US012564617B2

(12) United States Patent
Jaynes et al.

(10) Patent No.: US 12,564,617 B2
(45) Date of Patent: Mar. 3, 2026

(54) METHODS FOR MODULATING MACROPHAGE ACTIVITY

(71) Applicant: Riptide Bioscience, Inc., Vallejo, CA (US)

(72) Inventors: Jesse Jaynes, Auburn, AL (US); Henry Wilfred Lopez, Napa, CA (US); George R. Martin, Rockville, MD (US); Clayton Yates, Auburn, AL (US); Balasubramanyam Karanam, Auburn, AL (US)

(73) Assignee: Riptide Bioscience, Inc., Vallejo, CA (US)

( * ) Notice: Subject to any disclaimer, the term of this patent is extended or adjusted under 35 U.S.C. 154(b) by 1022 days.

(21) Appl. No.: 17/478,042

(22) Filed: Sep. 17, 2021

(65) Prior Publication Data

US 2022/0062373 A1 Mar. 3, 2022

Related U.S. Application Data

(63) Continuation of application No. PCT/US2020/027672, filed on Apr. 10, 2020.

(60) Provisional application No. 62/966,961, filed on Jan. 28, 2020, provisional application No. 62/833,352, filed on Apr. 12, 2019.

(51) Int. Cl.

| | |
|---|---|
| ***A61K 38/08*** | (2019.01) |
| ***A61P 35/00*** | (2006.01) |
| ***C12N 5/0786*** | (2010.01) |

(52) U.S. Cl.

CPC .............. *A61K 38/08* (2013.01); *A61P 35/00* (2018.01); *C12N 5/0645* (2013.01)

(58) Field of Classification Search

CPC ..... A61K 38/08; A61P 35/00; C12N 2501/50; C12N 2501/59; C12N 5/0645; G01N 2333/70596; G01N 33/5055; G01N 33/57407

See application file for complete search history.

(56) References Cited

U.S. PATENT DOCUMENTS

| | | | |
|---|---|---|---|
| 5,561,107 | A | 10/1996 | Jaynes et al. |
| 5,717,064 | A | 2/1998 | Julian et al. |
| 5,861,478 | A | 1/1999 | Jaynes |
| 5,955,573 | A | 9/1999 | Garbarino et al. |
| 5,962,410 | A | 10/1999 | Jaynes et al. |
| 6,001,805 | A | 12/1999 | Jaynes et al. |
| 6,084,156 | A | 7/2000 | Garbarino et al. |
| 6,191,110 | B1 | 2/2001 | Jaynes et al. |
| 6,255,282 | B1 | 7/2001 | Jaynes |
| 6,432,415 | B1 | 8/2002 | Osborne et al. |
| 6,514,692 | B2 | 2/2003 | Jaynes |
| 6,559,281 | B1 | 5/2003 | Jaynes |
| 6,635,740 | B1 | 10/2003 | Enright et al. |
| 6,680,058 | B1 | 1/2004 | Enright et al. |
| 7,288,622 | B1 | 10/2007 | Jaynes et al. |
| 7,566,777 | B2 | 7/2009 | Enright et al. |
| 7,803,755 | B2 | 9/2010 | Jaynes |
| 8,258,100 | B2 | 9/2012 | Enright et al. |
| 8,569,230 | B2 | 10/2013 | Yount et al. |
| 8,734,775 | B2 | 5/2014 | Yates-Binder et al. |
| 9,090,655 | B2 | 7/2015 | Cheng et al. |
| 9,492,499 | B2 * | 11/2016 | Jaynes .................... A61P 11/00 |
| 10,016,480 | B2 | 7/2018 | Rudloff et al. |
| 10,017,542 | B2 | 7/2018 | Jaynes et al. |
| 10,285,938 | B2 | 5/2019 | Isanaka et al. |
| 10,548,944 | B1 | 2/2020 | Jaynes et al. |
| 2002/0155132 | A1 | 10/2002 | Jaynes |
| 2003/0109452 | A1 | 6/2003 | Owen |
| 2004/0018967 | A1 | 1/2004 | Enright et al. |
| 2005/0187151 | A1 | 8/2005 | Strom et al. |
| 2005/0244916 | A1 | 11/2005 | Yeaman et al. |
| 2008/0153748 | A1 | 6/2008 | Jaynes |
| 2010/0015116 | A1 | 1/2010 | Oyler et al. |
| 2010/0016227 | A1 | 1/2010 | Enright et al. |
| 2012/0270770 | A1 | 10/2012 | Jaynes |
| 2012/0329720 | A1 | 12/2012 | May et al. |
| 2013/0052213 | A1 | 2/2013 | Kjaer et al. |
| 2013/0052258 | A1 | 2/2013 | Kalle et al. |

(Continued)

FOREIGN PATENT DOCUMENTS

| | | |
|---|---|---|
| EP | 3354274 A1 | 8/2018 |
| JP | H8-134075 A | 5/1996 |

(Continued)

OTHER PUBLICATIONS

Gupta et al (Computational Biology and Chemistry, vol. 76, Oct. 2018, pp. 210-217) (Year: 2018).*
Philips et al (Open access peer-reviewed chapter Has Molecular Docking Ever Brought us a Medicine? Molecular Docking, Book, published: Jul. 11, 2018) (Year: 2018).*
Furukawa et al (BBA—Reviews on Cancer 1875 (2021) 188486, pp. 1-15) (Year: 2021).*
Jaynes et al (Sci Transl Med. Feb. 12, 2020; 12(530)) (Year: 2020).*
Ray et al (J. Exp. Med. 2025 vol. 222 No. 1, pp. 1-18) (Year: 2025).*
Rannikko et al (British Journal of Cancer (2024) 131:627-640) (Year: 2024).*
Cancer Newsletter (Cancer myths and questions•May 12, 2025) (Year: 2025).*

(Continued)

*Primary Examiner* — Jean P Cornet
(74) *Attorney, Agent, or Firm* — Travis Young; Andrew R. Guzman; Bret E. Field

(57) ABSTRACT

Methods according to certain embodiments include contacting a macrophage with a mannose receptor (CD206) binding agent in a manner sufficient to modulate activity of the macrophage. Methods for converting a phenotype of a macrophage from an M2 phenotype to an M1 phenotype are also provided. Methods for inhibiting growth of a CD206-expressing cell as well as methods for treating a subject for a neoplastic condition (e.g., cancer) or a condition associated with chronic inflammation are described. Immuno-modulating peptides suitable for use in the subject methods are also presented.

14 Claims, 138 Drawing Sheets

Specification includes a Sequence Listing.

(56) References Cited

U.S. PATENT DOCUMENTS

| | | | |
|---|---|---|---|
| 2014/0128312 | A1 | 5/2014 | Jaynes |
| 2014/0329753 | A1 | 11/2014 | Jaynes |
| 2016/0083482 | A1 | 3/2016 | Martini et al. |
| 2016/0101150 | A1 | 4/2016 | Jaynes et al. |
| 2016/0296594 | A1 | 10/2016 | Jaynes et al. |
| 2017/0020956 | A1 | 1/2017 | Jaynes et al. |
| 2019/0046601 | A1 | 2/2019 | Jaynes et al. |
| 2019/0151304 | A1 | 5/2019 | Tan et al. |
| 2021/0340132 | A1 | 11/2021 | Schafer et al. |
| 2022/0143130 | A1 | 5/2022 | Jaynes et al. |

FOREIGN PATENT DOCUMENTS

| | | | |
|---|---|---|---|
| JP | 2000-513209 | A | 10/2000 |
| JP | 2001-520639 | A | 10/2001 |
| JP | 2010-536714 | A | 12/2010 |
| WO | WO1990012866 | A1 | 11/1990 |
| WO | WO1993003749 | A1 | 3/1993 |
| WO | WO9516776 | A1 | 6/1995 |
| WO | WO1995028832 | A1 | 11/1995 |
| WO | WO1996003519 | A1 | 2/1996 |
| WO | WO1996003522 | A1 | 2/1996 |
| WO | WO1998042364 | A1 | 10/1998 |
| WO | WO1998042365 | A1 | 10/1998 |
| WO | WO1998042634 | A1 | 10/1998 |
| WO | WO2000073433 | A1 | 12/2000 |
| WO | WO2004033715 | A1 | 4/2004 |
| WO | WO2005046714 | A2 | 5/2005 |
| WO | WO2006100096 | A3 | 9/2006 |
| WO | WO2007072037 | A1 | 6/2007 |
| WO | WO2007106951 | A1 | 9/2007 |
| WO | WO2008014414 | A2 | 1/2008 |
| WO | WO2008022444 | A1 | 2/2008 |
| WO | WO2009059379 | A1 | 5/2009 |
| WO | WO2010038220 | A1 | 4/2010 |
| WO | WO2011020188 | A1 | 2/2011 |
| WO | WO2012050892 | A2 | 4/2012 |
| WO | WO2013174537 | A1 | 11/2013 |
| WO | WO2018007827 | A1 | 1/2018 |
| WO | WO2020046835 | A1 | 3/2020 |
| WO | WO2021126923 | A1 | 6/2021 |

OTHER PUBLICATIONS

Mayo Clinic, Feb. 15, 2024 (Year: 2024).*

Sharma et al (Adv. Nano Biomed Res. Jan. 2021, pp. 1-21) (Year: 2021).*

Liddiard et al (Nature Medicine vol. 21, pp. 119-120 (2015)) (Year: 2015).*

Antibacterial Protein PR-39 Precursor [Sus Scrofa], from https://www.ncbi.nlm.nih.gov/protein/NP_999615.1, p. 1-3, accessed Sep. 4, 2019.

Blondelle et al., Optimization and High-Throughput Screening of Antimicrobial Peptides, Current Pharmaceutical Design, vol. 16, No. 28, Sep. 1, 2010, p. 3204-3211.

Clemens et al., Designed Host Defense Peptides for the Treatment of Bacterial Keratitis, Investigative Ophthalmology and Visual Science, vol. 58, No. 14, Dec. 2017, p. 6273-6281.

Isaacs et al., A Lipid-Peptide Microbicide Inactivates Herpes Simplex Virus, Antimicrobial Agents and Chemotherapy, Aug. 2004, vol. 48, No. 8, p. 3182-3184.

Jankowski et al., Anti-Inflammatory Effect of Oxytocin in Rat Myocardial Infarction, Basic Research in Cardiology, Mar. 2010, vol. 105, No. 2, p. 205-218.

Jaynes et al., Structure/Function Link Between Cytokine Domains and Natural and Designed Lytic Peptides: Medical Promise, Apr. 2012, American Chemical Society, p. 21-45.

Ko et al., FOLFIRINOX A Small Step or a Great Leap Forward?, Journal of Clinical Oncology, vol. 29, No. 28, Oct. 1, 2011, p. 3727-3729.

Ma et al., Inhibitory Activity of Synthetic Peptide Antibiotics on Feline Immunodeficiency Virus Infectivity in Vitro, Journal of Virology, Oct. 2002, vol. 76, No. 19, p. 9952-9961.

Muta et al., Tachyplesins Isolated from Hemocytes of Southeast Asian Horseshoe Crabs (*Carcinoscorpis rotundicauda* and *Tachypleus gigas*): Identification of a New Tachyplesin, Tachyplesin III, and a Processing Intermediate of its Precursor, Journal of Biochemistry, Aug. 1990, p. 261-266.

Oxytocin, NCBI, PRF:229114, GI:229114, Jul. 10, 1992, p. 1, also available at http://www.ncbi.nlm.nig.gov/protein/229114, accessed Jan. 28, 2016.

Panda et al., Hypothetical Protein KCO_01177 [*Pectobacterium carotovorum* Subsp. *brasiliensis* ICMP 19477], Genbank entry [online], Jun. 24, 2015 [retrieved Dec. 14, 2018], <URL: https://www.ncbi.nlm.nih.gov/protein/KMK85879.1>, p. 1-2.

Park et al., Melittin Inhibits Inflammatory Target Gene Expression and Mediator Generation Via Interaction with KappaB Kinase, Biochemical Pharmacology, Sep. 29, 2006, vol. 73, No. 2, p. 237-247.

Partial Supplementary European Search Report for European Application No. EP15851584, dated May 30, 2018, 17 pages.

Raventos et al., Improving on Nature's Defenses: Optimization and High Throughput Screening of Antimicrobial Peptides, Combinatorial Chemistry and High Throughput Screening, vol. 8, No. 3, Jun. 2005, p. 219-233.

Sawabe et al., Hypothetical Protein JCM19233_786 [*Vibrio* sp. C7], Genbank entry [online], Oct. 17, 2014 [retrieved Dec. 14, 2018], <URL: https://www.ncbi.nlm.nih.gov/protein/GAL09809.1>, p. 1.

Schwab et al., In Vitro Activities of Designed Antimicrobial Peptides Against Multidrug-Resistant Cystic Fibrosis Pathogens, Antimicrobial Agents and Chemotherapy, Jun. 1999, vol. 43, No. 6, p. 1435-1440.

Smith et al., Effects of Synthetic Amphiphilic α-Helical Peptides on the Electrochemical and Structural Properties of Supported Hybrid Bilayers on Gold, Langmuir, Jan. 20, 2006, vol. 22, No. 4, p. 1919-1927.

Stover et al., Screening Antimicrobial Peptides In Vitro for Use in Developing Transgenic Citrus Resistant to Huanglongbing and Citrus Canker, Journal of the American Society for Horticultural Science, Mar. 2013, vol. 138, No. 2, p. 142-148.

Visser et al., A Transient Expression Assay for the In Planta Efficacy Screening of an Antimicrobial Peptide Against Grapevine Bacterial Pathogens, Letters in Applied Microbiology, Jun. 2012, vol. 54, No. 6, p. 543-551.

Wang et al., A Cell-Penetrating Peptide Suppresses Inflammation by Inhibiting NF-Kappa-Beta Signaling, Molecular Therapy, May 10, 2011, vol. 19, No. 10, p. 1849-1857.

Wang, Human Antimicrobial Peptides and Proteins, Pharmaceuticals, May 2014, vol. 7, No. 5, p. 545-594.

Water, from https://www.biology-online.org/dictionary/Water, p. 1-3, accessed Sep. 4, 2019.

Yates et al., LHRH-Conjugated Lytic Peptides Directly Target Prostate Cancer Cells, Biochemical Pharmacology, Jan. 1, 2011, vol. 81, No. 1, p. 104-110.

Movahedi et al., Nanobody-Based Targeting of the Macrophage Mannose Receptor for Effective In Vivo Imaging ofTumor-Associated Macrophages, Cancer Research, Aug. 2012, vol. 72, No. 16, p. 4165-4177.

Antimicrobial Peptide AP00692, from http://aps.unmc.edu/AP/database/query_output.php?ID=00692, accessed Feb. 28, 2020, p. 1.

Parabens as Preservatives, Ueno Fine Chemicals Industry Ltd., pp. 1-13, accessed Feb. 2, 2020.

Nogami et al., Tailor-made Designer Helical Peptides That Induce Mitochondrion-Mediated Cell Death Without Necrosis, Chembiochem. Nov. 24, 2014;15(17):2571-6.

Feinberg et al., Structure of a C-type carbohydrate recognition domain from the macrophage mannose receptor, J Biol Chem. Jul. 14, 2000;275(28):21539-48.

Bork, Powers and pitfalls in sequence analysis: the 70% hurdle, Genome Res. Apr. 2000;10(4):398-400.

Bowie et al., Deciphering the message in protein sequences: tolerance to amino acid substitutions, Science Mar. 6, 1990: vol. 247, Issue 4948, pp. 1306-1310.

Burgess et al., Possible dissociation of the heparin-binding and mitogenic activities of heparin-binding (acidic fibroblast) growth

(56) References Cited

OTHER PUBLICATIONS factor-1 from its receptor-binding activities by site-directed mutagenesis of a single lysine residue, J Cell Biol. Nov. 1990;111(5 Pt 1):2129-38.
Lazar et al., Transforming growth factor alpha: mutation of aspartic acid 47 and leucine 48 results in different biological activities, Mol Cell Biol. Mar. 1988; 8(3): 1247-1252.
De La Fuente-Nunez et al., D-enantiomeric peptides that eradicate wild-type and multi-drug resistant biofilms and protect against lethal Pseudomonas aeruginosa infections, Chem Biol. Feb. 19, 2015; 22(2): 196-205.
Jahnsen et al., Characterization of a proteolytically stable multi-functional host defense peptidomimetic, Chem Biol. Oct. 24, 2013;20(10):1286-95.
Kozakov et al., How Good is Automated Protein Docking?, Proteins. Dec. 2013; 81(12): 2159-2166.
Porter et al., ClusPro PeptiDock: efficient global docking of peptide recognition motifs using FFT, Bioinformatics, 33(20), 2017, 3299-3301.
Laverty et al., The potential of antimicrobial peptides as biocides, Int J Mol Sci, 2011; 12(10):6566-96.
Adessi et al., Converting a peptide into a drug: strategies to improve stability and bioavailability, Curr Med Chem, May 2002; 9(9):963-78.
Haney et al., Peptide Design for Antimicrobial and Immunomodulatory Applications, Biopolymers, Nov. 2013; 100(6): 572-583.
Shiva-10 enzyme cut, from http://web.expasy.org/cgi-bin/peptide_cutter/peptidecutter.pl, pp. 1-3, accessed Nov. 4, 2021.
Dulmovits et al., Microvascular remodeling and wound healing: a role for pericytes, Int J Biochem Cell Biol, Nov. 2012, 44(11):1800-12.
Chalekson et al., Treatment of infected wounds with the antimicrobial peptide D2A21, J Trauma, Apr. 2003, 5(4):770-4.
Dangaj et al., Mannose receptor (MR) engagement by mesothelin GPI anchor polarizes tumor-associated macrophages and is blocked by anti-MR human recombinant antibody, PLoS One. 2011;6(12):e28386.
Boulman et al., Calcinosis in rheumatic diseases, Semin Arthritis Rheum, 34(6):805-12 (Jun. 2005).
Valenzuela et al., Calcinosis: pathophysiology and management, Curr Opin Rheumatol, 27(6):542-8 (Nov. 2015).

* cited by examiner

FIG. 2

| **HDP** | **Sequence** | **Molly** |
|---|---|---|
| CEC-F1 | IFKKIERVGQ |  |
| CEC-F2 | LFKKIEKVGQ | 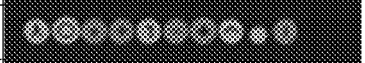 |
| LL37-F1 | FFRKSKEKIG |  |
| LL37-F2 | IGKEFKRIVQ | 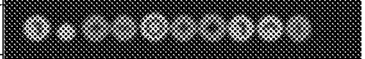 |
| PLEU-F | FFKKAAHVGK | 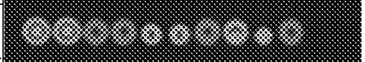 |
| PSEU-F | ALKKVFQGIH | 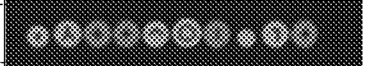 |
| MAG-F1 | FLHSAKKFGK | 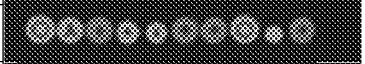 |
| CATH-F | LKKALPVAKK | 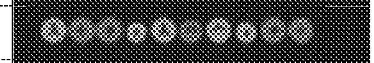 |
| MAG-F2 | HSAKKFGKAF | 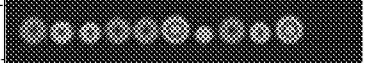 |
| LL37-F3 | RIKDFLRNLV | 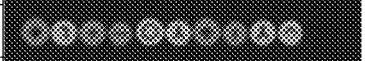 |
| LL37-F4 | RIVQRIKDFL | 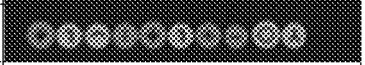 |
| **DHDP** | **Sequence** | **Molly** |
| RP-182 | KFRKAFKRFF | 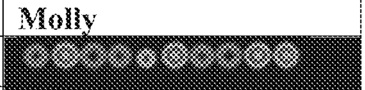 |
| RP-426 | KARKAAKRAF | 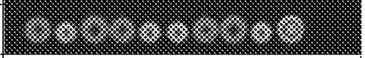 |
| **Virulence** | **Sequence** | **Molly** |
| AVP1-F | EKLSAFRNFF |  |
| CTPR-F | AVRRLAQRLA |  |
| MPCP-F | KEFLAFKRFF | 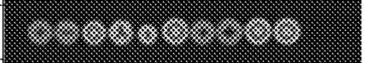 |
| TPRO-F | IENAAFKRFF | 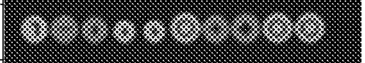 |
| PTTM-F | GFRELFRQLD |  |
| gp120-F | AIRRIPRRIR | 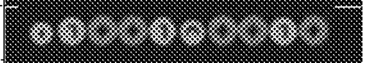 |
| FLAB-F | MVFRDVGNRN | 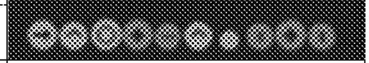 |
| **Collagen** | **Sequence** | **Molly** |
| COLI-F | DRGIKGHRGF | 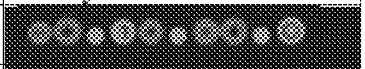 |
| COLIV-F | LRGQKGDRGF | 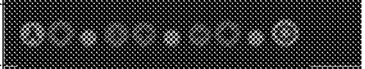 |
| COLV-F | EAGEKGDQGL | 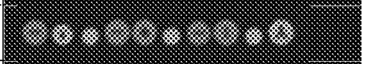 |
| COLVI-F | VLDAIRRLRL | 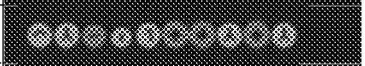 |
| COLVII-F | HVVQRGEHSL | 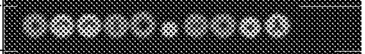 |
| COLXVIII-F | IVRRADRAAV | 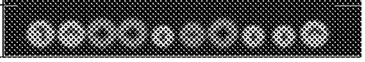 |

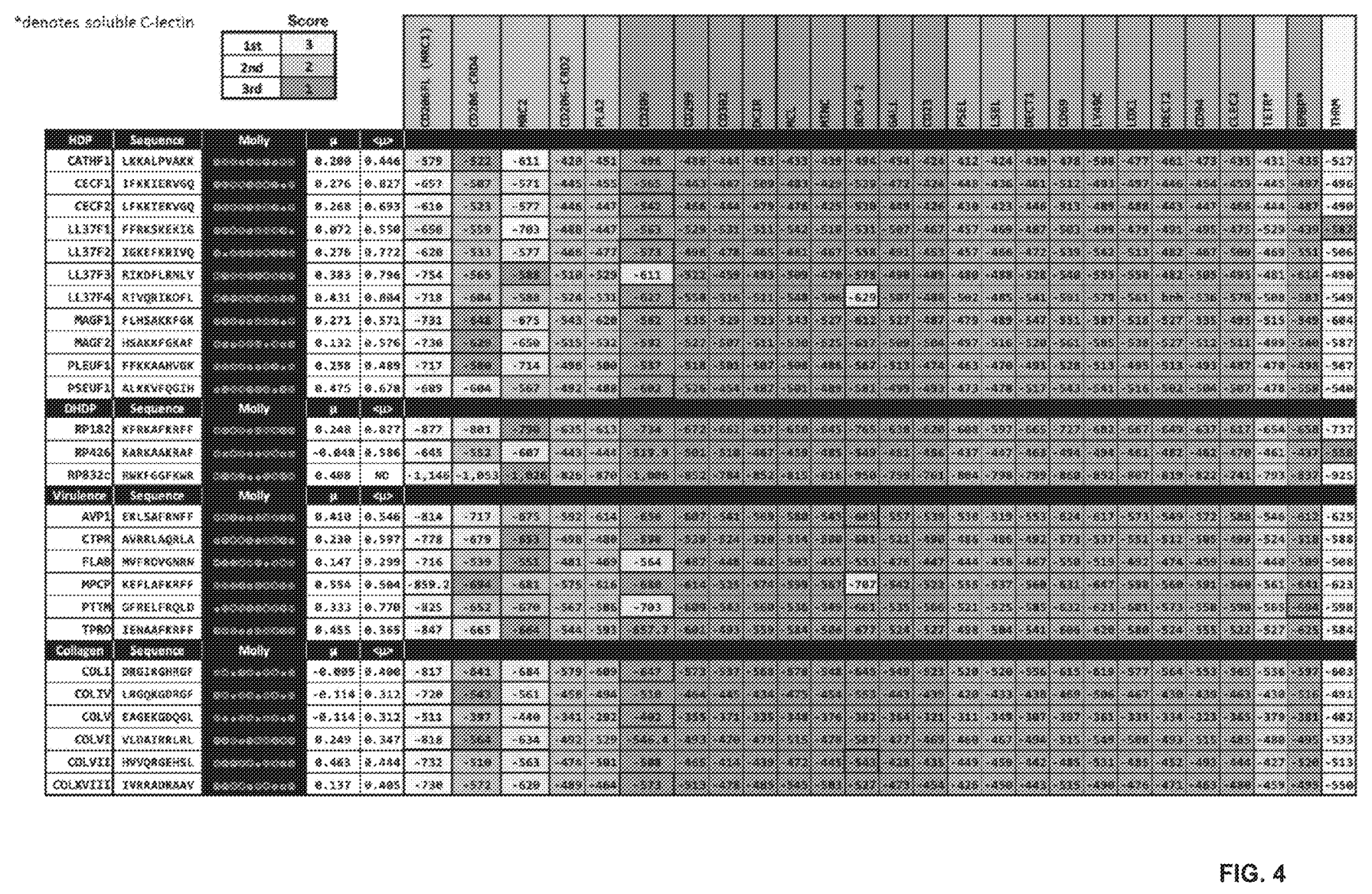

*denotes soluble C-lectin

| Score | |
|---|---|
| 1st | 3 |
| 2nd | 2 |
| 3rd | 1 |

| KDP | Sequence | Molly | μ | <μ> | CD206L (MRC1) | CD206-CRD4 | MRC2 | CD206-CRD2 | PLA2 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible]* | [illegible]* | THBM |
|---|---|---|---|---|---|---|---|---|---|---|---|---|---|---|---|---|---|---|---|---|---|---|---|---|---|---|---|---|---|---|
| CATHF1 | LKKALPVAKK | | 0.300 | 0.446 | -579 | [illegible] | -611 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -517 |
| CECF1 | IFKKIERVGQ | | 0.276 | 0.827 | -657 | [illegible] | -571 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -496 |
| CECF2 | LFKKIEKVGQ | | 0.268 | 0.693 | -610 | [illegible] | -577 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -490 |
| LL37F1 | FFRKSKEKIG | | 0.072 | 0.550 | -656 | [illegible] | -703 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] |
| LL37F2 | IGKEFKRIVQ | | 0.278 | 0.772 | -628 | [illegible] | -577 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -506 |
| LL37F3 | RIKDFLRNLV | | 0.383 | 0.796 | -754 | [illegible] | [illegible] | [illegible] | [illegible] | -611 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -490 |
| LL37F4 | RIVQRIKDFL | | 0.431 | 0.884 | -718 | [illegible] | [illegible] | [illegible] | [illegible] | [illegible] | [illegible] | [illegible] | [illegible] | [illegible] | [illegible] | -629 | [illegible] | [illegible] | [illegible] | [illegible] | [illegible] | [illegible] | [illegible] | [illegible] | [illegible] | [illegible] | [illegible] | [illegible] | [illegible] | -549 |
| MAGF1 | FLHSAKKFGK | | 0.271 | 0.571 | -731 | [illegible] | -675 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -604 |
| MAGF2 | HSAKKFGKAF | | 0.132 | 0.576 | -736 | [illegible] | -650 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -587 |
| PLEUF1 | FFKKAAHVGK | | 0.298 | 0.489 | -717 | [illegible] | -714 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -567 |
| PSEUF1 | ALKKVFQGIH | | 0.475 | 0.678 | -689 | -604 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -540 |
| **DHDP** | **Sequence** | **Molly** | **μ** | **<μ>** | | | | | | | | | | | | | | | | | | | | | | | | | | |
| RP182 | KFRKAFKRFF | | 0.248 | 0.827 | -877 | -801 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -737 |
| RP426 | KARKAAKKAF | | -0.048 | 0.586 | -645 | [illegible] | -687 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] |
| RP832c | HWKFGGFKWR | | 0.488 | ND | -1,146 | -1,093 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -925 |
| **Virulence** | **Sequence** | **Molly** | **μ** | **<μ>** | | | | | | | | | | | | | | | | | | | | | | | | | | |
| AVP1 | EKLSAFRNFF | | 0.410 | 0.546 | -814 | -717 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -625 |
| CTPR | AVRRLAQRLA | | 0.230 | 0.597 | -778 | -679 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -588 |
| FLAB | MVFRQVGNRN | | 0.147 | 0.299 | -716 | [illegible] | [illegible] | [illegible] | [illegible] | -564 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -508 |
| MPCP | KEFLAFKRFF | | 0.554 | 0.504 | -859.2 | [illegible] | [illegible] | [illegible] | [illegible] | [illegible] | [illegible] | [illegible] | [illegible] | [illegible] | [illegible] | -787 | [illegible] | [illegible] | [illegible] | [illegible] | [illegible] | [illegible] | [illegible] | [illegible] | [illegible] | [illegible] | [illegible] | [illegible] | [illegible] | -623 |
| PTTM | GFRELFRQLD | | 0.333 | 0.770 | -825 | [illegible] | -670 | [illegible] | [illegible] | -703 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -598 |
| TPRO | IENAAFKRFF | | 0.455 | 0.365 | -847 | -665 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -584 |
| **Collagen** | **Sequence** | **Molly** | **μ** | **<μ>** | | | | | | | | | | | | | | | | | | | | | | | | | | |
| COLI | DRGIKGHRGF | | -0.009 | 0.400 | -817 | [illegible] | -684 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -603 |
| COLIV | LRGQKGDRGF | | -0.114 | 0.312 | -720 | [illegible] | -561 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -491 |
| COLV | EAGEKGDQGL | | -0.114 | 0.312 | -513 | [illegible] | -440 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -482 |
| COLVI | VLDAIRRLRL | | 0.249 | 0.347 | -818 | [illegible] | -634 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -533 |
| COLVII | HVVQRGEHSL | | 0.463 | 0.444 | -732 | [illegible] | -563 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -513 |
| COLXVIII | IVRRADRAAV | | 0.137 | 0.405 | -738 | [illegible] | -620 | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | [illegible] | -550 |

FIG. 4

| Sample | Rg Guinier (Å) | Rg in reciprocal space (Å) | Rg in Real space (Å) | Dmax (Å) | MW' Vporod (kda) | MW' Vc (kda) |
|---|---|---|---|---|---|---|
| CD206 | 79 ± 3 | 81.9 | 82 ± 2 | 301 | 345 | 343 Q = 0.15 |

FIG. 7C
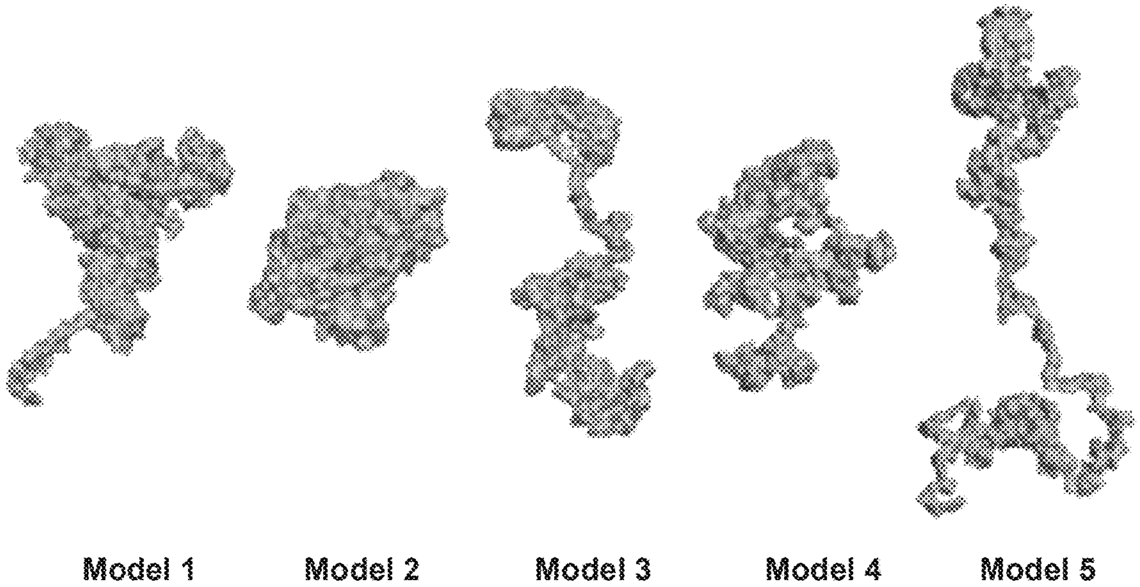
| | Model 1 | Model 2 | Model 3 | Model 4 | Model 5 |
|---|---|---|---|---|---|
| $X^2$ | 1.9409 | 40.026 | 3.9197 | 6.3528 | 3.9197 |
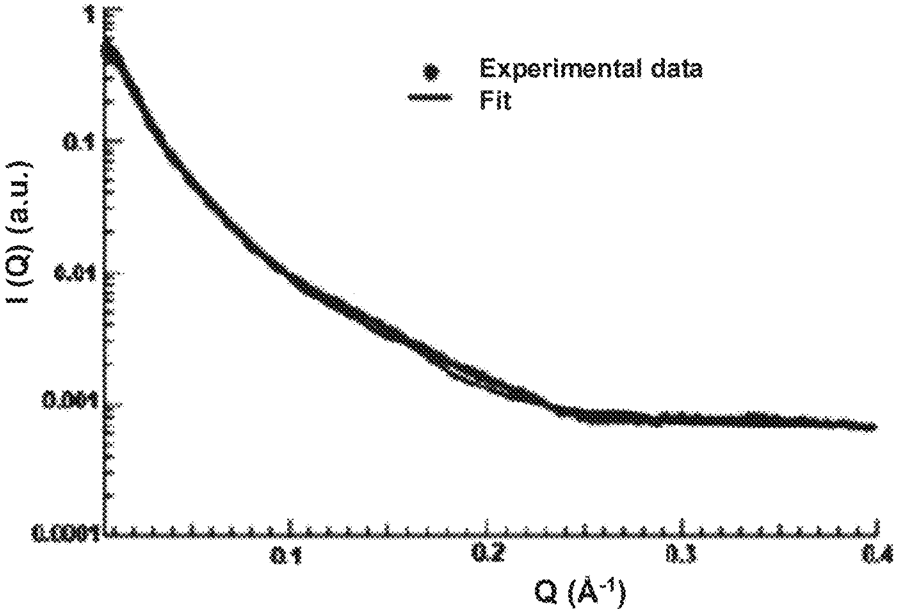

FIG. 9B
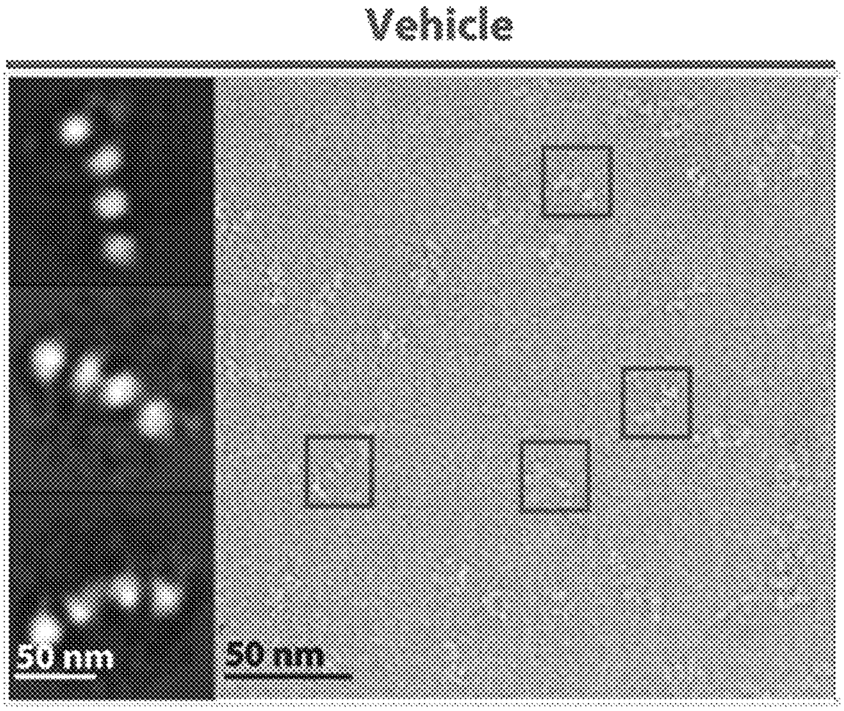
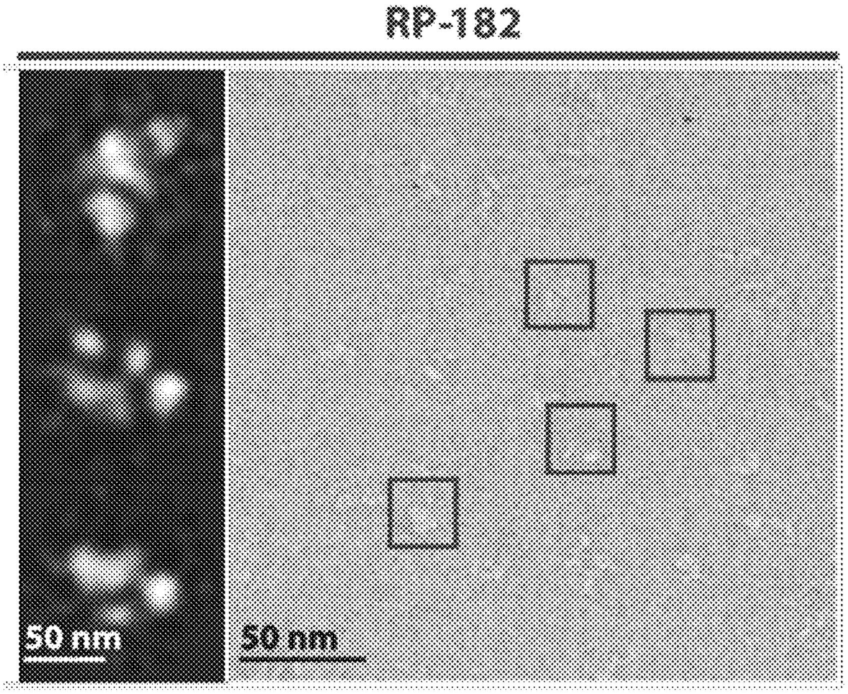

FIG. 10

| Complex | Ratio CD206:RP182 | Concentration of RP182 (μM) | Closed conformation (%) |
|---|---|---|---|
| CD206FL-RP182 | 1:1 | 0.65 | 5 |
| CD206FL-RP182 | 1:3 | 2 | 16 |
| CD206FL-RP182 | 1:9 | 6 | 40 |
| CD206FL-RP182 | 1:27 | 17.5 | 57 |
| CD206FL-RP182 | 1:91 | 59 | 74 |
| CD206FL-RP182 | 1:1900 | 160 | 95 |

FIG. 11

| Peptide | Closed CD206 complexes | |
|---|---|---|
| | Low concentration | High concentration |
| RP-182 | 56/100 | 100/100 |
| RP-832C | 45/100 | 100/100 |
| RP-185 | 41/100 | 63/100 |
| AVP1 | 44/100 | 46/100 |
| LL37F1 | 17/100 | 25/100 |
| RP-426 | 17/100 | 15/100 |

FIG. 12A
RP-185
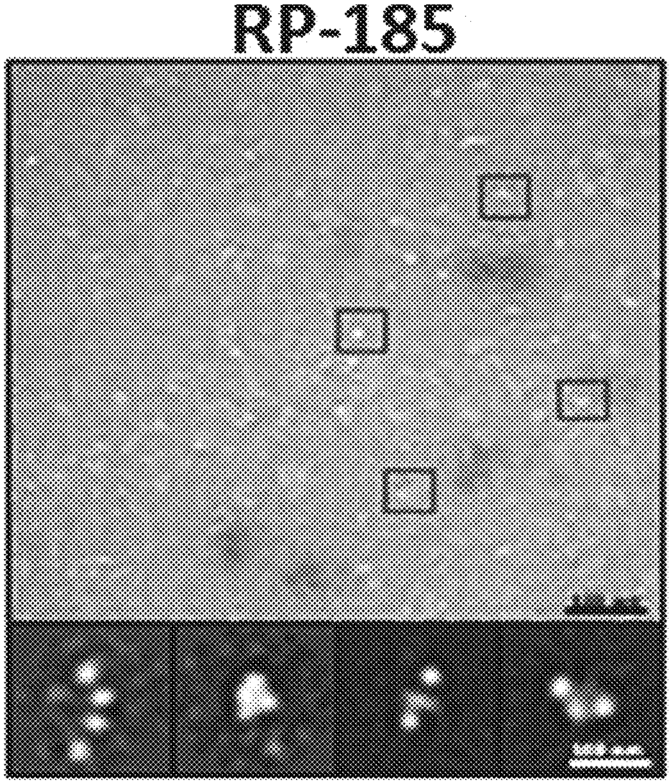
AVP1
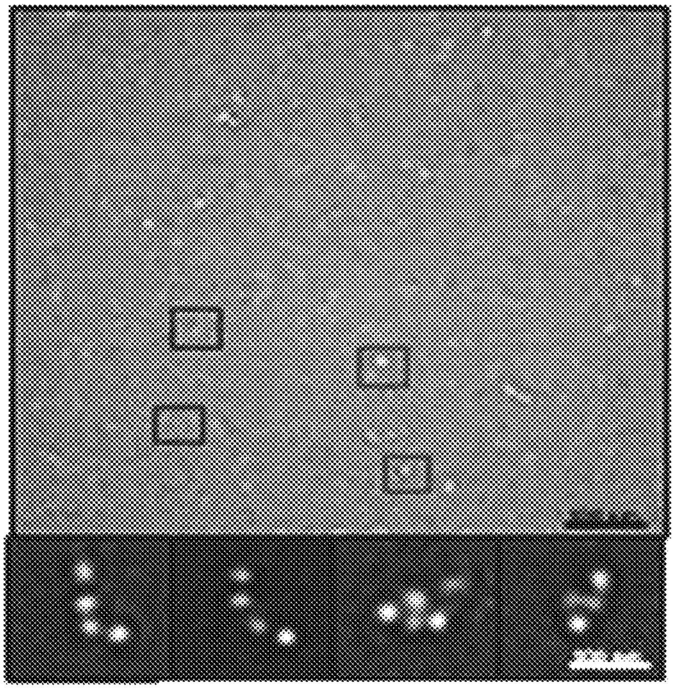

A Human peripheral blood monocyte-dervied macrophage polarization protocol

B Cellular Thermal Shift Assay (CETSA) of human macrophages

| Treatment | Tagg, °C |
|---|---|
| PBS | 52.20 |
| RP-182 | 47.95 |
| RP-426 | 52.42 |

C Murine bone marrow-derived macrophage (BMDM) polarization protocol

Cellular Thermal Shift Assay (CETSA) of murine macrophages

| Treatment | $T_{agg}$ |
|---|---|
| PBS | 54.52 |
| RP-182 | 50.48 |
| RP-426 | 54.72 |

(i). CsOH, Bu, NBr, $CH_2$ $Cl_2$, rt, 12hr, 65% (ii) TFA, rt, 2h, 93%
(ii) Chiral chromatography, 1NaOH, MeOH, 85% (iv) Fmoc-Cl, DIEA, THF, 70%

FIG. 15B
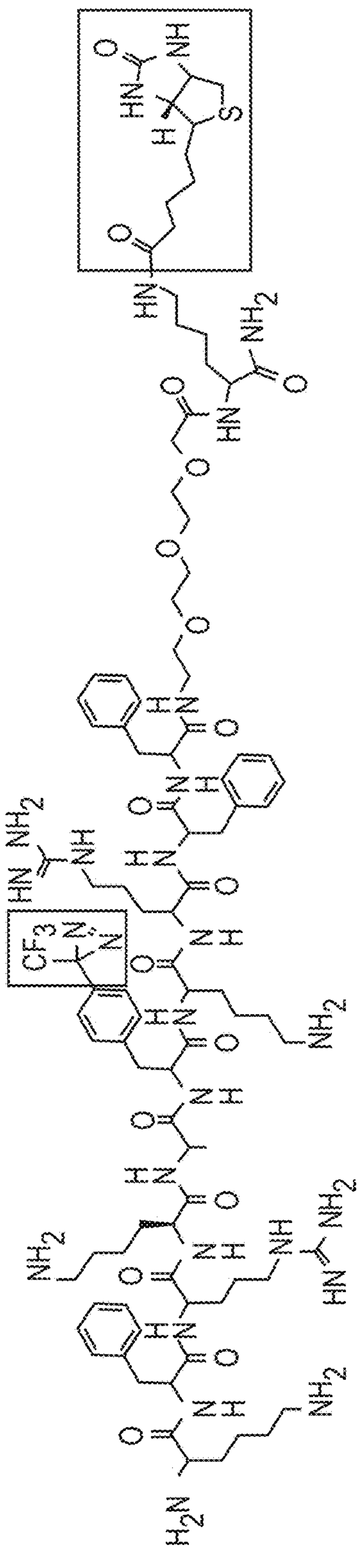
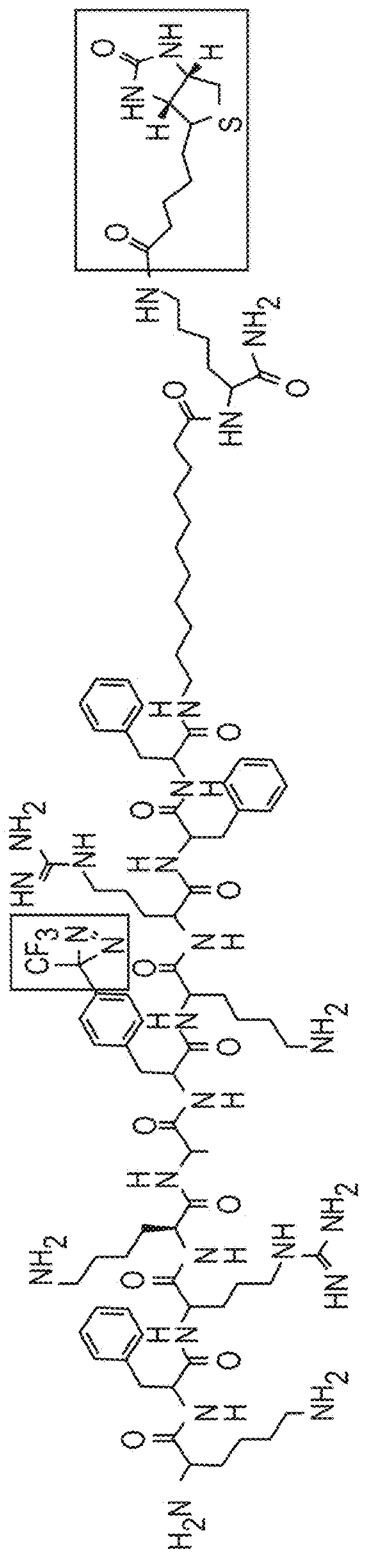

FIG. 15B (Cont.)
| | | | |
|---|---|---|---|
| KFRKAFKRFF, PEG linker | NCGC-00510433 | *9.00 μM (±5.45)* | 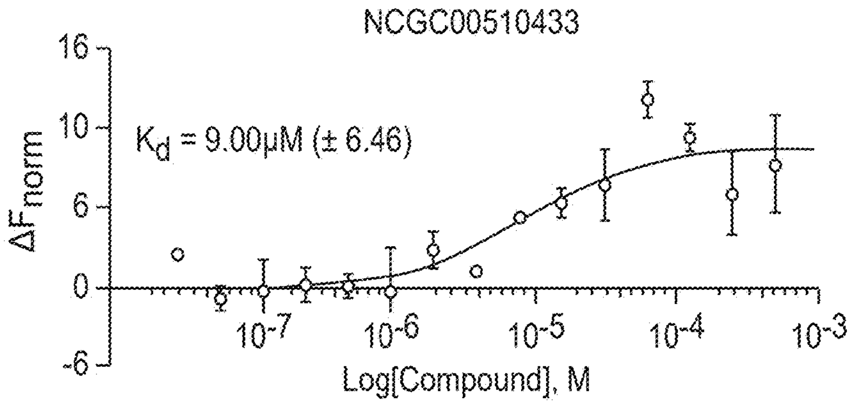 |
| KFRKAFKRFF, Hydrocarbon linker | NCGC-00510432 | *1.70 μM (±0.45)* | 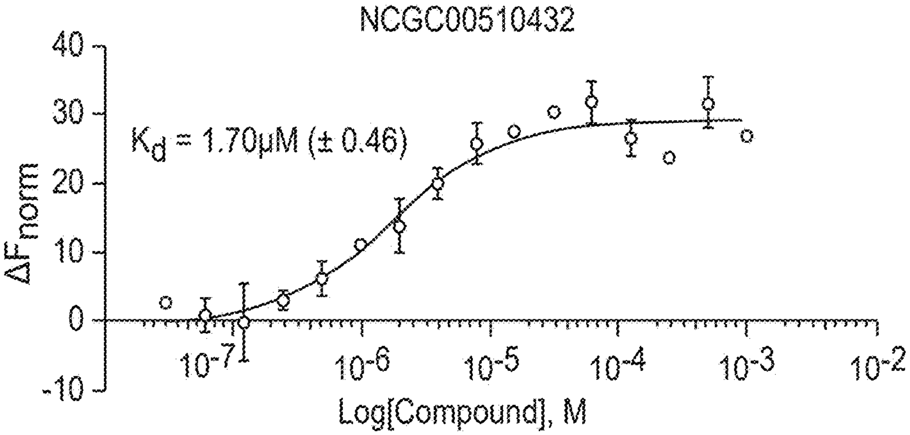 |

FIG. 15B (Cont.)
| | | | |
|---|---|---|---|
| KFRKAFKRFF, PEG linker | NCGC-00510435 | *76.46 μM (±10.95)* | 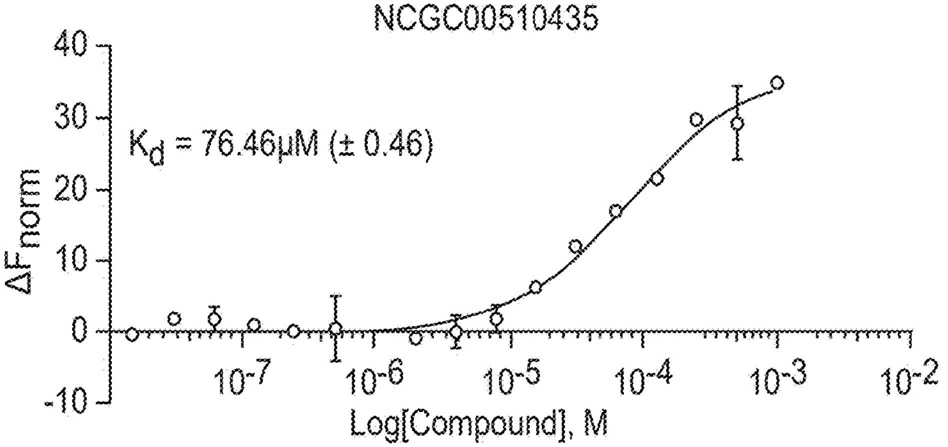 |
| KFRKAFKRFF, Hydrocarbon linker | NCGC-00510434 | *7.01 μM (±2.96)* | 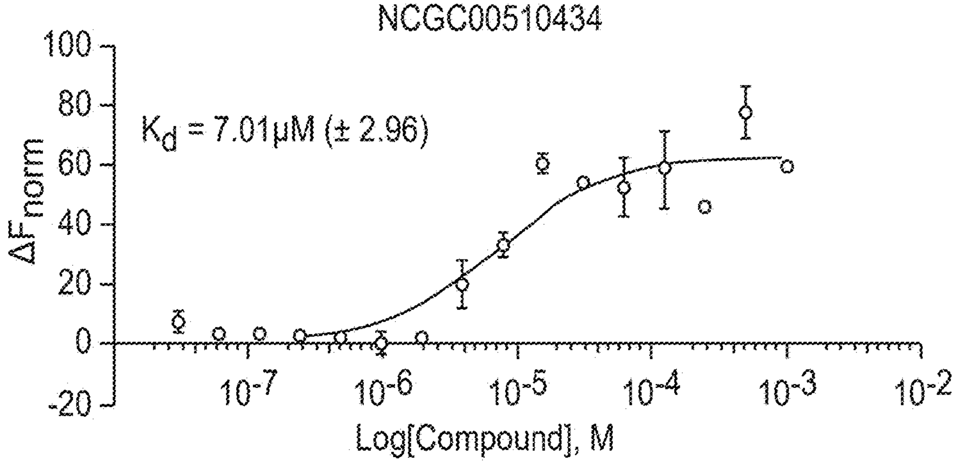 |

| Sample | EdgeR |
|---|---|
| M2 2h | 119 |
| M1 2h | 0 |
| M1 6h | 6 |
| M1 24h | 8 |

- FDR < 0.05
- -1 <Log2[FC] >1 for EdgeR

FIG. 21B

RP182 vs vehicle-treated M2 BMDM: Gene Selection Method

| Biological Process | NES | NOM p-val |
|---|---|---|
| Innate Immune Response | 1.5121943 | 0.005035247 |
| Regulation of Protein Secretion | 1.4837614 | 0.01010101 |
| Regulation of Cytokine Secretion | 1.5302026 | 0.01344364 |
| Immune Response | 1.3335506 | 0.019 |
| Positive Regulation of Cytokine Production | 1.404566 | 0.02004008 |
| Response to Bacterium | 1.3361756 | 0.022 |
| Positive Regulation of Immune System Process | 1.3449228 | 0.023023022 |
| Defense Response | 1.2754207 | 0.025 |
| Positive Regulation of NF KappaB TF Activity | 1.5162232 | 0.026943006 |
| Positive Regulation of Establishment of Protein Localization | 1.4145086 | 0.027162978 |
| Defense Response to Other Organism | 1.4783081 | 0.02749491 |
| Positive Regulation of Multicellular Organismal Process | 1.291472 | 0.03 |
| Regulation of Immune System Process | 1.2597538 | 0.031 |
| Regulation of Secretion | 1.4092323 | 0.03109328 |
| Regulation of Sequence Specific DNA Binding Transcription Factor Activity | 1.4006019 | 0.03137652 |
| Positive Regulation of Sequence Specific DNA Binding Transcription Factor Binding | 1.4850513 | 0.031664964 |
| Regulation of Protein Localization | 1.3489579 | 0.032 |
| Response to Lipid | 1.2966526 | 0.034 |
| Response to Biotic Stimulus | 1.3144593 | 0.035 |
| Regulation of Transport | 1.2829467 | 0.039 |
| Activation of Innate Immune Response | 1.4573423 | 0.039553754 |
| Immune System Process | 1.2223215 | 0.04 |
| Regulation of Immune Response | 1.3094363 | 0.04308617 |
| Lymphocyte Activation | 1.4584979 | 0.046296295 |
| Positive Regulation of Immune Response | 1.3799728 | 0.04904905 |

FIG. 21D

RP182 Treated M2 Protein Pull Down: Gene Selection Method

| Biological Process | NES | NOM - val |
|---|---|---|
| Cytoskeleton Organization | 1.8106458 | 0.001023541 |
| Protein Complex Subunit Organization | 1.7975897 | 0.001 |
| Actin Filament Based Process | 1.6858648 | 0.009193054 |
| Regulation Of Cytoskeleton Organization | 1.6780076 | 0.02012712 |
| Movement Of Cell Or Subcellular Component | 1.6758994 | 0.011293635 |
| Regulation Of GTPase Activity | 1.5549008 | 0.04278075 |
| Positive Regulation Of Hydrolase Activity | 1.5470825 | 0.048596114 |
| Regulation Of Hydrolase Activity | 1. 5200257 | 0.049788136 |
| Positive Regulation Of Molecular Function | 1.473363 | 0.058641974 |
| Macromolecular Complex Assembly | 1.4618286 | 0.08220603 |
| Locomotion | 1.4499347 | 0.08550574 |
| Regulation Of Organelle Organization | 1.431553 | 0.0687885 |
| Phosphate Containing Compound Metabolic Process | 1.4239783 | 0.10085837 |
| Cell Cycle | 1.4000933 | 0.12150538 |
| Intracellular Signal Transduction | 1.3988564 | 0.100926876 |
| Positive Regulation Of Catalytic Activity | 1.3934673 | 0.10103093 |
| Cellular Component Morphogenesis | 1.3591273 | 0.1372756 |
| Response To External Stimulus | 1.3327377 | 0.15828878 |
| Cell Projection Organization | 1.2906903 | 0.17913593 |
| Cell Development | 1.2322806 | 0.22839506 |

Proteins within the MS pull down assay were pre-ranked (by protein spectrum matches ratio-RP182/ control) and input into GSEA to assess GO | Biological Process enrichment. NES - Normalized Enrichment Score

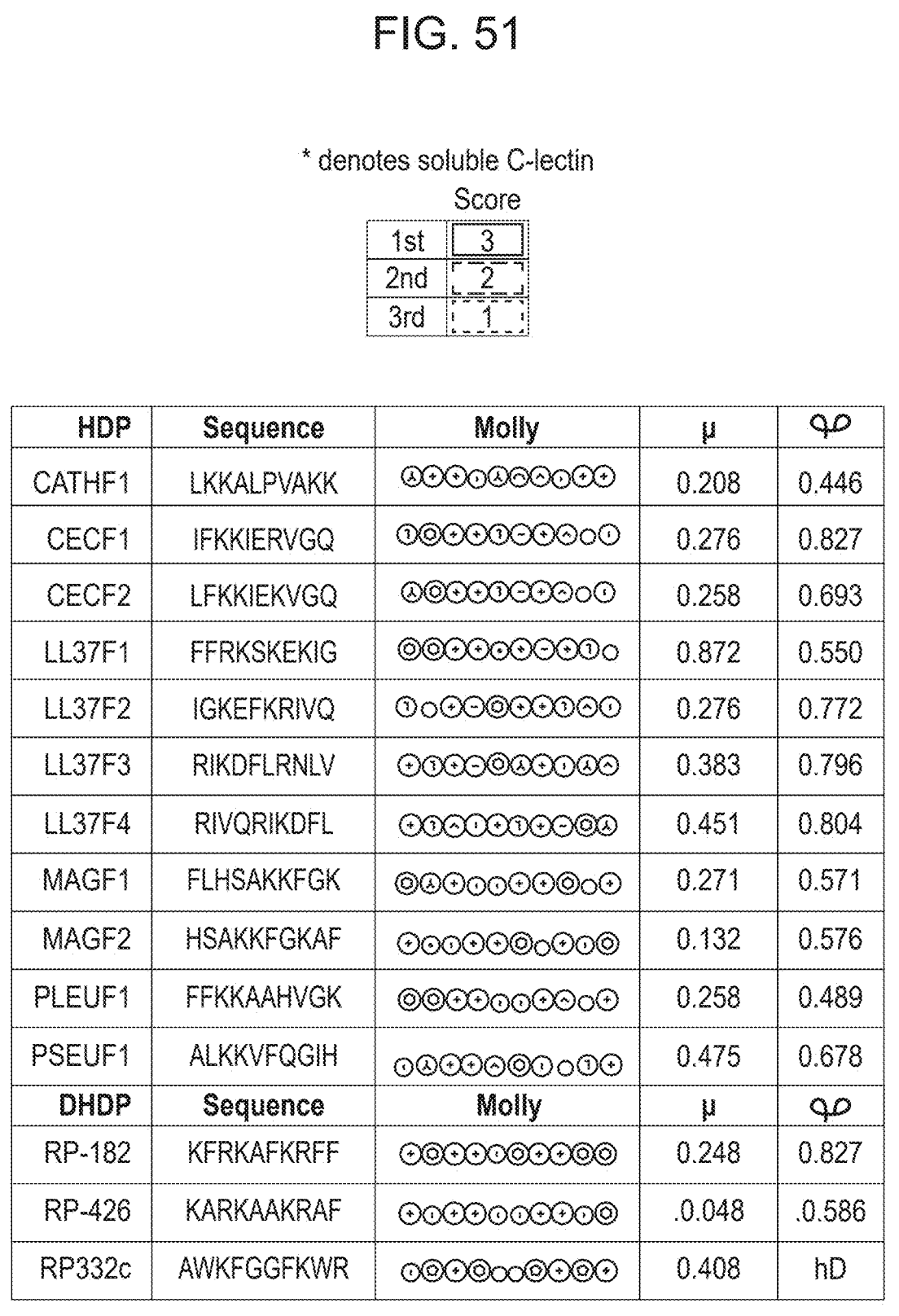

FIG. 51
* denotes soluble C-lectin
| | Score |
|---|---|
| 1st | 3 |
| 2nd | 2 |
| 3rd | 1 |
| HDP | Sequence | Molly | μ | φ |
|---|---|---|---|---|
| CATHF1 | LKKALPVAKK |  | 0.208 | 0.446 |
| CECF1 | IFKKIERVGQ |  | 0.276 | 0.827 |
| CECF2 | LFKKIEKVGQ |  | 0.258 | 0.693 |
| LL37F1 | FFRKSKEKIG |  | 0.872 | 0.550 |
| LL37F2 | IGKEFKRIVQ |  | 0.276 | 0.772 |
| LL37F3 | RIKDFLRNLV |  | 0.383 | 0.796 |
| LL37F4 | RIVQRIKDFL |  | 0.451 | 0.804 |
| MAGF1 | FLHSAKKFGK |  | 0.271 | 0.571 |
| MAGF2 | HSAKKFGKAF |  | 0.132 | 0.576 |
| PLEUF1 | FFKKAAHVGK |  | 0.258 | 0.489 |
| PSEUF1 | ALKKVFQGIH |  | 0.475 | 0.678 |
| **DHDP** | **Sequence** | **Molly** | **μ** | **φ** |
| RP-182 | KFRKAFKRFF |  | 0.248 | 0.827 |
| RP-426 | KARKAAKRAF |  | .0.048 | .0.586 |
| RP332c | AWKFGGFKWR |  | 0.408 | hD |

FIG. 51 (Cont.)

* denotes soluble C-lectin

| | Score |
|---|---|
| 1st | 3 |
| 2nd | 2 |
| 3rd | 1 |

| | CD206FL (MRC1) | CD206-CRD4 | MRC2 | CD206-CRD2 | PLA2 | CD209 | PSEL | LSEL |
|---|---|---|---|---|---|---|---|---|
| **HDP** | | | | | | | | |
| CATHF1 | -579 | -522 | -611 | -420 | -451 | -496 | -412 | -424 |
| CECF1 | -657 | -507 | -571 | -445 | -455 | -565 | -448 | -436 |
| CECF2 | -610 | -523 | -577 | -446 | -447 | -542 | -430 | -423 |
| LL37F1 | -650 | -559 | -703 | -488 | -447 | -563 | -457 | -469 |
| LL37F2 | -620 | -533 | -577 | -466 | -477 | -573 | -457 | -466 |
| LL37F3 | -754 | -565 | -588 | -510 | -529 | -611 | -480 | -488 |
| LL37F4 | -718 | -604 | -588 | -524 | -551 | -627 | -502 | -485 |
| MAGF1 | -731 | -648 | -675 | -543 | -620 | -562 | -479 | -489 |
| MAGF2 | -730 | -629 | -650 | -515 | -532 | -592 | -497 | -516 |
| PLEUF1 | -717 | -580 | -714 | -496 | -500 | -537 | -463 | -470 |
| PSEUF1 | -689 | -604 | -567 | -492 | -488 | -602 | -473 | -478 |
| **DHDP** | | | | | | | | |
| RP-182 | -877 | -801 | -790 | -635 | -613 | -734 | -608 | -597 |
| RP-426 | -645 | -552 | -607 | -443 | -444 | -519.9 | -437 | -447 |
| RP332c | -1,145 | -1,053 | -1,026 | -826 | -870 | -1,006 | -804 | -798 |

FIG. 51 (Cont.)

* denotes soluble C-lectin

| | Score |
|---|---|
| 1st | 3 |
| 2nd | 2 |
| 3rd | 1 |

| | CD299 | CD302 | DCIR | MCL | MINC | BDCA-2 | GALL | CD23 |
|---|---|---|---|---|---|---|---|---|
| **HDP** | | | | | | | | |
| CATHF1 | -486 | -444 | -453 | -433 | -439 | -494 | -454 | -424 |
| CECF1 | -443 | -447 | -509 | -483 | -429 | -539 | -472 | -424 |
| CECF2 | -466 | -444 | -479 | -476 | -425 | -530 | -449 | -426 |
| LL37F1 | -529 | -531 | -511 | -542 | -518 | -531 | -507 | -467 |
| LL37F2 | -498 | -478 | -465 | -481 | -467 | -558 | -491 | -453 |
| LL37F3 | -522 | -459 | -493 | -509 | -470 | -578 | -490 | -489 |
| LL37F4 | -558 | -516 | -511 | -548 | -506 | -629 | -507 | -488 |
| MAGF1 | -535 | -529 | -523 | -543 | -527 | -612 | -527 | -487 |
| MAGF2 | -527 | -507 | -511 | -530 | -525 | -617 | -509 | -504 |
| PLEUF1 | -518 | -501 | -507 | -508 | -486 | -567 | -513 | -474 |
| PSEUF1 | -526 | -454 | -487 | -501 | -489 | -581 | -499 | -493 |
| **DHDP** | | | | | | | | |
| RP-182 | -672 | -662 | -657 | -650 | -645 | -765 | -638 | -620 |
| RP-426 | -501 | -510 | -467 | -459 | -485 | -549 | -481 | -456 |
| RP332c | -852 | -784 | -852 | -815 | -816 | -950 | -759 | -761 |

FIG. 51 (Cont.)

* denotes soluble C-lectin

| | Score |
|---|---|
| 1st | 3 |
| 2nd | 2 |
| 3rd | 1 |

| | DECT1 | CD69 | LY49C | LOX1 | DECT2 | CD94 | CLEC2 | TETR* | ENBP* | THRM |
|---|---|---|---|---|---|---|---|---|---|---|
| **HDP** | | | | | | | | | | |
| CATHF1 | -430 | -478 | -508 | -477 | -461 | -473 | -435 | -431 | -435 | -517 |
| CECF1 | -461 | -512 | -493 | -497 | -446 | -454 | -459 | -445 | -497 | -496 |
| CECF2 | -446 | -513 | -489 | -488 | -443 | -447 | -466 | -444 | -487 | -490 |
| LL37F1 | -487 | -503 | -499 | -479 | -491 | -495 | -475 | -529 | -439 | -587 |
| LL37F2 | -472 | -539 | -542 | -513 | -482 | -467 | -509 | -469 | -551 | -586 |
| LL37F3 | -528 | -540 | -555 | -558 | -492 | -505 | -495 | -481 | -614 | -490 |
| LL37F4 | -541 | -591 | -579 | -561 | bnh | -536 | -570 | -508 | -583 | -549 |
| MAGF1 | -547 | -551 | -587 | -518 | -527 | -535 | -495 | -515 | -549 | -604 |
| MAGF2 | -520 | -561 | -585 | -538 | -527 | -512 | -511 | -499 | -540 | -587 |
| PLEUF1 | -493 | -528 | -513 | -495 | -513 | -493 | -487 | -470 | -498 | -567 |
| PSEUF1 | -517 | -543 | -541 | -516 | -502 | -504 | -507 | -478 | -558 | -540 |
| **DHDP** | | | | | | | | | | |
| RP-182 | -665 | -727 | -682 | -667 | -649 | -637 | -617 | -654 | -658 | -737 |
| RP-426 | -463 | -494 | -494 | -461 | -482 | -462 | -470 | -461 | -437 | -558 |
| RP332c | -799 | -860 | -852 | -887 | -819 | -822 | -741 | -793 | -837 | -925 |

FIG. 51 (Cont.)
* denotes soluble C-lectin
| | Score |
|---|---|
| 1st | 3 |
| 2nd | 2 |
| 3rd | 1 |
| Virulence | Sequence | Molly | μ | φ |
|---|---|---|---|---|
| AVP1 | EKLSAFRNFF |  | 0.410 | 0.546 |
| CTPR | AVRRLAQRLA |  | 0.230 | 0.597 |
| FLAB | MVFRDVGNRN |  | 0.147 | 0.299 |
| MPCP | KEFLAFKRFF |  | 0.554 | 0.584 |
| PTTM | GFRELFRQLD |  | 0.333 | 0.770 |
| TPRO | IENAAFKRFF |  | 0.455 | 0.365 |
| **Collagen** | **Sequence** | **Molly** | **μ** | **φ** |
| COLI | DRGIKGHRGF |  | -0.005 | -0.480 |
| COLIV | LRGQKGDRGF |  | -0.114 | -0.312 |
| COLV | EAGEKGDQGL |  | -0.114 | -0.312 |
| COLVI | VLDAIRRLRL |  | 0.249 | 0.347 |
| COLVII | HVVQRGEHSL |  | 0.453 | 0.444 |
| COLXVIII | IVRRADRAAV |  | 0.137 | 0.485 |

FIG. 51 (Cont.)

* denotes soluble C-lectin

| | Score |
|---|---|
| 1st | 3 |
| 2nd | 2 |
| 3rd | 1 |

| | CD206FL (MRC1) | CD206-CRD4 | MRC2 | CD206 -CRD2 | PLA2 | CD209 | PSEL | LSEL |
|---|---|---|---|---|---|---|---|---|
| **Virulence** | | | | | | | | |
| AVP1 | -814 | -717 | -675 | -592 | -624 | -656 | -538 | -519 |
| CTPR | -778 | -679 | -653 | -498 | -488 | -590 | -486 | -486 |
| FLAB | -716 | -539 | -551 | -481 | -469 | -564 | -444 | -458 |
| MPCP | -859.2 | -694 | -681 | -575 | -616 | -680 | -555 | -537 |
| PTTM | -825 | -652 | -670 | -567 | -586 | -783 | -521 | -525 |
| TPRO | -847 | -665 | -664 | -544 | -593 | -657.7 | -498 | -504 |
| **Collagen** | | | | | | | | |
| COLI | -817 | -641 | -684 | -579 | -609 | -647 | -520 | -520 |
| COLIV | -720 | -543 | -561 | -458 | -494 | -510 | -420 | -433 |
| COLV | -511 | -397 | -440 | -341 | -292 | -482 | -311 | -349 |
| COLVI | -818 | -564 | -634 | -492 | -529 | -546.4 | -460 | -467 |
| COLVII | -732 | -518 | -563 | -474 | -501 | -588 | -449 | -459 |
| COLXVIII | -730 | -572 | -620 | -489 | -464 | -573 | -426 | -458 |

FIG. 51 (Cont.)

* denotes soluble C-lectin

| | Score |
|---|---|
| 1st | 3 |
| 2nd | 2 |
| 3rd | 1 |

| | CD299 | CD302 | DCIR | MCL | MINC | BDCA -2 | GALL | CD23 |
|---|---|---|---|---|---|---|---|---|
| **Virulence** | | | | | | | | |
| AVP1 | -607 | -541 | -569 | -580 | -545 | -683 | -557 | -539 |
| CTPR | -539 | -524 | -520 | -554 | -500 | -601 | -521 | -490 |
| FLAB | -487 | -448 | -462 | -503 | -455 | -553 | -476 | -447 |
| MPCP | -614 | -525 | -574 | -599 | -567 | -787 | -542 | -522 |
| PTTM | -689 | -543 | -568 | -536 | -549 | -661 | -535 | -566 |
| TPRO | -601 | -493 | -559 | -584 | -506 | -677 | -524 | -527 |
| **Collagen** | | | | | | | | |
| COLI | -573 | -537 | -568 | -578 | -548 | -645 | -549 | -523 |
| COLIV | -464 | -445 | -434 | -475 | -454 | -553 | -443 | -439 |
| COLV | -355 | -371 | -335 | -348 | -376 | -382 | -364 | -321 |
| COLVI | -493 | -470 | -479 | -515 | -478 | -587 | -477 | -469 |
| COLVII | -465 | -414 | -439 | -472 | -445 | -543 | -428 | -435 |
| COLXVIII | -513 | -478 | -485 | -545 | -503 | -527 | -473 | -454 |

FIG. 51 (Cont.)

* denotes soluble C-lectin

| | Score |
|---|---|
| 1st | 3 |
| 2nd | 2 |
| 3rd | 1 |

| | DECT1 | CD69 | LY49C | LOX1 | DECT2 | CD94 | CLEC2 | TETR* | ENBP* | THRM |
|---|---|---|---|---|---|---|---|---|---|---|
| **Virulence** | | | | | | | | | | |
| AVP1 | -553 | -624 | -617 | -573 | -549 | -572 | -588 | -546 | -612 | -625 |
| CTPR | -492 | -573 | -537 | -551 | -512 | -505 | -499 | -524 | -518 | -588 |
| FLAB | -467 | -550 | -519 | -492 | -474 | -459 | -485 | -440 | -509 | -508 |
| MPCP | -568 | -631 | -647 | -598 | -560 | -591 | -560 | -561 | -641 | -623 |
| PTTM | -585 | -632 | -623 | -681 | -573 | -558 | -598 | -565 | -694 | -598 |
| TPRO | -541 | -606 | -620 | -580 | -524 | -555 | -522 | -527 | -625 | -584 |
| **Collagen** | | | | | | | | | | |
| COLI | -556 | -615 | -619 | -577 | -564 | -553 | -565 | -536 | -597 | -603 |
| COLIV | -438 | -469 | -506 | -467 | -430 | -439 | -463 | -430 | -516 | -491 |
| COLV | -307 | -397 | -361 | -335 | -334 | -323 | -365 | -379 | -381 | -402 |
| COLVI | -494 | -515 | -549 | -588 | -493 | -515 | -485 | -480 | -495 | -533 |
| COLVII | -442 | -485 | -531 | -485 | -452 | -493 | -444 | -427 | -520 | -513 |
| COLXVIII | -443 | -515 | -490 | -476 | -471 | -463 | -480 | -459 | -495 | -550 |

FIG. 67B
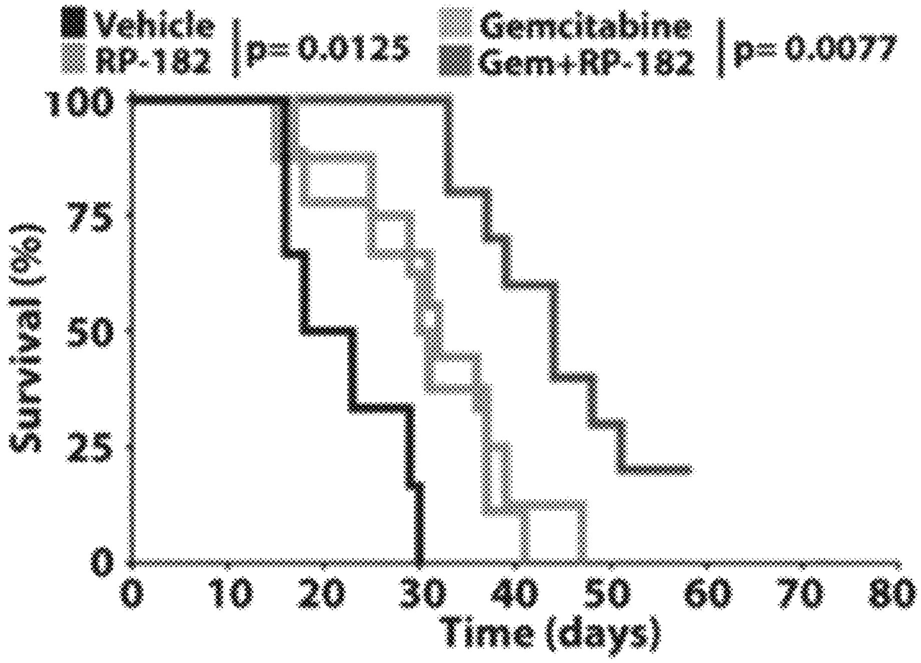
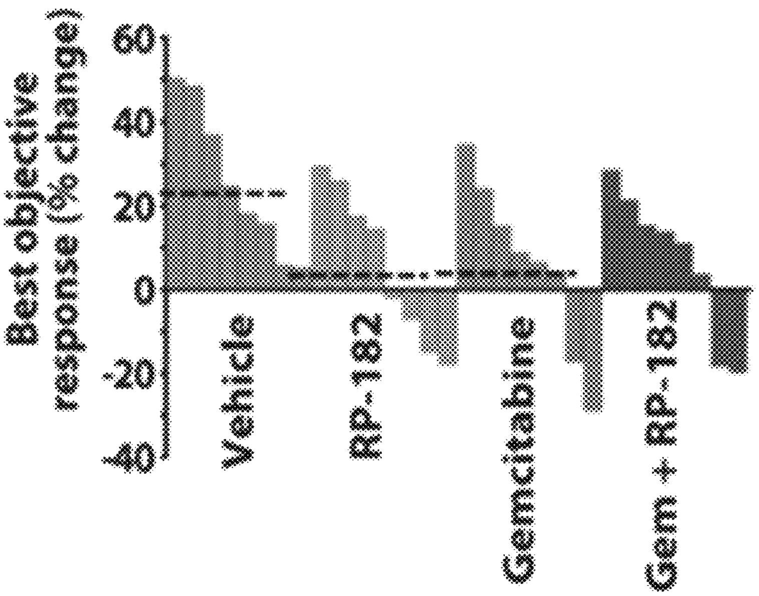

| | KPC vehicle | KPC RP-182 |
|---|---|---|
| Median OS (days) | 26 | 33 |

| | KPC CD206 KO vehicle | KPC CD206 KO RP-182 |
|---|---|---|
| Median OS (days) | 25 | 21 |

| Flow cytometry (% CFSE+ cells) | BMDM M2 | |
|---|---|---|
| | vehicle | RP - 182 |
| % of CD11b $^+$/Gr1$^-$/F4/80$^+$/CD86 $^+$ | 21.7 | 37.5 |
| % of CD11b$^+$/Gr1$^-$/F4/80$^+$ CFSE $^+$/CD206 $^+$ | 1.08 | 2.84 |

FIG. 97
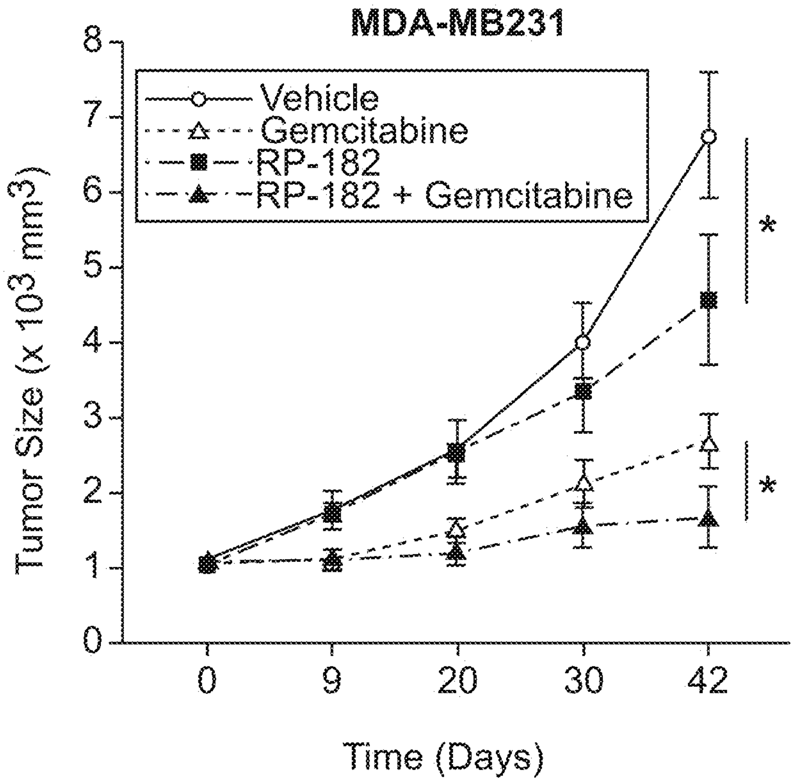
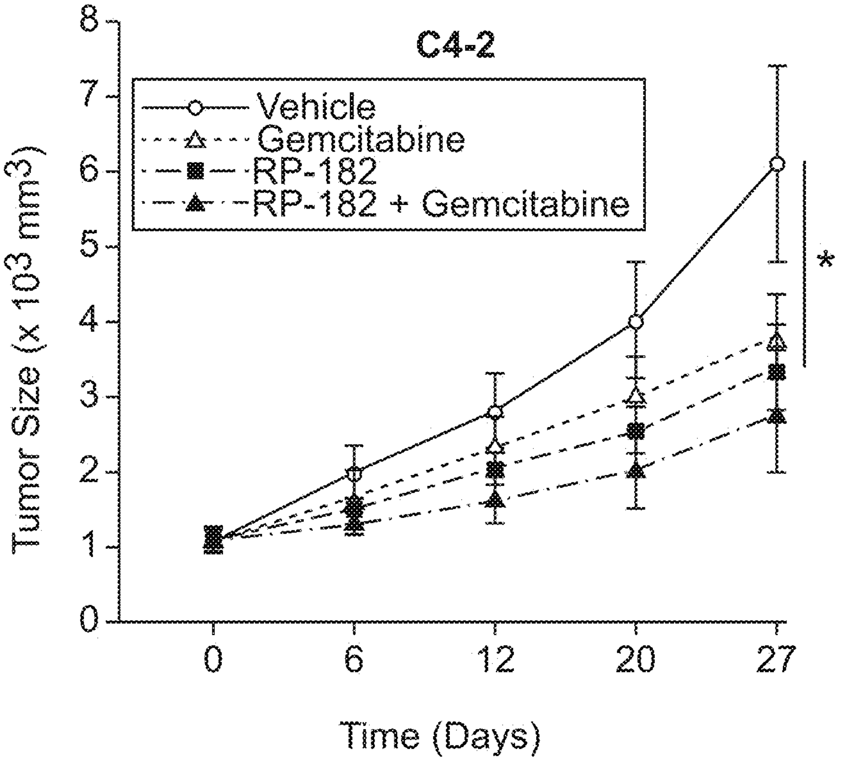

SEQUENCE LISTING

```
<160> NUMBER OF SEQ ID NOS: 1218

<210> SEQ ID NO 1
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently
      selected from phenylalanine, tryptophan, alanine, valine, and
      glycine
<220> FEATURE:
<221> NAME/KEY: MISC_FEATURE
<222> LOCATION: (3)..(4)
<223> OTHER INFORMATION: Xaa at positions 3 and 4 are each independently
      selected from lysine, arginine, histidine, aspartic acid, glutamic
      acid, asparagine and glutamine.
```

<220> FEATURE:
<221> NAME/KEY: MISC_FEATURE
<222> LOCATION: (5)..(6)
<223> OTHER INFORMATION: Xaa at positions 5 and 6 are each independently selected from phenylalanine, tryptophan, alanine, valine, and glycine
<220> FEATURE:
<221> NAME/KEY: MISC_FEATURE
<222> LOCATION: (7)..(8)
<223> OTHER INFORMATION: Xaa at positions 7 and 8 are each independently selected from lysine, arginine, histidine, aspartic acid, glutamic acid, asparagine and glutamine.
<220> FEATURE:
<221> NAME/KEY: MISC_FEATURE
<222> LOCATION: (9)..(9)
<223> OTHER INFORMATION: Xaa is selected from phenylalanine, tryptophan, alanine, valine, and glycine
<220> FEATURE:
<221> NAME/KEY: MISC_FEATURE
<222> LOCATION: (10)..(10)
<223> OTHER INFORMATION: Xaa is selected from lysine, arginine, histidine, aspartic acid, glutamic acid, asparagine and glutamine.

<400> SEQUENCE: 1

Xaa Xaa Xaa Xaa Xaa Xaa Xaa Xaa Xaa Xaa
1 5 10

<210> SEQ ID NO 2
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is independently selected from lysine, arginine, histidine, aspartic acid, glutamic acid, asparagine and glutamine.
<220> FEATURE:
<221> NAME/KEY: MISC_FEATURE
<222> LOCATION: (2)..(2)
<223> OTHER INFORMATION: Xaa is independently selected from phenylalanine, tryptophan, alanine, valine, and glycine.
<220> FEATURE:
<221> NAME/KEY: MISC_FEATURE
<222> LOCATION: (3)..(4)
<223> OTHER INFORMATION: Xaa at positions 3 and 4 are each independently selected from lysine, arginine, histidine, aspartic acid, glutamic acid, asparagine and glutamine
<220> FEATURE:
<221> NAME/KEY: MISC_FEATURE
<222> LOCATION: (5)..(6)
<223> OTHER INFORMATION: Xaa at positions 5 and 6 are each independently selected from phenylalanine, tryptophan, alanine, valine, and glycine
<220> FEATURE:
<221> NAME/KEY: MISC_FEATURE
<222> LOCATION: (7)..(8)
<223> OTHER INFORMATION: Xaa at positions 7 and 8 are each independently selected from lysine, arginine, histidine, aspartic acid, glutamic acid, asparagine and glutamine
<220> FEATURE:
<221> NAME/KEY: MISC_FEATURE
<222> LOCATION: (9)..(10)
<223> OTHER INFORMATION: Xaa at positions 9 and 10 are each independently selected from phenylalanine, tryptophan, alanine, valine, and glycine

<400> SEQUENCE: 2

Xaa Xaa Xaa Xaa Xaa Xaa Xaa Xaa Xaa Xaa
1 5 10

<210> SEQ ID NO 3
<211> LENGTH: 10

<212> TYPE: PRT
<213> ORGANISM: Artificial sequence
<220> FEATURE:
<223> OTHER INFORMATION: synthetic sequence

<400> SEQUENCE: 3

Lys Phe Arg Lys Ala Phe Lys Arg Phe Phe
1 5 10

<210> SEQ ID NO 4
<211> LENGTH: 10
<212> TYPE: PRT
<213> ORGANISM: Artificial sequence
<220> FEATURE:
<223> OTHER INFORMATION: synthetic sequence

<400> SEQUENCE: 4

Phe Phe Arg Lys Phe Ala Lys Arg Phe Lys
1 5 10

<210> SEQ ID NO 5
<211> LENGTH: 10
<212> TYPE: PRT
<213> ORGANISM: Artificial sequence
<220> FEATURE:
<223> OTHER INFORMATION: synthetic sequence

<400> SEQUENCE: 5

Phe Phe Lys Lys Phe Phe Lys Lys Phe Lys
1 5 10

<210> SEQ ID NO 6
<211> LENGTH: 10
<212> TYPE: PRT
<213> ORGANISM: Artificial sequence
<220> FEATURE:
<223> OTHER INFORMATION: synthetic sequence

<400> SEQUENCE: 6

Phe Phe Lys Lys Phe Phe Lys Lys Phe Lys
1 5 10

<210> SEQ ID NO 7
<211> LENGTH: 10
<212> TYPE: PRT
<213> ORGANISM: Artificial sequence
<220> FEATURE:
<223> OTHER INFORMATION: synthetic sequence

<400> SEQUENCE: 7

Phe Phe Lys Lys Phe Phe Lys Lys Phe Lys
1 5 10

<210> SEQ ID NO 8
<211> LENGTH: 10
<212> TYPE: PRT
<213> ORGANISM: Artificial sequence
<220> FEATURE:
<223> OTHER INFORMATION: synthetic sequence

<400> SEQUENCE: 8

Arg Trp Lys Phe Gly Gly Phe Lys Trp Arg
1 5 10

<210> SEQ ID NO 9
<211> LENGTH: 10
<212> TYPE: PRT

<213> ORGANISM: Artificial sequence
<220> FEATURE:
<223> OTHER INFORMATION: synthetic sequence

<400> SEQUENCE: 9

Phe Lys Trp Arg Gly Gly Arg Trp Lys Phe
1 5 10

<210> SEQ ID NO 10
<211> LENGTH: 10
<212> TYPE: PRT
<213> ORGANISM: Artificial sequence
<220> FEATURE:
<223> OTHER INFORMATION: synthetic sequence

<400> SEQUENCE: 10

Phe Trp Lys Arg Gly Gly Arg Lys Trp Phe
1 5 10

<210> SEQ ID NO 11
<211> LENGTH: 6
<212> TYPE: PRT
<213> ORGANISM: Artificial sequence
<220> FEATURE:
<223> OTHER INFORMATION: synthetic sequence

<400> SEQUENCE: 11

Phe Trp Lys Arg Phe Val
1 5

<210> SEQ ID NO 12
<211> LENGTH: 6
<212> TYPE: PRT
<213> ORGANISM: Artificial sequence
<220> FEATURE:
<223> OTHER INFORMATION: synthetic sequence

<400> SEQUENCE: 12

Phe Val Arg Lys Trp Arg
1 5

<210> SEQ ID NO 13
<211> LENGTH: 5
<212> TYPE: PRT
<213> ORGANISM: Artificial sequence
<220> FEATURE:
<223> OTHER INFORMATION: synthetic sequence

<400> SEQUENCE: 13

Phe Ala Phe Ala Phe
1 5

<210> SEQ ID NO 14
<211> LENGTH: 10
<212> TYPE: PRT
<213> ORGANISM: Artificial sequence
<220> FEATURE:
<223> OTHER INFORMATION: synthetic sequence

<400> SEQUENCE: 14

Phe Trp Lys Arg Phe Val Arg Lys Trp Arg
1 5 10

<210> SEQ ID NO 15
<211> LENGTH: 10
<212> TYPE: PRT
<213> ORGANISM: Artificial sequence -continued
<220> FEATURE:
<223> OTHER INFORMATION: synthetic sequence

<400> SEQUENCE: 15

Phe Trp Lys Lys Phe Val Lys Lys Trp Lys
1               5                   10

<210> SEQ ID NO 16
<211> LENGTH: 10
<212> TYPE: PRT
<213> ORGANISM: Artificial sequence
<220> FEATURE:
<223> OTHER INFORMATION: synthetic sequence

<400> SEQUENCE: 16

Trp Trp His His Trp Trp His His Trp His
1               5                   10

<210> SEQ ID NO 17
<211> LENGTH: 10
<212> TYPE: PRT
<213> ORGANISM: Artificial sequence
<220> FEATURE:
<223> OTHER INFORMATION: synthetic sequence

<400> SEQUENCE: 17

Trp Trp Arg His Trp Trp His Arg Trp Arg
1               5                   10

<210> SEQ ID NO 18
<211> LENGTH: 10
<212> TYPE: PRT
<213> ORGANISM: Artificial sequence
<220> FEATURE:
<223> OTHER INFORMATION: synthetic sequence

<400> SEQUENCE: 18

Trp Trp Lys His Trp Trp His Lys Trp Lys
1               5                   10

<210> SEQ ID NO 19
<211> LENGTH: 11
<212> TYPE: PRT
<213> ORGANISM: Artificial sequence
<220> FEATURE:
<223> OTHER INFORMATION: synthetic sequence

<400> SEQUENCE: 19

Gly Asp Arg Gly Ile Lys Gly His Arg Gly Phe
1               5                   10

<210> SEQ ID NO 20
<211> LENGTH: 10
<212> TYPE: PRT
<213> ORGANISM: Artificial sequence
<220> FEATURE:
<223> OTHER INFORMATION: synthetic sequence

<400> SEQUENCE: 20

Leu Tyr Lys Lys Ile Ile Lys Lys Leu Leu
1               5                   10

<210> SEQ ID NO 21
<211> LENGTH: 10
<212> TYPE: PRT
<213> ORGANISM: Artificial sequence
<220> FEATURE:

<223> OTHER INFORMATION: synthetic sequence

<400> SEQUENCE: 21

Phe Tyr Pro Asp Phe Phe Lys Lys Phe Phe
1               5                   10

<210> SEQ ID NO 22
<211> LENGTH: 10
<212> TYPE: PRT
<213> ORGANISM: Artificial sequence
<220> FEATURE:
<223> OTHER INFORMATION: synthetic sequence

<400> SEQUENCE: 22

Phe Phe Arg Lys Ser Lys Glu Lys Ile Gly
1               5                   10

<210> SEQ ID NO 23
<211> LENGTH: 10
<212> TYPE: PRT
<213> ORGANISM: Artificial sequence
<220> FEATURE:
<223> OTHER INFORMATION: synthetic sequence

<400> SEQUENCE: 23

Phe Phe Arg His Phe Ala Thr His Leu Asp
1               5                   10

<210> SEQ ID NO 24
<211> LENGTH: 10
<212> TYPE: PRT
<213> ORGANISM: Artificial sequence
<220> FEATURE:
<223> OTHER INFORMATION: synthetic sequence

<400> SEQUENCE: 24

Glu Lys Leu Ser Ala Phe Arg Asn Phe Phe
1               5                   10

<210> SEQ ID NO 25
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(4)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (5)..(5)
<223> OTHER INFORMATION: Xaa is selected from lysine, arginine,

```
      histidine, aspartic acid, glutamic acid, asparagine and glutamine
<220> FEATURE:
<221> NAME/KEY: MISC_FEATURE
<222> LOCATION: (6)..(6)
<223> OTHER INFORMATION: Xaa is selected from phenylalanine, tryptophan,
      alanine, valine, leucine, isoleucine, methionine, tyrosine,
      threonine, serine, cysteine, proline, and glycine

<400> SEQUENCE: 25

Xaa Xaa Xaa Xaa Xaa Xaa
1               5


<210> SEQ ID NO 26
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (2)..(2)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (3)..(3)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (5)..(5)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (6)..(6)
<223> OTHER INFORMATION: Xaa is selected from lysine, arginine,
      histidine, aspartic acid, glutamic acid, asparagine and glutamine

<400> SEQUENCE: 26

Xaa Xaa Xaa Xaa Xaa Xaa
1               5


<210> SEQ ID NO 27
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently
      selected from phenylalanine, tryptophan, alanine, valine, leucine,
      isoleucine, methionine, tyrosine, threonine, serine, cysteine,
      proline, and glycine
<220> FEATURE:
<221> NAME/KEY: MISC_FEATURE
<222> LOCATION: (3)..(4)
<223> OTHER INFORMATION: Xaa at positions 3 and 4 are each independently
      selected from lysine, arginine, histidine, aspartic acid, glutamic
      acid, asparagine and glutamine
```

```
<220> FEATURE:
<221> NAME/KEY: MISC_FEATURE
<222> LOCATION: (5)..(6)
<223> OTHER INFORMATION: Xaa at positions 5 and 6 are each independently
      selected from phenylalanine, tryptophan, alanine, valine, leucine,
      isoleucine, methionine, tyrosine, threonine, serine, cysteine,
      proline, and glycine

<400> SEQUENCE: 27

Xaa Xaa Xaa Xaa Xaa Xaa
1               5


<210> SEQ ID NO 28
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently
      selected from phenylalanine, tryptophan, alanine, valine, leucine,
      isoleucine, methionine, tyrosine, threonine, serine, cysteine,
      proline, and glycine
<220> FEATURE:
<221> NAME/KEY: MISC_FEATURE
<222> LOCATION: (3)..(4)
<223> OTHER INFORMATION: Xaa at positions 3 and 4 are each independently
      selected from lysine, arginine, histidine, aspartic acid, glutamic
      acid, asparagine and glutamine
<220> FEATURE:
<221> NAME/KEY: MISC_FEATURE
<222> LOCATION: (5)..(5)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (6)..(6)
<223> OTHER INFORMATION: Xaa is selected from lysine, arginine,
      histidine, aspartic acid, glutamic acid, asparagine and glutamine

<400> SEQUENCE: 28

Xaa Xaa Xaa Xaa Xaa Xaa
1               5


<210> SEQ ID NO 29
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (3)..(4)
<223> OTHER INFORMATION: Xaa at positions 3 and 4 are each independently
      selected from lysine, arginine, histidine, aspartic acid, glutamic
      acid, asparagine and glutamine
<220> FEATURE:
<221> NAME/KEY: MISC_FEATURE
<222> LOCATION: (5)..(6)
<223> OTHER INFORMATION: Xaa at positions 5 and 6 are each independently
      selected from phenylalanine, tryptophan, alanine, valine, leucine,
```

isoleucine, methionine, tyrosine, threonine, serine, cysteine, proline, and glycine

<400> SEQUENCE: 29

Xaa Xaa Xaa Xaa Xaa Xaa
1 5

<210> SEQ ID NO 30
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(5)
<223> OTHER INFORMATION: Xaa at positions 4 and 5 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (6)..(6)
<223> OTHER INFORMATION: Xaa is selected from lysine, arginine, histidine, aspartic acid, glutamic acid, asparagine and glutamine

<400> SEQUENCE: 30

Xaa Xaa Xaa Xaa Xaa Xaa
1 5

<210> SEQ ID NO 31
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(3)
<223> OTHER INFORMATION: Xaa at positions 2 and 3 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (5)..(6)
<223> OTHER INFORMATION: Xaa at positions 5 and 6 are each independently selected from phenylalanine, tryptophan, alanine, valine, leucine, isoleucine, methionine, tyrosine, threonine, serine, cysteine, proline, and glycine

<400> SEQUENCE: 31

Xaa Xaa Xaa Xaa Xaa Xaa
1 5

<210> SEQ ID NO 32
<211> LENGTH: 6
<212> TYPE: PRT
<213> ORGANISM: Artificial sequence
<220> FEATURE:
<223> OTHER INFORMATION: synthetic sequence

<400> SEQUENCE: 32

Ala Phe Lys Arg Phe Phe
1 5

<210> SEQ ID NO 33
<211> LENGTH: 6
<212> TYPE: PRT
<213> ORGANISM: Artificial sequence
<220> FEATURE:
<223> OTHER INFORMATION: synthetic sequence

<400> SEQUENCE: 33

Phe Phe Lys Lys Phe Phe
1 5

<210> SEQ ID NO 34
<211> LENGTH: 6
<212> TYPE: PRT
<213> ORGANISM: Artificial sequence
<220> FEATURE:
<223> OTHER INFORMATION: synthetic sequence

<400> SEQUENCE: 34

Phe Trp Lys Arg Phe Val
1 5

<210> SEQ ID NO 35
<211> LENGTH: 6
<212> TYPE: PRT
<213> ORGANISM: Artificial sequence
<220> FEATURE:
<223> OTHER INFORMATION: synthetic sequence

<400> SEQUENCE: 35

Trp Val Arg Arg Val Val
1 5

<210> SEQ ID NO 36
<211> LENGTH: 6
<212> TYPE: PRT
<213> ORGANISM: Artificial sequence
<220> FEATURE:
<223> OTHER INFORMATION: synthetic sequence

<400> SEQUENCE: 36

Ile Phe Lys Lys Ile Glu
1 5

<210> SEQ ID NO 37
<211> LENGTH: 6
<212> TYPE: PRT
<213> ORGANISM: Artificial sequence
<220> FEATURE:
<223> OTHER INFORMATION: synthetic sequence

<400> SEQUENCE: 37

Phe Leu Arg Asn Leu Val 1 5

<210> SEQ ID NO 38
<211> LENGTH: 6
<212> TYPE: PRT
<213> ORGANISM: Artificial sequence
<220> FEATURE:
<223> OTHER INFORMATION: synthetic sequence

<400> SEQUENCE: 38

Phe Leu His Ser Ala Lys
1 5

<210> SEQ ID NO 39
<211> LENGTH: 6
<212> TYPE: PRT
<213> ORGANISM: Artificial sequence
<220> FEATURE:
<223> OTHER INFORMATION: synthetic sequence

<400> SEQUENCE: 39

Phe Phe His His Ile Phe
1 5

<210> SEQ ID NO 40
<211> LENGTH: 6
<212> TYPE: PRT
<213> ORGANISM: Artificial sequence
<220> FEATURE:
<223> OTHER INFORMATION: synthetic sequence

<400> SEQUENCE: 40

Phe Phe Lys Lys Ala Ala
1 5

<210> SEQ ID NO 41
<211> LENGTH: 6
<212> TYPE: PRT
<213> ORGANISM: Artificial sequence
<220> FEATURE:
<223> OTHER INFORMATION: synthetic sequence

<400> SEQUENCE: 41

Ala Leu Lys Lys Val Phe
1 5

<210> SEQ ID NO 42
<211> LENGTH: 6
<212> TYPE: PRT
<213> ORGANISM: Artificial sequence
<220> FEATURE:
<223> OTHER INFORMATION: synthetic sequence

<400> SEQUENCE: 42

Leu Tyr Lys Lys Ile Ile
1 5

<210> SEQ ID NO 43
<211> LENGTH: 6
<212> TYPE: PRT
<213> ORGANISM: Artificial sequence
<220> FEATURE:
<223> OTHER INFORMATION: synthetic sequence

<400> SEQUENCE: 43

Leu Phe Arg Arg Ala Phe
1 5

<210> SEQ ID NO 44
<211> LENGTH: 6
<212> TYPE: PRT
<213> ORGANISM: Artificial sequence
<220> FEATURE:
<223> OTHER INFORMATION: synthetic sequence

<400> SEQUENCE: 44

Phe Leu Lys Arg Leu Leu
1               5

<210> SEQ ID NO 45
<211> LENGTH: 6
<212> TYPE: PRT
<213> ORGANISM: Artificial sequence
<220> FEATURE:
<223> OTHER INFORMATION: synthetic sequence

<400> SEQUENCE: 45

Phe Phe Arg Arg Phe Ala
1               5

<210> SEQ ID NO 46
<211> LENGTH: 6
<212> TYPE: PRT
<213> ORGANISM: Artificial sequence
<220> FEATURE:
<223> OTHER INFORMATION: synthetic sequence

<400> SEQUENCE: 46

Phe Phe Arg His Phe Ala
1               5

<210> SEQ ID NO 47
<211> LENGTH: 6
<212> TYPE: PRT
<213> ORGANISM: Artificial sequence
<220> FEATURE:
<223> OTHER INFORMATION: synthetic sequence

<400> SEQUENCE: 47

Ala Ile Arg Arg Ile Pro
1               5

<210> SEQ ID NO 48
<211> LENGTH: 6
<212> TYPE: PRT
<213> ORGANISM: Artificial sequence
<220> FEATURE:
<223> OTHER INFORMATION: synthetic sequence

<400> SEQUENCE: 48

Ala Phe His Arg Phe Phe
1               5

<210> SEQ ID NO 49
<211> LENGTH: 6
<212> TYPE: PRT
<213> ORGANISM: Artificial sequence
<220> FEATURE:
<223> OTHER INFORMATION: synthetic sequence

<400> SEQUENCE: 49

Phe Phe Asn Arg Phe Ala
1               5

<210> SEQ ID NO 50
<211> LENGTH: 6
<212> TYPE: PRT
<213> ORGANISM: Artificial sequence
<220> FEATURE:
<223> OTHER INFORMATION: synthetic sequence

<400> SEQUENCE: 50

Ala Phe Lys Arg Phe Phe
1               5

<210> SEQ ID NO 51
<211> LENGTH: 6
<212> TYPE: PRT
<213> ORGANISM: Artificial sequence
<220> FEATURE:
<223> OTHER INFORMATION: synthetic sequence

<400> SEQUENCE: 51

Ala Phe Lys Arg Phe Phe
1               5

<210> SEQ ID NO 52
<211> LENGTH: 6
<212> TYPE: PRT
<213> ORGANISM: Artificial sequence
<220> FEATURE:
<223> OTHER INFORMATION: synthetic sequence

<400> SEQUENCE: 52

Ile Val Arg Arg Ala Asp
1               5

<210> SEQ ID NO 53
<211> LENGTH: 6
<212> TYPE: PRT
<213> ORGANISM: Artificial sequence
<220> FEATURE:
<223> OTHER INFORMATION: synthetic sequence

<400> SEQUENCE: 53

Phe Trp Arg Trp Phe Lys
1               5

<210> SEQ ID NO 54
<211> LENGTH: 6
<212> TYPE: PRT
<213> ORGANISM: Artificial sequence
<220> FEATURE:
<223> OTHER INFORMATION: synthetic sequence

<400> SEQUENCE: 54

Lys Phe Trp Arg Trp Phe
1               5

<210> SEQ ID NO 55
<211> LENGTH: 6
<212> TYPE: PRT
<213> ORGANISM: Artificial sequence
<220> FEATURE:
<223> OTHER INFORMATION: synthetic sequence

<400> SEQUENCE: 55

Trp Phe Arg Phe Trp Lys
1               5

<210> SEQ ID NO 56
<211> LENGTH: 6
<212> TYPE: PRT
<213> ORGANISM: Artificial sequence
<220> FEATURE:
<223> OTHER INFORMATION: synthetic sequence

<400> SEQUENCE: 56

Lys Trp Phe Arg Phe Trp
1               5

<210> SEQ ID NO 57
<211> LENGTH: 6
<212> TYPE: PRT
<213> ORGANISM: Artificial sequence
<220> FEATURE:
<223> OTHER INFORMATION: synthetic sequence

<400> SEQUENCE: 57

Ala Phe His His Phe Phe
1               5

<210> SEQ ID NO 58
<211> LENGTH: 6
<212> TYPE: PRT
<213> ORGANISM: Artificial sequence
<220> FEATURE:
<223> OTHER INFORMATION: synthetic sequence

<400> SEQUENCE: 58

Phe Phe Arg Asn Phe Ala
1               5

<210> SEQ ID NO 59
<211> LENGTH: 6
<212> TYPE: PRT
<213> ORGANISM: Artificial sequence
<220> FEATURE:
<223> OTHER INFORMATION: synthetic sequence

<400> SEQUENCE: 59

Ala Phe His Arg Phe Phe
1               5

<210> SEQ ID NO 60
<211> LENGTH: 6
<212> TYPE: PRT
<213> ORGANISM: Artificial sequence
<220> FEATURE:
<223> OTHER INFORMATION: synthetic sequence

<400> SEQUENCE: 60

Phe Phe Arg Gln Phe Ala
1               5

<210> SEQ ID NO 61
<211> LENGTH: 6
<212> TYPE: PRT
<213> ORGANISM: Artificial sequence
<220> FEATURE:
<223> OTHER INFORMATION: synthetic sequence

<400> SEQUENCE: 61

Ala Phe Asn Arg Phe Phe
1               5

<210> SEQ ID NO 62

-continued

<211> LENGTH: 6
<212> TYPE: PRT
<213> ORGANISM: Artificial sequence
<220> FEATURE:
<223> OTHER INFORMATION: synthetic sequence

<400> SEQUENCE: 62

Trp Ile Gln Arg Met Met
1 5

<210> SEQ ID NO 63
<211> LENGTH: 6
<212> TYPE: PRT
<213> ORGANISM: Artificial sequence
<220> FEATURE:
<223> OTHER INFORMATION: synthetic sequence

<400> SEQUENCE: 63

Trp Val Gln Arg Val Val
1 5

<210> SEQ ID NO 64
<211> LENGTH: 6
<212> TYPE: PRT
<213> ORGANISM: Artificial sequence
<220> FEATURE:
<223> OTHER INFORMATION: synthetic sequence

<400> SEQUENCE: 64

Ala Phe Arg Asn Phe Phe
1 5

<210> SEQ ID NO 65
<211> LENGTH: 6
<212> TYPE: PRT
<213> ORGANISM: Artificial sequence
<220> FEATURE:
<223> OTHER INFORMATION: synthetic sequence

<400> SEQUENCE: 65

Thr Leu Arg Arg Phe Met
1 5

<210> SEQ ID NO 66
<211> LENGTH: 6
<212> TYPE: PRT
<213> ORGANISM: Artificial sequence
<220> FEATURE:
<223> OTHER INFORMATION: synthetic sequence

<400> SEQUENCE: 66

Asp Val Arg Met Arg Leu
1 5

<210> SEQ ID NO 67
<211> LENGTH: 6
<212> TYPE: PRT
<213> ORGANISM: Artificial sequence
<220> FEATURE:
<223> OTHER INFORMATION: synthetic sequence

<400> SEQUENCE: 67

Arg Arg Ala Glu Leu Gly
1 5

<210> SEQ ID NO 68
<211> LENGTH: 6

<212> TYPE: PRT
<213> ORGANISM: Artificial sequence
<220> FEATURE:
<223> OTHER INFORMATION: synthetic sequence

<400> SEQUENCE: 68

Phe Trp Arg Trp Phe Ala
1 5

<210> SEQ ID NO 69
<211> LENGTH: 6
<212> TYPE: PRT
<213> ORGANISM: Artificial sequence
<220> FEATURE:
<223> OTHER INFORMATION: synthetic sequence

<400> SEQUENCE: 69

Ala Phe Trp Arg Trp Phe
1 5

<210> SEQ ID NO 70
<211> LENGTH: 6
<212> TYPE: PRT
<213> ORGANISM: Artificial sequence
<220> FEATURE:
<223> OTHER INFORMATION: synthetic sequence

<400> SEQUENCE: 70

Trp Phe Arg Phe Trp Ala
1 5

<210> SEQ ID NO 71
<211> LENGTH: 6
<212> TYPE: PRT
<213> ORGANISM: Artificial sequence
<220> FEATURE:
<223> OTHER INFORMATION: synthetic sequence

<400> SEQUENCE: 71

Ala Trp Phe Arg Phe Trp
1 5

<210> SEQ ID NO 72
<211> LENGTH: 6
<212> TYPE: PRT
<213> ORGANISM: Artificial sequence
<220> FEATURE:
<223> OTHER INFORMATION: synthetic sequence

<400> SEQUENCE: 72

Val Ala Val Arg Ile Trp
1 5

<210> SEQ ID NO 73
<211> LENGTH: 6
<212> TYPE: PRT
<213> ORGANISM: Artificial sequence
<220> FEATURE:
<223> OTHER INFORMATION: synthetic sequence

<400> SEQUENCE: 73

Phe Phe Arg Phe Phe Ala
1 5

<210> SEQ ID NO 74
<211> LENGTH: 6
<212> TYPE: PRT

<213> ORGANISM: Artificial sequence
<220> FEATURE:
<223> OTHER INFORMATION: synthetic sequence

<400> SEQUENCE: 74

Ala Phe Phe Arg Phe Phe
1               5

<210> SEQ ID NO 75
<211> LENGTH: 6
<212> TYPE: PRT
<213> ORGANISM: Artificial sequence
<220> FEATURE:
<223> OTHER INFORMATION: synthetic sequence

<400> SEQUENCE: 75

Trp Trp Lys Lys Phe Phe
1               5

<210> SEQ ID NO 76
<211> LENGTH: 6
<212> TYPE: PRT
<213> ORGANISM: Artificial sequence
<220> FEATURE:
<223> OTHER INFORMATION: synthetic sequence

<400> SEQUENCE: 76

Phe Trp Lys Lys Trp Phe
1               5

<210> SEQ ID NO 77
<211> LENGTH: 6
<212> TYPE: PRT
<213> ORGANISM: Artificial sequence
<220> FEATURE:
<223> OTHER INFORMATION: synthetic sequence

<400> SEQUENCE: 77

Phe Phe Lys Lys Trp Trp
1               5

<210> SEQ ID NO 78
<211> LENGTH: 6
<212> TYPE: PRT
<213> ORGANISM: Artificial sequence
<220> FEATURE:
<223> OTHER INFORMATION: synthetic sequence

<400> SEQUENCE: 78

Trp Trp Lys Lys Trp Trp
1               5

<210> SEQ ID NO 79
<211> LENGTH: 6
<212> TYPE: PRT
<213> ORGANISM: Artificial sequence
<220> FEATURE:
<223> OTHER INFORMATION: synthetic sequence

<400> SEQUENCE: 79

Tyr Tyr Lys Lys Tyr Tyr
1               5

<210> SEQ ID NO 80
<211> LENGTH: 6
<212> TYPE: PRT
<213> ORGANISM: Artificial sequence
<220> FEATURE:
<223> OTHER INFORMATION: synthetic sequence

<400> SEQUENCE: 80

Ile Ile Lys Lys Tyr Tyr
1 5

<210> SEQ ID NO 81
<211> LENGTH: 6
<212> TYPE: PRT
<213> ORGANISM: Artificial sequence
<220> FEATURE:
<223> OTHER INFORMATION: synthetic sequence

<400> SEQUENCE: 81

Tyr Ile Lys Lys Ile Tyr
1 5

<210> SEQ ID NO 82
<211> LENGTH: 6
<212> TYPE: PRT
<213> ORGANISM: Artificial sequence
<220> FEATURE:
<223> OTHER INFORMATION: synthetic sequence

<400> SEQUENCE: 82

Tyr Tyr Lys Lys Ile Ile
1 5

<210> SEQ ID NO 83
<211> LENGTH: 6
<212> TYPE: PRT
<213> ORGANISM: Artificial sequence
<220> FEATURE:
<223> OTHER INFORMATION: synthetic sequence

<400> SEQUENCE: 83

Ile Ile Lys Lys Ile Ile
1 5

<210> SEQ ID NO 84
<211> LENGTH: 6
<212> TYPE: PRT
<213> ORGANISM: Artificial sequence
<220> FEATURE:
<223> OTHER INFORMATION: synthetic sequence

<400> SEQUENCE: 84

Met Met Lys Lys Met Met
1 5

<210> SEQ ID NO 85
<211> LENGTH: 6
<212> TYPE: PRT
<213> ORGANISM: Artificial sequence
<220> FEATURE:
<223> OTHER INFORMATION: synthetic sequence

<400> SEQUENCE: 85

Leu Leu Lys Lys Met Met
1 5

<210> SEQ ID NO 86
<211> LENGTH: 6
<212> TYPE: PRT
<213> ORGANISM: Artificial sequence
<220> FEATURE:

<223> OTHER INFORMATION: synthetic sequence

<400> SEQUENCE: 86

Met Leu Lys Lys Leu Met
1 5

<210> SEQ ID NO 87
<211> LENGTH: 6
<212> TYPE: PRT
<213> ORGANISM: Artificial sequence
<220> FEATURE:
<223> OTHER INFORMATION: synthetic sequence

<400> SEQUENCE: 87

Met Met Lys Lys Leu Leu
1 5

<210> SEQ ID NO 88
<211> LENGTH: 6
<212> TYPE: PRT
<213> ORGANISM: Artificial sequence
<220> FEATURE:
<223> OTHER INFORMATION: synthetic sequence

<400> SEQUENCE: 88

Leu Leu Lys Lys Leu Leu
1 5

<210> SEQ ID NO 89
<211> LENGTH: 6
<212> TYPE: PRT
<213> ORGANISM: Artificial sequence
<220> FEATURE:
<223> OTHER INFORMATION: synthetic sequence

<400> SEQUENCE: 89

Val Val Lys Lys Val Val
1 5

<210> SEQ ID NO 90
<211> LENGTH: 6
<212> TYPE: PRT
<213> ORGANISM: Artificial sequence
<220> FEATURE:
<223> OTHER INFORMATION: synthetic sequence

<400> SEQUENCE: 90

Ala Ala Lys Lys Val Val
1 5

<210> SEQ ID NO 91
<211> LENGTH: 6
<212> TYPE: PRT
<213> ORGANISM: Artificial sequence
<220> FEATURE:
<223> OTHER INFORMATION: synthetic sequence

<400> SEQUENCE: 91

Val Ala Lys Lys Ala Val
1 5

<210> SEQ ID NO 92
<211> LENGTH: 6
<212> TYPE: PRT
<213> ORGANISM: Artificial sequence
<220> FEATURE:
<223> OTHER INFORMATION: synthetic sequence

<400> SEQUENCE: 92

Val Val Lys Lys Ala Ala
1 5

<210> SEQ ID NO 93
<211> LENGTH: 6
<212> TYPE: PRT
<213> ORGANISM: Artificial sequence
<220> FEATURE:
<223> OTHER INFORMATION: synthetic sequence

<400> SEQUENCE: 93

Ala Ala Lys Lys Ala Ala
1 5

<210> SEQ ID NO 94
<211> LENGTH: 6
<212> TYPE: PRT
<213> ORGANISM: Artificial sequence
<220> FEATURE:
<223> OTHER INFORMATION: synthetic sequence

<400> SEQUENCE: 94

Gly Gly Lys Lys Gly Gly
1 5

<210> SEQ ID NO 95
<211> LENGTH: 6
<212> TYPE: PRT
<213> ORGANISM: Artificial sequence
<220> FEATURE:
<223> OTHER INFORMATION: synthetic sequence

<400> SEQUENCE: 95

Thr Thr Lys Lys Gly Gly
1 5

<210> SEQ ID NO 96
<211> LENGTH: 6
<212> TYPE: PRT
<213> ORGANISM: Artificial sequence
<220> FEATURE:
<223> OTHER INFORMATION: synthetic sequence

<400> SEQUENCE: 96

Gly Thr Lys Lys Thr Gly
1 5

<210> SEQ ID NO 97
<211> LENGTH: 6
<212> TYPE: PRT
<213> ORGANISM: Artificial sequence
<220> FEATURE:
<223> OTHER INFORMATION: synthetic sequence

<400> SEQUENCE: 97

Gly Gly Lys Lys Thr Thr
1 5

<210> SEQ ID NO 98
<211> LENGTH: 6
<212> TYPE: PRT
<213> ORGANISM: Artificial sequence
<220> FEATURE:
<223> OTHER INFORMATION: synthetic sequence -continued

<400> SEQUENCE: 98

Thr Thr Lys Lys Thr Thr
1 5

<210> SEQ ID NO 99
<211> LENGTH: 6
<212> TYPE: PRT
<213> ORGANISM: Artificial sequence
<220> FEATURE:
<223> OTHER INFORMATION: synthetic sequence

<400> SEQUENCE: 99

Ser Ser Lys Lys Ser Ser
1 5

<210> SEQ ID NO 100
<211> LENGTH: 6
<212> TYPE: PRT
<213> ORGANISM: Artificial sequence
<220> FEATURE:
<223> OTHER INFORMATION: synthetic sequence

<400> SEQUENCE: 100

Cys Cys Lys Lys Ser Ser
1 5

<210> SEQ ID NO 101
<211> LENGTH: 6
<212> TYPE: PRT
<213> ORGANISM: Artificial sequence
<220> FEATURE:
<223> OTHER INFORMATION: synthetic sequence

<400> SEQUENCE: 101

Ser Cys Lys Lys Cys Ser
1 5

<210> SEQ ID NO 102
<211> LENGTH: 6
<212> TYPE: PRT
<213> ORGANISM: Artificial sequence
<220> FEATURE:
<223> OTHER INFORMATION: synthetic sequence

<400> SEQUENCE: 102

Ser Ser Lys Lys Cys Cys
1 5

<210> SEQ ID NO 103
<211> LENGTH: 6
<212> TYPE: PRT
<213> ORGANISM: Artificial sequence
<220> FEATURE:
<223> OTHER INFORMATION: synthetic sequence

<400> SEQUENCE: 103

Cys Cys Lys Lys Cys Cys
1 5

<210> SEQ ID NO 104
<211> LENGTH: 6
<212> TYPE: PRT
<213> ORGANISM: Artificial sequence
<220> FEATURE:
<223> OTHER INFORMATION: synthetic sequence

<400> SEQUENCE: 104

Phe Lys Phe Lys Phe Lys
1 5

<210> SEQ ID NO 105
<211> LENGTH: 6
<212> TYPE: PRT
<213> ORGANISM: Artificial sequence
<220> FEATURE:
<223> OTHER INFORMATION: synthetic sequence

<400> SEQUENCE: 105

Trp Lys Trp Lys Trp Lys
1 5

<210> SEQ ID NO 106
<211> LENGTH: 6
<212> TYPE: PRT
<213> ORGANISM: Artificial sequence
<220> FEATURE:
<223> OTHER INFORMATION: synthetic sequence

<400> SEQUENCE: 106

Tyr Lys Tyr Lys Tyr Lys
1 5

<210> SEQ ID NO 107
<211> LENGTH: 6
<212> TYPE: PRT
<213> ORGANISM: Artificial sequence
<220> FEATURE:
<223> OTHER INFORMATION: synthetic sequence

<400> SEQUENCE: 107

Ile Lys Ile Lys Ile Lys
1 5

<210> SEQ ID NO 108
<211> LENGTH: 6
<212> TYPE: PRT
<213> ORGANISM: Artificial sequence
<220> FEATURE:
<223> OTHER INFORMATION: synthetic sequence

<400> SEQUENCE: 108

Met Lys Met Lys Met Lys
1 5

<210> SEQ ID NO 109
<211> LENGTH: 6
<212> TYPE: PRT
<213> ORGANISM: Artificial sequence
<220> FEATURE:
<223> OTHER INFORMATION: synthetic sequence

<400> SEQUENCE: 109

Leu Lys Leu Lys Leu Lys
1 5

<210> SEQ ID NO 110
<211> LENGTH: 6
<212> TYPE: PRT
<213> ORGANISM: Artificial sequence
<220> FEATURE:
<223> OTHER INFORMATION: synthetic sequence

<400> SEQUENCE: 110

Val Lys Val Lys Val Lys
1 5

<210> SEQ ID NO 111
<211> LENGTH: 6
<212> TYPE: PRT
<213> ORGANISM: Artificial sequence
<220> FEATURE:
<223> OTHER INFORMATION: synthetic sequence

<400> SEQUENCE: 111

Ala Lys Ala Lys Ala Lys
1 5

<210> SEQ ID NO 112
<211> LENGTH: 6
<212> TYPE: PRT
<213> ORGANISM: Artificial sequence
<220> FEATURE:
<223> OTHER INFORMATION: synthetic sequence

<400> SEQUENCE: 112

Gly Lys Gly Lys Gly Lys
1 5

<210> SEQ ID NO 113
<211> LENGTH: 6
<212> TYPE: PRT
<213> ORGANISM: Artificial sequence
<220> FEATURE:
<223> OTHER INFORMATION: synthetic sequence

<400> SEQUENCE: 113

Thr Lys Thr Lys Thr Lys
1 5

<210> SEQ ID NO 114
<211> LENGTH: 6
<212> TYPE: PRT
<213> ORGANISM: Artificial sequence
<220> FEATURE:
<223> OTHER INFORMATION: synthetic sequence

<400> SEQUENCE: 114

Ser Lys Ser Lys Ser Lys
1 5

<210> SEQ ID NO 115
<211> LENGTH: 6
<212> TYPE: PRT
<213> ORGANISM: Artificial sequence
<220> FEATURE:
<223> OTHER INFORMATION: synthetic sequence

<400> SEQUENCE: 115

Cys Lys Cys Lys Cys Lys
1 5

<210> SEQ ID NO 116
<211> LENGTH: 6
<212> TYPE: PRT
<213> ORGANISM: Artificial sequence
<220> FEATURE:
<223> OTHER INFORMATION: synthetic sequence

<400> SEQUENCE: 116

Lys Phe Lys Phe Lys Phe 1 5

<210> SEQ ID NO 117
<211> LENGTH: 6
<212> TYPE: PRT
<213> ORGANISM: Artificial sequence
<220> FEATURE:
<223> OTHER INFORMATION: synthetic sequence

<400> SEQUENCE: 117

Lys Trp Lys Trp Lys Trp
1 5

<210> SEQ ID NO 118
<211> LENGTH: 6
<212> TYPE: PRT
<213> ORGANISM: Artificial sequence
<220> FEATURE:
<223> OTHER INFORMATION: synthetic sequence

<400> SEQUENCE: 118

Lys Tyr Lys Tyr Lys Tyr
1 5

<210> SEQ ID NO 119
<211> LENGTH: 6
<212> TYPE: PRT
<213> ORGANISM: Artificial sequence
<220> FEATURE:
<223> OTHER INFORMATION: synthetic sequence

<400> SEQUENCE: 119

Lys Ile Lys Ile Lys Ile
1 5

<210> SEQ ID NO 120
<211> LENGTH: 6
<212> TYPE: PRT
<213> ORGANISM: Artificial sequence
<220> FEATURE:
<223> OTHER INFORMATION: synthetic sequence

<400> SEQUENCE: 120

Lys Met Lys Met Lys Met
1 5

<210> SEQ ID NO 121
<211> LENGTH: 6
<212> TYPE: PRT
<213> ORGANISM: Artificial sequence
<220> FEATURE:
<223> OTHER INFORMATION: synthetic sequence

<400> SEQUENCE: 121

Lys Leu Lys Leu Lys Leu
1 5

<210> SEQ ID NO 122
<211> LENGTH: 6
<212> TYPE: PRT
<213> ORGANISM: Artificial sequence
<220> FEATURE:
<223> OTHER INFORMATION: synthetic sequence

<400> SEQUENCE: 122

Lys Val Lys Val Lys Val
1 5

<210> SEQ ID NO 123
<211> LENGTH: 6
<212> TYPE: PRT
<213> ORGANISM: Artificial sequence
<220> FEATURE:
<223> OTHER INFORMATION: synthetic sequence

<400> SEQUENCE: 123

Lys Ala Lys Ala Lys Ala
1               5

<210> SEQ ID NO 124
<211> LENGTH: 6
<212> TYPE: PRT
<213> ORGANISM: Artificial sequence
<220> FEATURE:
<223> OTHER INFORMATION: synthetic sequence

<400> SEQUENCE: 124

Lys Gly Lys Gly Lys Gly
1               5

<210> SEQ ID NO 125
<211> LENGTH: 6
<212> TYPE: PRT
<213> ORGANISM: Artificial sequence
<220> FEATURE:
<223> OTHER INFORMATION: synthetic sequence

<400> SEQUENCE: 125

Lys Thr Lys Thr Lys Thr
1               5

<210> SEQ ID NO 126
<211> LENGTH: 6
<212> TYPE: PRT
<213> ORGANISM: Artificial sequence
<220> FEATURE:
<223> OTHER INFORMATION: synthetic sequence

<400> SEQUENCE: 126

Lys Ser Lys Ser Lys Ser
1               5

<210> SEQ ID NO 127
<211> LENGTH: 6
<212> TYPE: PRT
<213> ORGANISM: Artificial sequence
<220> FEATURE:
<223> OTHER INFORMATION: synthetic sequence

<400> SEQUENCE: 127

Lys Cys Lys Cys Lys Cys
1               5

<210> SEQ ID NO 128
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is independently selected from
      phenylalanine, tryptophan, alanine, valine, leucine, isoleucine,
      methionine, tyrosine, threonine, serine, cysteine, proline, and glycine
<220> FEATURE:
<221> NAME/KEY: MISC_FEATURE
<222> LOCATION: (2)..(2)
<223> OTHER INFORMATION: Xaa is independently selected from lysine, arginine, histidine, aspartic acid, glutamic acid, asparagine and glutamine
<220> FEATURE:
<221> NAME/KEY: MISC_FEATURE
<222> LOCATION: (3)..(3)
<223> OTHER INFORMATION: Xaa is independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (4)..(4)
<223> OTHER INFORMATION: Xaa is independently selected from lysine, arginine, histidine, aspartic acid, glutamic acid, asparagine and glutamine
<220> FEATURE:
<221> NAME/KEY: MISC_FEATURE
<222> LOCATION: (5)..(5)
<223> OTHER INFORMATION: Xaa is independently selected from phenylalanine, tryptophan, alanine, valine, leucine, isoleucine, methionine, tyrosine, threonine, serine, cysteine, proline, and glycine

<400> SEQUENCE: 128

Xaa Xaa Xaa Xaa Xaa
1 5

<210> SEQ ID NO 129
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is independently selected from lysine, arginine, histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(4)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (5)..(5)
<223> OTHER INFORMATION: Xaa is selected from lysine, arginine, histidine, aspartic acid, glutamic acid, asparagine and glutamine

<400> SEQUENCE: 129

Xaa Xaa Xaa Xaa Xaa
1 5

<210> SEQ ID NO 130
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(5)
<223> OTHER INFORMATION: Xaa at positions 4 and 5 are each independently selected from phenylalanine, tryptophan, alanine, valine, leucine, isoleucine, methionine, tyrosine, threonine, serine, cysteine, proline, and glycine

<400> SEQUENCE: 130

```
Xaa Xaa Xaa Xaa Xaa
1               5
```

<210> SEQ ID NO 131
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(4)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (5)..(5)
<223> OTHER INFORMATION: Xaa is selected from lysine, arginine, histidine, aspartic acid, glutamic acid, asparagine and glutamine

<400> SEQUENCE: 131

```
Xaa Xaa Xaa Xaa Xaa
1               5
```

<210> SEQ ID NO 132
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine.

<220> FEATURE:
<221> NAME/KEY: MISC_FEATURE
<222> LOCATION: (2)..(3)
<223> OTHER INFORMATION: Xaa at positions 2 and 3 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine, histidine, aspartic acid, glutamic acid, asparagine and glutamine.
<220> FEATURE:
<221> NAME/KEY: MISC_FEATURE
<222> LOCATION: (5)..(5)
<223> OTHER INFORMATION: Xaa is selected from phenylalanine, tryptophan, alanine, valine, leucine, isoleucine, methionine, tyrosine, threonine, serine, cysteine, proline, and glycine

<400> SEQUENCE: 132

```
Xaa Xaa Xaa Xaa Xaa
1               5
```

<210> SEQ ID NO 133
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (2)..(2)
<223> OTHER INFORMATION: Xaa is selected from lysine, arginine, histidine, aspartic acid, glutamic acid, asparagine and glutamine.
<220> FEATURE:
<221> NAME/KEY: MISC_FEATURE
<222> LOCATION: (3)..(4)
<223> OTHER INFORMATION: Xaa at positions 3 and 4 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (5)..(5)
<223> OTHER INFORMATION: Xaa is selected from lysine, arginine, histidine, aspartic acid, glutamic acid, asparagine and glutamine.

<400> SEQUENCE: 133

```
Xaa Xaa Xaa Xaa Xaa
1               5
```

<210> SEQ ID NO 134
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine.
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(5)
<223> OTHER INFORMATION: Xaa at positions 4 and 5 are each independently selected from phenylalanine, tryptophan, alanine, valine, leucine, isoleucine, methionine, tyrosine, threonine, serine, cysteine, proline, and glycine.

<400> SEQUENCE: 134

Xaa Xaa Xaa Xaa Xaa
1 5

<210> SEQ ID NO 135
<211> LENGTH: 5
<212> TYPE: PRT
<213> ORGANISM: Artificial sequence
<220> FEATURE:
<223> OTHER INFORMATION: synthetic sequence

<400> SEQUENCE: 135

Ala Phe Lys Arg Phe
1 5

<210> SEQ ID NO 136
<211> LENGTH: 5
<212> TYPE: PRT
<213> ORGANISM: Artificial sequence
<220> FEATURE:
<223> OTHER INFORMATION: synthetic sequence

<400> SEQUENCE: 136

Phe Phe Lys Lys Phe
1 5

<210> SEQ ID NO 137
<211> LENGTH: 5
<212> TYPE: PRT
<213> ORGANISM: Artificial sequence
<220> FEATURE:
<223> OTHER INFORMATION: synthetic sequence

<400> SEQUENCE: 137

Phe Trp Lys Arg Phe
1 5

<210> SEQ ID NO 138
<211> LENGTH: 5
<212> TYPE: PRT
<213> ORGANISM: Artificial sequence
<220> FEATURE:
<223> OTHER INFORMATION: synthetic sequence

<400> SEQUENCE: 138

Trp Val Arg Arg Val
1 5

<210> SEQ ID NO 139
<211> LENGTH: 5
<212> TYPE: PRT
<213> ORGANISM: Artificial sequence
<220> FEATURE:
<223> OTHER INFORMATION: synthetic sequence

<400> SEQUENCE: 139

Ile Phe Lys Lys Ile
1 5

<210> SEQ ID NO 140
<211> LENGTH: 5
<212> TYPE: PRT
<213> ORGANISM: Artificial sequence
<220> FEATURE:
<223> OTHER INFORMATION: synthetic sequence

<400> SEQUENCE: 140

Phe Leu Arg Asn Leu
1               5

<210> SEQ ID NO 141
<211> LENGTH: 5
<212> TYPE: PRT
<213> ORGANISM: Artificial sequence
<220> FEATURE:
<223> OTHER INFORMATION: synthetic sequence

<400> SEQUENCE: 141

Phe Leu His Ser Ala
1               5

<210> SEQ ID NO 142
<211> LENGTH: 5
<212> TYPE: PRT
<213> ORGANISM: Artificial sequence
<220> FEATURE:
<223> OTHER INFORMATION: synthetic sequence

<400> SEQUENCE: 142

Phe Phe His His Ile
1               5

<210> SEQ ID NO 143
<211> LENGTH: 5
<212> TYPE: PRT
<213> ORGANISM: Artificial sequence
<220> FEATURE:
<223> OTHER INFORMATION: synthetic sequence

<400> SEQUENCE: 143

Phe Phe Lys Lys Ala
1               5

<210> SEQ ID NO 144
<211> LENGTH: 5
<212> TYPE: PRT
<213> ORGANISM: Artificial sequence
<220> FEATURE:
<223> OTHER INFORMATION: synthetic sequence

<400> SEQUENCE: 144

Ala Leu Lys Lys Val
1               5

<210> SEQ ID NO 145
<211> LENGTH: 5
<212> TYPE: PRT
<213> ORGANISM: Artificial sequence
<220> FEATURE:
<223> OTHER INFORMATION: synthetic sequence

<400> SEQUENCE: 145

Leu Tyr Lys Lys Ile
1               5

<210> SEQ ID NO 146

<211> LENGTH: 5
<212> TYPE: PRT
<213> ORGANISM: Artificial sequence
<220> FEATURE:
<223> OTHER INFORMATION: synthetic sequence

<400> SEQUENCE: 146

Leu Phe Arg Arg Ala
1               5

<210> SEQ ID NO 147
<211> LENGTH: 5
<212> TYPE: PRT
<213> ORGANISM: Artificial sequence
<220> FEATURE:
<223> OTHER INFORMATION: synthetic sequence

<400> SEQUENCE: 147

Phe Leu Lys Arg Leu
1               5

<210> SEQ ID NO 148
<211> LENGTH: 5
<212> TYPE: PRT
<213> ORGANISM: Artificial sequence
<220> FEATURE:
<223> OTHER INFORMATION: synthetic sequence

<400> SEQUENCE: 148

Phe Phe Arg Arg Phe
1               5

<210> SEQ ID NO 149
<211> LENGTH: 5
<212> TYPE: PRT
<213> ORGANISM: Artificial sequence
<220> FEATURE:
<223> OTHER INFORMATION: synthetic sequence

<400> SEQUENCE: 149

Phe Phe Arg His Phe
1               5

<210> SEQ ID NO 150
<211> LENGTH: 5
<212> TYPE: PRT
<213> ORGANISM: Artificial sequence
<220> FEATURE:
<223> OTHER INFORMATION: synthetic sequence

<400> SEQUENCE: 150

Ala Ile Arg Arg Ile
1               5

<210> SEQ ID NO 151
<211> LENGTH: 5
<212> TYPE: PRT
<213> ORGANISM: Artificial sequence
<220> FEATURE:
<223> OTHER INFORMATION: synthetic sequence

<400> SEQUENCE: 151

Ala Phe His Arg Phe
1               5

<210> SEQ ID NO 152
<211> LENGTH: 5

<212> TYPE: PRT
<213> ORGANISM: Artificial sequence
<220> FEATURE:
<223> OTHER INFORMATION: synthetic sequence

<400> SEQUENCE: 152

Phe Phe Asn Arg Phe
1               5

<210> SEQ ID NO 153
<211> LENGTH: 5
<212> TYPE: PRT
<213> ORGANISM: Artificial sequence
<220> FEATURE:
<223> OTHER INFORMATION: synthetic sequence

<400> SEQUENCE: 153

Ile Val Arg Arg Ala
1               5

<210> SEQ ID NO 154
<211> LENGTH: 5
<212> TYPE: PRT
<213> ORGANISM: Artificial sequence
<220> FEATURE:
<223> OTHER INFORMATION: synthetic sequence

<400> SEQUENCE: 154

Phe Trp Arg Trp Phe
1               5

<210> SEQ ID NO 155
<211> LENGTH: 5
<212> TYPE: PRT
<213> ORGANISM: Artificial sequence
<220> FEATURE:
<223> OTHER INFORMATION: synthetic sequence

<400> SEQUENCE: 155

Lys Phe Trp Arg Trp
1               5

<210> SEQ ID NO 156
<211> LENGTH: 5
<212> TYPE: PRT
<213> ORGANISM: Artificial sequence
<220> FEATURE:
<223> OTHER INFORMATION: synthetic sequence

<400> SEQUENCE: 156

Trp Phe Arg Phe Trp
1               5

<210> SEQ ID NO 157
<211> LENGTH: 5
<212> TYPE: PRT
<213> ORGANISM: Artificial sequence
<220> FEATURE:
<223> OTHER INFORMATION: synthetic sequence

<400> SEQUENCE: 157

Lys Trp Phe Arg Phe
1               5

<210> SEQ ID NO 158
<211> LENGTH: 5
<212> TYPE: PRT

<213> ORGANISM: Artificial sequence
<220> FEATURE:
<223> OTHER INFORMATION: synthetic sequence

<400> SEQUENCE: 158

Ala Phe His His Phe
1               5

<210> SEQ ID NO 159
<211> LENGTH: 5
<212> TYPE: PRT
<213> ORGANISM: Artificial sequence
<220> FEATURE:
<223> OTHER INFORMATION: synthetic sequence

<400> SEQUENCE: 159

Phe Phe Arg Asn Phe
1               5

<210> SEQ ID NO 160
<211> LENGTH: 5
<212> TYPE: PRT
<213> ORGANISM: Artificial sequence
<220> FEATURE:
<223> OTHER INFORMATION: synthetic sequence

<400> SEQUENCE: 160

Phe Phe Arg Gln Phe
1               5

<210> SEQ ID NO 161
<211> LENGTH: 5
<212> TYPE: PRT
<213> ORGANISM: Artificial sequence
<220> FEATURE:
<223> OTHER INFORMATION: synthetic sequence

<400> SEQUENCE: 161

Ala Phe Asn Arg Phe
1               5

<210> SEQ ID NO 162
<211> LENGTH: 5
<212> TYPE: PRT
<213> ORGANISM: Artificial sequence
<220> FEATURE:
<223> OTHER INFORMATION: synthetic sequence

<400> SEQUENCE: 162

Trp Ile Gln Arg Met
1               5

<210> SEQ ID NO 163
<211> LENGTH: 5
<212> TYPE: PRT
<213> ORGANISM: Artificial sequence
<220> FEATURE:
<223> OTHER INFORMATION: synthetic sequence

<400> SEQUENCE: 163

Trp Val Gln Arg Val
1               5

<210> SEQ ID NO 164
<211> LENGTH: 5
<212> TYPE: PRT
<213> ORGANISM: Artificial sequence
<220> FEATURE:
<223> OTHER INFORMATION: synthetic sequence

<400> SEQUENCE: 164

Ala Phe Arg Asn Phe
1 5

<210> SEQ ID NO 165
<211> LENGTH: 5
<212> TYPE: PRT
<213> ORGANISM: Artificial sequence
<220> FEATURE:
<223> OTHER INFORMATION: synthetic sequence

<400> SEQUENCE: 165

Thr Leu Arg Arg Phe
1 5

<210> SEQ ID NO 166
<211> LENGTH: 5
<212> TYPE: PRT
<213> ORGANISM: Artificial sequence
<220> FEATURE:
<223> OTHER INFORMATION: synthetic sequence

<400> SEQUENCE: 166

Phe Lys Arg Phe Phe
1 5

<210> SEQ ID NO 167
<211> LENGTH: 5
<212> TYPE: PRT
<213> ORGANISM: Artificial sequence
<220> FEATURE:
<223> OTHER INFORMATION: synthetic sequence

<400> SEQUENCE: 167

Phe Lys Lys Phe Phe
1 5

<210> SEQ ID NO 168
<211> LENGTH: 5
<212> TYPE: PRT
<213> ORGANISM: Artificial sequence
<220> FEATURE:
<223> OTHER INFORMATION: synthetic sequence

<400> SEQUENCE: 168

Trp Lys Arg Phe Val
1 5

<210> SEQ ID NO 169
<211> LENGTH: 5
<212> TYPE: PRT
<213> ORGANISM: Artificial sequence
<220> FEATURE:
<223> OTHER INFORMATION: synthetic sequence

<400> SEQUENCE: 169

Val Arg Arg Val Val
1 5

<210> SEQ ID NO 170
<211> LENGTH: 5
<212> TYPE: PRT
<213> ORGANISM: Artificial sequence
<220> FEATURE:

<223> OTHER INFORMATION: synthetic sequence

<400> SEQUENCE: 170

Phe Lys Lys Ile Glu
1 5

<210> SEQ ID NO 171
<211> LENGTH: 5
<212> TYPE: PRT
<213> ORGANISM: Artificial sequence
<220> FEATURE:
<223> OTHER INFORMATION: synthetic sequence

<400> SEQUENCE: 171

Leu Arg Asn Leu Val
1 5

<210> SEQ ID NO 172
<211> LENGTH: 5
<212> TYPE: PRT
<213> ORGANISM: Artificial sequence
<220> FEATURE:
<223> OTHER INFORMATION: synthetic sequence

<400> SEQUENCE: 172

Leu His Ser Ala Lys
1 5

<210> SEQ ID NO 173
<211> LENGTH: 5
<212> TYPE: PRT
<213> ORGANISM: Artificial sequence
<220> FEATURE:
<223> OTHER INFORMATION: synthetic sequence

<400> SEQUENCE: 173

Phe His His Ile Phe
1 5

<210> SEQ ID NO 174
<211> LENGTH: 5
<212> TYPE: PRT
<213> ORGANISM: Artificial sequence
<220> FEATURE:
<223> OTHER INFORMATION: synthetic sequence

<400> SEQUENCE: 174

Phe Lys Lys Ala Ala
1 5

<210> SEQ ID NO 175
<211> LENGTH: 5
<212> TYPE: PRT
<213> ORGANISM: Artificial sequence
<220> FEATURE:
<223> OTHER INFORMATION: synthetic sequence

<400> SEQUENCE: 175

Leu Lys Lys Val Phe
1 5

<210> SEQ ID NO 176
<211> LENGTH: 5
<212> TYPE: PRT
<213> ORGANISM: Artificial sequence
<220> FEATURE:
<223> OTHER INFORMATION: synthetic sequence

<400> SEQUENCE: 176

Tyr Lys Lys Ile Ile
1 5

<210> SEQ ID NO 177
<211> LENGTH: 5
<212> TYPE: PRT
<213> ORGANISM: Artificial sequence
<220> FEATURE:
<223> OTHER INFORMATION: synthetic sequence

<400> SEQUENCE: 177

Phe Arg Arg Ala Phe
1 5

<210> SEQ ID NO 178
<211> LENGTH: 5
<212> TYPE: PRT
<213> ORGANISM: Artificial sequence
<220> FEATURE:
<223> OTHER INFORMATION: synthetic sequence

<400> SEQUENCE: 178

Leu Lys Arg Leu Leu
1 5

<210> SEQ ID NO 179
<211> LENGTH: 5
<212> TYPE: PRT
<213> ORGANISM: Artificial sequence
<220> FEATURE:
<223> OTHER INFORMATION: synthetic sequence

<400> SEQUENCE: 179

Phe Arg Arg Phe Ala
1 5

<210> SEQ ID NO 180
<211> LENGTH: 5
<212> TYPE: PRT
<213> ORGANISM: Artificial sequence
<220> FEATURE:
<223> OTHER INFORMATION: synthetic sequence

<400> SEQUENCE: 180

Phe Arg His Phe Ala
1 5

<210> SEQ ID NO 181
<211> LENGTH: 5
<212> TYPE: PRT
<213> ORGANISM: Artificial sequence
<220> FEATURE:
<223> OTHER INFORMATION: synthetic sequence

<400> SEQUENCE: 181

Ile Arg Arg Ile Pro
1 5

<210> SEQ ID NO 182
<211> LENGTH: 5
<212> TYPE: PRT
<213> ORGANISM: Artificial sequence
<220> FEATURE:
<223> OTHER INFORMATION: synthetic sequence

<400> SEQUENCE: 182

Phe His Arg Phe Phe
1               5

<210> SEQ ID NO 183
<211> LENGTH: 5
<212> TYPE: PRT
<213> ORGANISM: Artificial sequence
<220> FEATURE:
<223> OTHER INFORMATION: synthetic sequence

<400> SEQUENCE: 183

Phe Asn Arg Phe Ala
1               5

<210> SEQ ID NO 184
<211> LENGTH: 5
<212> TYPE: PRT
<213> ORGANISM: Artificial sequence
<220> FEATURE:
<223> OTHER INFORMATION: synthetic sequence

<400> SEQUENCE: 184

Val Arg Arg Ala Asp
1               5

<210> SEQ ID NO 185
<211> LENGTH: 5
<212> TYPE: PRT
<213> ORGANISM: Artificial sequence
<220> FEATURE:
<223> OTHER INFORMATION: synthetic sequence

<400> SEQUENCE: 185

Trp Arg Trp Phe Lys
1               5

<210> SEQ ID NO 186
<211> LENGTH: 5
<212> TYPE: PRT
<213> ORGANISM: Artificial sequence
<220> FEATURE:
<223> OTHER INFORMATION: synthetic sequence

<400> SEQUENCE: 186

Phe Arg Phe Trp Lys
1               5

<210> SEQ ID NO 187
<211> LENGTH: 5
<212> TYPE: PRT
<213> ORGANISM: Artificial sequence
<220> FEATURE:
<223> OTHER INFORMATION: synthetic sequence

<400> SEQUENCE: 187

Phe His His Phe Phe
1               5

<210> SEQ ID NO 188
<211> LENGTH: 5
<212> TYPE: PRT
<213> ORGANISM: Artificial sequence
<220> FEATURE:
<223> OTHER INFORMATION: synthetic sequence

<400> SEQUENCE: 188

Phe Arg Asn Phe Ala
1 5

<210> SEQ ID NO 189
<211> LENGTH: 5
<212> TYPE: PRT
<213> ORGANISM: Artificial sequence
<220> FEATURE:
<223> OTHER INFORMATION: synthetic sequence

<400> SEQUENCE: 189

Phe Arg Gln Phe Ala
1 5

<210> SEQ ID NO 190
<211> LENGTH: 5
<212> TYPE: PRT
<213> ORGANISM: Artificial sequence
<220> FEATURE:
<223> OTHER INFORMATION: synthetic sequence

<400> SEQUENCE: 190

Phe Asn Arg Phe Phe
1 5

<210> SEQ ID NO 191
<211> LENGTH: 5
<212> TYPE: PRT
<213> ORGANISM: Artificial sequence
<220> FEATURE:
<223> OTHER INFORMATION: synthetic sequence

<400> SEQUENCE: 191

Ile Gln Arg Met Met
1 5

<210> SEQ ID NO 192
<211> LENGTH: 5
<212> TYPE: PRT
<213> ORGANISM: Artificial sequence
<220> FEATURE:
<223> OTHER INFORMATION: synthetic sequence

<400> SEQUENCE: 192

Val Gln Arg Val Val
1 5

<210> SEQ ID NO 193
<211> LENGTH: 5
<212> TYPE: PRT
<213> ORGANISM: Artificial sequence
<220> FEATURE:
<223> OTHER INFORMATION: synthetic sequence

<400> SEQUENCE: 193

Phe Arg Asn Phe Phe
1 5

<210> SEQ ID NO 194
<211> LENGTH: 5
<212> TYPE: PRT
<213> ORGANISM: Artificial sequence
<220> FEATURE:
<223> OTHER INFORMATION: synthetic sequence

<400> SEQUENCE: 194

Leu Arg Arg Phe Met
1 5

<210> SEQ ID NO 195
<211> LENGTH: 5
<212> TYPE: PRT
<213> ORGANISM: Artificial sequence
<220> FEATURE:
<223> OTHER INFORMATION: synthetic sequence

<400> SEQUENCE: 195

Asp Val Arg Met Arg
1 5

<210> SEQ ID NO 196
<211> LENGTH: 5
<212> TYPE: PRT
<213> ORGANISM: Artificial sequence
<220> FEATURE:
<223> OTHER INFORMATION: synthetic sequence

<400> SEQUENCE: 196

Val Arg Met Arg Leu
1 5

<210> SEQ ID NO 197
<211> LENGTH: 5
<212> TYPE: PRT
<213> ORGANISM: Artificial sequence
<220> FEATURE:
<223> OTHER INFORMATION: synthetic sequence

<400> SEQUENCE: 197

Arg Arg Ala Glu Leu
1 5

<210> SEQ ID NO 198
<211> LENGTH: 5
<212> TYPE: PRT
<213> ORGANISM: Artificial sequence
<220> FEATURE:
<223> OTHER INFORMATION: synthetic sequence

<400> SEQUENCE: 198

Arg Ala Glu Leu Gly
1 5

<210> SEQ ID NO 199
<211> LENGTH: 5
<212> TYPE: PRT
<213> ORGANISM: Artificial sequence
<220> FEATURE:
<223> OTHER INFORMATION: synthetic sequence

<400> SEQUENCE: 199

Arg Trp Lys Phe Gly
1 5

<210> SEQ ID NO 200
<211> LENGTH: 5
<212> TYPE: PRT
<213> ORGANISM: Artificial sequence
<220> FEATURE:
<223> OTHER INFORMATION: synthetic sequence

<400> SEQUENCE: 200

Ala Phe Trp Arg Trp 1 5

<210> SEQ ID NO 201
<211> LENGTH: 5
<212> TYPE: PRT
<213> ORGANISM: Artificial sequence
<220> FEATURE:
<223> OTHER INFORMATION: synthetic sequence

<400> SEQUENCE: 201

Ala Trp Phe Arg Phe
1 5

<210> SEQ ID NO 202
<211> LENGTH: 5
<212> TYPE: PRT
<213> ORGANISM: Artificial sequence
<220> FEATURE:
<223> OTHER INFORMATION: synthetic sequence

<400> SEQUENCE: 202

Val Ala Val Arg Ile
1 5

<210> SEQ ID NO 203
<211> LENGTH: 5
<212> TYPE: PRT
<213> ORGANISM: Artificial sequence
<220> FEATURE:
<223> OTHER INFORMATION: synthetic sequence

<400> SEQUENCE: 203

Phe Phe Arg Phe Phe
1 5

<210> SEQ ID NO 204
<211> LENGTH: 5
<212> TYPE: PRT
<213> ORGANISM: Artificial sequence
<220> FEATURE:
<223> OTHER INFORMATION: synthetic sequence

<400> SEQUENCE: 204

Ala Phe Phe Arg Phe
1 5

<210> SEQ ID NO 205
<211> LENGTH: 5
<212> TYPE: PRT
<213> ORGANISM: Artificial sequence
<220> FEATURE:
<223> OTHER INFORMATION: synthetic sequence

<400> SEQUENCE: 205

Trp Arg Trp Phe Ala
1 5

<210> SEQ ID NO 206
<211> LENGTH: 5
<212> TYPE: PRT
<213> ORGANISM: Artificial sequence
<220> FEATURE:
<223> OTHER INFORMATION: synthetic sequence

<400> SEQUENCE: 206

Phe Arg Phe Trp Ala
1 5

<210> SEQ ID NO 207
<211> LENGTH: 5
<212> TYPE: PRT
<213> ORGANISM: Artificial sequence
<220> FEATURE:
<223> OTHER INFORMATION: synthetic sequence

<400> SEQUENCE: 207

Ala Val Arg Ile Trp
1               5

<210> SEQ ID NO 208
<211> LENGTH: 5
<212> TYPE: PRT
<213> ORGANISM: Artificial sequence
<220> FEATURE:
<223> OTHER INFORMATION: synthetic sequence

<400> SEQUENCE: 208

Phe Arg Phe Phe Ala
1               5

<210> SEQ ID NO 209
<211> LENGTH: 5
<212> TYPE: PRT
<213> ORGANISM: Artificial sequence
<220> FEATURE:
<223> OTHER INFORMATION: synthetic sequence

<400> SEQUENCE: 209

Phe Phe Lys Lys Phe
1               5

<210> SEQ ID NO 210
<211> LENGTH: 5
<212> TYPE: PRT
<213> ORGANISM: Artificial sequence
<220> FEATURE:
<223> OTHER INFORMATION: synthetic sequence

<400> SEQUENCE: 210

Trp Trp Lys Lys Phe
1               5

<210> SEQ ID NO 211
<211> LENGTH: 5
<212> TYPE: PRT
<213> ORGANISM: Artificial sequence
<220> FEATURE:
<223> OTHER INFORMATION: synthetic sequence

<400> SEQUENCE: 211

Phe Trp Lys Lys Trp
1               5

<210> SEQ ID NO 212
<211> LENGTH: 5
<212> TYPE: PRT
<213> ORGANISM: Artificial sequence
<220> FEATURE:
<223> OTHER INFORMATION: synthetic sequence

<400> SEQUENCE: 212

Phe Phe Lys Lys Trp
1               5

<210> SEQ ID NO 213
<211> LENGTH: 5
<212> TYPE: PRT
<213> ORGANISM: Artificial sequence
<220> FEATURE:
<223> OTHER INFORMATION: synthetic sequence

<400> SEQUENCE: 213

Trp Trp Lys Lys Trp
1 5

<210> SEQ ID NO 214
<211> LENGTH: 5
<212> TYPE: PRT
<213> ORGANISM: Artificial sequence
<220> FEATURE:
<223> OTHER INFORMATION: synthetic sequence

<400> SEQUENCE: 214

Tyr Tyr Lys Lys Tyr
1 5

<210> SEQ ID NO 215
<211> LENGTH: 5
<212> TYPE: PRT
<213> ORGANISM: Artificial sequence
<220> FEATURE:
<223> OTHER INFORMATION: synthetic sequence

<400> SEQUENCE: 215

Ile Ile Lys Lys Tyr
1 5

<210> SEQ ID NO 216
<211> LENGTH: 5
<212> TYPE: PRT
<213> ORGANISM: Artificial sequence
<220> FEATURE:
<223> OTHER INFORMATION: synthetic sequence

<400> SEQUENCE: 216

Tyr Ile Lys Lys Ile
1 5

<210> SEQ ID NO 217
<211> LENGTH: 5
<212> TYPE: PRT
<213> ORGANISM: Artificial sequence
<220> FEATURE:
<223> OTHER INFORMATION: synthetic sequence

<400> SEQUENCE: 217

Tyr Tyr Lys Lys Ile
1 5

<210> SEQ ID NO 218
<211> LENGTH: 5
<212> TYPE: PRT
<213> ORGANISM: Artificial sequence
<220> FEATURE:
<223> OTHER INFORMATION: synthetic sequence

<400> SEQUENCE: 218

Ile Ile Lys Lys Ile
1 5

<210> SEQ ID NO 219
<211> LENGTH: 5
<212> TYPE: PRT
<213> ORGANISM: Artificial sequence
<220> FEATURE:
<223> OTHER INFORMATION: synthetic sequence

<400> SEQUENCE: 219

Met Met Lys Lys Met
1               5

<210> SEQ ID NO 220
<211> LENGTH: 5
<212> TYPE: PRT
<213> ORGANISM: Artificial sequence
<220> FEATURE:
<223> OTHER INFORMATION: synthetic sequence

<400> SEQUENCE: 220

Leu Leu Lys Lys Met
1               5

<210> SEQ ID NO 221
<211> LENGTH: 5
<212> TYPE: PRT
<213> ORGANISM: Artificial sequence
<220> FEATURE:
<223> OTHER INFORMATION: synthetic sequence

<400> SEQUENCE: 221

Met Leu Lys Lys Leu
1               5

<210> SEQ ID NO 222
<211> LENGTH: 5
<212> TYPE: PRT
<213> ORGANISM: Artificial sequence
<220> FEATURE:
<223> OTHER INFORMATION: synthetic sequence

<400> SEQUENCE: 222

Met Met Lys Lys Leu
1               5

<210> SEQ ID NO 223
<211> LENGTH: 5
<212> TYPE: PRT
<213> ORGANISM: Artificial sequence
<220> FEATURE:
<223> OTHER INFORMATION: synthetic sequence

<400> SEQUENCE: 223

Leu Leu Lys Lys Leu
1               5

<210> SEQ ID NO 224
<211> LENGTH: 5
<212> TYPE: PRT
<213> ORGANISM: Artificial sequence
<220> FEATURE:
<223> OTHER INFORMATION: synthetic sequence

<400> SEQUENCE: 224

Val Val Lys Lys Val
1               5

<210> SEQ ID NO 225

<211> LENGTH: 5
<212> TYPE: PRT
<213> ORGANISM: Artificial sequence
<220> FEATURE:
<223> OTHER INFORMATION: synthetic sequence

<400> SEQUENCE: 225

Ala Ala Lys Lys Val
1               5

<210> SEQ ID NO 226
<211> LENGTH: 5
<212> TYPE: PRT
<213> ORGANISM: Artificial sequence
<220> FEATURE:
<223> OTHER INFORMATION: synthetic sequence

<400> SEQUENCE: 226

Val Ala Lys Lys Ala
1               5

<210> SEQ ID NO 227
<211> LENGTH: 5
<212> TYPE: PRT
<213> ORGANISM: Artificial sequence
<220> FEATURE:
<223> OTHER INFORMATION: synthetic sequence

<400> SEQUENCE: 227

Val Val Lys Lys Ala
1               5

<210> SEQ ID NO 228
<211> LENGTH: 5
<212> TYPE: PRT
<213> ORGANISM: Artificial sequence
<220> FEATURE:
<223> OTHER INFORMATION: synthetic sequence

<400> SEQUENCE: 228

Ala Ala Lys Lys Ala
1               5

<210> SEQ ID NO 229
<211> LENGTH: 5
<212> TYPE: PRT
<213> ORGANISM: Artificial sequence
<220> FEATURE:
<223> OTHER INFORMATION: synthetic sequence

<400> SEQUENCE: 229

Gly Gly Lys Lys Gly
1               5

<210> SEQ ID NO 230
<211> LENGTH: 5
<212> TYPE: PRT
<213> ORGANISM: Artificial sequence
<220> FEATURE:
<223> OTHER INFORMATION: synthetic sequence

<400> SEQUENCE: 230

Thr Thr Lys Lys Gly
1               5

<210> SEQ ID NO 231
<211> LENGTH: 5

<212> TYPE: PRT
<213> ORGANISM: Artificial sequence
<220> FEATURE:
<223> OTHER INFORMATION: synthetic sequence

<400> SEQUENCE: 231

Gly Thr Lys Lys Thr
1 5

<210> SEQ ID NO 232
<211> LENGTH: 5
<212> TYPE: PRT
<213> ORGANISM: Artificial sequence
<220> FEATURE:
<223> OTHER INFORMATION: synthetic sequence

<400> SEQUENCE: 232

Gly Gly Lys Lys Thr
1 5

<210> SEQ ID NO 233
<211> LENGTH: 5
<212> TYPE: PRT
<213> ORGANISM: Artificial sequence
<220> FEATURE:
<223> OTHER INFORMATION: synthetic sequence

<400> SEQUENCE: 233

Thr Thr Lys Lys Thr
1 5

<210> SEQ ID NO 234
<211> LENGTH: 5
<212> TYPE: PRT
<213> ORGANISM: Artificial sequence
<220> FEATURE:
<223> OTHER INFORMATION: synthetic sequence

<400> SEQUENCE: 234

Ser Ser Lys Lys Ser
1 5

<210> SEQ ID NO 235
<211> LENGTH: 5
<212> TYPE: PRT
<213> ORGANISM: Artificial sequence
<220> FEATURE:
<223> OTHER INFORMATION: synthetic sequence

<400> SEQUENCE: 235

Cys Cys Lys Lys Ser
1 5

<210> SEQ ID NO 236
<211> LENGTH: 5
<212> TYPE: PRT
<213> ORGANISM: Artificial sequence
<220> FEATURE:
<223> OTHER INFORMATION: synthetic sequence

<400> SEQUENCE: 236

Ser Cys Lys Lys Cys
1 5

<210> SEQ ID NO 237
<211> LENGTH: 5
<212> TYPE: PRT

<213> ORGANISM: Artificial sequence
<220> FEATURE:
<223> OTHER INFORMATION: synthetic sequence

<400> SEQUENCE: 237

Ser Ser Lys Lys Cys
1 5

<210> SEQ ID NO 238
<211> LENGTH: 5
<212> TYPE: PRT
<213> ORGANISM: Artificial sequence
<220> FEATURE:
<223> OTHER INFORMATION: synthetic sequence

<400> SEQUENCE: 238

Cys Cys Lys Lys Cys
1 5

<210> SEQ ID NO 239
<211> LENGTH: 5
<212> TYPE: PRT
<213> ORGANISM: Artificial sequence
<220> FEATURE:
<223> OTHER INFORMATION: synthetic sequence

<400> SEQUENCE: 239

Phe Lys Lys Phe Phe
1 5

<210> SEQ ID NO 240
<211> LENGTH: 5
<212> TYPE: PRT
<213> ORGANISM: Artificial sequence
<220> FEATURE:
<223> OTHER INFORMATION: synthetic sequence

<400> SEQUENCE: 240

Trp Lys Lys Phe Phe
1 5

<210> SEQ ID NO 241
<211> LENGTH: 5
<212> TYPE: PRT
<213> ORGANISM: Artificial sequence
<220> FEATURE:
<223> OTHER INFORMATION: synthetic sequence

<400> SEQUENCE: 241

Trp Lys Lys Trp Phe
1 5

<210> SEQ ID NO 242
<211> LENGTH: 5
<212> TYPE: PRT
<213> ORGANISM: Artificial sequence
<220> FEATURE:
<223> OTHER INFORMATION: synthetic sequence

<400> SEQUENCE: 242

Phe Lys Lys Trp Trp
1 5

<210> SEQ ID NO 243
<211> LENGTH: 5
<212> TYPE: PRT
<213> ORGANISM: Artificial sequence
<220> FEATURE:
<223> OTHER INFORMATION: synthetic sequence

<400> SEQUENCE: 243

Trp Lys Lys Trp Trp
1 5

<210> SEQ ID NO 244
<211> LENGTH: 5
<212> TYPE: PRT
<213> ORGANISM: Artificial sequence
<220> FEATURE:
<223> OTHER INFORMATION: synthetic sequence

<400> SEQUENCE: 244

Tyr Lys Lys Tyr Tyr
1 5

<210> SEQ ID NO 245
<211> LENGTH: 5
<212> TYPE: PRT
<213> ORGANISM: Artificial sequence
<220> FEATURE:
<223> OTHER INFORMATION: synthetic sequence

<400> SEQUENCE: 245

Ile Lys Lys Tyr Tyr
1 5

<210> SEQ ID NO 246
<211> LENGTH: 5
<212> TYPE: PRT
<213> ORGANISM: Artificial sequence
<220> FEATURE:
<223> OTHER INFORMATION: synthetic sequence

<400> SEQUENCE: 246

Ile Lys Lys Ile Tyr
1 5

<210> SEQ ID NO 247
<211> LENGTH: 5
<212> TYPE: PRT
<213> ORGANISM: Artificial sequence
<220> FEATURE:
<223> OTHER INFORMATION: synthetic sequence

<400> SEQUENCE: 247

Tyr Lys Lys Ile Ile
1 5

<210> SEQ ID NO 248
<211> LENGTH: 5
<212> TYPE: PRT
<213> ORGANISM: Artificial sequence
<220> FEATURE:
<223> OTHER INFORMATION: synthetic sequence

<400> SEQUENCE: 248

Ile Lys Lys Ile Ile
1 5

<210> SEQ ID NO 249
<211> LENGTH: 5
<212> TYPE: PRT
<213> ORGANISM: Artificial sequence
<220> FEATURE:

<223> OTHER INFORMATION: synthetic sequence

<400> SEQUENCE: 249

Met Lys Lys Met Met
1 5

<210> SEQ ID NO 250
<211> LENGTH: 5
<212> TYPE: PRT
<213> ORGANISM: Artificial sequence
<220> FEATURE:
<223> OTHER INFORMATION: synthetic sequence

<400> SEQUENCE: 250

Leu Lys Lys Met Met
1 5

<210> SEQ ID NO 251
<211> LENGTH: 5
<212> TYPE: PRT
<213> ORGANISM: Artificial sequence
<220> FEATURE:
<223> OTHER INFORMATION: synthetic sequence

<400> SEQUENCE: 251

Leu Lys Lys Leu Met
1 5

<210> SEQ ID NO 252
<211> LENGTH: 5
<212> TYPE: PRT
<213> ORGANISM: Artificial sequence
<220> FEATURE:
<223> OTHER INFORMATION: synthetic sequence

<400> SEQUENCE: 252

Met Lys Lys Leu Leu
1 5

<210> SEQ ID NO 253
<211> LENGTH: 5
<212> TYPE: PRT
<213> ORGANISM: Artificial sequence
<220> FEATURE:
<223> OTHER INFORMATION: synthetic sequence

<400> SEQUENCE: 253

Leu Lys Lys Leu Leu
1 5

<210> SEQ ID NO 254
<211> LENGTH: 5
<212> TYPE: PRT
<213> ORGANISM: Artificial sequence
<220> FEATURE:
<223> OTHER INFORMATION: synthetic sequence

<400> SEQUENCE: 254

Val Lys Lys Val Val
1 5

<210> SEQ ID NO 255
<211> LENGTH: 5
<212> TYPE: PRT
<213> ORGANISM: Artificial sequence
<220> FEATURE:
<223> OTHER INFORMATION: synthetic sequence

<400> SEQUENCE: 255

Ala Lys Lys Val Val
1               5

<210> SEQ ID NO 256
<211> LENGTH: 5
<212> TYPE: PRT
<213> ORGANISM: Artificial sequence
<220> FEATURE:
<223> OTHER INFORMATION: synthetic sequence

<400> SEQUENCE: 256

Ala Lys Lys Ala Val
1               5

<210> SEQ ID NO 257
<211> LENGTH: 5
<212> TYPE: PRT
<213> ORGANISM: Artificial sequence
<220> FEATURE:
<223> OTHER INFORMATION: synthetic sequence

<400> SEQUENCE: 257

Val Lys Lys Ala Ala
1               5

<210> SEQ ID NO 258
<211> LENGTH: 5
<212> TYPE: PRT
<213> ORGANISM: Artificial sequence
<220> FEATURE:
<223> OTHER INFORMATION: synthetic sequence

<400> SEQUENCE: 258

Ala Lys Lys Ala Ala
1               5

<210> SEQ ID NO 259
<211> LENGTH: 5
<212> TYPE: PRT
<213> ORGANISM: Artificial sequence
<220> FEATURE:
<223> OTHER INFORMATION: synthetic sequence

<400> SEQUENCE: 259

Gly Lys Lys Gly Gly
1               5

<210> SEQ ID NO 260
<211> LENGTH: 5
<212> TYPE: PRT
<213> ORGANISM: Artificial sequence
<220> FEATURE:
<223> OTHER INFORMATION: synthetic sequence

<400> SEQUENCE: 260

Thr Lys Lys Gly Gly
1               5

<210> SEQ ID NO 261
<211> LENGTH: 5
<212> TYPE: PRT
<213> ORGANISM: Artificial sequence
<220> FEATURE:
<223> OTHER INFORMATION: synthetic sequence

<400> SEQUENCE: 261

Thr Lys Lys Thr Gly
1 5

<210> SEQ ID NO 262
<211> LENGTH: 5
<212> TYPE: PRT
<213> ORGANISM: Artificial sequence
<220> FEATURE:
<223> OTHER INFORMATION: synthetic sequence

<400> SEQUENCE: 262

Gly Lys Lys Thr Thr
1 5

<210> SEQ ID NO 263
<211> LENGTH: 5
<212> TYPE: PRT
<213> ORGANISM: Artificial sequence
<220> FEATURE:
<223> OTHER INFORMATION: synthetic sequence

<400> SEQUENCE: 263

Thr Lys Lys Thr Thr
1 5

<210> SEQ ID NO 264
<211> LENGTH: 5
<212> TYPE: PRT
<213> ORGANISM: Artificial sequence
<220> FEATURE:
<223> OTHER INFORMATION: synthetic sequence

<400> SEQUENCE: 264

Ser Lys Lys Ser Ser
1 5

<210> SEQ ID NO 265
<211> LENGTH: 5
<212> TYPE: PRT
<213> ORGANISM: Artificial sequence
<220> FEATURE:
<223> OTHER INFORMATION: synthetic sequence

<400> SEQUENCE: 265

Cys Lys Lys Ser Ser
1 5

<210> SEQ ID NO 266
<211> LENGTH: 5
<212> TYPE: PRT
<213> ORGANISM: Artificial sequence
<220> FEATURE:
<223> OTHER INFORMATION: synthetic sequence

<400> SEQUENCE: 266

Cys Lys Lys Cys Ser
1 5

<210> SEQ ID NO 267
<211> LENGTH: 5
<212> TYPE: PRT
<213> ORGANISM: Artificial sequence
<220> FEATURE:
<223> OTHER INFORMATION: synthetic sequence

<400> SEQUENCE: 267

Ser Lys Lys Cys Cys
1 5

<210> SEQ ID NO 268
<211> LENGTH: 5
<212> TYPE: PRT
<213> ORGANISM: Artificial sequence
<220> FEATURE:
<223> OTHER INFORMATION: synthetic sequence

<400> SEQUENCE: 268

Cys Lys Lys Cys Cys
1 5

<210> SEQ ID NO 269
<211> LENGTH: 5
<212> TYPE: PRT
<213> ORGANISM: Artificial sequence
<220> FEATURE:
<223> OTHER INFORMATION: synthetic sequence

<400> SEQUENCE: 269

Phe Lys Phe Lys Phe
1 5

<210> SEQ ID NO 270
<211> LENGTH: 5
<212> TYPE: PRT
<213> ORGANISM: Artificial sequence
<220> FEATURE:
<223> OTHER INFORMATION: synthetic sequence

<400> SEQUENCE: 270

Trp Lys Trp Lys Trp
1 5

<210> SEQ ID NO 271
<211> LENGTH: 5
<212> TYPE: PRT
<213> ORGANISM: Artificial sequence
<220> FEATURE:
<223> OTHER INFORMATION: synthetic sequence

<400> SEQUENCE: 271

Tyr Lys Tyr Lys Tyr
1 5

<210> SEQ ID NO 272
<211> LENGTH: 5
<212> TYPE: PRT
<213> ORGANISM: Artificial sequence
<220> FEATURE:
<223> OTHER INFORMATION: synthetic sequence

<400> SEQUENCE: 272

Ile Lys Ile Lys Ile
1 5

<210> SEQ ID NO 273
<211> LENGTH: 5
<212> TYPE: PRT
<213> ORGANISM: Artificial sequence
<220> FEATURE:
<223> OTHER INFORMATION: synthetic sequence

<400> SEQUENCE: 273

Met Lys Met Lys Met
1 5

<210> SEQ ID NO 274
<211> LENGTH: 5
<212> TYPE: PRT
<213> ORGANISM: Artificial sequence
<220> FEATURE:
<223> OTHER INFORMATION: synthetic sequence

<400> SEQUENCE: 274

Leu Lys Leu Lys Leu
1 5

<210> SEQ ID NO 275
<211> LENGTH: 5
<212> TYPE: PRT
<213> ORGANISM: Artificial sequence
<220> FEATURE:
<223> OTHER INFORMATION: synthetic sequence

<400> SEQUENCE: 275

Val Lys Val Lys Val
1 5

<210> SEQ ID NO 276
<211> LENGTH: 5
<212> TYPE: PRT
<213> ORGANISM: Artificial sequence
<220> FEATURE:
<223> OTHER INFORMATION: synthetic sequence

<400> SEQUENCE: 276

Ala Lys Ala Lys Ala
1 5

<210> SEQ ID NO 277
<211> LENGTH: 5
<212> TYPE: PRT
<213> ORGANISM: Artificial sequence
<220> FEATURE:
<223> OTHER INFORMATION: synthetic sequence

<400> SEQUENCE: 277

Gly Lys Gly Lys Gly
1 5

<210> SEQ ID NO 278
<211> LENGTH: 5
<212> TYPE: PRT
<213> ORGANISM: Artificial sequence
<220> FEATURE:
<223> OTHER INFORMATION: synthetic sequence

<400> SEQUENCE: 278

Thr Lys Thr Lys Thr
1 5

<210> SEQ ID NO 279
<211> LENGTH: 5
<212> TYPE: PRT
<213> ORGANISM: Artificial sequence
<220> FEATURE:
<223> OTHER INFORMATION: synthetic sequence

<400> SEQUENCE: 279

Ser Lys Ser Lys Ser 1 5

<210> SEQ ID NO 280
<211> LENGTH: 5
<212> TYPE: PRT
<213> ORGANISM: Artificial sequence
<220> FEATURE:
<223> OTHER INFORMATION: synthetic sequence

<400> SEQUENCE: 280

Cys Lys Cys Lys Cys
1 5

<210> SEQ ID NO 281
<211> LENGTH: 5
<212> TYPE: PRT
<213> ORGANISM: Artificial sequence
<220> FEATURE:
<223> OTHER INFORMATION: synthetic sequence

<400> SEQUENCE: 281

Lys Phe Lys Phe Lys
1 5

<210> SEQ ID NO 282
<211> LENGTH: 5
<212> TYPE: PRT
<213> ORGANISM: Artificial sequence
<220> FEATURE:
<223> OTHER INFORMATION: synthetic sequence

<400> SEQUENCE: 282

Lys Trp Lys Trp Lys
1 5

<210> SEQ ID NO 283
<211> LENGTH: 5
<212> TYPE: PRT
<213> ORGANISM: Artificial sequence
<220> FEATURE:
<223> OTHER INFORMATION: synthetic sequence

<400> SEQUENCE: 283

Lys Tyr Lys Tyr Lys
1 5

<210> SEQ ID NO 284
<211> LENGTH: 5
<212> TYPE: PRT
<213> ORGANISM: Artificial sequence
<220> FEATURE:
<223> OTHER INFORMATION: synthetic sequence

<400> SEQUENCE: 284

Lys Ile Lys Ile Lys
1 5

<210> SEQ ID NO 285
<211> LENGTH: 5
<212> TYPE: PRT
<213> ORGANISM: Artificial sequence
<220> FEATURE:
<223> OTHER INFORMATION: synthetic sequence

<400> SEQUENCE: 285

Lys Met Lys Met Lys
1 5

<210> SEQ ID NO 286
<211> LENGTH: 5
<212> TYPE: PRT
<213> ORGANISM: Artificial sequence
<220> FEATURE:
<223> OTHER INFORMATION: synthetic sequence

<400> SEQUENCE: 286

Lys Leu Lys Leu Lys
1               5

<210> SEQ ID NO 287
<211> LENGTH: 5
<212> TYPE: PRT
<213> ORGANISM: Artificial sequence
<220> FEATURE:
<223> OTHER INFORMATION: synthetic sequence

<400> SEQUENCE: 287

Lys Val Lys Val Lys
1               5

<210> SEQ ID NO 288
<211> LENGTH: 5
<212> TYPE: PRT
<213> ORGANISM: Artificial sequence
<220> FEATURE:
<223> OTHER INFORMATION: synthetic sequence

<400> SEQUENCE: 288

Lys Ala Lys Ala Lys
1               5

<210> SEQ ID NO 289
<211> LENGTH: 5
<212> TYPE: PRT
<213> ORGANISM: Artificial sequence
<220> FEATURE:
<223> OTHER INFORMATION: synthetic sequence

<400> SEQUENCE: 289

Lys Gly Lys Gly Lys
1               5

<210> SEQ ID NO 290
<211> LENGTH: 5
<212> TYPE: PRT
<213> ORGANISM: Artificial sequence
<220> FEATURE:
<223> OTHER INFORMATION: synthetic sequence

<400> SEQUENCE: 290

Lys Thr Lys Thr Lys
1               5

<210> SEQ ID NO 291
<211> LENGTH: 5
<212> TYPE: PRT
<213> ORGANISM: Artificial sequence
<220> FEATURE:
<223> OTHER INFORMATION: synthetic sequence

<400> SEQUENCE: 291

Lys Ser Lys Ser Lys
1               5

```
<210> SEQ ID NO 292
<211> LENGTH: 5
<212> TYPE: PRT
<213> ORGANISM: Artificial sequence
<220> FEATURE:
<223> OTHER INFORMATION: synthetic sequence

<400> SEQUENCE: 292

Lys Cys Lys Cys Lys
1               5


<210> SEQ ID NO 293
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (2)..(4)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (3)..(3)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine,
      histidine, aspartic acid, glutamic acid, asparagine and glutamine

<400> SEQUENCE: 293

Xaa Xaa Xaa Xaa
1


<210> SEQ ID NO 294
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (4)..(4)
<223> OTHER INFORMATION: Xaa is selected from phenylalanine, tryptophan,
      alanine, valine, leucine, isoleucine, methionine, tyrosine,
      threonine, serine, cysteine, proline, and glycine

<400> SEQUENCE: 294
```

Xaa Xaa Xaa Xaa
1

<210> SEQ ID NO 295
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from lysine, arginine, histidine, aspartic acid, glutamic acid, asparagine and glutamine
<220> FEATURE:
<221> NAME/KEY: MISC_FEATURE
<222> LOCATION: (3)..(4)
<223> OTHER INFORMATION: Xaa at positions 3 and 4 are each independently selected from phenylalanine, tryptophan, alanine, valine, leucine, isoleucine, methionine, tyrosine, threonine, serine, cysteine, proline, and glycine

<400> SEQUENCE: 295

Xaa Xaa Xaa Xaa
1

<210> SEQ ID NO 296
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(4)
<223> OTHER INFORMATION: Xaa at positions 3 and 4 are each independently selected from lysine, arginine, histidine, aspartic acid, glutamic acid, asparagine and glutamine

<400> SEQUENCE: 296

Xaa Xaa Xaa Xaa
1

<210> SEQ ID NO 297
<211> LENGTH: 4
<212> TYPE: PRT
<213> ORGANISM: Artificial sequence
<220> FEATURE:
<223> OTHER INFORMATION: synthetic sequence

<400> SEQUENCE: 297

Ala Phe Lys Arg
1

<210> SEQ ID NO 298
<211> LENGTH: 4
<212> TYPE: PRT
<213> ORGANISM: Artificial sequence
<220> FEATURE:
<223> OTHER INFORMATION: synthetic sequence

<400> SEQUENCE: 298

-continued

Phe Phe Lys Lys
1

<210> SEQ ID NO 299
<211> LENGTH: 4
<212> TYPE: PRT
<213> ORGANISM: Artificial sequence
<220> FEATURE:
<223> OTHER INFORMATION: synthetic sequence

<400> SEQUENCE: 299

Phe Trp Lys Arg
1

<210> SEQ ID NO 300
<211> LENGTH: 4
<212> TYPE: PRT
<213> ORGANISM: Artificial sequence
<220> FEATURE:
<223> OTHER INFORMATION: synthetic sequence

<400> SEQUENCE: 300

Trp Val Arg Arg
1

<210> SEQ ID NO 301
<211> LENGTH: 4
<212> TYPE: PRT
<213> ORGANISM: Artificial sequence
<220> FEATURE:
<223> OTHER INFORMATION: synthetic sequence

<400> SEQUENCE: 301

Ile Phe Lys Lys
1

<210> SEQ ID NO 302
<211> LENGTH: 4
<212> TYPE: PRT
<213> ORGANISM: Artificial sequence
<220> FEATURE:
<223> OTHER INFORMATION: synthetic sequence

<400> SEQUENCE: 302

Phe Leu Arg Asn
1

<210> SEQ ID NO 303
<211> LENGTH: 4
<212> TYPE: PRT
<213> ORGANISM: Artificial sequence
<220> FEATURE:
<223> OTHER INFORMATION: synthetic sequence

<400> SEQUENCE: 303

Phe Leu His Ser
1

<210> SEQ ID NO 304
<211> LENGTH: 4
<212> TYPE: PRT
<213> ORGANISM: Artificial sequence
<220> FEATURE:
<223> OTHER INFORMATION: synthetic sequence

<400> SEQUENCE: 304

Phe Phe His His

1

<210> SEQ ID NO 305
<211> LENGTH: 4
<212> TYPE: PRT
<213> ORGANISM: Artificial sequence
<220> FEATURE:
<223> OTHER INFORMATION: synthetic sequence

<400> SEQUENCE: 305

Ala Leu Lys Lys
1

<210> SEQ ID NO 306
<211> LENGTH: 4
<212> TYPE: PRT
<213> ORGANISM: Artificial sequence
<220> FEATURE:
<223> OTHER INFORMATION: synthetic sequence

<400> SEQUENCE: 306

Leu Tyr Lys Lys
1

<210> SEQ ID NO 307
<211> LENGTH: 4
<212> TYPE: PRT
<213> ORGANISM: Artificial sequence
<220> FEATURE:
<223> OTHER INFORMATION: synthetic sequence

<400> SEQUENCE: 307

Leu Phe Arg Arg
1

<210> SEQ ID NO 308
<211> LENGTH: 4
<212> TYPE: PRT
<213> ORGANISM: Artificial sequence
<220> FEATURE:
<223> OTHER INFORMATION: synthetic sequence

<400> SEQUENCE: 308

Phe Leu Lys Arg
1

<210> SEQ ID NO 309
<211> LENGTH: 4
<212> TYPE: PRT
<213> ORGANISM: Artificial sequence
<220> FEATURE:
<223> OTHER INFORMATION: synthetic sequence

<400> SEQUENCE: 309

Phe Phe Arg Arg
1

<210> SEQ ID NO 310
<211> LENGTH: 4
<212> TYPE: PRT
<213> ORGANISM: Artificial sequence
<220> FEATURE:
<223> OTHER INFORMATION: synthetic sequence

<400> SEQUENCE: 310

Phe Phe Arg His
1

<210> SEQ ID NO 311
<211> LENGTH: 4
<212> TYPE: PRT
<213> ORGANISM: Artificial sequence
<220> FEATURE:
<223> OTHER INFORMATION: synthetic sequence

<400> SEQUENCE: 311

Ala Ile Arg Arg
1

<210> SEQ ID NO 312
<211> LENGTH: 4
<212> TYPE: PRT
<213> ORGANISM: Artificial sequence
<220> FEATURE:
<223> OTHER INFORMATION: synthetic sequence

<400> SEQUENCE: 312

Ala Phe His Arg
1

<210> SEQ ID NO 313
<211> LENGTH: 4
<212> TYPE: PRT
<213> ORGANISM: Artificial sequence
<220> FEATURE:
<223> OTHER INFORMATION: synthetic sequence

<400> SEQUENCE: 313

Phe Phe Asn Arg
1

<210> SEQ ID NO 314
<211> LENGTH: 4
<212> TYPE: PRT
<213> ORGANISM: Artificial sequence
<220> FEATURE:
<223> OTHER INFORMATION: synthetic sequence

<400> SEQUENCE: 314

Ile Val Arg Arg
1

<210> SEQ ID NO 315
<211> LENGTH: 4
<212> TYPE: PRT
<213> ORGANISM: Artificial sequence
<220> FEATURE:
<223> OTHER INFORMATION: synthetic sequence

<400> SEQUENCE: 315

Phe Trp Arg Trp
1

<210> SEQ ID NO 316
<211> LENGTH: 4
<212> TYPE: PRT
<213> ORGANISM: Artificial sequence
<220> FEATURE:
<223> OTHER INFORMATION: synthetic sequence

<400> SEQUENCE: 316

Lys Phe Trp Arg
1

<210> SEQ ID NO 317
<211> LENGTH: 4
<212> TYPE: PRT
<213> ORGANISM: Artificial sequence
<220> FEATURE:
<223> OTHER INFORMATION: synthetic sequence

<400> SEQUENCE: 317

Trp Phe Arg Phe
1

<210> SEQ ID NO 318
<211> LENGTH: 4
<212> TYPE: PRT
<213> ORGANISM: Artificial sequence
<220> FEATURE:
<223> OTHER INFORMATION: synthetic sequence

<400> SEQUENCE: 318

Lys Trp Phe Arg
1

<210> SEQ ID NO 319
<211> LENGTH: 4
<212> TYPE: PRT
<213> ORGANISM: Artificial sequence
<220> FEATURE:
<223> OTHER INFORMATION: synthetic sequence

<400> SEQUENCE: 319

Ala Phe His His
1

<210> SEQ ID NO 320
<211> LENGTH: 4
<212> TYPE: PRT
<213> ORGANISM: Artificial sequence
<220> FEATURE:
<223> OTHER INFORMATION: synthetic sequence

<400> SEQUENCE: 320

Phe Phe Arg Asn
1

<210> SEQ ID NO 321
<211> LENGTH: 4
<212> TYPE: PRT
<213> ORGANISM: Artificial sequence
<220> FEATURE:
<223> OTHER INFORMATION: synthetic sequence

<400> SEQUENCE: 321

Phe Phe Arg Gln
1

<210> SEQ ID NO 322
<211> LENGTH: 4
<212> TYPE: PRT
<213> ORGANISM: Artificial sequence
<220> FEATURE:
<223> OTHER INFORMATION: synthetic sequence

<400> SEQUENCE: 322

Ala Phe Asn Arg
1

<210> SEQ ID NO 323
<211> LENGTH: 4
<212> TYPE: PRT
<213> ORGANISM: Artificial sequence
<220> FEATURE:
<223> OTHER INFORMATION: synthetic sequence

<400> SEQUENCE: 323

Trp Ile Gln Arg
1

<210> SEQ ID NO 324
<211> LENGTH: 4
<212> TYPE: PRT
<213> ORGANISM: Artificial sequence
<220> FEATURE:
<223> OTHER INFORMATION: synthetic sequence

<400> SEQUENCE: 324

Trp Val Gln Arg
1

<210> SEQ ID NO 325
<211> LENGTH: 4
<212> TYPE: PRT
<213> ORGANISM: Artificial sequence
<220> FEATURE:
<223> OTHER INFORMATION: synthetic sequence

<400> SEQUENCE: 325

Ala Phe Arg Asn
1

<210> SEQ ID NO 326
<211> LENGTH: 4
<212> TYPE: PRT
<213> ORGANISM: Artificial sequence
<220> FEATURE:
<223> OTHER INFORMATION: synthetic sequence

<400> SEQUENCE: 326

Thr Leu Arg Arg
1

<210> SEQ ID NO 327
<211> LENGTH: 4
<212> TYPE: PRT
<213> ORGANISM: Artificial sequence
<220> FEATURE:
<223> OTHER INFORMATION: synthetic sequence

<400> SEQUENCE: 327

Lys Arg Phe Phe
1

<210> SEQ ID NO 328
<211> LENGTH: 4
<212> TYPE: PRT
<213> ORGANISM: Artificial sequence
<220> FEATURE:
<223> OTHER INFORMATION: synthetic sequence

<400> SEQUENCE: 328

Lys Lys Phe Phe
1

<210> SEQ ID NO 329

<211> LENGTH: 4
<212> TYPE: PRT
<213> ORGANISM: Artificial sequence
<220> FEATURE:
<223> OTHER INFORMATION: synthetic sequence

<400> SEQUENCE: 329

Lys Arg Phe Val
1

<210> SEQ ID NO 330
<211> LENGTH: 4
<212> TYPE: PRT
<213> ORGANISM: Artificial sequence
<220> FEATURE:
<223> OTHER INFORMATION: synthetic sequence

<400> SEQUENCE: 330

Arg Arg Val Val
1

<210> SEQ ID NO 331
<211> LENGTH: 4
<212> TYPE: PRT
<213> ORGANISM: Artificial sequence
<220> FEATURE:
<223> OTHER INFORMATION: synthetic sequence

<400> SEQUENCE: 331

Lys Lys Ile Glu
1

<210> SEQ ID NO 332
<211> LENGTH: 4
<212> TYPE: PRT
<213> ORGANISM: Artificial sequence
<220> FEATURE:
<223> OTHER INFORMATION: synthetic sequence

<400> SEQUENCE: 332

Arg Asn Leu Val
1

<210> SEQ ID NO 333
<211> LENGTH: 4
<212> TYPE: PRT
<213> ORGANISM: Artificial sequence
<220> FEATURE:
<223> OTHER INFORMATION: synthetic sequence

<400> SEQUENCE: 333

His Ser Ala Lys
1

<210> SEQ ID NO 334
<211> LENGTH: 4
<212> TYPE: PRT
<213> ORGANISM: Artificial sequence
<220> FEATURE:
<223> OTHER INFORMATION: synthetic sequence

<400> SEQUENCE: 334

His His Ile Phe
1

<210> SEQ ID NO 335
<211> LENGTH: 4

<212> TYPE: PRT
<213> ORGANISM: Artificial sequence
<220> FEATURE:
<223> OTHER INFORMATION: synthetic sequence

<400> SEQUENCE: 335

Lys Lys Ala Ala
1

<210> SEQ ID NO 336
<211> LENGTH: 4
<212> TYPE: PRT
<213> ORGANISM: Artificial sequence
<220> FEATURE:
<223> OTHER INFORMATION: synthetic sequence

<400> SEQUENCE: 336

Lys Lys Val Phe
1

<210> SEQ ID NO 337
<211> LENGTH: 4
<212> TYPE: PRT
<213> ORGANISM: Artificial sequence
<220> FEATURE:
<223> OTHER INFORMATION: synthetic sequence

<400> SEQUENCE: 337

Lys Lys Ile Ile
1

<210> SEQ ID NO 338
<211> LENGTH: 4
<212> TYPE: PRT
<213> ORGANISM: Artificial sequence
<220> FEATURE:
<223> OTHER INFORMATION: synthetic sequence

<400> SEQUENCE: 338

Arg Arg Ala Phe
1

<210> SEQ ID NO 339
<211> LENGTH: 4
<212> TYPE: PRT
<213> ORGANISM: Artificial sequence
<220> FEATURE:
<223> OTHER INFORMATION: synthetic sequence

<400> SEQUENCE: 339

Lys Arg Leu Leu
1

<210> SEQ ID NO 340
<211> LENGTH: 4
<212> TYPE: PRT
<213> ORGANISM: Artificial sequence
<220> FEATURE:
<223> OTHER INFORMATION: synthetic sequence

<400> SEQUENCE: 340

Arg Arg Phe Ala
1

<210> SEQ ID NO 341
<211> LENGTH: 4
<212> TYPE: PRT

<213> ORGANISM: Artificial sequence
<220> FEATURE:
<223> OTHER INFORMATION: synthetic sequence

<400> SEQUENCE: 341

Arg His Phe Ala
1

<210> SEQ ID NO 342
<211> LENGTH: 4
<212> TYPE: PRT
<213> ORGANISM: Artificial sequence
<220> FEATURE:
<223> OTHER INFORMATION: synthetic sequence

<400> SEQUENCE: 342

Arg Arg Ile Pro
1

<210> SEQ ID NO 343
<211> LENGTH: 4
<212> TYPE: PRT
<213> ORGANISM: Artificial sequence
<220> FEATURE:
<223> OTHER INFORMATION: synthetic sequence

<400> SEQUENCE: 343

His Arg Phe Phe
1

<210> SEQ ID NO 344
<211> LENGTH: 4
<212> TYPE: PRT
<213> ORGANISM: Artificial sequence
<220> FEATURE:
<223> OTHER INFORMATION: synthetic sequence

<400> SEQUENCE: 344

Asn Arg Phe Ala
1

<210> SEQ ID NO 345
<211> LENGTH: 4
<212> TYPE: PRT
<213> ORGANISM: Artificial sequence
<220> FEATURE:
<223> OTHER INFORMATION: synthetic sequence

<400> SEQUENCE: 345

Arg Arg Ala Asp
1

<210> SEQ ID NO 346
<211> LENGTH: 4
<212> TYPE: PRT
<213> ORGANISM: Artificial sequence
<220> FEATURE:
<223> OTHER INFORMATION: synthetic sequence

<400> SEQUENCE: 346

Arg Trp Phe Lys
1

<210> SEQ ID NO 347
<211> LENGTH: 4
<212> TYPE: PRT
<213> ORGANISM: Artificial sequence
<220> FEATURE:
<223> OTHER INFORMATION: synthetic sequence

<400> SEQUENCE: 347

Arg Phe Trp Lys
1

<210> SEQ ID NO 348
<211> LENGTH: 4
<212> TYPE: PRT
<213> ORGANISM: Artificial sequence
<220> FEATURE:
<223> OTHER INFORMATION: synthetic sequence

<400> SEQUENCE: 348

His His Phe Phe
1

<210> SEQ ID NO 349
<211> LENGTH: 4
<212> TYPE: PRT
<213> ORGANISM: Artificial sequence
<220> FEATURE:
<223> OTHER INFORMATION: synthetic sequence

<400> SEQUENCE: 349

Arg Asn Phe Ala
1

<210> SEQ ID NO 350
<211> LENGTH: 4
<212> TYPE: PRT
<213> ORGANISM: Artificial sequence
<220> FEATURE:
<223> OTHER INFORMATION: synthetic sequence

<400> SEQUENCE: 350

Arg Gln Phe Ala
1

<210> SEQ ID NO 351
<211> LENGTH: 4
<212> TYPE: PRT
<213> ORGANISM: Artificial sequence
<220> FEATURE:
<223> OTHER INFORMATION: synthetic sequence

<400> SEQUENCE: 351

Asn Arg Phe Phe
1

<210> SEQ ID NO 352
<211> LENGTH: 4
<212> TYPE: PRT
<213> ORGANISM: Artificial sequence
<220> FEATURE:
<223> OTHER INFORMATION: synthetic sequence

<400> SEQUENCE: 352

Gln Arg Met Met
1

<210> SEQ ID NO 353
<211> LENGTH: 4
<212> TYPE: PRT
<213> ORGANISM: Artificial sequence
<220> FEATURE:

<223> OTHER INFORMATION: synthetic sequence

<400> SEQUENCE: 353

Gln Arg Val Val
1

<210> SEQ ID NO 354
<211> LENGTH: 4
<212> TYPE: PRT
<213> ORGANISM: Artificial sequence
<220> FEATURE:
<223> OTHER INFORMATION: synthetic sequence

<400> SEQUENCE: 354

Arg Asn Phe Phe
1

<210> SEQ ID NO 355
<211> LENGTH: 4
<212> TYPE: PRT
<213> ORGANISM: Artificial sequence
<220> FEATURE:
<223> OTHER INFORMATION: synthetic sequence

<400> SEQUENCE: 355

Arg Arg Phe Met
1

<210> SEQ ID NO 356
<211> LENGTH: 4
<212> TYPE: PRT
<213> ORGANISM: Artificial sequence
<220> FEATURE:
<223> OTHER INFORMATION: synthetic sequence

<400> SEQUENCE: 356

Val Arg Met Arg
1

<210> SEQ ID NO 357
<211> LENGTH: 4
<212> TYPE: PRT
<213> ORGANISM: Artificial sequence
<220> FEATURE:
<223> OTHER INFORMATION: synthetic sequence

<400> SEQUENCE: 357

Arg Met Arg Leu
1

<210> SEQ ID NO 358
<211> LENGTH: 4
<212> TYPE: PRT
<213> ORGANISM: Artificial sequence
<220> FEATURE:
<223> OTHER INFORMATION: synthetic sequence

<400> SEQUENCE: 358

Arg Ala Glu Leu
1

<210> SEQ ID NO 359
<211> LENGTH: 4
<212> TYPE: PRT
<213> ORGANISM: Artificial sequence
<220> FEATURE:
<223> OTHER INFORMATION: synthetic sequence

<400> SEQUENCE: 359

Ala Glu Leu Gly
1

<210> SEQ ID NO 360
<211> LENGTH: 4
<212> TYPE: PRT
<213> ORGANISM: Artificial sequence
<220> FEATURE:
<223> OTHER INFORMATION: synthetic sequence

<400> SEQUENCE: 360

Trp Lys Phe Gly
1

<210> SEQ ID NO 361
<211> LENGTH: 4
<212> TYPE: PRT
<213> ORGANISM: Artificial sequence
<220> FEATURE:
<223> OTHER INFORMATION: synthetic sequence

<400> SEQUENCE: 361

Phe Trp Arg Trp
1

<210> SEQ ID NO 362
<211> LENGTH: 4
<212> TYPE: PRT
<213> ORGANISM: Artificial sequence
<220> FEATURE:
<223> OTHER INFORMATION: synthetic sequence

<400> SEQUENCE: 362

Ala Phe Trp Arg
1

<210> SEQ ID NO 363
<211> LENGTH: 4
<212> TYPE: PRT
<213> ORGANISM: Artificial sequence
<220> FEATURE:
<223> OTHER INFORMATION: synthetic sequence

<400> SEQUENCE: 363

Trp Phe Arg Phe
1

<210> SEQ ID NO 364
<211> LENGTH: 4
<212> TYPE: PRT
<213> ORGANISM: Artificial sequence
<220> FEATURE:
<223> OTHER INFORMATION: synthetic sequence

<400> SEQUENCE: 364

Ala Trp Phe Arg
1

<210> SEQ ID NO 365
<211> LENGTH: 4
<212> TYPE: PRT
<213> ORGANISM: Artificial sequence
<220> FEATURE:
<223> OTHER INFORMATION: synthetic sequence

<400> SEQUENCE: 365

Val Ala Val Arg
1

<210> SEQ ID NO 366
<211> LENGTH: 4
<212> TYPE: PRT
<213> ORGANISM: Artificial sequence
<220> FEATURE:
<223> OTHER INFORMATION: synthetic sequence

<400> SEQUENCE: 366

Phe Phe Arg Phe
1

<210> SEQ ID NO 367
<211> LENGTH: 4
<212> TYPE: PRT
<213> ORGANISM: Artificial sequence
<220> FEATURE:
<223> OTHER INFORMATION: synthetic sequence

<400> SEQUENCE: 367

Ala Phe Phe Arg
1

<210> SEQ ID NO 368
<211> LENGTH: 4
<212> TYPE: PRT
<213> ORGANISM: Artificial sequence
<220> FEATURE:
<223> OTHER INFORMATION: synthetic sequence

<400> SEQUENCE: 368

Arg Trp Phe Ala
1

<210> SEQ ID NO 369
<211> LENGTH: 4
<212> TYPE: PRT
<213> ORGANISM: Artificial sequence
<220> FEATURE:
<223> OTHER INFORMATION: synthetic sequence

<400> SEQUENCE: 369

Trp Arg Trp Phe
1

<210> SEQ ID NO 370
<211> LENGTH: 4
<212> TYPE: PRT
<213> ORGANISM: Artificial sequence
<220> FEATURE:
<223> OTHER INFORMATION: synthetic sequence

<400> SEQUENCE: 370

Arg Phe Trp Ala
1

<210> SEQ ID NO 371
<211> LENGTH: 4
<212> TYPE: PRT
<213> ORGANISM: Artificial sequence
<220> FEATURE:
<223> OTHER INFORMATION: synthetic sequence

<400> SEQUENCE: 371

Phe Arg Phe Trp
1

<210> SEQ ID NO 372
<211> LENGTH: 4
<212> TYPE: PRT
<213> ORGANISM: Artificial sequence
<220> FEATURE:
<223> OTHER INFORMATION: synthetic sequence

<400> SEQUENCE: 372

Val Arg Ile Trp
1

<210> SEQ ID NO 373
<211> LENGTH: 4
<212> TYPE: PRT
<213> ORGANISM: Artificial sequence
<220> FEATURE:
<223> OTHER INFORMATION: synthetic sequence

<400> SEQUENCE: 373

Arg Phe Phe Ala
1

<210> SEQ ID NO 374
<211> LENGTH: 4
<212> TYPE: PRT
<213> ORGANISM: Artificial sequence
<220> FEATURE:
<223> OTHER INFORMATION: synthetic sequence

<400> SEQUENCE: 374

Phe Arg Phe Phe
1

<210> SEQ ID NO 375
<211> LENGTH: 4
<212> TYPE: PRT
<213> ORGANISM: Artificial sequence
<220> FEATURE:
<223> OTHER INFORMATION: synthetic sequence

<400> SEQUENCE: 375

Phe Phe Lys Lys
1

<210> SEQ ID NO 376
<211> LENGTH: 4
<212> TYPE: PRT
<213> ORGANISM: Artificial sequence
<220> FEATURE:
<223> OTHER INFORMATION: synthetic sequence

<400> SEQUENCE: 376

Trp Trp Lys Lys
1

<210> SEQ ID NO 377
<211> LENGTH: 4
<212> TYPE: PRT
<213> ORGANISM: Artificial sequence
<220> FEATURE:
<223> OTHER INFORMATION: synthetic sequence

<400> SEQUENCE: 377

Phe Trp Lys Lys
1

<210> SEQ ID NO 378
<211> LENGTH: 4
<212> TYPE: PRT
<213> ORGANISM: Artificial sequence
<220> FEATURE:
<223> OTHER INFORMATION: synthetic sequence

<400> SEQUENCE: 378

Tyr Tyr Lys Lys
1

<210> SEQ ID NO 379
<211> LENGTH: 4
<212> TYPE: PRT
<213> ORGANISM: Artificial sequence
<220> FEATURE:
<223> OTHER INFORMATION: synthetic sequence

<400> SEQUENCE: 379

Ile Ile Lys Lys
1

<210> SEQ ID NO 380
<211> LENGTH: 4
<212> TYPE: PRT
<213> ORGANISM: Artificial sequence
<220> FEATURE:
<223> OTHER INFORMATION: synthetic sequence

<400> SEQUENCE: 380

Tyr Ile Lys Lys
1

<210> SEQ ID NO 381
<211> LENGTH: 4
<212> TYPE: PRT
<213> ORGANISM: Artificial sequence
<220> FEATURE:
<223> OTHER INFORMATION: synthetic sequence

<400> SEQUENCE: 381

Met Met Lys Lys
1

<210> SEQ ID NO 382
<211> LENGTH: 4
<212> TYPE: PRT
<213> ORGANISM: Artificial sequence
<220> FEATURE:
<223> OTHER INFORMATION: synthetic sequence

<400> SEQUENCE: 382

Leu Leu Lys Lys
1

<210> SEQ ID NO 383
<211> LENGTH: 4
<212> TYPE: PRT
<213> ORGANISM: Artificial sequence
<220> FEATURE:
<223> OTHER INFORMATION: synthetic sequence

<400> SEQUENCE: 383

Met Leu Lys Lys

1

<210> SEQ ID NO 384
<211> LENGTH: 4
<212> TYPE: PRT
<213> ORGANISM: Artificial sequence
<220> FEATURE:
<223> OTHER INFORMATION: synthetic sequence

<400> SEQUENCE: 384

Val Val Lys Lys
1

<210> SEQ ID NO 385
<211> LENGTH: 4
<212> TYPE: PRT
<213> ORGANISM: Artificial sequence
<220> FEATURE:
<223> OTHER INFORMATION: synthetic sequence

<400> SEQUENCE: 385

Ala Ala Lys Lys
1

<210> SEQ ID NO 386
<211> LENGTH: 4
<212> TYPE: PRT
<213> ORGANISM: Artificial sequence
<220> FEATURE:
<223> OTHER INFORMATION: synthetic sequence

<400> SEQUENCE: 386

Val Ala Lys Lys
1

<210> SEQ ID NO 387
<211> LENGTH: 4
<212> TYPE: PRT
<213> ORGANISM: Artificial sequence
<220> FEATURE:
<223> OTHER INFORMATION: synthetic sequence

<400> SEQUENCE: 387

Gly Gly Lys Lys
1

<210> SEQ ID NO 388
<211> LENGTH: 4
<212> TYPE: PRT
<213> ORGANISM: Artificial sequence
<220> FEATURE:
<223> OTHER INFORMATION: synthetic sequence

<400> SEQUENCE: 388

Thr Thr Lys Lys
1

<210> SEQ ID NO 389
<211> LENGTH: 4
<212> TYPE: PRT
<213> ORGANISM: Artificial sequence
<220> FEATURE:
<223> OTHER INFORMATION: synthetic sequence

<400> SEQUENCE: 389

Gly Thr Lys Lys
1

<210> SEQ ID NO 390
<211> LENGTH: 4
<212> TYPE: PRT
<213> ORGANISM: Artificial sequence
<220> FEATURE:
<223> OTHER INFORMATION: synthetic sequence

<400> SEQUENCE: 390

Ser Ser Lys Lys
1

<210> SEQ ID NO 391
<211> LENGTH: 4
<212> TYPE: PRT
<213> ORGANISM: Artificial sequence
<220> FEATURE:
<223> OTHER INFORMATION: synthetic sequence

<400> SEQUENCE: 391

Cys Cys Lys Lys
1

<210> SEQ ID NO 392
<211> LENGTH: 4
<212> TYPE: PRT
<213> ORGANISM: Artificial sequence
<220> FEATURE:
<223> OTHER INFORMATION: synthetic sequence

<400> SEQUENCE: 392

Ser Cys Lys Lys
1

<210> SEQ ID NO 393
<211> LENGTH: 4
<212> TYPE: PRT
<213> ORGANISM: Artificial sequence
<220> FEATURE:
<223> OTHER INFORMATION: synthetic sequence

<400> SEQUENCE: 393

Lys Lys Phe Phe
1

<210> SEQ ID NO 394
<211> LENGTH: 4
<212> TYPE: PRT
<213> ORGANISM: Artificial sequence
<220> FEATURE:
<223> OTHER INFORMATION: synthetic sequence

<400> SEQUENCE: 394

Lys Lys Trp Phe
1

<210> SEQ ID NO 395
<211> LENGTH: 4
<212> TYPE: PRT
<213> ORGANISM: Artificial sequence
<220> FEATURE:
<223> OTHER INFORMATION: synthetic sequence

<400> SEQUENCE: 395

Lys Lys Trp Trp
1

<210> SEQ ID NO 396
<211> LENGTH: 4
<212> TYPE: PRT
<213> ORGANISM: Artificial sequence
<220> FEATURE:
<223> OTHER INFORMATION: synthetic sequence

<400> SEQUENCE: 396

Lys Lys Tyr Tyr
1

<210> SEQ ID NO 397
<211> LENGTH: 4
<212> TYPE: PRT
<213> ORGANISM: Artificial sequence
<220> FEATURE:
<223> OTHER INFORMATION: synthetic sequence

<400> SEQUENCE: 397

Lys Lys Ile Tyr
1

<210> SEQ ID NO 398
<211> LENGTH: 4
<212> TYPE: PRT
<213> ORGANISM: Artificial sequence
<220> FEATURE:
<223> OTHER INFORMATION: synthetic sequence

<400> SEQUENCE: 398

Lys Lys Ile Ile
1

<210> SEQ ID NO 399
<211> LENGTH: 4
<212> TYPE: PRT
<213> ORGANISM: Artificial sequence
<220> FEATURE:
<223> OTHER INFORMATION: synthetic sequence

<400> SEQUENCE: 399

Lys Lys Met Met
1

<210> SEQ ID NO 400
<211> LENGTH: 4
<212> TYPE: PRT
<213> ORGANISM: Artificial sequence
<220> FEATURE:
<223> OTHER INFORMATION: synthetic sequence

<400> SEQUENCE: 400

Lys Lys Leu Met
1

<210> SEQ ID NO 401
<211> LENGTH: 4
<212> TYPE: PRT
<213> ORGANISM: Artificial sequence
<220> FEATURE:
<223> OTHER INFORMATION: synthetic sequence

<400> SEQUENCE: 401

Lys Lys Leu Leu
1

<210> SEQ ID NO 402
<211> LENGTH: 4
<212> TYPE: PRT
<213> ORGANISM: Artificial sequence
<220> FEATURE:
<223> OTHER INFORMATION: synthetic sequence

<400> SEQUENCE: 402

Lys Lys Val Val
1

<210> SEQ ID NO 403
<211> LENGTH: 4
<212> TYPE: PRT
<213> ORGANISM: Artificial sequence
<220> FEATURE:
<223> OTHER INFORMATION: synthetic sequence

<400> SEQUENCE: 403

Lys Lys Ala Val
1

<210> SEQ ID NO 404
<211> LENGTH: 4
<212> TYPE: PRT
<213> ORGANISM: Artificial sequence
<220> FEATURE:
<223> OTHER INFORMATION: synthetic sequence

<400> SEQUENCE: 404

Lys Lys Ala Ala
1

<210> SEQ ID NO 405
<211> LENGTH: 4
<212> TYPE: PRT
<213> ORGANISM: Artificial sequence
<220> FEATURE:
<223> OTHER INFORMATION: synthetic sequence

<400> SEQUENCE: 405

Lys Lys Gly Gly
1

<210> SEQ ID NO 406
<211> LENGTH: 4
<212> TYPE: PRT
<213> ORGANISM: Artificial sequence
<220> FEATURE:
<223> OTHER INFORMATION: synthetic sequence

<400> SEQUENCE: 406

Lys Lys Thr Gly
1

<210> SEQ ID NO 407
<211> LENGTH: 4
<212> TYPE: PRT
<213> ORGANISM: Artificial sequence
<220> FEATURE:
<223> OTHER INFORMATION: synthetic sequence

<400> SEQUENCE: 407

Lys Lys Thr Thr
1

<210> SEQ ID NO 408

<211> LENGTH: 4
<212> TYPE: PRT
<213> ORGANISM: Artificial sequence
<220> FEATURE:
<223> OTHER INFORMATION: synthetic sequence

<400> SEQUENCE: 408

Lys Lys Ser Ser
1

<210> SEQ ID NO 409
<211> LENGTH: 4
<212> TYPE: PRT
<213> ORGANISM: Artificial sequence
<220> FEATURE:
<223> OTHER INFORMATION: synthetic sequence

<400> SEQUENCE: 409

Lys Lys Cys Ser
1

<210> SEQ ID NO 410
<211> LENGTH: 4
<212> TYPE: PRT
<213> ORGANISM: Artificial sequence
<220> FEATURE:
<223> OTHER INFORMATION: synthetic sequence

<400> SEQUENCE: 410

Lys Lys Cys Cys
1

<210> SEQ ID NO 411
<211> LENGTH: 4
<212> TYPE: PRT
<213> ORGANISM: Artificial sequence
<220> FEATURE:
<223> OTHER INFORMATION: synthetic sequence

<400> SEQUENCE: 411

Phe Lys Phe Lys
1

<210> SEQ ID NO 412
<211> LENGTH: 4
<212> TYPE: PRT
<213> ORGANISM: Artificial sequence
<220> FEATURE:
<223> OTHER INFORMATION: synthetic sequence

<400> SEQUENCE: 412

Trp Lys Trp Lys
1

<210> SEQ ID NO 413
<211> LENGTH: 4
<212> TYPE: PRT
<213> ORGANISM: Artificial sequence
<220> FEATURE:
<223> OTHER INFORMATION: synthetic sequence

<400> SEQUENCE: 413

Tyr Lys Tyr Lys
1

<210> SEQ ID NO 414
<211> LENGTH: 4

<212> TYPE: PRT
<213> ORGANISM: Artificial sequence
<220> FEATURE:
<223> OTHER INFORMATION: synthetic sequence

<400> SEQUENCE: 414

Ile Lys Ile Lys
1

<210> SEQ ID NO 415
<211> LENGTH: 4
<212> TYPE: PRT
<213> ORGANISM: Artificial sequence
<220> FEATURE:
<223> OTHER INFORMATION: synthetic sequence

<400> SEQUENCE: 415

Met Lys Met Lys
1

<210> SEQ ID NO 416
<211> LENGTH: 4
<212> TYPE: PRT
<213> ORGANISM: Artificial sequence
<220> FEATURE:
<223> OTHER INFORMATION: synthetic sequence

<400> SEQUENCE: 416

Leu Lys Leu Lys
1

<210> SEQ ID NO 417
<211> LENGTH: 4
<212> TYPE: PRT
<213> ORGANISM: Artificial sequence
<220> FEATURE:
<223> OTHER INFORMATION: synthetic sequence

<400> SEQUENCE: 417

Val Lys Val Lys
1

<210> SEQ ID NO 418
<211> LENGTH: 4
<212> TYPE: PRT
<213> ORGANISM: Artificial sequence
<220> FEATURE:
<223> OTHER INFORMATION: synthetic sequence

<400> SEQUENCE: 418

Ala Lys Ala Lys
1

<210> SEQ ID NO 419
<211> LENGTH: 4
<212> TYPE: PRT
<213> ORGANISM: Artificial sequence
<220> FEATURE:
<223> OTHER INFORMATION: synthetic sequence

<400> SEQUENCE: 419

Gly Lys Gly Lys
1

<210> SEQ ID NO 420
<211> LENGTH: 4
<212> TYPE: PRT

<213> ORGANISM: Artificial sequence
<220> FEATURE:
<223> OTHER INFORMATION: synthetic sequence

<400> SEQUENCE: 420

Thr Lys Thr Lys
1

<210> SEQ ID NO 421
<211> LENGTH: 4
<212> TYPE: PRT
<213> ORGANISM: Artificial sequence
<220> FEATURE:
<223> OTHER INFORMATION: synthetic sequence

<400> SEQUENCE: 421

Ser Lys Ser Lys
1

<210> SEQ ID NO 422
<211> LENGTH: 4
<212> TYPE: PRT
<213> ORGANISM: Artificial sequence
<220> FEATURE:
<223> OTHER INFORMATION: synthetic sequence

<400> SEQUENCE: 422

Cys Lys Cys Lys
1

<210> SEQ ID NO 423
<211> LENGTH: 4
<212> TYPE: PRT
<213> ORGANISM: Artificial sequence
<220> FEATURE:
<223> OTHER INFORMATION: synthetic sequence

<400> SEQUENCE: 423

Lys Phe Lys Phe
1

<210> SEQ ID NO 424
<211> LENGTH: 4
<212> TYPE: PRT
<213> ORGANISM: Artificial sequence
<220> FEATURE:
<223> OTHER INFORMATION: synthetic sequence

<400> SEQUENCE: 424

Lys Trp Lys Trp
1

<210> SEQ ID NO 425
<211> LENGTH: 4
<212> TYPE: PRT
<213> ORGANISM: Artificial sequence
<220> FEATURE:
<223> OTHER INFORMATION: synthetic sequence

<400> SEQUENCE: 425

Lys Tyr Lys Tyr
1

<210> SEQ ID NO 426
<211> LENGTH: 4
<212> TYPE: PRT
<213> ORGANISM: Artificial sequence
<220> FEATURE:
<223> OTHER INFORMATION: synthetic sequence

<400> SEQUENCE: 426

Lys Ile Lys Ile
1

<210> SEQ ID NO 427
<211> LENGTH: 4
<212> TYPE: PRT
<213> ORGANISM: Artificial sequence
<220> FEATURE:
<223> OTHER INFORMATION: synthetic sequence

<400> SEQUENCE: 427

Lys Met Lys Met
1

<210> SEQ ID NO 428
<211> LENGTH: 4
<212> TYPE: PRT
<213> ORGANISM: Artificial sequence
<220> FEATURE:
<223> OTHER INFORMATION: synthetic sequence

<400> SEQUENCE: 428

Lys Leu Lys Leu
1

<210> SEQ ID NO 429
<211> LENGTH: 4
<212> TYPE: PRT
<213> ORGANISM: Artificial sequence
<220> FEATURE:
<223> OTHER INFORMATION: synthetic sequence

<400> SEQUENCE: 429

Lys Val Lys Val
1

<210> SEQ ID NO 430
<211> LENGTH: 4
<212> TYPE: PRT
<213> ORGANISM: Artificial sequence
<220> FEATURE:
<223> OTHER INFORMATION: synthetic sequence

<400> SEQUENCE: 430

Lys Ala Lys Ala
1

<210> SEQ ID NO 431
<211> LENGTH: 4
<212> TYPE: PRT
<213> ORGANISM: Artificial sequence
<220> FEATURE:
<223> OTHER INFORMATION: synthetic sequence

<400> SEQUENCE: 431

Lys Gly Lys Gly
1

<210> SEQ ID NO 432
<211> LENGTH: 4
<212> TYPE: PRT
<213> ORGANISM: Artificial sequence
<220> FEATURE:

<223> OTHER INFORMATION: synthetic sequence

<400> SEQUENCE: 432

Lys Thr Lys Thr
1

<210> SEQ ID NO 433
<211> LENGTH: 4
<212> TYPE: PRT
<213> ORGANISM: Artificial sequence
<220> FEATURE:
<223> OTHER INFORMATION: synthetic sequence

<400> SEQUENCE: 433

Lys Ser Lys Ser
1

<210> SEQ ID NO 434
<211> LENGTH: 4
<212> TYPE: PRT
<213> ORGANISM: Artificial sequence
<220> FEATURE:
<223> OTHER INFORMATION: synthetic sequence

<400> SEQUENCE: 434

Lys Cys Lys Cys
1

<210> SEQ ID NO 435
<211> LENGTH: 15
<212> TYPE: PRT
<213> ORGANISM: Artificial sequence
<220> FEATURE:
<223> OTHER INFORMATION: synthetic sequence

<400> SEQUENCE: 435

Asn Phe Gly Asp Leu Val Ser Ile Gln Ser Glu Ser Glu Lys Lys
1 5 10 15

<210> SEQ ID NO 436
<211> LENGTH: 15
<212> TYPE: PRT
<213> ORGANISM: Artificial sequence
<220> FEATURE:
<223> OTHER INFORMATION: synthetic sequence

<400> SEQUENCE: 436

Asn Asp Ala Gln Ser Ala Tyr Phe Ile Gly Leu Leu Ile Ser Leu
1 5 10 15

<210> SEQ ID NO 437
<211> LENGTH: 13
<212> TYPE: PRT
<213> ORGANISM: Artificial sequence
<220> FEATURE:
<223> OTHER INFORMATION: synthetic sequence

<400> SEQUENCE: 437

Ser Lys Glu Lys Glu Thr Met Asp Asn Ala Arg Ala Phe
1 5 10

<210> SEQ ID NO 438
<211> LENGTH: 16
<212> TYPE: PRT
<213> ORGANISM: Artificial sequence
<220> FEATURE:
<223> OTHER INFORMATION: synthetic sequence

<400> SEQUENCE: 438

Glu Asp Glu Asn Cys Val Thr Met Tyr Ser Asn Ser Gly Phe Trp Asn
1 5 10 15

<210> SEQ ID NO 439
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, and glycine
<220> FEATURE:
<221> NAME/KEY: MISC_FEATURE
<222> LOCATION: (3)..(4)
<223> OTHER INFORMATION: Xaa at positions 3 and 4 are each independently selected from lysine, arginine, histidine, aspartic acid, glutamic acid, asparagine and glutamine
<220> FEATURE:
<221> NAME/KEY: MISC_FEATURE
<222> LOCATION: (5)..(6)
<223> OTHER INFORMATION: Xaa at positions 5 and 6 are each independently selected from phenylalanine, tryptophan, alanine, valine, and glycine
<220> FEATURE:
<221> NAME/KEY: MISC_FEATURE
<222> LOCATION: (7)..(8)
<223> OTHER INFORMATION: Xaa at positions 7 and 8 are each independently selected from lysine, arginine, histidine, aspartic acid, glutamic acid, asparagine and glutamine
<220> FEATURE:
<221> NAME/KEY: MISC_FEATURE
<222> LOCATION: (9)..(10)
<223> OTHER INFORMATION: Xaa at positions 9 and 10 are each independently selected from phenylalanine, tryptophan, alanine, valine, and glycine

<400> SEQUENCE: 439

Xaa Xaa Xaa Xaa Xaa Xaa Xaa Xaa Xaa Xaa
1 5 10

<210> SEQ ID NO 440
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa at position 1 is selected from lysine, arginine, histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa at position 2 is selected from phenylalanine, tryptophan, alanine, valine, and glycine
<220> FEATURE:
<221> NAME/KEY: MISC_FEATURE
<222> LOCATION: (3)..(4)
<223> OTHER INFORMATION: Xaa at position 3 and 4 are each independently selected from lysine, arginine, histidine, aspartic acid, glutamic acid, asparagine and glutamine
<220> FEATURE:
<221> NAME/KEY: MISC_FEATURE
<222> LOCATION: (5)..(6)
<223> OTHER INFORMATION: Xaa at positions 5 and 6 are each independently selected from phenylalanine, tryptophan, alanine, valine, and glycine

```
<220> FEATURE:
<221> NAME/KEY: MISC_FEATURE
<222> LOCATION: (7)..(8)
<223> OTHER INFORMATION: Xaa at position 7 and 8 are each independently
      selected from lysine, arginine, histidine, aspartic acid, glutamic
      acid, asparagine and glutamine
<220> FEATURE:
<221> NAME/KEY: MISC_FEATURE
<222> LOCATION: (9)..(10)
<223> OTHER INFORMATION: Xaa at positions 9 and 10 are each
      independently selected from phenylalanine, tryptophan, alanine,
      valine, and glycine

<400> SEQUENCE: 440

Xaa Xaa Xaa Xaa Xaa Xaa Xaa Xaa Xaa Xaa
1               5                   10


<210> SEQ ID NO 441
<211> LENGTH: 10
<212> TYPE: PRT
<213> ORGANISM: Artificial sequence
<220> FEATURE:
<223> OTHER INFORMATION: synthetic sequence

<400> SEQUENCE: 441

Lys Phe Arg Lys Ala Phe Lys Arg Phe Phe
1               5                   10


<210> SEQ ID NO 442
<211> LENGTH: 10
<212> TYPE: PRT
<213> ORGANISM: Artificial sequence
<220> FEATURE:
<223> OTHER INFORMATION: synthetic sequence

<400> SEQUENCE: 442

Phe Phe Arg Lys Phe Ala Lys Arg Phe Lys
1               5                   10


<210> SEQ ID NO 443
<211> LENGTH: 10
<212> TYPE: PRT
<213> ORGANISM: Artificial sequence
<220> FEATURE:
<223> OTHER INFORMATION: synthetic sequence

<400> SEQUENCE: 443

Phe Phe Lys Lys Phe Phe Lys Lys Phe Lys
1               5                   10


<210> SEQ ID NO 444
<211> LENGTH: 10
<212> TYPE: PRT
<213> ORGANISM: Artificial sequence
<220> FEATURE:
<223> OTHER INFORMATION: synthetic sequence

<400> SEQUENCE: 444

Phe Phe Lys Lys Phe Phe Lys Lys Phe Lys
1               5                   10


<210> SEQ ID NO 445
<211> LENGTH: 10
<212> TYPE: PRT
<213> ORGANISM: Artificial sequence
<220> FEATURE:
<223> OTHER INFORMATION: synthetic sequence

<400> SEQUENCE: 445
```

Phe Phe Lys Lys Phe Phe Lys Lys Phe Lys
1 5 10

<210> SEQ ID NO 446
<211> LENGTH: 10
<212> TYPE: PRT
<213> ORGANISM: Artificial sequence
<220> FEATURE:
<223> OTHER INFORMATION: synthetic sequence

<400> SEQUENCE: 446

Lys Phe Arg Lys Ala Phe Lys Arg Phe Phe
1 5 10

<210> SEQ ID NO 447
<211> LENGTH: 10
<212> TYPE: PRT
<213> ORGANISM: Artificial sequence
<220> FEATURE:
<223> OTHER INFORMATION: synthetic sequence

<400> SEQUENCE: 447

Phe Phe Arg Lys Phe Ala Lys Arg Phe Lys
1 5 10

<210> SEQ ID NO 448
<211> LENGTH: 10
<212> TYPE: PRT
<213> ORGANISM: Artificial sequence
<220> FEATURE:
<223> OTHER INFORMATION: synthetic sequence

<400> SEQUENCE: 448

Phe Phe Lys Lys Phe Phe Lys Lys Phe Lys
1 5 10

<210> SEQ ID NO 449
<211> LENGTH: 10
<212> TYPE: PRT
<213> ORGANISM: Artificial sequence
<220> FEATURE:
<223> OTHER INFORMATION: synthetic sequence

<400> SEQUENCE: 449

Arg Trp Lys Phe Gly Gly Phe Lys Trp Arg
1 5 10

<210> SEQ ID NO 450
<211> LENGTH: 10
<212> TYPE: PRT
<213> ORGANISM: Artificial sequence
<220> FEATURE:
<223> OTHER INFORMATION: synthetic sequence

<400> SEQUENCE: 450

Phe Lys Trp Arg Gly Gly Arg Trp Lys Phe
1 5 10

<210> SEQ ID NO 451
<211> LENGTH: 10
<212> TYPE: PRT
<213> ORGANISM: Artificial sequence
<220> FEATURE:
<223> OTHER INFORMATION: synthetic sequence

<400> SEQUENCE: 451

```
Phe Trp Lys Arg Gly Gly Arg Lys Trp Phe
1               5                   10


<210> SEQ ID NO 452
<211> LENGTH: 6
<212> TYPE: PRT
<213> ORGANISM: Artificial sequence
<220> FEATURE:
<223> OTHER INFORMATION: synthetic sequence

<400> SEQUENCE: 452

Phe Trp Lys Arg Phe Val
1               5


<210> SEQ ID NO 453
<211> LENGTH: 6
<212> TYPE: PRT
<213> ORGANISM: Artificial sequence
<220> FEATURE:
<223> OTHER INFORMATION: synthetic sequence

<400> SEQUENCE: 453

Phe Val Arg Lys Trp Arg
1               5


<210> SEQ ID NO 454
<211> LENGTH: 5
<212> TYPE: PRT
<213> ORGANISM: Artificial sequence
<220> FEATURE:
<223> OTHER INFORMATION: synthetic sequence

<400> SEQUENCE: 454

Phe Ala Phe Ala Phe
1               5


<210> SEQ ID NO 455
<211> LENGTH: 10
<212> TYPE: PRT
<213> ORGANISM: Artificial sequence
<220> FEATURE:
<223> OTHER INFORMATION: synthetic sequence

<400> SEQUENCE: 455

Phe Trp Lys Arg Phe Val Arg Lys Trp Arg
1               5                   10


<210> SEQ ID NO 456
<211> LENGTH: 10
<212> TYPE: PRT
<213> ORGANISM: Artificial sequence
<220> FEATURE:
<223> OTHER INFORMATION: synthetic sequence

<400> SEQUENCE: 456

Phe Trp Lys Lys Phe Val Lys Lys Trp Lys
1               5                   10


<210> SEQ ID NO 457
<211> LENGTH: 10
<212> TYPE: PRT
<213> ORGANISM: Artificial sequence
<220> FEATURE:
<223> OTHER INFORMATION: synthetic sequence

<400> SEQUENCE: 457

Trp Trp His His Trp Trp His His Trp His
```

-continued 1 5 10

<210> SEQ ID NO 458
<211> LENGTH: 10
<212> TYPE: PRT
<213> ORGANISM: Artificial sequence
<220> FEATURE:
<223> OTHER INFORMATION: synthetic sequence

<400> SEQUENCE: 458

Trp Trp Arg His Trp Trp His Arg Trp Arg
1 5 10

<210> SEQ ID NO 459
<211> LENGTH: 10
<212> TYPE: PRT
<213> ORGANISM: Artificial sequence
<220> FEATURE:
<223> OTHER INFORMATION: synthetic sequence

<400> SEQUENCE: 459

Trp Trp Lys His Trp Trp His Lys Trp Lys
1 5 10

<210> SEQ ID NO 460
<211> LENGTH: 11
<212> TYPE: PRT
<213> ORGANISM: Artificial sequence
<220> FEATURE:
<223> OTHER INFORMATION: synthetic sequence

<400> SEQUENCE: 460

Gly Asp Arg Gly Ile Lys Gly His Arg Gly Phe
1 5 10

<210> SEQ ID NO 461
<211> LENGTH: 10
<212> TYPE: PRT
<213> ORGANISM: Artificial sequence
<220> FEATURE:
<223> OTHER INFORMATION: synthetic sequence

<400> SEQUENCE: 461

Leu Tyr Lys Lys Ile Ile Lys Lys Leu Leu
1 5 10

<210> SEQ ID NO 462
<211> LENGTH: 10
<212> TYPE: PRT
<213> ORGANISM: Artificial sequence
<220> FEATURE:
<223> OTHER INFORMATION: synthetic sequence

<400> SEQUENCE: 462

Phe Tyr Pro Asp Phe Phe Lys Lys Phe Phe
1 5 10

<210> SEQ ID NO 463
<211> LENGTH: 10
<212> TYPE: PRT
<213> ORGANISM: Artificial sequence
<220> FEATURE:
<223> OTHER INFORMATION: synthetic sequence

<400> SEQUENCE: 463

Phe Phe Arg Lys Ser Lys Glu Lys Ile Gly
1 5 10

<210> SEQ ID NO 464
<211> LENGTH: 10
<212> TYPE: PRT
<213> ORGANISM: Artificial sequence
<220> FEATURE:
<223> OTHER INFORMATION: synthetic sequence

<400> SEQUENCE: 464

Phe Phe Arg His Phe Ala Thr His Leu Asp
1 5 10

<210> SEQ ID NO 465
<211> LENGTH: 10
<212> TYPE: PRT
<213> ORGANISM: Artificial sequence
<220> FEATURE:
<223> OTHER INFORMATION: synthetic sequence

<400> SEQUENCE: 465

Glu Lys Leu Ser Ala Phe Arg Asn Phe Phe
1 5 10

<210> SEQ ID NO 466
<211> LENGTH: 10
<212> TYPE: PRT
<213> ORGANISM: Artificial sequence
<220> FEATURE:
<223> OTHER INFORMATION: synthetic sequence

<400> SEQUENCE: 466

Arg Trp Lys Phe Gly Gly Phe Lys Trp Arg
1 5 10

<210> SEQ ID NO 467
<211> LENGTH: 10
<212> TYPE: PRT
<213> ORGANISM: Artificial sequence
<220> FEATURE:
<223> OTHER INFORMATION: synthetic sequence

<400> SEQUENCE: 467

Phe Lys Trp Arg Gly Gly Arg Trp Lys Phe
1 5 10

<210> SEQ ID NO 468
<211> LENGTH: 10
<212> TYPE: PRT
<213> ORGANISM: Artificial sequence
<220> FEATURE:
<223> OTHER INFORMATION: synthetic sequence

<400> SEQUENCE: 468

Phe Trp Lys Arg Gly Gly Arg Lys Trp Phe
1 5 10

<210> SEQ ID NO 469
<211> LENGTH: 6
<212> TYPE: PRT
<213> ORGANISM: Artificial sequence
<220> FEATURE:
<223> OTHER INFORMATION: synthetic sequence

<400> SEQUENCE: 469

Phe Trp Lys Arg Phe Val
1 5

<210> SEQ ID NO 470
<211> LENGTH: 6
<212> TYPE: PRT
<213> ORGANISM: Artificial sequence
<220> FEATURE:
<223> OTHER INFORMATION: synthetic sequence

<400> SEQUENCE: 470

Phe Val Arg Lys Trp Arg
1               5

<210> SEQ ID NO 471
<211> LENGTH: 5
<212> TYPE: PRT
<213> ORGANISM: Artificial sequence
<220> FEATURE:
<223> OTHER INFORMATION: synthetic sequence

<400> SEQUENCE: 471

Phe Ala Phe Ala Phe
1               5

<210> SEQ ID NO 472
<211> LENGTH: 10
<212> TYPE: PRT
<213> ORGANISM: Artificial sequence
<220> FEATURE:
<223> OTHER INFORMATION: synthetic sequence

<400> SEQUENCE: 472

Phe Trp Lys Arg Phe Val Arg Lys Trp Arg
1               5                   10

<210> SEQ ID NO 473
<211> LENGTH: 10
<212> TYPE: PRT
<213> ORGANISM: Artificial sequence
<220> FEATURE:
<223> OTHER INFORMATION: synthetic sequence

<400> SEQUENCE: 473

Phe Trp Lys Lys Phe Val Lys Lys Trp Lys
1               5                   10

<210> SEQ ID NO 474
<211> LENGTH: 10
<212> TYPE: PRT
<213> ORGANISM: Artificial sequence
<220> FEATURE:
<223> OTHER INFORMATION: synthetic sequence

<400> SEQUENCE: 474

Trp Trp His His Trp Trp His His Trp His
1               5                   10

<210> SEQ ID NO 475
<211> LENGTH: 10
<212> TYPE: PRT
<213> ORGANISM: Artificial sequence
<220> FEATURE:
<223> OTHER INFORMATION: synthetic sequence

<400> SEQUENCE: 475

Trp Trp Arg His Trp Trp His Arg Trp Arg
1               5                   10

<210> SEQ ID NO 476
<211> LENGTH: 10
<212> TYPE: PRT
<213> ORGANISM: Artificial sequence
<220> FEATURE:
<223> OTHER INFORMATION: synthetic sequence

<400> SEQUENCE: 476

Trp Trp Lys His Trp Trp His Lys Trp Lys
1 5 10

<210> SEQ ID NO 477
<211> LENGTH: 10
<212> TYPE: PRT
<213> ORGANISM: Artificial sequence
<220> FEATURE:
<223> OTHER INFORMATION: synthetic sequence

<400> SEQUENCE: 477

Leu Tyr Lys Lys Ile Ile Lys Lys Leu Leu
1 5 10

<210> SEQ ID NO 478
<211> LENGTH: 10
<212> TYPE: PRT
<213> ORGANISM: Artificial sequence
<220> FEATURE:
<223> OTHER INFORMATION: synthetic sequence

<400> SEQUENCE: 478

Phe Tyr Pro Asp Phe Phe Lys Lys Phe Phe
1 5 10

<210> SEQ ID NO 479
<211> LENGTH: 10
<212> TYPE: PRT
<213> ORGANISM: Artificial sequence
<220> FEATURE:
<223> OTHER INFORMATION: synthetic sequence

<400> SEQUENCE: 479

Phe Phe Arg Lys Ser Lys Glu Lys Ile Gly
1 5 10

<210> SEQ ID NO 480
<211> LENGTH: 10
<212> TYPE: PRT
<213> ORGANISM: Artificial sequence
<220> FEATURE:
<223> OTHER INFORMATION: synthetic sequence

<400> SEQUENCE: 480

Phe Phe Arg His Phe Ala Thr His Leu Asp
1 5 10

<210> SEQ ID NO 481
<211> LENGTH: 10
<212> TYPE: PRT
<213> ORGANISM: Artificial sequence
<220> FEATURE:
<223> OTHER INFORMATION: synthetic sequence

<400> SEQUENCE: 481

Phe Phe Arg Lys Ser Lys Glu Lys Ile Gly
1 5 10

<210> SEQ ID NO 482

```
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (4)..(4)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (5)..(5)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (6)..(6)
<223> OTHER INFORMATION: Xaa is selected from phenylalanine, tryptophan,
      alanine, valine, leucine, isoleucine, methionine, tyrosine,
      threonine, serine, cysteine, proline, and glycine

<400> SEQUENCE: 482

Xaa Xaa Xaa Xaa Xaa Xaa
1               5


<210> SEQ ID NO 483
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (2)..(2)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (3)..(3)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (5)..(5)
<223> OTHER INFORMATION: Xaa is selected from phenylalanine, tryptophan,
      alanine, valine, leucine, isoleucine, methionine, tyrosine,
      threonine, serine, cysteine, proline, and glycine
```

<220> FEATURE:
<221> NAME/KEY: MISC_FEATURE
<222> LOCATION: (6)..(6)
<223> OTHER INFORMATION: Xaa is selected from lysine, arginine, histidine, aspartic acid, glutamic acid, asparagine and glutamine

<400> SEQUENCE: 483

Xaa Xaa Xaa Xaa Xaa Xaa
1               5

<210> SEQ ID NO 484
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (2)..(2)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(4)
<223> OTHER INFORMATION: Xaa at positions 3 and 4 are each independently selected from lysine, arginine, histidine, aspartic acid, glutamic acid, asparagine and glutamine
<220> FEATURE:
<221> NAME/KEY: MISC_FEATURE
<222> LOCATION: (5)..(6)
<223> OTHER INFORMATION: Xaa at positions 5 and 6 are each independently selected from phenylalanine, tryptophan, alanine, valine, leucine, isoleucine, methionine, tyrosine, threonine, serine, cysteine, proline, and glycine

<400> SEQUENCE: 484

Xaa Xaa Xaa Xaa Xaa Xaa
1               5

<210> SEQ ID NO 485
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(4)
<223> OTHER INFORMATION: Xaa at positions 3 and 4 are each independently selected from lysine, arginine, histidine, aspartic acid, glutamic acid, asparagine and glutamine
<220> FEATURE:
<221> NAME/KEY: MISC_FEATURE
<222> LOCATION: (5)..(5)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (6)..(6)
<223> OTHER INFORMATION: Xaa is selected from lysine, arginine, histidine, aspartic acid, glutamic acid, asparagine and glutamine

<400> SEQUENCE: 485

Xaa Xaa Xaa Xaa Xaa Xaa
1 5

<210> SEQ ID NO 486
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(4)
<223> OTHER INFORMATION: Xaa at positions 3 and 4 are each independently selected from lysine, arginine, histidine, aspartic acid, glutamic acid, asparagine and glutamine
<220> FEATURE:
<221> NAME/KEY: MISC_FEATURE
<222> LOCATION: (5)..(6)
<223> OTHER INFORMATION: Xaa at positions 5 and 6 are each independently selected from phenylalanine, tryptophan, alanine, valine, leucine, isoleucine, methionine, tyrosine, threonine, serine, cysteine, proline, and glycine

<400> SEQUENCE: 486

Xaa Xaa Xaa Xaa Xaa Xaa
1 5

<210> SEQ ID NO 487
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(5)
<223> OTHER INFORMATION: Xaa at positions 4 and 5 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (6)..(6)
<223> OTHER INFORMATION: Xaa is selected from lysine, arginine, histidine, aspartic acid, glutamic acid, asparagine and glutamine

<400> SEQUENCE: 487

Xaa Xaa Xaa Xaa Xaa Xaa 1 5

<210> SEQ ID NO 488
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(3)
<223> OTHER INFORMATION: Xaa at positions 2 and 3 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (5)..(6)
<223> OTHER INFORMATION: Xaa at positions 5 and 6 are each independently selected from phenylalanine, tryptophan, alanine, valine, leucine, isoleucine, methionine, tyrosine, threonine, serine, cysteine, proline, and glycine

<400> SEQUENCE: 488

Xaa Xaa Xaa Xaa Xaa Xaa
1 5

<210> SEQ ID NO 489
<211> LENGTH: 6
<212> TYPE: PRT
<213> ORGANISM: Artificial sequence
<220> FEATURE:
<223> OTHER INFORMATION: synthetic sequence

<400> SEQUENCE: 489

Ala Phe Lys Arg Phe Phe
1 5

<210> SEQ ID NO 490
<211> LENGTH: 6
<212> TYPE: PRT
<213> ORGANISM: Artificial sequence
<220> FEATURE:
<223> OTHER INFORMATION: synthetic sequence

<400> SEQUENCE: 490

Phe Phe Lys Lys Phe Phe
1 5

<210> SEQ ID NO 491
<211> LENGTH: 6
<212> TYPE: PRT
<213> ORGANISM: Artificial sequence
<220> FEATURE:
<223> OTHER INFORMATION: synthetic sequence

<400> SEQUENCE: 491

Phe Trp Lys Arg Phe Val
1 5

<210> SEQ ID NO 492
<211> LENGTH: 6
<212> TYPE: PRT
<213> ORGANISM: Artificial sequence
<220> FEATURE:
<223> OTHER INFORMATION: synthetic sequence

<400> SEQUENCE: 492

Trp Val Arg Arg Val Val
1 5

<210> SEQ ID NO 493
<211> LENGTH: 6
<212> TYPE: PRT
<213> ORGANISM: Artificial sequence
<220> FEATURE:
<223> OTHER INFORMATION: synthetic sequence

<400> SEQUENCE: 493

Ile Phe Lys Lys Ile Glu
1 5

<210> SEQ ID NO 494
<211> LENGTH: 6
<212> TYPE: PRT
<213> ORGANISM: Artificial sequence
<220> FEATURE:
<223> OTHER INFORMATION: synthetic sequence

<400> SEQUENCE: 494

Phe Leu Arg Asn Leu Val
1 5

<210> SEQ ID NO 495
<211> LENGTH: 6
<212> TYPE: PRT
<213> ORGANISM: Artificial sequence
<220> FEATURE:
<223> OTHER INFORMATION: synthetic sequence

<400> SEQUENCE: 495

Phe Leu His Ser Ala Lys
1 5

<210> SEQ ID NO 496
<211> LENGTH: 6
<212> TYPE: PRT
<213> ORGANISM: Artificial sequence
<220> FEATURE:
<223> OTHER INFORMATION: synthetic sequence

<400> SEQUENCE: 496

Phe Phe His His Ile Phe
1 5

<210> SEQ ID NO 497
<211> LENGTH: 6
<212> TYPE: PRT
<213> ORGANISM: Artificial sequence
<220> FEATURE:
<223> OTHER INFORMATION: synthetic sequence

<400> SEQUENCE: 497

Phe Phe Lys Lys Ala Ala
1 5

<210> SEQ ID NO 498

<211> LENGTH: 6
<212> TYPE: PRT
<213> ORGANISM: Artificial sequence
<220> FEATURE:
<223> OTHER INFORMATION: synthetic sequence

<400> SEQUENCE: 498

Ala Leu Lys Lys Val Phe
1               5

<210> SEQ ID NO 499
<211> LENGTH: 6
<212> TYPE: PRT
<213> ORGANISM: Artificial sequence
<220> FEATURE:
<223> OTHER INFORMATION: synthetic sequence

<400> SEQUENCE: 499

Leu Tyr Lys Lys Ile Ile
1               5

<210> SEQ ID NO 500
<211> LENGTH: 6
<212> TYPE: PRT
<213> ORGANISM: Artificial sequence
<220> FEATURE:
<223> OTHER INFORMATION: synthetic sequence

<400> SEQUENCE: 500

Leu Phe Arg Arg Ala Phe
1               5

<210> SEQ ID NO 501
<211> LENGTH: 6
<212> TYPE: PRT
<213> ORGANISM: Artificial sequence
<220> FEATURE:
<223> OTHER INFORMATION: synthetic sequence

<400> SEQUENCE: 501

Phe Leu Lys Arg Leu Leu
1               5

<210> SEQ ID NO 502
<211> LENGTH: 6
<212> TYPE: PRT
<213> ORGANISM: Artificial sequence
<220> FEATURE:
<223> OTHER INFORMATION: synthetic sequence

<400> SEQUENCE: 502

Phe Phe Arg Arg Phe Ala
1               5

<210> SEQ ID NO 503
<211> LENGTH: 6
<212> TYPE: PRT
<213> ORGANISM: Artificial sequence
<220> FEATURE:
<223> OTHER INFORMATION: synthetic sequence

<400> SEQUENCE: 503

Phe Phe Arg His Phe Ala
1               5

<210> SEQ ID NO 504
<211> LENGTH: 6

<212> TYPE: PRT
<213> ORGANISM: Artificial sequence
<220> FEATURE:
<223> OTHER INFORMATION: synthetic sequence

<400> SEQUENCE: 504

Ala Ile Arg Arg Ile Pro
1               5

<210> SEQ ID NO 505
<211> LENGTH: 6
<212> TYPE: PRT
<213> ORGANISM: Artificial sequence
<220> FEATURE:
<223> OTHER INFORMATION: synthetic sequence

<400> SEQUENCE: 505

Ala Phe His Arg Phe Phe
1               5

<210> SEQ ID NO 506
<211> LENGTH: 6
<212> TYPE: PRT
<213> ORGANISM: Artificial sequence
<220> FEATURE:
<223> OTHER INFORMATION: synthetic sequence

<400> SEQUENCE: 506

Phe Phe Asn Arg Phe Ala
1               5

<210> SEQ ID NO 507
<211> LENGTH: 6
<212> TYPE: PRT
<213> ORGANISM: Artificial sequence
<220> FEATURE:
<223> OTHER INFORMATION: synthetic sequence

<400> SEQUENCE: 507

Ala Phe Lys Arg Phe Phe
1               5

<210> SEQ ID NO 508
<211> LENGTH: 6
<212> TYPE: PRT
<213> ORGANISM: Artificial sequence
<220> FEATURE:
<223> OTHER INFORMATION: synthetic sequence

<400> SEQUENCE: 508

Ala Phe Lys Arg Phe Phe
1               5

<210> SEQ ID NO 509
<211> LENGTH: 6
<212> TYPE: PRT
<213> ORGANISM: Artificial sequence
<220> FEATURE:
<223> OTHER INFORMATION: synthetic sequence

<400> SEQUENCE: 509

Ile Val Arg Arg Ala Asp
1               5

<210> SEQ ID NO 510
<211> LENGTH: 6
<212> TYPE: PRT

<213> ORGANISM: Artificial sequence
<220> FEATURE:
<223> OTHER INFORMATION: synthetic sequence

<400> SEQUENCE: 510

Phe Trp Arg Trp Phe Lys
1 5

<210> SEQ ID NO 511
<211> LENGTH: 6
<212> TYPE: PRT
<213> ORGANISM: Artificial sequence
<220> FEATURE:
<223> OTHER INFORMATION: synthetic sequence

<400> SEQUENCE: 511

Lys Phe Trp Arg Trp Phe
1 5

<210> SEQ ID NO 512
<211> LENGTH: 6
<212> TYPE: PRT
<213> ORGANISM: Artificial sequence
<220> FEATURE:
<223> OTHER INFORMATION: synthetic sequence

<400> SEQUENCE: 512

Trp Phe Arg Phe Trp Lys
1 5

<210> SEQ ID NO 513
<211> LENGTH: 6
<212> TYPE: PRT
<213> ORGANISM: Artificial sequence
<220> FEATURE:
<223> OTHER INFORMATION: synthetic sequence

<400> SEQUENCE: 513

Lys Trp Phe Arg Phe Trp
1 5

<210> SEQ ID NO 514
<211> LENGTH: 6
<212> TYPE: PRT
<213> ORGANISM: Artificial sequence
<220> FEATURE:
<223> OTHER INFORMATION: synthetic sequence

<400> SEQUENCE: 514

Ala Phe His His Phe Phe
1 5

<210> SEQ ID NO 515
<211> LENGTH: 6
<212> TYPE: PRT
<213> ORGANISM: Artificial sequence
<220> FEATURE:
<223> OTHER INFORMATION: synthetic sequence

<400> SEQUENCE: 515

Phe Phe Arg Asn Phe Ala
1 5

<210> SEQ ID NO 516
<211> LENGTH: 6
<212> TYPE: PRT
<213> ORGANISM: Artificial sequence
<220> FEATURE:
<223> OTHER INFORMATION: synthetic sequence

<400> SEQUENCE: 516

Ala Phe His Arg Phe Phe
1 5

<210> SEQ ID NO 517
<211> LENGTH: 6
<212> TYPE: PRT
<213> ORGANISM: Artificial sequence
<220> FEATURE:
<223> OTHER INFORMATION: synthetic sequence

<400> SEQUENCE: 517

Phe Phe Arg Gln Phe Ala
1 5

<210> SEQ ID NO 518
<211> LENGTH: 6
<212> TYPE: PRT
<213> ORGANISM: Artificial sequence
<220> FEATURE:
<223> OTHER INFORMATION: synthetic sequence

<400> SEQUENCE: 518

Ala Phe Asn Arg Phe Phe
1 5

<210> SEQ ID NO 519
<211> LENGTH: 6
<212> TYPE: PRT
<213> ORGANISM: Artificial sequence
<220> FEATURE:
<223> OTHER INFORMATION: synthetic sequence

<400> SEQUENCE: 519

Trp Ile Gln Arg Met Met
1 5

<210> SEQ ID NO 520
<211> LENGTH: 6
<212> TYPE: PRT
<213> ORGANISM: Artificial sequence
<220> FEATURE:
<223> OTHER INFORMATION: synthetic sequence

<400> SEQUENCE: 520

Trp Val Gln Arg Val Val
1 5

<210> SEQ ID NO 521
<211> LENGTH: 6
<212> TYPE: PRT
<213> ORGANISM: Artificial sequence
<220> FEATURE:
<223> OTHER INFORMATION: synthetic sequence

<400> SEQUENCE: 521

Ala Phe Arg Asn Phe Phe
1 5

<210> SEQ ID NO 522
<211> LENGTH: 6
<212> TYPE: PRT
<213> ORGANISM: Artificial sequence
<220> FEATURE:

<223> OTHER INFORMATION: synthetic sequence

<400> SEQUENCE: 522

Thr Leu Arg Arg Phe Met
1 5

<210> SEQ ID NO 523
<211> LENGTH: 6
<212> TYPE: PRT
<213> ORGANISM: Artificial sequence
<220> FEATURE:
<223> OTHER INFORMATION: synthetic sequence

<400> SEQUENCE: 523

Asp Val Arg Met Arg Leu
1 5

<210> SEQ ID NO 524
<211> LENGTH: 6
<212> TYPE: PRT
<213> ORGANISM: Artificial sequence
<220> FEATURE:
<223> OTHER INFORMATION: synthetic sequence

<400> SEQUENCE: 524

Arg Arg Ala Glu Leu Gly
1 5

<210> SEQ ID NO 525
<211> LENGTH: 6
<212> TYPE: PRT
<213> ORGANISM: Artificial sequence
<220> FEATURE:
<223> OTHER INFORMATION: synthetic sequence

<400> SEQUENCE: 525

Phe Trp Arg Trp Phe Ala
1 5

<210> SEQ ID NO 526
<211> LENGTH: 6
<212> TYPE: PRT
<213> ORGANISM: Artificial sequence
<220> FEATURE:
<223> OTHER INFORMATION: synthetic sequence

<400> SEQUENCE: 526

Ala Phe Trp Arg Trp Phe
1 5

<210> SEQ ID NO 527
<211> LENGTH: 6
<212> TYPE: PRT
<213> ORGANISM: Artificial sequence
<220> FEATURE:
<223> OTHER INFORMATION: synthetic sequence

<400> SEQUENCE: 527

Trp Phe Arg Phe Trp Ala
1 5

<210> SEQ ID NO 528
<211> LENGTH: 6
<212> TYPE: PRT
<213> ORGANISM: Artificial sequence
<220> FEATURE:
<223> OTHER INFORMATION: synthetic sequence

<400> SEQUENCE: 528

Ala Trp Phe Arg Phe Trp
1               5

<210> SEQ ID NO 529
<211> LENGTH: 6
<212> TYPE: PRT
<213> ORGANISM: Artificial sequence
<220> FEATURE:
<223> OTHER INFORMATION: synthetic sequence

<400> SEQUENCE: 529

Val Ala Val Arg Ile Trp
1               5

<210> SEQ ID NO 530
<211> LENGTH: 6
<212> TYPE: PRT
<213> ORGANISM: Artificial sequence
<220> FEATURE:
<223> OTHER INFORMATION: synthetic sequence

<400> SEQUENCE: 530

Phe Phe Arg Phe Phe Ala
1               5

<210> SEQ ID NO 531
<211> LENGTH: 6
<212> TYPE: PRT
<213> ORGANISM: Artificial sequence
<220> FEATURE:
<223> OTHER INFORMATION: synthetic sequence

<400> SEQUENCE: 531

Ala Phe Phe Arg Phe Phe
1               5

<210> SEQ ID NO 532
<211> LENGTH: 6
<212> TYPE: PRT
<213> ORGANISM: Artificial sequence
<220> FEATURE:
<223> OTHER INFORMATION: synthetic sequence

<400> SEQUENCE: 532

Phe Phe Lys Lys Phe Phe
1               5

<210> SEQ ID NO 533
<211> LENGTH: 6
<212> TYPE: PRT
<213> ORGANISM: Artificial sequence
<220> FEATURE:
<223> OTHER INFORMATION: synthetic sequence

<400> SEQUENCE: 533

Trp Trp Lys Lys Phe Phe
1               5

<210> SEQ ID NO 534
<211> LENGTH: 6
<212> TYPE: PRT
<213> ORGANISM: Artificial sequence
<220> FEATURE:
<223> OTHER INFORMATION: synthetic sequence -continued

<400> SEQUENCE: 534

Phe Trp Lys Lys Trp Phe
1               5

<210> SEQ ID NO 535
<211> LENGTH: 6
<212> TYPE: PRT
<213> ORGANISM: Artificial sequence
<220> FEATURE:
<223> OTHER INFORMATION: synthetic sequence

<400> SEQUENCE: 535

Phe Phe Lys Lys Trp Trp
1               5

<210> SEQ ID NO 536
<211> LENGTH: 6
<212> TYPE: PRT
<213> ORGANISM: Artificial sequence
<220> FEATURE:
<223> OTHER INFORMATION: synthetic sequence

<400> SEQUENCE: 536

Trp Trp Lys Lys Trp Trp
1               5

<210> SEQ ID NO 537
<211> LENGTH: 6
<212> TYPE: PRT
<213> ORGANISM: Artificial sequence
<220> FEATURE:
<223> OTHER INFORMATION: synthetic sequence

<400> SEQUENCE: 537

Tyr Tyr Lys Lys Tyr Tyr
1               5

<210> SEQ ID NO 538
<211> LENGTH: 6
<212> TYPE: PRT
<213> ORGANISM: Artificial sequence
<220> FEATURE:
<223> OTHER INFORMATION: synthetic sequence

<400> SEQUENCE: 538

Ile Ile Lys Lys Tyr Tyr
1               5

<210> SEQ ID NO 539
<211> LENGTH: 6
<212> TYPE: PRT
<213> ORGANISM: Artificial sequence
<220> FEATURE:
<223> OTHER INFORMATION: synthetic sequence

<400> SEQUENCE: 539

Tyr Ile Lys Lys Ile Tyr
1               5

<210> SEQ ID NO 540
<211> LENGTH: 6
<212> TYPE: PRT
<213> ORGANISM: Artificial sequence
<220> FEATURE:
<223> OTHER INFORMATION: synthetic sequence

<400> SEQUENCE: 540

Tyr Tyr Lys Lys Ile Ile
1 5

<210> SEQ ID NO 541
<211> LENGTH: 6
<212> TYPE: PRT
<213> ORGANISM: Artificial sequence
<220> FEATURE:
<223> OTHER INFORMATION: synthetic sequence

<400> SEQUENCE: 541

Ile Ile Lys Lys Ile Ile
1 5

<210> SEQ ID NO 542
<211> LENGTH: 6
<212> TYPE: PRT
<213> ORGANISM: Artificial sequence
<220> FEATURE:
<223> OTHER INFORMATION: synthetic sequence

<400> SEQUENCE: 542

Met Met Lys Lys Met Met
1 5

<210> SEQ ID NO 543
<211> LENGTH: 6
<212> TYPE: PRT
<213> ORGANISM: Artificial sequence
<220> FEATURE:
<223> OTHER INFORMATION: synthetic sequence

<400> SEQUENCE: 543

Leu Leu Lys Lys Met Met
1 5

<210> SEQ ID NO 544
<211> LENGTH: 6
<212> TYPE: PRT
<213> ORGANISM: Artificial sequence
<220> FEATURE:
<223> OTHER INFORMATION: synthetic sequence

<400> SEQUENCE: 544

Met Leu Lys Lys Leu Met
1 5

<210> SEQ ID NO 545
<211> LENGTH: 6
<212> TYPE: PRT
<213> ORGANISM: Artificial sequence
<220> FEATURE:
<223> OTHER INFORMATION: synthetic sequence

<400> SEQUENCE: 545

Met Met Lys Lys Leu Leu
1 5

<210> SEQ ID NO 546
<211> LENGTH: 6
<212> TYPE: PRT
<213> ORGANISM: Artificial sequence
<220> FEATURE:
<223> OTHER INFORMATION: synthetic sequence

<400> SEQUENCE: 546

-continued

Leu Leu Lys Lys Leu Leu
1 5

<210> SEQ ID NO 547
<211> LENGTH: 6
<212> TYPE: PRT
<213> ORGANISM: Artificial sequence
<220> FEATURE:
<223> OTHER INFORMATION: synthetic sequence

<400> SEQUENCE: 547

Val Val Lys Lys Val Val
1 5

<210> SEQ ID NO 548
<211> LENGTH: 6
<212> TYPE: PRT
<213> ORGANISM: Artificial sequence
<220> FEATURE:
<223> OTHER INFORMATION: synthetic sequence

<400> SEQUENCE: 548

Ala Ala Lys Lys Val Val
1 5

<210> SEQ ID NO 549
<211> LENGTH: 6
<212> TYPE: PRT
<213> ORGANISM: Artificial sequence
<220> FEATURE:
<223> OTHER INFORMATION: synthetic sequence

<400> SEQUENCE: 549

Val Ala Lys Lys Ala Val
1 5

<210> SEQ ID NO 550
<211> LENGTH: 6
<212> TYPE: PRT
<213> ORGANISM: Artificial sequence
<220> FEATURE:
<223> OTHER INFORMATION: synthetic sequence

<400> SEQUENCE: 550

Val Val Lys Lys Ala Ala
1 5

<210> SEQ ID NO 551
<211> LENGTH: 6
<212> TYPE: PRT
<213> ORGANISM: Artificial sequence
<220> FEATURE:
<223> OTHER INFORMATION: synthetic sequence

<400> SEQUENCE: 551

Ala Ala Lys Lys Ala Ala
1 5

<210> SEQ ID NO 552
<211> LENGTH: 6
<212> TYPE: PRT
<213> ORGANISM: Artificial sequence
<220> FEATURE:
<223> OTHER INFORMATION: synthetic sequence

<400> SEQUENCE: 552

Gly Gly Lys Lys Gly Gly 1 5

<210> SEQ ID NO 553
<211> LENGTH: 6
<212> TYPE: PRT
<213> ORGANISM: Artificial sequence
<220> FEATURE:
<223> OTHER INFORMATION: synthetic sequence

<400> SEQUENCE: 553

Thr Thr Lys Lys Gly Gly
1 5

<210> SEQ ID NO 554
<211> LENGTH: 6
<212> TYPE: PRT
<213> ORGANISM: Artificial sequence
<220> FEATURE:
<223> OTHER INFORMATION: synthetic sequence

<400> SEQUENCE: 554

Gly Thr Lys Lys Thr Gly
1 5

<210> SEQ ID NO 555
<211> LENGTH: 6
<212> TYPE: PRT
<213> ORGANISM: Artificial sequence
<220> FEATURE:
<223> OTHER INFORMATION: synthetic sequence

<400> SEQUENCE: 555

Gly Gly Lys Lys Thr Thr
1 5

<210> SEQ ID NO 556
<211> LENGTH: 6
<212> TYPE: PRT
<213> ORGANISM: Artificial sequence
<220> FEATURE:
<223> OTHER INFORMATION: synthetic sequence

<400> SEQUENCE: 556

Thr Thr Lys Lys Thr Thr
1 5

<210> SEQ ID NO 557
<211> LENGTH: 6
<212> TYPE: PRT
<213> ORGANISM: Artificial sequence
<220> FEATURE:
<223> OTHER INFORMATION: synthetic sequence

<400> SEQUENCE: 557

Ser Ser Lys Lys Ser Ser
1 5

<210> SEQ ID NO 558
<211> LENGTH: 6
<212> TYPE: PRT
<213> ORGANISM: Artificial sequence
<220> FEATURE:
<223> OTHER INFORMATION: synthetic sequence

<400> SEQUENCE: 558

Cys Cys Lys Lys Ser Ser
1 5

<210> SEQ ID NO 559
<211> LENGTH: 6
<212> TYPE: PRT
<213> ORGANISM: Artificial sequence
<220> FEATURE:
<223> OTHER INFORMATION: synthetic sequence

<400> SEQUENCE: 559

Ser Cys Lys Lys Cys Ser
1               5

<210> SEQ ID NO 560
<211> LENGTH: 6
<212> TYPE: PRT
<213> ORGANISM: Artificial sequence
<220> FEATURE:
<223> OTHER INFORMATION: synthetic sequence

<400> SEQUENCE: 560

Ser Ser Lys Lys Cys Cys
1               5

<210> SEQ ID NO 561
<211> LENGTH: 6
<212> TYPE: PRT
<213> ORGANISM: Artificial sequence
<220> FEATURE:
<223> OTHER INFORMATION: synthetic sequence

<400> SEQUENCE: 561

Cys Cys Lys Lys Cys Cys
1               5

<210> SEQ ID NO 562
<211> LENGTH: 6
<212> TYPE: PRT
<213> ORGANISM: Artificial sequence
<220> FEATURE:
<223> OTHER INFORMATION: synthetic sequence

<400> SEQUENCE: 562

Phe Lys Phe Lys Phe Lys
1               5

<210> SEQ ID NO 563
<211> LENGTH: 6
<212> TYPE: PRT
<213> ORGANISM: Artificial sequence
<220> FEATURE:
<223> OTHER INFORMATION: synthetic sequence

<400> SEQUENCE: 563

Trp Lys Trp Lys Trp Lys
1               5

<210> SEQ ID NO 564
<211> LENGTH: 6
<212> TYPE: PRT
<213> ORGANISM: Artificial sequence
<220> FEATURE:
<223> OTHER INFORMATION: synthetic sequence

<400> SEQUENCE: 564

Tyr Lys Tyr Lys Tyr Lys
1               5

```
<210> SEQ ID NO 565
<211> LENGTH: 6
<212> TYPE: PRT
<213> ORGANISM: Artificial sequence
<220> FEATURE:
<223> OTHER INFORMATION: synthetic sequence

<400> SEQUENCE: 565

Ile Lys Ile Lys Ile Lys
1               5


<210> SEQ ID NO 566
<211> LENGTH: 6
<212> TYPE: PRT
<213> ORGANISM: Artificial sequence
<220> FEATURE:
<223> OTHER INFORMATION: synthetic sequence

<400> SEQUENCE: 566

Met Lys Met Lys Met Lys
1               5


<210> SEQ ID NO 567
<211> LENGTH: 6
<212> TYPE: PRT
<213> ORGANISM: Artificial sequence
<220> FEATURE:
<223> OTHER INFORMATION: synthetic sequence

<400> SEQUENCE: 567

Leu Lys Leu Lys Leu Lys
1               5


<210> SEQ ID NO 568
<211> LENGTH: 6
<212> TYPE: PRT
<213> ORGANISM: Artificial sequence
<220> FEATURE:
<223> OTHER INFORMATION: synthetic sequence

<400> SEQUENCE: 568

Val Lys Val Lys Val Lys
1               5


<210> SEQ ID NO 569
<211> LENGTH: 6
<212> TYPE: PRT
<213> ORGANISM: Artificial sequence
<220> FEATURE:
<223> OTHER INFORMATION: synthetic sequence

<400> SEQUENCE: 569

Ala Lys Ala Lys Ala Lys
1               5


<210> SEQ ID NO 570
<211> LENGTH: 6
<212> TYPE: PRT
<213> ORGANISM: Artificial sequence
<220> FEATURE:
<223> OTHER INFORMATION: synthetic sequence

<400> SEQUENCE: 570

Gly Lys Gly Lys Gly Lys
1               5
```

<210> SEQ ID NO 571
<211> LENGTH: 6
<212> TYPE: PRT
<213> ORGANISM: Artificial sequence
<220> FEATURE:
<223> OTHER INFORMATION: synthetic sequence

<400> SEQUENCE: 571

Thr Lys Thr Lys Thr Lys
1               5

<210> SEQ ID NO 572
<211> LENGTH: 6
<212> TYPE: PRT
<213> ORGANISM: Artificial sequence
<220> FEATURE:
<223> OTHER INFORMATION: synthetic sequence

<400> SEQUENCE: 572

Ser Lys Ser Lys Ser Lys
1               5

<210> SEQ ID NO 573
<211> LENGTH: 6
<212> TYPE: PRT
<213> ORGANISM: Artificial sequence
<220> FEATURE:
<223> OTHER INFORMATION: synthetic sequence

<400> SEQUENCE: 573

Cys Lys Cys Lys Cys Lys
1               5

<210> SEQ ID NO 574
<211> LENGTH: 6
<212> TYPE: PRT
<213> ORGANISM: Artificial sequence
<220> FEATURE:
<223> OTHER INFORMATION: synthetic sequence

<400> SEQUENCE: 574

Lys Phe Lys Phe Lys Phe
1               5

<210> SEQ ID NO 575
<211> LENGTH: 6
<212> TYPE: PRT
<213> ORGANISM: Artificial sequence
<220> FEATURE:
<223> OTHER INFORMATION: synthetic sequence

<400> SEQUENCE: 575

Lys Trp Lys Trp Lys Trp
1               5

<210> SEQ ID NO 576
<211> LENGTH: 6
<212> TYPE: PRT
<213> ORGANISM: Artificial sequence
<220> FEATURE:
<223> OTHER INFORMATION: synthetic sequence

<400> SEQUENCE: 576

Lys Tyr Lys Tyr Lys Tyr
1               5

<210> SEQ ID NO 577

<211> LENGTH: 6
<212> TYPE: PRT
<213> ORGANISM: Artificial sequence
<220> FEATURE:
<223> OTHER INFORMATION: synthetic sequence

<400> SEQUENCE: 577

Lys Ile Lys Ile Lys Ile
1 5

<210> SEQ ID NO 578
<211> LENGTH: 6
<212> TYPE: PRT
<213> ORGANISM: Artificial sequence
<220> FEATURE:
<223> OTHER INFORMATION: synthetic sequence

<400> SEQUENCE: 578

Lys Met Lys Met Lys Met
1 5

<210> SEQ ID NO 579
<211> LENGTH: 6
<212> TYPE: PRT
<213> ORGANISM: Artificial sequence
<220> FEATURE:
<223> OTHER INFORMATION: synthetic sequence

<400> SEQUENCE: 579

Lys Leu Lys Leu Lys Leu
1 5

<210> SEQ ID NO 580
<211> LENGTH: 6
<212> TYPE: PRT
<213> ORGANISM: Artificial sequence
<220> FEATURE:
<223> OTHER INFORMATION: synthetic sequence

<400> SEQUENCE: 580

Lys Val Lys Val Lys Val
1 5

<210> SEQ ID NO 581
<211> LENGTH: 6
<212> TYPE: PRT
<213> ORGANISM: Artificial sequence
<220> FEATURE:
<223> OTHER INFORMATION: synthetic sequence

<400> SEQUENCE: 581

Lys Ala Lys Ala Lys Ala
1 5

<210> SEQ ID NO 582
<211> LENGTH: 6
<212> TYPE: PRT
<213> ORGANISM: Artificial sequence
<220> FEATURE:
<223> OTHER INFORMATION: synthetic sequence

<400> SEQUENCE: 582

Lys Gly Lys Gly Lys Gly
1 5

<210> SEQ ID NO 583
<211> LENGTH: 6

<212> TYPE: PRT
<213> ORGANISM: Artificial sequence
<220> FEATURE:
<223> OTHER INFORMATION: synthetic sequence

<400> SEQUENCE: 583

Lys Thr Lys Thr Lys Thr
1               5

<210> SEQ ID NO 584
<211> LENGTH: 6
<212> TYPE: PRT
<213> ORGANISM: Artificial sequence
<220> FEATURE:
<223> OTHER INFORMATION: synthetic sequence

<400> SEQUENCE: 584

Lys Ser Lys Ser Lys Ser
1               5

<210> SEQ ID NO 585
<211> LENGTH: 6
<212> TYPE: PRT
<213> ORGANISM: Artificial sequence
<220> FEATURE:
<223> OTHER INFORMATION: synthetic sequence

<400> SEQUENCE: 585

Lys Cys Lys Cys Lys Cys
1               5

<210> SEQ ID NO 586
<211> LENGTH: 6
<212> TYPE: PRT
<213> ORGANISM: Artificial sequence
<220> FEATURE:
<223> OTHER INFORMATION: synthetic sequence

<400> SEQUENCE: 586

Phe Phe His His Phe Phe
1               5

<210> SEQ ID NO 587
<211> LENGTH: 6
<212> TYPE: PRT
<213> ORGANISM: Artificial sequence
<220> FEATURE:
<223> OTHER INFORMATION: synthetic sequence

<400> SEQUENCE: 587

Phe Phe Arg His Phe Phe
1               5

<210> SEQ ID NO 588
<211> LENGTH: 6
<212> TYPE: PRT
<213> ORGANISM: Artificial sequence
<220> FEATURE:
<223> OTHER INFORMATION: synthetic sequence

<400> SEQUENCE: 588

Phe Phe Lys Asn Phe Phe
1               5

<210> SEQ ID NO 589
<211> LENGTH: 6
<212> TYPE: PRT

<213> ORGANISM: Artificial sequence
<220> FEATURE:
<223> OTHER INFORMATION: synthetic sequence

<400> SEQUENCE: 589

Leu Trp His His Trp Pro
1               5

<210> SEQ ID NO 590
<211> LENGTH: 6
<212> TYPE: PRT
<213> ORGANISM: Artificial sequence
<220> FEATURE:
<223> OTHER INFORMATION: synthetic sequence

<400> SEQUENCE: 590

Phe Phe Arg His Phe Ala
1               5

<210> SEQ ID NO 591
<211> LENGTH: 6
<212> TYPE: PRT
<213> ORGANISM: Artificial sequence
<220> FEATURE:
<223> OTHER INFORMATION: synthetic sequence

<400> SEQUENCE: 591

Phe Phe Arg Asn Phe Phe
1               5

<210> SEQ ID NO 592
<211> LENGTH: 6
<212> TYPE: PRT
<213> ORGANISM: Artificial sequence
<220> FEATURE:
<223> OTHER INFORMATION: synthetic sequence

<400> SEQUENCE: 592

Phe Phe His His Ile Phe
1               5

<210> SEQ ID NO 593
<211> LENGTH: 6
<212> TYPE: PRT
<213> ORGANISM: Artificial sequence
<220> FEATURE:
<223> OTHER INFORMATION: synthetic sequence

<400> SEQUENCE: 593

Phe Phe Asn Gly Tyr Pro
1               5

<210> SEQ ID NO 594
<211> LENGTH: 6
<212> TYPE: PRT
<213> ORGANISM: Artificial sequence
<220> FEATURE:
<223> OTHER INFORMATION: synthetic sequence

<400> SEQUENCE: 594

Phe Phe His Asn Phe Phe
1               5

<210> SEQ ID NO 595
<211> LENGTH: 6
<212> TYPE: PRT
<213> ORGANISM: Artificial sequence
<220> FEATURE:
<223> OTHER INFORMATION: synthetic sequence

<400> SEQUENCE: 595

Phe Phe Gln His Phe Phe
1 5

<210> SEQ ID NO 596
<211> LENGTH: 6
<212> TYPE: PRT
<213> ORGANISM: Artificial sequence
<220> FEATURE:
<223> OTHER INFORMATION: synthetic sequence

<400> SEQUENCE: 596

Phe Phe Arg Gln Phe Phe
1 5

<210> SEQ ID NO 597
<211> LENGTH: 6
<212> TYPE: PRT
<213> ORGANISM: Artificial sequence
<220> FEATURE:
<223> OTHER INFORMATION: synthetic sequence

<400> SEQUENCE: 597

Trp Phe Arg Asp Val Phe
1 5

<210> SEQ ID NO 598
<211> LENGTH: 6
<212> TYPE: PRT
<213> ORGANISM: Artificial sequence
<220> FEATURE:
<223> OTHER INFORMATION: synthetic sequence

<400> SEQUENCE: 598

Trp Phe Arg Phe Trp Ala
1 5

<210> SEQ ID NO 599
<211> LENGTH: 6
<212> TYPE: PRT
<213> ORGANISM: Artificial sequence
<220> FEATURE:
<223> OTHER INFORMATION: synthetic sequence

<400> SEQUENCE: 599

Phe Phe Asn His Phe Phe
1 5

<210> SEQ ID NO 600
<211> LENGTH: 6
<212> TYPE: PRT
<213> ORGANISM: Artificial sequence
<220> FEATURE:
<223> OTHER INFORMATION: synthetic sequence

<400> SEQUENCE: 600

Leu Phe His Thr Leu Phe
1 5

<210> SEQ ID NO 601
<211> LENGTH: 6
<212> TYPE: PRT
<213> ORGANISM: Artificial sequence
<220> FEATURE:

<223> OTHER INFORMATION: synthetic sequence

<400> SEQUENCE: 601

Ala Trp Phe Arg Phe Trp
1 5

<210> SEQ ID NO 602
<211> LENGTH: 6
<212> TYPE: PRT
<213> ORGANISM: Artificial sequence
<220> FEATURE:
<223> OTHER INFORMATION: synthetic sequence

<400> SEQUENCE: 602

Phe Leu His His Met Val
1 5

<210> SEQ ID NO 603
<211> LENGTH: 6
<212> TYPE: PRT
<213> ORGANISM: Artificial sequence
<220> FEATURE:
<223> OTHER INFORMATION: synthetic sequence

<400> SEQUENCE: 603

Phe Phe His Gln Phe Phe
1 5

<210> SEQ ID NO 604
<211> LENGTH: 6
<212> TYPE: PRT
<213> ORGANISM: Artificial sequence
<220> FEATURE:
<223> OTHER INFORMATION: synthetic sequence

<400> SEQUENCE: 604

Phe Trp Arg Trp Phe Ala
1 5

<210> SEQ ID NO 605
<211> LENGTH: 6
<212> TYPE: PRT
<213> ORGANISM: Artificial sequence
<220> FEATURE:
<223> OTHER INFORMATION: synthetic sequence

<400> SEQUENCE: 605

Ala Phe His Arg Phe Phe
1 5

<210> SEQ ID NO 606
<211> LENGTH: 6
<212> TYPE: PRT
<213> ORGANISM: Artificial sequence
<220> FEATURE:
<223> OTHER INFORMATION: synthetic sequence

<400> SEQUENCE: 606

Ala Phe His Arg Phe Phe
1 5

<210> SEQ ID NO 607
<211> LENGTH: 6
<212> TYPE: PRT
<213> ORGANISM: Artificial sequence
<220> FEATURE:
<223> OTHER INFORMATION: synthetic sequence

<400> SEQUENCE: 607

Phe Phe Thr Gly Phe Phe
1               5

<210> SEQ ID NO 608
<211> LENGTH: 6
<212> TYPE: PRT
<213> ORGANISM: Artificial sequence
<220> FEATURE:
<223> OTHER INFORMATION: synthetic sequence

<400> SEQUENCE: 608

Phe Phe Thr Ser Phe Phe
1               5

<210> SEQ ID NO 609
<211> LENGTH: 6
<212> TYPE: PRT
<213> ORGANISM: Artificial sequence
<220> FEATURE:
<223> OTHER INFORMATION: synthetic sequence

<400> SEQUENCE: 609

Phe Phe Lys His Phe Phe
1               5

<210> SEQ ID NO 610
<211> LENGTH: 6
<212> TYPE: PRT
<213> ORGANISM: Artificial sequence
<220> FEATURE:
<223> OTHER INFORMATION: synthetic sequence

<400> SEQUENCE: 610

Phe Phe Gln Asn Phe Phe
1               5

<210> SEQ ID NO 611
<211> LENGTH: 6
<212> TYPE: PRT
<213> ORGANISM: Artificial sequence
<220> FEATURE:
<223> OTHER INFORMATION: synthetic sequence

<400> SEQUENCE: 611

Tyr Phe Thr Arg Leu Phe
1               5

<210> SEQ ID NO 612
<211> LENGTH: 6
<212> TYPE: PRT
<213> ORGANISM: Artificial sequence
<220> FEATURE:
<223> OTHER INFORMATION: synthetic sequence

<400> SEQUENCE: 612

Phe Phe Lys Gln Phe Phe
1               5

<210> SEQ ID NO 613
<211> LENGTH: 6
<212> TYPE: PRT
<213> ORGANISM: Artificial sequence
<220> FEATURE:
<223> OTHER INFORMATION: synthetic sequence

<400> SEQUENCE: 613

Phe Phe Ser Thr Phe Phe
1               5

<210> SEQ ID NO 614
<211> LENGTH: 6
<212> TYPE: PRT
<213> ORGANISM: Artificial sequence
<220> FEATURE:
<223> OTHER INFORMATION: synthetic sequence

<400> SEQUENCE: 614

Phe Leu Arg Asn Leu Val
1               5

<210> SEQ ID NO 615
<211> LENGTH: 6
<212> TYPE: PRT
<213> ORGANISM: Artificial sequence
<220> FEATURE:
<223> OTHER INFORMATION: synthetic sequence

<400> SEQUENCE: 615

Phe Phe Gln Asn Ile Phe
1               5

<210> SEQ ID NO 616
<211> LENGTH: 6
<212> TYPE: PRT
<213> ORGANISM: Artificial sequence
<220> FEATURE:
<223> OTHER INFORMATION: synthetic sequence

<400> SEQUENCE: 616

Phe Phe Asn Asn Phe Phe
1               5

<210> SEQ ID NO 617
<211> LENGTH: 6
<212> TYPE: PRT
<213> ORGANISM: Artificial sequence
<220> FEATURE:
<223> OTHER INFORMATION: synthetic sequence

<400> SEQUENCE: 617

Phe Phe Gly Thr Phe Phe
1               5

<210> SEQ ID NO 618
<211> LENGTH: 6
<212> TYPE: PRT
<213> ORGANISM: Artificial sequence
<220> FEATURE:
<223> OTHER INFORMATION: synthetic sequence

<400> SEQUENCE: 618

Ser Trp His Arg Leu Phe
1               5

<210> SEQ ID NO 619
<211> LENGTH: 6
<212> TYPE: PRT
<213> ORGANISM: Artificial sequence
<220> FEATURE:
<223> OTHER INFORMATION: synthetic sequence

<400> SEQUENCE: 619

Ile Met Asn His Met Ile
1 5

<210> SEQ ID NO 620
<211> LENGTH: 6
<212> TYPE: PRT
<213> ORGANISM: Artificial sequence
<220> FEATURE:
<223> OTHER INFORMATION: synthetic sequence

<400> SEQUENCE: 620

Phe Phe Gln Lys Phe Phe
1 5

<210> SEQ ID NO 621
<211> LENGTH: 6
<212> TYPE: PRT
<213> ORGANISM: Artificial sequence
<220> FEATURE:
<223> OTHER INFORMATION: synthetic sequence

<400> SEQUENCE: 621

Phe Phe Gly Ser Phe Phe
1 5

<210> SEQ ID NO 622
<211> LENGTH: 6
<212> TYPE: PRT
<213> ORGANISM: Artificial sequence
<220> FEATURE:
<223> OTHER INFORMATION: synthetic sequence

<400> SEQUENCE: 622

Leu Phe Arg Asn Tyr Ala
1 5

<210> SEQ ID NO 623
<211> LENGTH: 6
<212> TYPE: PRT
<213> ORGANISM: Artificial sequence
<220> FEATURE:
<223> OTHER INFORMATION: synthetic sequence

<400> SEQUENCE: 623

Lys Trp Phe Arg Phe Trp
1 5

<210> SEQ ID NO 624
<211> LENGTH: 6
<212> TYPE: PRT
<213> ORGANISM: Artificial sequence
<220> FEATURE:
<223> OTHER INFORMATION: synthetic sequence

<400> SEQUENCE: 624

Phe Phe Gly Gly Phe Phe
1 5

<210> SEQ ID NO 625
<211> LENGTH: 6
<212> TYPE: PRT
<213> ORGANISM: Artificial sequence
<220> FEATURE:
<223> OTHER INFORMATION: synthetic sequence

<400> SEQUENCE: 625

Ile Phe Ser Asp Met Phe
1 5

<210> SEQ ID NO 626
<211> LENGTH: 6
<212> TYPE: PRT
<213> ORGANISM: Artificial sequence
<220> FEATURE:
<223> OTHER INFORMATION: synthetic sequence

<400> SEQUENCE: 626

Tyr Leu Lys Ser Phe Phe
1 5

<210> SEQ ID NO 627
<211> LENGTH: 6
<212> TYPE: PRT
<213> ORGANISM: Artificial sequence
<220> FEATURE:
<223> OTHER INFORMATION: synthetic sequence

<400> SEQUENCE: 627

Val Phe Asp Ser Ile Phe
1 5

<210> SEQ ID NO 628
<211> LENGTH: 6
<212> TYPE: PRT
<213> ORGANISM: Artificial sequence
<220> FEATURE:
<223> OTHER INFORMATION: synthetic sequence

<400> SEQUENCE: 628

Leu Trp Gln Thr Leu Leu
1 5

<210> SEQ ID NO 629
<211> LENGTH: 6
<212> TYPE: PRT
<213> ORGANISM: Artificial sequence
<220> FEATURE:
<223> OTHER INFORMATION: synthetic sequence

<400> SEQUENCE: 629

Tyr Tyr Thr His Ala Ala
1 5

<210> SEQ ID NO 630
<211> LENGTH: 6
<212> TYPE: PRT
<213> ORGANISM: Artificial sequence
<220> FEATURE:
<223> OTHER INFORMATION: synthetic sequence

<400> SEQUENCE: 630

Trp Phe Arg Phe Trp Lys
1 5

<210> SEQ ID NO 631
<211> LENGTH: 6
<212> TYPE: PRT
<213> ORGANISM: Artificial sequence
<220> FEATURE:
<223> OTHER INFORMATION: synthetic sequence

<400> SEQUENCE: 631

Ala Phe Trp Arg Trp Phe 1 5

<210> SEQ ID NO 632
<211> LENGTH: 6
<212> TYPE: PRT
<213> ORGANISM: Artificial sequence
<220> FEATURE:
<223> OTHER INFORMATION: synthetic sequence

<400> SEQUENCE: 632

Val Tyr Thr Ser Val Val
1 5

<210> SEQ ID NO 633
<211> LENGTH: 6
<212> TYPE: PRT
<213> ORGANISM: Artificial sequence
<220> FEATURE:
<223> OTHER INFORMATION: synthetic sequence

<400> SEQUENCE: 633

Tyr Val Gln Gln Ile Phe
1 5

<210> SEQ ID NO 634
<211> LENGTH: 6
<212> TYPE: PRT
<213> ORGANISM: Artificial sequence
<220> FEATURE:
<223> OTHER INFORMATION: synthetic sequence

<400> SEQUENCE: 634

Phe Phe Arg Arg Phe Ala
1 5

<210> SEQ ID NO 635
<211> LENGTH: 6
<212> TYPE: PRT
<213> ORGANISM: Artificial sequence
<220> FEATURE:
<223> OTHER INFORMATION: synthetic sequence

<400> SEQUENCE: 635

Tyr Leu Asp His Tyr Phe
1 5

<210> SEQ ID NO 636
<211> LENGTH: 6
<212> TYPE: PRT
<213> ORGANISM: Artificial sequence
<220> FEATURE:
<223> OTHER INFORMATION: synthetic sequence

<400> SEQUENCE: 636

Phe Met Gln Ser Phe Ile
1 5

<210> SEQ ID NO 637
<211> LENGTH: 6
<212> TYPE: PRT
<213> ORGANISM: Artificial sequence
<220> FEATURE:
<223> OTHER INFORMATION: synthetic sequence

<400> SEQUENCE: 637

Leu Leu Ser Gly Ile Val
1 5

<210> SEQ ID NO 638
<211> LENGTH: 6
<212> TYPE: PRT
<213> ORGANISM: Artificial sequence
<220> FEATURE:
<223> OTHER INFORMATION: synthetic sequence

<400> SEQUENCE: 638

Ala Phe Arg Asn Phe Phe
1               5

<210> SEQ ID NO 639
<211> LENGTH: 6
<212> TYPE: PRT
<213> ORGANISM: Artificial sequence
<220> FEATURE:
<223> OTHER INFORMATION: synthetic sequence

<400> SEQUENCE: 639

Val Tyr Gly Gly Trp Phe
1               5

<210> SEQ ID NO 640
<211> LENGTH: 6
<212> TYPE: PRT
<213> ORGANISM: Artificial sequence
<220> FEATURE:
<223> OTHER INFORMATION: synthetic sequence

<400> SEQUENCE: 640

Phe Trp Lys Arg Phe Val
1               5

<210> SEQ ID NO 641
<211> LENGTH: 6
<212> TYPE: PRT
<213> ORGANISM: Artificial sequence
<220> FEATURE:
<223> OTHER INFORMATION: synthetic sequence

<400> SEQUENCE: 641

Tyr Val Thr Asn Phe Ile
1               5

<210> SEQ ID NO 642
<211> LENGTH: 6
<212> TYPE: PRT
<213> ORGANISM: Artificial sequence
<220> FEATURE:
<223> OTHER INFORMATION: synthetic sequence

<400> SEQUENCE: 642

Phe Phe Gly Glu Met Phe
1               5

<210> SEQ ID NO 643
<211> LENGTH: 6
<212> TYPE: PRT
<213> ORGANISM: Artificial sequence
<220> FEATURE:
<223> OTHER INFORMATION: synthetic sequence

<400> SEQUENCE: 643

Ile Ile Asn Arg Ile Ile
1               5

<210> SEQ ID NO 644
<211> LENGTH: 6
<212> TYPE: PRT
<213> ORGANISM: Artificial sequence
<220> FEATURE:
<223> OTHER INFORMATION: synthetic sequence

<400> SEQUENCE: 644

Thr Leu Arg Ser Tyr Leu
1               5

<210> SEQ ID NO 645
<211> LENGTH: 6
<212> TYPE: PRT
<213> ORGANISM: Artificial sequence
<220> FEATURE:
<223> OTHER INFORMATION: synthetic sequence

<400> SEQUENCE: 645

Ala Val His His Trp Ala
1               5

<210> SEQ ID NO 646
<211> LENGTH: 6
<212> TYPE: PRT
<213> ORGANISM: Artificial sequence
<220> FEATURE:
<223> OTHER INFORMATION: synthetic sequence

<400> SEQUENCE: 646

Leu Phe Arg Arg Ala Phe
1               5

<210> SEQ ID NO 647
<211> LENGTH: 6
<212> TYPE: PRT
<213> ORGANISM: Artificial sequence
<220> FEATURE:
<223> OTHER INFORMATION: synthetic sequence

<400> SEQUENCE: 647

Thr Tyr Arg Ser Tyr Val
1               5

<210> SEQ ID NO 648
<211> LENGTH: 6
<212> TYPE: PRT
<213> ORGANISM: Artificial sequence
<220> FEATURE:
<223> OTHER INFORMATION: synthetic sequence

<400> SEQUENCE: 648

Val Thr Arg Arg Phe Ile
1               5

<210> SEQ ID NO 649
<211> LENGTH: 6
<212> TYPE: PRT
<213> ORGANISM: Artificial sequence
<220> FEATURE:
<223> OTHER INFORMATION: synthetic sequence

<400> SEQUENCE: 649

Phe Tyr Asp Asp Ile Val
1               5

<210> SEQ ID NO 650
<211> LENGTH: 6
<212> TYPE: PRT
<213> ORGANISM: Artificial sequence
<220> FEATURE:
<223> OTHER INFORMATION: synthetic sequence

<400> SEQUENCE: 650

Leu Tyr Thr Gln Leu Phe
1 5

<210> SEQ ID NO 651
<211> LENGTH: 6
<212> TYPE: PRT
<213> ORGANISM: Artificial sequence
<220> FEATURE:
<223> OTHER INFORMATION: synthetic sequence

<400> SEQUENCE: 651

Phe Leu Ser Gln Tyr Phe
1 5

<210> SEQ ID NO 652
<211> LENGTH: 6
<212> TYPE: PRT
<213> ORGANISM: Artificial sequence
<220> FEATURE:
<223> OTHER INFORMATION: synthetic sequence

<400> SEQUENCE: 652

Phe Leu Lys Asp Leu Val
1 5

<210> SEQ ID NO 653
<211> LENGTH: 6
<212> TYPE: PRT
<213> ORGANISM: Artificial sequence
<220> FEATURE:
<223> OTHER INFORMATION: synthetic sequence

<400> SEQUENCE: 653

Ile Thr Gln Asn Ile Val
1 5

<210> SEQ ID NO 654
<211> LENGTH: 6
<212> TYPE: PRT
<213> ORGANISM: Artificial sequence
<220> FEATURE:
<223> OTHER INFORMATION: synthetic sequence

<400> SEQUENCE: 654

Leu Leu Arg Asn Thr Pro
1 5

<210> SEQ ID NO 655
<211> LENGTH: 6
<212> TYPE: PRT
<213> ORGANISM: Artificial sequence
<220> FEATURE:
<223> OTHER INFORMATION: synthetic sequence

<400> SEQUENCE: 655

Ile Ile Arg Asn Tyr Tyr
1 5

<210> SEQ ID NO 656

<211> LENGTH: 6
<212> TYPE: PRT
<213> ORGANISM: Artificial sequence
<220> FEATURE:
<223> OTHER INFORMATION: synthetic sequence

<400> SEQUENCE: 656

Phe Met Gln Asn Phe Val
1 5

<210> SEQ ID NO 657
<211> LENGTH: 6
<212> TYPE: PRT
<213> ORGANISM: Artificial sequence
<220> FEATURE:
<223> OTHER INFORMATION: synthetic sequence

<400> SEQUENCE: 657

Leu Ser Thr Gln Ile Phe
1 5

<210> SEQ ID NO 658
<211> LENGTH: 6
<212> TYPE: PRT
<213> ORGANISM: Artificial sequence
<220> FEATURE:
<223> OTHER INFORMATION: synthetic sequence

<400> SEQUENCE: 658

Phe Phe Ser Ser Leu Ala
1 5

<210> SEQ ID NO 659
<211> LENGTH: 6
<212> TYPE: PRT
<213> ORGANISM: Artificial sequence
<220> FEATURE:
<223> OTHER INFORMATION: synthetic sequence

<400> SEQUENCE: 659

Tyr Phe Gln Glu Tyr Ile
1 5

<210> SEQ ID NO 660
<211> LENGTH: 6
<212> TYPE: PRT
<213> ORGANISM: Artificial sequence
<220> FEATURE:
<223> OTHER INFORMATION: synthetic sequence

<400> SEQUENCE: 660

Ala Tyr Gly Gly Val Leu
1 5

<210> SEQ ID NO 661
<211> LENGTH: 6
<212> TYPE: PRT
<213> ORGANISM: Artificial sequence
<220> FEATURE:
<223> OTHER INFORMATION: synthetic sequence

<400> SEQUENCE: 661

Leu Tyr Gln Gln Met Ala
1 5

<210> SEQ ID NO 662
<211> LENGTH: 6

<212> TYPE: PRT
<213> ORGANISM: Artificial sequence
<220> FEATURE:
<223> OTHER INFORMATION: synthetic sequence

<400> SEQUENCE: 662

Met Leu Ser Ser Ala Met
1 5

<210> SEQ ID NO 663
<211> LENGTH: 6
<212> TYPE: PRT
<213> ORGANISM: Artificial sequence
<220> FEATURE:
<223> OTHER INFORMATION: synthetic sequence

<400> SEQUENCE: 663

Phe Phe Gly Asp Phe Val
1 5

<210> SEQ ID NO 664
<211> LENGTH: 6
<212> TYPE: PRT
<213> ORGANISM: Artificial sequence
<220> FEATURE:
<223> OTHER INFORMATION: synthetic sequence

<400> SEQUENCE: 664

Leu Ile Asn Thr Met Pro
1 5

<210> SEQ ID NO 665
<211> LENGTH: 6
<212> TYPE: PRT
<213> ORGANISM: Artificial sequence
<220> FEATURE:
<223> OTHER INFORMATION: synthetic sequence

<400> SEQUENCE: 665

Leu Leu Asp Arg Phe Tyr
1 5

<210> SEQ ID NO 666
<211> LENGTH: 6
<212> TYPE: PRT
<213> ORGANISM: Artificial sequence
<220> FEATURE:
<223> OTHER INFORMATION: synthetic sequence

<400> SEQUENCE: 666

Leu Phe Ser Gln Ala Gly
1 5

<210> SEQ ID NO 667
<211> LENGTH: 6
<212> TYPE: PRT
<213> ORGANISM: Artificial sequence
<220> FEATURE:
<223> OTHER INFORMATION: synthetic sequence

<400> SEQUENCE: 667

Met Ala Thr Arg Gly Leu
1 5

<210> SEQ ID NO 668
<211> LENGTH: 6
<212> TYPE: PRT

<213> ORGANISM: Artificial sequence
<220> FEATURE:
<223> OTHER INFORMATION: synthetic sequence

<400> SEQUENCE: 668

Ile Phe Arg Asn Thr Ala
1               5

<210> SEQ ID NO 669
<211> LENGTH: 6
<212> TYPE: PRT
<213> ORGANISM: Artificial sequence
<220> FEATURE:
<223> OTHER INFORMATION: synthetic sequence

<400> SEQUENCE: 669

Met Leu Arg Asn Tyr Tyr
1               5

<210> SEQ ID NO 670
<211> LENGTH: 6
<212> TYPE: PRT
<213> ORGANISM: Artificial sequence
<220> FEATURE:
<223> OTHER INFORMATION: synthetic sequence

<400> SEQUENCE: 670

Met Leu Thr Gly Ala Phe
1               5

<210> SEQ ID NO 671
<211> LENGTH: 6
<212> TYPE: PRT
<213> ORGANISM: Artificial sequence
<220> FEATURE:
<223> OTHER INFORMATION: synthetic sequence

<400> SEQUENCE: 671

Leu Met Asn Gly Met Met
1               5

<210> SEQ ID NO 672
<211> LENGTH: 6
<212> TYPE: PRT
<213> ORGANISM: Artificial sequence
<220> FEATURE:
<223> OTHER INFORMATION: synthetic sequence

<400> SEQUENCE: 672

Val Ala His His Tyr Ala
1               5

<210> SEQ ID NO 673
<211> LENGTH: 6
<212> TYPE: PRT
<213> ORGANISM: Artificial sequence
<220> FEATURE:
<223> OTHER INFORMATION: synthetic sequence

<400> SEQUENCE: 673

Phe Phe Ser Lys Leu Pro
1               5

<210> SEQ ID NO 674
<211> LENGTH: 6
<212> TYPE: PRT
<213> ORGANISM: Artificial sequence
<220> FEATURE:
<223> OTHER INFORMATION: synthetic sequence

<400> SEQUENCE: 674

Leu Ala Arg Gln Val Val
1               5

<210> SEQ ID NO 675
<211> LENGTH: 6
<212> TYPE: PRT
<213> ORGANISM: Artificial sequence
<220> FEATURE:
<223> OTHER INFORMATION: synthetic sequence

<400> SEQUENCE: 675

Ala Phe Asn Asn Phe Phe
1               5

<210> SEQ ID NO 676
<211> LENGTH: 6
<212> TYPE: PRT
<213> ORGANISM: Artificial sequence
<220> FEATURE:
<223> OTHER INFORMATION: synthetic sequence

<400> SEQUENCE: 676

Ala Tyr Gln Asn Phe Leu
1               5

<210> SEQ ID NO 677
<211> LENGTH: 6
<212> TYPE: PRT
<213> ORGANISM: Artificial sequence
<220> FEATURE:
<223> OTHER INFORMATION: synthetic sequence

<400> SEQUENCE: 677

Phe Leu Asn Asn Leu Ile
1               5

<210> SEQ ID NO 678
<211> LENGTH: 6
<212> TYPE: PRT
<213> ORGANISM: Artificial sequence
<220> FEATURE:
<223> OTHER INFORMATION: synthetic sequence

<400> SEQUENCE: 678

Ala Trp His Asp Val Ala
1               5

<210> SEQ ID NO 679
<211> LENGTH: 6
<212> TYPE: PRT
<213> ORGANISM: Artificial sequence
<220> FEATURE:
<223> OTHER INFORMATION: synthetic sequence

<400> SEQUENCE: 679

Val Phe Asn Glu Leu Tyr
1               5

<210> SEQ ID NO 680
<211> LENGTH: 6
<212> TYPE: PRT
<213> ORGANISM: Artificial sequence
<220> FEATURE:

<223> OTHER INFORMATION: synthetic sequence

<400> SEQUENCE: 680

Val Phe Glu Gln Leu Tyr
1 5

<210> SEQ ID NO 681
<211> LENGTH: 6
<212> TYPE: PRT
<213> ORGANISM: Artificial sequence
<220> FEATURE:
<223> OTHER INFORMATION: synthetic sequence

<400> SEQUENCE: 681

Phe Val Ser Gly Val Tyr
1 5

<210> SEQ ID NO 682
<211> LENGTH: 6
<212> TYPE: PRT
<213> ORGANISM: Artificial sequence
<220> FEATURE:
<223> OTHER INFORMATION: synthetic sequence

<400> SEQUENCE: 682

Ala Leu Gln Ser Phe Met
1 5

<210> SEQ ID NO 683
<211> LENGTH: 6
<212> TYPE: PRT
<213> ORGANISM: Artificial sequence
<220> FEATURE:
<223> OTHER INFORMATION: synthetic sequence

<400> SEQUENCE: 683

Ala Phe Lys Arg Phe Phe
1 5

<210> SEQ ID NO 684
<211> LENGTH: 6
<212> TYPE: PRT
<213> ORGANISM: Artificial sequence
<220> FEATURE:
<223> OTHER INFORMATION: synthetic sequence

<400> SEQUENCE: 684

Met Ala Ser Gln Met Val
1 5

<210> SEQ ID NO 685
<211> LENGTH: 6
<212> TYPE: PRT
<213> ORGANISM: Artificial sequence
<220> FEATURE:
<223> OTHER INFORMATION: synthetic sequence

<400> SEQUENCE: 685

Ala Leu Ser Lys Met Met
1 5

<210> SEQ ID NO 686
<211> LENGTH: 6
<212> TYPE: PRT
<213> ORGANISM: Artificial sequence
<220> FEATURE:
<223> OTHER INFORMATION: synthetic sequence

<400> SEQUENCE: 686

Phe Thr Asp Asn Phe Tyr
1               5

<210> SEQ ID NO 687
<211> LENGTH: 6
<212> TYPE: PRT
<213> ORGANISM: Artificial sequence
<220> FEATURE:
<223> OTHER INFORMATION: synthetic sequence

<400> SEQUENCE: 687

Pro Leu Gln Lys Met Val
1               5

<210> SEQ ID NO 688
<211> LENGTH: 6
<212> TYPE: PRT
<213> ORGANISM: Artificial sequence
<220> FEATURE:
<223> OTHER INFORMATION: synthetic sequence

<400> SEQUENCE: 688

Leu Leu Lys Asn Ile Leu
1               5

<210> SEQ ID NO 689
<211> LENGTH: 6
<212> TYPE: PRT
<213> ORGANISM: Artificial sequence
<220> FEATURE:
<223> OTHER INFORMATION: synthetic sequence

<400> SEQUENCE: 689

Val Val Asp Arg Ala Leu
1               5

<210> SEQ ID NO 690
<211> LENGTH: 6
<212> TYPE: PRT
<213> ORGANISM: Artificial sequence
<220> FEATURE:
<223> OTHER INFORMATION: synthetic sequence

<400> SEQUENCE: 690

Val Ala Ser Glu Met Val
1               5

<210> SEQ ID NO 691
<211> LENGTH: 6
<212> TYPE: PRT
<213> ORGANISM: Artificial sequence
<220> FEATURE:
<223> OTHER INFORMATION: synthetic sequence

<400> SEQUENCE: 691

Ile Tyr Gln Arg Tyr Ser
1               5

<210> SEQ ID NO 692
<211> LENGTH: 6
<212> TYPE: PRT
<213> ORGANISM: Artificial sequence
<220> FEATURE:
<223> OTHER INFORMATION: synthetic sequence

<400> SEQUENCE: 692

Phe Ala Gly Asp Met Met
1 5

<210> SEQ ID NO 693
<211> LENGTH: 6
<212> TYPE: PRT
<213> ORGANISM: Artificial sequence
<220> FEATURE:
<223> OTHER INFORMATION: synthetic sequence

<400> SEQUENCE: 693

Phe Gly Gln Asn Ile Tyr
1 5

<210> SEQ ID NO 694
<211> LENGTH: 6
<212> TYPE: PRT
<213> ORGANISM: Artificial sequence
<220> FEATURE:
<223> OTHER INFORMATION: synthetic sequence

<400> SEQUENCE: 694

Ala Leu Asp Gly Ile Phe
1 5

<210> SEQ ID NO 695
<211> LENGTH: 6
<212> TYPE: PRT
<213> ORGANISM: Artificial sequence
<220> FEATURE:
<223> OTHER INFORMATION: synthetic sequence

<400> SEQUENCE: 695

Tyr Val Ser Glu Leu Pro
1 5

<210> SEQ ID NO 696
<211> LENGTH: 6
<212> TYPE: PRT
<213> ORGANISM: Artificial sequence
<220> FEATURE:
<223> OTHER INFORMATION: synthetic sequence

<400> SEQUENCE: 696

Trp Trp Gly Asn Ser Tyr
1 5

<210> SEQ ID NO 697
<211> LENGTH: 6
<212> TYPE: PRT
<213> ORGANISM: Artificial sequence
<220> FEATURE:
<223> OTHER INFORMATION: synthetic sequence

<400> SEQUENCE: 697

Ile Leu Gly Lys Ile Ala
1 5

<210> SEQ ID NO 698
<211> LENGTH: 6
<212> TYPE: PRT
<213> ORGANISM: Artificial sequence
<220> FEATURE:
<223> OTHER INFORMATION: synthetic sequence

<400> SEQUENCE: 698

Trp Leu Lys Gln Ser Val
1 5

<210> SEQ ID NO 699
<211> LENGTH: 6
<212> TYPE: PRT
<213> ORGANISM: Artificial sequence
<220> FEATURE:
<223> OTHER INFORMATION: synthetic sequence

<400> SEQUENCE: 699

Tyr Phe Gln Glu Tyr Leu
1 5

<210> SEQ ID NO 700
<211> LENGTH: 6
<212> TYPE: PRT
<213> ORGANISM: Artificial sequence
<220> FEATURE:
<223> OTHER INFORMATION: synthetic sequence

<400> SEQUENCE: 700

Gly Leu Lys Arg Met Phe
1 5

<210> SEQ ID NO 701
<211> LENGTH: 6
<212> TYPE: PRT
<213> ORGANISM: Artificial sequence
<220> FEATURE:
<223> OTHER INFORMATION: synthetic sequence

<400> SEQUENCE: 701

Met Phe Asp Arg Ala Thr
1 5

<210> SEQ ID NO 702
<211> LENGTH: 6
<212> TYPE: PRT
<213> ORGANISM: Artificial sequence
<220> FEATURE:
<223> OTHER INFORMATION: synthetic sequence

<400> SEQUENCE: 702

Thr Ala Gln Arg Tyr Leu
1 5

<210> SEQ ID NO 703
<211> LENGTH: 6
<212> TYPE: PRT
<213> ORGANISM: Artificial sequence
<220> FEATURE:
<223> OTHER INFORMATION: synthetic sequence

<400> SEQUENCE: 703

Trp Leu Asn Glu Phe Gly
1 5

<210> SEQ ID NO 704
<211> LENGTH: 6
<212> TYPE: PRT
<213> ORGANISM: Artificial sequence
<220> FEATURE:
<223> OTHER INFORMATION: synthetic sequence

<400> SEQUENCE: 704

Ile Ala Asp Arg Val Phe
1 5

<210> SEQ ID NO 705
<211> LENGTH: 6
<212> TYPE: PRT
<213> ORGANISM: Artificial sequence
<220> FEATURE:
<223> OTHER INFORMATION: synthetic sequence

<400> SEQUENCE: 705

Leu Leu Asp Arg Tyr Tyr
1 5

<210> SEQ ID NO 706
<211> LENGTH: 6
<212> TYPE: PRT
<213> ORGANISM: Artificial sequence
<220> FEATURE:
<223> OTHER INFORMATION: synthetic sequence

<400> SEQUENCE: 706

Phe Ser Lys Glu Ile Phe
1 5

<210> SEQ ID NO 707
<211> LENGTH: 6
<212> TYPE: PRT
<213> ORGANISM: Artificial sequence
<220> FEATURE:
<223> OTHER INFORMATION: synthetic sequence

<400> SEQUENCE: 707

Ala Phe Asn Gln Phe Leu
1 5

<210> SEQ ID NO 708
<211> LENGTH: 6
<212> TYPE: PRT
<213> ORGANISM: Artificial sequence
<220> FEATURE:
<223> OTHER INFORMATION: synthetic sequence

<400> SEQUENCE: 708

Ala Val Glu Arg Tyr Leu
1 5

<210> SEQ ID NO 709
<211> LENGTH: 6
<212> TYPE: PRT
<213> ORGANISM: Artificial sequence
<220> FEATURE:
<223> OTHER INFORMATION: synthetic sequence

<400> SEQUENCE: 709

Ala Val Arg Gly Ile Phe
1 5

<210> SEQ ID NO 710
<211> LENGTH: 6
<212> TYPE: PRT
<213> ORGANISM: Artificial sequence
<220> FEATURE:
<223> OTHER INFORMATION: synthetic sequence

<400> SEQUENCE: 710

Leu Thr Gln Gln Phe Thr 1 5

<210> SEQ ID NO 711
<211> LENGTH: 6
<212> TYPE: PRT
<213> ORGANISM: Artificial sequence
<220> FEATURE:
<223> OTHER INFORMATION: synthetic sequence

<400> SEQUENCE: 711

Ala Phe Ser Asp Ile Leu
1 5

<210> SEQ ID NO 712
<211> LENGTH: 6
<212> TYPE: PRT
<213> ORGANISM: Artificial sequence
<220> FEATURE:
<223> OTHER INFORMATION: synthetic sequence

<400> SEQUENCE: 712

Tyr Leu Asp Asn Val Ser
1 5

<210> SEQ ID NO 713
<211> LENGTH: 6
<212> TYPE: PRT
<213> ORGANISM: Artificial sequence
<220> FEATURE:
<223> OTHER INFORMATION: synthetic sequence

<400> SEQUENCE: 713

Tyr Ile Ser Asp Phe Thr
1 5

<210> SEQ ID NO 714
<211> LENGTH: 6
<212> TYPE: PRT
<213> ORGANISM: Artificial sequence
<220> FEATURE:
<223> OTHER INFORMATION: synthetic sequence

<400> SEQUENCE: 714

Ser Tyr Asn Asn Trp Tyr
1 5

<210> SEQ ID NO 715
<211> LENGTH: 6
<212> TYPE: PRT
<213> ORGANISM: Artificial sequence
<220> FEATURE:
<223> OTHER INFORMATION: synthetic sequence

<400> SEQUENCE: 715

Met Phe Asn Asn Ile Trp
1 5

<210> SEQ ID NO 716
<211> LENGTH: 6
<212> TYPE: PRT
<213> ORGANISM: Artificial sequence
<220> FEATURE:
<223> OTHER INFORMATION: synthetic sequence

<400> SEQUENCE: 716

Ser Trp Gln Glu Val Val
1 5

<210> SEQ ID NO 717
<211> LENGTH: 6
<212> TYPE: PRT
<213> ORGANISM: Artificial sequence
<220> FEATURE:
<223> OTHER INFORMATION: synthetic sequence

<400> SEQUENCE: 717

Ala Leu Ser Glu Ile Ile
1               5

<210> SEQ ID NO 718
<211> LENGTH: 6
<212> TYPE: PRT
<213> ORGANISM: Artificial sequence
<220> FEATURE:
<223> OTHER INFORMATION: synthetic sequence

<400> SEQUENCE: 718

Gly Leu Lys Arg Val Val
1               5

<210> SEQ ID NO 719
<211> LENGTH: 6
<212> TYPE: PRT
<213> ORGANISM: Artificial sequence
<220> FEATURE:
<223> OTHER INFORMATION: synthetic sequence

<400> SEQUENCE: 719

Leu Tyr Arg Lys Ile Val
1               5

<210> SEQ ID NO 720
<211> LENGTH: 6
<212> TYPE: PRT
<213> ORGANISM: Artificial sequence
<220> FEATURE:
<223> OTHER INFORMATION: synthetic sequence

<400> SEQUENCE: 720

Ala Leu Lys Gln Val Leu
1               5

<210> SEQ ID NO 721
<211> LENGTH: 6
<212> TYPE: PRT
<213> ORGANISM: Artificial sequence
<220> FEATURE:
<223> OTHER INFORMATION: synthetic sequence

<400> SEQUENCE: 721

Gly Thr Lys Arg Leu Phe
1               5

<210> SEQ ID NO 722
<211> LENGTH: 6
<212> TYPE: PRT
<213> ORGANISM: Artificial sequence
<220> FEATURE:
<223> OTHER INFORMATION: synthetic sequence

<400> SEQUENCE: 722

Pro Pro Arg Asn Tyr Ile
1               5

<210> SEQ ID NO 723
<211> LENGTH: 6
<212> TYPE: PRT
<213> ORGANISM: Artificial sequence
<220> FEATURE:
<223> OTHER INFORMATION: synthetic sequence

<400> SEQUENCE: 723

Leu Leu Arg Lys Ala Met
1 5

<210> SEQ ID NO 724
<211> LENGTH: 6
<212> TYPE: PRT
<213> ORGANISM: Artificial sequence
<220> FEATURE:
<223> OTHER INFORMATION: synthetic sequence

<400> SEQUENCE: 724

Ile Ala Ser Lys Leu Leu
1 5

<210> SEQ ID NO 725
<211> LENGTH: 6
<212> TYPE: PRT
<213> ORGANISM: Artificial sequence
<220> FEATURE:
<223> OTHER INFORMATION: synthetic sequence

<400> SEQUENCE: 725

Gly Leu Lys Arg Ile Phe
1 5

<210> SEQ ID NO 726
<211> LENGTH: 6
<212> TYPE: PRT
<213> ORGANISM: Artificial sequence
<220> FEATURE:
<223> OTHER INFORMATION: synthetic sequence

<400> SEQUENCE: 726

Ala Ile Thr Arg Leu Ser
1 5

<210> SEQ ID NO 727
<211> LENGTH: 6
<212> TYPE: PRT
<213> ORGANISM: Artificial sequence
<220> FEATURE:
<223> OTHER INFORMATION: synthetic sequence

<400> SEQUENCE: 727

Ile Leu Gln Gln Ala Gly
1 5

<210> SEQ ID NO 728
<211> LENGTH: 6
<212> TYPE: PRT
<213> ORGANISM: Artificial sequence
<220> FEATURE:
<223> OTHER INFORMATION: synthetic sequence

<400> SEQUENCE: 728

Ala Ala Ser Lys Trp Leu
1 5

<210> SEQ ID NO 729
<211> LENGTH: 6
<212> TYPE: PRT
<213> ORGANISM: Artificial sequence
<220> FEATURE:
<223> OTHER INFORMATION: synthetic sequence

<400> SEQUENCE: 729

Met Met Ser Glu Val Pro
1               5

<210> SEQ ID NO 730
<211> LENGTH: 6
<212> TYPE: PRT
<213> ORGANISM: Artificial sequence
<220> FEATURE:
<223> OTHER INFORMATION: synthetic sequence

<400> SEQUENCE: 730

Leu Ile Pro Arg Phe Ala
1               5

<210> SEQ ID NO 731
<211> LENGTH: 6
<212> TYPE: PRT
<213> ORGANISM: Artificial sequence
<220> FEATURE:
<223> OTHER INFORMATION: synthetic sequence

<400> SEQUENCE: 731

Ala Phe Gly Gly Ala Leu
1               5

<210> SEQ ID NO 732
<211> LENGTH: 6
<212> TYPE: PRT
<213> ORGANISM: Artificial sequence
<220> FEATURE:
<223> OTHER INFORMATION: synthetic sequence

<400> SEQUENCE: 732

Ala Ala Gln Glu Val Ile
1               5

<210> SEQ ID NO 733
<211> LENGTH: 6
<212> TYPE: PRT
<213> ORGANISM: Artificial sequence
<220> FEATURE:
<223> OTHER INFORMATION: synthetic sequence

<400> SEQUENCE: 733

Thr Leu Asp Lys Ala Leu
1               5

<210> SEQ ID NO 734
<211> LENGTH: 6
<212> TYPE: PRT
<213> ORGANISM: Artificial sequence
<220> FEATURE:
<223> OTHER INFORMATION: synthetic sequence

<400> SEQUENCE: 734

Leu Leu Gln Gln Val Gly
1               5

<210> SEQ ID NO 735

<211> LENGTH: 6
<212> TYPE: PRT
<213> ORGANISM: Artificial sequence
<220> FEATURE:
<223> OTHER INFORMATION: synthetic sequence

<400> SEQUENCE: 735

Ala Phe Asn Asp Tyr Leu
1 5

<210> SEQ ID NO 736
<211> LENGTH: 6
<212> TYPE: PRT
<213> ORGANISM: Artificial sequence
<220> FEATURE:
<223> OTHER INFORMATION: synthetic sequence

<400> SEQUENCE: 736

Ala Ala Lys Gln Met Val
1 5

<210> SEQ ID NO 737
<211> LENGTH: 6
<212> TYPE: PRT
<213> ORGANISM: Artificial sequence
<220> FEATURE:
<223> OTHER INFORMATION: synthetic sequence

<400> SEQUENCE: 737

Gly Leu Lys Asn Met Phe
1 5

<210> SEQ ID NO 738
<211> LENGTH: 6
<212> TYPE: PRT
<213> ORGANISM: Artificial sequence
<220> FEATURE:
<223> OTHER INFORMATION: synthetic sequence

<400> SEQUENCE: 738

Ala Ile Glu Arg Leu Ser
1 5

<210> SEQ ID NO 739
<211> LENGTH: 6
<212> TYPE: PRT
<213> ORGANISM: Artificial sequence
<220> FEATURE:
<223> OTHER INFORMATION: synthetic sequence

<400> SEQUENCE: 739

Val Ala Lys Glu Phe Leu
1 5

<210> SEQ ID NO 740
<211> LENGTH: 6
<212> TYPE: PRT
<213> ORGANISM: Artificial sequence
<220> FEATURE:
<223> OTHER INFORMATION: synthetic sequence

<400> SEQUENCE: 740

Leu Ile Asn Asn Tyr Leu
1 5

<210> SEQ ID NO 741
<211> LENGTH: 6

<212> TYPE: PRT
<213> ORGANISM: Artificial sequence
<220> FEATURE:
<223> OTHER INFORMATION: synthetic sequence

<400> SEQUENCE: 741

Ala Ala Asn Glu Ile Ile
1               5

<210> SEQ ID NO 742
<211> LENGTH: 6
<212> TYPE: PRT
<213> ORGANISM: Artificial sequence
<220> FEATURE:
<223> OTHER INFORMATION: synthetic sequence

<400> SEQUENCE: 742

Phe Leu Ser Ser Ala Thr
1               5

<210> SEQ ID NO 743
<211> LENGTH: 6
<212> TYPE: PRT
<213> ORGANISM: Artificial sequence
<220> FEATURE:
<223> OTHER INFORMATION: synthetic sequence

<400> SEQUENCE: 743

Val Pro Gln Gln Val Leu
1               5

<210> SEQ ID NO 744
<211> LENGTH: 6
<212> TYPE: PRT
<213> ORGANISM: Artificial sequence
<220> FEATURE:
<223> OTHER INFORMATION: synthetic sequence

<400> SEQUENCE: 744

Thr Leu Asp Gly Phe Phe
1               5

<210> SEQ ID NO 745
<211> LENGTH: 6
<212> TYPE: PRT
<213> ORGANISM: Artificial sequence
<220> FEATURE:
<223> OTHER INFORMATION: synthetic sequence

<400> SEQUENCE: 745

Ala Phe Asn Asp Tyr Ser
1               5

<210> SEQ ID NO 746
<211> LENGTH: 6
<212> TYPE: PRT
<213> ORGANISM: Artificial sequence
<220> FEATURE:
<223> OTHER INFORMATION: synthetic sequence

<400> SEQUENCE: 746

Val Val Glu Gly Phe Leu
1               5

<210> SEQ ID NO 747
<211> LENGTH: 6
<212> TYPE: PRT

<213> ORGANISM: Artificial sequence
<220> FEATURE:
<223> OTHER INFORMATION: synthetic sequence

<400> SEQUENCE: 747

Ala Ile Ser Asn Ile Trp
1 5

<210> SEQ ID NO 748
<211> LENGTH: 6
<212> TYPE: PRT
<213> ORGANISM: Artificial sequence
<220> FEATURE:
<223> OTHER INFORMATION: synthetic sequence

<400> SEQUENCE: 748

Phe Phe Lys Lys Phe Phe
1 5

<210> SEQ ID NO 749
<211> LENGTH: 6
<212> TYPE: PRT
<213> ORGANISM: Artificial sequence
<220> FEATURE:
<223> OTHER INFORMATION: synthetic sequence

<400> SEQUENCE: 749

Thr Thr Gln Asn Val Leu
1 5

<210> SEQ ID NO 750
<211> LENGTH: 6
<212> TYPE: PRT
<213> ORGANISM: Artificial sequence
<220> FEATURE:
<223> OTHER INFORMATION: synthetic sequence

<400> SEQUENCE: 750

Gly Phe Lys Arg Ile Phe
1 5

<210> SEQ ID NO 751
<211> LENGTH: 6
<212> TYPE: PRT
<213> ORGANISM: Artificial sequence
<220> FEATURE:
<223> OTHER INFORMATION: synthetic sequence

<400> SEQUENCE: 751

Ile Leu Gly Gln Ala Met
1 5

<210> SEQ ID NO 752
<211> LENGTH: 6
<212> TYPE: PRT
<213> ORGANISM: Artificial sequence
<220> FEATURE:
<223> OTHER INFORMATION: synthetic sequence

<400> SEQUENCE: 752

Leu Met Asn Asp Tyr Ile
1 5

<210> SEQ ID NO 753
<211> LENGTH: 6
<212> TYPE: PRT
<213> ORGANISM: Artificial sequence
<220> FEATURE:
<223> OTHER INFORMATION: synthetic sequence

<400> SEQUENCE: 753

Ile Leu Asp Glu Ala Trp
1               5

<210> SEQ ID NO 754
<211> LENGTH: 6
<212> TYPE: PRT
<213> ORGANISM: Artificial sequence
<220> FEATURE:
<223> OTHER INFORMATION: synthetic sequence

<400> SEQUENCE: 754

Gly Ile Lys Arg Met Phe
1               5

<210> SEQ ID NO 755
<211> LENGTH: 6
<212> TYPE: PRT
<213> ORGANISM: Artificial sequence
<220> FEATURE:
<223> OTHER INFORMATION: synthetic sequence

<400> SEQUENCE: 755

Ile Ala Lys Asn Ile Phe
1               5

<210> SEQ ID NO 756
<211> LENGTH: 6
<212> TYPE: PRT
<213> ORGANISM: Artificial sequence
<220> FEATURE:
<223> OTHER INFORMATION: synthetic sequence

<400> SEQUENCE: 756

Leu Ile Gly Lys Ala Ile
1               5

<210> SEQ ID NO 757
<211> LENGTH: 6
<212> TYPE: PRT
<213> ORGANISM: Artificial sequence
<220> FEATURE:
<223> OTHER INFORMATION: synthetic sequence

<400> SEQUENCE: 757

Leu Ile Gly Lys Ala Ile
1               5

<210> SEQ ID NO 758
<211> LENGTH: 6
<212> TYPE: PRT
<213> ORGANISM: Artificial sequence
<220> FEATURE:
<223> OTHER INFORMATION: synthetic sequence

<400> SEQUENCE: 758

Ser Leu Gly Thr Ala Ile
1               5

<210> SEQ ID NO 759
<211> LENGTH: 6
<212> TYPE: PRT
<213> ORGANISM: Artificial sequence
<220> FEATURE:

<223> OTHER INFORMATION: synthetic sequence

<400> SEQUENCE: 759

Val Pro Lys His Val Tyr
1 5

<210> SEQ ID NO 760
<211> LENGTH: 6
<212> TYPE: PRT
<213> ORGANISM: Artificial sequence
<220> FEATURE:
<223> OTHER INFORMATION: synthetic sequence

<400> SEQUENCE: 760

Ile Ile Gln Gln Ala Gly
1 5

<210> SEQ ID NO 761
<211> LENGTH: 6
<212> TYPE: PRT
<213> ORGANISM: Artificial sequence
<220> FEATURE:
<223> OTHER INFORMATION: synthetic sequence

<400> SEQUENCE: 761

Thr Leu Lys Ser Ala Leu
1 5

<210> SEQ ID NO 762
<211> LENGTH: 6
<212> TYPE: PRT
<213> ORGANISM: Artificial sequence
<220> FEATURE:
<223> OTHER INFORMATION: synthetic sequence

<400> SEQUENCE: 762

Ile Ile Asp Lys Ile Phe
1 5

<210> SEQ ID NO 763
<211> LENGTH: 6
<212> TYPE: PRT
<213> ORGANISM: Artificial sequence
<220> FEATURE:
<223> OTHER INFORMATION: synthetic sequence

<400> SEQUENCE: 763

Phe Met Asp Lys Tyr Ile
1 5

<210> SEQ ID NO 764
<211> LENGTH: 6
<212> TYPE: PRT
<213> ORGANISM: Artificial sequence
<220> FEATURE:
<223> OTHER INFORMATION: synthetic sequence

<400> SEQUENCE: 764

Ile Thr Asn Lys Ala Ala
1 5

<210> SEQ ID NO 765
<211> LENGTH: 6
<212> TYPE: PRT
<213> ORGANISM: Artificial sequence
<220> FEATURE:
<223> OTHER INFORMATION: synthetic sequence

<400> SEQUENCE: 765

Ile Val Ser Thr Ala Ala
1 5

<210> SEQ ID NO 766
<211> LENGTH: 6
<212> TYPE: PRT
<213> ORGANISM: Artificial sequence
<220> FEATURE:
<223> OTHER INFORMATION: synthetic sequence

<400> SEQUENCE: 766

Ala Phe Ser Glu Ala Trp
1 5

<210> SEQ ID NO 767
<211> LENGTH: 6
<212> TYPE: PRT
<213> ORGANISM: Artificial sequence
<220> FEATURE:
<223> OTHER INFORMATION: synthetic sequence

<400> SEQUENCE: 767

Met Ser Gly Gly Tyr Leu
1 5

<210> SEQ ID NO 768
<211> LENGTH: 6
<212> TYPE: PRT
<213> ORGANISM: Artificial sequence
<220> FEATURE:
<223> OTHER INFORMATION: synthetic sequence

<400> SEQUENCE: 768

Gly Ile Ala Lys Met Phe
1 5

<210> SEQ ID NO 769
<211> LENGTH: 6
<212> TYPE: PRT
<213> ORGANISM: Artificial sequence
<220> FEATURE:
<223> OTHER INFORMATION: synthetic sequence

<400> SEQUENCE: 769

Met Ile Lys Thr Ala Phe
1 5

<210> SEQ ID NO 770
<211> LENGTH: 6
<212> TYPE: PRT
<213> ORGANISM: Artificial sequence
<220> FEATURE:
<223> OTHER INFORMATION: synthetic sequence

<400> SEQUENCE: 770

Val Leu Lys Gln Leu Ala
1 5

<210> SEQ ID NO 771
<211> LENGTH: 6
<212> TYPE: PRT
<213> ORGANISM: Artificial sequence
<220> FEATURE:
<223> OTHER INFORMATION: synthetic sequence

<400> SEQUENCE: 771

Ala Phe Asp Glu Val Met
1 5

<210> SEQ ID NO 772
<211> LENGTH: 6
<212> TYPE: PRT
<213> ORGANISM: Artificial sequence
<220> FEATURE:
<223> OTHER INFORMATION: synthetic sequence

<400> SEQUENCE: 772

Val Ile Asp Glu Ala Ile
1 5

<210> SEQ ID NO 773
<211> LENGTH: 6
<212> TYPE: PRT
<213> ORGANISM: Artificial sequence
<220> FEATURE:
<223> OTHER INFORMATION: synthetic sequence

<400> SEQUENCE: 773

Ile Val Gly Gly Leu Val
1 5

<210> SEQ ID NO 774
<211> LENGTH: 6
<212> TYPE: PRT
<213> ORGANISM: Artificial sequence
<220> FEATURE:
<223> OTHER INFORMATION: synthetic sequence

<400> SEQUENCE: 774

Met Ala Lys Glu Met Ser
1 5

<210> SEQ ID NO 775
<211> LENGTH: 6
<212> TYPE: PRT
<213> ORGANISM: Artificial sequence
<220> FEATURE:
<223> OTHER INFORMATION: synthetic sequence

<400> SEQUENCE: 775

Ser Phe Asp Asn Tyr Ile
1 5

<210> SEQ ID NO 776
<211> LENGTH: 6
<212> TYPE: PRT
<213> ORGANISM: Artificial sequence
<220> FEATURE:
<223> OTHER INFORMATION: synthetic sequence

<400> SEQUENCE: 776

Gly Ala Gln Ser Ala Val
1 5

<210> SEQ ID NO 777
<211> LENGTH: 6
<212> TYPE: PRT
<213> ORGANISM: Artificial sequence
<220> FEATURE:
<223> OTHER INFORMATION: synthetic sequence

<400> SEQUENCE: 777

Phe Thr Lys Lys Met Val
1               5

<210> SEQ ID NO 778
<211> LENGTH: 6
<212> TYPE: PRT
<213> ORGANISM: Artificial sequence
<220> FEATURE:
<223> OTHER INFORMATION: synthetic sequence

<400> SEQUENCE: 778

Thr Ile Thr Asp Tyr Val
1               5

<210> SEQ ID NO 779
<211> LENGTH: 6
<212> TYPE: PRT
<213> ORGANISM: Artificial sequence
<220> FEATURE:
<223> OTHER INFORMATION: synthetic sequence

<400> SEQUENCE: 779

Ile Ser Lys Asp Phe Phe
1               5

<210> SEQ ID NO 780
<211> LENGTH: 6
<212> TYPE: PRT
<213> ORGANISM: Artificial sequence
<220> FEATURE:
<223> OTHER INFORMATION: synthetic sequence

<400> SEQUENCE: 780

Val Ala Glu Glu Leu Tyr
1               5

<210> SEQ ID NO 781
<211> LENGTH: 6
<212> TYPE: PRT
<213> ORGANISM: Artificial sequence
<220> FEATURE:
<223> OTHER INFORMATION: synthetic sequence

<400> SEQUENCE: 781

Ala Ile Asn Asn Ala Ile
1               5

<210> SEQ ID NO 782
<211> LENGTH: 6
<212> TYPE: PRT
<213> ORGANISM: Artificial sequence
<220> FEATURE:
<223> OTHER INFORMATION: synthetic sequence

<400> SEQUENCE: 782

Val Ala Asp Glu Leu Leu
1               5

<210> SEQ ID NO 783
<211> LENGTH: 6
<212> TYPE: PRT
<213> ORGANISM: Artificial sequence
<220> FEATURE:
<223> OTHER INFORMATION: synthetic sequence

<400> SEQUENCE: 783

Ile Val Gly Gly Leu Ile
1 5

<210> SEQ ID NO 784
<211> LENGTH: 6
<212> TYPE: PRT
<213> ORGANISM: Artificial sequence
<220> FEATURE:
<223> OTHER INFORMATION: synthetic sequence

<400> SEQUENCE: 784

Ala Phe Lys Asp Val Val
1 5

<210> SEQ ID NO 785
<211> LENGTH: 5
<212> TYPE: PRT
<213> ORGANISM: Artificial sequence
<220> FEATURE:
<223> OTHER INFORMATION: synthetic sequence

<400> SEQUENCE: 785

Met Lys Asn Leu Phe
1 5

<210> SEQ ID NO 786
<211> LENGTH: 6
<212> TYPE: PRT
<213> ORGANISM: Artificial sequence
<220> FEATURE:
<223> OTHER INFORMATION: synthetic sequence

<400> SEQUENCE: 786

Ala Phe Thr Asp Gly Ala
1 5

<210> SEQ ID NO 787
<211> LENGTH: 6
<212> TYPE: PRT
<213> ORGANISM: Artificial sequence
<220> FEATURE:
<223> OTHER INFORMATION: synthetic sequence

<400> SEQUENCE: 787

Val Gly Ser Lys Leu Tyr
1 5

<210> SEQ ID NO 788
<211> LENGTH: 6
<212> TYPE: PRT
<213> ORGANISM: Artificial sequence
<220> FEATURE:
<223> OTHER INFORMATION: synthetic sequence

<400> SEQUENCE: 788

Met Ile Arg Lys Tyr Tyr
1 5

<210> SEQ ID NO 789
<211> LENGTH: 6
<212> TYPE: PRT
<213> ORGANISM: Artificial sequence
<220> FEATURE:
<223> OTHER INFORMATION: synthetic sequence

<400> SEQUENCE: 789

Ser Val Gln Gln Ala Ala 1 5

<210> SEQ ID NO 790
<211> LENGTH: 6
<212> TYPE: PRT
<213> ORGANISM: Artificial sequence
<220> FEATURE:
<223> OTHER INFORMATION: synthetic sequence

<400> SEQUENCE: 790

Met Ala Glu Lys Ala Tyr
1 5

<210> SEQ ID NO 791
<211> LENGTH: 6
<212> TYPE: PRT
<213> ORGANISM: Artificial sequence
<220> FEATURE:
<223> OTHER INFORMATION: synthetic sequence

<400> SEQUENCE: 791

Ala Ser Asp Lys Leu Phe
1 5

<210> SEQ ID NO 792
<211> LENGTH: 6
<212> TYPE: PRT
<213> ORGANISM: Artificial sequence
<220> FEATURE:
<223> OTHER INFORMATION: synthetic sequence

<400> SEQUENCE: 792

Pro Pro Gln Asp Tyr Val
1 5

<210> SEQ ID NO 793
<211> LENGTH: 6
<212> TYPE: PRT
<213> ORGANISM: Artificial sequence
<220> FEATURE:
<223> OTHER INFORMATION: synthetic sequence

<400> SEQUENCE: 793

Ile Tyr Lys Lys Phe Tyr
1 5

<210> SEQ ID NO 794
<211> LENGTH: 6
<212> TYPE: PRT
<213> ORGANISM: Artificial sequence
<220> FEATURE:
<223> OTHER INFORMATION: synthetic sequence

<400> SEQUENCE: 794

Met Met Lys Asn Val Tyr
1 5

<210> SEQ ID NO 795
<211> LENGTH: 6
<212> TYPE: PRT
<213> ORGANISM: Artificial sequence
<220> FEATURE:
<223> OTHER INFORMATION: synthetic sequence

<400> SEQUENCE: 795

Leu Val Lys Arg Gly Val
1 5

<210> SEQ ID NO 796
<211> LENGTH: 6
<212> TYPE: PRT
<213> ORGANISM: Artificial sequence
<220> FEATURE:
<223> OTHER INFORMATION: synthetic sequence

<400> SEQUENCE: 796

Gly Ser Ala Asn Val Tyr
1               5

<210> SEQ ID NO 797
<211> LENGTH: 6
<212> TYPE: PRT
<213> ORGANISM: Artificial sequence
<220> FEATURE:
<223> OTHER INFORMATION: synthetic sequence

<400> SEQUENCE: 797

Ala Ile Asp Asn Leu Phe
1               5

<210> SEQ ID NO 798
<211> LENGTH: 6
<212> TYPE: PRT
<213> ORGANISM: Artificial sequence
<220> FEATURE:
<223> OTHER INFORMATION: synthetic sequence

<400> SEQUENCE: 798

Ser Ile Asn Asp Leu Tyr
1               5

<210> SEQ ID NO 799
<211> LENGTH: 6
<212> TYPE: PRT
<213> ORGANISM: Artificial sequence
<220> FEATURE:
<223> OTHER INFORMATION: synthetic sequence

<400> SEQUENCE: 799

Leu Tyr Lys Lys Ile Ile
1               5

<210> SEQ ID NO 800
<211> LENGTH: 6
<212> TYPE: PRT
<213> ORGANISM: Artificial sequence
<220> FEATURE:
<223> OTHER INFORMATION: synthetic sequence

<400> SEQUENCE: 800

Thr Thr Gly Lys Tyr Tyr
1               5

<210> SEQ ID NO 801
<211> LENGTH: 6
<212> TYPE: PRT
<213> ORGANISM: Artificial sequence
<220> FEATURE:
<223> OTHER INFORMATION: synthetic sequence

<400> SEQUENCE: 801

Thr Tyr Lys Lys Tyr Tyr
1               5

<210> SEQ ID NO 802
<211> LENGTH: 6
<212> TYPE: PRT
<213> ORGANISM: Artificial sequence
<220> FEATURE:
<223> OTHER INFORMATION: synthetic sequence

<400> SEQUENCE: 802

Ala Ala Gly Lys Met Gly
1 5

<210> SEQ ID NO 803
<211> LENGTH: 6
<212> TYPE: PRT
<213> ORGANISM: Artificial sequence
<220> FEATURE:
<223> OTHER INFORMATION: synthetic sequence

<400> SEQUENCE: 803

Val Met Glu Lys Leu Gly
1 5

<210> SEQ ID NO 804
<211> LENGTH: 6
<212> TYPE: PRT
<213> ORGANISM: Artificial sequence
<220> FEATURE:
<223> OTHER INFORMATION: synthetic sequence

<400> SEQUENCE: 804

Leu Met Ser Lys Phe Gly
1 5

<210> SEQ ID NO 805
<211> LENGTH: 6
<212> TYPE: PRT
<213> ORGANISM: Artificial sequence
<220> FEATURE:
<223> OTHER INFORMATION: synthetic sequence

<400> SEQUENCE: 805

Ala Leu Asp Glu Ala Ile
1 5

<210> SEQ ID NO 806
<211> LENGTH: 6
<212> TYPE: PRT
<213> ORGANISM: Artificial sequence
<220> FEATURE:
<223> OTHER INFORMATION: synthetic sequence

<400> SEQUENCE: 806

Arg Arg Ala Glu Leu Gly
1 5

<210> SEQ ID NO 807
<211> LENGTH: 6
<212> TYPE: PRT
<213> ORGANISM: Artificial sequence
<220> FEATURE:
<223> OTHER INFORMATION: synthetic sequence

<400> SEQUENCE: 807

Ala Ile Asn Lys Val Ser
1 5

<210> SEQ ID NO 808
<211> LENGTH: 6
<212> TYPE: PRT
<213> ORGANISM: Artificial sequence
<220> FEATURE:
<223> OTHER INFORMATION: synthetic sequence

<400> SEQUENCE: 808

Ala Ala Gly Gln Ala Ile
1               5

<210> SEQ ID NO 809
<211> LENGTH: 6
<212> TYPE: PRT
<213> ORGANISM: Artificial sequence
<220> FEATURE:
<223> OTHER INFORMATION: synthetic sequence

<400> SEQUENCE: 809

Met Phe Lys Lys Ile Leu
1               5

<210> SEQ ID NO 810
<211> LENGTH: 6
<212> TYPE: PRT
<213> ORGANISM: Artificial sequence
<220> FEATURE:
<223> OTHER INFORMATION: synthetic sequence

<400> SEQUENCE: 810

Pro Pro Arg Lys Tyr Ile
1               5

<210> SEQ ID NO 811
<211> LENGTH: 6
<212> TYPE: PRT
<213> ORGANISM: Artificial sequence
<220> FEATURE:
<223> OTHER INFORMATION: synthetic sequence

<400> SEQUENCE: 811

Ser Leu Lys Gly Ala Met
1               5

<210> SEQ ID NO 812
<211> LENGTH: 6
<212> TYPE: PRT
<213> ORGANISM: Artificial sequence
<220> FEATURE:
<223> OTHER INFORMATION: synthetic sequence

<400> SEQUENCE: 812

Ala Met Gly Asn Ala Met
1               5

<210> SEQ ID NO 813
<211> LENGTH: 6
<212> TYPE: PRT
<213> ORGANISM: Artificial sequence
<220> FEATURE:
<223> OTHER INFORMATION: synthetic sequence

<400> SEQUENCE: 813

Leu Ala Asn Gln Ser Ala
1               5

<210> SEQ ID NO 814

<211> LENGTH: 6
<212> TYPE: PRT
<213> ORGANISM: Artificial sequence
<220> FEATURE:
<223> OTHER INFORMATION: synthetic sequence

<400> SEQUENCE: 814

Thr Ala Asp Ser Trp Phe
1               5

<210> SEQ ID NO 815
<211> LENGTH: 6
<212> TYPE: PRT
<213> ORGANISM: Artificial sequence
<220> FEATURE:
<223> OTHER INFORMATION: synthetic sequence

<400> SEQUENCE: 815

Ala Met Glu Lys Leu Ser
1               5

<210> SEQ ID NO 816
<211> LENGTH: 6
<212> TYPE: PRT
<213> ORGANISM: Artificial sequence
<220> FEATURE:
<223> OTHER INFORMATION: synthetic sequence

<400> SEQUENCE: 816

Ile Phe Lys Lys Ile Glu
1               5

<210> SEQ ID NO 817
<211> LENGTH: 6
<212> TYPE: PRT
<213> ORGANISM: Artificial sequence
<220> FEATURE:
<223> OTHER INFORMATION: synthetic sequence

<400> SEQUENCE: 817

Leu Leu Lys Lys Phe Ser
1               5

<210> SEQ ID NO 818
<211> LENGTH: 6
<212> TYPE: PRT
<213> ORGANISM: Artificial sequence
<220> FEATURE:
<223> OTHER INFORMATION: synthetic sequence

<400> SEQUENCE: 818

Ala Ile Lys Asp Thr Tyr
1               5

<210> SEQ ID NO 819
<211> LENGTH: 6
<212> TYPE: PRT
<213> ORGANISM: Artificial sequence
<220> FEATURE:
<223> OTHER INFORMATION: synthetic sequence

<400> SEQUENCE: 819

Phe Phe Lys Lys Ala Ala
1               5

<210> SEQ ID NO 820
<211> LENGTH: 6

<212> TYPE: PRT
<213> ORGANISM: Artificial sequence
<220> FEATURE:
<223> OTHER INFORMATION: synthetic sequence

<400> SEQUENCE: 820

Trp Lys Phe Lys Trp Arg
1               5

<210> SEQ ID NO 821
<211> LENGTH: 6
<212> TYPE: PRT
<213> ORGANISM: Artificial sequence
<220> FEATURE:
<223> OTHER INFORMATION: synthetic sequence

<400> SEQUENCE: 821

Phe Phe Gln Arg Phe Phe
1               5

<210> SEQ ID NO 822
<211> LENGTH: 6
<212> TYPE: PRT
<213> ORGANISM: Artificial sequence
<220> FEATURE:
<223> OTHER INFORMATION: synthetic sequence

<400> SEQUENCE: 822

Phe Phe Glu Ser Ile Phe
1               5

<210> SEQ ID NO 823
<211> LENGTH: 6
<212> TYPE: PRT
<213> ORGANISM: Artificial sequence
<220> FEATURE:
<223> OTHER INFORMATION: synthetic sequence

<400> SEQUENCE: 823

Trp Leu Thr Asn Met Ile
1               5

<210> SEQ ID NO 824
<211> LENGTH: 6
<212> TYPE: PRT
<213> ORGANISM: Artificial sequence
<220> FEATURE:
<223> OTHER INFORMATION: synthetic sequence

<400> SEQUENCE: 824

Phe Phe Ser Gly Phe Phe
1               5

<210> SEQ ID NO 825
<211> LENGTH: 6
<212> TYPE: PRT
<213> ORGANISM: Artificial sequence
<220> FEATURE:
<223> OTHER INFORMATION: synthetic sequence

<400> SEQUENCE: 825

Gly Trp Arg Thr Tyr Val
1               5

<210> SEQ ID NO 826
<211> LENGTH: 6
<212> TYPE: PRT

<213> ORGANISM: Artificial sequence
<220> FEATURE:
<223> OTHER INFORMATION: synthetic sequence

<400> SEQUENCE: 826

Phe Phe Ser Ser Phe Phe
1               5

<210> SEQ ID NO 827
<211> LENGTH: 6
<212> TYPE: PRT
<213> ORGANISM: Artificial sequence
<220> FEATURE:
<223> OTHER INFORMATION: synthetic sequence

<400> SEQUENCE: 827

Phe Phe Thr Thr Phe Phe
1               5

<210> SEQ ID NO 828
<211> LENGTH: 6
<212> TYPE: PRT
<213> ORGANISM: Artificial sequence
<220> FEATURE:
<223> OTHER INFORMATION: synthetic sequence

<400> SEQUENCE: 828

Phe Phe Asn Arg Phe Phe
1               5

<210> SEQ ID NO 829
<211> LENGTH: 6
<212> TYPE: PRT
<213> ORGANISM: Artificial sequence
<220> FEATURE:
<223> OTHER INFORMATION: synthetic sequence

<400> SEQUENCE: 829

Phe Phe Arg Arg Phe Phe
1               5

<210> SEQ ID NO 830
<211> LENGTH: 6
<212> TYPE: PRT
<213> ORGANISM: Artificial sequence
<220> FEATURE:
<223> OTHER INFORMATION: synthetic sequence

<400> SEQUENCE: 830

Phe Phe Pro Ser Leu Phe
1               5

<210> SEQ ID NO 831
<211> LENGTH: 6
<212> TYPE: PRT
<213> ORGANISM: Artificial sequence
<220> FEATURE:
<223> OTHER INFORMATION: synthetic sequence

<400> SEQUENCE: 831

Pro Tyr His His Ile Ile
1               5

<210> SEQ ID NO 832
<211> LENGTH: 6
<212> TYPE: PRT
<213> ORGANISM: Artificial sequence
<220> FEATURE:
<223> OTHER INFORMATION: synthetic sequence

<400> SEQUENCE: 832

Thr Leu His Arg Met Met
1 5

<210> SEQ ID NO 833
<211> LENGTH: 6
<212> TYPE: PRT
<213> ORGANISM: Artificial sequence
<220> FEATURE:
<223> OTHER INFORMATION: synthetic sequence

<400> SEQUENCE: 833

Val Val Arg His Trp Thr
1 5

<210> SEQ ID NO 834
<211> LENGTH: 6
<212> TYPE: PRT
<213> ORGANISM: Artificial sequence
<220> FEATURE:
<223> OTHER INFORMATION: synthetic sequence

<400> SEQUENCE: 834

Ala Phe Arg His Phe Ala
1 5

<210> SEQ ID NO 835
<211> LENGTH: 6
<212> TYPE: PRT
<213> ORGANISM: Artificial sequence
<220> FEATURE:
<223> OTHER INFORMATION: synthetic sequence

<400> SEQUENCE: 835

Leu Phe Thr Thr Leu Leu
1 5

<210> SEQ ID NO 836
<211> LENGTH: 6
<212> TYPE: PRT
<213> ORGANISM: Artificial sequence
<220> FEATURE:
<223> OTHER INFORMATION: synthetic sequence

<400> SEQUENCE: 836

Tyr Leu Arg Asp Val Tyr
1 5

<210> SEQ ID NO 837
<211> LENGTH: 6
<212> TYPE: PRT
<213> ORGANISM: Artificial sequence
<220> FEATURE:
<223> OTHER INFORMATION: synthetic sequence

<400> SEQUENCE: 837

Ala Tyr Arg His Phe Ala
1 5

<210> SEQ ID NO 838
<211> LENGTH: 6
<212> TYPE: PRT
<213> ORGANISM: Artificial sequence
<220> FEATURE:

<223> OTHER INFORMATION: synthetic sequence

<400> SEQUENCE: 838

Trp Ile Gln Arg Met Met
1 5

<210> SEQ ID NO 839
<211> LENGTH: 6
<212> TYPE: PRT
<213> ORGANISM: Artificial sequence
<220> FEATURE:
<223> OTHER INFORMATION: synthetic sequence

<400> SEQUENCE: 839

Ala Phe His Arg Tyr Ala
1 5

<210> SEQ ID NO 840
<211> LENGTH: 6
<212> TYPE: PRT
<213> ORGANISM: Artificial sequence
<220> FEATURE:
<223> OTHER INFORMATION: synthetic sequence

<400> SEQUENCE: 840

Phe Phe Gln Gln Phe Phe
1 5

<210> SEQ ID NO 841
<211> LENGTH: 6
<212> TYPE: PRT
<213> ORGANISM: Artificial sequence
<220> FEATURE:
<223> OTHER INFORMATION: synthetic sequence

<400> SEQUENCE: 841

Val Leu Ser Arg Leu Trp
1 5

<210> SEQ ID NO 842
<211> LENGTH: 6
<212> TYPE: PRT
<213> ORGANISM: Artificial sequence
<220> FEATURE:
<223> OTHER INFORMATION: synthetic sequence

<400> SEQUENCE: 842

Val Ala Val Arg Ile Trp
1 5

<210> SEQ ID NO 843
<211> LENGTH: 6
<212> TYPE: PRT
<213> ORGANISM: Artificial sequence
<220> FEATURE:
<223> OTHER INFORMATION: synthetic sequence

<400> SEQUENCE: 843

Leu Trp Asn Asn Leu Leu
1 5

<210> SEQ ID NO 844
<211> LENGTH: 6
<212> TYPE: PRT
<213> ORGANISM: Artificial sequence
<220> FEATURE:
<223> OTHER INFORMATION: synthetic sequence

<400> SEQUENCE: 844

Trp Leu Gly His Leu Met
1 5

<210> SEQ ID NO 845
<211> LENGTH: 6
<212> TYPE: PRT
<213> ORGANISM: Artificial sequence
<220> FEATURE:
<223> OTHER INFORMATION: synthetic sequence

<400> SEQUENCE: 845

Ile Leu Arg Arg Val Phe
1 5

<210> SEQ ID NO 846
<211> LENGTH: 6
<212> TYPE: PRT
<213> ORGANISM: Artificial sequence
<220> FEATURE:
<223> OTHER INFORMATION: synthetic sequence

<400> SEQUENCE: 846

Val Trp Arg Gly Ile Thr
1 5

<210> SEQ ID NO 847
<211> LENGTH: 6
<212> TYPE: PRT
<213> ORGANISM: Artificial sequence
<220> FEATURE:
<223> OTHER INFORMATION: synthetic sequence

<400> SEQUENCE: 847

Met Tyr Arg His Val Leu
1 5

<210> SEQ ID NO 848
<211> LENGTH: 6
<212> TYPE: PRT
<213> ORGANISM: Artificial sequence
<220> FEATURE:
<223> OTHER INFORMATION: synthetic sequence

<400> SEQUENCE: 848

Phe Phe Glu Gln Phe Phe
1 5

<210> SEQ ID NO 849
<211> LENGTH: 6
<212> TYPE: PRT
<213> ORGANISM: Artificial sequence
<220> FEATURE:
<223> OTHER INFORMATION: synthetic sequence

<400> SEQUENCE: 849

Phe Trp Arg Trp Phe Lys
1 5

<210> SEQ ID NO 850
<211> LENGTH: 6
<212> TYPE: PRT
<213> ORGANISM: Artificial sequence
<220> FEATURE:
<223> OTHER INFORMATION: synthetic sequence

<400> SEQUENCE: 850

Phe Phe Asn Gln Phe Phe
1 5

<210> SEQ ID NO 851
<211> LENGTH: 6
<212> TYPE: PRT
<213> ORGANISM: Artificial sequence
<220> FEATURE:
<223> OTHER INFORMATION: synthetic sequence

<400> SEQUENCE: 851

Tyr Leu Thr Glu Ile Ile
1 5

<210> SEQ ID NO 852
<211> LENGTH: 6
<212> TYPE: PRT
<213> ORGANISM: Artificial sequence
<220> FEATURE:
<223> OTHER INFORMATION: synthetic sequence

<400> SEQUENCE: 852

Leu Leu Asp Arg Phe Phe
1 5

<210> SEQ ID NO 853
<211> LENGTH: 6
<212> TYPE: PRT
<213> ORGANISM: Artificial sequence
<220> FEATURE:
<223> OTHER INFORMATION: synthetic sequence

<400> SEQUENCE: 853

Ile Trp Asn Asn Met Thr
1 5

<210> SEQ ID NO 854
<211> LENGTH: 6
<212> TYPE: PRT
<213> ORGANISM: Artificial sequence
<220> FEATURE:
<223> OTHER INFORMATION: synthetic sequence

<400> SEQUENCE: 854

Phe Phe Arg Lys Phe Phe
1 5

<210> SEQ ID NO 855
<211> LENGTH: 6
<212> TYPE: PRT
<213> ORGANISM: Artificial sequence
<220> FEATURE:
<223> OTHER INFORMATION: synthetic sequence

<400> SEQUENCE: 855

Trp Pro Glu Arg Val Phe
1 5

<210> SEQ ID NO 856
<211> LENGTH: 6
<212> TYPE: PRT
<213> ORGANISM: Artificial sequence
<220> FEATURE:
<223> OTHER INFORMATION: synthetic sequence

<400> SEQUENCE: 856

Trp Ser His Gly Ile Tyr
1 5

<210> SEQ ID NO 857
<211> LENGTH: 6
<212> TYPE: PRT
<213> ORGANISM: Artificial sequence
<220> FEATURE:
<223> OTHER INFORMATION: synthetic sequence

<400> SEQUENCE: 857

Ala Phe Asn Arg Phe Val
1 5

<210> SEQ ID NO 858
<211> LENGTH: 6
<212> TYPE: PRT
<213> ORGANISM: Artificial sequence
<220> FEATURE:
<223> OTHER INFORMATION: synthetic sequence

<400> SEQUENCE: 858

Ala Thr Arg His Ile Ile
1 5

<210> SEQ ID NO 859
<211> LENGTH: 6
<212> TYPE: PRT
<213> ORGANISM: Artificial sequence
<220> FEATURE:
<223> OTHER INFORMATION: synthetic sequence

<400> SEQUENCE: 859

Val Val Glu Arg Met Val
1 5

<210> SEQ ID NO 860
<211> LENGTH: 6
<212> TYPE: PRT
<213> ORGANISM: Artificial sequence
<220> FEATURE:
<223> OTHER INFORMATION: synthetic sequence

<400> SEQUENCE: 860

Phe Leu His Lys Thr Leu
1 5

<210> SEQ ID NO 861
<211> LENGTH: 6
<212> TYPE: PRT
<213> ORGANISM: Artificial sequence
<220> FEATURE:
<223> OTHER INFORMATION: synthetic sequence

<400> SEQUENCE: 861

Lys Phe Trp Arg Trp Phe
1 5

<210> SEQ ID NO 862
<211> LENGTH: 6
<212> TYPE: PRT
<213> ORGANISM: Artificial sequence
<220> FEATURE:
<223> OTHER INFORMATION: synthetic sequence

<400> SEQUENCE: 862

Ala Thr Arg Asn Phe Val
1 5

<210> SEQ ID NO 863
<211> LENGTH: 6
<212> TYPE: PRT
<213> ORGANISM: Artificial sequence
<220> FEATURE:
<223> OTHER INFORMATION: synthetic sequence

<400> SEQUENCE: 863

Phe Val Arg Glu Ser Phe
1 5

<210> SEQ ID NO 864
<211> LENGTH: 6
<212> TYPE: PRT
<213> ORGANISM: Artificial sequence
<220> FEATURE:
<223> OTHER INFORMATION: synthetic sequence

<400> SEQUENCE: 864

Trp Tyr Ser Glu Ile Met
1 5

<210> SEQ ID NO 865
<211> LENGTH: 6
<212> TYPE: PRT
<213> ORGANISM: Artificial sequence
<220> FEATURE:
<223> OTHER INFORMATION: synthetic sequence

<400> SEQUENCE: 865

Tyr Leu Gly Arg Tyr Met
1 5

<210> SEQ ID NO 866
<211> LENGTH: 6
<212> TYPE: PRT
<213> ORGANISM: Artificial sequence
<220> FEATURE:
<223> OTHER INFORMATION: synthetic sequence

<400> SEQUENCE: 866

Leu Ala Gln His Ile Val
1 5

<210> SEQ ID NO 867
<211> LENGTH: 6
<212> TYPE: PRT
<213> ORGANISM: Artificial sequence
<220> FEATURE:
<223> OTHER INFORMATION: synthetic sequence

<400> SEQUENCE: 867

Ile Ser Asp Arg Met Leu
1 5

<210> SEQ ID NO 868
<211> LENGTH: 6
<212> TYPE: PRT
<213> ORGANISM: Artificial sequence
<220> FEATURE:
<223> OTHER INFORMATION: synthetic sequence

<400> SEQUENCE: 868

Val Met Arg Asn Phe Val 1 5

<210> SEQ ID NO 869
<211> LENGTH: 6
<212> TYPE: PRT
<213> ORGANISM: Artificial sequence
<220> FEATURE:
<223> OTHER INFORMATION: synthetic sequence

<400> SEQUENCE: 869

Val Phe Arg Glu Met Tyr
1 5

<210> SEQ ID NO 870
<211> LENGTH: 6
<212> TYPE: PRT
<213> ORGANISM: Artificial sequence
<220> FEATURE:
<223> OTHER INFORMATION: synthetic sequence

<400> SEQUENCE: 870

Ala Tyr Asn Ser Leu Ile
1 5

<210> SEQ ID NO 871
<211> LENGTH: 6
<212> TYPE: PRT
<213> ORGANISM: Artificial sequence
<220> FEATURE:
<223> OTHER INFORMATION: synthetic sequence

<400> SEQUENCE: 871

Ile Met Glu Arg Ile Phe
1 5

<210> SEQ ID NO 872
<211> LENGTH: 6
<212> TYPE: PRT
<213> ORGANISM: Artificial sequence
<220> FEATURE:
<223> OTHER INFORMATION: synthetic sequence

<400> SEQUENCE: 872

Gly Tyr Thr Arg Ile Leu
1 5

<210> SEQ ID NO 873
<211> LENGTH: 6
<212> TYPE: PRT
<213> ORGANISM: Artificial sequence
<220> FEATURE:
<223> OTHER INFORMATION: synthetic sequence

<400> SEQUENCE: 873

Phe Phe Lys Arg Phe Phe
1 5

<210> SEQ ID NO 874
<211> LENGTH: 6
<212> TYPE: PRT
<213> ORGANISM: Artificial sequence
<220> FEATURE:
<223> OTHER INFORMATION: synthetic sequence

<400> SEQUENCE: 874

Ala Trp Arg Gln Ala Ala
1 5

<210> SEQ ID NO 875
<211> LENGTH: 6
<212> TYPE: PRT
<213> ORGANISM: Artificial sequence
<220> FEATURE:
<223> OTHER INFORMATION: synthetic sequence

<400> SEQUENCE: 875

Trp Val Gln Arg Val Val
1               5

<210> SEQ ID NO 876
<211> LENGTH: 6
<212> TYPE: PRT
<213> ORGANISM: Artificial sequence
<220> FEATURE:
<223> OTHER INFORMATION: synthetic sequence

<400> SEQUENCE: 876

Ser Gly His His Leu Leu
1               5

<210> SEQ ID NO 877
<211> LENGTH: 6
<212> TYPE: PRT
<213> ORGANISM: Artificial sequence
<220> FEATURE:
<223> OTHER INFORMATION: synthetic sequence

<400> SEQUENCE: 877

Met Val Glu Arg Met Val
1               5

<210> SEQ ID NO 878
<211> LENGTH: 6
<212> TYPE: PRT
<213> ORGANISM: Artificial sequence
<220> FEATURE:
<223> OTHER INFORMATION: synthetic sequence

<400> SEQUENCE: 878

Ile Met Arg Asp Met Tyr
1               5

<210> SEQ ID NO 879
<211> LENGTH: 6
<212> TYPE: PRT
<213> ORGANISM: Artificial sequence
<220> FEATURE:
<223> OTHER INFORMATION: synthetic sequence

<400> SEQUENCE: 879

Phe Phe Asn Lys Phe Phe
1               5

<210> SEQ ID NO 880
<211> LENGTH: 6
<212> TYPE: PRT
<213> ORGANISM: Artificial sequence
<220> FEATURE:
<223> OTHER INFORMATION: synthetic sequence

<400> SEQUENCE: 880

Tyr Val Thr Asp Leu Pro
1               5

<210> SEQ ID NO 881
<211> LENGTH: 6
<212> TYPE: PRT
<213> ORGANISM: Artificial sequence
<220> FEATURE:
<223> OTHER INFORMATION: synthetic sequence

<400> SEQUENCE: 881

Tyr Phe His Gln Pro Leu
1               5

<210> SEQ ID NO 882
<211> LENGTH: 6
<212> TYPE: PRT
<213> ORGANISM: Artificial sequence
<220> FEATURE:
<223> OTHER INFORMATION: synthetic sequence

<400> SEQUENCE: 882

Ala Ala Arg Asn Ile Trp
1               5

<210> SEQ ID NO 883
<211> LENGTH: 6
<212> TYPE: PRT
<213> ORGANISM: Artificial sequence
<220> FEATURE:
<223> OTHER INFORMATION: synthetic sequence

<400> SEQUENCE: 883

Phe Leu His Ser Ala Lys
1               5

<210> SEQ ID NO 884
<211> LENGTH: 6
<212> TYPE: PRT
<213> ORGANISM: Artificial sequence
<220> FEATURE:
<223> OTHER INFORMATION: synthetic sequence

<400> SEQUENCE: 884

Thr Tyr His Glu Phe Ala
1               5

<210> SEQ ID NO 885
<211> LENGTH: 6
<212> TYPE: PRT
<213> ORGANISM: Artificial sequence
<220> FEATURE:
<223> OTHER INFORMATION: synthetic sequence

<400> SEQUENCE: 885

Val Tyr Thr Asp Phe Tyr
1               5

<210> SEQ ID NO 886
<211> LENGTH: 6
<212> TYPE: PRT
<213> ORGANISM: Artificial sequence
<220> FEATURE:
<223> OTHER INFORMATION: synthetic sequence

<400> SEQUENCE: 886

Pro Val Arg Gln Leu Leu
1               5

<210> SEQ ID NO 887
<211> LENGTH: 6
<212> TYPE: PRT
<213> ORGANISM: Artificial sequence
<220> FEATURE:
<223> OTHER INFORMATION: synthetic sequence

<400> SEQUENCE: 887

Leu Phe Arg Arg Phe Gly
1 5

<210> SEQ ID NO 888
<211> LENGTH: 6
<212> TYPE: PRT
<213> ORGANISM: Artificial sequence
<220> FEATURE:
<223> OTHER INFORMATION: synthetic sequence

<400> SEQUENCE: 888

Phe Phe Glu Thr Ala Leu
1 5

<210> SEQ ID NO 889
<211> LENGTH: 6
<212> TYPE: PRT
<213> ORGANISM: Artificial sequence
<220> FEATURE:
<223> OTHER INFORMATION: synthetic sequence

<400> SEQUENCE: 889

Phe Phe Glu Ser Ala Leu
1 5

<210> SEQ ID NO 890
<211> LENGTH: 6
<212> TYPE: PRT
<213> ORGANISM: Artificial sequence
<220> FEATURE:
<223> OTHER INFORMATION: synthetic sequence

<400> SEQUENCE: 890

Leu Tyr Asp Asn Leu Val
1 5

<210> SEQ ID NO 891
<211> LENGTH: 6
<212> TYPE: PRT
<213> ORGANISM: Artificial sequence
<220> FEATURE:
<223> OTHER INFORMATION: synthetic sequence

<400> SEQUENCE: 891

Met Tyr Gln Gln Leu Phe
1 5

<210> SEQ ID NO 892
<211> LENGTH: 6
<212> TYPE: PRT
<213> ORGANISM: Artificial sequence
<220> FEATURE:
<223> OTHER INFORMATION: synthetic sequence

<400> SEQUENCE: 892

Ile Met Glu His Val Leu
1 5

<210> SEQ ID NO 893

<211> LENGTH: 6
<212> TYPE: PRT
<213> ORGANISM: Artificial sequence
<220> FEATURE:
<223> OTHER INFORMATION: synthetic sequence

<400> SEQUENCE: 893

Ile Val Arg Arg Ala Asp
1               5

<210> SEQ ID NO 894
<211> LENGTH: 6
<212> TYPE: PRT
<213> ORGANISM: Artificial sequence
<220> FEATURE:
<223> OTHER INFORMATION: synthetic sequence

<400> SEQUENCE: 894

Ser Tyr Gln Asn Phe Leu
1               5

<210> SEQ ID NO 895
<211> LENGTH: 6
<212> TYPE: PRT
<213> ORGANISM: Artificial sequence
<220> FEATURE:
<223> OTHER INFORMATION: synthetic sequence

<400> SEQUENCE: 895

Tyr Tyr Lys Gln Leu Tyr
1               5

<210> SEQ ID NO 896
<211> LENGTH: 6
<212> TYPE: PRT
<213> ORGANISM: Artificial sequence
<220> FEATURE:
<223> OTHER INFORMATION: synthetic sequence

<400> SEQUENCE: 896

Ala Ala Arg Asp Met Met
1               5

<210> SEQ ID NO 897
<211> LENGTH: 6
<212> TYPE: PRT
<213> ORGANISM: Artificial sequence
<220> FEATURE:
<223> OTHER INFORMATION: synthetic sequence

<400> SEQUENCE: 897

Thr Ala Arg Gly Tyr Leu
1               5

<210> SEQ ID NO 898
<211> LENGTH: 6
<212> TYPE: PRT
<213> ORGANISM: Artificial sequence
<220> FEATURE:
<223> OTHER INFORMATION: synthetic sequence

<400> SEQUENCE: 898

Met Leu Asn Lys Ile Pro
1               5

<210> SEQ ID NO 899
<211> LENGTH: 6

<212> TYPE: PRT
<213> ORGANISM: Artificial sequence
<220> FEATURE:
<223> OTHER INFORMATION: synthetic sequence

<400> SEQUENCE: 899

Thr Leu Asn Thr Leu Phe
1 5

<210> SEQ ID NO 900
<211> LENGTH: 6
<212> TYPE: PRT
<213> ORGANISM: Artificial sequence
<220> FEATURE:
<223> OTHER INFORMATION: synthetic sequence

<400> SEQUENCE: 900

Ile Leu Glu Asn Tyr Tyr
1 5

<210> SEQ ID NO 901
<211> LENGTH: 6
<212> TYPE: PRT
<213> ORGANISM: Artificial sequence
<220> FEATURE:
<223> OTHER INFORMATION: synthetic sequence

<400> SEQUENCE: 901

Phe Pro Asp Asn Met Leu
1 5

<210> SEQ ID NO 902
<211> LENGTH: 6
<212> TYPE: PRT
<213> ORGANISM: Artificial sequence
<220> FEATURE:
<223> OTHER INFORMATION: synthetic sequence

<400> SEQUENCE: 902

Phe Leu Ser Gln Leu Ala
1 5

<210> SEQ ID NO 903
<211> LENGTH: 6
<212> TYPE: PRT
<213> ORGANISM: Artificial sequence
<220> FEATURE:
<223> OTHER INFORMATION: synthetic sequence

<400> SEQUENCE: 903

Phe Gly Arg Arg Ile Ala
1 5

<210> SEQ ID NO 904
<211> LENGTH: 6
<212> TYPE: PRT
<213> ORGANISM: Artificial sequence
<220> FEATURE:
<223> OTHER INFORMATION: synthetic sequence

<400> SEQUENCE: 904

Phe Phe Asp Gln Leu Ile
1 5

<210> SEQ ID NO 905
<211> LENGTH: 6
<212> TYPE: PRT

<213> ORGANISM: Artificial sequence
<220> FEATURE:
<223> OTHER INFORMATION: synthetic sequence

<400> SEQUENCE: 905

Ala Tyr Asp Arg Val Met
1 5

<210> SEQ ID NO 906
<211> LENGTH: 6
<212> TYPE: PRT
<213> ORGANISM: Artificial sequence
<220> FEATURE:
<223> OTHER INFORMATION: synthetic sequence

<400> SEQUENCE: 906

Ala Leu Ser Thr Pro Val
1 5

<210> SEQ ID NO 907
<211> LENGTH: 6
<212> TYPE: PRT
<213> ORGANISM: Artificial sequence
<220> FEATURE:
<223> OTHER INFORMATION: synthetic sequence

<400> SEQUENCE: 907

Trp Val Arg Arg Val Val
1 5

<210> SEQ ID NO 908
<211> LENGTH: 6
<212> TYPE: PRT
<213> ORGANISM: Artificial sequence
<220> FEATURE:
<223> OTHER INFORMATION: synthetic sequence

<400> SEQUENCE: 908

Ala Thr Glu His Phe Phe
1 5

<210> SEQ ID NO 909
<211> LENGTH: 6
<212> TYPE: PRT
<213> ORGANISM: Artificial sequence
<220> FEATURE:
<223> OTHER INFORMATION: synthetic sequence

<400> SEQUENCE: 909

Phe Tyr Asp Gln Leu Met
1 5

<210> SEQ ID NO 910
<211> LENGTH: 6
<212> TYPE: PRT
<213> ORGANISM: Artificial sequence
<220> FEATURE:
<223> OTHER INFORMATION: synthetic sequence

<400> SEQUENCE: 910

Tyr Thr Lys Glu Leu Phe
1 5

<210> SEQ ID NO 911
<211> LENGTH: 6
<212> TYPE: PRT
<213> ORGANISM: Artificial sequence
<220> FEATURE:
<223> OTHER INFORMATION: synthetic sequence

<400> SEQUENCE: 911

Met Val Arg Asn Tyr Tyr
1 5

<210> SEQ ID NO 912
<211> LENGTH: 6
<212> TYPE: PRT
<213> ORGANISM: Artificial sequence
<220> FEATURE:
<223> OTHER INFORMATION: synthetic sequence

<400> SEQUENCE: 912

Leu Ile Arg Glu Ala Met
1 5

<210> SEQ ID NO 913
<211> LENGTH: 6
<212> TYPE: PRT
<213> ORGANISM: Artificial sequence
<220> FEATURE:
<223> OTHER INFORMATION: synthetic sequence

<400> SEQUENCE: 913

Ala Tyr Asp Ser Met Thr
1 5

<210> SEQ ID NO 914
<211> LENGTH: 6
<212> TYPE: PRT
<213> ORGANISM: Artificial sequence
<220> FEATURE:
<223> OTHER INFORMATION: synthetic sequence

<400> SEQUENCE: 914

Ile Ala Asn Arg Phe Thr
1 5

<210> SEQ ID NO 915
<211> LENGTH: 6
<212> TYPE: PRT
<213> ORGANISM: Artificial sequence
<220> FEATURE:
<223> OTHER INFORMATION: synthetic sequence

<400> SEQUENCE: 915

Leu Leu Gly Lys Leu Met
1 5

<210> SEQ ID NO 916
<211> LENGTH: 6
<212> TYPE: PRT
<213> ORGANISM: Artificial sequence
<220> FEATURE:
<223> OTHER INFORMATION: synthetic sequence

<400> SEQUENCE: 916

Leu Leu Lys Ser Leu Ile
1 5

<210> SEQ ID NO 917
<211> LENGTH: 6
<212> TYPE: PRT
<213> ORGANISM: Artificial sequence
<220> FEATURE:

<223> OTHER INFORMATION: synthetic sequence

<400> SEQUENCE: 917

Tyr Phe Asp Gly Phe Val
1               5

<210> SEQ ID NO 918
<211> LENGTH: 6
<212> TYPE: PRT
<213> ORGANISM: Artificial sequence
<220> FEATURE:
<223> OTHER INFORMATION: synthetic sequence

<400> SEQUENCE: 918

Met Ala Ser Glu Ile Val
1               5

<210> SEQ ID NO 919
<211> LENGTH: 6
<212> TYPE: PRT
<213> ORGANISM: Artificial sequence
<220> FEATURE:
<223> OTHER INFORMATION: synthetic sequence

<400> SEQUENCE: 919

Tyr Thr Gln Arg Leu Ala
1               5

<210> SEQ ID NO 920
<211> LENGTH: 6
<212> TYPE: PRT
<213> ORGANISM: Artificial sequence
<220> FEATURE:
<223> OTHER INFORMATION: synthetic sequence

<400> SEQUENCE: 920

Gly Trp Asp Ser Ile Ile
1               5

<210> SEQ ID NO 921
<211> LENGTH: 6
<212> TYPE: PRT
<213> ORGANISM: Artificial sequence
<220> FEATURE:
<223> OTHER INFORMATION: synthetic sequence

<400> SEQUENCE: 921

Ala Val Ser His Ala Ala
1               5

<210> SEQ ID NO 922
<211> LENGTH: 6
<212> TYPE: PRT
<213> ORGANISM: Artificial sequence
<220> FEATURE:
<223> OTHER INFORMATION: synthetic sequence

<400> SEQUENCE: 922

Val Gly Asp Asp Tyr Tyr
1               5

<210> SEQ ID NO 923
<211> LENGTH: 6
<212> TYPE: PRT
<213> ORGANISM: Artificial sequence
<220> FEATURE:
<223> OTHER INFORMATION: synthetic sequence

<400> SEQUENCE: 923

Ile Ile Asn Asn Phe Ile
1 5

<210> SEQ ID NO 924
<211> LENGTH: 6
<212> TYPE: PRT
<213> ORGANISM: Artificial sequence
<220> FEATURE:
<223> OTHER INFORMATION: synthetic sequence

<400> SEQUENCE: 924

Met Tyr Glu Ser Met Ala
1 5

<210> SEQ ID NO 925
<211> LENGTH: 6
<212> TYPE: PRT
<213> ORGANISM: Artificial sequence
<220> FEATURE:
<223> OTHER INFORMATION: synthetic sequence

<400> SEQUENCE: 925

Ile Leu Asp Asn Tyr Tyr
1 5

<210> SEQ ID NO 926
<211> LENGTH: 6
<212> TYPE: PRT
<213> ORGANISM: Artificial sequence
<220> FEATURE:
<223> OTHER INFORMATION: synthetic sequence

<400> SEQUENCE: 926

Ala Leu Gln Thr Ala Val
1 5

<210> SEQ ID NO 927
<211> LENGTH: 6
<212> TYPE: PRT
<213> ORGANISM: Artificial sequence
<220> FEATURE:
<223> OTHER INFORMATION: synthetic sequence

<400> SEQUENCE: 927

Phe Ile Thr Asn Tyr Leu
1 5

<210> SEQ ID NO 928
<211> LENGTH: 6
<212> TYPE: PRT
<213> ORGANISM: Artificial sequence
<220> FEATURE:
<223> OTHER INFORMATION: synthetic sequence

<400> SEQUENCE: 928

Gly Trp Asp Ser Ile Val
1 5

<210> SEQ ID NO 929
<211> LENGTH: 6
<212> TYPE: PRT
<213> ORGANISM: Artificial sequence
<220> FEATURE:
<223> OTHER INFORMATION: synthetic sequence -continued

<400> SEQUENCE: 929

Met Met Thr Ser Leu Ile
1 5

<210> SEQ ID NO 930
<211> LENGTH: 6
<212> TYPE: PRT
<213> ORGANISM: Artificial sequence
<220> FEATURE:
<223> OTHER INFORMATION: synthetic sequence

<400> SEQUENCE: 930

Tyr Phe Asp Gly Leu Val
1 5

<210> SEQ ID NO 931
<211> LENGTH: 6
<212> TYPE: PRT
<213> ORGANISM: Artificial sequence
<220> FEATURE:
<223> OTHER INFORMATION: synthetic sequence

<400> SEQUENCE: 931

Met Met Thr Asp Tyr Ile
1 5

<210> SEQ ID NO 932
<211> LENGTH: 6
<212> TYPE: PRT
<213> ORGANISM: Artificial sequence
<220> FEATURE:
<223> OTHER INFORMATION: synthetic sequence

<400> SEQUENCE: 932

Met Thr Arg Asp Tyr Tyr
1 5

<210> SEQ ID NO 933
<211> LENGTH: 6
<212> TYPE: PRT
<213> ORGANISM: Artificial sequence
<220> FEATURE:
<223> OTHER INFORMATION: synthetic sequence

<400> SEQUENCE: 933

Thr Tyr Gln Lys Tyr Leu
1 5

<210> SEQ ID NO 934
<211> LENGTH: 6
<212> TYPE: PRT
<213> ORGANISM: Artificial sequence
<220> FEATURE:
<223> OTHER INFORMATION: synthetic sequence

<400> SEQUENCE: 934

Ile Leu Gln Gln Ala Ala
1 5

<210> SEQ ID NO 935
<211> LENGTH: 6
<212> TYPE: PRT
<213> ORGANISM: Artificial sequence
<220> FEATURE:
<223> OTHER INFORMATION: synthetic sequence

<400> SEQUENCE: 935

Leu Ile Ser Asn Tyr Val
1 5

<210> SEQ ID NO 936
<211> LENGTH: 6
<212> TYPE: PRT
<213> ORGANISM: Artificial sequence
<220> FEATURE:
<223> OTHER INFORMATION: synthetic sequence

<400> SEQUENCE: 936

Phe Tyr Glu Lys Leu Ile
1 5

<210> SEQ ID NO 937
<211> LENGTH: 6
<212> TYPE: PRT
<213> ORGANISM: Artificial sequence
<220> FEATURE:
<223> OTHER INFORMATION: synthetic sequence

<400> SEQUENCE: 937

Phe Tyr Ser Ser Ala Gly
1 5

<210> SEQ ID NO 938
<211> LENGTH: 6
<212> TYPE: PRT
<213> ORGANISM: Artificial sequence
<220> FEATURE:
<223> OTHER INFORMATION: synthetic sequence

<400> SEQUENCE: 938

Phe Ile Gln Lys Gly Tyr
1 5

<210> SEQ ID NO 939
<211> LENGTH: 6
<212> TYPE: PRT
<213> ORGANISM: Artificial sequence
<220> FEATURE:
<223> OTHER INFORMATION: synthetic sequence

<400> SEQUENCE: 939

Ala Met Glu Arg Ile Ser
1 5

<210> SEQ ID NO 940
<211> LENGTH: 6
<212> TYPE: PRT
<213> ORGANISM: Artificial sequence
<220> FEATURE:
<223> OTHER INFORMATION: synthetic sequence

<400> SEQUENCE: 940

Leu Leu Lys Asp Val Leu
1 5

<210> SEQ ID NO 941
<211> LENGTH: 6
<212> TYPE: PRT
<213> ORGANISM: Artificial sequence
<220> FEATURE:
<223> OTHER INFORMATION: synthetic sequence

<400> SEQUENCE: 941

Met Leu His Asn Leu Ala
1 5

<210> SEQ ID NO 942
<211> LENGTH: 6
<212> TYPE: PRT
<213> ORGANISM: Artificial sequence
<220> FEATURE:
<223> OTHER INFORMATION: synthetic sequence

<400> SEQUENCE: 942

Tyr Phe Lys Arg Val Phe
1 5

<210> SEQ ID NO 943
<211> LENGTH: 5
<212> TYPE: PRT
<213> ORGANISM: Artificial sequence
<220> FEATURE:
<223> OTHER INFORMATION: synthetic sequence

<400> SEQUENCE: 943

Met Lys Arg Val Ile
1 5

<210> SEQ ID NO 944
<211> LENGTH: 6
<212> TYPE: PRT
<213> ORGANISM: Artificial sequence
<220> FEATURE:
<223> OTHER INFORMATION: synthetic sequence

<400> SEQUENCE: 944

Phe Ser Glu Gln Phe Leu
1 5

<210> SEQ ID NO 945
<211> LENGTH: 6
<212> TYPE: PRT
<213> ORGANISM: Artificial sequence
<220> FEATURE:
<223> OTHER INFORMATION: synthetic sequence

<400> SEQUENCE: 945

Pro Phe Arg Lys Trp Leu
1 5

<210> SEQ ID NO 946
<211> LENGTH: 6
<212> TYPE: PRT
<213> ORGANISM: Artificial sequence
<220> FEATURE:
<223> OTHER INFORMATION: synthetic sequence

<400> SEQUENCE: 946

Gly Gly Asn Lys Leu Leu
1 5

<210> SEQ ID NO 947
<211> LENGTH: 6
<212> TYPE: PRT
<213> ORGANISM: Artificial sequence
<220> FEATURE:
<223> OTHER INFORMATION: synthetic sequence

<400> SEQUENCE: 947

Gly Ile Arg Asp Ala Ile 1 5

<210> SEQ ID NO 948
<211> LENGTH: 6
<212> TYPE: PRT
<213> ORGANISM: Artificial sequence
<220> FEATURE:
<223> OTHER INFORMATION: synthetic sequence

<400> SEQUENCE: 948

Tyr Trp Ser Glu Tyr Phe
1 5

<210> SEQ ID NO 949
<211> LENGTH: 6
<212> TYPE: PRT
<213> ORGANISM: Artificial sequence
<220> FEATURE:
<223> OTHER INFORMATION: synthetic sequence

<400> SEQUENCE: 949

Ile Leu Arg Lys Ala Ile
1 5

<210> SEQ ID NO 950
<211> LENGTH: 6
<212> TYPE: PRT
<213> ORGANISM: Artificial sequence
<220> FEATURE:
<223> OTHER INFORMATION: synthetic sequence

<400> SEQUENCE: 950

Phe Ile Asp Asp Tyr Ile
1 5

<210> SEQ ID NO 951
<211> LENGTH: 6
<212> TYPE: PRT
<213> ORGANISM: Artificial sequence
<220> FEATURE:
<223> OTHER INFORMATION: synthetic sequence

<400> SEQUENCE: 951

Phe Leu Lys Arg Leu Leu
1 5

<210> SEQ ID NO 952
<211> LENGTH: 6
<212> TYPE: PRT
<213> ORGANISM: Artificial sequence
<220> FEATURE:
<223> OTHER INFORMATION: synthetic sequence

<400> SEQUENCE: 952

Tyr Phe Arg Arg Thr Gly
1 5

<210> SEQ ID NO 953
<211> LENGTH: 6
<212> TYPE: PRT
<213> ORGANISM: Artificial sequence
<220> FEATURE:
<223> OTHER INFORMATION: synthetic sequence

<400> SEQUENCE: 953

Val Tyr Glu Asn Val Val
1 5

<210> SEQ ID NO 954
<211> LENGTH: 6
<212> TYPE: PRT
<213> ORGANISM: Artificial sequence
<220> FEATURE:
<223> OTHER INFORMATION: synthetic sequence

<400> SEQUENCE: 954

Thr Ala Gln Asn Trp Ile
1               5

<210> SEQ ID NO 955
<211> LENGTH: 6
<212> TYPE: PRT
<213> ORGANISM: Artificial sequence
<220> FEATURE:
<223> OTHER INFORMATION: synthetic sequence

<400> SEQUENCE: 955

Ile Leu Glu Asp Val Ala
1               5

<210> SEQ ID NO 956
<211> LENGTH: 6
<212> TYPE: PRT
<213> ORGANISM: Artificial sequence
<220> FEATURE:
<223> OTHER INFORMATION: synthetic sequence

<400> SEQUENCE: 956

Leu Ile Lys Ser Trp Val
1               5

<210> SEQ ID NO 957
<211> LENGTH: 6
<212> TYPE: PRT
<213> ORGANISM: Artificial sequence
<220> FEATURE:
<223> OTHER INFORMATION: synthetic sequence

<400> SEQUENCE: 957

Leu Phe Gly Glu Leu Leu
1               5

<210> SEQ ID NO 958
<211> LENGTH: 6
<212> TYPE: PRT
<213> ORGANISM: Artificial sequence
<220> FEATURE:
<223> OTHER INFORMATION: synthetic sequence

<400> SEQUENCE: 958

Gly Ile Lys Arg Leu Phe
1               5

<210> SEQ ID NO 959
<211> LENGTH: 6
<212> TYPE: PRT
<213> ORGANISM: Artificial sequence
<220> FEATURE:
<223> OTHER INFORMATION: synthetic sequence

<400> SEQUENCE: 959

Met Ala Lys Glu Met Met
1               5

<210> SEQ ID NO 960
<211> LENGTH: 6
<212> TYPE: PRT
<213> ORGANISM: Artificial sequence
<220> FEATURE:
<223> OTHER INFORMATION: synthetic sequence

<400> SEQUENCE: 960

Thr Ala Thr Asn Tyr Met
1 5

<210> SEQ ID NO 961
<211> LENGTH: 6
<212> TYPE: PRT
<213> ORGANISM: Artificial sequence
<220> FEATURE:
<223> OTHER INFORMATION: synthetic sequence

<400> SEQUENCE: 961

Gly Phe Lys Asn Met Phe
1 5

<210> SEQ ID NO 962
<211> LENGTH: 6
<212> TYPE: PRT
<213> ORGANISM: Artificial sequence
<220> FEATURE:
<223> OTHER INFORMATION: synthetic sequence

<400> SEQUENCE: 962

Ser Leu Asn Asp Leu Trp
1 5

<210> SEQ ID NO 963
<211> LENGTH: 6
<212> TYPE: PRT
<213> ORGANISM: Artificial sequence
<220> FEATURE:
<223> OTHER INFORMATION: synthetic sequence

<400> SEQUENCE: 963

Ala Gly Gln Lys Leu Met
1 5

<210> SEQ ID NO 964
<211> LENGTH: 6
<212> TYPE: PRT
<213> ORGANISM: Artificial sequence
<220> FEATURE:
<223> OTHER INFORMATION: synthetic sequence

<400> SEQUENCE: 964

Ser Leu Asp Asp Ile Trp
1 5

<210> SEQ ID NO 965
<211> LENGTH: 6
<212> TYPE: PRT
<213> ORGANISM: Artificial sequence
<220> FEATURE:
<223> OTHER INFORMATION: synthetic sequence

<400> SEQUENCE: 965

Val Leu Gln Gln Ala Gly
1 5

<210> SEQ ID NO 966
<211> LENGTH: 6
<212> TYPE: PRT
<213> ORGANISM: Artificial sequence
<220> FEATURE:
<223> OTHER INFORMATION: synthetic sequence

<400> SEQUENCE: 966

Ile Ile Arg Asp Ala Gly
1               5

<210> SEQ ID NO 967
<211> LENGTH: 6
<212> TYPE: PRT
<213> ORGANISM: Artificial sequence
<220> FEATURE:
<223> OTHER INFORMATION: synthetic sequence

<400> SEQUENCE: 967

Ile Leu Asp Ser Leu Thr
1               5

<210> SEQ ID NO 968
<211> LENGTH: 6
<212> TYPE: PRT
<213> ORGANISM: Artificial sequence
<220> FEATURE:
<223> OTHER INFORMATION: synthetic sequence

<400> SEQUENCE: 968

Ser Thr Gln Asn Val Leu
1               5

<210> SEQ ID NO 969
<211> LENGTH: 6
<212> TYPE: PRT
<213> ORGANISM: Artificial sequence
<220> FEATURE:
<223> OTHER INFORMATION: synthetic sequence

<400> SEQUENCE: 969

Pro Leu Asp Gln Leu Leu
1               5

<210> SEQ ID NO 970
<211> LENGTH: 6
<212> TYPE: PRT
<213> ORGANISM: Artificial sequence
<220> FEATURE:
<223> OTHER INFORMATION: synthetic sequence

<400> SEQUENCE: 970

Gly Val Lys Asn Leu Phe
1               5

<210> SEQ ID NO 971
<211> LENGTH: 6
<212> TYPE: PRT
<213> ORGANISM: Artificial sequence
<220> FEATURE:
<223> OTHER INFORMATION: synthetic sequence

<400> SEQUENCE: 971

Ala Ile Lys Ser Trp Val
1               5

<210> SEQ ID NO 972

<211> LENGTH: 6
<212> TYPE: PRT
<213> ORGANISM: Artificial sequence
<220> FEATURE:
<223> OTHER INFORMATION: synthetic sequence

<400> SEQUENCE: 972

Ala Pro Lys Asn Met Leu
1               5

<210> SEQ ID NO 973
<211> LENGTH: 6
<212> TYPE: PRT
<213> ORGANISM: Artificial sequence
<220> FEATURE:
<223> OTHER INFORMATION: synthetic sequence

<400> SEQUENCE: 973

Leu Ile Ser Thr Leu Leu
1               5

<210> SEQ ID NO 974
<211> LENGTH: 6
<212> TYPE: PRT
<213> ORGANISM: Artificial sequence
<220> FEATURE:
<223> OTHER INFORMATION: synthetic sequence

<400> SEQUENCE: 974

Ala Val Lys Arg Ile Val
1               5

<210> SEQ ID NO 975
<211> LENGTH: 6
<212> TYPE: PRT
<213> ORGANISM: Artificial sequence
<220> FEATURE:
<223> OTHER INFORMATION: synthetic sequence

<400> SEQUENCE: 975

Val Leu Asn Lys Leu Phe
1               5

<210> SEQ ID NO 976
<211> LENGTH: 6
<212> TYPE: PRT
<213> ORGANISM: Artificial sequence
<220> FEATURE:
<223> OTHER INFORMATION: synthetic sequence

<400> SEQUENCE: 976

Leu Pro Gln Gln Val Leu
1               5

<210> SEQ ID NO 977
<211> LENGTH: 6
<212> TYPE: PRT
<213> ORGANISM: Artificial sequence
<220> FEATURE:
<223> OTHER INFORMATION: synthetic sequence

<400> SEQUENCE: 977

Val Tyr Ser Asp Ala Met
1               5

<210> SEQ ID NO 978
<211> LENGTH: 6

<212> TYPE: PRT
<213> ORGANISM: Artificial sequence
<220> FEATURE:
<223> OTHER INFORMATION: synthetic sequence

<400> SEQUENCE: 978

Tyr Ala Thr Glu Val Ser
1 5

<210> SEQ ID NO 979
<211> LENGTH: 6
<212> TYPE: PRT
<213> ORGANISM: Artificial sequence
<220> FEATURE:
<223> OTHER INFORMATION: synthetic sequence

<400> SEQUENCE: 979

Phe Ile Gln Gln Ala Leu
1 5

<210> SEQ ID NO 980
<211> LENGTH: 6
<212> TYPE: PRT
<213> ORGANISM: Artificial sequence
<220> FEATURE:
<223> OTHER INFORMATION: synthetic sequence

<400> SEQUENCE: 980

Ile Ile Lys Asn Leu Tyr
1 5

<210> SEQ ID NO 981
<211> LENGTH: 6
<212> TYPE: PRT
<213> ORGANISM: Artificial sequence
<220> FEATURE:
<223> OTHER INFORMATION: synthetic sequence

<400> SEQUENCE: 981

Thr Val Asn Asn Val Ala
1 5

<210> SEQ ID NO 982
<211> LENGTH: 6
<212> TYPE: PRT
<213> ORGANISM: Artificial sequence
<220> FEATURE:
<223> OTHER INFORMATION: synthetic sequence

<400> SEQUENCE: 982

Val Leu Arg Lys Tyr Leu
1 5

<210> SEQ ID NO 983
<211> LENGTH: 6
<212> TYPE: PRT
<213> ORGANISM: Artificial sequence
<220> FEATURE:
<223> OTHER INFORMATION: synthetic sequence

<400> SEQUENCE: 983

Gly Gly Arg Lys Leu Leu
1 5

<210> SEQ ID NO 984
<211> LENGTH: 6
<212> TYPE: PRT

<213> ORGANISM: Artificial sequence
<220> FEATURE:
<223> OTHER INFORMATION: synthetic sequence

<400> SEQUENCE: 984

Ala Leu Gly Thr Ala Ile
1               5

<210> SEQ ID NO 985
<211> LENGTH: 6
<212> TYPE: PRT
<213> ORGANISM: Artificial sequence
<220> FEATURE:
<223> OTHER INFORMATION: synthetic sequence

<400> SEQUENCE: 985

Leu Met Lys Thr Phe Pro
1               5

<210> SEQ ID NO 986
<211> LENGTH: 6
<212> TYPE: PRT
<213> ORGANISM: Artificial sequence
<220> FEATURE:
<223> OTHER INFORMATION: synthetic sequence

<400> SEQUENCE: 986

Val Gly Gln Asn Leu Val
1               5

<210> SEQ ID NO 987
<211> LENGTH: 6
<212> TYPE: PRT
<213> ORGANISM: Artificial sequence
<220> FEATURE:
<223> OTHER INFORMATION: synthetic sequence

<400> SEQUENCE: 987

Gly Gly Arg Lys Leu Leu
1               5

<210> SEQ ID NO 988
<211> LENGTH: 6
<212> TYPE: PRT
<213> ORGANISM: Artificial sequence
<220> FEATURE:
<223> OTHER INFORMATION: synthetic sequence

<400> SEQUENCE: 988

Leu Ala Ser Lys Val Ala
1               5

<210> SEQ ID NO 989
<211> LENGTH: 6
<212> TYPE: PRT
<213> ORGANISM: Artificial sequence
<220> FEATURE:
<223> OTHER INFORMATION: synthetic sequence

<400> SEQUENCE: 989

Ala Thr Lys Asn Ile Phe
1               5

<210> SEQ ID NO 990
<211> LENGTH: 6
<212> TYPE: PRT
<213> ORGANISM: Artificial sequence
<220> FEATURE:
<223> OTHER INFORMATION: synthetic sequence

<400> SEQUENCE: 990

Leu Pro Glu Asp Val Trp
1               5

<210> SEQ ID NO 991
<211> LENGTH: 6
<212> TYPE: PRT
<213> ORGANISM: Artificial sequence
<220> FEATURE:
<223> OTHER INFORMATION: synthetic sequence

<400> SEQUENCE: 991

Leu Ala Arg Lys Leu Ala
1               5

<210> SEQ ID NO 992
<211> LENGTH: 6
<212> TYPE: PRT
<213> ORGANISM: Artificial sequence
<220> FEATURE:
<223> OTHER INFORMATION: synthetic sequence

<400> SEQUENCE: 992

Thr Ala Thr Asp Ile Phe
1               5

<210> SEQ ID NO 993
<211> LENGTH: 6
<212> TYPE: PRT
<213> ORGANISM: Artificial sequence
<220> FEATURE:
<223> OTHER INFORMATION: synthetic sequence

<400> SEQUENCE: 993

Met Ile Gln Thr Ala Ser
1               5

<210> SEQ ID NO 994
<211> LENGTH: 6
<212> TYPE: PRT
<213> ORGANISM: Artificial sequence
<220> FEATURE:
<223> OTHER INFORMATION: synthetic sequence

<400> SEQUENCE: 994

Ala Leu Lys Lys Leu Ile
1               5

<210> SEQ ID NO 995
<211> LENGTH: 6
<212> TYPE: PRT
<213> ORGANISM: Artificial sequence
<220> FEATURE:
<223> OTHER INFORMATION: synthetic sequence

<400> SEQUENCE: 995

Gly Ile Lys Asn Leu Tyr
1               5

<210> SEQ ID NO 996
<211> LENGTH: 6
<212> TYPE: PRT
<213> ORGANISM: Artificial sequence
<220> FEATURE:

<223> OTHER INFORMATION: synthetic sequence

<400> SEQUENCE: 996

Ile Ile Glu Glu Ala Trp
1 5

<210> SEQ ID NO 997
<211> LENGTH: 6
<212> TYPE: PRT
<213> ORGANISM: Artificial sequence
<220> FEATURE:
<223> OTHER INFORMATION: synthetic sequence

<400> SEQUENCE: 997

Ile Ala Gln Asn Leu Ala
1 5

<210> SEQ ID NO 998
<211> LENGTH: 6
<212> TYPE: PRT
<213> ORGANISM: Artificial sequence
<220> FEATURE:
<223> OTHER INFORMATION: synthetic sequence

<400> SEQUENCE: 998

Ala Leu Asn Lys Leu Gly
1 5

<210> SEQ ID NO 999
<211> LENGTH: 6
<212> TYPE: PRT
<213> ORGANISM: Artificial sequence
<220> FEATURE:
<223> OTHER INFORMATION: synthetic sequence

<400> SEQUENCE: 999

Met Thr Arg Lys Gly Leu
1 5

<210> SEQ ID NO 1000
<211> LENGTH: 6
<212> TYPE: PRT
<213> ORGANISM: Artificial sequence
<220> FEATURE:
<223> OTHER INFORMATION: synthetic sequence

<400> SEQUENCE: 1000

Pro Ala Asp Glu Ile Leu
1 5

<210> SEQ ID NO 1001
<211> LENGTH: 6
<212> TYPE: PRT
<213> ORGANISM: Artificial sequence
<220> FEATURE:
<223> OTHER INFORMATION: synthetic sequence

<400> SEQUENCE: 1001

Ala Ile Lys Asp Trp Val
1 5

<210> SEQ ID NO 1002
<211> LENGTH: 6
<212> TYPE: PRT
<213> ORGANISM: Artificial sequence
<220> FEATURE:
<223> OTHER INFORMATION: synthetic sequence

<400> SEQUENCE: 1002

Leu Ala Ser Lys Tyr Phe
1 5

<210> SEQ ID NO 1003
<211> LENGTH: 6
<212> TYPE: PRT
<213> ORGANISM: Artificial sequence
<220> FEATURE:
<223> OTHER INFORMATION: synthetic sequence

<400> SEQUENCE: 1003

Ile Ile Asp Glu Ala Trp
1 5

<210> SEQ ID NO 1004
<211> LENGTH: 6
<212> TYPE: PRT
<213> ORGANISM: Artificial sequence
<220> FEATURE:
<223> OTHER INFORMATION: synthetic sequence

<400> SEQUENCE: 1004

Met Met Asp Asp Val Pro
1 5

<210> SEQ ID NO 1005
<211> LENGTH: 6
<212> TYPE: PRT
<213> ORGANISM: Artificial sequence
<220> FEATURE:
<223> OTHER INFORMATION: synthetic sequence

<400> SEQUENCE: 1005

Val Leu Lys Lys Leu Ile
1 5

<210> SEQ ID NO 1006
<211> LENGTH: 6
<212> TYPE: PRT
<213> ORGANISM: Artificial sequence
<220> FEATURE:
<223> OTHER INFORMATION: synthetic sequence

<400> SEQUENCE: 1006

Val Ala Lys Asp Ile Ser
1 5

<210> SEQ ID NO 1007
<211> LENGTH: 6
<212> TYPE: PRT
<213> ORGANISM: Artificial sequence
<220> FEATURE:
<223> OTHER INFORMATION: synthetic sequence

<400> SEQUENCE: 1007

Ala Ala Lys Arg Ala Phe
1 5

<210> SEQ ID NO 1008
<211> LENGTH: 6
<212> TYPE: PRT
<213> ORGANISM: Artificial sequence
<220> FEATURE:
<223> OTHER INFORMATION: synthetic sequence

<400> SEQUENCE: 1008

Gly Ile Lys Arg Ile Phe
1 5

<210> SEQ ID NO 1009
<211> LENGTH: 6
<212> TYPE: PRT
<213> ORGANISM: Artificial sequence
<220> FEATURE:
<223> OTHER INFORMATION: synthetic sequence

<400> SEQUENCE: 1009

Val Tyr Asp Glu Met Gly
1 5

<210> SEQ ID NO 1010
<211> LENGTH: 6
<212> TYPE: PRT
<213> ORGANISM: Artificial sequence
<220> FEATURE:
<223> OTHER INFORMATION: synthetic sequence

<400> SEQUENCE: 1010

Thr Ala Asp Lys Ala Met
1 5

<210> SEQ ID NO 1011
<211> LENGTH: 6
<212> TYPE: PRT
<213> ORGANISM: Artificial sequence
<220> FEATURE:
<223> OTHER INFORMATION: synthetic sequence

<400> SEQUENCE: 1011

Trp Phe Lys Arg Gly Leu
1 5

<210> SEQ ID NO 1012
<211> LENGTH: 6
<212> TYPE: PRT
<213> ORGANISM: Artificial sequence
<220> FEATURE:
<223> OTHER INFORMATION: synthetic sequence

<400> SEQUENCE: 1012

Met Met Lys Asn Ile Tyr
1 5

<210> SEQ ID NO 1013
<211> LENGTH: 6
<212> TYPE: PRT
<213> ORGANISM: Artificial sequence
<220> FEATURE:
<223> OTHER INFORMATION: synthetic sequence

<400> SEQUENCE: 1013

Met Leu Lys Lys Tyr Phe
1 5

<210> SEQ ID NO 1014
<211> LENGTH: 6
<212> TYPE: PRT
<213> ORGANISM: Artificial sequence
<220> FEATURE:
<223> OTHER INFORMATION: synthetic sequence

<400> SEQUENCE: 1014

Ala Tyr Asn Asp Ala Pro
1               5

<210> SEQ ID NO 1015
<211> LENGTH: 6
<212> TYPE: PRT
<213> ORGANISM: Artificial sequence
<220> FEATURE:
<223> OTHER INFORMATION: synthetic sequence

<400> SEQUENCE: 1015

Leu Leu Asp Glu Ala Leu
1               5

<210> SEQ ID NO 1016
<211> LENGTH: 6
<212> TYPE: PRT
<213> ORGANISM: Artificial sequence
<220> FEATURE:
<223> OTHER INFORMATION: synthetic sequence

<400> SEQUENCE: 1016

Trp Ile Asp Lys Gly Gly
1               5

<210> SEQ ID NO 1017
<211> LENGTH: 6
<212> TYPE: PRT
<213> ORGANISM: Artificial sequence
<220> FEATURE:
<223> OTHER INFORMATION: synthetic sequence

<400> SEQUENCE: 1017

Ile Ile Lys Gly Tyr Ile
1               5

<210> SEQ ID NO 1018
<211> LENGTH: 6
<212> TYPE: PRT
<213> ORGANISM: Artificial sequence
<220> FEATURE:
<223> OTHER INFORMATION: synthetic sequence

<400> SEQUENCE: 1018

Met Ile Lys Asn Ile Gly
1               5

<210> SEQ ID NO 1019
<211> LENGTH: 6
<212> TYPE: PRT
<213> ORGANISM: Artificial sequence
<220> FEATURE:
<223> OTHER INFORMATION: synthetic sequence

<400> SEQUENCE: 1019

Phe Tyr Lys Lys Ile Val
1               5

<210> SEQ ID NO 1020
<211> LENGTH: 6
<212> TYPE: PRT
<213> ORGANISM: Artificial sequence
<220> FEATURE:
<223> OTHER INFORMATION: synthetic sequence

<400> SEQUENCE: 1020

Phe Ala Lys Lys Phe Ala
1 5

<210> SEQ ID NO 1021
<211> LENGTH: 6
<212> TYPE: PRT
<213> ORGANISM: Artificial sequence
<220> FEATURE:
<223> OTHER INFORMATION: synthetic sequence

<400> SEQUENCE: 1021

Ser Ala Asp Arg Tyr Tyr
1 5

<210> SEQ ID NO 1022
<211> LENGTH: 6
<212> TYPE: PRT
<213> ORGANISM: Artificial sequence
<220> FEATURE:
<223> OTHER INFORMATION: synthetic sequence

<400> SEQUENCE: 1022

Phe Phe Lys Phe Lys Phe
1 5

<210> SEQ ID NO 1023
<211> LENGTH: 6
<212> TYPE: PRT
<213> ORGANISM: Artificial sequence
<220> FEATURE:
<223> OTHER INFORMATION: synthetic sequence

<400> SEQUENCE: 1023

Met Met Lys Lys Ile Ile
1 5

<210> SEQ ID NO 1024
<211> LENGTH: 6
<212> TYPE: PRT
<213> ORGANISM: Artificial sequence
<220> FEATURE:
<223> OTHER INFORMATION: synthetic sequence

<400> SEQUENCE: 1024

Ala Leu Lys Lys Val Phe
1 5

<210> SEQ ID NO 1025
<211> LENGTH: 6
<212> TYPE: PRT
<213> ORGANISM: Artificial sequence
<220> FEATURE:
<223> OTHER INFORMATION: synthetic sequence

<400> SEQUENCE: 1025

Ala Ala Asp Asn Ala Ile
1 5

<210> SEQ ID NO 1026
<211> LENGTH: 6
<212> TYPE: PRT
<213> ORGANISM: Artificial sequence
<220> FEATURE:
<223> OTHER INFORMATION: synthetic sequence

<400> SEQUENCE: 1026

Ala Tyr Lys Lys Val Phe 1 5

<210> SEQ ID NO 1027
<211> LENGTH: 6
<212> TYPE: PRT
<213> ORGANISM: Artificial sequence
<220> FEATURE:
<223> OTHER INFORMATION: synthetic sequence

<400> SEQUENCE: 1027

Phe Phe Arg Phe His Phe
1 5

<210> SEQ ID NO 1028
<211> LENGTH: 6
<212> TYPE: PRT
<213> ORGANISM: Artificial sequence
<220> FEATURE:
<223> OTHER INFORMATION: synthetic sequence

<400> SEQUENCE: 1028

Met Phe Lys Lys Thr Leu
1 5

<210> SEQ ID NO 1029
<211> LENGTH: 6
<212> TYPE: PRT
<213> ORGANISM: Artificial sequence
<220> FEATURE:
<223> OTHER INFORMATION: synthetic sequence

<400> SEQUENCE: 1029

Leu Leu Lys Lys Phe Gly
1 5

<210> SEQ ID NO 1030
<211> LENGTH: 6
<212> TYPE: PRT
<213> ORGANISM: Artificial sequence
<220> FEATURE:
<223> OTHER INFORMATION: synthetic sequence

<400> SEQUENCE: 1030

Phe Arg Phe His Phe Phe
1 5

<210> SEQ ID NO 1031
<211> LENGTH: 6
<212> TYPE: PRT
<213> ORGANISM: Artificial sequence
<220> FEATURE:
<223> OTHER INFORMATION: synthetic sequence

<400> SEQUENCE: 1031

Phe Lys Phe Lys Phe Phe
1 5

<210> SEQ ID NO 1032
<211> LENGTH: 6
<212> TYPE: PRT
<213> ORGANISM: Artificial sequence
<220> FEATURE:
<223> OTHER INFORMATION: synthetic sequence

<400> SEQUENCE: 1032

Tyr Ala Lys Lys Tyr Gly
1 5

<210> SEQ ID NO 1033
<211> LENGTH: 6
<212> TYPE: PRT
<213> ORGANISM: Artificial sequence
<220> FEATURE:
<223> OTHER INFORMATION: synthetic sequence

<400> SEQUENCE: 1033

Ala Ile Asp Asp Phe Gly
1 5

<210> SEQ ID NO 1034
<211> LENGTH: 6
<212> TYPE: PRT
<213> ORGANISM: Artificial sequence
<220> FEATURE:
<223> OTHER INFORMATION: synthetic sequence

<400> SEQUENCE: 1034

Ala Ile Lys Lys Ile Ile
1 5

<210> SEQ ID NO 1035
<211> LENGTH: 6
<212> TYPE: PRT
<213> ORGANISM: Artificial sequence
<220> FEATURE:
<223> OTHER INFORMATION: synthetic sequence

<400> SEQUENCE: 1035

Gly Gly Lys Lys Gly Gly
1 5

<210> SEQ ID NO 1036
<211> LENGTH: 6
<212> TYPE: PRT
<213> ORGANISM: Artificial sequence
<220> FEATURE:
<223> OTHER INFORMATION: synthetic sequence

<400> SEQUENCE: 1036

Lys Gly Gly Gly Gly Lys
1 5

<210> SEQ ID NO 1037
<211> LENGTH: 6
<212> TYPE: PRT
<213> ORGANISM: Artificial sequence
<220> FEATURE:
<223> OTHER INFORMATION: synthetic sequence

<400> SEQUENCE: 1037

Ala Met Lys Lys Val Val
1 5

<210> SEQ ID NO 1038
<211> LENGTH: 6
<212> TYPE: PRT
<213> ORGANISM: Artificial sequence
<220> FEATURE:
<223> OTHER INFORMATION: synthetic sequence

<400> SEQUENCE: 1038

Ser Ala Gly Gly Val Ala
1 5

<210> SEQ ID NO 1039
<211> LENGTH: 6
<212> TYPE: PRT
<213> ORGANISM: Artificial sequence
<220> FEATURE:
<223> OTHER INFORMATION: synthetic sequence

<400> SEQUENCE: 1039

Ala Met Lys Lys Leu Ala
1               5

<210> SEQ ID NO 1040
<211> LENGTH: 6
<212> TYPE: PRT
<213> ORGANISM: Artificial sequence
<220> FEATURE:
<223> OTHER INFORMATION: synthetic sequence

<400> SEQUENCE: 1040

Ala Ala Asp Asp Ala Ala
1               5

<210> SEQ ID NO 1041
<211> LENGTH: 6
<212> TYPE: PRT
<213> ORGANISM: Artificial sequence
<220> FEATURE:
<223> OTHER INFORMATION: synthetic sequence

<400> SEQUENCE: 1041

Arg Lys Met Leu Arg His
1               5

<210> SEQ ID NO 1042
<211> LENGTH: 6
<212> TYPE: PRT
<213> ORGANISM: Artificial sequence
<220> FEATURE:
<223> OTHER INFORMATION: synthetic sequence

<400> SEQUENCE: 1042

Ser Tyr Arg Arg Ile Thr
1               5

<210> SEQ ID NO 1043
<211> LENGTH: 6
<212> TYPE: PRT
<213> ORGANISM: Artificial sequence
<220> FEATURE:
<223> OTHER INFORMATION: synthetic sequence

<400> SEQUENCE: 1043

Trp Val Gln Asp Ser Met
1               5

<210> SEQ ID NO 1044
<211> LENGTH: 6
<212> TYPE: PRT
<213> ORGANISM: Artificial sequence
<220> FEATURE:
<223> OTHER INFORMATION: synthetic sequence

<400> SEQUENCE: 1044

Trp Val Gln Glu Tyr Val
1               5

<210> SEQ ID NO 1045
<211> LENGTH: 6
<212> TYPE: PRT
<213> ORGANISM: Artificial sequence
<220> FEATURE:
<223> OTHER INFORMATION: synthetic sequence

<400> SEQUENCE: 1045

Ser Tyr Arg Arg Ile Thr
1               5

<210> SEQ ID NO 1046
<211> LENGTH: 6
<212> TYPE: PRT
<213> ORGANISM: Artificial sequence
<220> FEATURE:
<223> OTHER INFORMATION: synthetic sequence

<400> SEQUENCE: 1046

Trp Val Gln Asp Ser Met
1               5

<210> SEQ ID NO 1047
<211> LENGTH: 6
<212> TYPE: PRT
<213> ORGANISM: Artificial sequence
<220> FEATURE:
<223> OTHER INFORMATION: synthetic sequence

<400> SEQUENCE: 1047

Trp Val Gln Lys Tyr Ile
1               5

<210> SEQ ID NO 1048
<211> LENGTH: 6
<212> TYPE: PRT
<213> ORGANISM: Artificial sequence
<220> FEATURE:
<223> OTHER INFORMATION: synthetic sequence

<400> SEQUENCE: 1048

Trp Val Lys Asp Ala Met
1               5

<210> SEQ ID NO 1049
<211> LENGTH: 6
<212> TYPE: PRT
<213> ORGANISM: Artificial sequence
<220> FEATURE:
<223> OTHER INFORMATION: synthetic sequence

<400> SEQUENCE: 1049

Met Val Lys Lys Ile Ile
1               5

<210> SEQ ID NO 1050
<211> LENGTH: 6
<212> TYPE: PRT
<213> ORGANISM: Artificial sequence
<220> FEATURE:
<223> OTHER INFORMATION: synthetic sequence

<400> SEQUENCE: 1050

Ile Ile Glu Lys Met Leu
1               5

<210> SEQ ID NO 1051

<211> LENGTH: 6
<212> TYPE: PRT
<213> ORGANISM: Artificial sequence
<220> FEATURE:
<223> OTHER INFORMATION: synthetic sequence

<400> SEQUENCE: 1051

Lys Lys Ile Val Gln Lys
1 5

<210> SEQ ID NO 1052
<211> LENGTH: 6
<212> TYPE: PRT
<213> ORGANISM: Artificial sequence
<220> FEATURE:
<223> OTHER INFORMATION: synthetic sequence

<400> SEQUENCE: 1052

Trp Val Gln Arg Val Val
1 5

<210> SEQ ID NO 1053
<211> LENGTH: 6
<212> TYPE: PRT
<213> ORGANISM: Artificial sequence
<220> FEATURE:
<223> OTHER INFORMATION: synthetic sequence

<400> SEQUENCE: 1053

Val Val Glu Lys Phe Leu
1 5

<210> SEQ ID NO 1054
<211> LENGTH: 6
<212> TYPE: PRT
<213> ORGANISM: Artificial sequence
<220> FEATURE:
<223> OTHER INFORMATION: synthetic sequence

<400> SEQUENCE: 1054

Lys Glu Leu Ile Lys Lys
1 5

<210> SEQ ID NO 1055
<211> LENGTH: 6
<212> TYPE: PRT
<213> ORGANISM: Artificial sequence
<220> FEATURE:
<223> OTHER INFORMATION: synthetic sequence

<400> SEQUENCE: 1055

Ala Ile Lys Asn Leu Leu
1 5

<210> SEQ ID NO 1056
<211> LENGTH: 6
<212> TYPE: PRT
<213> ORGANISM: Artificial sequence
<220> FEATURE:
<223> OTHER INFORMATION: synthetic sequence

<400> SEQUENCE: 1056

Phe Leu Asn Arg Trp Ile
1 5

<210> SEQ ID NO 1057
<211> LENGTH: 6

<212> TYPE: PRT
<213> ORGANISM: Artificial sequence
<220> FEATURE:
<223> OTHER INFORMATION: synthetic sequence

<400> SEQUENCE: 1057

Thr Leu Gln Glu Ile Ile
1               5

<210> SEQ ID NO 1058
<211> LENGTH: 6
<212> TYPE: PRT
<213> ORGANISM: Artificial sequence
<220> FEATURE:
<223> OTHER INFORMATION: synthetic sequence

<400> SEQUENCE: 1058

Thr Leu Glu Asn Phe Leu
1               5

<210> SEQ ID NO 1059
<211> LENGTH: 6
<212> TYPE: PRT
<213> ORGANISM: Artificial sequence
<220> FEATURE:
<223> OTHER INFORMATION: synthetic sequence

<400> SEQUENCE: 1059

Trp Leu Gln Asp Met Thr
1               5

<210> SEQ ID NO 1060
<211> LENGTH: 6
<212> TYPE: PRT
<213> ORGANISM: Artificial sequence
<220> FEATURE:
<223> OTHER INFORMATION: synthetic sequence

<400> SEQUENCE: 1060

Ser Phe Lys Glu Phe Leu
1               5

<210> SEQ ID NO 1061
<211> LENGTH: 6
<212> TYPE: PRT
<213> ORGANISM: Artificial sequence
<220> FEATURE:
<223> OTHER INFORMATION: synthetic sequence

<400> SEQUENCE: 1061

Phe Ser Glu Arg Leu Ser
1               5

<210> SEQ ID NO 1062
<211> LENGTH: 6
<212> TYPE: PRT
<213> ORGANISM: Artificial sequence
<220> FEATURE:
<223> OTHER INFORMATION: synthetic sequence

<400> SEQUENCE: 1062

Tyr Leu Glu Glu Val Met
1               5

<210> SEQ ID NO 1063
<211> LENGTH: 6
<212> TYPE: PRT

<213> ORGANISM: Artificial sequence
<220> FEATURE:
<223> OTHER INFORMATION: synthetic sequence

<400> SEQUENCE: 1063

Leu Arg Leu Arg Leu Arg
1 5

<210> SEQ ID NO 1064
<211> LENGTH: 6
<212> TYPE: PRT
<213> ORGANISM: Artificial sequence
<220> FEATURE:
<223> OTHER INFORMATION: synthetic sequence

<400> SEQUENCE: 1064

Ala Ser Arg Lys Thr Ser
1 5

<210> SEQ ID NO 1065
<211> LENGTH: 6
<212> TYPE: PRT
<213> ORGANISM: Artificial sequence
<220> FEATURE:
<223> OTHER INFORMATION: synthetic sequence

<400> SEQUENCE: 1065

Thr Ile Asp Arg Val Met
1 5

<210> SEQ ID NO 1066
<211> LENGTH: 6
<212> TYPE: PRT
<213> ORGANISM: Artificial sequence
<220> FEATURE:
<223> OTHER INFORMATION: synthetic sequence

<400> SEQUENCE: 1066

Thr Val Glu Asn Leu Ile
1 5

<210> SEQ ID NO 1067
<211> LENGTH: 6
<212> TYPE: PRT
<213> ORGANISM: Artificial sequence
<220> FEATURE:
<223> OTHER INFORMATION: synthetic sequence

<400> SEQUENCE: 1067

Leu Phe Glu Asp Met Thr
1 5

<210> SEQ ID NO 1068
<211> LENGTH: 6
<212> TYPE: PRT
<213> ORGANISM: Artificial sequence
<220> FEATURE:
<223> OTHER INFORMATION: synthetic sequence

<400> SEQUENCE: 1068

Leu Leu Arg His Leu Leu
1 5

<210> SEQ ID NO 1069
<211> LENGTH: 6
<212> TYPE: PRT
<213> ORGANISM: Artificial sequence
<220> FEATURE:
<223> OTHER INFORMATION: synthetic sequence

<400> SEQUENCE: 1069

Thr Leu Arg Lys Ile Ser
1               5

<210> SEQ ID NO 1070
<211> LENGTH: 6
<212> TYPE: PRT
<213> ORGANISM: Artificial sequence
<220> FEATURE:
<223> OTHER INFORMATION: synthetic sequence

<400> SEQUENCE: 1070

Trp Met Gln Lys Phe Tyr
1               5

<210> SEQ ID NO 1071
<211> LENGTH: 6
<212> TYPE: PRT
<213> ORGANISM: Artificial sequence
<220> FEATURE:
<223> OTHER INFORMATION: synthetic sequence

<400> SEQUENCE: 1071

Lys Arg Leu Leu Glu Lys
1               5

<210> SEQ ID NO 1072
<211> LENGTH: 6
<212> TYPE: PRT
<213> ORGANISM: Artificial sequence
<220> FEATURE:
<223> OTHER INFORMATION: synthetic sequence

<400> SEQUENCE: 1072

Tyr Met Lys His Tyr Phe
1               5

<210> SEQ ID NO 1073
<211> LENGTH: 6
<212> TYPE: PRT
<213> ORGANISM: Artificial sequence
<220> FEATURE:
<223> OTHER INFORMATION: synthetic sequence

<400> SEQUENCE: 1073

Ala Ile His Glu Leu Ile
1               5

<210> SEQ ID NO 1074
<211> LENGTH: 6
<212> TYPE: PRT
<213> ORGANISM: Artificial sequence
<220> FEATURE:
<223> OTHER INFORMATION: synthetic sequence

<400> SEQUENCE: 1074

Met Ser Arg Lys Ala Phe
1               5

<210> SEQ ID NO 1075
<211> LENGTH: 6
<212> TYPE: PRT
<213> ORGANISM: Artificial sequence
<220> FEATURE:

<223> OTHER INFORMATION: synthetic sequence

<400> SEQUENCE: 1075

Trp Ser Lys Asp Ile Gly
1 5

<210> SEQ ID NO 1076
<211> LENGTH: 6
<212> TYPE: PRT
<213> ORGANISM: Artificial sequence
<220> FEATURE:
<223> OTHER INFORMATION: synthetic sequence

<400> SEQUENCE: 1076

Ser Leu Lys Lys Gly Tyr
1 5

<210> SEQ ID NO 1077
<211> LENGTH: 6
<212> TYPE: PRT
<213> ORGANISM: Artificial sequence
<220> FEATURE:
<223> OTHER INFORMATION: synthetic sequence

<400> SEQUENCE: 1077

Asn Asn Leu Met Asn Gln
1 5

<210> SEQ ID NO 1078
<211> LENGTH: 6
<212> TYPE: PRT
<213> ORGANISM: Artificial sequence
<220> FEATURE:
<223> OTHER INFORMATION: synthetic sequence

<400> SEQUENCE: 1078

Ser Gly Lys Asp Val Phe
1 5

<210> SEQ ID NO 1079
<211> LENGTH: 6
<212> TYPE: PRT
<213> ORGANISM: Artificial sequence
<220> FEATURE:
<223> OTHER INFORMATION: synthetic sequence

<400> SEQUENCE: 1079

Leu Gly Arg Arg Gly Phe
1 5

<210> SEQ ID NO 1080
<211> LENGTH: 6
<212> TYPE: PRT
<213> ORGANISM: Artificial sequence
<220> FEATURE:
<223> OTHER INFORMATION: synthetic sequence

<400> SEQUENCE: 1080

Ala Leu Arg Lys Gly Val
1 5

<210> SEQ ID NO 1081
<211> LENGTH: 6
<212> TYPE: PRT
<213> ORGANISM: Artificial sequence
<220> FEATURE:
<223> OTHER INFORMATION: synthetic sequence

<400> SEQUENCE: 1081

Trp Val Gln Lys Tyr Val
1 5

<210> SEQ ID NO 1082
<211> LENGTH: 6
<212> TYPE: PRT
<213> ORGANISM: Artificial sequence
<220> FEATURE:
<223> OTHER INFORMATION: synthetic sequence

<400> SEQUENCE: 1082

Trp Val Arg Glu Tyr Ile
1 5

<210> SEQ ID NO 1083
<211> LENGTH: 6
<212> TYPE: PRT
<213> ORGANISM: Artificial sequence
<220> FEATURE:
<223> OTHER INFORMATION: synthetic sequence

<400> SEQUENCE: 1083

Ile Ser Arg Arg Gly Thr
1 5

<210> SEQ ID NO 1084
<211> LENGTH: 6
<212> TYPE: PRT
<213> ORGANISM: Artificial sequence
<220> FEATURE:
<223> OTHER INFORMATION: synthetic sequence

<400> SEQUENCE: 1084

Ser Tyr Arg Arg Thr Thr
1 5

<210> SEQ ID NO 1085
<211> LENGTH: 6
<212> TYPE: PRT
<213> ORGANISM: Artificial sequence
<220> FEATURE:
<223> OTHER INFORMATION: synthetic sequence

<400> SEQUENCE: 1085

Trp Val Arg Asp Ser Met
1 5

<210> SEQ ID NO 1086
<211> LENGTH: 6
<212> TYPE: PRT
<213> ORGANISM: Artificial sequence
<220> FEATURE:
<223> OTHER INFORMATION: synthetic sequence

<400> SEQUENCE: 1086

Ile Ser Lys Arg Gly Phe
1 5

<210> SEQ ID NO 1087
<211> LENGTH: 6
<212> TYPE: PRT
<213> ORGANISM: Artificial sequence
<220> FEATURE:
<223> OTHER INFORMATION: synthetic sequence -continued

<400> SEQUENCE: 1087

Ser Tyr Arg Arg Ile Thr
1               5

<210> SEQ ID NO 1088
<211> LENGTH: 6
<212> TYPE: PRT
<213> ORGANISM: Artificial sequence
<220> FEATURE:
<223> OTHER INFORMATION: synthetic sequence

<400> SEQUENCE: 1088

Trp Val Gln Asn Tyr Met
1               5

<210> SEQ ID NO 1089
<211> LENGTH: 6
<212> TYPE: PRT
<213> ORGANISM: Artificial sequence
<220> FEATURE:
<223> OTHER INFORMATION: synthetic sequence

<400> SEQUENCE: 1089

Trp Val Gln Asp Tyr Ile
1               5

<210> SEQ ID NO 1090
<211> LENGTH: 6
<212> TYPE: PRT
<213> ORGANISM: Artificial sequence
<220> FEATURE:
<223> OTHER INFORMATION: synthetic sequence

<400> SEQUENCE: 1090

Trp Val Arg Asp Val Val
1               5

<210> SEQ ID NO 1091
<211> LENGTH: 14
<212> TYPE: PRT
<213> ORGANISM: Artificial sequence
<220> FEATURE:
<223> OTHER INFORMATION: synthetic sequence

<400> SEQUENCE: 1091

Met Val Gln Lys Ile Ile Glu Lys Ile Leu Asn Lys Gly Ser
1               5                   10

<210> SEQ ID NO 1092
<211> LENGTH: 10
<212> TYPE: PRT
<213> ORGANISM: Artificial sequence
<220> FEATURE:
<223> OTHER INFORMATION: synthetic sequence

<400> SEQUENCE: 1092

Leu Tyr Lys Lys Ile Ile Lys Lys Leu Leu
1               5                   10

<210> SEQ ID NO 1093
<211> LENGTH: 10
<212> TYPE: PRT
<213> ORGANISM: Artificial sequence
<220> FEATURE:
<223> OTHER INFORMATION: synthetic sequence

<400> SEQUENCE: 1093

Phe Leu Lys Lys Val Ile Gln Lys Ile Leu
1 5 10

<210> SEQ ID NO 1094
<211> LENGTH: 10
<212> TYPE: PRT
<213> ORGANISM: Artificial sequence
<220> FEATURE:
<223> OTHER INFORMATION: synthetic sequence

<400> SEQUENCE: 1094

Phe Leu Lys Lys Val Ile Gln Lys Ile Leu
1 5 10

<210> SEQ ID NO 1095
<211> LENGTH: 6
<212> TYPE: PRT
<213> ORGANISM: Artificial sequence
<220> FEATURE:
<223> OTHER INFORMATION: synthetic sequence

<400> SEQUENCE: 1095

Arg Arg Phe Ile Asp Arg
1 5

<210> SEQ ID NO 1096
<211> LENGTH: 6
<212> TYPE: PRT
<213> ORGANISM: Artificial sequence
<220> FEATURE:
<223> OTHER INFORMATION: synthetic sequence

<400> SEQUENCE: 1096

Ser Thr Lys Arg Phe Ile
1 5

<210> SEQ ID NO 1097
<211> LENGTH: 6
<212> TYPE: PRT
<213> ORGANISM: Artificial sequence
<220> FEATURE:
<223> OTHER INFORMATION: synthetic sequence

<400> SEQUENCE: 1097

Leu Ile Lys Asn Ile Met
1 5

<210> SEQ ID NO 1098
<211> LENGTH: 6
<212> TYPE: PRT
<213> ORGANISM: Artificial sequence
<220> FEATURE:
<223> OTHER INFORMATION: synthetic sequence

<400> SEQUENCE: 1098

Trp Val Gln Glu Leu Met
1 5

<210> SEQ ID NO 1099
<211> LENGTH: 6
<212> TYPE: PRT
<213> ORGANISM: Artificial sequence
<220> FEATURE:
<223> OTHER INFORMATION: synthetic sequence

<400> SEQUENCE: 1099

Tyr Phe Glu Gln Ser Trp
1 5

<210> SEQ ID NO 1100
<211> LENGTH: 6
<212> TYPE: PRT
<213> ORGANISM: Artificial sequence
<220> FEATURE:
<223> OTHER INFORMATION: synthetic sequence

<400> SEQUENCE: 1100

Phe Glu Leu Asn Ile Asn
1 5

<210> SEQ ID NO 1101
<211> LENGTH: 6
<212> TYPE: PRT
<213> ORGANISM: Artificial sequence
<220> FEATURE:
<223> OTHER INFORMATION: synthetic sequence

<400> SEQUENCE: 1101

Thr Leu Asp Gln Trp Gly
1 5

<210> SEQ ID NO 1102
<211> LENGTH: 6
<212> TYPE: PRT
<213> ORGANISM: Artificial sequence
<220> FEATURE:
<223> OTHER INFORMATION: synthetic sequence

<400> SEQUENCE: 1102

Met Ile Asp Glu Ile Ile
1 5

<210> SEQ ID NO 1103
<211> LENGTH: 6
<212> TYPE: PRT
<213> ORGANISM: Artificial sequence
<220> FEATURE:
<223> OTHER INFORMATION: synthetic sequence

<400> SEQUENCE: 1103

Leu Val Lys Glu Thr Leu
1 5

<210> SEQ ID NO 1104
<211> LENGTH: 6
<212> TYPE: PRT
<213> ORGANISM: Artificial sequence
<220> FEATURE:
<223> OTHER INFORMATION: synthetic sequence

<400> SEQUENCE: 1104

Phe Leu Lys Arg Leu Leu
1 5

<210> SEQ ID NO 1105
<211> LENGTH: 6
<212> TYPE: PRT
<213> ORGANISM: Artificial sequence
<220> FEATURE:
<223> OTHER INFORMATION: synthetic sequence

<400> SEQUENCE: 1105

Trp Leu Arg Arg Ala Gly 1 5

<210> SEQ ID NO 1106
<211> LENGTH: 6
<212> TYPE: PRT
<213> ORGANISM: Artificial sequence
<220> FEATURE:
<223> OTHER INFORMATION: synthetic sequence

<400> SEQUENCE: 1106

Ala Ser Arg Lys Thr Ser
1 5

<210> SEQ ID NO 1107
<211> LENGTH: 6
<212> TYPE: PRT
<213> ORGANISM: Artificial sequence
<220> FEATURE:
<223> OTHER INFORMATION: synthetic sequence

<400> SEQUENCE: 1107

Lys Lys Leu Phe Arg Glu
1 5

<210> SEQ ID NO 1108
<211> LENGTH: 6
<212> TYPE: PRT
<213> ORGANISM: Artificial sequence
<220> FEATURE:
<223> OTHER INFORMATION: synthetic sequence

<400> SEQUENCE: 1108

Leu Leu Lys Glu Ala Val
1 5

<210> SEQ ID NO 1109
<211> LENGTH: 6
<212> TYPE: PRT
<213> ORGANISM: Artificial sequence
<220> FEATURE:
<223> OTHER INFORMATION: synthetic sequence

<400> SEQUENCE: 1109

Lys Lys Leu Ile Glu Glu
1 5

<210> SEQ ID NO 1110
<211> LENGTH: 6
<212> TYPE: PRT
<213> ORGANISM: Artificial sequence
<220> FEATURE:
<223> OTHER INFORMATION: synthetic sequence

<400> SEQUENCE: 1110

Ile Val His His Val Ala
1 5

<210> SEQ ID NO 1111
<211> LENGTH: 6
<212> TYPE: PRT
<213> ORGANISM: Artificial sequence
<220> FEATURE:
<223> OTHER INFORMATION: synthetic sequence

<400> SEQUENCE: 1111

Tyr Val Asp Arg Val Phe
1 5

<210> SEQ ID NO 1112
<211> LENGTH: 6
<212> TYPE: PRT
<213> ORGANISM: Artificial sequence
<220> FEATURE:
<223> OTHER INFORMATION: synthetic sequence

<400> SEQUENCE: 1112

Lys Glu Phe Leu Glu Arg
1 5

<210> SEQ ID NO 1113
<211> LENGTH: 6
<212> TYPE: PRT
<213> ORGANISM: Artificial sequence
<220> FEATURE:
<223> OTHER INFORMATION: synthetic sequence

<400> SEQUENCE: 1113

Ile Thr Asn Arg Thr Phe
1 5

<210> SEQ ID NO 1114
<211> LENGTH: 6
<212> TYPE: PRT
<213> ORGANISM: Artificial sequence
<220> FEATURE:
<223> OTHER INFORMATION: synthetic sequence

<400> SEQUENCE: 1114

Phe Tyr Glu Lys Leu Leu
1 5

<210> SEQ ID NO 1115
<211> LENGTH: 6
<212> TYPE: PRT
<213> ORGANISM: Artificial sequence
<220> FEATURE:
<223> OTHER INFORMATION: synthetic sequence

<400> SEQUENCE: 1115

Thr Ser Glu Glu Leu Leu
1 5

<210> SEQ ID NO 1116
<211> LENGTH: 6
<212> TYPE: PRT
<213> ORGANISM: Artificial sequence
<220> FEATURE:
<223> OTHER INFORMATION: synthetic sequence

<400> SEQUENCE: 1116

Phe Met Glu Asp Val Phe
1 5

<210> SEQ ID NO 1117
<211> LENGTH: 6
<212> TYPE: PRT
<213> ORGANISM: Artificial sequence
<220> FEATURE:
<223> OTHER INFORMATION: synthetic sequence

<400> SEQUENCE: 1117

Leu Ala Arg Lys Leu Leu
1 5

<210> SEQ ID NO 1118
<211> LENGTH: 6
<212> TYPE: PRT
<213> ORGANISM: Artificial sequence
<220> FEATURE:
<223> OTHER INFORMATION: synthetic sequence

<400> SEQUENCE: 1118

Ala Leu Glu Asp Val Leu
1               5

<210> SEQ ID NO 1119
<211> LENGTH: 6
<212> TYPE: PRT
<213> ORGANISM: Artificial sequence
<220> FEATURE:
<223> OTHER INFORMATION: synthetic sequence

<400> SEQUENCE: 1119

Gln Lys Ile Val Glu Glu
1               5

<210> SEQ ID NO 1120
<211> LENGTH: 6
<212> TYPE: PRT
<213> ORGANISM: Artificial sequence
<220> FEATURE:
<223> OTHER INFORMATION: synthetic sequence

<400> SEQUENCE: 1120

Glu Arg Phe Tyr Asp Lys
1               5

<210> SEQ ID NO 1121
<211> LENGTH: 6
<212> TYPE: PRT
<213> ORGANISM: Artificial sequence
<220> FEATURE:
<223> OTHER INFORMATION: synthetic sequence

<400> SEQUENCE: 1121

Arg Glu Thr Thr Lys Arg
1               5

<210> SEQ ID NO 1122
<211> LENGTH: 6
<212> TYPE: PRT
<213> ORGANISM: Artificial sequence
<220> FEATURE:
<223> OTHER INFORMATION: synthetic sequence

<400> SEQUENCE: 1122

Ser Ser Gln Lys Met Val
1               5

<210> SEQ ID NO 1123
<211> LENGTH: 10
<212> TYPE: PRT
<213> ORGANISM: Artificial sequence
<220> FEATURE:
<223> OTHER INFORMATION: synthetic sequence

<400> SEQUENCE: 1123

Val Leu His Glu Leu Ile Gln Gln Ile Phe
1               5                   10

<210> SEQ ID NO 1124
<211> LENGTH: 6
<212> TYPE: PRT
<213> ORGANISM: Artificial sequence
<220> FEATURE:
<223> OTHER INFORMATION: synthetic sequence

<400> SEQUENCE: 1124

Ala Tyr Lys Glu Leu Ser
1 5

<210> SEQ ID NO 1125
<211> LENGTH: 6
<212> TYPE: PRT
<213> ORGANISM: Artificial sequence
<220> FEATURE:
<223> OTHER INFORMATION: synthetic sequence

<400> SEQUENCE: 1125

Leu Ser Lys Gln Met Val
1 5

<210> SEQ ID NO 1126
<211> LENGTH: 6
<212> TYPE: PRT
<213> ORGANISM: Artificial sequence
<220> FEATURE:
<223> OTHER INFORMATION: synthetic sequence

<400> SEQUENCE: 1126

Thr Val Gln Glu Ala Thr
1 5

<210> SEQ ID NO 1127
<211> LENGTH: 6
<212> TYPE: PRT
<213> ORGANISM: Artificial sequence
<220> FEATURE:
<223> OTHER INFORMATION: synthetic sequence

<400> SEQUENCE: 1127

Met Gly Lys Arg Ala Leu
1 5

<210> SEQ ID NO 1128
<211> LENGTH: 6
<212> TYPE: PRT
<213> ORGANISM: Artificial sequence
<220> FEATURE:
<223> OTHER INFORMATION: synthetic sequence

<400> SEQUENCE: 1128

Val Val Lys His Phe Tyr
1 5

<210> SEQ ID NO 1129
<211> LENGTH: 10
<212> TYPE: PRT
<213> ORGANISM: Artificial sequence
<220> FEATURE:
<223> OTHER INFORMATION: synthetic sequence

<400> SEQUENCE: 1129

Leu Lys Leu Asp Thr Arg Ile Lys Thr Arg
1 5 10

<210> SEQ ID NO 1130

<211> LENGTH: 6
<212> TYPE: PRT
<213> ORGANISM: Artificial sequence
<220> FEATURE:
<223> OTHER INFORMATION: synthetic sequence

<400> SEQUENCE: 1130

Trp Val Gln Arg Tyr Met
1 5

<210> SEQ ID NO 1131
<211> LENGTH: 6
<212> TYPE: PRT
<213> ORGANISM: Artificial sequence
<220> FEATURE:
<223> OTHER INFORMATION: synthetic sequence

<400> SEQUENCE: 1131

Val Leu Arg Arg Ala Trp
1 5

<210> SEQ ID NO 1132
<211> LENGTH: 6
<212> TYPE: PRT
<213> ORGANISM: Artificial sequence
<220> FEATURE:
<223> OTHER INFORMATION: synthetic sequence

<400> SEQUENCE: 1132

Trp Val Gln Lys Tyr Ile
1 5

<210> SEQ ID NO 1133
<211> LENGTH: 6
<212> TYPE: PRT
<213> ORGANISM: Artificial sequence
<220> FEATURE:
<223> OTHER INFORMATION: synthetic sequence

<400> SEQUENCE: 1133

Met Leu Arg Lys Met Gly
1 5

<210> SEQ ID NO 1134
<211> LENGTH: 12
<212> TYPE: PRT
<213> ORGANISM: Artificial sequence
<220> FEATURE:
<223> OTHER INFORMATION: synthetic sequence

<400> SEQUENCE: 1134

Val Ser His His Ile Ser Arg Arg Leu Leu Glu Arg
1 5 10

<210> SEQ ID NO 1135
<211> LENGTH: 6
<212> TYPE: PRT
<213> ORGANISM: Artificial sequence
<220> FEATURE:
<223> OTHER INFORMATION: synthetic sequence

<400> SEQUENCE: 1135

Trp Val Arg Asp Val Val
1 5

<210> SEQ ID NO 1136
<211> LENGTH: 6

<212> TYPE: PRT
<213> ORGANISM: Artificial sequence
<220> FEATURE:
<223> OTHER INFORMATION: synthetic sequence

<400> SEQUENCE: 1136

Trp Val Glu Arg Ile Ile
1               5

<210> SEQ ID NO 1137
<211> LENGTH: 6
<212> TYPE: PRT
<213> ORGANISM: Artificial sequence
<220> FEATURE:
<223> OTHER INFORMATION: synthetic sequence

<400> SEQUENCE: 1137

Tyr Thr Asp Arg Ile Leu
1               5

<210> SEQ ID NO 1138
<211> LENGTH: 6
<212> TYPE: PRT
<213> ORGANISM: Artificial sequence
<220> FEATURE:
<223> OTHER INFORMATION: synthetic sequence

<400> SEQUENCE: 1138

Trp Val Gln Gln Leu Met
1               5

<210> SEQ ID NO 1139
<211> LENGTH: 10
<212> TYPE: PRT
<213> ORGANISM: Artificial sequence
<220> FEATURE:
<223> OTHER INFORMATION: synthetic sequence

<400> SEQUENCE: 1139

Lys Leu Leu Lys Trp Leu Lys Lys Leu Leu
1               5                   10

<210> SEQ ID NO 1140
<211> LENGTH: 10
<212> TYPE: PRT
<213> ORGANISM: Artificial sequence
<220> FEATURE:
<223> OTHER INFORMATION: synthetic sequence

<400> SEQUENCE: 1140

Leu Trp Lys Asp Ile Leu Lys Asn Val Gly
1               5                   10

<210> SEQ ID NO 1141
<211> LENGTH: 10
<212> TYPE: PRT
<213> ORGANISM: Artificial sequence
<220> FEATURE:
<223> OTHER INFORMATION: synthetic sequence

<400> SEQUENCE: 1141

Lys Val Val Asn Val Leu Lys Asn Leu Phe
1               5                   10

<210> SEQ ID NO 1142
<211> LENGTH: 10
<212> TYPE: PRT

<213> ORGANISM: Artificial sequence
<220> FEATURE:
<223> OTHER INFORMATION: synthetic sequence

<400> SEQUENCE: 1142

Lys Phe Lys Lys Leu Phe Lys Lys Leu Ser
1               5                   10

<210> SEQ ID NO 1143
<211> LENGTH: 10
<212> TYPE: PRT
<213> ORGANISM: Artificial sequence
<220> FEATURE:
<223> OTHER INFORMATION: synthetic sequence

<400> SEQUENCE: 1143

Leu Ser Asp Arg Gly Arg Arg Leu Gly Glu
1               5                   10

<210> SEQ ID NO 1144
<211> LENGTH: 10
<212> TYPE: PRT
<213> ORGANISM: Artificial sequence
<220> FEATURE:
<223> OTHER INFORMATION: synthetic sequence

<400> SEQUENCE: 1144

Lys Gly Lys Glu Met Leu Lys Asp Tyr Ala
1               5                   10

<210> SEQ ID NO 1145
<211> LENGTH: 10
<212> TYPE: PRT
<213> ORGANISM: Artificial sequence
<220> FEATURE:
<223> OTHER INFORMATION: synthetic sequence

<400> SEQUENCE: 1145

Lys Leu Val Lys Lys Val Lys His Thr Ile
1               5                   10

<210> SEQ ID NO 1146
<211> LENGTH: 10
<212> TYPE: PRT
<213> ORGANISM: Artificial sequence
<220> FEATURE:
<223> OTHER INFORMATION: synthetic sequence

<400> SEQUENCE: 1146

Lys Val Phe Lys Arg Leu Glu Lys Leu Phe
1               5                   10

<210> SEQ ID NO 1147
<211> LENGTH: 10
<212> TYPE: PRT
<213> ORGANISM: Artificial sequence
<220> FEATURE:
<223> OTHER INFORMATION: synthetic sequence

<400> SEQUENCE: 1147

Arg Lys Leu Lys Lys Leu Arg Asn Ala Leu
1               5                   10

<210> SEQ ID NO 1148
<211> LENGTH: 10
<212> TYPE: PRT
<213> ORGANISM: Artificial sequence
<220> FEATURE:
<223> OTHER INFORMATION: synthetic sequence

<400> SEQUENCE: 1148

Ser Leu Gln Arg Gly Gly Gln Lys Ile Leu
1 5 10

<210> SEQ ID NO 1149
<211> LENGTH: 10
<212> TYPE: PRT
<213> ORGANISM: Artificial sequence
<220> FEATURE:
<223> OTHER INFORMATION: synthetic sequence

<400> SEQUENCE: 1149

Lys Leu Leu Asp Ala Ala Lys Gln Ile Leu
1 5 10

<210> SEQ ID NO 1150
<211> LENGTH: 10
<212> TYPE: PRT
<213> ORGANISM: Artificial sequence
<220> FEATURE:
<223> OTHER INFORMATION: synthetic sequence

<400> SEQUENCE: 1150

Arg Ile Lys Asp Phe Leu Arg Asn Leu Val
1 5 10

<210> SEQ ID NO 1151
<211> LENGTH: 10
<212> TYPE: PRT
<213> ORGANISM: Artificial sequence
<220> FEATURE:
<223> OTHER INFORMATION: synthetic sequence

<400> SEQUENCE: 1151

Arg Ile Val Gln Arg Ile Lys Asp Phe Leu
1 5 10

<210> SEQ ID NO 1152
<211> LENGTH: 10
<212> TYPE: PRT
<213> ORGANISM: Artificial sequence
<220> FEATURE:
<223> OTHER INFORMATION: synthetic sequence

<400> SEQUENCE: 1152

Lys Val Lys His Ala Gly Arg Arg Val Leu
1 5 10

<210> SEQ ID NO 1153
<211> LENGTH: 10
<212> TYPE: PRT
<213> ORGANISM: Artificial sequence
<220> FEATURE:
<223> OTHER INFORMATION: synthetic sequence

<400> SEQUENCE: 1153

Leu Gly Lys Arg Ala Leu Lys Lys Ile Ile
1 5 10

<210> SEQ ID NO 1154
<211> LENGTH: 10
<212> TYPE: PRT
<213> ORGANISM: Artificial sequence
<220> FEATURE:

<223> OTHER INFORMATION: synthetic sequence

<400> SEQUENCE: 1154

Lys Val Arg Lys Gly Phe Lys Glu Ala Ser
1 5 10

<210> SEQ ID NO 1155
<211> LENGTH: 10
<212> TYPE: PRT
<213> ORGANISM: Artificial sequence
<220> FEATURE:
<223> OTHER INFORMATION: synthetic sequence

<400> SEQUENCE: 1155

Ser Met Ala Lys Lys Leu Lys Glu Tyr Met
1 5 10

<210> SEQ ID NO 1156
<211> LENGTH: 10
<212> TYPE: PRT
<213> ORGANISM: Artificial sequence
<220> FEATURE:
<223> OTHER INFORMATION: synthetic sequence

<400> SEQUENCE: 1156

Thr Ala Lys Asn Val Ala Lys Asn Val Ala
1 5 10

<210> SEQ ID NO 1157
<211> LENGTH: 10
<212> TYPE: PRT
<213> ORGANISM: Artificial sequence
<220> FEATURE:
<223> OTHER INFORMATION: synthetic sequence

<400> SEQUENCE: 1157

Arg Gln Gly Trp Arg Ala His Lys Val Val
1 5 10

<210> SEQ ID NO 1158
<211> LENGTH: 10
<212> TYPE: PRT
<213> ORGANISM: Artificial sequence
<220> FEATURE:
<223> OTHER INFORMATION: synthetic sequence

<400> SEQUENCE: 1158

Arg Val Val Arg Val Val Arg Arg Trp Val
1 5 10

<210> SEQ ID NO 1159
<211> LENGTH: 10
<212> TYPE: PRT
<213> ORGANISM: Artificial sequence
<220> FEATURE:
<223> OTHER INFORMATION: synthetic sequence

<400> SEQUENCE: 1159

Lys Ile Phe Glu Lys Val Lys Asn Leu Val
1 5 10

<210> SEQ ID NO 1160
<211> LENGTH: 10
<212> TYPE: PRT
<213> ORGANISM: Artificial sequence
<220> FEATURE:
<223> OTHER INFORMATION: synthetic sequence

<400> SEQUENCE: 1160

Lys Ile Gly Gln Arg Ile Arg Asp Phe Phe
1 5 10

<210> SEQ ID NO 1161
<211> LENGTH: 10
<212> TYPE: PRT
<213> ORGANISM: Artificial sequence
<220> FEATURE:
<223> OTHER INFORMATION: synthetic sequence

<400> SEQUENCE: 1161

Phe Ile Lys Lys Phe Tyr Lys Gln Ile Met
1 5 10

<210> SEQ ID NO 1162
<211> LENGTH: 10
<212> TYPE: PRT
<213> ORGANISM: Artificial sequence
<220> FEATURE:
<223> OTHER INFORMATION: synthetic sequence

<400> SEQUENCE: 1162

Arg Leu Leu Lys Ser Val Arg Arg Ala Val
1 5 10

<210> SEQ ID NO 1163
<211> LENGTH: 9
<212> TYPE: PRT
<213> ORGANISM: Artificial sequence
<220> FEATURE:
<223> OTHER INFORMATION: synthetic sequence

<400> SEQUENCE: 1163

Lys Trp Arg Arg Trp Val Arg Trp Ile
1 5

<210> SEQ ID NO 1164
<211> LENGTH: 10
<212> TYPE: PRT
<213> ORGANISM: Artificial sequence
<220> FEATURE:
<223> OTHER INFORMATION: synthetic sequence

<400> SEQUENCE: 1164

Lys Leu Phe Lys Lys Ile Leu Lys Tyr Leu
1 5 10

<210> SEQ ID NO 1165
<211> LENGTH: 10
<212> TYPE: PRT
<213> ORGANISM: Artificial sequence
<220> FEATURE:
<223> OTHER INFORMATION: synthetic sequence

<400> SEQUENCE: 1165

Lys Phe Trp Lys Lys Val Leu Asn Gly Ala
1 5 10

<210> SEQ ID NO 1166
<211> LENGTH: 10
<212> TYPE: PRT
<213> ORGANISM: Artificial sequence
<220> FEATURE:
<223> OTHER INFORMATION: synthetic sequence

<400> SEQUENCE: 1166

Leu Trp Lys Glu Val Leu Lys Asn Ala Gly
1 5 10

<210> SEQ ID NO 1167
<211> LENGTH: 10
<212> TYPE: PRT
<213> ORGANISM: Artificial sequence
<220> FEATURE:
<223> OTHER INFORMATION: synthetic sequence

<400> SEQUENCE: 1167

Lys Ile Lys Lys Gly Phe Arg Lys Ile Phe
1 5 10

<210> SEQ ID NO 1168
<211> LENGTH: 10
<212> TYPE: PRT
<213> ORGANISM: Artificial sequence
<220> FEATURE:
<223> OTHER INFORMATION: synthetic sequence

<400> SEQUENCE: 1168

Lys Gly Lys Glu Leu Leu Arg Asp Tyr Ala
1 5 10

<210> SEQ ID NO 1169
<211> LENGTH: 10
<212> TYPE: PRT
<213> ORGANISM: Artificial sequence
<220> FEATURE:
<223> OTHER INFORMATION: synthetic sequence

<400> SEQUENCE: 1169

Gly Leu Phe Asp Ile Ile Lys Lys Ile Ala
1 5 10

<210> SEQ ID NO 1170
<211> LENGTH: 10
<212> TYPE: PRT
<213> ORGANISM: Artificial sequence
<220> FEATURE:
<223> OTHER INFORMATION: synthetic sequence

<400> SEQUENCE: 1170

Gly Leu Phe Asp Ile Val Lys Lys Val Val
1 5 10

<210> SEQ ID NO 1171
<211> LENGTH: 10
<212> TYPE: PRT
<213> ORGANISM: Artificial sequence
<220> FEATURE:
<223> OTHER INFORMATION: synthetic sequence

<400> SEQUENCE: 1171

Gly Leu Lys Asn Val Gly Lys Glu Val Gly
1 5 10

<210> SEQ ID NO 1172
<211> LENGTH: 10
<212> TYPE: PRT
<213> ORGANISM: Artificial sequence
<220> FEATURE:
<223> OTHER INFORMATION: synthetic sequence

<400> SEQUENCE: 1172

Gly Leu Arg Arg Leu Gly Arg Lys Ile Ala
1 5 10

<210> SEQ ID NO 1173
<211> LENGTH: 10
<212> TYPE: PRT
<213> ORGANISM: Artificial sequence
<220> FEATURE:
<223> OTHER INFORMATION: synthetic sequence

<400> SEQUENCE: 1173

Gly Trp Lys Asp Trp Ala Lys Lys Ala Gly
1 5 10

<210> SEQ ID NO 1174
<211> LENGTH: 10
<212> TYPE: PRT
<213> ORGANISM: Artificial sequence
<220> FEATURE:
<223> OTHER INFORMATION: synthetic sequence

<400> SEQUENCE: 1174

Gly Lys Val Arg Ala Lys Ala Lys Thr Arg
1 5 10

<210> SEQ ID NO 1175
<211> LENGTH: 10
<212> TYPE: PRT
<213> ORGANISM: Artificial sequence
<220> FEATURE:
<223> OTHER INFORMATION: synthetic sequence

<400> SEQUENCE: 1175

Lys Phe Phe Arg Lys Leu Lys Lys Ser Val
1 5 10

<210> SEQ ID NO 1176
<211> LENGTH: 8
<212> TYPE: PRT
<213> ORGANISM: Artificial sequence
<220> FEATURE:
<223> OTHER INFORMATION: synthetic sequence

<400> SEQUENCE: 1176

Gly Lys Ser Lys Ile Lys Trp Gln
1 5

<210> SEQ ID NO 1177
<211> LENGTH: 10
<212> TYPE: PRT
<213> ORGANISM: Artificial sequence
<220> FEATURE:
<223> OTHER INFORMATION: synthetic sequence

<400> SEQUENCE: 1177

Ala Phe Gln Asp Thr Ile Arg Lys Phe Leu
1 5 10

<210> SEQ ID NO 1178
<211> LENGTH: 10
<212> TYPE: PRT
<213> ORGANISM: Artificial sequence
<220> FEATURE:
<223> OTHER INFORMATION: synthetic sequence

<400> SEQUENCE: 1178

```
Ile Leu Lys Lys Val Gly Lys Glu Ala Val
1               5                   10


<210> SEQ ID NO 1179
<211> LENGTH: 10
<212> TYPE: PRT
<213> ORGANISM: Artificial sequence
<220> FEATURE:
<223> OTHER INFORMATION: synthetic sequence

<400> SEQUENCE: 1179

Lys Phe Phe Lys Lys Val Lys Lys Ser Val
1               5                   10


<210> SEQ ID NO 1180
<211> LENGTH: 10
<212> TYPE: PRT
<213> ORGANISM: Artificial sequence
<220> FEATURE:
<223> OTHER INFORMATION: synthetic sequence

<400> SEQUENCE: 1180

Ala Met Glu Lys Ile Ala Glu Lys Val Gly
1               5                   10


<210> SEQ ID NO 1181
<211> LENGTH: 7
<212> TYPE: PRT
<213> ORGANISM: Artificial sequence
<220> FEATURE:
<223> OTHER INFORMATION: synthetic sequence

<400> SEQUENCE: 1181

Ile Arg Trp Arg Ile Arg Val
1               5


<210> SEQ ID NO 1182
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (2)..(2)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (3)..(3)
<223> OTHER INFORMATION: Xaa is selected from phenylalanine, tryptophan,
      alanine, valine, leucine, isoleucine, methionine, tyrosine,
      threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine,
      histidine, aspartic acid, glutamic acid, asparagine and glutamine
<220> FEATURE:
<221> NAME/KEY: MISC_FEATURE
<222> LOCATION: (5)..(5)
<223> OTHER INFORMATION: Xaa is selected from phenylalanine, tryptophan,
      alanine, valine, leucine, isoleucine, methionine, tyrosine,
      threonine, serine, cysteine, proline, and glycine

<400> SEQUENCE: 1182
```

Xaa Xaa Xaa Xaa Xaa
1 5

<210> SEQ ID NO 1183
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(4)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (5)..(5)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (6)..(6)
<223> OTHER INFORMATION: Xaa is selected from phenylalanine, tryptophan, alanine, valine, leucine, isoleucine, methionine, tyrosine, threonine, serine, cysteine, proline, and glycine

<400> SEQUENCE: 1183

Xaa Xaa Xaa Xaa Xaa
1 5

<210> SEQ ID NO 1184
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(5)
<223> OTHER INFORMATION: Xaa at positions 4 and 5 are each independently selected from phenylalanine, tryptophan, alanine, valine, leucine, isoleucine, methionine, tyrosine, threonine, serine, cysteine, proline, and glycine

<400> SEQUENCE: 1184

Xaa Xaa Xaa Xaa Xaa
1 5

<210> SEQ ID NO 1185
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(4)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (5)..(5)
<223> OTHER INFORMATION: Xaa is selected from lysine, arginine, histidine, aspartic acid, glutamic acid, asparagine and glutamine

<400> SEQUENCE: 1185

Xaa Xaa Xaa Xaa Xaa
1 5

<210> SEQ ID NO 1186
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(3)
<223> OTHER INFORMATION: Xaa at positions 2 and 3 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (5)..(5)
<223> OTHER INFORMATION: Xaa is selected from phenylalanine, tryptophan, alanine, valine, leucine, isoleucine, methionine, tyrosine, threonine, serine, cysteine, proline, and glycine

<400> SEQUENCE: 1186

Xaa Xaa Xaa Xaa Xaa
1 5

<210> SEQ ID NO 1187
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (2)..(2)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (3)..(4)
<223> OTHER INFORMATION: Xaa at positions 3 and 4 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (5)..(5)
<223> OTHER INFORMATION: Xaa is selected from lysine, arginine, histidine, aspartic acid, glutamic acid, asparagine and glutamine

<400> SEQUENCE: 1187

Xaa Xaa Xaa Xaa Xaa
1               5

<210> SEQ ID NO 1188
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(5)
<223> OTHER INFORMATION: Xaa at positions 4 and 5 are each independently selected from phenylalanine, tryptophan, alanine, valine, leucine, isoleucine, methionine, tyrosine, threonine, serine, cysteine, proline, and glycine

<400> SEQUENCE: 1188

Xaa Xaa Xaa Xaa Xaa
1               5

<210> SEQ ID NO 1189
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa at position 1 is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (2)..(2)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (3)..(3)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (4)..(4)
<223> OTHER INFORMATION: Xaa is selected from lysine, arginine, histidine, aspartic acid, glutamic acid, asparagine and glutamine

<400> SEQUENCE: 1189

Xaa Xaa Xaa Xaa
1

<210> SEQ ID NO 1190
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (2)..(2)
<223> OTHER INFORMATION: Xaa is selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(3)
<223> OTHER INFORMATION: Xaa is selected from lysine, arginine, histidine, aspartic acid, glutamic acid, asparagine and glutamine
<220> FEATURE:
<221> NAME/KEY: MISC_FEATURE
<222> LOCATION: (4)..(4)
<223> OTHER INFORMATION: Xaa is selected from phenylalanine, tryptophan, alanine, valine, leucine, isoleucine, methionine, tyrosine, threonine, serine, cysteine, proline, and glycine

<400> SEQUENCE: 1190

Xaa Xaa Xaa Xaa
1

<210> SEQ ID NO 1191
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from lysine, arginine, histidine, aspartic acid, glutamic acid, asparagine and glutamine
<220> FEATURE:
<221> NAME/KEY: MISC_FEATURE
<222> LOCATION: (3)..(4)
<223> OTHER INFORMATION: Xaa at positions 3 and 4 are each independently selected from phenylalanine, tryptophan, alanine, valine, leucine, isoleucine, methionine, tyrosine, threonine, serine, cysteine, proline, and glycine

<400> SEQUENCE: 1191

Xaa Xaa Xaa Xaa
1

<210> SEQ ID NO 1192
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(2)
<223> OTHER INFORMATION: Xaa at positions 1 and 2 are each independently selected from phenylalanine, tryptophan, alanine, valine, leucine, isoleucine, methionine, tyrosine, threonine, serine, cysteine, proline, and glycine
<220> FEATURE:
<221> NAME/KEY: MISC_FEATURE
<222> LOCATION: (3)..(4)
<223> OTHER INFORMATION: Xaa at positions 3 and 4 are each independently selected from lysine, arginine, histidine, aspartic acid, glutamic acid, asparagine and glutamine

<400> SEQUENCE: 1192

Xaa Xaa Xaa Xaa
1

<210> SEQ ID NO 1193
<211> LENGTH: 10
<212> TYPE: PRT
<213> ORGANISM: Artificial sequence
<220> FEATURE:
<223> OTHER INFORMATION: synthetic sequence

<400> SEQUENCE: 1193

Ile Phe Lys Lys Ile Glu Arg Val Gly Gln
1 5 10

<210> SEQ ID NO 1194
<211> LENGTH: 10
<212> TYPE: PRT
<213> ORGANISM: Artificial sequence
<220> FEATURE:
<223> OTHER INFORMATION: synthetic sequence

<400> SEQUENCE: 1194

Leu Phe Lys Lys Ile Glu Lys Val Gly Gln
1 5 10

<210> SEQ ID NO 1195
<211> LENGTH: 10
<212> TYPE: PRT
<213> ORGANISM: Artificial sequence
<220> FEATURE:
<223> OTHER INFORMATION: synthetic sequence

<400> SEQUENCE: 1195

Phe Phe Arg Lys Ser Lys Glu Lys Ile Gly
1 5 10

<210> SEQ ID NO 1196
<211> LENGTH: 10
<212> TYPE: PRT
<213> ORGANISM: Artificial sequence
<220> FEATURE:
<223> OTHER INFORMATION: synthetic sequence

<400> SEQUENCE: 1196

Ile Gly Lys Glu Phe Lys Arg Ile Val Gln
1 5 10

<210> SEQ ID NO 1197
<211> LENGTH: 10
<212> TYPE: PRT
<213> ORGANISM: Artificial sequence
<220> FEATURE:
<223> OTHER INFORMATION: synthetic sequence

<400> SEQUENCE: 1197

Phe Phe Lys Lys Ala Ala His Val Gly Lys
1 5 10

<210> SEQ ID NO 1198
<211> LENGTH: 10
<212> TYPE: PRT
<213> ORGANISM: Artificial sequence
<220> FEATURE:
<223> OTHER INFORMATION: synthetic sequence

<400> SEQUENCE: 1198

Ala Leu Lys Lys Val Phe Gln Gly Ile His
1 5 10

<210> SEQ ID NO 1199
<211> LENGTH: 10
<212> TYPE: PRT
<213> ORGANISM: Artificial sequence
<220> FEATURE:
<223> OTHER INFORMATION: synthetic sequence

<400> SEQUENCE: 1199

Phe Leu His Ser Ala Lys Lys Phe Gly Lys
1 5 10

<210> SEQ ID NO 1200
<211> LENGTH: 10
<212> TYPE: PRT
<213> ORGANISM: Artificial sequence
<220> FEATURE:
<223> OTHER INFORMATION: synthetic sequence

<400> SEQUENCE: 1200

Leu Lys Lys Ala Leu Pro Val Ala Lys Lys
1 5 10

<210> SEQ ID NO 1201
<211> LENGTH: 10
<212> TYPE: PRT
<213> ORGANISM: Artificial sequence
<220> FEATURE:
<223> OTHER INFORMATION: synthetic sequence

<400> SEQUENCE: 1201

His Ser Ala Lys Lys Phe Gly Lys Ala Phe
1 5 10

<210> SEQ ID NO 1202
<211> LENGTH: 10
<212> TYPE: PRT
<213> ORGANISM: Artificial sequence
<220> FEATURE:
<223> OTHER INFORMATION: synthetic sequence

<400> SEQUENCE: 1202

Arg Ile Lys Asp Phe Leu Arg Asn Leu Val
1 5 10

<210> SEQ ID NO 1203
<211> LENGTH: 10
<212> TYPE: PRT
<213> ORGANISM: Artificial sequence
<220> FEATURE:
<223> OTHER INFORMATION: synthetic sequence

<400> SEQUENCE: 1203

Arg Ile Val Gln Arg Ile Lys Asp Phe Leu
1 5 10

<210> SEQ ID NO 1204
<211> LENGTH: 10
<212> TYPE: PRT
<213> ORGANISM: Artificial sequence
<220> FEATURE:
<223> OTHER INFORMATION: synthetic sequence

<400> SEQUENCE: 1204

Lys Phe Arg Lys Ala Phe Lys Arg Phe Phe
1 5 10

<210> SEQ ID NO 1205
<211> LENGTH: 10
<212> TYPE: PRT
<213> ORGANISM: Artificial sequence
<220> FEATURE:
<223> OTHER INFORMATION: synthetic sequence

<400> SEQUENCE: 1205

Lys Ala Arg Lys Ala Ala Lys Arg Ala Phe
1 5 10

<210> SEQ ID NO 1206
<211> LENGTH: 10
<212> TYPE: PRT
<213> ORGANISM: Artificial sequence
<220> FEATURE:
<223> OTHER INFORMATION: synthetic sequence

<400> SEQUENCE: 1206

Glu Lys Leu Ser Ala Phe Arg Asn Phe Phe
1 5 10

<210> SEQ ID NO 1207
<211> LENGTH: 10
<212> TYPE: PRT
<213> ORGANISM: Artificial sequence
<220> FEATURE:
<223> OTHER INFORMATION: synthetic sequence

<400> SEQUENCE: 1207

Ala Val Arg Arg Leu Ala Gln Arg Leu Ala
1 5 10

<210> SEQ ID NO 1208
<211> LENGTH: 10
<212> TYPE: PRT
<213> ORGANISM: Artificial sequence
<220> FEATURE:
<223> OTHER INFORMATION: synthetic sequence

<400> SEQUENCE: 1208

Lys Glu Phe Leu Ala Phe Lys Arg Phe Phe
1 5 10

<210> SEQ ID NO 1209
<211> LENGTH: 10
<212> TYPE: PRT
<213> ORGANISM: Artificial sequence
<220> FEATURE:
<223> OTHER INFORMATION: synthetic sequence

<400> SEQUENCE: 1209

Ile Glu Asn Ala Ala Phe Lys Arg Phe Phe
1 5 10

<210> SEQ ID NO 1210
<211> LENGTH: 10
<212> TYPE: PRT
<213> ORGANISM: Artificial sequence
<220> FEATURE:
<223> OTHER INFORMATION: synthetic sequence

<400> SEQUENCE: 1210

Gly Phe Arg Glu Leu Phe Arg Gln Leu Asp
1 5 10

<210> SEQ ID NO 1211
<211> LENGTH: 10
<212> TYPE: PRT
<213> ORGANISM: Artificial sequence
<220> FEATURE:
<223> OTHER INFORMATION: synthetic sequence

<400> SEQUENCE: 1211

Ala Ile Arg Arg Ile Pro Arg Arg Ile Arg
1 5 10

<210> SEQ ID NO 1212
<211> LENGTH: 10
<212> TYPE: PRT
<213> ORGANISM: Artificial sequence
<220> FEATURE:
<223> OTHER INFORMATION: synthetic sequence

<400> SEQUENCE: 1212

Met Val Phe Arg Asp Val Gly Asn Arg Asn
1 5 10

<210> SEQ ID NO 1213
<211> LENGTH: 10
<212> TYPE: PRT
<213> ORGANISM: Artificial sequence
<220> FEATURE:
<223> OTHER INFORMATION: synthetic sequence

<400> SEQUENCE: 1213

Asp Arg Gly Ile Lys Gly His Arg Gly Phe
1 5 10

<210> SEQ ID NO 1214
<211> LENGTH: 10
<212> TYPE: PRT
<213> ORGANISM: Artificial sequence
<220> FEATURE:
<223> OTHER INFORMATION: synthetic sequence

<400> SEQUENCE: 1214

-continued

```
Leu Arg Gly Gln Lys Gly Asp Arg Gly Phe
1               5                   10


<210> SEQ ID NO 1215
<211> LENGTH: 10
<212> TYPE: PRT
<213> ORGANISM: Artificial sequence
<220> FEATURE:
<223> OTHER INFORMATION: synthetic sequence

<400> SEQUENCE: 1215

Glu Ala Gly Glu Lys Gly Asp Gln Gly Leu
1               5                   10


<210> SEQ ID NO 1216
<211> LENGTH: 10
<212> TYPE: PRT
<213> ORGANISM: Artificial sequence
<220> FEATURE:
<223> OTHER INFORMATION: synthetic sequence

<400> SEQUENCE: 1216

Val Leu Asp Ala Ile Arg Arg Leu Arg Leu
1               5                   10


<210> SEQ ID NO 1217
<211> LENGTH: 10
<212> TYPE: PRT
<213> ORGANISM: Artificial sequence
<220> FEATURE:
<223> OTHER INFORMATION: synthetic sequence

<400> SEQUENCE: 1217

His Val Val Gln Arg Gly Glu His Ser Leu
1               5                   10


<210> SEQ ID NO 1218
<211> LENGTH: 10
<212> TYPE: PRT
<213> ORGANISM: Artificial sequence
<220> FEATURE:
<223> OTHER INFORMATION: synthetic sequence

<400> SEQUENCE: 1218

Ile Val Arg Arg Ala Asp Arg Ala Ala Val
1               5                   10
```

METHODS FOR MODULATING MACROPHAGE ACTIVITY

CROSS-REFERENCE TO RELATED APPLICATIONS

This application is a continuation of PCT Application No. PCT/US2020/027672 filed Apr. 10, 2020, which application, pursuant to 35 U.S.C. § 119 (e), claims priority to the filing dates of U.S. Provisional Patent Application Ser. No. 62/966,961 filed Jan. 28, 2020 and U.S. Provisional Patent Application Ser. No. 62/833,352 filed Apr. 12, 2019; the disclosures of which applications are herein incorporated by reference.

INTRODUCTION

Cancer remains one of the leading causes of death globally, with an estimated 12.7 million annual cases around the world affecting both sexes. This number is expected to increase to 21 million by 2030.

Recent advances in immunotherapy have transformed the care of many cancer patients. Immunotherapy approaches in the form of checkpoint inhibitor monoclonal antibody (CIMA) therapy or chimeric antigen receptor (CAR) T cell therapy have become first- or second-line treatment options, and afford some patients sustained, durable treatment responses generally not observed with standard systemic chemotherapy. To date, these positive findings are limited to a small number of immunologically 'hot' cancers. This is in stark contrast to the majority of solid organ cancers classified as immunologically 'cold', where the promise of immunotherapy via T cell activation has largely evaded patients. These tumors create an immune milieu, which excludes cytotoxic T cells or induces an exhausted T cell phenotype through an abundance of immune evasive cues, frequently involving innate immune cells such as tumor-associated macrophages (TAMs) or immature myeloid-derived suppressor cells (MDSCs).

Macrophages are one of the primary innate immune cell populations and play a pivotal role in many human diseases including cancer, where tumor-associated macrophages (TAMs) are a major driver of cancer biology. Tumor cells attract and reprogram myeloid cells to support tumor growth and metastatic spread. While the dichotomous M1 versus M2 classification omits to capture the ontogeny and tissue-specific cues and stress responses in macrophages, in general terms. TAMs in the early stages of tumorigenesis are more frequently M1-like, secreting proinflammatory type I cytokines and inhibit immune evasion, whereas M2-tumor associated macrophages often become the predominant phenotype during tumor progression and further evolved tumor stages. M2-like TAMs may harness tumor growth directly via the excretion of type II cancer-promoting factors, or indirectly via promotion of angiogenesis, the nurturing of cancer stem cells affording resistance to cytotoxic chemotherapy, or the generation of an immune-evasive tumor microenvironment.

SUMMARY

Aspects of the present disclosure include methods for modulating macrophage activity. Methods according to certain embodiments include contacting a macrophage with a mannose receptor (CD206) binding agent in a manner sufficient to modulate activity of the macrophage. Methods for converting a phenotype of a macrophage from an M2 phenotype to an M1 phenotype are also provided. Methods for inhibiting growth of a CD206-expressing cell as well as methods for treating a subject for a neoplastic condition (e.g., cancer) or a condition associated with chronic inflammation are described. As used herein "inhibiting growth of a CD206-expressing cell includes killing the cell, or reprogramming the cell. In some embodiments, methods include killing a CD206-expressing cell. In other embodiments, methods include reprogramming a CD206-expressing cell. Immuno-modulating peptides suitable for use in the subject methods are also presented. Aspects of the present disclosure also include active agents for binding to an activity modulating domain of CD206. Methods for determining whether a compound binds to an activity modulating domain of CD206 are also provided.

In certain embodiments, methods include modulating a macrophage activity. Methods according to certain embodiments include contacting a macrophage with a CD206-binding agent to modulate activity of the macrophage. In these embodiments, the CD206-binding agent binds to a site selected from the fibronectin II domain of CD206, C-type lectin carbohydrate recognition domain 3 (CRD3) of CD206. C-type lectin carbohydrate recognition domain 4 (CRD4) of CD206 and C-type lectin carbohydrate recognition domain 5 (CRD5) of CD206. In some instances, the CD206-binding agent binds to CD206 with a binding energy of at least −650 kcal/mol. In some instances, the macrophage activity that is modulated is macrophage polarization. In other instances, the macrophage viability is reduced. The macrophage according to certain embodiments is a macrophage with an M2 phenotype. In other embodiments, the macrophage is a tumor associated macrophage. In some embodiments, the CD206-binding agent inhibits macrophage activity. In other embodiments, the CD206-binding agent induces apoptosis of the macrophage. In still other embodiments, the CD206-binding agent stimulates phagocytosis. The macrophage may be contacted in vivo or in vitro.

In other embodiments, methods include inhibiting growth of a CD206-expressing cell. Methods according to certain embodiments include contacting a target CD206-expressing cell with a CD206-binding agent to inhibit growth of the cell. In some instances, the target CD206-expressing cell is a cancer cell. For example, the cancer cell may be a pancreatic cancer cell, a prostate cancer cell, a colon cancer cell, a skin cancer cell or breast cancer cell.

In certain embodiments, methods include treating a subject for a neoplastic condition. Methods according to certain embodiments include administering a therapeutically effective amount of a CD206-binding agent to a subject diagnosed as having a neoplastic condition to treat the neoplastic condition in the subject. In these embodiments, the neoplastic condition may be a solid-tumor cancer. For example, the neoplastic condition may be a cancer selected from pancreatic cancer, prostate cancer, colon cancer, breast cancer and skin cancer. In some instances, methods further include administering an effective amount of a chemotherapeutic agent, antibody agent or cell therapy to the subject. For example, the chemotherapeutic agent, antibody agent or cell therapy may be selected from steroids, anthracyclines, thyroid hormone replacement drugs, thymidylate-targeted drugs, antibodies, checkpoint inhibitor drugs, Chimeric Antigen Receptor/T cell therapies, and other cell therapies. In some embodiments, the chemotherapeutic agent is a non-peptidic compound that reduces proliferation of cancer cells. For example, the chemotherapeutic agent may be a compound selected from alkylating agents, metal complexes, nitrosoureas, antimetabolites, antitumor antibiotics, plant (*vinca*) alkaloids, hormone modulators, and steroid hormones. In some instances, the antibody agent is a chemotherapeutic antibody agent. For example, the antibody agent may be an antibody raised against a tumor-associated antigen selected from the group consisting of CD20, CD30, CD33, CD52, CD47, EpCAM, CEA, gpA33, Mucins, TAG-72, CAIX, PSMA, Folate-binding protein. Gangliosides (e.g., GD2, GD3, GM2, etc.), Le y. VEGF, VEGFR, Integrin alpha-V-beta-3, Integrin alpha-5-beta-1, EGFR, ERBB2, ERBB3, MET, IGF1R. EPHA3, TRAILR1, TRAILR2, RANKL, FAP and Tenascin. In certain embodiments, methods include administering a checkpoint inhibitor. For example, the checkpoint inhibitor may be an inhibitory compound that targets one or more of PD1, PD-L1, CTLA4, TIM3, LAG3, VISTA, BTLA, TIGIT, LAIR1, CD160, 2B4 and TGFRβ.

In yet other embodiments, methods include treating a subject for a condition associated with chronic inflammation. Methods according to certain embodiments include administering a therapeutically effective amount of a CD206-binding agent to a subject to treat the subject for the condition associated with chronic inflammation. In some embodiments, the condition associated with chronic inflammation is selected from scleroderma or multiple sclerosis, irritable bowel disease, ulcerative colitis, colitis, Crohn's disease, idiopathic pulmonary fibrosis, asthma, keratitis, arthritis, osteoarthritis, rheumatoid arthritis, auto-immune diseases, a feline or human immunodeficiency virus (FIV or HIV) infection, cancer, age-related inflammation and/or stem cell dysfunction, graft-versus-host disease (GVHD), keloids, obesity, diabetes, diabetic wounds, other chronic wounds, atherosclerosis, Parkinson's disease, Alzheimer's disease, macular degeneration, gout, gastric ulcers, gastritis, mucositis, toxoplasmosis, and chronic viral or microbial infections.

In still other embodiments, methods include converting a phenotype of a macrophage from an M2 phenotype to an M1 phenotype. Methods according to certain embodiments include contacting a macrophage having an M2 phenotype with a CD206-binding agent in a manner sufficient to convert the phenotype of the macrophage to an M1 phenotype. In some instances, contacting the CD206-binding agent induces a conformational change in a CD206 receptor of the macrophage sufficient to convert the phenotype of the macrophage to an M1 phenotype. In some instances, converting the phenotype of the macrophage includes inducing expression of CD86 by the macrophage. In other instances, converting the phenotype of the macrophage includes reducing expression of CD206 by the macrophage. In other instances, converting the phenotype of the macrophage includes reducing expression of CD163 by the macrophage. In still other instances, converting the phenotype of the macrophage includes converting the macrophage to a phenotype that exhibits upregulation of M1 cytokines and markers. For example, the M1 cytokine and marker is selected from the group consisting of IL-1β, IL-12, TNFα and nitric oxide synthetase. In other instances, converting the phenotype of the macrophage includes converting the macrophage to a phenotype that exhibits decreased expression of signal regulatory protein a (SIRPα).

In certain embodiments, there is provided an active agent that binds to an activity modulating domain of CD206. In these embodiments, the active agent binds to an activity modulating domain of CD206 selected from the fibronectin 11 domain of CD206. C-type lectin carbohydrate recognition domain 3 (CRD3) of CD206. C-type lectin carbohydrate recognition domain 4 (CRD4) of CD206 and C-type lectin carbohydrate recognition domain 5 (CRD5) of CD206. In some instances, the active agent binds to the CRD5 domain of CD206. In some instances, the active agent binds to the fibronectin II domain of CD206. In some other instances, the active agent binds to the CRD3 domain of CD206.

In certain embodiments, the methods include determining if an active agent binds to an activity modulating domain of CD206. In these embodiments, the methods include contacting a macrophage comprising CD206 with a compound, and determining whether the compound binds to an activity modulating domain of CD206. In some instances, the method includes determining the activity modulating domain of CD20 that binds the compound. In certain instances of these methods, the macrophage is a macrophage comprising one or more mutations in the activity modulating domains of CD206. In certain embodiments, the activity modulating domain of CD206 is selected from the fibronectin II domain of CD206, C-type lectin carbohydrate recognition domain 3 (CRD3) of CD206, C-type lectin carbohydrate recognition domain 4 (CRD4) of CD206 and C-type lectin carbohydrate recognition domain 5 (CRD5) of CD206. In certain cases, the activity modulating domain of CD206 is the CRD5 domain. In certain instances, the activity modulating domain of CD206 is the fibronectin II domain. In certain other cases, the activity modulating domain of CD206 is the CRD3 domain.

The CD206-binding agent according to certain embodiments of the present disclosure is an immunomodulatory peptide. In some instances, the immunomodulatory peptide is of 5 to 18 amino acid residues in length and includes a striapathic region of alternating hydrophilic and hydrophobic modules that adopts an amphipathic conformation under physiological conditions. In these instances, the striapathic region may include 3 or more hydrophobic modules; and 2 or more hydrophilic modules each comprising at least one cationic residue. In some embodiments, the immunomodulatory peptide includes a sequence defined by one of the formulae:

$$[J_{1a}J_{1b}]-[X_{1a}X_{1b}]-[J_{2a}J_{2b}]-[X_{2a}X_{2b}]-[J_{3a}]-[X_{3a}]; \text{ and}$$

$$[X_{3a}]-[J_{3a}]-[X_{2b}X_{2a}]-[J_{2b}J_{2a}]-[X_{1b}X_{1a}]-[J_{1b}J_{1a}];$$

wherein:

$J_{1a}$, $J_{1b}$, $J_{2a}$, $J_{2b}$ and $J_{3a}$ are each independently selected from phenylalanine, tryptophan, alanine, valine, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine. In some instances, $J_{1a}$, $J_{1b}$, $J_{2a}$, $J_{2b}$ and $J_{3a}$ are each phenylalanine; and $X_{1a}$, $X_{1b}$, $X_{2a}$, $X_{2b}$ and $X_{3a}$ are each independently selected from lysine and arginine. In certain embodiments, the immunomodulatory peptide includes: a) a sequence selected from: KFRKAFKRFF (RP182); FFRKFAKRFK (RP183); FFKKFFKKFK (RP185); FFKKFFKKFK (RP186); and FFKKFFKKFK (RP233); or b) a sequence having one or two amino acid substitutions relative to the sequence defined in a). In other embodiments, the immunomodulatory peptide includes: a) a peptide sequence selected from: RWKFGGFKWR (RP832C); FKWRGGRWKF (RP837C); FWKRGGRKWF (RP837A); FWKRFV (RP837N); FVRKWR (RP837C1); FAOOFAOOFO (RP850); FWKRFVRKWR (RP837); FWKKFVKKWK (RP841); WWHHWWWHHWH (RP847); WWRHWWHRWR (RP848); WWKHWWHKWK (RP849); GDRGIKGHRGF (RP842); LYKKIIKKLL (RP846); FYPDFFKKFF (RP844); FFRKSKEKIG (RP853); FFRHFATHLD (RP845); and EKLSAFRNFF (RP843); or b) a sequence having one or two amino acid substitutions relative to the sequence defined in a).

CD206-binding agent according to certain embodiments of the present disclosure also includes immunomodulatory peptides including a sequence defined by one of the formulae:

$[X_{1a}]$-$[J_{2a}]$-$[X_{2a}]$-$[J_{2a}]$-$[X_{3a}]$-$[J_{3a}]$ $[J_{3a}]$-$[X_{3a}]$-$[J_{2a}]$-$[X_{2a}]$-$[J_{1a}]$-$[X_{1a}]$ $[J_{1a}J_{1b}]$-$[X_{1a}X_{1b}]$-$[J_{2a}J_{2b}]$;

$[J_{1a}J_{1b}]$-$[X_{1a}X_{1b}]$-$[J_{2a}]$-$[X_{2a}]$;

$[X_{3a}]$-$[J_{3a}]$-$[X_{2b}X_{2a}]$-$[J_{2b}J_{2a}]$;

$[J_{1a}J_{1b}]$-$[X_{1a}]$-$[J_{2a}J_{2b}]$-$[X_{2a}]$; and $[X_{1a}]$-$[J_{1a}J_{1b}]$-$[X_{2a}]$-$[J_{2a}J_{2b}]$;

wherein:

$J_{1a}$, $J_{1b}$, $J_{2a}$, $J_{2b}$ and $J_{3a}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, $X_{2b}$, and $X_{3a}$ are each independently selected from lysine, arginine, histidine, aspartic acid, glutamic acid, asparagine and glutamine. In certain embodiments, the immunomodulatory peptide includes: a) a sequence selected from: AFKRFF (182-FN6); FFKKFF (185-FN6); FWKRFV (837-FN6); WVRRVV (WLUB-F1-N6); IFKKIE (CEC-F1-N6) FLRNLV (LL37F-3-N6); FLHSAK (MAG-F1-N6); FFHHIF (PISC-F-N6); FFKKAA (PLEU-F-N6); ALKKVF (PSEU-F-N6); LYKKII (CXCL4-F-N6); LFRRAF (IL24-FN6); FLKRLL (IL7-FN6); FFRRFA (ABCP-FN6); FFRHFA (E1P-FN6); AIRRIP (gP120-FN6); AFHRFF (GP2B-FN6); FFNRFA (MCPH-FN6); AFKRFF (SPRA-FN6); AFKRFF (TPRO-FN6); IVRRAD (COL18-FN6); FWRWFK (HX5/CPAP); KFWRWF (HX6/YJPA); WFRFWK (HX7/CLPB) KWFRFW (HX8/ATG1); AFHHFF (HEX16F/STPK); FFRNFA (HEXF13/SIF1); AFHRFF (HEX9F/THIF); FFRQFA (HEXF1/ATPB); AFNRFF (HEX2F/AATF); WIQRMM (CXCL13-FN6); WVQRVV (CXCL8-FN6); AFRNFF (HEX3F/FBNA); and TLRRFM (HEX18/HSHK); or b) a sequence having one or two amino acid substitutions relative to the sequence defined in a). In other embodiments, the immunomodulatory peptide includes: a) a sequence selected from: DVRMRL (MCMV-FN6); and RRAELG (TONB-FN6) or b) a sequence having one or two amino acid substitutions relative to the sequence defined in a). In some other embodiments, the immunomodulatory peptide includes: a) a sequence selected from: FWRWFA (HX1/MMPL); AFWRWF (HX2/ABCT); WFRFWA (HX3/GTRF); AWFRFW (HX4/AXES); VAVRIW (HX9/IDRF/AMIA); FFRFFA (HEXF2/AMT1); and AFFRFF (HEX13F/TGME); or b) a sequence having one or two amino acid substitutions relative to the sequence defined in a). In other embodiments, the immunomodulatory peptide includes: a sequence selected from: FFKKFF; WWKKFF; FWKKWF; FFKKWW; WWKKWW; YYKKYY; IIKKYY; YIKKIY; YYKKII; IIKKII; MMKKMM; LLKKMM; MLKKLM; MMKKLL; LLKKLL; VVKKVV; AAKKVV; VAKKAV; VVKKAA; AAKKAA; GGKKGG; TTKKGG; GTKKTG; GGKKTT; TTKKTT; SSKKSS; CCKKSS; SCKKCS; SSKKCC; and CCKKCC; or b) a sequence having one or two amino acid substitutions relative to the sequence defined in a). In certain other cases, the immunomodulatory peptide includes: a sequence selected from: FKFKFK; WKWKWK; YKYKYK; IKIKIK; MKMKMK; LKLKLK; VKVKVK; AKAKAK; GKGKGK; TKTKTK; SKSKSK; CKCKCK; KFKFKF; KWKWKW; KYKYKY; KIKIKI; KMKMKM; KLKLKL; KVKVKV; KAKAKA; KGKGKG; KTKTKT; KSKSKS; and KCKCKC; or b) a sequence having one or two amino acid substitutions relative to the sequence defined in a).

CD206-binding agent according to certain embodiments of the present disclosure also includes immunomodulatory peptides including a sequence defined by one of the formulae:

$[J_{1a}]$-$[X_{2a}]$-$[J_{2a}]$-$[X_{3a}]$-$[J_{3a}]$ $[X_{1a}]$-$[J_{1a}]$-$[X_{2a}]$-$[J_{2a}]$-$[X_{3a}]$ $[X_{1a}]$-$[J_{1a}]$-$[X_{2a}]$-$[J_{2a}J_{2b}]$;

$[J_{1a}J_{1b}]$-$[X_{1a}]$-$[J_{2a}]$-$[X_{2a}]$;

$[X_{1a}]$-$[J_{1a}J_{1b}]$-$[X_{2a}]$-$[J_{2a}]$;

$[J_{1a}]$-$[X_{1a}]$-$[J_{2a}J_{2b}]$-$[X_{2a}]$; and $[J_{1a}J_{1b}]$-$[X_{2a}]$-$[J_{2a}J_{2b}]$;

wherein:

$J_{1a}$, $J_{1b}$, $J_{2a}$, $J_{2b}$ and $J_{3a}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine. In certain embodiments, the immunomodulatory peptide includes: a) a sequence selected from: AFKRF; FFKKF; FWKRF; WVRRV; IFKKI; FLRNL; FLHSA; FFHHI; FFKKA; ALKKV; LYKKI; LFRRA; FLKRL; FFRRF; FFRHF; AIRRI; AFHRF; FFNRF; IVRRA; FWRWF; KFWRW; WFRFW; KWFRF; AFHHF: FFRNF; FFRQF; AFNRF; WIQRM: WVQRV; AFRNF; TLRRF; FKRFF; FKKFF; WKRFV; VRRVV; FKKIE; LRNLV; LHSAK; FHHIF; FKKAA; LKKVF; YKKII; FRRAF; LKRLL; FRRFA; FRHFA; IRRIP; FHRFF; FNRFA; VRRAD; WRWFK; FRFWK; FHHFF; FRNFA; FRQFA; FNRFF; IQRMM; VQRVV; FRNFF; LRRFM; DVRMR; VRMRL; RRAEL; RAELG; and RWKFG; or b) a sequence having one or two amino acid substitutions relative to the sequence defined in a). In other embodiments, the immunomodulatory peptide includes: a) a peptide sequence selected from: AFWRW; AWFRF; VAVRI; FFRFF; AFFRF; WRWFA; FRFWA; AVRIW; and FRFFA; or b) a sequence having one or two amino acid substitutions relative to the sequence defined in a). In other embodiments, the immunomodulatory peptide includes: a) a peptide sequence selected from: FFKKF; WWKKF; FWKKW; FFKKW; WWKKW; YYKKY;

IHKKY; YIKKI; YYKKI; IIKKI; MMKKM; LLKKM; MLKKL; MMKKL; LLKKL; VVKKV; AAKKV; VAKKA; VVKKA; AAKKA; GGKKG; TTKKG; GTKKT; GGKKT; TTKKT; SSKKS; CCKKS; SCKKC; SSKKC; and CCKKC; FKKFF: WKKFF; WKKWF; FKKWW; WKKWW; YKKYY: IKKYY; IKKIY; YKKII; IKKII; MKKMM; LKKMM; LKKLM; MKKLL; LKKLL; VKKVV; AKKVV; AKKAV; VKKAA; AKKAA; GKKGG; TKKGG; TKKTG; GKKTT; TKKTT; SKKSS; CKKSS; CKKCS; SKKCC; and CKKCC; or b) a sequence having one or two amino acid substitutions relative to the sequence defined in a). In certain other cases, the immunomodulatory peptide includes: a sequence selected from: a) a peptide sequence selected from: FKFKF; WKWKW; YKYKY; IKIKI; MKMKM; LKLKL; VKVKV; AKAKA; GKGKG; TKTKT; SKSKS; CKCKC; KFKFK; KWKWK; KYKYK; KIKIK; KMKMK; KLKLK; KVKVK; KAKAK; KGKGK; KTKTK; KSKSK; and KCKCK; or b) a sequence having one or two amino acid substitutions relative to the sequence defined in a).

CD206-binding agent according to certain embodiments of the present disclosure also includes immunomodulatory peptides including a sequence defined by one of the formulae:

$[J_{1a}]$-$[X_{1a}]$-$[J_{2a}]$-$[X_{2a}]$ $[X_{1a}]$-$[J_{1a}]$-$[X_{2a}]$-$[J_{2a}]$ $[X_{1a}X_{2a}]$-$[J_{2a}J_{2b}]$; and $[J_{1a}J_{1b}]$-$[X_{1a}X_{2a}]$;

wherein:

$J_{1a}$, $J_{1b}$, $J_{2a}$, and $J_{2b}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, and $X_{2b}$ are each independently selected from lysine, arginine, histidine, aspartic acid, glutamic acid, asparagine and glutamine. In certain embodiments, the immunomodulatory peptide includes: a) a sequence selected from: AFKR; FFKK; FWKR; WVRR; IFKK; FLRN; FLHS; FFHH; ALKK; LYKK; LFRR; FLKR; FFRR; FFRH; AIRR; AFHR; FFNR; IVRR; FWRW; KFWR; WFRF; KWFR; AFHH; FFRN; FFRQ; AFNR; WIQR; WVQR; AFRN; TLRR; KRFF; KKFF; KRFV; RRVV; KKIE; RNLV; HSAK; HHIF; KKAA; KKVF; KKII; RRAF; KRLL; RRFA; RHFA; RRIP; HRFF; NRFA; RRAD; RWFK; RFWK; HHFF; RNFA; RQFA; NRFF; QRMM; QRVV; RNFF; RRFM; VRMR; RMRL; RAEL; AELG; and WKFG; or b) a sequence having one or two amino acid substitutions relative to the sequence defined in a). In other embodiments, the immunomodulatory peptide includes: a) a peptide sequence selected from: FWRW; AFWR; WFRF; AWFR; VAVR; FFRF; AFFR; RWFA; WRWF; RFWA; FRFW; VRIW; RFFA; and FRFF; or b) a sequence having one or two amino acid substitutions relative to the sequence defined in a). In other embodiments, the immunomodulatory peptide includes: a) a peptide sequence selected from: FFKK; WWKK; FWKK; YYKK; IIKK; YIKK; MMKK; LLKK; MLKK; VVKK; AAKK; VAKK; CGKK; TTKK; GTKK; SSKK; CCKK; SCKK; KKFF; KKWF; KKWW; KKYY; KKIY; KKII; KKMM; KKLM; KKLL; KKVV; KKAV; KKAA; KKGG; KKTG; KKTT; KKSS; KKCS; and KKCC; or b) a sequence having one or two amino acid substitutions relative to the sequence defined in a). In certain other cases, the immunomodulatory peptide includes: a sequence selected from: a) a peptide sequence selected from: FKFK; WKWK; YKYK; IKIK; MKMK; LKLK; VKVK; AKAK; GKGK; TKTK; SKSK; CKCK; KFKF; KWKW; KYKY; KIKI; KMKM; KLKL; KVKV; KAKA; KGKG; KTKT; KSKS; and KCKC; or b) a sequence having one or two amino acid substitutions relative to the sequence defined in a).

CD206-binding agent according to certain embodiments of the present disclosure also includes small molecule active agents. In certain instances, the small molecule active agent is described by formula (I):

(I)

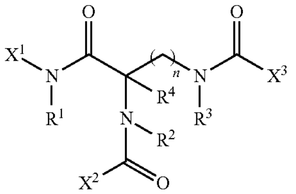

wherein:

$R^1$-$R^4$ are each independently selected from hydrogen, alkyl and substituted alkyl;

$X^1$ is selected from alkyl, substituted alkyl, aryl, substituted aryl, aralkyl, substituted aralkyl, heterocycle, substituted heterocycle, heteroaryl, substituted heteroaryl;

$X^2$ is selected from alkyl, substituted alkyl, aryl, substituted aryl, amino, substituted amino, heteroaryl, substituted heteroaryl, heterocycle, substituted heteroaryl;

$X^3$ is selected from alkyl, substituted alkyl, aryl, substituted aryl, naphthyl, substituted naphthyl, heterocycle, substituted heterocycle, heteroaryl, substituted heteroaryl, aryl heterocycle, substituted aryl heterocycle; and n is an integer from 1 to 10, or a pharmaceutically acceptable salt or solvate thereof.

A CD206-binding agent according to certain embodiments of the present disclosure also includes small molecule active agents described by formula (II):

(II)

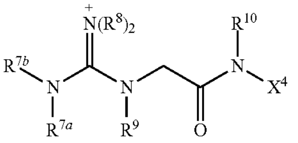

wherein:

$R^{7a}$, $R^{7b}$, $R^8$, $R^9$ and $R^{10}$ are each independently selected from hydrogen, alkyl and substituted alkyl; and $X^4$ is selected from alkyl, aryl, aralkyl, heterocycle, and heteroaryl, acyl, wherein X° is optionally further substituted with one or more groups selected from, alkyl, substituted alkyl, aryl, substituted aryl, amino, substituted amino, carboxamide, substituted carboxamide, heterocycle, substituted heterocycle, and a second compound of formula (II)

or a pharmaceutically acceptable salt or solvate thereof.

CD206-binding agent according to certain embodiments of the present disclosure also includes small molecule active agents described by formula (III):

(III)

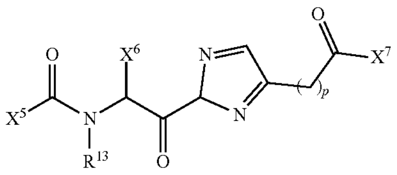

wherein:

$R^{13}$ is selected from hydrogen, alkyl and substituted alkyl;

$X^5$ is selected from alkyl, substituted alkyl, aryl, substituted aryl, amino, substituted amino, heteroaryl, substituted heteroaryl, heterocycle, substituted heteroaryl;

$X^6$ is selected from alkyl, substituted alkyl, aryl, substituted aryl, aralkyl, substituted aralkyl, heterocycle, substituted heterocycle, heteroaryl, substituted heteroaryl;

$X^7$ is selected from alkyl, substituted alkyl, aryl, substituted aryl, naphthyl, substituted naphthyl, heterocycle, substituted heterocycle, heteroaryl, substituted heteroaryl, aryl heterocycle, substituted aryl heterocycle; and p is an integer from 1 to 10.

or a pharmaceutically acceptable salt or solvate thereof.

A CD206-binding agent according to certain embodiments of the present disclosure also includes specific binding members. In certain cases, the specific binding pair is an antibody, or a binding fragment thereof. In certain cases, the specific binding member targets a sequence of CD206 selected from NFGDLVSIQSESEKK, NDAQSAYFIGLLISL, SKEKETMDNARAF, and EDENCVTMYSNSGFWN.

BRIEF DESCRIPTION OF THE DRAWINGS

FIG. 2 shows biophysical homology screening using the Molly font, which identifies conservation of a 10mer structural motif across representative HDPs, outer surface virulence factors, and collagens. Conservation of the 10mer structural motif with secondary α-helical structure with amphiphilic surface topology of hydrophobic and hydrophilic faces across representative HDPs, outer surface virulence factors, and collagens, is shown by Molly font. "DHDP" designates a designed host defense peptide.

FIG. 4 shows relative binding affinities (BE; in kcal/mol) of individual 10mer homology sequence ligand-lectin receptor combinations by ClusPro®, identifying MRC1/CD206 as the top binding target.

FIG. 7C shows a full length MRC1/CD206 model. C. 5 top-ranking human MRC1/CD206 models created by I-TASSER tested for best fit with experimental SAXS data. The discrepancy between models and experimental curves ($\chi^2$) are in the bottom table. In the fitting, MRC1/CD206 dimer models were used based on Model1-5 as monomer, respectively.

FIG. 9B shows another negatively stained electron microscopy micrographs of full length CD206 proteins incubated with vehicle (blue squares) and RP-182 (red squares) and corresponding 2D classes (inlets), schematic of open 'elongated' and 'closed' conformations on left.

FIG. 10 shows that RP-182 binds to MRC1/CD206. A. Dose-response relationship of increasing concentrations of RP-182 and the induction of the closed conformation of the CD206 receptor. Percent closed conformation of 100 examined CD206 particles on negatively stained EM micrographs of CD206 full length proteins at increasing concentrations of RP-182 (in p M).

FIG. 11 shows ratios of closed vs open conformations of MRC1/CD206 (low, CD206: peptide ratio 1:40, high, 1:500).

FIG. 12A shows that RP-182 binds to MRC1/CD206. Induction of the closed conformation of the CD206 receptor by 10mer homology motifs. Representative micrographs of full length CD206 incubated with 10mer biophysical homology peptides RP-185. RP-832C, AVP1, LL37F, and control peptide RP-426, 2D classes are shown on bottom.

FIG. 21B shows RP182 vs. vehicle-treated M2 BMDM FIG. 21D shows RP182 treated M2 protein pull down

FIG. 51 shows characterization of binding partners of CD206 induced by RP-182 in M2 macrophages. Proteomic analysis of CD206 pulled down from M2 BMDMs incubated with biotinylated RP-182 coupled to beads versus beads alone. PSM, peptide-spectrum match. Applied cut-off criteria included ratio of RP-182 to control was ≥5, MS identified peptides covered more than 10% of the protein sequence, and FDR<0.01 yielding 119 proteins (attached separately).

FIG. 67B shows survival and anti-tumor activity in KPC mice.

DETAILED DESCRIPTION OF THE INVENTION

Figure 1:
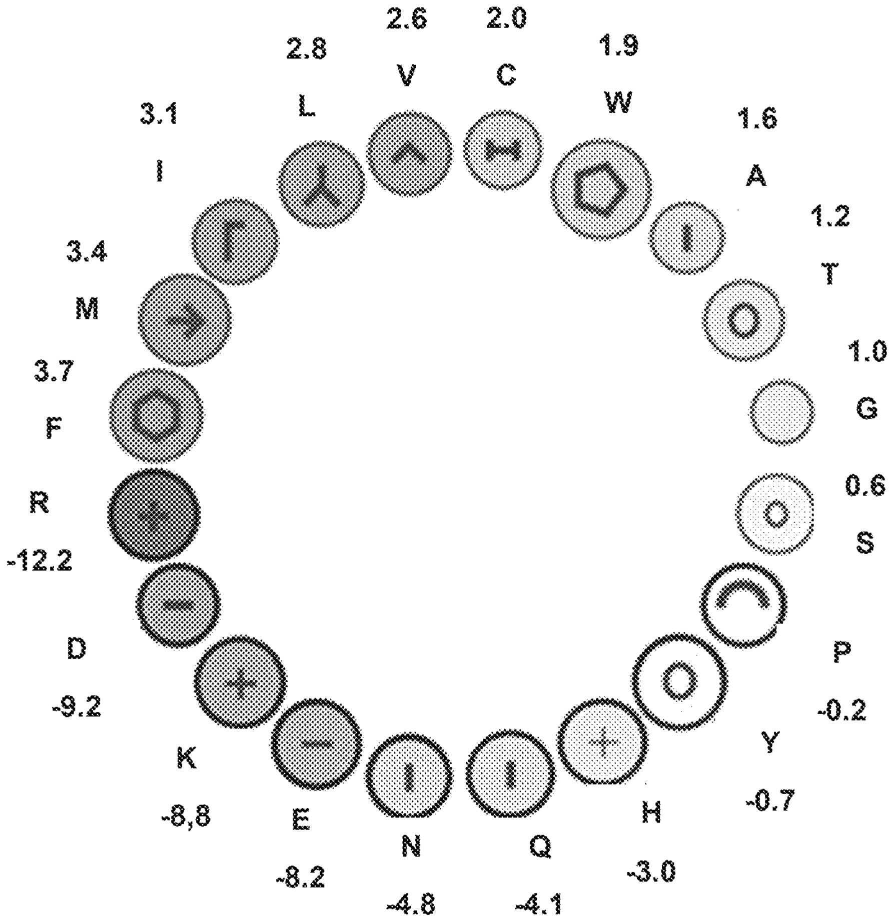
FIG. 1 shows biophysical homology screening using the Molly font, which identifies conservation of 10mer structural motif across representative HDPs, outer surface virulence factors, and collagens. A. Molly font heuristic denoting the chemical nature of amino acids for biophysical homology comparisons. The size of the circle indicates the proportional steric amino acid volumes in water, and the hydrophobicity/hydrophilicity of each amino acid is indicated by a color scale in which the most hydrophobic amino acids are the most intense cyan color, and those that are less hydrophobic are proportionally less concentrated cyan. Amino acids that are most hydrophilic possess the deepest magenta color, and a graduated scale of less intense magenta color indicates amino acids of lower hydrophilic character. Mnemonic glyphs used to capture biophysical relationships and further characterize chemical properties of amino acids include thickness depicting dissociation constant of their ionizable protons and charge, with charged amino acids having a "+" or a "−" sign incorporated within their glyph. Numerical values encode the energy in kcal/mol required to move the amino acid side chain from the interior of a lipid bilayer to the outside aqueous environment.

Aspects of the present disclosure include methods for modulating macrophage activity. Methods according to certain embodiments include contacting a macrophage with a mannose receptor (CD206) binding agent in a manner sufficient to modulate activity of the macrophage. Methods for converting a phenotype of a macrophage from an M2 phenotype to an M1 phenotype are also provided. Methods for inhibiting growth of a CD206-expressing cell as well as methods for treating a subject for a neoplastic condition (e.g., cancer) or a condition associated with chronic inflammation are described. Immuno-modulating peptides suitable for use in the subject methods are also presented. Aspects of the present disclosure also include active agents for binding to an activity modulating domain of CD206. Methods for determining if a compound binds to an activity modulating domain of CD206 are also provided.

Before the present invention is described in greater detail, it is to be understood that this invention is not limited to particular embodiments described, which as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely." "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Methods for Modulating Macrophage Activity

Methods for modulating macrophage activity and for converting a phenotype of a macrophage from an M2 phenotype to an M1 phenotype, methods of inhibiting growth of a CD206-expressing cell, methods for treating a neoplastic condition or a condition associated with chronic inflammation as well as combination therapy methods are described in greater detail, along with examples, as set forth below.

In some embodiments, methods include modulating macrophage activity: the method including contacting a macrophage with a CD206-binding agent (e.g., as described herein) to modulate activity of the macrophage.

In certain cases, the CD206-binding agent binds to a site selected from fibronectin II domain of CD206, C-type lectin carbohydrate recognition domain 3 (CRD3) of CD206. C-type lectin carbohydrate recognition domain 4 (CRD4) of CD206 and C-type lectin carbohydrate recognition domain 5 (CRD5) of CD206. In certain cases, the site is fibronectin II domain of CD206. In certain cases, the site is C-type lectin carbohydrate recognition domain 3 (CRD3) of CD206. In certain other cases, the site is C-type lectin carbohydrate recognition domain 5 (CRD5) of CD206.

In certain embodiments, the CD206-binding agent binds to CD206 with a binding energy of at least −650 kcal/mol, such as at least −700 kcal/mol, and in certain embodiments at least −750, −800, −900, −1000, −1100, −1200, −1250, −1300, −1350, −1400, −1425, −1450, −1475, −1500, −1525, −1550, −1575, −1600 kcal/mol, or greater. The energy of binding can be determined, e.g., in silico, in vitro, or in vivo, using methods well-known in the art (e.g., using the ClusPro™ algorithm).

In certain embodiments, of the methods of modulating macrophage activity, the macrophage activity that is modulated is macrophage polarization. In certain embodiments of the method, the viability of the macrophage is reduced. In certain embodiments, of the methods of modulating macrophage activity, the macrophage is an M2 macrophage or a tumor associated macrophage (TAM). In certain embodiments of the methods of modulating macrophage activity, the CD206-binding agent (e.g., as described herein) inhibits macrophage activity. In certain embodiments of the method, the CD206-binding agent induces apoptosis of the macrophage. In certain embodiments of the method, the CD206-binding agent stimulates phagocytosis.

In certain embodiments of the methods of modulating macrophage activity, the macrophage is in vitro. In certain other embodiments, the macrophage is in vivo. In still other embodiments, methods include converting a phenotype of a macrophage from an M2 phenotype to an M1 phenotype. Methods according to certain embodiments include contacting a macrophage having an M2 phenotype with a CD206-binding agent in a manner sufficient to convert the phenotype of the macrophage to an M1 phenotype. In some instances, contacting the CD206-binding agent induces a conformational change in a CD206 receptor of the macrophage sufficient to convert the phenotype of the macrophage to an M1 phenotype. In some instances, converting the phenotype of the macrophage includes inducing expression of CD86 by the macrophage. In other instances, converting the phenotype of the macrophage includes reducing expression of CD206 by the macrophage. In still other instances, converting the phenotype of the macrophage includes converting the macrophage to a phenotype that exhibits upregulation of M1 cytokines and markers. For example, the M1 cytokine and marker may be selected from the group consisting of IL-10, IL-12, TNFα and nitric oxide synthetase. In other instances, converting the phenotype of the macrophage includes converting the macrophage to a phenotype that exhibits decreased expression of signal regulatory protein α (SIRPα).

In certain embodiments of the methods of converting a phenotype of a macrophage from an M2 phenotype to an M1 phenotype, the CD206-binding agent binds to a site selected from fibronectin II domain of CD206, C-type lectin carbohydrate recognition domain 3 (CRD3) of CD206, C-type lectin carbohydrate recognition domain 4 (CRD4) of CD206 and C-type lectin carbohydrate recognition domain 5 (CRD5) of CD206. In certain cases, the site is fibronectin II domain of CD206. In certain cases, the site is C-type lectin carbohydrate recognition domain 3 (CRD3) of CD206. In certain other cases, the site is C-type lectin carbohydrate recognition domain 5 (CRD5) of CD206.

In certain embodiments of the methods of converting a phenotype of a macrophage from an M2 phenotype to an M1 phenotype, the macrophage is contacted with the CD206-binding agent in vitro. In certain other embodiments, the macrophage is contacted with the CD206-binding agent in vivo.

In some embodiments, methods include inhibiting growth of a CD206-expressing cell: the method including contacting a target CD206-expressing cell with a CD-206-binding agent (e.g., as described herein) to inhibit growth of the cell. In certain instances, the cell is a cancer cell. Cancer cells include, without limitation, a pancreatic cancer cell, a prostate cancer cell, a colon cancer cell, a skin cancer cell or a breast cancer cell. In certain cases, the cancer is a solid tumor cancer. Solid tumor cancers include, without limitation, pancreatic, prostate, colon, breast, or skin tumors. In certain embodiments, of the methods of inhibiting growth of a CD206-expressing cell, the contacting of the target CD206-expressing cell comprises administering to a subject in need thereof a therapeutically effective amount of the CD206-binding agent (e.g., as described herein), to treat the subject for a cancer. In some embodiments, methods include treating a subject for a condition associated with chronic inflammation. Methods according to certain embodiments include administering a therapeutically effective amount of a CD206-binding agent to a subject to treat the subject for the condition associated with chronic inflammation. In some embodiments, the condition associated with chronic inflammation is selected from scleroderma or multiple sclerosis, irritable bowel disease, ulcerative colitis, colitis, Crohn's disease, idiopathic pulmonary fibrosis, asthma, keratitis, arthritis, osteoarthritis, rheumatoid arthritis, auto-immune diseases, a feline or human immunodeficiency virus (FIV or HIV) infection, cancer, age-related inflammation and/or stem cell dysfunction, graft-versus-host disease (GVHD), keloids, obesity, diabetes, diabetic wounds, other chronic wounds, atherosclerosis, Parkinson's disease, Alzheimer's disease, macular degeneration, gout, gastric ulcers, gastritis, mucositis, toxoplasmosis, an ophthalmic inflammatory condition (e.g., keratitis), a skin disease (e.g., atopic dermatitis, or psoriasis), an inflammatory condition such as sinusitis or otitis media, a parasitic infection (e.g., malaria), and chronic viral or microbial infections.

In certain embodiments of methods for treating chronic inflammation, the CD206-binding agent (e.g., as described herein) is administered in conjunction with another drug known to be effective in treating the condition. In some instances, the condition is cancer. In some instances, the cancer includes, without limitation, pancreatic, prostate, colon, breast or skin cancer. In certain cases, the methods further include administering an effective amount of a chemotherapeutic agent, antibody agent, or cell therapy to the subject. In certain cases, the chemotherapeutic agent, antibody agent or cell therapy is selected from steroids, anthracyclines, thyroid hormone replacement drugs, thymidylate-targeted drugs, antibodies, checkpoint inhibitor drugs, Chimeric Antigen Receptor/T cell therapies, and other cell therapies.

In some embodiments of the methods of treating chronic inflammation, the condition associated with chronic inflammation is a fibrosis. In some instances, the condition associated with chronic inflammation is scleroderma.

In some embodiments, methods include treating a subject for a neoplastic condition, such as cancer (e.g., a solid tumor cancer). The methods of the present disclosure may be employed to target and treat a variety of cancers, including e.g., primary cancer, secondary cancers, re-growing cancers, recurrent cancers, refractory cancers and the like. For example, in some instances, the methods of the present disclosure may be employed as an initial treatment of a primary cancer identified in a subject. In some instances, the methods of the present disclosure may be employed as a non-primary (e.g., secondary or later) treatment, e.g., in a subject with a cancer that is refractory to a prior treatment, in a subject with a cancer that is re-growing following a prior treatment, in a subject with a mixed response to a prior treatment (e.g., a positive response to at least one tumor in the subject and a negative or neutral response to at least a second tumor in the subject), and the like.

In some instances, the method of the present disclosure may be employed to target, treat or clear a subject for minimal residual disease (MRD) remaining after a prior cancer therapy. Targeting, treating and/or clearance of MRD may be pursued using the instant methods whether the MRD is or has been determined to be refractory to the prior treatment or not. In some instances, a method of the present disclosure may be employed to target, treat and/or clear a subject of MRD following a determination that the MRD is refractory to a prior treatment or one or more available treatment options.

Cancers of interest associated with commonly mutated genes include e.g., ABI1, ABL1, ABL2, ACKR3, ACSL3, ACSL6, AFF1, AFF3, AFF4, AKAP9, AKT1, AKT2, ALDH2, ALK, AMER1, APC, ARHGAP26, ARHGEF12, ARID1A, ARID2, ARNT, ASPSCR1. ASXL1, ATF1, ATIC, ATM, ATP1A1, ATP2B3, ATRX, AXIN1, BAP1, BCL10, BCL11A, BCL11B, BCL2, BCL3, BCL6, BCL7A, BCL9, BCOR, BCR, BIRC3, BLM, BMPR1A, BRAF, BRCA1, BRCA2, BRD3, BRD4, BRIP1, BTG1, BUB1B, C15orf65, C2orf44, CACNA1D, CALR, CAMTA1, CANT1, CARD11, CARS, CASC5, CASP8, CBFA2T3, CBFB, CBL, CBLB, CBLC, CCDC6, CCNB1IP1, CCND1, CCND2, CCND3, CCNE1, CD274, CD74, CD79A, CD79B, CDC73, CDH1, CDH11, CDK12, CDK4, CDK6, CDKN2A, CDKN2C, CDX2, CEBPA, CEP89, CHCHD7, CHEK2, CHIC2, CHN1, CIC, CIITA, CLIP1, CLP1, CLTC, CLTCL1, CNBP, CNOT3, CNTRL, COLIA1, COL2A1, COX6C, CREB1, CREB3L1, CREB3L2, CREBBP, CRLF2, CRTC1, CRTC3, CSF3R, CTNNB1, CUX1, CYLD, DAXX, DCTN1, DDB2, DDIT3, DDX10, DDX5, DDX6, DEK, DICER1, DNM2, DNMT3A, EBF1, ECT2L, EGFR, EIF3E, EIF4A2, ELF4, ELK4, ELL, ELN, EML4, EP300, EPS15, ERBB2, ERC1, ERCC2, ERCC3, ERCC4, ERCC5, ERG, ETV1, ETV4, ETV5, ETV6, EWSR1, EXT1, EXT2, EZH2, EZR, FAM46C, FANCA, FANCC, FANCD2, FANCE, FANCF, FANCG, FAS, FBXO11, FBXW7, FCGR2B, FCRL4, FEV, FGFR1, FGFR1OP, FGFR2, FGFR3, FH, FHIT, FIPIL1, FLCN, FLI1, FLT3, FNBP1, FOXA1, FOXL2, FOXO1, FOXO3, FOXO4, FOXP1, FSTL3, FUBP1, FUS, GAS7, GATA1, GATA2, GATA3, GMPS, GNA11, GNAQ, GNAS, GOLGA5, GOPC, GPC3, GPHN, H3F3A, H3F3B, HERPUD1, HEY1, HIP1, HIST1H4I, HLA-A, HLF, HMGA1, HMGA2, HNF1A, HNRNPA2B1, HOOK3, HOXA11, HOXA13, HOXA9, HOXC11, HOXC13, HOXD11, HOXD13, HRAS, HSP90AA1, HSP90AB1, IDH1, IDH2, IKZF1, IL2, IL21R, IL6ST, IL7R, IRF4, ITK, JAK1, JAK2, JAK3, JAZF1, JUN, KAT6A, KAT6B, KCNJ5, KDM5A, KDM5C, KDM6A, KDR, KDSR, KIAA1549, KIAA1598, KIF5B, KIT, KLF4, KLF6, KLK2, KMT2A, KMT2C, KMT2D, KRAS, KTN1, LASP1, LCK, LCP1, LHFP, LIFR, LMNA, LMO1, LMO2, LPP, LRIG3, LSM14A, LYL1, MAF, MAFB, MALT1, MAML2, MAP2K1, MAP2K2, MAP2K4, MAX, MDM2, MDM4, MECOM, MED12, MEN1, MET, MITF, MKL1, MLF1, MLH1, MLLT1, MLLT10, MLLT11, MLLT3. MLLT4, MLLT6, MN1, MNX1, MPL, MSH2, MSH6, MSI2, MSN, MTCP1, MUC1, MUTYH, MYB, MYC, MYCL, MYCN, MYD88, MYH11, MYH9, MYO5A, NAB2, NACA, NBN, NCKIPSD, NCOA1, NCOA2, NCOA4, NDRG1, NF1, NF2, NFATC2, NFE2L2, NFIB, NFKB2, NIN, NKX2-1, NONO, NOTCH1, NOTCH2, NPM1, NR4A3, NRAS, NRG1, NSD1, NT5C2, NTRK1, NTRK3, NUMA1, NUP214, NUP98, NUTM1, NUTM2A, NUTM2B, OLIG2, OMD, P2RY8, PAFAH1B2, PALB2, PATZ1, PAX3, PAX5, PAX7, PAX8, PBRM1, PBX1, PCM1, PCSK7, PDCD1LG2, PDE4DIP, PDGFB, PDGFRA, PDGFRB, PER1, PHF6, PHOX2B, PICALM, PIK3CA, PIK3R1, PIM1, PLAG1, PLCG1, PML, PMS1, PMS2, POT1, POU2AF1, POU5F1, PPARG, PPFIBP1, PPP2R1A, PRCC, PRDM1, PRDM16, PRF1, PRKAR1A, PRRX1, PSIP1, PTCH1, PTEN, PTPN11, PTPRB, PTPRC, PTPRK, PWWP2A, RABEP1, RAC1, RAD21, RAD51B, RAF1, RALGDS, RANBP17, RAP1GDS1, RARA, RB1, RBM15, RECQL4, REL, RET, RHOH, RMI2, RNF213, RNF43, ROS1, RPL10, RPL22, RPL5, RPN1, RSPO2, RSPO3, RUNX1, RUNX1T1, SBDS, SDC4, SDHAF2, SDHB, SDHC, SDHD, SEPT5, SEPT6, SEPT9, SET, SETBP1, SETD2, SF3B1, SFPQ, SH2B3, SH3GL1, SLC34A2, SLC45A3, SMAD4, SMARCA4, SMARCB1, SMARCE1, SMO, SOCS1, SOX2, SPECC1, SRGAP3, SRSF2, SRSF3, SS18, SS18L1, SSX1, SSX2, SSX2B, SSX4, SSX4B, STAG2, STAT3, STAT5B, STAT6, STIL, STK11, SUFU, SUZ12, SYK, TAF15, TAL1, TAL2, TBL1XR1, TCEA1, TCF12, TCF3, TCF7L2, TCL1A, TERT, TET1, TET2, TFE3, TFEB, TFG, TFPT, TFRC, THRAP3, TLX1, TLX3, TMPRSS2, TNFAIP3, TNFRSF14, TNFRSF17, TOP1, TP53, TPM3, TPM4, TPR, TRAF7, TRIM24, TRIM27, TRIM33, TRIP11, TRRAP, TSC1, TSC2, TSHR, TTL, U2AF1, UBR5, USP6, VHL, VTI1A, WAS, WHSC1, WHSC1L1, WIF1, WRN, WT1, WWTR1, XPA, XPC, XPO1, YWHAE, ZBTB16, ZCCHC8, ZMYM2, ZNF331, ZNF384, ZNF521 and ZRSR2.

Cancers of interest for treatment according to embodiments of the present disclosure include but are not limited to, e.g., Acute Lymphoblastic Leukemia (ALL). Acute Myeloid Leukemia (AML), Adrenocortical Carcinoma, AIDS-Related Cancers (e.g., Kaposi Sarcoma, Lymphoma, etc.), Anal Cancer. Appendix Cancer, Astrocytomas. Atypical Teratoid/Rhabdoid Tumor. Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.). Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.). Ductal Carcinoma In Situ (DCIS), Embryonal Tumors. Endometrial Cancer. Ependymoma, Esophageal Cancer, Esthesioneuroblastoma, Ewing Sarcoma, Extracranial Germ Cell Tumor, Extragonadal Germ Cell Tumor. Extrahepatic Bile Duct Cancer. Eye Cancer (e.g., Intraocular Melanoma. Retinoblastoma, etc.), Fibrous Histiocytoma of Bone (e.g., Malignant, Osteosarcoma, etc.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia. Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis. Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin. Primary Central Nervous System (CNS), etc.). Macroglobulinemia (e.g., Waldenstrom, etc.). Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer. Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor. Low Malignant Potential Tumor, etc.). Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor. Pleuropulmonary Blastoma. Primary Central Nervous System (CNS) Lymphoma. Prostate Cancer. Rectal Cancer, Renal Cell (Kidney) Cancer, Renal Pelvis and Ureter, Transitional Cell Cancer, Retinoblastoma, Rhabdomyosarcoma. Salivary Gland Cancer. Sarcoma (e.g., Ewing, Kaposi, Osteosarcoma, Rhabdomyosarcoma, Soft Tissue, Uterine, etc.), Sézary Syndrome, Skin Cancer (e.g., Childhood. Melanoma, Merkel Cell Carcinoma, Nonmelanoma, etc.), Small Cell Lung Cancer. Small Intestine Cancer, Soft Tissue Sarcoma. Squamous Cell Carcinoma, Squamous Neck Cancer (e.g., with Occult Primary, Metastatic, etc.), Stomach (Gastric) Cancer. T-Cell Lymphoma, Testicular Cancer. Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.). Uterine Sarcoma. Vaginal Cancer, Vulvar Cancer, Waldenström Macroglobulinemia, Wilms Tumor, and the like.

The methods of treating described herein may, in some instances, be performed in a subject that has previously undergone one or more conventional treatments. For example, in the case of oncology, the methods described herein may, in some instances, be performed following a conventional cancer therapy including but not limited to e.g., conventional chemotherapy, conventional radiation therapy, conventional immunotherapy, surgery, etc. In some instances, the methods described herein may be used when a subject has not responded to or is refractory to a conventional therapy.

With respect to the cancer as a whole, desired effects of the described treatments may result in a reduction in the number of cells in the cancer, a reduction in the size of a tumor, a reduction in the overall proliferation of the cancer, a reduction in the overall growth rate of a tumor, etc. For example, an effective treatment is in some cases a treatment that, when administered in one or more doses to an individual in need thereof, reduces the number of cancer cells in the individual and/or reduces tumor mass in the individual, by at least about 10%, at least about 15%, at least about 20%, at least about 25%, at least about 30%, at least about 40%, at least about 50%, at least about 75%, or more than 75%, compared to the number of cancer cells and/or tumor mass in the absence of the treatment.

In some embodiments, an effective treatment is a treatment that, when administered alone (e.g., in monotherapy) or in combination (e.g., in combination therapy) with one or more additional therapeutic agents, in one or more doses, is effective to reduce one or more of tumor growth rate, cancer cell number, and tumor mass, by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the tumor growth rate, cancer cell number, or tumor mass in the absence of the treatment.

In some instances, treatment may involve modulation, including induction, of the expression and/or secretion of a cytokine by an immune cell. Non-limiting examples of cytokines, the expression/secretion of which may be modulated, include but are not limited to e.g., Interleukins and related (e.g., IL-1-like, IL-1α, IL-1β, IL-1RA, IL-18, IL-2, IL-4, IL-7, IL-9, IL-13, IL-15, IL-3, IL-5, GM-CSF, IL-6-like, IL-6, IL-11, G-CSF, IL-12, LIF, OSM, IL-10-like, IL-10, IL-20, IL-14, IL-16, IL-17, etc.). Interferons (e.g., IFN-α, IFN-β, IFN-γ, etc.). TNF family (e.g., CD154, LT-D, TNF-α, TNF-β, 4-1BBL, APRIL. CD70, CD153. CD178, GITRL, LIGHT, OX40L, TALL-1, TRAIL, TWEAK, TRANCE, etc.), TGF-β family (e.g., TGF-β1, TGF-β2, TGF-β3, etc.) and the like. The amount of the increase may vary and may range from a 10% or greater increase, including but not limited to e.g., 10% or greater, 25% or greater, 50% or greater, 75% or greater, 100% or greater, 150% or greater, 200% or greater, 250% or greater, 300% or greater, 350% or greater 400% or greater, etc.

Chemotherapeutic Agents and Combination Therapy

As will be readily understood, the methods of treating by administering a therapeutically effective amount of a CD206-binding agent to a subject described herein may, in some instances, be combined with one or more conventional treatments. For example, in the case of oncology, the methods described herein may, in some instances, be combined with a conventional cancer therapy including but not limited to e.g., conventional chemotherapy, conventional radiation therapy, conventional immunotherapy, surgery, etc.

In conjunction with any of the subject methods, the CD206-binding agent (e.g., as described herein) (or pharmaceutical compositions comprising such compounds) can be administered in combination with another drug designed to reduce or prevent inflammation, treat or prevent chronic inflammation, or treat cancer. In some embodiments, the condition associated with chronic inflammation is a fibrosis. In some instances, the condition associated with chronic inflammation is scleroderma. For example, the CD206- binding agent may be combined with a conventional agent or therapy for treating chronic inflammation or fibrosis, including but limited to e.g., pirfenidone, nintedanib, a nonsteroidal anti-inflammatory drug (NSADs), a steroidal agent, standard scleroderma treatments. In each case, the CD206-binding agent can be administered prior to, at the same time as, or after the administration of the other drug.

In some instances, the methods described herein may be used before or after a conventional therapy. For example, the methods described herein may be used as an adjuvant therapy, e.g., after a subject has seen improvement from a conventional therapy, or may be used when a subject has not responded to a conventional therapy. In some instances, the methods described herein may be used prior to an additional therapy, e.g., to prepare a subject for an additional therapy, e.g., a conventional therapy as described herein.

Standard cancer therapies include surgery (e.g., surgical removal of cancerous tissue), radiation therapy, bone marrow transplantation, chemotherapeutic treatment, antibody treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastin™), cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), 90Y-labelled ibritumomab tiuxetan (Zevalin™), 131I-labelled tositumoma (Bexxar™), etc. Suitable antibodies for use in cancer treatment include, but are not limited to, antibodies raised against tumor-associated antigens. Such antigens include, but are not limited to, CD20. CD30, CD33, CD52, EpCAM, CEA, gpA33, Mucins, TAG-72, CAIX, PSMA, Folate-binding protein, Gangliosides (e.g., GD2, GD3, GM2, etc.), Le y, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, etc.

Conventional cancer therapies also include targeted therapies for cancer including but not limited to e.g., Ado-trastuzumab emtansine (Kadcyla) targeting HER2 (ERBB2/neu) (approved for use in Breast cancer); Afatinib (Gilotrif) targeting EGFR (HER1/ERBB1), HER2 (ERBB2/neu) (approved for use in Non-small cell lung cancer); Aldesleukin (Proleukin) targeting (approved for use in Renal cell carcinoma, Melanoma); Alectinib (Alecensa) targeting ALK (approved for use in Non-small cell lung cancer); Alemtuzumab (Campath) targeting CD52 (approved for use in B-cell chronic lymphocytic leukemia); Atezolizumab (Tecentriq) targeting PD-L1 (approved for use in Urothelial carcinoma, Non-small cell lung cancer); Avelumab (Bavencio) targeting PD-L1 (approved for use in Merkel cell carcinoma); Axitinib (Inlyta) targeting KIT, PDGFRβ, VEGFR1/2/3 (approved for use in Renal cell carcinoma); Belimumab (Benlysta) targeting BAFF (approved for use in Lupus erythematosus); Belinostat (Beleodaq) targeting HDAC (approved for use in Peripheral T-cell lymphoma); Bevacizumab (Avastin) targeting VEGF ligand (approved for use in Cervical cancer, Colorectal cancer. Fallopian tube cancer, Glioblastoma, Non-small cell lung cancer. Ovarian cancer, Peritoneal cancer, Renal cell carcinoma); Blinatumomab (Blincyto) targeting CD19/CD3 (approved for use in Acute lymphoblastic leukemia (precursor B-cell)); Bortezomib (Velcade) targeting Proteasome (approved for use in Multiple myeloma, Mantle cell lymphoma); Bosutinib (Bosulif) targeting ABL (approved for use in Chronic myelogenous leukemia): Brentuximab vedotin (Adcetris) targeting CD30 (approved for use in Hodgkin lymphoma, Anaplastic large cell lymphoma); Brigatinib (Alunbrig) targeting ALK (approved for use in Non-small cell lung cancer (ALK+)); Cabozantinib (Cabometyx, Cometriq) targeting FLT3, KIT. MET, RET, VEGFR2 (approved for use in Medullary thyroid cancer, Renal cell carcinoma); Carfilzomib (Kyprolis) targeting Proteasome (approved for use in Multiple myeloma); Ceritinib (Zykadia) targeting ALK (approved for use in Non-small cell lung cancer); Cetuximab (Erbitux) targeting EGFR (HER1/ERBB1) (approved for use in Colorectal cancer, Squamous cell cancer of the head and neck); Cobimetinib (Cotellic) targeting MEK (approved for use in Melanoma); Crizotinib (Xalkori) targeting ALK, MET, ROS1 (approved for use in Non-small cell lung cancer); Dabrafenib (Tafinlar) targeting BRAF (approved for use in Melanoma. Non-small cell lung cancer); Daratumumab (Darzalex) targeting CD38 (approved for use in Multiple myeloma); Dasatinib (Sprycel) targeting ABL (approved for use in Chronic myelogenous leukemia. Acute lymphoblastic leukemia); Denosumab (Xgeva) targeting RANKL (approved for use in Giant cell tumor of the bone); Dinutuximab (Unituxin) targeting B4GALNT1 (GD2) (approved for use in Pediatric neuroblastoma); Durvalumab (Imfinzi) targeting PD-L1 (approved for use in Urothelial carcinoma); Elotuzumab (Empliciti) targeting SLAMF7 (CSI/CD319/CRACC) (approved for use in Multiple myeloma); Enasidenib (Idhifa) targeting IDH2 (approved for use in Acute myeloid leukemia); Erlotinib (Tarceva) targeting EGFR (HER1/ERBB1) (approved for use in Non-small cell lung cancer, Pancreatic cancer); Everolimus (Afinitor) targeting mTOR (approved for use in Pancreatic, gastrointestinal, or lung origin neuroendocrine tumor. Renal cell carcinoma, Nonresectable subependymal giant cell astrocytoma. Breast cancer); Gefitinib (Iressa) targeting EGFR (HER1/ERBB1) (approved for use in Non-small cell lung cancer); Ibritumomab tiuxetan (Zevalin) targeting CD20 (approved for use in Non-Hodgkin's lymphoma): Ibrutinib (Imbruvica) targeting BTK (approved for use in Mantle cell lymphoma, Chronic lymphocytic leukemia, Waldenstrom's macroglobulinemia); Idelalisib (Zydelig) targeting PI3Kδ (approved for use in Chronic lymphocytic leukemia, Follicular B-cell non-Hodgkin lymphoma. Small lymphocytic lymphoma); Imatinib (Gleevec) targeting KIT, PDGFR, ABL (approved for use in GI stromal tumor (KIT+), Dermatofibrosarcoma protuberans. Multiple hematologic malignancies); Ipilimumab (Yervoy) targeting CTLA-4 (approved for use in Melanoma); Ixazomib (Ninlaro) targeting Proteasome (approved for use in Multiple Myeloma); Lapatinib (Tykerb) targeting HER2 (ERBB2/neu), EGFR (HER1/ERBB1) (approved for use in Breast cancer (HER2+)); Lenvatinib (Lenvima) targeting VEGFR2 (approved for use in Renal cell carcinoma, Thyroid cancer); Midostaurin (Rydapt) targeting FLT3 (approved for use in acute myeloid leukemia (FLT3+)); Necitumumab (Portrazza) targeting EGFR (HER1/ERBB1) (approved for use in Squamous non-small cell lung cancer); Neratinib (Nerlynx) targeting HER2 (ERBB2/neu) (approved for use in Breast cancer); Nilotinib (Tasigna) targeting ABL (approved for use in Chronic myelogenous leukemia); Niraparib (Zejula) targeting PARP (approved for use in Ovarian cancer, Fallopian tube cancer, Peritoneal cancer); Nivolumab (Opdivo) targeting PD-1 (approved for use in Colorectal cancer, Head and neck squamous cell carcinoma. Hodgkin lymphoma, Melanoma. Non-small cell lung cancer. Renal cell carminoma, Urothelial carcinoma); Obinutuzumab (Gazyva) targeting CD20 (approved for use in Chronic lymphocytic leukemia. Follicular lymphoma); Ofatumumab (Arzerra, HuMax-CD20) targeting CD20 (approved for use in Chronic lymphocytic leukemia); Olaparib (Lynparza) targeting PARP (approved for use in Ovarian cancer); Olaratumab (Lartruvo) targeting PDGFRα (approved for use in Soft tissue sarcoma); Osimertinib (Tagrisso) targeting EGFR (approved for use in Non-small cell lung cancer); Palbociclib (Ibrance) targeting CDK4, CDK6 (approved for use in Breast cancer); Panitumumab (Vectibix) targeting EGFR (HER1/ERBB1) (approved for use in Colorectal cancer); Panobinostat (Farydak) targeting HDAC (approved for use in Multiple myeloma); Pazopanib (Votrient) targeting VEGFR, PDGFR, KIT (approved for use in Renal cell carcinoma); Pembrolizumab (Keytruda) targeting PD-1 (approved for use in Classical Hodgkin lymphoma, Melanoma, Non-small cell lung cancer (PD-L1+), Head and neck squamous cell carcinoma, Solid tumors (MSI-H)); Pertuzumab (Perjeta) targeting HER2 (ERBB2/neu) (approved for use in Breast cancer (HER2+)); Ponatinib (Iclusig) targeting ABL, FGFR1-3, FLT3, VEGFR2 (approved for use in Chronic myelogenous leukemia. Acute lymphoblastic leukemia); Ramucirumab (Cyramza) targeting VEGFR2 (approved for use in Colorectal cancer, Gastric cancer or Gastroesophageal junction (GEJ) adenocarcinoma, Non-small cell lung cancer); Regorafenib (Stivarga) targeting KIT, PDGFRβ, RAF, RET, VEGFR1/2/3 (approved for use in Colorectal cancer, Gastrointestinal stromal tumors, Hepatocellular carcinoma); Ribociclib (Kisqali) targeting CDK4, CDK6 (approved for use in Breast cancer (HR+, HER2−)); Rituximab (Rituxan, Mabthera) targeting CD20 (approved for use in Non-Hodgkin's lymphoma, Chronic lymphocytic leukemia, Rheumatoid arthritis, Granulomatosis with polyangiitis); Rituximab/hyaluronidase human (Rituxan Hycela) targeting CD20 (approved for use in Chronic lymphocytic leukemia, Diffuse large B-cell lymphoma, Follicular lymphoma); Romidepsin (Istodax) targeting HDAC (approved for use in Cutaneous T-cell lymphoma, Peripheral T-cell lymphoma); Rucaparib (Rubraca) targeting PARP (approved for use in Ovarian cancer); Ruxolitinib (Jakafi) targeting JAK1/2 (approved for use in Myelofibrosis); Siltuximab (Sylvant) targeting IL-6 (approved for use in Multicentric Castleman's disease); Sipuleucel-T (Provenge) targeting (approved for use in Prostate cancer); Sonidegib (Odomzo) targeting Smoothened (approved for use in Basal cell carcinoma); Sorafenib (Nexavar) targeting VEGFR, PDGFR, KIT, RAF (approved for use in Hepatocellular carcinoma. Renal cell carcinoma, Thyroid carcinoma); Temsirolimus (Torisel) targeting mTOR (approved for use in Renal cell carcinoma); Tositumomab (Bexxar) targeting CD20 (approved for use in Non-Hodgkin's lymphoma); Trametinib (Mekinist) targeting MEK (approved for use in Melanoma, Non-small cell lung cancer); Trastuzumab (Herceptin) targeting HER2 (ERBB2/neu) (approved for use in Breast cancer (HER2+), Gastric cancer (HER2+)); Vandetanib (Caprelsa) targeting EGFR (HER1/ERBB1), RET, VEGFR2 (approved for use in Medullary thyroid cancer); Vemurafenib (Zelboraf) targeting BRAF (approved for use in Melanoma); Venetoclax (Venclexta) targeting BCL2 (approved for use in Chronic lymphocytic leukemia); Vismodegib (Erivedge) targeting PTCH, Smoothened (approved for use in Basal cell carcinoma); Vorinostat (Zolinza) targeting HDAC (approved for use in Cutaneous T-cell lymphoma); Ziv-aflibercept (Zaltrap) targeting PIGF, VEGFA/B (approved for use in Colorectal cancer); and the like.

Biological response modifiers suitable for use in connection with the methods of the present disclosure include, but are not limited to, (1) inhibitors of tyrosine kinase (RTK) activity: (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5.8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids. e.g. vincristine, vinblastine, vinorelbine, vindesine, etc.; podophyllotoxins, e.g. etoposide, teniposide, etc.; antibiotics. e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyinolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042). Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chtorotrianisene, hydroxyprogesterone, aminoglutethimide, estramustine, medroxyprogesterone acetate, leuprolide, Flutamide (Drogenil), Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

“Taxanes” include paclitaxel, as well as any active taxane derivative or pro-drug. “Paclitaxel” (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882. WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (17402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term “taxane” are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In some instances, methods of treating a subject for cancer may further include administering an agent which enhances the activity of the treatment. Such agents that enhance the activity of the treatment will vary widely and may include but are not limited to e.g., agents that inhibit an inhibitor molecule. Suitable inhibitory molecules that may be targeted include but are not limited to e.g., PD1, PD-L1, CTLA4, TIM3, LAG3, VISTA, BTLA, TIGIT, LAIR1, CD160, 2B4 and TGFR beta.

Inhibiting of inhibitory molecules may be achieved by any convenient method including but not limited to e.g., the administration of a direct inhibitor of the inhibitory molecule (e.g., an antibody that binds the inhibitory molecule, a small molecule antagonist of the inhibitory molecule, etc.), administration of an agent that inhibits expression of the inhibitory molecule (e.g., an inhibitory nucleic acid, e.g., a dsRNA, e.g., an siRNA or shRNA targeting a nucleic acid encoding the inhibitory molecule), an indirect inhibitor of the inhibitory signaling, and the like. In some instances, an agent that may be administered may be an antibody or antibody fragment that binds to an inhibitory molecule. For example, the agent can be an antibody or antibody fragment that binds to PD1, PD-L1. PD-L2 or CTLA4 (e.g., ipilimumab (also referred to as MDX-010 and MDX-101, and marketed as Yervoy (Bristol-Myers Squibb)), Tremelimumab (Pfizer, formerly known as ticilimumab, CP-675, 206)), TIM3, LAG3, or the like.

In some embodiments, methods include administering to the subject an immune checkpoint inhibitors like anti-CTLA4 or anti-PD-1 and anti-PD-1L agents. The immune system depends on multiple checkpoints to avoid overactivation of the immune system on healthy cells, and tumor cells often take advantage of these checkpoints in order to escape detection by the immune system. CTLA-4, shown to be aberrantly upregulated and present on the surface of T cells in certain cancers, and PD-1, also upregulated in certain tumors and found to inhibit T-cell function, are checkpoints that have been studied as targets for cancer therapy (Pardoll, D. M. 2012 *Nat Rev Cancer* 12(4):252-264; Sharma, et al. 2011 *Nat Rev Cancer* 11(11):805-812).

In some instances, the methods of the instant disclosure may be used without any additional conventional therapy including e.g., where the method described herein is the sole method used to treat the subject. For example, in the case of oncology, the methods described herein may, in some instances, be the sole method used to treat the subject for a cancer.

Determining when combination therapies, e.g., involving the administration of one or more agents that ameliorates one or more side effects of a therapy described herein or involving the administration of one or more agents that enhances a therapy described herein, are indicated and the specifics of the administration of such combination therapies are within the skill of the relevant medical practitioner. In some instances, dosage regimens and treatment schedules of combination therapies may be determined through clinical trials.

In some instances, a subject may be evaluated, in certain contexts, through one or more of the following diagnostics procedures: 3D CT angiography, Angiography, Anoscopy, Autofluorescence bronchoscopy/fluorescence bronchoscopy, Barium swallow or enema. Biopsy, Bone Marrow Aspiration and Biopsy, Bone Scan. Bronchoscopy, CA-125 test, CAD for mammography, CTC Test, Chest x-ray, Colonoscopy, Complete Blood Count Test. Computed Tomography Scan, CT-guided biopsy, DEXA scan, Digital Breast Tomosynthesis, Electrocardiogram, Endobronchial ultrasound, Endoscopic ultrasound, ERCP, Flow cytometry, Full-field digital mammography, Genetic testing. Large bore CT scanner/RT with simulation, Lumbar puncture, Magnetic Resonance Imaging, Mammography, Miraluma breast imaging. MRI-Guided Breast Biopsy. Multi-detector CT scanner, Multiple-gated acquisition (MUGA) scan, Navigational Bronchoscopy, Nuclear Medicine Imaging, Oncotype DX Test, Pap test, Pelvic exam, PET Scan, PET-CT Scan, Radiofrequency ablation, Sentinel lymph node biopsy, Spiral CT, Tumor marker testing, Tumor molecular profiling, Ultrasound, Video Capsule Endoscopy, X-ray, and the like.

Diagnostic procedures may be performed for a variety of reasons including but not limited to e.g., to screen for cancer or precancerous conditions before a person has any symptoms of disease; to help diagnose cancer; to provide information about the stage of a cancer; to provide information about the malignancy of a tumor; to provide information about the size and/or extent of a primary tumor; to provide information about whether or not a tumor has metastasized; to plan treatment; to monitor a patient's general health during treatment; to check for potential side effects of the treatment; to determine whether a cancer is responding to treatment; to find out whether a cancer has recurred; etc.

Active Agents

The active agent for binding to an activity modulating domain of CD206, also referred to herein as a CD206-binding agent, can include any convenient compound. According to certain embodiments disclosed herein, the active agent can be an immunomodulatory peptide, a small molecule active agent, or a specific binding member.

Immunomodulatory Peptides

In certain embodiments of the present disclosure the CD206-binding agent is an immunomodulatory peptide. The terms "immune-modulatory" and "immunomodulatory" are used interchangeably herein. In some cases, an immunomodulatory peptide described herein can be referred to as an anti-inflammatory peptide and vice versa. In certain instances, the immunomodulatory peptide (e.g., as described herein) is an anti-inflammatory peptide, e.g., the peptide has at least one anti-inflammatory property.

Certain aspects of immunomodulatory polypeptides of interest which may be applied to, or adapted for use with, the peptides of the present disclosure are described by Jaynes et al. in WO2016/061133, the disclosure of which is herein incorporated by reference in its entirety.

The terms "peptide" and "polypeptide" are used synonymously herein to refer to polymers constructed from amino acid residues. The term "amino acid residue," as used herein, refers to any naturally occurring amino acid, non-naturally occurring amino acid, or amino acid mimetic (such as a peptoid monomer). An amino acid residue can be in an L- or D-form.

This disclosure includes immunomodulatory peptides having a striapathic region that comprises at least 25% of the length of the polypeptide and at least one immunomodulatory property. The term "striapathic region," refers to a region or portion of a peptide sequence that is composed of a sequence of alternating hydrophobic and hydrophilic modules. A "hydrophobic module" is a peptide sequence consisting of one to five (e.g., 1 to 3 or 1 to 2) hydrophobic amino acid residues, e.g., 1, 2, 3, 4 or 5 hydrophobic amino acid residues. A "hydrophilic module" is a peptide sequence consisting of one to five (e.g., 1 to 3 or 1 to 2) hydrophilic amino acid residues. e.g., 1, 2, 3, 4 or 5 hydrophilic amino acid residues.

A striapathic region can thus be represented by the formulae $(X_{1-5}Y_{1-5})_n$ or $(J_{1-5}J_{1-5})_n$, where each X signifies a hydrophilic amino acid residue, each J signifies a hydrophobic amino acid residue, and each n is an integer from 1 to 10, such as 2 to 10, 2 to 8, 3 to 8, 4 to 8, or 5 to 10. As described in further detail below, aspects of the present disclosure include immunomodulatory peptides having a striapathic region having a specific degree of cationic charge. Immunomodulatory peptides of this disclosure can include a striapathic region having a cationic surface. In certain embodiments, the striapathic region has a cationic charge (i.e., charge>0, e.g., +1, +2, +3, +4, +5, +6 or more). In certain embodiments, the immunomodulatory peptide includes a tail region (e.g., a hydrophobic tail sequence). In certain embodiments, an immunomodulatory peptide includes two or more striapathic regions. In such embodiments, two amphipathic regions of the peptide are in the form of a dimer, where the two amphipathic regions can have the same or different amino acid sequences (i.e., be a homodimer or a heterodimer). In certain embodiments, the two (or more) striapathic regions are connected via a linker or linking region. The linker can be a contiguous (or in-line) amino acid sequence or a non-amino acid moiety as desired.

Hydrophobic amino acid residues are characterized by a sidechain group that has predominantly non-polar chemical or physical properties, e.g., in an environment in which a peptide finds use, e.g., physiological conditions. Such hydrophobic amino acid residues can be naturally occurring or non-naturally occurring. A hydrophobic amino acid residue can be a mimetic of a naturally occurring amino acid that is characterized by a sidechain group that has predominantly non-polar chemical or physical properties. Conversely, hydrophilic amino acid residues are characterized by a sidechain group that is predominantly polar (e.g., charged or neutral hydrophilic), e.g., in an environment in which a peptide finds use, e.g., physiological conditions. Such hydrophilic amino acid residues can be naturally occurring or non-naturally occurring. A hydrophilic amino acid residues can be a mimetic of a naturally occurring amino acid characterized by a sidechain group that is predominantly hydrophilic (charged or neutral polar). Examples of hydrophilic and hydrophobic amino acid residues are shown in Table 1, below. Suitable non-naturally occurring amino acid residues and amino acid mimetics are known in the art. See, e.g., Liang et al. (2013), "An Index for Characterization of Natural and Non-Natural Amino Acids for Peptidomimetics," PLoS ONE 8(7):e67844.

Although most amino acid residues can be considered as either hydrophobic or hydrophilic, a few, depending on their context, can behave as either hydrophobic or hydrophilic. For example, due to their relatively weak non-polar characteristics, glycine, proline, serine and/or cysteine can sometimes function as hydrophilic amino acid residues. Conversely, due to their bulky, slightly hydrophobic side chains, histidine and arginine can sometimes function as hydrophobic amino acid residues.

TABLE 1

| Hydrophobic and Hydrophilic Amino Acid Residues | |
|---|---|
| Hydrophilic Residues (X) | Hydrophobic Residues (J) |
| Arginine | Tryptophan |
| Histidine | Phenylalanine |
| Lysine | Tyrosine |
| Aspartic Acid | Isoleucine |
| Glutamic Acid | Leucine |
| Asparagine | Valine |
| Glutamine | Methionine |
| Pyrrolysine | Cysteine |
| Ornithine | Threonine |

TABLE 1-continued

| Hydrophobic and Hydrophilic Amino Acid Residues | |
|---|---|
| Hydrophilic Residues (X) | Hydrophobic Residues (J) |
| | Serine |
| | Alanine |
| | Proline |
| | Glycine |
| | Selenocysteine |
| | N-formylmethionine |
| | Norleucine |
| | Norvaline |

In some instances, the immunomodulatory peptide is of 5 to 18 amino acid residues in length and includes a striapathic region of alternating hydrophilic and hydrophobic modules that adopts an amphipathic conformation under physiological conditions. In these instances, the striapathic region may include 3 or more hydrophobic modules; and 2 or more hydrophilic modules each comprising at least one cationic residue. In some embodiments, the immunomodulatory peptide includes a sequence defined by one of the formulae:

$[J_{1a}J_{1b}]$-$[X_{1a}X_{1b}]$-$[J_{2a}J_{2b}]$-$[X_{2a}X_{2b}]$-$[J_{3a}]$-$[J_{3a}]$; and $[X_{3a}]$-$[Y_{3a}]$-$[X_{2b}X_{2a}]$-$[J_{2b}J_{2a}]$-$[X_{1b}X_{1a}]$-$[J_{1b}J_{1a}]$;

wherein:

$J_{1a}$, $J_{1b}$, $J_{2a}$, $J_{2b}$ and $J_{3a}$ are each independently selected from phenylalanine, tryptophan, alanine, valine, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine. In some instances, $J_{1a}$, $J_{1b}$, $J_{2a}$, and $J_{3a}$ are each phenylalanine; and $X_{1a}$, $X_{1b}$, $X_{2a}$, $X_{2b}$ and $X_{3a}$ are each independently selected from lysine and arginine.

In certain embodiments, the immunomodulatory peptide includes: a) a sequence selected from: KFRKAFKRFF (RP182); FFRKFAKRFK (RP183); FFKKFFKKFK (RP185); FFKKFFKKFK (RP186); and FFKKFFKKFK (RP233); or b) a sequence having one or two amino acid substitutions relative to the sequence defined in a). In certain embodiments, the immunomodulatory peptide includes the amino acid sequence KFRKAFKRFF (RP182). In certain instances, the immunomodulatory peptide includes the amino acid sequence FFRKFAKRFK (RP183). In certain instances, the immunomodulatory peptide includes the amino acid sequence FFKKFFKKFK (RP185).

In other embodiments, the immunomodulatory peptide includes: a) a peptide sequence selected from: RWKFGGFKWR (RP832C); FKWRGGRWKF (RP837C); FWKRGGRKWF (RP837A); FWKRFV (RP837N); FVRKWR (RP837C1); FAOOFAOOFO (RP850); FWKRFVRKWR (RP837); FWKKFVKKWK (RP841); WWHHWWHHWH (RP847); WWRHWWHRWR (RP848); WWKHWWHKWK (RP849); GDRGIKGHRGF (RP842); LYKKIIKKLL (RP846); FYPDFFKKFF (RP844); FFRKSKEKIG (RP853); FFRHFATHLD (RP845); and EKLSAFRNFF (RP843); or b) a sequence having one or two amino acid substitutions relative to the sequence defined in a). In certain embodiments, the immunomodulatory peptide includes the amino acid sequence selected from: RWKFGGFKWR (RP832C), FKWRGGRWKF (RP837C) and FWKRGGRKWF (RP837A). In certain instances, the immunomodulatory peptide includes the amino acid sequence selected from FWKRFV (RP837N) and FVRKWR (RP837C1). In certain instances, the immunomodulatory peptide includes the amino acid sequence selected from FAOOFAOOFO (RP850), FWKRFVRKWR (RP837) and FWKKFVKKWK (RP841). In certain instances, the immunomodulatory peptide includes the amino acid sequence selected from WWHHWWHHWH, WWRHWWHRWR and WWKHWWHKWK (RP847-849).

In certain embodiments, the immunomodulatory peptide includes the amino acid sequence LYKKIIKKLL (RP846). In certain instances, the immunomodulatory peptide includes the amino acid sequence FYPDFFKKFF (RP844). In certain instances, the immunomodulatory peptide includes the amino acid sequence FFRKSKEKIG (RP853). In certain instances, the immunomodulatory peptide includes the amino acid sequence FFRHFATHLD (RP845). In certain instances, the immunomodulatory peptide includes the amino acid sequence FFRKSKEKIG (RP853).

In some embodiments, the immunomodulatory peptide includes a sequence defined by one of the formulae:

$[X_{1a}]$-$[J_{2a}]$-$[X_{2a}]$-$[J_{2a}]$-$[X_{3a}]$-$[J_{3a}]$ $[J_{3a}]$-$[X_{3a}]$-$[J_{2a}]$-$[X_{2a}]$-$[J_{1a}]$-$[X_{1a}]$ $[J_{1a}J_{1b}]$-$[X_{1a}X_{1b}]$-$[J_{2a}J_{2b}]$;

$[J_{1a}J_{1b}]$-$[X_{1a}X_{1b}]$-$[J_{2a}]$-$[X_{2a}]$;

$[X_{3a}]$-$[J_{3a}]$-$[X_{2b}X_{2a}]$-$[J_{2b}J_{2a}]$;

$[J_{1a}J_{1b}]$-$[X_{1a}]$-$[J_{2a}J_{2b}]$-$[X_{2a}]$; and $[X_{1a}]$-$[J_{1a}J_{1b}]$-$[X_{2a}]$-$[J_{2a}J_{2b}]$;

wherein:

$J_{1a}$, $J_{1b}$, $J_{2a}$, $J_{2b}$ and $J_{3a}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine. In certain embodiments, the immunomodulatory peptide includes: a) a sequence selected from: AFKRFF (182-FN6); FFKKIFF (185-FN6); FWKRFV (837-FN6); WVRRVV (WLUB-F1-N6); IFKKIE (CEC-F1-N6) FLRNLV (LL37F-3-N6); FLHSAK (MAG-F1-N6); FFHHIF (PISC-F-N6); FFKKAA (PLEU-F-N6); ALKKVF (PSEU-F-N6); LYKKII (CXCL4-F-N6); LFRRAF (IL24-FN6); FLKRLL (IL7-FN6); FFRRFA (ABCP-FN6); FFRHFA (E1P-FN6); AIRRIP (gP120-FN6); AFHRFF (GP2B-FN6); FFNRFA (MCPH-FN6); AFKRFF (SPRA-FN6); AFKRFF (TPRO-FN6); IVRRAD (COL18-FN6); FWRWFK (HX5/CPAP); KFWRWF (HX6/YJPA); WFRFWK (HX7/CLPB) KWFRFW (HX8/ATG1); AFHHFF (HEX16F/STPK); FFRNFA (HEXF13/SIF1); AFHRFF (HEX9F/THIF); FFRQFA (HEXF1/ATPB); AFNRFF (HEX2F/AATF); WIQRMM (CXCL13-FN6); WVQRVV (CXCL8-FN6); AFRNFF (HEX3F/FBNA); and TLRRFM (HEX18/HSHK); or b) a sequence having one or two amino acid substitutions relative to the sequence defined in a). In other embodiments, the immunomodulatory peptide includes: a) a sequence selected from: DVRMRL (MCMV-FN6); and RRAELG (TONB-FN6) or b) a sequence having one or two amino acid substitutions relative to the sequence defined in a). In some other embodiments, the immunomodulatory peptide includes: a) a sequence selected from: FWRWFA (HX1/MMPL); AFWRWF (HX2/ABCT); WFRFWA (HX3/GTRF); AWFRFW (HX4/AXES); VAVRIW (HX9/IDRF/AMIA); FFRFFA (HEXF2/AMT1); and AFFRFF (HEX13FiTGME); or b) a sequence having one or two amino acid substitutions relative to the sequence defined in a). In other embodiments, the immunomodulatory peptide includes: a sequence selected from: FFKKFF; WWKKFF; FWKKWF; FFKKWW; WWKKWW; YYKKYY; IIKKYY; YIKKIY; YYKKII; IIKKII; MMKKMM; LLKKMM; MLKKLM; MMKKLL; LLKKLL; VVKKVV; AAKKVV; VAKKAV; VVKKAA; AAKKAA; GGKKGG; TTKKGG; GTKKTG; GGKKTT; TTKKTT; SSKKSS; CCKKSS; SCKKCS; SSKKCC; and CCKKCC; or b) a sequence having one or two amino acid substitutions relative to the sequence defined in a). In certain other cases, the immunomodulatory peptide includes: a sequence selected from: FKFKFK; WKWKWK; YKYKYK; IKIKIK; MKMKMK; LKLKLK; VKVKVK; AKAKAK; GKGKGK; TKTKTK; SKSKSK; CKCKCK; KFKFKF; KWKWKW; KYKYKY; KIKIKI; KMKMKM; KLKLKL; KVKVKV; KAKAKA; KGKGKG; KTKTKT; KSKSKS; and KCKCKC; or b) a sequence having one or two amino acid substitutions relative to the sequence defined in a).

In certain embodiments, the immunomodulatory peptide comprises a peptide sequence as described in Tables 2A-2C.

Tables 2A-2C: Exemplary immunomodulatory peptides sequences including 6 or 10 amino acids.

TABLE 2A

| Name | Sequence | Name | Sequence |
|---|---|---|---|
| FF13FF | FFHHFF | FF21FF | FFQRFF |
| FF3FF | FFRHFF | SPRA2 | FFESIF |
| FF11FF | FFKNFF | SPRA16 | WLTNMI |
| FLAG23 | LWHHWP | FF32FF | FFSGFF |
| E1P-FN6 | FFRHFA | TRAC8 | GWRTYV |
| FF4FF | FFRNFF | FF28FF | FFSSFF |
| PISC-FN6 | FFHHIF | FF27FF | FFTTFF |
| PFMB6 | FFNGYP | FF16FF | FFNRFF |
| FF14FF | FFHNFF | FF1FF | FFRRFF |
| FF23FF | FFQHFF | SPRA3 | FFPSLF |
| FF5FF | FFRQFF | TRAG59 | PYHHII |
| PREV17 | WFRDVF | TRAG63 | TLHRMM |
| HX3/GTRF | WFRFWA | RHSP10 | VVRHWT |
| FF18FF | FFNHFF | SEQ3 | AFRHFA |
| TRAC10 | LFHTLF | FIMH14 | LFTTLL |
| HX4/AXES | AWFRFW | TRAC67 | YLRDVY |
| FIBR6 | FLHHMV | SEQ4 | AYRHFA |
| FF15FF | FFHQFF | CXCL13-F | WIQRMM |
| HX1/MMPL | FWRWFA | SEQ5 | AFHRYA |
| GP2B-FN6 | AFHRFF | FF25FF | FFQQFF |
| SEQ1 | AFHRFF | TRAC8 | VLSRLW |
| FF34FF | FFTGFF | HX9/IDRF/AMIA | VAVRIW |
| FF30FF | FFTSFF | TRAC41 | LWNNLL |
| FF8FF | FFKHFF | TRAG71 | WLGHLM |
| FF24FF | FFQNFF | PFMB10 | ILRRVF |
| FLHB28 | YFTRLF | PFMB18 | VWRGIT |
| FF12FF | FFKQFF | FLHB25 | MYRHVL |
| FF29FF | FFSTFF | PREV2 | FFEQFF |
| LL37-3FN6 | FLRNLV | HX5/CPAP | FWRWFK |
| PREV9 | FFQNIF | FF20FF | FFNQFF |
| FF19FF | FFNNFF | SPRA18 | YLTEII |
| FF33FF | FFGTFF | FIBR14 | LLDRFF |
| TRAC52 | SWHRLF | HIV4 | IWNNMT |
| TRAC24 | IMNHMI | FF2FF | FFRKFF |
| FF22FF | FFQKFF | TRAC24 | WPERVF |
| FF31FF | FFGSFF | FIMH33 | WSHGIY |
| TRAG33 | LFRNYA | PREV8 | AFNRFV |
| HX8/ATG1 | KWFRFW | TRAC11 | ATRHII |
| FF26FF | FFGGFF | YOPB26 | VVERMV |

TABLE 2A-continued

| Name | Sequence | Name | Sequence |
|---|---|---|---|
| TRAG20 | IFSDMF | SPRA4 | FLHKTL |
| ADHE16 | YLKSFF | HX6/YJPA | KFWRWF |
| PREV16 | VFDSIF | TRAC1 | ATRNFV |
| FIMH19 | LWQTLL | FLHB3 | FVRESF |
| TRAC70 | YYTHAA | TRAC63 | WYSEIM |
| HX7/CLPB | WFRFWK | TRAG79 | YLGRYM |
| HX2/ABCT | AFWRWF | TRAC31 | LAQHIV |
| FLAG39 | VYTSVV | FLAG17 | ISDRML |
| TRAG81 | YVQQIF | FLHB26 | VMRNFV |
| ABCP-FN6 | FFRRFA | SPRA15 | VFREMY |
| SPRA17 | YLDHYF | FLID4 | AYNSLI |
| PORPH2 | FMQSFI | YOPB2 | IMERIF |
| HIV6 | LLSGIV | ADHE20 | GYTRIL |
| FIBR2 | AFRNFF | FF6FF | FFKRFF |
| VIRB59 | VYGGWF | RHSP4 | AWRQAA |
| 837-FN6 | FWKRFV | CXCL8-F | WVQRVV |
| ADHE53 | YVTNFI | RHSP5 | SGHHLL |
| FLHB2 | FFGEMF | YOPB19 | MVERMV |
| ADHE23 | IINRII | TRAC25 | IMRDMY |
| VIRB58 | TLRSYL | FF17FF | FFNKFF |
| RHSP17 | AVHHWA | FIMH38 | YVTDLP |
| HIV5 | LFRRAF | RHSP6 | YFHQPL |
| FIMH27 | TYRSYV | TRAC2 | AARNIW |
| ADHE47 | VTRRFI | MAG1-FN | FLHSAK |
| FIBR9 | FYDDIV | FLAG33 | TYHEFA |
| TRAG46 | LYTQLF | SIPD2 | VYTDFY |
| SPRA5 | FLSQYF | TRAC18 | PVRQLL |
| ADHE12 | FLKDLV | TRAG35 | LFRRFG |
| TRAC28 | ITQNIV | TRAG9 | FFETAL |
| FIMH16 | LLRNTP | TRAG8 | FFESAL |
| SPRA8 | IRNYY | SIPD5 | LYDNLV |
| PORPH1 | FMQNFV | TRAG55 | MYQQLF |
| FIMH18 | LSTQIF | YOPB7 | IMEHVL |
| ADHE11 | FFSSLA | COL18-FN6 | IVRRAD |
| FIMH34 | YFQEYI | PREV1 | SYQNFL |
| FIMH6 | AYGGVL | TRAG82 | YYKQLY |
| VIRB56 | LYQQMA | TRAG1 | AARDMM |
| VIRB57 | MLSSAM | FIMH24 | TARGYL |
| TRAG10 | FFGDFV | PREV10 | MLNKIP |
| TRAC11 | LINTMP | TRAC20 | TLNTLF |
| FIBR15 | LLDRFY | FIBR12 | ILENYY |
| FIMH13 | LFSQAG | ADHE15 | FPDNML |
| YOPB15 | MATRGL | TRAC5 | FLSQLA |
| FIMH11 | IFRNTA | RHSP19 | FGRRIA |
| PREV12 | MLRNYY | TRAG7 | FFDQLI |
| FLAG28 | MLTGAF | TRAC2 | AYDRVM |
| TRAG43 | LMNGMM | FIMH4 | ALSTPV |
| RHSP13 | VAHHYA | WLUB-F1-N6 | WVRRVV |
| RHSP9 | FFSKLP | ADHE8 | ATEHFF |
| YOPB8 | LARQVV | SPRA7 | FYDQLM |
| SEQ2 | AFNNFF | PREV15 | YTKELF |
| PREV7 | AYQNFL | PREV3 | MVRNYY |
| TRAC17 | FLNNLI | FLHB20 | LIREAM |
| PFMB4 | AWHDVA | TRAC3 | AYDSMT |
| SPRA14 | VFNELY | FLIC21 | IANRFT |
| PREV14 | VFEQLY | YOPB12 | LLGKLM |
| FIMH7 | FVSGVY | FLHB21 | LLKSLI |
| FLID3 | ALQSFM | RHSP16 | YFDGFV |
| 182-FN6 | AFKRFF | FLAG26 | MASEIV |
| FLAG27 | MASQMV | FIMH36 | YTQRLA |
| SIPB3 | ALSKMM | FIMH9 | GWDSII |
| SPRA6 | FTDNFY | PFMB3 | AVSHAA |
| SIPD4 | PLQKMV | FLIC34 | VGDDYY |
| ADHE31 | LLKNIL | TRAG24 | IINNFI |
| FLAG38 | VVDRAL | TRAC17 | MYESMA |
| FLIC33 | VASEMV | FIBR11 | ILDNYY |
| FLAG19 | IYQRYS | YOPB3 | ALQTAV |
| TRAC14 | FAGDMM | PFMB7 | FITNYL |
| FLAG11 | FGQNIY | FIMH10 | GWDSIV |
| FIBR3 | ALDGIF | YOPB18 | MMTSLI |
| FIMH37 | YVSELP | RHSP18 | YFDGLV |
| PFMB19 | WWGNSY | FIMH21 | MMTDYI |
| YOPB6 | ILGKIA | PREV13 | MTRDYY |
| YOPB27 | WLKQSV | SPRA12 | TYQKYL |
| FIMH35 | YFQEYL | FLAG16 | ILQQAA |
| FLHB14 | GLKRMF | YOPB11 | LISNYV |
| FLHB23 | MFDRAT | TRAC7 | FYEKLI |
| FLAG31 | TAQRYL | VIRB54 | FYSSAG |

TABLE 2A-continued

| Name | Sequence | Name | Sequence |
|---|---|---|---|
| TRAG72 | WLNEFG | TRAC16 | FIQKGY |
| TRAG18 | IADRVF | FLAG8 | AMERIS |
| FIBR16 | LLDRYY | TRAC36 | LLKDVL |
| FIBR7 | FSKEIF | YOPB17 | MLHNLA |
| PORPH3 | AFNQFL | FLHB27 | YFKRVF |
| HIV1 | AVERYL | PFMB14 | MKRVI |
| FLAG10 | AVRGIF | PREV6 | FSEQFL |
| FLID7 | LTQQFT | TRAC46 | PFRKWL |
| SIPD3 | AFSDIL | FLAG12 | GGNKLL |
| RHSP3 | YLDNVS | FLID5 | GIRDAI |
| VIRB510 | YISDFT | FIMH39 | YWSEYF |
| ADHE43 | SYNNWY | TRAC23 | ILRKAI |
| TRAG48 | MFNNIW | TRAC4 | FIDDYI |
| TRAC19 | SWQEVV | IL7-F | FLKRLL |
| FLAG2 | ALSEII | TRAC25 | YFRRTG |
| RHSP8 | GLKRVV | SIPD1 | VYENVV |
| ADHE34 | LYRKIV | PFMB16 | TAQNWI |
| TRAC7 | ALKQVL | RHSP14 | ILEDVA |
| FLHB15 | GTKRLF | PFMB11 | LIKSWV |
| FIMH22 | PPRNYI | FIBR13 | LFGELL |
| RHSP15 | LLRKAM | FLHB10 | GIKRLF |
| ADHE22 | IASKLL | FLIC24 | MAKEMM |
| FLHB13 | GLKRIF | FLAG32 | TATNYM |
| FLIC12 | AITRLS | FLHB6 | GFKNMF |
| FLIC22 | ILQQAG | YOPB20 | SLNDLW |
| TRAC3 | AASKWL | SPRA1 | AGQKLM |
| FLAG29 | MMSEVP | HIV7 | SLDDIW |
| FLHB19 | LIPRFA | FLAG37 | VLQQAG |
| FIMH1 | AFGGAL | PFMB9 | HIRDAG |
| ADHE1 | AAQEVI | FLID6 | ILDSLT |
| FLIC29 | TLDKAL | FLIC28 | STQNVL |
| ADHE32 | LLQQVG | FLID8 | PLDQLL |
| FIMH2 | AFNDYL | FLHB16 | GVKNLF |
| FLIC5 | AAKQMV | FLID2 | AIKSWV |
| FLHB12 | GLKNMF | ADHE7 | APKNML |
| FLIC8 | AIERLS | FLAG22 | LISTLL |
| SPRA13 | VAKEFL | FIMH5 | AVKRIV |
| TRAC33 | LINNYL | YOPB23 | VLNKLF |
| FLIC6 | AANEII | FLIC23 | LPQQVL |
| TRAC6 | FLSSAT | TRAC23 | VYSDAM |
| FLIC36 | VPQQVL | FLIC37 | YATEVS |
| PFMB17 | TLDGFF | YOPB5 | FIQQAL |
| FIMH3 | AFNDYS | PFMB8 | NKNLY |
| YOPB25 | VVEGFL | FLID10 | TVNNVA |
| ADHE5 | AISNIW | FIBR20 | VLRKYL |
| 185-FN6 | FFKKFF | FLIC20 | GGRKLL |
| FLIC31 | TTQNVL | FLIC14 | ALGTAI |
| FLHB7 | GFKRIF | FIMH17 | LMKTFP |
| FIMH12 | ILGQAM | FIMH29 | VGQNLV |
| TRAC39 | LMNDYI | FLAG13 | GGRKLL |
| TRAC22 | ILDEAW | YOPB9 | LASKVA |
| FLHB11 | GIKRMF | FIBR5 | ATKNIF |
| FIBR10 | IAKNIF | TRAC12 | LPEDVW |
| SIPB6 | LIGKAI | FLHB18 | LARKLA |
| YOPB10 | LIGKAI | FIMH25 | TATDIF |
| FLIC27 | SLGTAI | FLIC25 | MIQTAS |
| FIMH31 | VPKHVY | FIBR4 | ALKKLI |
| FLAG15 | HIQQAG | ADHE17 | GIKNLY |
| FLID9 | TLKSAL | TRAC21 | IIEEAW |
| TRAG21 | IDKIF | TRAC9 | IAQNLA |
| ADHE14 | FMDKYI | FLIC15 | ALNKLG |
| FLAG18 | ITNKAA | RHSP12 | MTRKGL |
| VIRB55 | IVSTAA | FLIC26 | PADEIL |
| TRAG3 | AFSEAW | FLID1 | AIKDWV |
| TRAC16 | MSGGYL | TRAG29 | LASKYF |
| FLHB8 | GIAKMF | TRAC20 | IDEAW |
| SPRA10 | MIKTAF | FLHB24 | MMDDVP |
| SIPB7 | VLKQLA | FLAG36 | VLKKLI |
| FIBR1 | AFDEVM | FIMH28 | VAKDIS |
| FLIC35 | VIDEAI | RP426-FN6 | AAKRAF |
| HIV3 | IVGGLV | FLHB9 | GIKRIF |
| FLAG25 | MAKEMS | RHSP7 | VYDEMG |
| FLAG30 | SFDNYI | FLAG1 | TADKAM |
| FLIC19 | GAQSAV | ADHE49 | WFKRGL |
| FIBR8 | FTKKMV | SPRA11 | MMKNIY |
| FIMH26 | TITDYV | FIRB19 | MLKKYF |
| FLHB17 | ISKDFF | FLIC18 | AYNDAP |
| FLAG34 | VAEELY | FIMH15 | LLDEAL |

TABLE 2A-continued

| Name | Sequence | Name | Sequence |
|---|---|---|---|
| FLIC11 | AINNAI | RHSP1 | WIDKGG |
| FLIC32 | VADELL | TRAG23 | IIKGYI |
| HIV2 | IVGGLI | SPRA9 | MIKNIG |
| YOPB1 | AFKDVV | FLHB5 | FYKKIV |
| PFMB13 | MKNLF | RHSP2/107 | FAKKFA |
| FLIC7 | AFTDGA | TRAC48 | SADRYY |
| FIMH30 | VGSKLY | CFC5/185B2 | FFKFKF |
| TRAG51 | MIRKYY | FIMH20 | MMKKII |
| YOPB21 | SVQQAA | PSEU-FN6. | ALKKVF |
| TRAC14 | MAEKAY | FLIC2 | AADNAI |
| FLIC17 | ASDKLF | PFMB5 | AYKKVF |
| ADHE38 | PPQDYV | CFC4/ADB2 | FFRFHF |
| ADHE26 | TYKKFY | PFMB12 | MFKKTL |
| PREV4 | MMKNVY | FIBR17 | LLKKFG |
| YOPB14 | LVKRGV | CFC3/ADB1 | FRFHFF |
| FIMH8 | GSANVY | CFC5/185B1 | FKFKFF |
| FLAG6 | AIDNLF | TRAG31 | YAKKYG |
| TRAC49 | SINDLY | PFMB1 | AIDDFG |
| CXCL4-F | LYKKII | ADHE3 | AIKKII |
| FLIC30 | TTGKYY | CFC1 | GGKKGG |
| TRAC54 | TYKKYY | CFC2 | KGGGGK |
| FLIC3 | AAGKMG | PFMB2 | AMKKVV |
| YOPB24 | VMEKLG | FIMH23 | SAGGVA |
| YOPB13 | LMSKFG | FLAG9 | AMKKLA |
| FLIC13 | ALDEAI | FLIC1 | AADDAA |
| TONB-FN6 | RRAELG | | |
| FLIC10 | AINKVS | | |
| FLIC4 | AAGQAI | | |
| YOPB16 | MFKKIL | | |
| ADHE39 | PPRKYI | | |
| FLAG4 | SLKGAM | | |
| FLHB1 | AMGNAM | | |
| FLAG20 | LANQSA | | |
| PFMB15 | TADSWF | | |
| FLIC16 | AMEKLS | | |
| CEC1-FN6 | IFKKIE | | |
| FIBR18 | LLKKFS | | |
| FLIC9 | AIKDTY | | |
| PLEU-FN6 | FFKKAA | | |
| 832c-FN6 | WKFKWR | | |

TABLE 2B

| Origin | Sequence | Origin | Sequence |
|---|---|---|---|
| CCL1 | RKMLRH | XCL2 | wvrdvv |
| MCP-1-A | SYRRIT | CXCL3 | mvqkiiekilnkgs |
| MCP-1-B | WVQDSM | CXCL4 | lYkkiikkll |
| (CCL4) | WVQEYV | CXCL5 | flkkviqkil |
| CCL11-A | SYRRIT | CXCL6 | flkkviqkil |
| CCL11-B | WVQDSM | CXCL13 | rrfidr |
| CCL18 | WVQKYI | CXCL14 | stkrfi |
| CX3CL1 | WVKDAM | LIG15-MSE | liknim |
| CXCL1-A | MVKKII | CXCL16 | wvqelm |
| CXCL1-B | IIEKML | IL-1F10 | Yfeqsw |
| CXCL7 | KKIVQK | IL-1F9 | felnin |
| CXCL8-A | WVQRVV | IL-1F8 | tldqwg |
| CXCL8-B | VVEKFL | IL-3 | mideii |
| CXCL9 | KELIKK | IL-5 | lvketl |
| CXCL10 | AIKNLL | IL-7 | flkrll |
| IL-2 | FLNRWI | IL-11 | wlrrag |
| IL-4-A | TLQEII | IL-12 | asrkts |
| IL-4-B | TLENFL | IL-13 | kklfre |
| IL-6-A | WLQDMT | TAXILLIN | llkeav |
| IL-6-B | SFKEFL | IL-16 | kkliee |
| IL-9 | FSERLS | IL-17A | ivhhva |
| IL-10-A | YLEEVM | IL-19 | Yvdrvf |
| IL-10-B | LRLRLR | IL-21 | kefler |
| IL-12-A | ASRKTS | IL-22 | itnrtf |
| IL-12-B | TIDRVM | IL-23 | fYekll |
| IL-15 | TVENLI | IL-25 | tseell |
| IL-18 | LFEDMT | IL-26 | fmedvf |
| IL-20-A | LLRHLL | IL-27 | larkll |
| IL-20-B | TLRKIS | IL-29 | aledvl |
| IL-24 | WMQKFY | IL-31 | qkivee |

TABLE 2B-continued

| Origin | Sequence | Origin | Sequence |
|---|---|---|---|
| IL-28 | KRLLEK | IL-32 | erfYdk |
| IL-34 | YMKHYF | IL-33 | rettkr |
| IFN-gamma | AIHELI | TNF-BETA | ssqkmv |
| CRP-A | MSRKAF | IFN-ALPHA | vlheliqqif |
| CRP-B | WSKDIG | SCF | aYkels |
| CRP-C | SLKKGY | NGF | lskqmv |
| LIF-A | NNLMNQ | HGCSF | tvqeat |
| LIF-B | SGKDVF | TachYkinin | mgkral |
| ONCSTN-A | LGRRGF | CCL22 | vvkhfY |
| ONCSTN-B | ALRKGV | CCL23 | lkldtriktr |
| (CCL3) | wvqkYv | CCL24 | wvqrYm |
| CCL5 | wvreYi | CCL25 | vlrraw |
| CCL6 | isrrgt | CCL26 | wvqkYi |
| CCL7 | sYrrtt | CCL27 | mirkmg |
| CCL8 | wvrdsm | CCL28 | vshhisrrller |
| LIG-9 MSE | iskrgf | XCL1 | wvrdvv |
| CCL12 | sYrrit | CCL19 | wverii |
| CCL13 | wvqnYm | CCL20 | Ytdril |
| (CCL14) | wvqdYi | CCL21 | wvqqlm |

TABLE 2C

| Name | Sequence | Name | Sequence |
|---|---|---|---|
| AP00143 | KLLKWLKKLL | AP02253 | FIKKFYKQIM |
| AP00163 | LWKDILKNVG | AP02569 | RLLKSVRRAV |
| AP00325 | KVVNVLKNLF | AP02664 | KWRRWVRWI |
| AP00366 | KFKKLFKKLS | AP02671 | KLFKKILKYL |
| AP00371 | LSDRGRRLGE | AP02899 | KFWKKVLNGA |
| AP00385 | KGKEMLKDYA | AP02924 | LWKEVLKNAG |
| AP00484 | KLVKKVKHTI | AP02964 | KIKKGFRKIF |
| AP00496 | KVFKRLEKLF | AP02981 | KGKELLRDYA |
| AP01010 | RKLKKLRNAL | AP00012 | GLFDIIKKIA |
| AP00680 | SLQRGGQKIL | AP00016 | GLFDIVKKVV |
| AP00541 | KLLDAAKQIL | AP00082 | GLKNVGKEVG |
| AP00624 | RIKDFLRNLV | AP00155 | GLRRLGRKIA |
| AP00629 | RIVQRIKDFL | AP00376 | GWKDWAKKAG |
| AP00691 | KVKHAGRRVL | AP00555 | GKVRAKAKTR |
| AP00722 | LGKRALKKII | AP01239 | KFFRKLKKSV |
| AP00774 | KVRKGFKEAS | AP01456 | GKSKIKWQ |
| AP01012 | SMAKKLKEYM | AP01540 | AFQDTIRKFL |
| AP01295 | TAKNVAKNVA | AP02318 | ILKKVGKEAV |
| AP01377 | RQGWRAHKVV | AP02424 | KFFKKVKKSV |
| AP01633 | RVVRVVRRWV | AP02749 | AMEKIAEKVG |
| AP01634 | KIFEKVKNLV | AP02776 | IRWRIRV |
| AP01768 | KIGQRIRDFF | | |

In some embodiments, the immunomodulatory peptide includes a sequence defined by one of the formulae:

$[J_{1a}]$-$[X_{2a}]$-$[J_{2a}]$-$[X_{3a}]$-$[J_{3a}]$ $[X_{1a}]$-$[J_{1a}]$-$[X_{2a}]$-$[J_{2a}]$-$[X_{3a}]$ $[X_{1a}]$-$[J_{1a}]$-$[X_{2a}]$-$[J_{2a}J_{2b}]$;

$[J_{1a}J_{1b}]$-$[X_{1a}]$-$[J_{2a}]$-$[X_{2a}]$;

$[X_{1a}]$-$[J_{1a}J_{1b}]$-$[X_{2a}]$-$[J_{2a}]$;

$[J_{1a}]$-$[X_{1a}]$-$[J_{2a}J_{2b}]$-$[X_{2a}]$; and $[J_{1a}J_{1b}]$-$[X_{2a}]$-$[J_{2a}J_{2b}]$;

wherein:

$J_{1a}$, $J_{1b}$, $J_{2a}$, $J_{2b}$ and $J_{3a}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine. In certain embodiments, the immunomodulatory peptide includes: a) a sequence selected from: AFKRF; FFKKF; FWKRF; WVRRV; IFKKI; FLRNL; FLHSA; FFHHI; FFKKA; ALKKV; LYKKI; LFRRA; FLKRL; FFRRF; FFRHF; AIRRI; AFHRF; FFNRF; IVRRA; FWRWF; KFWRW; WFRFW; KWFRF; AFHHF; FFRNF; FFRQF; AFNRF; WIQRM; WVQRV; AFRNF; TLRRF; FKRFF; FKKFF; WKRFV; VRRVV; FKKIE; LRNLV; LHSAK; FHHIF; FKKAA; LKKVF; YKKII; FRRAF; LKRLL; FRRFA; FRHFA; IRRIP; FHRFF; FNRFA; VRRAD; WRWFK; FRFWK; FHHFF; FRNFA; FRQFA; FNRFF; IQRMM; VQRVV; FRNFF; LRRFM; DVRMR; VRMRL; RRAEL; RAELG; and RWKFG; or b) a sequence having one or two amino acid substitutions relative to the sequence defined in a). In other embodiments, the immunomodulatory peptide includes: a) a peptide sequence selected from: AFWRW; AWFRF; VAVRI; FFRFF; AFFRF; WRWFA; FRFWA; AVRIW; and FRFFA; or b) a sequence having one or two amino acid substitutions relative to the sequence defined in a). In other embodiments, the immunomodulatory peptide includes: a) a peptide sequence selected from: FFKKF; WWKKF; FWKKW; FFKKW; WWKKW; YYKKY; IIKKY; YIKKI; YYKKI; IIKKI; MMKKM; LLKKM; MLKKL; MMKKL; LLKKL; VVKKV; AAKKV; VAKKA; VVKKA; AAKKA; GGKKG; TTKKG; GTKKT; GGKKT; TTKKT; SSKKS; CCKKS; SCKKC; SSKKC; and CCKKC; FKKFF; WKKFF; WKKWF; FKKWW; WKKWW; YKKYY; IKKYY; IKKIY; YKKII; IKKII; MKKMM; LKKMM; LKKLM; MKKLL; LKKLL; VKKVV; AKKVV; AKKAV; VKKAA; AKKAA; GKKGG; TKKGG; TKKTG; GKKTT; TKKTT; SKKSS; CKKSS; CKKCS; SKKCC; and CKKCC; or b) a sequence having one or two amino acid substitutions relative to the sequence defined in a). In certain other cases, the immunomodulatory peptide includes: a sequence selected from: a) a peptide sequence selected from: FKFKF; WKWKW; YKYKY; IKIKI; MKMKM; LKLKL; VKVKV; AKAKA; GKGKG; TKTKT; SKSKS; CKCKC; KFKFK; KWKWK; KYKYK; KIKIK; KMKMK; KLKLK; KVKVK; KAKAK; KGKGK; KTKTK; KSKSK; and KCKCK; or b) a sequence having one or two amino acid substitutions relative to the sequence defined in a).

In certain embodiments, the immunomodulatory peptide comprises a peptide sequence as described in Table 2, truncated by 1 amino acid at the N-terminus. In some other instances, the immunomodulatory peptide comprises a peptide sequence as described in Table 2, truncated by 1 amino acid at the C-terminus.

In some embodiments, the immunomodulatory peptide includes a sequence defined by one of the formulae:

$[J_{1a}]$-$[X_{1a}]$-$[J_{2a}]$-$[X_{2a}]$ $[X_{1a}]$-$[J_{1a}]$-$[X_{2a}]$-$[J_{2a}]$ $[X_{1a}X_{2a}]$-$[J_{2a}J_{2b}]$; and $[J_{1a}J_{1b}]$-$[X_{1a}X_{2a}]$;

wherein:

$J_{1a}$, $J_{1b}$, $J_{2a}$, and $J_{2b}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, and $X_{2b}$ are each independently selected from lysine, arginine, histidine, aspartic acid, glutamic acid, asparagine and glutamine. In certain embodiments, the immunomodulatory peptide includes: a) a sequence selected from: AFKR; FFKK; FWKR; WVRR; IFKK; FLRN; FLHS; FFHH; ALKK; LYKK; LFRR; FLKR; FFRR; FFRH; AIRR; AFHR; FFNR; IVRR; FWRW; KFWR; WFRF; KWFR; AFHH; FFRN; FFRQ; AFNR; WIQR; WVQR; AFRN; TLRR; KRFF; KKFF; KRFV; RRVV; KKIE; RNLV; HSAK; HHIF; KKAA; KKVF; KKII; RRAF; KRLL; RRFA; RHFA; RRIP; HRFF; NRFA; RRAD; RWFK; RFWK; HHFF; RNFA; RQFA; NRFF; QRMM; QRVV; RNFF; RRFM; VRMR; RMRL; RAEL; AELG; and WKFG; or b) a sequence having one or two amino acid substitutions relative to the sequence defined in a). In other embodiments, the immunomodulatory peptide includes: a) a peptide sequence selected from: FWRW; AFWR; WFRF; AWFR; VAVR; FFRF; AFFR; RWFA; WRWF; RFWA; FRFW; VRIW; RFFA; and FRFF; or b) a sequence having one or two amino acid substitutions relative to the sequence defined in a). In other embodiments, the immunomodulatory peptide includes: a) a peptide sequence selected from: FFKK; WWKK; FWKK; YYKK; IIKK; YIKK; MMKK; LLKK; MLKK; VVKK; AAKK; VAKK; GGKK; TTKK; GTKK; SSKK; CCKK; SCKK; KKFF; KKWF; KKWW; KKYY; KKIY; KKII; KKMM; KKLM; KKLL; KKVV; KKAV; KKAA; KKGG; KKTG; KKTT; KKSS; KKCS; and KKCC; or b) a sequence having one or two amino acid substitutions relative to the sequence defined in a). In certain other cases, the immunomodulatory peptide includes: a sequence selected from: a) a peptide sequence selected from: FKFK; WKWK; YKYK; IKIK; MKMK; LKLK; VKVK; AKAK; GKGK; TKTK; SKSK; CKCK; KFKF; KWKW; KYKY; KIKI; KMKM; KLKL; KVKV; KAKA; KGKG; KTKT; KSKS; and KCKC; or b) a sequence having one or two amino acid substitutions relative to the sequence defined in a).

In certain embodiments, the immunomodulatory peptide comprises a peptide sequence as described in Table 2, truncated by 2 amino acid at the N-terminus. In some other instances, the immunomodulatory peptide comprises a peptide sequence as described in Table 2, truncated by 2 amino acid at the C-terminus.

The exemplary immunomodulatory peptide sequences described herein are merely examples and are not the only immunomodulatory polypeptides provided herein. Indeed, fragments and variants of the sequences of the disclosed peptides are also within the scope of the present disclosure.

The present disclosure provides immunomodulatory polypeptides, sometimes referred to as "RP peptides," that satisfy one or more of the structural formulae described above. The present disclosure also provides immunomodulatory polypeptides that share a minimum degree of homology with any of the exemplary RP peptides disclosed herein, or variant thereof, or a fragment thereof. Thus, a peptide or polypeptide of the present disclosure is an immunomodulatory peptide that satisfies one of the formulae described herein or shares a minimum degree of homology with any of the exemplary RP peptides disclosed herein.

A "fragment" of the invention includes at least 4, 5, 6, 7, 8, 9, 10, 11, 12, 13, 14, 15, 16, 17, 18, 19, 20, 21, 22, or 23 contiguous amino acid residues of a peptide disclosed herein (or up to one less than the number of amino acid residues in the subject peptide) and retains at least one immunomodulatory property of the subject peptide. Thus, fragments of the invention include peptides that are missing one, two, three, four, or more amino acids from the N-terminus and/or the C-terminus relative to a parent immunomodulatory peptide disclosed herein.

A "variant" of the invention is a polypeptide that is substantially similar to a polypeptide disclosed herein and retains at least one immunomodulatory property of the subject polypeptide. Variants can include deletions (i.e., truncations) of one or more amino acid residues at the N-terminus or the C-terminus of a subject polypeptide disclosed herein; deletion and/or addition of one or more amino acid residues at one or more internal sites in the subject polypeptide disclosed herein; and/or substitution of one or more amino acid residues (e.g., one, two, three, or even more) at one or more positions in the subject polypeptide disclosed herein. For subject polypeptides that are 12 amino acid residues in length or shorter, variant polypeptides can include three or fewer (e.g., three, two, one, or none) deleted amino acid residues, whether located internally, at the N-terminal end, and/or at the C-terminal end.

Accordingly, the invention further provides immunomodulatory polypeptides that are at least 50% identical (i.e., at least 50% sequence identity) (e.g., at least 60%, at least 70%, at least 80%, at least 85%, at least 90%, at least 95% or more) to any one of the immunomodulatory polypeptides disclosed herein (e.g., Table 2) and still retain at least one immunomodulatory property. Sequence identity is based on a comparison of two peptide sequences or fragments thereof of the same or similar length.

As such, in certain embodiments, this disclosure provides polypeptides that include an amino acid sequence having from 1 to 10 amino acid differences (e.g., 10 or fewer, 9 or fewer, 8 or fewer, 7 or fewer, 6 or fewer, 5 or fewer, 4 or fewer, 3 or fewer, 2 or fewer, or 1 amino acid difference) to any one of the polypeptides disclosed herein and still retain at least one immunomodulatory property. An "amino acid difference" as used herein includes: an amino acid substitution, an amino acid insertion, a terminal amino acid addition, an amino acid deletion, a terminal amino acid truncation, or any combination thereof.

In some embodiments, any of the peptides disclosed herein can be 1 or 2 amino acids shorter at the N-terminus. In some embodiments, any of the peptides disclosed herein can be 1 or 2 amino acids shorter at the C-terminus. In some instances, any of the peptides disclosed in (able 21 may be 1 or 2 amino acids shorter at the N-terminus. In some other instances, any of the peptides disclosed in table 2 may be 1 or 2 amino acids shorter at the C-terminus.

In some embodiments the peptides disclosed herein can include deletions, additions, and/or substitutions of amino acid residues, as discussed herein. Substituted amino acid residues can be unrelated to the amino acid residue being replaced (e.g., unrelated in terms or hydrophobicity/hydrophilicity, size, charge, polarity, etc.), or the substituted amino acid residues can constitute similar, conservative, or highly conservative amino acid substitutions. As used herein. "similar," "conservative," and "highly conservative" amino acid substitutions are defined as shown in Table 3, below. The determination of whether an amino acid residue substitution is similar, conservative, or highly conservative is based exclusively on the side chain of the amino acid residue and not the peptide backbone, which may be modified to increase peptide stability, as discussed below.

TABLE 3

| Classification of Amino Acid Substitutions | | | |
|---|---|---|---|
| Amino Acid in Subject Polypeptide | Similar Amino Acid Substitutions | Conservative Amino Acid Substitutions | Highly Conservative Amino Acid Substitutions |
| Glycine (G) | A, S, N | A | n/a |
| Alanine (A) | S, G, T, V, C, P, Q | S, G, T | S |
| Serine (S) | T, A, N, G, Q | T, A, N | T, A |
| Threonine (T) | S, A, V, N, M | S, A, V, N | S |
| Cysteine (C) | A, S, T, V, I | A | n/a |
| Proline (P) | A, S, T, K | A | n/a |
| Methionine (M) | L, I, V, F | L, I, V | L, I |
| Valine (V) | I, L, M, T, A | I, L, M | I |
| Leucine (L) | M, I, V, F, T, A | M, I, V, F | M, I |
| Isoleucine (I) | V, L, M, F, T, C | V, L, M, F | V, L, M |
| Phenylalanine (F) | W, Y, L, M, I, V | W, L | n/a |
| Tyrosine (Y) | F, W, H, L, I | F, W | F |
| Tryptophan (W) | F, L, V | F | n/a |
| Asparagine (N) | Q | Q | Q |
| Glutamine (Q) | N | N | N |
| Aspartic Acid (D) | E | E | E |
| Glutamic Acid (E) | D | D | D |
| Histidine (H) | R, K | R, K | R, K |
| Lysine (K) | R, H, O | R, H, O | R, O |
| Arginine (R) | K, H, O | K, H, O | K, O |
| Ornithine (O) | R, H, K | R, H, K | K, R |

The "length" of a subject peptide or polypeptide is the number of amino acid residues linked end-to-end that constitute the peptide or polypeptide, excluding any non-peptide linkers and/or modifications that the peptide or polypeptide may contain. In some embodiments, the peptide is of 5 to 30 amino acid residues (e.g., 5 to 25, 10 to 20 or 5 to 18, 5 to 12 or 5 to 10, or 6 to 30, 6 to 25, 6 to 20, 6 to 18, 6 to 12, 6 to 10 or 7 to 12, or 7 to 10 amino acid residues) in length, and comprises a striapathic region of alternating hydrophilic and hydrophobic modules that adopts an amphipathic conformation under physiological conditions (e.g., as described herein). In some embodiments, the peptide is of 4 to 12 amino acid residues (e.g., 4, 5, 6, 7, 8, 9 or 10 amino acid residues) in length, and comprises a striapathic region of alternating hydrophilic and hydrophobic modules that adopts an amphipathic conformation under physiological conditions. In certain instances, a striapathic region of the peptide is of 5 to 18 amino acid residues in length (e.g., 6 to 18, 6 to 14, 6 to 12, 7 to 12, or 5, 6, 7, 8, 9, 10, 11 or 12 amino acids in length), wherein the peptide is optionally further modified (e.g., as described herein). The striapathic region can comprise: 2 or more (e.g., 3 or more or 4 or more) hydrophobic modules; and one or more (e.g., 2 or more, 3 or more, or 4 or more) hydrophilic modules (e.g., each comprising at least one cationic residue). In some instances, the striapathic region of the peptide has a length of 4 to 10 amino acid residues, such as 4 to 6. In some instances, the striapathic region of the peptide has a length of 2 to 3 amino acid residues.

The hydrophobic modules can consist of any convenient residues. In certain instances, the hydrophobic modules include amino acid residues selected from phenylalanine, tryptophan, alanine, valine, and glycine. The striapathic region can include 1, 2 or more cationic amino acid residues in total, such as 3 or more, 4 or more, 5 or more, 6 or more, or even more. The immunomodulatory peptide can comprise 2, 3 or more hydrophilic modules that consist of any convenient residues. In some instances, the hydrophilic modules include amino acid residues selected from lysine, arginine, histidine, aspartic acid, glutamic acid, asparagine and glutamine.

In the formula described herein, J(N) is used to refer to a particular hydrophobic module, where N is indicates a position within the linear formula. Similarly, X(N) is used to refer to a particular hydrophilic module, where N is indicates a position within the linear formula.

In the formula described herein, $J_{(nx)}$ is used to refer to a particular hydrophobic amino acid residue, where n indicates which module the residue is located in and x indicates its position within the module. Similarly, $X_{(nx)}$ is used to refer to a particular hydrophilic amino acid residue, where n indicates which module the residue is located in and x indicates its position within the module.

Small Molecules

In certain embodiments of the present disclosure the CD206-binding agent is a small molecule. Small molecules of interest include, but are not limited to, small organic or inorganic compounds having a molecular weight (MW) of more than 50 and less than about 2,500 daltons (Da), such as more than 50 and less than about 1000 Da, or more than 50 and less than about 500 Da. "Small molecules" encompasses numerous biological and chemical classes, including synthetic, semi-synthetic, or naturally-occurring inorganic or organic molecules, including synthetic, recombinant or naturally-occurring nucleic acids. Small molecules of interest can comprise functional groups necessary for structural interaction with proteins, particularly hydrogen bonding, and can include at least an amine, carbonyl, hydroxyl or carboxyl group, and can contain at least two of the functional chemical groups. The small molecules can comprise cyclical carbon or heterocyclic structures and/or aromatic or polyaromatic structures substituted with one or more of the above functional groups. Small molecules are also found among biomolecules including saccharides, fatty acids, steroids, purines, pyrimidines, derivatives, structural analogs or combinations thereof.

Some molecules of interest can comprise a backbone comprising one or more carboxamide functional groups. In some instances, the small molecule of interest comprises a backbone comprising one or more urea functional groups. In some instances, the small molecule of interest comprises one or more carboxamide functional groups and one or more urea functional groups. In certain instances, the small molecule of interest includes one or more optionally substituted aryl groups. In certain instances, the small molecule of interest includes one or more optionally substituted naphthyl groups. In certain instances, the small molecule of interest includes one or more optionally substituted heterocyclic groups. In certain cases, the small molecule of interest includes one or more optionally substituted carbazole groups.

In some embodiments, the small molecule active agent is described by formula (I):

(I)

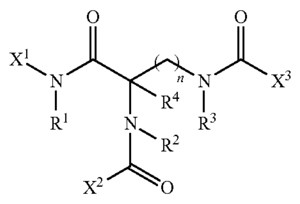

wherein:

$R^1$-$R^4$ are each independently selected from hydrogen, alkyl and substituted alkyl;

$X^1$ is selected from alkyl, substituted alkyl, aryl, substituted aryl, aralkyl, substituted aralkyl, heterocycle, substituted heterocycle, heteroaryl, substituted heteroaryl;

$X^2$ is selected from alkyl, substituted alkyl, aryl, substituted aryl, amino, substituted amino, heteroaryl, substituted heteroaryl, heterocycle, substituted heterocycle;

$X^3$ is selected from alkyl, substituted alkyl, aryl, substituted aryl, naphthyl, substituted naphthyl, heterocycle, substituted heterocycle, heteroaryl, substituted heteroaryl, aryl heterocycle, substituted aryl heterocycle; and n is an integer from 1 to 10, or a pharmaceutically acceptable salt or solvate thereof.

In certain embodiments of a compound of formula (I), $X^1$ is alkyl or substituted alkyl. In certain cases. $X^1$ is aryl or substituted aryl. In certain cases $X^1$ is selected from heterocycle, substituted heterocycle, heteroaryl, and substituted heteroaryl. In certain cases. $X^1$ is an optionally substituted carbazole. In certain cases, $X^1$ is an optionally substituted naphthyl. In certain cases. $X^1$ is phenol. In some cases. $X^1$ is phenyl. In certain cases. $X^1$ is aralkyl or substituted aralkyl. In certain cases, $X^1$ is an aralkyl including one or more aryl groups. In certain cases, the aralkyl includes a $C_1$-$C_{10}$ alkyl chain including one or more optionally substituted phenyl groups. In certain cases, $X^1$ is a $C_1$-$C_{10}$ alkyl chain including at least two optionally substituted phenyl groups. In certain cases, the alkyl chain terminates in at least two optionally substituted phenyl groups. In certain cases, the phenyl groups are unsubstituted. In certain cases the phenyl group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases $X^1$ is a $C_1$-$C_6$ alkyl chain substituted with two optionally substituted phenyl groups. In certain cases, the alkyl chain terminates in the two optionally substituted phenyl groups.

In certain embodiments of a compound of formula (I). $X^1$ is alkyl or substituted alkyl. In certain cases $X^2$ is $C_1$-$C_6$ alkyl. In certain cases, $X^2$ is methyl. In certain cases, $X^2$ is a $C_1$-$C_6$ alkyl group substituted by one or more groups. In certain cases the alkyl group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases, the alkyl group is substituted with a guanidine group. In certain cases, $X^2$ is aryl or substituted aryl. In certain cases $X^2$ is selected from heterocycle, substituted heterocycle, heteroaryl, and substituted heteroaryl. In certain cases, $X^2$ is an optionally substituted carbazole. In certain cases, $X^2$ is an optionally substituted naphthyl. In certain cases, $X^2$ is phenol. In some cases, $X^2$ is phenyl. In certain cases. $X^2$ is amino or substituted amino. In certain cases, $X^2$ is an amino group substituted by one or more aryl groups. In certain cases, the amino group is substituted by one or more optionally substituted phenyl groups. In certain cases, $X^2$ is an amino group substituted by one on more phenol groups.

In certain embodiments of a compound of formula (I). $X^3$ is alkyl or substituted alkyl. In certain cases, $X^3$ is aryl or substituted aryl. In certain cases, $X^3$ is selected from heterocycle, substituted heterocycle, heteroaryl, and substituted heteroaryl. In certain cases, $X^3$ is aryl heterocycle or substituted aryl heterocycle. In certain cases, $X^3$ is an optionally substituted carbazole. In certain cases, $X^3$ is an optionally substituted naphthyl. In certain cases, $X^3$ is phenol. In some cases, $X^3$ is phenyl. In certain cases the $X^3$ group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases $X^3$ is a carbazole substituted with one or two hydroxyl groups. In certain cases, $X^3$ is an unsubstituted carbazole. In certain cases $X^3$ is a naphthyl substituted with one or two hydroxyl groups. In certain cases, $X^3$ is an unsubstituted naphthyl.

In certain embodiments of a compound of formula (I), n is an integer less than 10, such as 9 or less, 8 or less, 7 or less, 6 or less, 5 or less, 4 or less, 3 or less, or even less. In some instances, n is an integer from 1 to 6, such as 1-3 or 1-2. In certain cases, n is 1.

In some embodiments, the compound of formula (I), is described by the formula (Ia):

(Ia)

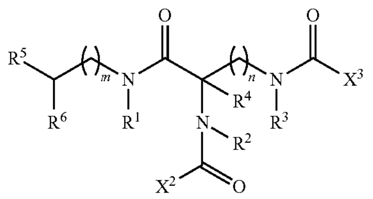

wherein:

$R^1$-$R^4$ are each independently selected from hydrogen, and alkyl;

$R^5$-$R^6$ are each independently selected from aryl and substituted aryl;

$X^2$ is selected from alkyl, substituted alkyl, and $NR^{2a}R^{2b}$, where $R^{2a}$ and $R^{2b}$ are independently selected from hydrogen, aryl, and substituted aryl;

$X^3$ is selected from aryl, substituted aryl, naphthyl, substituted naphthyl, carbazole, and substituted carbazole;

n is an integer from 1 to 6; and m is an integer from 1 to 6.

In certain embodiments of formula (I) or (Ia). $R^1$-$R^4$ are each hydrogen. In certain cases, at least one of $R^1$-$R^4$ is alkyl. In certain cases. $R^1$ is alkyl and each of $R^1$-$R^3$ is hydrogen. In certain cases. $R^2$ is alkyl and each of $R^1$, $R^3$ and $R^4$ are hydrogen. In certain cases, $R^3$ is alkyl, and each of $R^1$, $R^2$ and $R^4$ are hydrogen. In certain cases, $R^4$ is alkyl, and each of $R^1$-$R^3$ are hydrogen. In certain cases, $R^1$-$R^2$ are alkyl and $R^3$-$R^4$ are hydrogen. In certain cases, $R^1$ and $R^3$ are alkyl and $R^2$ and $R^4$ are hydrogen. In certain cases. $R^2R^3$ are alkyl and $R^1$ and $R^4$ are hydrogen. In certain cases, $R^3$-$R^4$ are alkyl and $R^1$-$R^2$ are hydrogen. In certain cases, $R^1$ is hydrogen and each of $R^1$-$R^3$ is alkyl. In certain cases, $R^2$ is hydrogen and each of $R^1$, $R^3$ and $R^4$ are alkyl. In certain cases, $R^3$ is hydrogen, and each of $R^1$, $R^2$ and $R^4$ are alkyl. In certain cases. $R^4$ is hydrogen, and each of $R^1$-$R^3$ are alkyl. In certain cases, $R^1$-$R^4$ are each alkyl. In certain cases, where at least one of $R^1$-$R^4$ is alkyl, the alkyl is $C_1$-$C_6$ alkyl (e.g., methyl, ethyl, propyl, butyl, pentyl, or hexyl). In certain cases, where at least one of $R^1$-$R^4$ is alkyl, the alkyl is methyl. In certain cases, where $R^4$ is alkyl, the compound is enantiomerically pure, and carbon to which $R^4$ is attached is of R-configuration. In certain cases, where $R^4$ is alkyl, the compound is enantiomerically pure, and the carbon to which $R^4$ is attached is of S-configuration. In certain cases, where $R^4$ is alkyl, the compound is a racemic mixture.

In certain embodiments of formula (Ia), each of $R^1$ and $R^6$ are aryl. In certain cases each of $R^5$ and $R^6$ are phenyl. In certain cases, at least one of $R^5$ or $R^e$ is substituted aryl. In certain cases at least one of $R^5$ or $R^6$ is an aryl group substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases, both $R^1$ and $R^6$ are substituted aryl. In certain cases, both $R^5$ and $R^6$ are substituted phenyl. In some cases, both $R^1$ and $R^6$ are phenol.

In certain embodiments of a compound of formula (Ia), m is an integer less than 6, such as 5 or less, 4 or less, 3 or less, or even less. In some instances, n is an integer from 1 to 4, such as 1-3 or 1-2. In certain cases, n is 1.

In certain embodiments of formula (Ia), $X^2$ is alkyl or substituted alkyl. In certain cases $X^2$ is $C_1$-$C_6$ alkyl. In certain cases, $X^2$ is methyl. In certain cases, $X^2$ is a $C_1$-$C_6$ alkyl group substituted by one or more groups. In certain cases the alkyl group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases, the alkyl group is substituted with a guanidine group. In certain cases, $X^2$ is $NR^{2a}R^{2b}$, where $R^{2a}$ and $R^{2b}$are independently selected from hydrogen, aryl, and substituted aryl. In certain cases both of $R^{2a}$ and $R^{2b}$ are hydrogen. In certain cases, both of $R^{2a}$ and $R^{2b}$ are aryl or substituted aryl. In certain cases. $R^{2a}$ is an optionally substituted aryl group and $R^{2b}$ is H. In certain cases the aryl group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases. $R^{2a}$ phenyl and $R^{2b}$ is H. In certain cases, $R^{2a}$ is phenol and $R^{2b}$ is H.

In certain embodiments of a compound of formula (Ia), $X^3$ is aryl or substituted aryl. In certain cases, $X^3$ is an optionally substituted carbazole. In certain cases, $X^3$ is an optionally substituted naphthyl. In certain cases, $X^3$ is phenol. In some cases, $X^3$ is phenyl. In certain cases the $X^3$ group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases $X^3$ is a carbazole substituted with one or two hydroxyl groups. In certain cases, $X^3$ is an unsubstituted carbazole. In certain cases $X^3$ is a naphthyl substituted with one or two hydroxyl groups. In certain cases, $X^3$ is an unsubstituted naphthyl.

In certain embodiments of a compound of formula (Ia), n is an integer less than 6, such as 5 or less, 4 or less, 3 or less, or even less. In some instances, n is an integer from 1 to 4, such as 1-3 or 1-2. In certain cases, n is 1.

In certain embodiments, the small molecule active agent is a compound selected from the group consisting of:

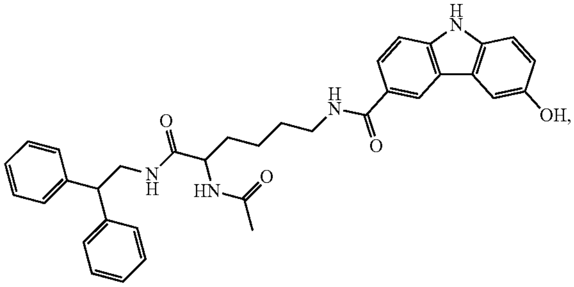
,

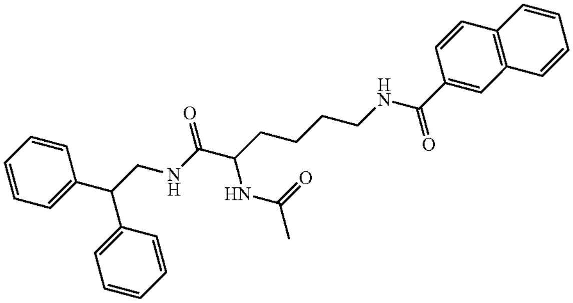

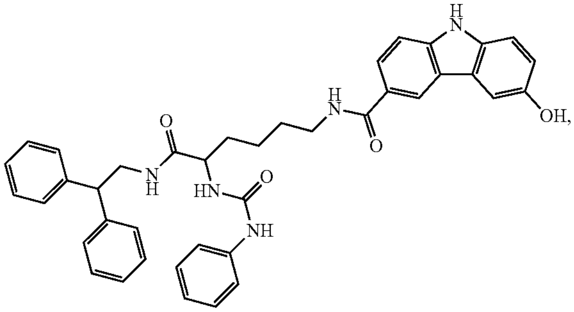
,

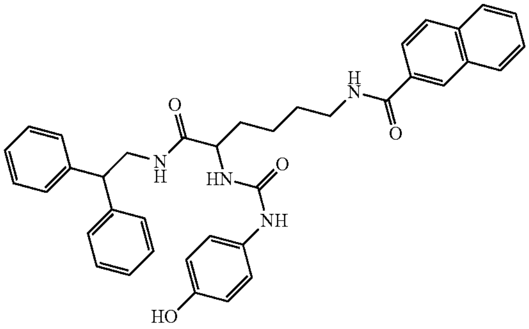
, and

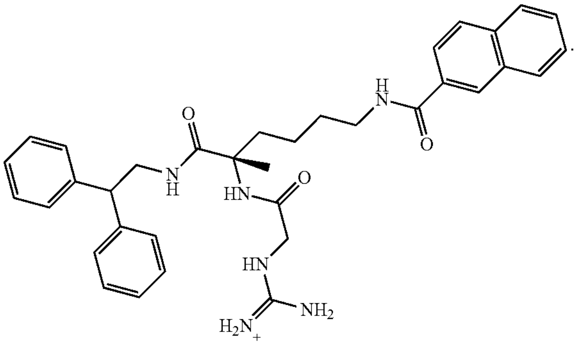
.

In certain other embodiments, the small molecule active agent is described by the formula (II):

(II)

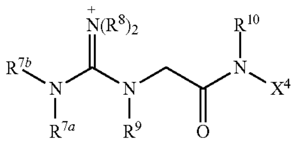

wherein:

$R^{7a}$, $R^{7b}$, $R^8$, $R^9$ and $R^{10}$ are each independently selected from hydrogen, alkyl and substituted alkyl; and $X^4$ is selected from alkyl, aryl, aralkyl, heterocycle, and heteroaryl, acyl, wherein $X^4$ is optionally further substituted with one or more groups selected from, alkyl, substituted alkyl, aryl, substituted aryl, amino, substituted amino, carboxamide, substituted carboxamide, heterocycle, substituted heterocycle, and a second compound of formula (II)

or a pharmaceutically acceptable salt or solvate thereof.

In certain embodiments of a compound of formula (II), $X^4$ is optionally substituted alkyl. In certain cases, $X^4$ is optionally substituted aryl. In certain cases $X^4$ is selected from heterocycle, and heteroaryl, wherein either are optionally substituted. In certain cases, $X^4$ is an optionally substituted aralkyl. In certain cases, $X^4$ is an optionally substituted acyl. In certain cases. $X^4$ is aralkyl or alkyl including one or more aryl groups. In certain cases, $X^4$ is an aralkyl includes a $C_1$-$C_{20}$ alkyl chain including one or more optionally substituted phenyl groups. In certain cases, $X^4$ is a $C_1$-$C_{20}$ alkyl chain including at least two optionally substituted phenyl groups. In certain cases, $X^4$ is an alkyl chain that attaches to the N atom at a central point and terminates at each end of the alkyl chain in at least two optionally substituted phenyl groups. In certain cases, the phenyl groups are unsubstituted. In certain cases the phenyl group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases $X^4$ is a $C_1$-$C_{20}$ alkyl chain substituted with two optionally substituted carboxamide groups. In certain cases, the alkyl chain attaches to the N atom at a central point and terminates at each end of the alkyl chain in the two optionally substituted carboxamide groups. In certain cases, the carboxamide groups are substituted with an aryl group. In certain cases, $X^4$ is a $C_1$-$C_{20}$ alkyl chain substituted with two optionally substituted acyl groups. In certain cases, the alkyl chain attaches to the N atom at a central point and terminates at each end of the alkyl chain in the two optionally substituted acyl groups. In certain cases, the acyl groups are substituted with an aryl group. In certain cases, $X^4$ is a $C_1$-$C_{20}$ alkyl chain substituted with at least one additional compound of formula (II). In some cases, the $C_{1-20}$ alkyl chain is further substituted with optionally substituted aryl groups. In some cases. $X^4$ is an optionally substituted acyl group. In some cases, the acyl group is substituted with a substituent that includes at least one additional compound of formula II). In some instances the acyl group is substituted with a substituent including a heterocyclic group.

In certain embodiments of the compound of formula (II), $X^4$ comprises a chelating group. In certain cases, the chelating group is a heterocyclic compound capable of coordinating a metal (e.g., iron) via at least two heteroatoms in the chelator. In certain cases the chelating group may be selected from any of 1,4,7,10-tetraazacyclododecane-1,4,7,10-tetraacetic acid (DOTA), triethylenetetramine (TETA), 1,4,7-triazacyclononane-1,4,7-triacetic acid (NOTA), 1,4,7-triazacyclononane-1,4-diacetic acid (NODA), (tert-Butyl)$_2$NODA, NETA, C-NETA, L-NETA, S-NETA, NODA-MPAA, and NODA-MPAEM. In certain cases. $X^4$ includes a chelator derived by 1,4,7,10-tetraazacyclododecane-1,4,7,10-tetraacetic acid (also known as DOTA, or tetraxetan) and can be attached to the compound of formula (II) via adaption of one of the pending acetic acid groups. In certain cases, $X^4$ includes a chelator derived from DOTA and is attached to 1, 2, 3 or 4 compounds of formula (II) via adaption of the pending acetic acid groups.

In certain embodiments, the compound of formula (II) is described by the formula (IIa):

(IIa)

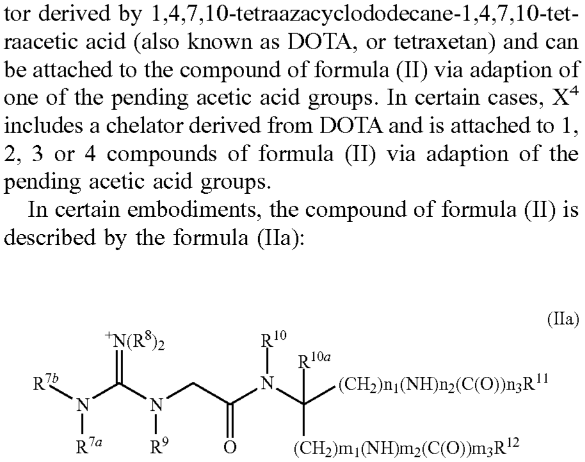

wherein:

$R^{7a}$, $R^{7b}$, $R^8$, $R^9$, $R^{10}$ and $R^{10a}$ are each independently selected from hydrogen, and alkyl;

$R^{11}$ and $R^{12}$ are each independently selected from aryl, substituted aryl, heteroaryl, substituted heteroaryl, naphthyl, substituted naphthyl, carbazole, and substituted carbazole;

$n_1$ and $m_1$ are each independently an integer from 1 to 10;

$n_2$ and $m_2$ are each independently 0 or 1; and $n_3$ and $m_3$ are each independently 0 or 1.

In certain embodiments of the compound of formula (II) or (IIa), $R^{7a}$, $R^{7b}$, $R^8$, $R^9$, $R^{10}$ and $R^{10a}$ are each hydrogen. In certain cases, at least one of $R^{7a}$, $R^{7b}$, $R^8$, $R^9$, $R^{10}$ and $R^{11}$ is alkyl. In certain cases, $R^{10}$ is alkyl and each of $R^{7a}$, $R^{7b}$, $R^8$, $R^9$ and $R^{10a}$ are hydrogen. In certain cases, $R^9$ is alkyl and each of $R^{7a}$, $R^{7b}$, $R^8$, $R^{10}$ and $R^{10a}$ are hydrogen. In certain cases. $R^{7a}$ is alkyl, and each of $R^9$, $R^{7b}$, $R^8$, $R^{10}$ and $R^{10a}$ are hydrogen. In certain cases, at least one of $R^8$ is alkyl, and each of $R^{7a}$, $R^{7b}$, $R^9$, $R^{10}$ and $R^{10a}$ are hydrogen. In certain cases, at least one of $R^{10a}$ is alkyl, and each of $R^{7a}$, $R^{7b}$, $R^9$, $R^{10}$ and $R^8$ are hydrogen. In certain cases, where at least one of $R^{7a}$, $R^{7b}$, $R^8$, $R^9$, $R^{10}$ and $R^{10a}$ is alkyl, the alkyl is methyl. In certain cases, where $R^{10a}$ is alkyl, the compound is enantiomerically pure, and carbon to which $R^{10a}$ is attached is of R-configuration. In certain cases, where $R^{10a}$ is alkyl, the compound is enantiomerically pure, and the carbon to which $R^{10a}$ is attached is of S-configuration. In certain cases, where $R^{10a}$ is alkyl, the compound is a racemic mixture.

In certain embodiments of the compound of formula (IIa), $n_1$ and $m_1$ are each independently at integer from 1 to 8, such as 1-7, 1-6 or 1-5. In some cases each of n, and m, are 10 or less, such as 9, 8, 7, 6, 5, 4, or less. In some cases each of $n_1$ and $m_1$ are 4-8, such as 5-7, such as 5-6. In some cases, $n_1$ and $m_1$ are both 5. In certain cases of formula (IIa), $n_2$ and $m_2$ are each 0. In some cases, at least one of $n_2$ and $m_2$ is 1. In some cases, each of $n_2$ and $m_2$ are 1. In some cases of formula (IIa), $n_3$ and $m_3$ are each 0. In some cases, at least one of $n_3$ and $m_3$ is 1. In some cases each of $n_3$ and $m_3$ are 1. In some cases, each of $n_1$ and $m_1$ is an integer from 1 to 10, each of $n_2$ and $m_2$ is 0; and each of $n_3$ and $m_3$ is 0. In some cases, each of $n_1$ and $m_1$ is an integer from 1 to 10, each of $n_2$ and $m_2$ is 1; and each of $n_3$ and $m_3$ is 0. In some cases, each of $n_1$ and $m_1$ is an integer from 1 to 10, each of $n_2$ and $m_2$ is 0; and each of $n_3$ and $m_3$ is 1. In some cases, each of n, and m, is an integer from 1 to 10, each of $n_2$ and $m_2$ is 1; and each of $n_3$ and $m_3$ is 1.

In certain embodiments of the compound formula (IIa). $R^{11}$ and $R^{12}$are each independently selected from aryl, or substituted aryl, In certain cases, $R^{11}$ and $R^{12}$ are each independently selected from heteroaryl, and substituted heteroaryl. In certain cases, at least one of $R^{11}$ and $R^{12}$ is an optionally substituted carbazole. In certain cases, at least one of $R^{11}$ and $R^{12}$ is an optionally substituted naphthyl. In certain cases, at least one of $R^{11}$ and $R^{12}$ is phenol. In some cases, at least one of $R^{11}$ and $R^{12}$ is phenyl. In some cases, each of $R^{11}$ and $R^{12}$ are phenyl. In certain cases $R^{11}$ and $R^{12}$ are each independently substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases at least one of $R^{11}$ and $R^{12}$ is a carbazole substituted with one or two hydroxyl groups. In certain cases, at least one of $R^{11}$ and $R^{12}$ is an unsubstituted carbazole. In certain cases at least one of $R^{11}$ and $R^{12}$ is a naphthyl substituted with one or two hydroxyl groups. In certain cases, at least one of $R^{11}$ and $R^{12}$ is an unsubstituted naphthyl.

In certain embodiments, the small molecule active agent is a compound selected from the group consisting of:

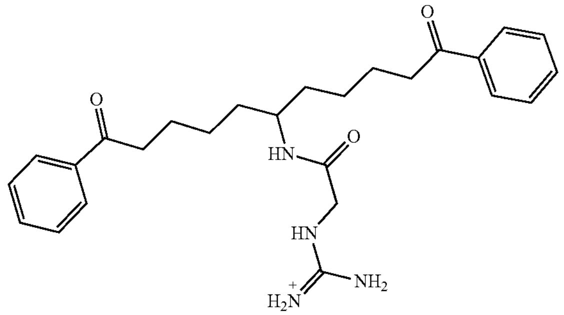

,

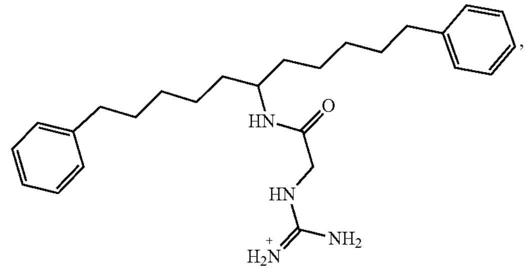

, and

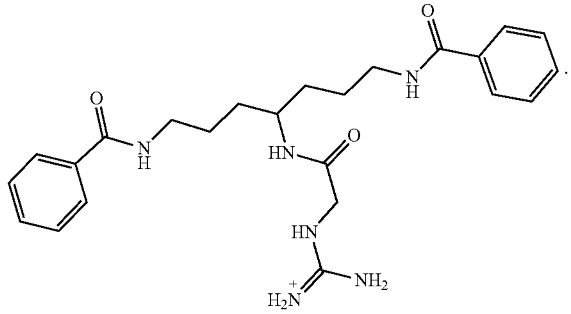

.

In certain embodiments, the small molecule active agent is a compound selected from the group consisting of:

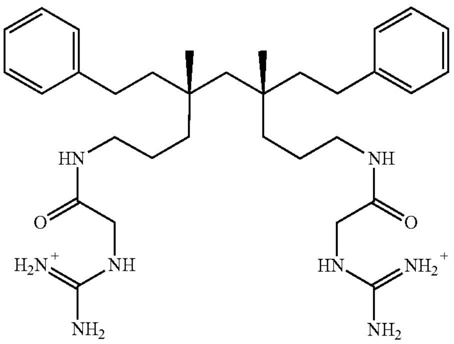

, and

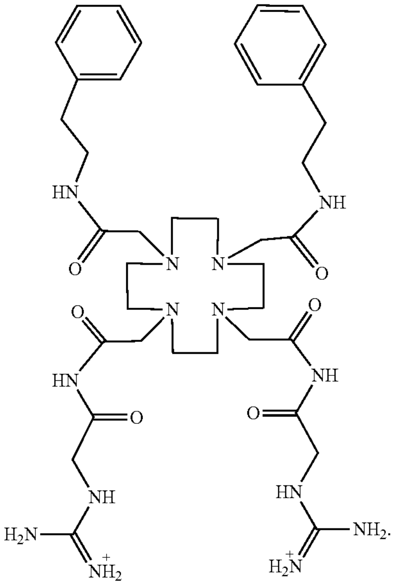

.

In certain other embodiments, the small molecule active agent is described by the formula (III):

(III)

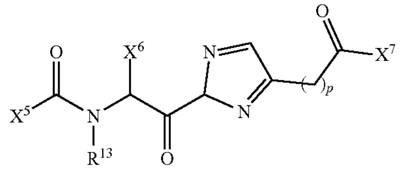

In certain embodiments of the compound of formula (III), $R^{13}$ is hydrogen. In other instances, $R^{13}$ is alkyl or substituted alkyl, such as $C_1$-$C_6$ alkyl. In some instances, $R^{13}$ is methyl.

In certain embodiments of a compound of formula (III), $X^5$ is alkyl or substituted alkyl. In certain cases, $X^5$ is aryl or substituted aryl. In certain cases, $X^5$ is selected from heterocycle, substituted heterocycle, heteroaryl, and substituted heteroaryl. In certain cases. $X^5$ is an optionally substituted carbazole. In certain cases, X is an optionally substituted naphthyl. In certain cases, X is phenol. In some cases, $X^5$ is phenyl. In certain cases. $X^5$ is amino or substituted amino. In certain cases, $X^5$ is an amino group substituted by one or more aryl groups. In certain cases, the amino group is substituted by one or more optionally substituted phenyl groups. In certain cases, $X^5$ is an amino group substituted by one on more phenol groups. In certain cases the $X^5$ group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro.

In certain embodiments of a compound of formula (III), $X^6$ is alkyl or substituted alkyl. In certain cases $X^6$ is $C_1$-$C_6$ alkyl. In certain cases. $X^6$ is methyl. In certain cases. $X^6$ is a $C_1$-$C_6$ alkyl group substituted by one or more groups. In certain cases the alkyl group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases, the alkyl group is substituted with a guanidine group. In certain cases, $X^6$ is aryl or substituted aryl. In certain cases $X^6$ is selected from heterocycle, substituted heterocycle, heteroaryl, and substituted heteroaryl. In certain cases, $X^6$ is an optionally substituted carbazole. In certain cases. $X^6$ is an optionally substituted naphthyl. In certain cases, $X^6$ is phenol. In some cases, $X^6$ is phenyl. In certain cases, $X^6$ is aralkyl or substituted aralkyl. In certain cases. $X^6$ is an aralkyl including one or more aryl groups. In certain cases, the aralkyl includes a $C_1$-$C_{10}$ alkyl chain including one or more optionally substituted phenyl groups. In certain cases, $X^6$ is a $C_1$-$C_{10}$ alkyl chain including at least one optionally substituted phenyl groups. In certain cases, the alkyl chain terminates in at least one optionally substituted phenyl groups. In certain cases, the phenyl group is unsubstituted. In certain cases the phenyl group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro.

In certain embodiments of a compound of formula (I). $X^7$ is alkyl or substituted alkyl. In certain cases, $X^7$ is aryl or substituted aryl. In certain cases, $X^7$ is selected from heterocycle, substituted heterocycle, heteroaryl, and substituted heteroaryl. In certain cases, $X^7$ is aryl heterocycle or substituted aryl heterocycle. In certain cases, $X^7$ is an optionally substituted carbazole. In certain cases, $X^7$ is an optionally substituted naphthyl. In certain cases, $X^7$ is phenol. In some cases. $X^7$ is phenyl. In certain cases the $X^7$ group is substituted with one or more groups selected from hydroxyl, amino, carboxamide, guanidine, acyl, halogen, alkyl, substituted alkyl, aryl, substituted aryl, heterocycle, substituted heterocycle, heteroaryl, substituted heteroaryl, nitrile and nitro. In certain cases $X^7$ is a carbazole substituted with one or two hydroxyl groups. In certain cases, $X^7$ is an unsubstituted carbazole. In certain cases $X^7$ is a naphthyl substituted with one or two hydroxyl groups. In certain cases, $X^7$ is an unsubstituted naphthyl.

In certain embodiments of a compound of formula (III), p is an integer less than 10, such as 9 or less, 8 or less, 7 or less, 6 or less, 5 or less, 4 or less, 3 or less, or even less. In some instances, p is an integer from 1 to 6, such as 1-3 or 1-2. In certain cases, p is 1.

In certain embodiments, the small molecule active agent is the following compound:

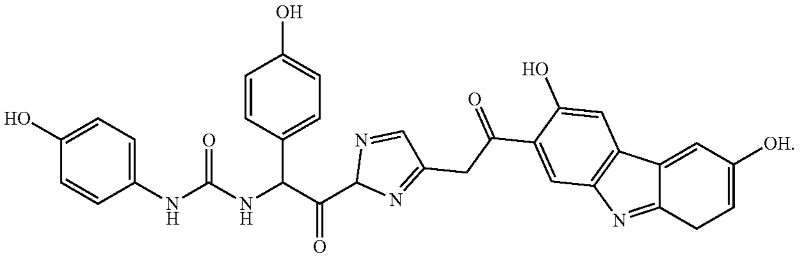 [SMILES: O=C(Nc1ccc(O)cc1)NC(C(=O)C1N=CC(CC(=O)c2cc3c(cc2O)C2=CC(O)=CCC2=N3)=N1)c1ccc(O)cc1]

It is understood that any of the compounds disclosed herein may be present in a salt form. In some cases, the salt form of the compound is a pharmaceutically acceptable salt. It is understood that any of the compounds disclosed herein may be present in a prodrug form.

Aspects of the present disclosure include small molecule active agents (e.g., as described herein), salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject small molecule active agent, or a prodrug form thereof, are provided in the form of pharmaceutically acceptable salts. Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)). In some cases, the promoiety is attached to a hydroxy group of the subject compounds. In certain cases, the promoiety is an acyl or substituted acyl group. In certain cases, the promoiety is an alkyl or substituted alkyl group, e.g., that forms an ester functional group when attached to a hydroxyl functional group of the subject compounds.

In some embodiments, the subject small molecule active agents, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

In some embodiments, the small molecule active agents are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

In some embodiments, the subject compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more.

Specific Binding Member

In certain embodiments of the present disclosure the CD206-binding agent is a specific binding member. The term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10\times10^{-9}$ M or less, such as $1\times10^{-9}$ M or less, $3\times10^{-10}$ M or less, $1\times10^{-10}$ M or less, $3\times10^{-11}$ M or less, $1\times10^{-11}$ M or less, $3\times10^{-12}$ M or less or $1\times10^{-12}$ M or less.

In some embodiments, the specific binding member is proteinaceous (e.g., composed of amino acid residues). In certain cases, the proteinaceous specific binding member is an antibody. In certain embodiments, the proteinaceous specific binding member is an antibody fragment, e.g., a binding fragment of an antibody that specific binds to a an activity modulating domain of CD206. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (I), and heavy chain genetic Ioci, which together comprise the myriad variable region genes, and the constant region genes mu (u), delta (d), gamma (g), sigma (e), and alpha (a) which encode the IgM, IgD, IgG. IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term antibody is meant to include full length antibodies and may refer to a natural antibody from any organism, an engineered antibody, or an antibody generated recombinantly for experimental, therapeutic, or other purposes as further defined herein. Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is an antibody. In certain embodiments, the specific binding member is a Fab fragment, a $F(ab')_2$ fragment, a scFv, a diabody or a triabody. In some cases, the specific binding member is a murine antibody or binding fragment thereof. In certain instances, the specific binding member is a recombinant antibody or binding fragment thereof.

In certain embodiments the specific binding member is an antibody, or a binding fragment thereof, that targets a sequence of CD206. In certain cases, the specific binding member targets a sequence of CD206 selected from the group consisting of NFGDLVSIQSESEKK, NDAQSAYFIGLLISL, SKEKETMDNARAF, and EDENCVTMYSNSGFWN. In some cases, the antibody or fragment thereof, targets a NFGDLVSIQSESEKK sequence of CD206. In some cases, the antibody, or binding fragment thereof, targets a NDAQSAYFIGLLISL sequence of CD206. In some cases, the antibody, or binding fragment thereof, targets a SKEKETMDNARAF sequence of CD206. In some cases, the antibody, or binding fragment thereof targets a EDENCVTMYSNSGFWN sequence of CD206.

Antibodies that can bind to an activity modulating domain of CD206 in connection with the present disclosure can encompass, but are not limited to, monoclonal antibodies, polyclonal antibodies, bispecific antibodies, Fab antibody fragments, $F(ab)_2$ antibody fragments, Fv antibody fragments (e.g., $V_H$ or $V_L$), single chain Fv antibody fragments and dsFv antibody fragments. Furthermore, the antibody molecules can be fully human antibodies, humanized antibodies, or chimeric antibodies. The antibodies that can be used in connection with the present disclosure can include any antibody variable region, mature or unprocessed, linked to any immunoglobulin constant region. Minor variations in the amino acid sequences of antibodies or immunoglobulin molecules are encompassed by the present disclosure, providing that the variations in the amino acid sequence maintain 75% or more, e.g., 80% or more, 90% or more, 95% or more, or 99% or more of the sequence.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes). e.g., IgG1, IgG2, IgG3. IgG4. IgA, and IgA2.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Antibodies that can be used in connection with the present disclosure thus can encompass monoclonal antibodies, polyclonal antibodies, bispecific antibodies, Fab antibody fragments, F(ab)2 antibody fragments, Fv antibody fragments (e.g., VH or VL), single chain Fv antibody fragments and dsFv antibody fragments. Furthermore, the antibody molecules can be fully human antibodies, humanized antibodies, or chimeric antibodies. In some embodiments, the antibody molecules are monoclonal, fully human antibodies.

The antibodies that can be used in connection with the present disclosure can include any antibody variable region, mature or unprocessed, linked to any immunoglobulin constant region. If a light chain variable region is linked to a constant region, it can be a kappa chain constant region. If a heavy chain variable region is linked to a constant region, it can be a human gamma 1, gamma 2, gamma 3 or gamma 4 constant region, more preferably, gamma 1, gamma 2 or gamma 4 and even more preferably gamma 1 or gamma 4.

Minor variations in the amino acid sequences of antibodies or immunoglobulin molecules are encompassed by the present invention, providing that the variations in the amino acid sequence maintain at least 75%, e.g., at least 80%, 90%, 95%, or 99% of the sequence. In particular, conservative amino acid replacements are contemplated (e.g., as described herein). Whether an amino acid change results in a functional peptide can readily be determined by assaying the specific activity of the polypeptide derivative. Fragments (or analogs) of antibodies or immunoglobulin molecules, can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Sequence motifs and structural conformations can be used to define structural and functional domains in accordance with the invention.

Non-limiting examples of antibodies which may find use in the present disclosure include Adecatumumab, Ascrinvacumab, Cixutumumab, Conatumumab. Daratumumab, Drozitumab, Duligotumab, Durvalumab, Dusigitumab, Enfortumab, Enoticumab, Figitumumab, Ganitumab, Glembatumumab, Intetumumab, Ipilimumab, Iratumumab. Icrucumab, Lexatumumab, Lucatumumab, Mapatumumab, Narnatumab, Necitumumab, Nesvacumab, Ofatumumab, Olaratumab, Panitumumab, Patritumab, Pritumumab, Radretumab, Ramucirumab, Rilotumumab. Robatumumab, Seribantumab, Tarextumab, Teprotumumab, Tovetumab, Vantictumab, Vesencumab, Votumumab, Zalutumumab, Flanvotumab, Altumomab, Anatumomab, Arcitumomab. Bectumomab, Blinatumomab, Detumomab, Ibritumomab. Minretumomab, Mitumomab, Moxetumomab, Naptumomab, Nofetumomab, Pemtumomab, Pintumomab, Racotumomab, Satumomab, Solitomab, Taplitumomab, Tenatumomab, Tositumomab, Tremelimumab. Abagovomab, Igovomab, Oregovomab, Capromab, Edrecolomab, Nacolomab. Amatuximab, Bavituximab, Brentuximab, Cetuximab, Derlotuximab, Dinutuximab, Ensituximab, Futuximab, Girentuximab. Indatuximab, Isatuximab. Margetuximab, Rituximab, Siltuximab, Ublituximab, Ecromeximab, Abituzumab, Alemtuzumab, Bevacizumab, Bivatuzumab, Brontictuzumab, Cantuzumab, Cantuzumab, Citatuzumab. Clivatuzumab. Dacetuzumab, Demcizumab, Dalotuzumab, Denintuzumab, Elotuzumab, Emactuzumab, Emibetuzumab, Enoblituzumab, Etaracizumab, Farletuzumab, Ficlatuzumab, Gemtuzumab, Imgatuzumab, Inotuzumab, Labetuzumab. Lifastuzumab, Lintuzumab, Lorvotuzumab, Lumretuzumab, Matuzumab, Milatuzumab, Nimotuzumab, Obinutuzumab, Ocaratuzumab. Otlertuzumab, Onartuzumab, Oportuzumab, Parsatuzumab, Pertuzumab, Pinatuzumab, Polatuzumab, Sibrotuzumab, Simtuzumab, Tacatuzumab, Tigatuzumab, Trastuzumab, Tucotuzumab, Vandortuzumab, Vanucizumab. Veltuzumab. Vorsetuzumab, Sofituzumab, Catumaxomab, Ertumaxomab. Depatuxizumab. Ontuxizumab, Blontuvetmab, Tamtuvetmab, or an antigen-binding variant thereof. As used herein, the term "variant" refers to an antibody that binds to a particular cognate antigen but has fewer or more amino acids than the parental antibody, has one or more amino acid substitutions relative to the parental antibody, is a single-chain variant (such as an scFv variant) of the parental antibody, or any combination thereof.

In certain embodiments, the specific binding member is an aptamer, a nucleic acid (e.g., a DNA, a RNA, or a nucleic acid analog).

In certain embodiments the specific binding member is an aptamer or a nucleic acid (e.g., a DNA, a RNA, or a nucleic acid analog), that targets a sequence of CD206. In certain cases, the specific binding member targets a sequence of CD206 selected from the group consisting of NFGDLVSIQSESEKK, NDAQSAYFIGLLISL, SKEKETMDNARAF, and EDENCVTMYSNSGFWN. In some cases, the an aptamer or a nucleic acid (e.g., a DNA, a RNA, or a nucleic acid analog), targets a NFGDLVSIQSESEKK sequence of CD206. In some cases, the an aptamer or a nucleic acid (e.g., a DNA, a RNA, or a nucleic acid analog), targets a NDAQSAYFIGLLISL sequence of CD206. In some cases, the an aptamer or a nucleic acid (e.g., a DNA, a RNA, or a nucleic acid analog), targets a SKEKETMDNARAF sequence of CD206. In some cases, the an aptamer or a nucleic acid (e.g., a DNA, a RNA, or a nucleic acid analog) targets a EDENCVTMYSNSGFWN sequence of CD206.

Conjugate Compounds

In certain embodiments of the present disclosure, the CD206-binding agent is conjugated to one or more other active agent compounds (such as for example one or more active agents described above for combination therapy). In some instances, the CD206-binding agent may be conjugated to two or more other active agent compounds, such as 3 or more and including 5 or more. The CD206-binding agent may be conjugated to the one or more active agents such as by hydrogen bonding or ionic interactions. In other embodiments, the CD206-binding agent is conjugated to the one or more active agents with one or more covalent bonds. The CD206-binding agent may be directly bonded to the active agent or may be bonded to the active agent through one or more linkers, where in certain instances, the CD206-binding agent and the active agent are bonded by linking chemistry that includes but is not limited to, maleimide/thiol, succimidylester (NHS ester)/amine, azide chemistry, carboxy/EDC (1-Ethyl-3-[3-dimethylaminopropyl]carbodiimide Hydrochloride)/amine, amine/Sulfo-SMCC (Sulfosuccinimidyl 4-[N-maleimidomethyl]cyclohexane-1-carboxylate)/thiol, and amine/BMPH (N-[β-Maleimidopropionic acid]hydrazide•TFA)/thiol.

Screening Methods

Aspects of the present disclosure also include assays configured to identify agents that find use in methods of the invention, e.g., as reviewed above. Aspects of the present disclosure include methods for identifying a candidate agent for the ability to bind to an activity modulating domain of CD206. In some instances, the method comprises: contacting a macrophage comprising CD206 with a compound; and determining if the compound binds to an activity modulating domain of CD206. In some cases, the method further includes determining the activity modulating domain of CD206 that binds to the compound. By assessing or determining is meant at least predicting that a given test compound will have a desirable binding, such that further testing of the compound in additional assays, such as animal model and/or clinical assays, may be desired.

In certain cases, the macrophage is a macrophage comprising one or more mutations in the activity modulating domains of CD206. In certain cases, the activity modulating domain of CD206 is selected from fibronectin II domain of CD206, C-type lectin carbohydrate recognition domain 3 (CRD3) of CD206, C-type lectin carbohydrate recognition domain 4 (CRD4) of CD206 and C-type lectin carbohydrate recognition domain 5 (CRD5) of CD206. In certain cases, the compound binds to the CRD5 activity modulating domain of CD206. In some cases, the compound binds to the fibronectin II activity modulating domain of CD206. In some cases, the compound binds to the CRD3 activity modulating domain of CD206.

The candidate compound can be: an immunomodulatory peptide, a small molecule, or a specific binding member (e.g., an antibody) as described herein. In some instances, the determining step comprises detecting a cellular parameter, wherein a change in the parameter in the cell as compared to in a cell not contacted with candidate compound indicates that the candidate compound specifically binds the activity modulating domain of CD206.

Compound screening may be performed using an in vitro model, a genetically altered cell a microorganism, or purified CD206 protein. One can identify ligands that compete with, modulate or mimic the action of a lead agent. Screening identifies compounds that bind to particular domains of a CD206 motif. A wide variety of assays may be used for this purpose, including labeled in vitro binding assays, electrophoretic mobility shift assays, immunoassays for protein binding, and the like. Knowledge of the 3-dimensional structure of CD206, and experimental data provided herein, can also lead to the rational design of compounds that specifically bind to an activity modulating domain of CD206.

The term "compound" as used herein describes any molecule, e.g., immunomodulatory peptide, small molecule, specific binding member (e.g., antibody or fragment thereof), with the capability of binding an activity modulating domain of CD206. Generally, a plurality of assay mixtures are run in parallel with different agent concentrations to obtain a differential response to the various concentrations. Typically one of these concentrations serves as a negative control, i.e., at zero concentration or below the level of detection.

Candidate compounds encompass numerous chemical classes, such as oligonucleotides, antibodies, peptides, polypeptides, and organic molecules, e.g., small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate small molecule compounds often comprise cyclical carbon or heterocyclic structures and/or aromatic or polyaromatic structures substituted with one or more of the above functional groups. Candidate compounds are also found among biomolecules including peptides, saccharides, fatty acids, steroids, purines, pyrimidines, derivatives, structural analogs or combinations thereof.

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Of interest in certain embodiments are compounds that pass the blood-brain barrier.

Where the screening assay is a binding assay, one or more of the molecules may be joined to a member of a signal producing system, e.g., a label, where the label can directly or indirectly provide a detectable signal. Various labels include, but are not limited to: radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. In some cases, between 1 and 48 hours will be sufficient.

In some embodiments, the screening step is performed at about 1 to about 1000 micromolar concentration of the compounds, such as about 10 to about 500 micromolar or about 10 to about 100 micromolar concentration. In some cases, a dose response curve is assessed for each of the compounds. In certain cases, the compounds are assessed for binding at a single concentration.

Compositions

In embodiments, compositions for use in treating a subject according to the present disclosure can be formulated according to any of the conventional methods known in the art and widely described in the literature. Thus, the active ingredient (e.g., CD206-binding agent as described herein) may be incorporated, optionally together with other active substances, with one or more conventional pharmaceutically acceptable carriers, diluents and/or excipients, etc., appropriate for the particular use of the composition, to produce conventional preparations that are suitable or can be made suitable for administration. They may be formulated as liquids, as semi-solids or solids, liquid solutions, dispersions, suspensions, and the like, depending on the intended mode of administration and therapeutic application. In some embodiments, the inventive composition is prepared in a form of an injectable or infusible solution.

In certain embodiments, the CD206-binding agent composition may include a carrier protein, such as serum albumin (e.g., HSA, BSA, and the like). The serum albumin can be purified or recombinantly produced. By mixing the CD206-binding agent in the pharmaceutical composition with serum albumin, the CD206-binding agent can be effectively "loaded" onto the serum albumin, allowing a greater amount of CD206-binding agent to be successfully.

In certain embodiments of the inventive treatment methods, administration is via any one of a variety of routes, including intravenous (IV), intramuscular (IM), intra-arterial, intramedullary, intrathecal, subcutaneous (SQ), intraventricular, transdermal, interdermal, intradermal, intratumoral, by intratracheal instillation, bronchial instillation, and/or inhalation; as a nasal spray, and/or aerosol, and/or through a portal vein catheter. In certain embodiments, intravenous injection, or infusion may be used. Any appropriate site of administration may be used. For example, the inventive composition may be administered locally and directly at the site where action is required or may be attached or otherwise associated, e.g. conjugated, with entities which will facilitate the targeting to an appropriate location in the body.

In certain embodiments, any physiologically compatible carrier, excipient, diluent, buffer or stabilizer can be used in the compositions of the invention. Examples of suitable carriers, excipients, diluents, buffers and stabilizers include one or more of water, saline, phosphate buffered saline, dextrose, glycerol, ethanol and the like, as well as combinations thereof. In some cases isotonic agents, e.g., sugars, polyalcohols (e.g., mannitol, sorbitol), or sodium chloride may be included. In certain embodiments, the compositions of the invention may be formulated so as to provide quick, sustained, or delayed release of the active ingredient (peptide A, peptide B. or variants thereof and/or additional drug(s)) after administration to the subject by employing procedures well known in the art. As described above, in certain embodiments, the composition is in a form suitable for injection and suitable carriers may be present at any appropriate concentration, but exemplary concentrations are from 1% to 20% or from 5% to 10%.

Therapeutic compositions typically must be sterile and stable under conditions of manufacture and storage. Appropriate ways of achieving such sterility and stability are well known and described in the art.

Pharmaceutical compositions are typically formulated in unit dosage form for ease of administration and uniformity of dosage. It will be understood, however, that the total daily (or other) usage of the compositions of the present invention will be decided by the attending physician within the scope of sound medical judgment. The specific therapeutically effective dosage level for any particular subject will depend upon a variety of factors including the activity of the composition employed; the half-life of the composition after administration; the age, body weight, general health, sex, and diet of the subject; the time of administration, route of administration, and rate of excretion of peptide A and (if used) the additional therapeutic agent employed; the duration of the treatment; drugs used in combination or coincidental with the specific compound employed; and like factors, well known in the medical arts. Furthermore, effective doses may be extrapolated from dose-response curves derived from in vitro and/or in vivo animal models.

Thus, suitable doses of the CD206-binding agent and other active ingredients (if included) will vary from patient to patient. In some embodiments, said dosages constitute a therapeutically effective amount or a prophylactically effective amount, depending on the nature of the treatment involved. The ability of the CD206-binding agent to elicit a desired response in the individual will also be a factor. Exemplary daily doses are: 0.1 to 250 mg/kg, or 0.1 to 200 or 100 mg/kg, or 0.5 to 100 mg/kg, or 1 to 50 or 1 to 10 mg/kg, of the active ingredient. This can be administered as a single unit dose or as multiple unit doses administered more than once a day, for example, subcutaneously, intraperitoneally, or intravenously. It is to be noted, however, that appropriate dosages may vary depending on the patient, and that for any particular subject, specific dosage regimes should be adjusted over time according to the individual needs of the patient. Thus, the dosage ranges set forth herein are to be regarded as exemplary and are not intended to limit the scope or practice of the claimed compositions or methods.

Kits

In one aspect, the present disclosure further provides kits the CD206-binding agent, or a composition formulated with the CD206-binding agent. Kits can include one or more other elements including, but not limited to, instructions for use; other therapeutic agents (for combination therapy); other reagents, e.g., a diluent, devices or other materials for preparing composition for administration; pharmaceutically acceptable carriers; and devices or other materials for administration to a subject. Instructions for use can include instructions for therapeutic application, including suggested dosages and/or modes of administration, e.g., in a human subject, as described herein. In some embodiments, said kits are for use in the methods and uses as described herein. e.g. therapeutic, diagnostic, or imaging methods, or are for use in in vitro assays or methods. The peptide(s) or variant in such kits may, in some embodiments, be a conjugate. e.g., may be conjugated to a detectable moiety.

EXAMPLES

Example 1: Biophysical Homology Screening

Native host defense peptides (HDPs) exist as short α-helices or β-sheets of 10 to 40 amino acids and frequently have a dichotomous amphipathic charge distribution with clusters of amino acids having polar charges arranged along an opposing plane of amino acids with hydrophobic residues A database of 431 α-helical antimicrobial peptides (AMPs) and HDPs (http://aps.unmc.edu/AP/main.php) were screened using Molly font under the hypothesis that phylogenetically conserved structural domains within naturally occurring HDPs harbor important innate immune functions, and that such select structure/function paradigm domains can be isolated and optimized for the design of novel therapeutics.

Instead of homology comparisons using primary amino acid alignments, Molly font (Molly Hydrophobicity Wheel) assesses the three key biophysical features: hydrophobicity, electrostatic charge of amino acids, and steric amino acid volume to detect structural homologies via their unique conserved biophysical nature (FIG. 1A). Out of the screened 431 peptides that were identified, 129 peptides, or 30%, were found to possess a preserved 10 amino acid domain consistent with the structural determinants of a secondary α-helical structure with amphiphilic surface topology (Table 4). Biophysically similar sequences were also identified in human collagens and various microbial virulence factors, possibly indicating peptide-structure involved in conserved, shared innate immune functionalities (FIG. 2 and Table 4).

TABLE 4

A

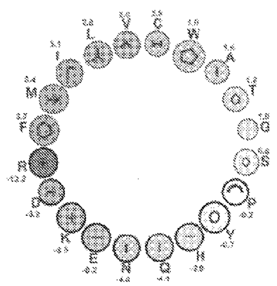

B

| HDP | Sequence | Virulence | Sequence |
|---|---|---|---|
| CEC-F1 | IFKKIERVGQ | AVP1-F | EKLSAFRNFF |
| CEC-F2 | LFKKIEKVGQ | CTPR-F | AVRRLAORLA |
| LL37-F1 | FFRKSKEKIG | MPCP-F | KEFLAFKRFF |
| LL37-F2 | IGKEFKRIVQ | TPRO-F | IENAAFKRFF |
| PLEU-F | FFKKAAHVGK | PTTM-F | GFRELFRQLD |
| PSEU-F | ALKKVFQGIH | gp120-F | AIRRIPRRIR |
| MAG-F1 | FLHSAKKFGK | FLAB-F | MVFRDVGNRN |
| CATH-F | LKKALPVAKK | Collagen | Sequence |
| MAG-F2 | HSAKKFGKAF | COLI-F | DRGIKGHRGF |
| LL37-F3 | RIKDFLRNLV | COLIV-F | LRGQKGDRGF |
| LL37-F4 | RIVQRIKDFL | COLV-F | EAGEKGDQGL |
| DHDP | Sequence | COLVI-F | VLDAIRRLRL |
| RP-182 | KFRKAFKRFF | COLVII-F | HVVQRGEHSL |
| RP-426 | KARKAAKRAF | COLXVIII-F | IVRRADRAAV |

TABLE 5

| HDP | Sequence | Origin |
|---|---|---|
| CATHF1 | LKKALPVAKK | ceratotoxin-A [Ceratitis capitata] Sequence ID: XP_004523341.1 |
| CECF1 | IFKKIERVGQ | cecropin A [Hyphantria cunea] Sequence ID: AID51414.1 |
| CECF2 | LFKKIEKVGQ | cecropin A [Hyalophora cecropia] Sequence ID: AAA29185.1 |
| LL37F1 | FFRKSKEKIG | cathelicidin antimicrobial peptide preproprotein [*Homo sapiens*] Sequence ID: NP_004336.3 |
| LL37F2 | IGKEFKRIVQ | cathelicidin antimicrobial peptide preproprotein [*Homo sapiens*] Sequence ID: NP_004336.3 |
| LL37F3 | RIKDFLRNLV | cathelicidin antimicrobial peptide preproprotein [*Homo sapiens*] Sequence ID: NP_004336.3 |
| LL37F4 | RIVQRIKDFL | catholicidin antimicrobial peptide preproprotein [*Homo sapiens*] Sequence ID: NP_004336.3 |
| MAGF1 | FLHSAKKFGK | magainins preproprotein [Xenopus laevis] Sequence ID: NP_001081306.1 |
| MAGF2 | HSAKKFGKAF | magainins preproprotein [Xenopus laevis] Sequence ID: NP_001081306.1 |
| PLEUF1 | FFKKAAHVGK | pleurocidin [Pleuronectes americanus] Sequence ID: Q90ZY0.1 |
| PSEUF1 | ALKKVFQGIH | pseudin-2 [Pseudis paradoxa] Sequence ID: P83189.1 |
| **DHDP** | **Sequence** | **Origin** |
| 182 | KFRKAFKRFF | designed |
| 426 | KARKAAKRAF | designed |
| **Virulence** | **Sequence** | **Origin** |
| AVP1 | EKLSAFRNFF | fibronectin-binding protein PavA [*Streptococcus pneumoniae*] Sequence ID: WP_079111036.1 |
| CTPR | AVRRLAQRLA | secretion protein [*Streptomyces*] Sequence ID: WP_079021188.1 MULTISPECIES |
| FLAB | MVFRDVGNRN | polar flagellin FlaB [*Vibrio vulnificus* YJ016] Sequence ID: BAC95256.1 |
| MPCP | KEFLAFKRFF | putative inner membrane protein [*Chlamydia psittaci* 06-1683] Sequence ID: EPJ33273.1 |
| PTTM | GFRELFRQLD | phage tail tape measure protein [*Mycobacterium obuense*] Sequence ID: WP_046363070.1 |
| TPRO | IENAAFKRFF | tail protein [*Acinetobacter baumannii*] Sequence ID: WP_031953720.1 |
| **Collagen** | **Sequence** | **Origin** |
| COLI | DRGIKGHRGF | pro alpha 1(I) collagen [*Homo sapiens*] Sequence ID: AAB94054.3 |
| COLIV | LRGQKGDRGF | collagen type IV a6 chain [*Homo sapiens*] Sequence ID: AAB19038.1 |
| COLV | EAGEKGDQGL | collagen type V alpha 3 chain [*Homo sapiens*] Sequence ID: AAF59902.1 |
| COLVII | HVVQRGEHSL | collagen alpha-1(VII) chain isoform X2 [*Homo sapiens*] Sequence ID: XP_016861177.1 |
| COLVII | VLDAIRRLRL | collagen alpha-3(VI) chain isoform X3 [*Homo sapiens*] Sequence ID: XP_005246122.1 |
| COLXVI | IVRRADRAAV | human type XVIII collagen [*Homo sapiens*] Sequence ID: CAB90482.1 |

Figure 3:
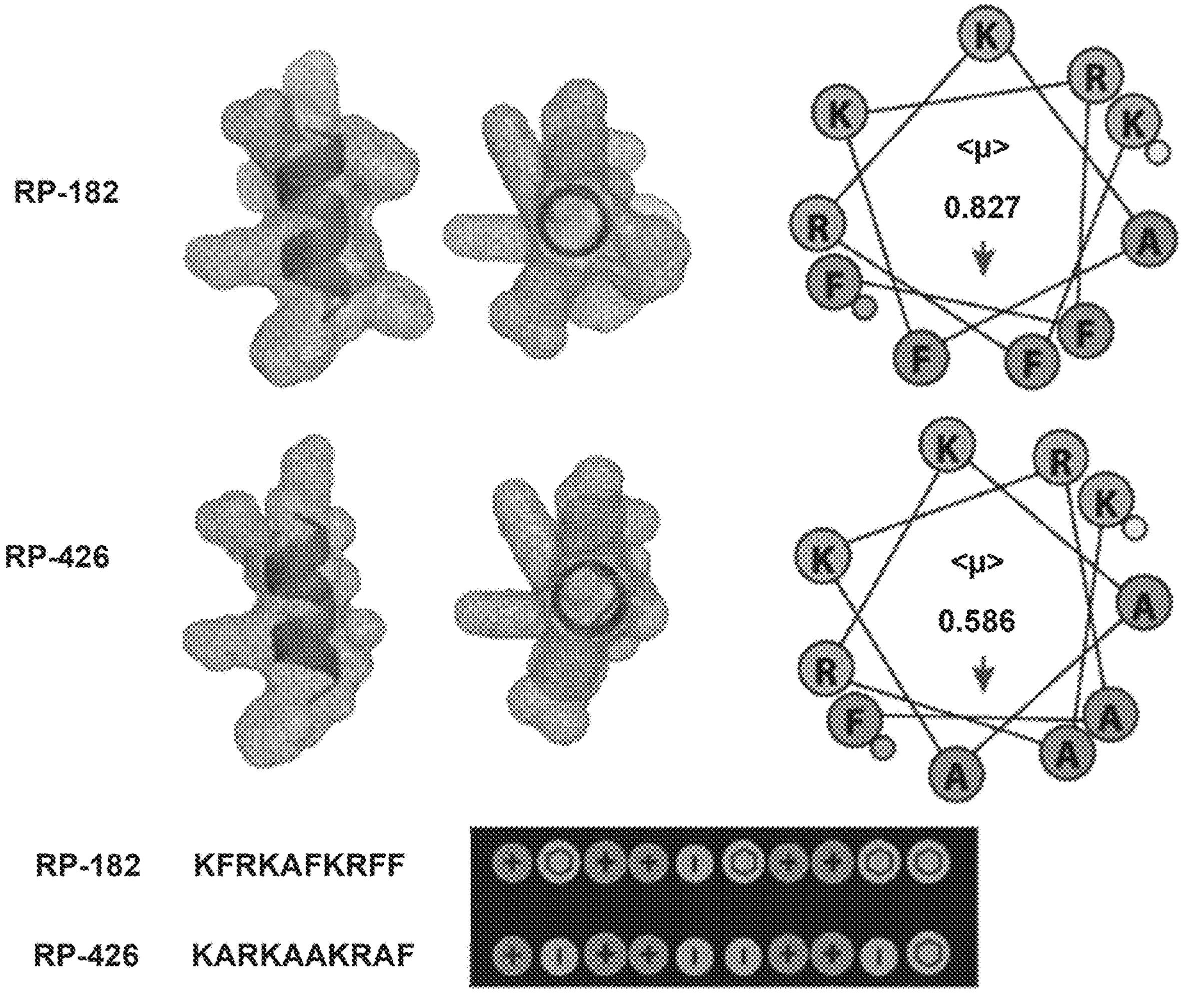
FIG. 3 shows secondary α-helical structures, helical hydrophobicity wheel projections, and Molly font alignments (bottom) of RP-182 and RP-426.

The synthetic design RP-182 was optimized for maximum amphipathy of the original conserved 10mer sequence by increasing hydrophobicity (hydrophobic moment vector <μ>) and positive charge density as visualized in Molly font (FIG. 3). RP-426 was designed as a control to test impact of hydrophobicity onto activity.

Figure 5:
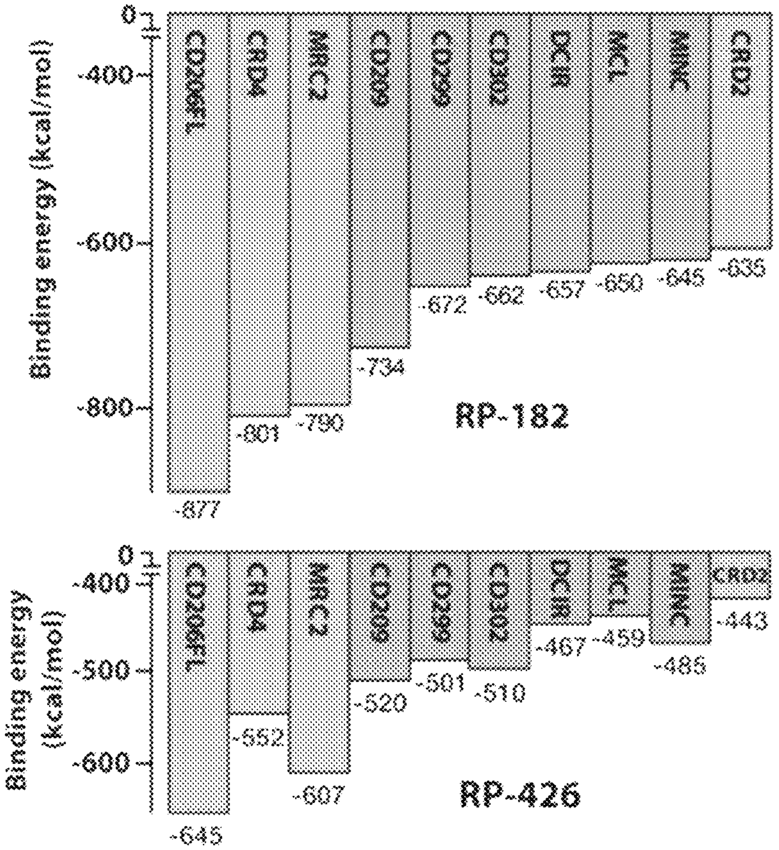
FIG. 5 shows relative binding energies to top ten C-type lectin receptors utilizing ClusPro®.
Figure 6:
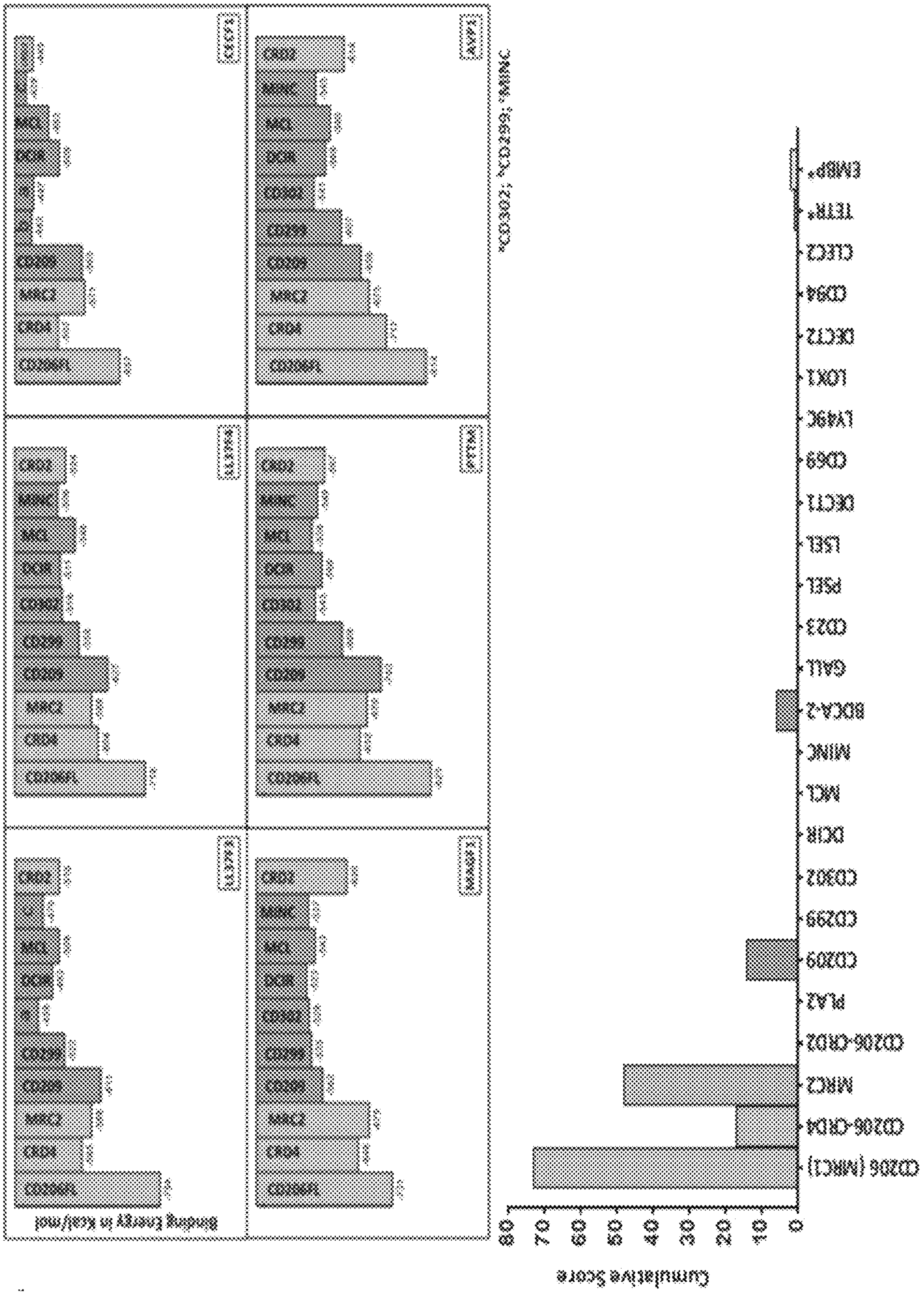
FIG. 6 shows the docking campaign of biophysical 10mer homology motifs and C-type lectin receptors. A. Relative binding energies, in kcal/mol, of top 10mer peptide motif ligand—C-type lectin receptor combinations utilizing ClusPro®. Origin of 10mer peptide sequence shown on bottom; predicted affinities to individual lectin receptors annotated on top. B. Mannose receptor CD206 shows the highest affinity to 10mer biophysical peptide sequences across all tested peptide-ligand receptor combinations. Cumulative score of the top three peptide ligand-receptor combinations is shown, with each receptor examined by 23 peptide ligand-receptor combinations. The receptor with the highest affinity (lowest −BE; in kcal/mol) was allocated three points, the second highest two, and the third highest one point. The plot shows the sum of points for each receptor across all peptides. CD206FL, full length CD206; CRD, carbohydrate recognition domain.
Figure 7A:
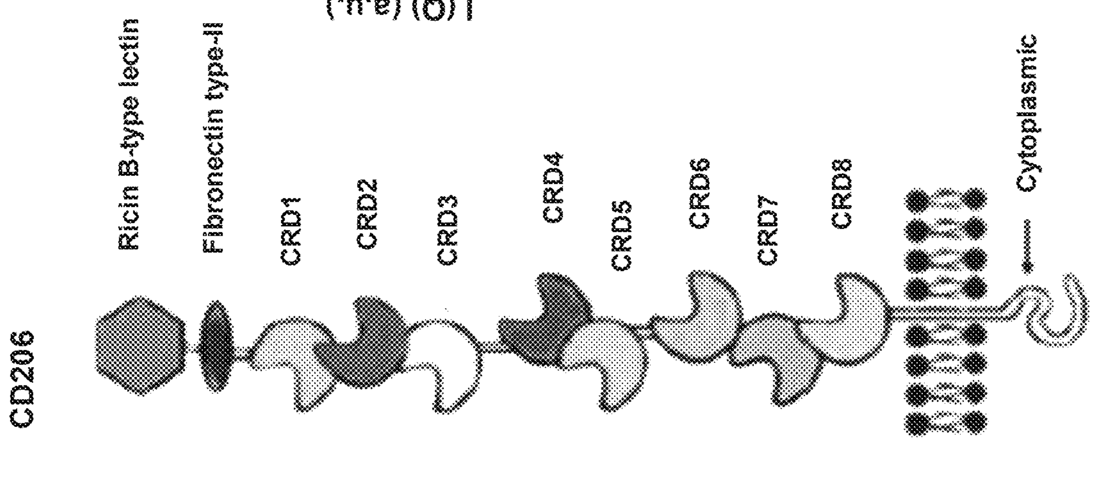
FIG. 7A shows a full length MRC1/CD206 model. Known functional domains of human MRC1/CD206. CRD, carbohydrate recognition domains 1-8.

Next, to identify possible lead % of putative binding partners of RP-182 and to examine whether RP-182 and the original 10mer homology sequences share common innate defense regulator function, we conducted in silico docking studies on human C-type lectin receptors which are target receptors of HDPs and major regulators of innate immune processes in higher organisms. The animal lectin database (http://www.imperial.ac.uk/research/animallectins/ctld/mammats/humanvmouscdata.htmi) contained 86 membrane-associated human C-type lectin-like domain (CTLD) containing proteins, of these had 24 crystal structures available. Using ClusPro®, the crystal structures were interrogated for binding to RP-182 and biophysically similar 10mer peptide fragments from 23 representative HDPs, virulence factors, and internal collagen sequences (FIG. 4). FIG. 5 shows the ten CTLD containing proteins with the highest predicted binding affinity to RP-182, and FIG. 6 binding affinities of top receptor/ligand combinations of other 10mer homology motifs, identifying the mannose receptor 1 (MRC1/CD206) as the target with the highest in silico affinity. MRC1/CD206 is a member of the group 6, C-type lectin receptor family and undergoes a conformational change from open, 'elongated' to closed state upon ligand binding or as pH in the surrounding environment decreases (FIG. 7A).

Figure 7B:
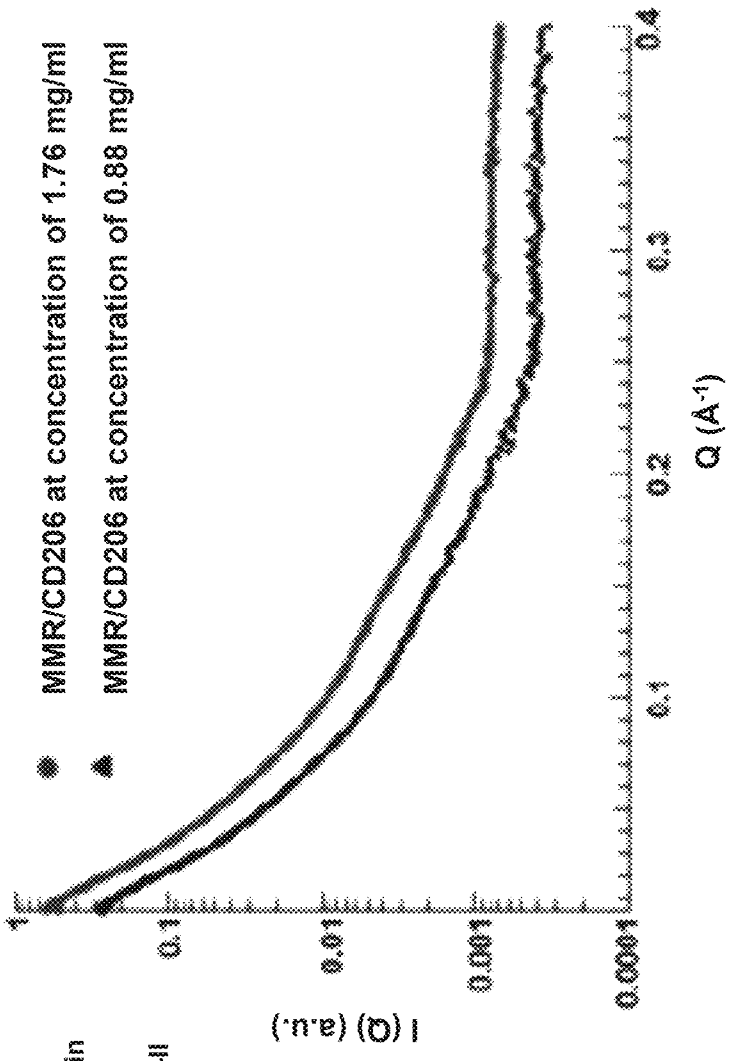
FIG. 7B shows a full length MRC1/CD206 model. SAXS profiles are shown as a function of concentration of the full length MRC1/CD206 protein where I(q) is scattering intensity and q (in Å-1) is the scattering vector. Structural parameters extracted from SAXS data are listed on bottom; Rg Guinier: the radius of gyration produced from Guinier plot of SAXS data extrapolated to 0 concentration; Rest Rg and Dmax (maximum dimension of the particle) are produced from GNOM (https://www.embl-hamburg.de/biosaxs/manuals/gnom.html). MW1 and MW2 are molecular weights estimated from SAXS data using Porod volume (Vporod) and correlation volume (Vc). For Vc calculation qmax=0.15 Å-1 was used. The results suggest that MRC1/CD206 forms a dimer in the solution.
Figure 7D:
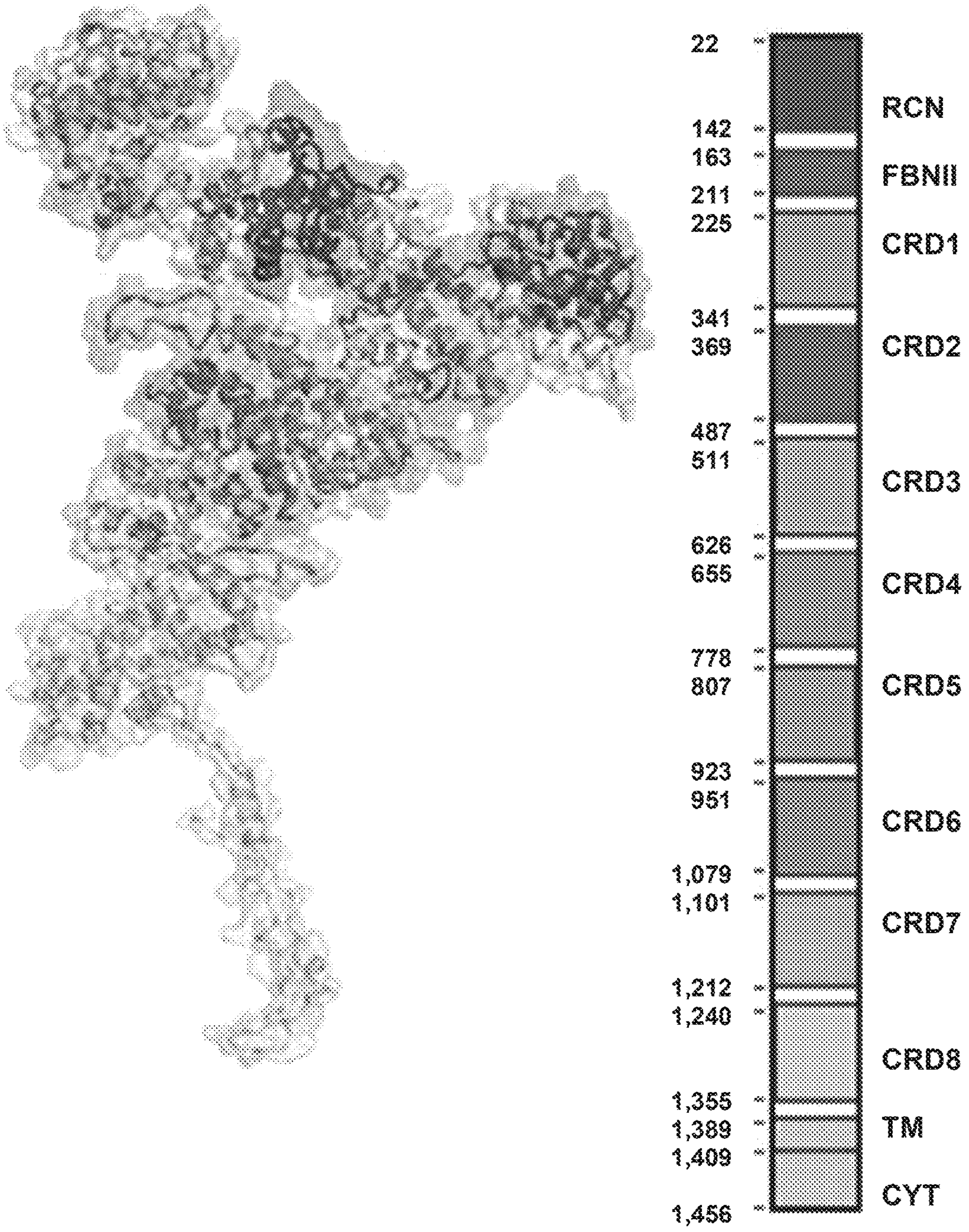
FIG. 7D shows a full length MRC1/CD206 model. C. 5 top-ranking human MRC1/CD206 models created by I-TASSER tested for best fit with experimental SAXS data. The discrepancy between models and experimental curves ($\chi^2$) are in the bottom table. In the fitting, MRC1/CD206 dimer models were used based on Model1-5 as monomer, respectively.
Figure 8A:
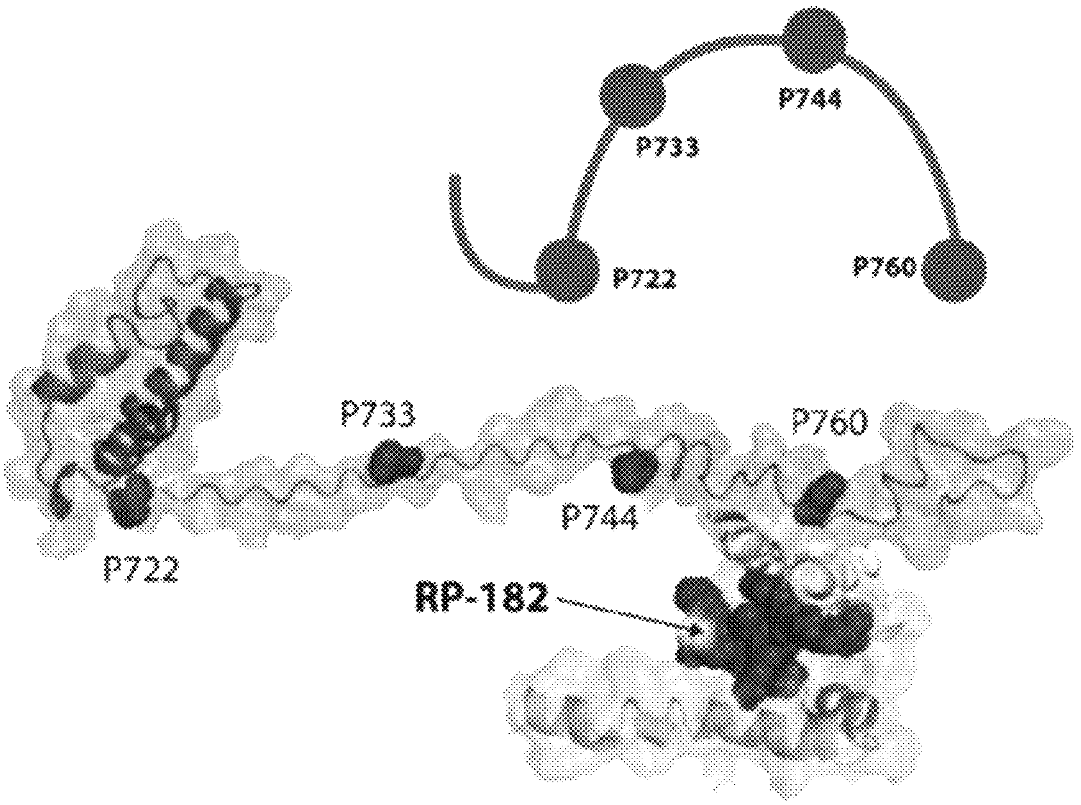
FIG. 8A shows a model of conformational bend in CRD4 and CRD5 of MRC1/CD206 induced by RP-182. Hydrophobic plane of RP-182 bound to CRD5 (cyan color).
Figure 8B:
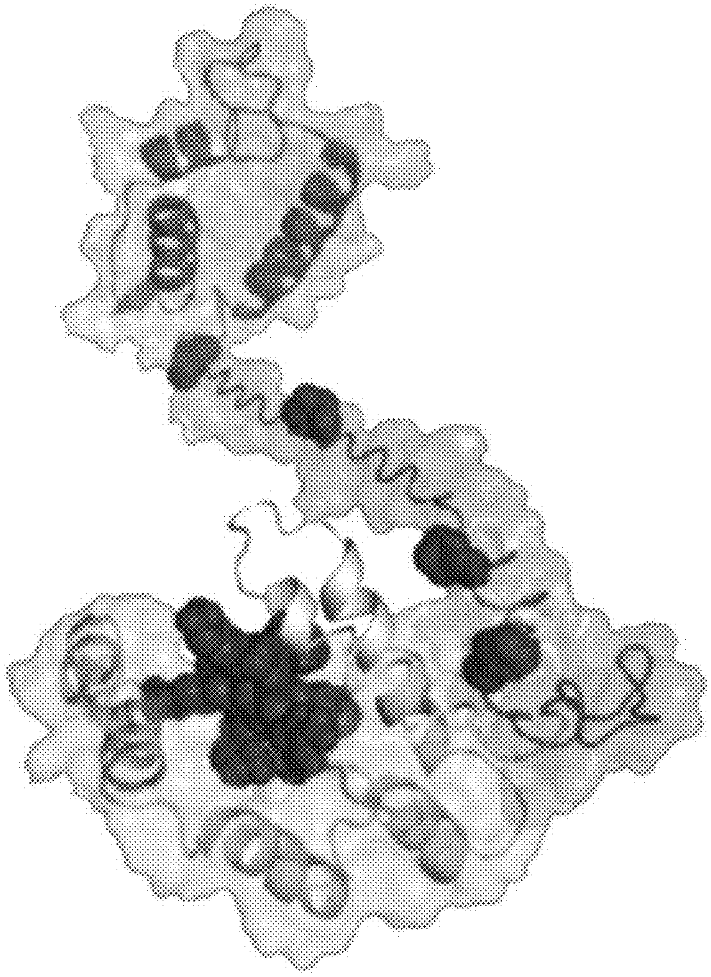
FIG. 8B shows another model of conformational bend in CRD4 and CRD5 of MRC1/CD206 induced by RP-182. Hydrophobic plane of RP-182 bound to CRD5 (cyan color).

Next, in silico models were created of full length human CD206 derived from I-TASSER which we aligned with small angle X-ray scattering (SAXS) data (FIGS. 7B-D). The molecular weight estimated by SAXS data revealed that CD206 forms a dimer in solution (FIG. 7B). The dimer of CD206 based on Model1 as monomer achieved the best fit (minimum $\chi^2$) to SAXS experimental data (FIGS. 7C-D). Therefore, Model1 was selected and used to repeat docking studies which confirmed full-length CD206 being the top binding partner of RP-182 and all except two of the 10mer peptide sequences with biophysical homology (FIG. 4). Based on Model1 RP-182 was predicted by ClusPro® to nestle into a cavity of CRD5 and to engage via three equidistantly spaced prolines (P722, P733 and P744) within CRD4. P760 acts as a fulcrum enabling bending of the CRD4 'handle' and rolling in of the receptor inducing the closed, 'globular' state of the receptor (FIGS. 8A-B).

Figure 9A:
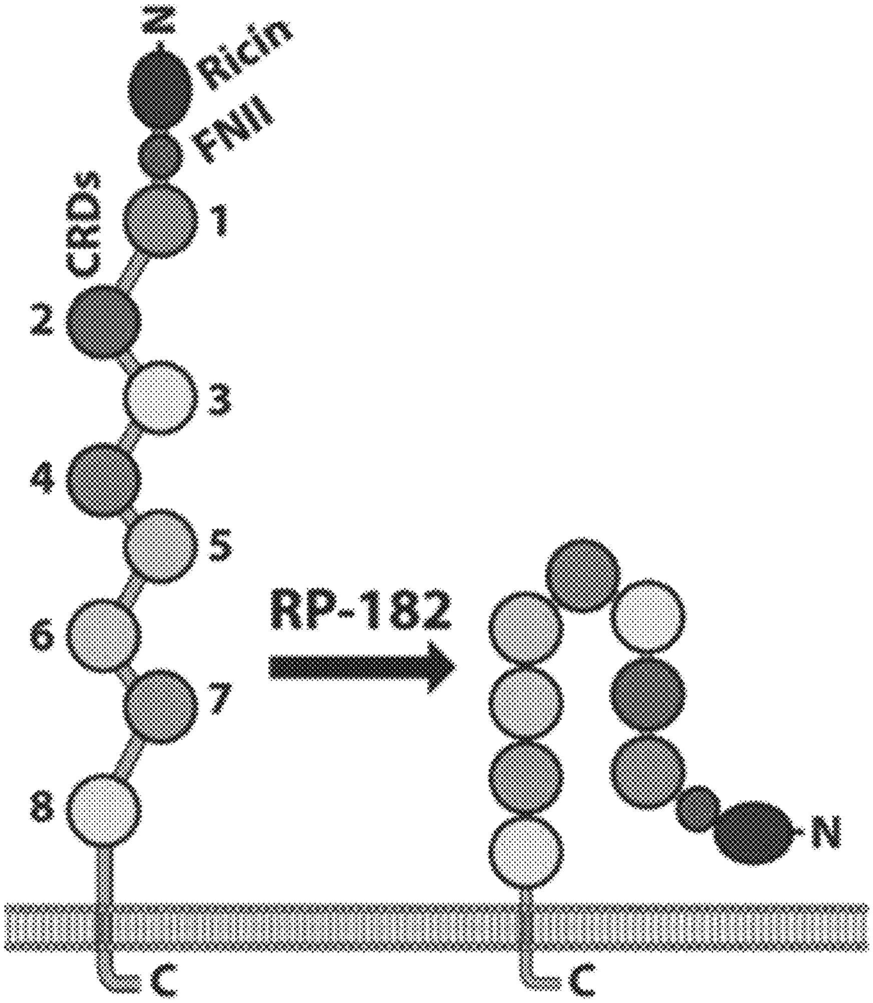
FIG. 9A shows negatively stained electron microscopy micrographs of full length CD206 proteins incubated with vehicle (blue squares) and RP-182 (red squares) and corresponding 2D classes (inlets), schematic of open 'elongated' and 'closed' conformations on left.
Figure 12B:
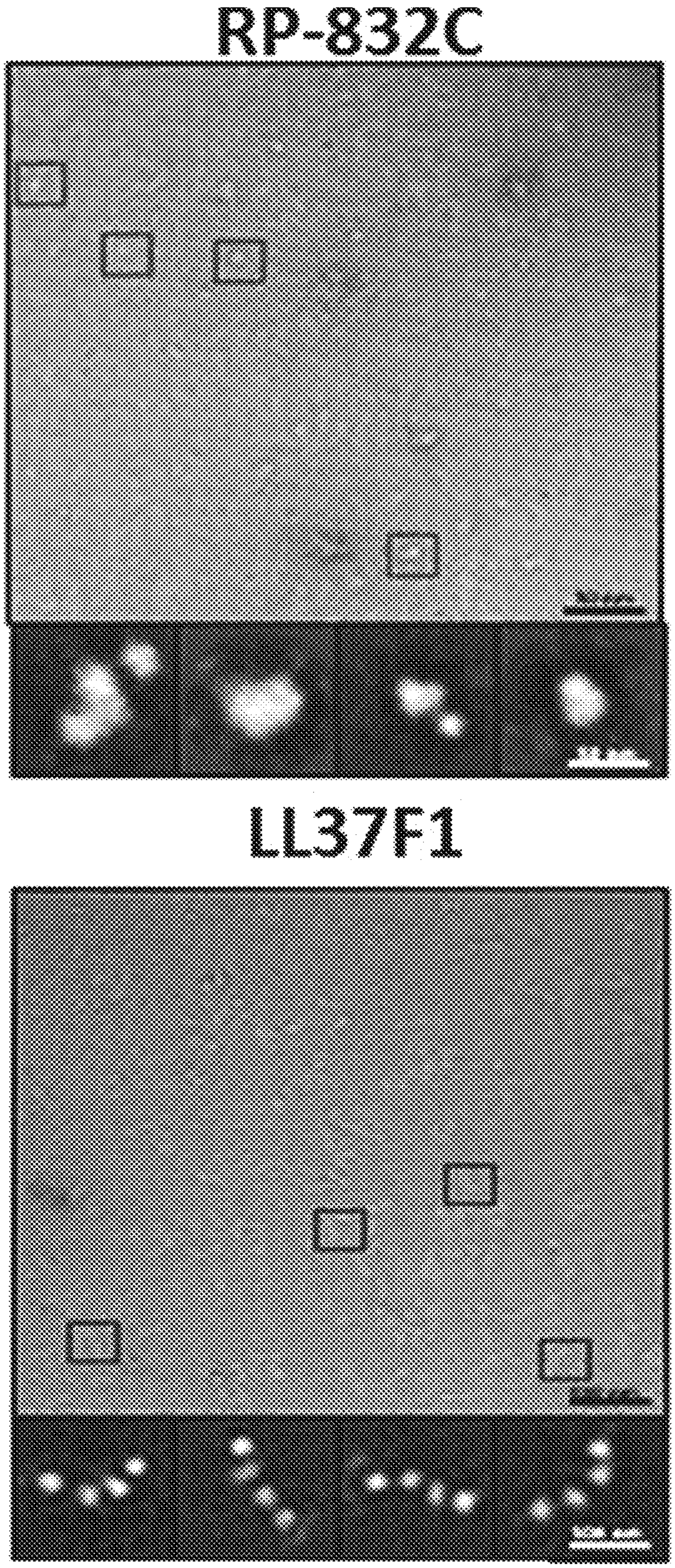
FIG. 12B shows additional views of RP-182 binding to MRC1/CD206. Induction of the closed conformation of the CD206 receptor by 10mer homology motifs. Representative micrographs of full length CD206 incubated with 10mer biophysical homology peptides RP-185, RP-832C. AVP1, LL37F. and control peptide RP-426, 2D classes are shown on bottom.
Figure 12C:
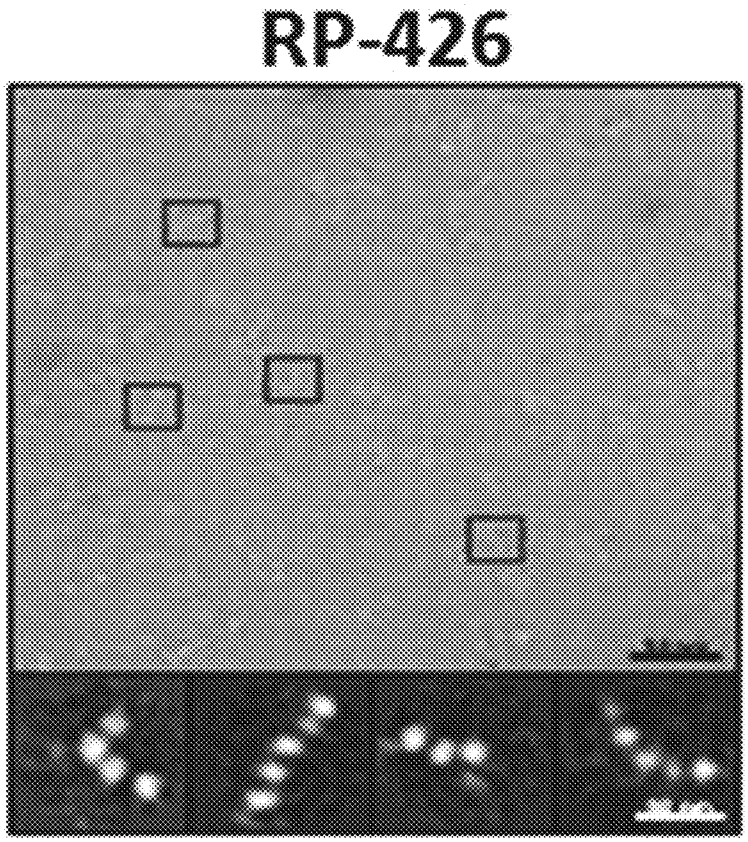
FIG. 12C shows an extra view of RP-182 binding to MRC1/CD206. Induction of the closed conformation of the CD206 receptor by 10mer homology motifs. Representative micrographs of full length CD206 incubated with 10mer biophysical homology peptides RP-185, RP-832C. AVP1, LL37F. and control peptide RP-426, 2D classes are shown on bottom.

To confirm the above binding studies, first ratios of open versus closed CD206 particles were determined by visualizing by electron microscopy incubated with RP-182 and controls. Upon incubation with RP-182 the open, 'elongated' conformation of CD206 switched to the closed, 'globular' conformation (FIGS. 9A-B). The half maximal effective concentration (EC50) of RP-182 to induce the closed conformation of CD206 measured ~11 μM, (FIG. 10). 10mer homology motifs from peptides LL37F1 or AVP1, predicted to bind less to CD206, had lower ratios of closed-to-open conformations compared to peptides RP-832C and RP-182, which were predicted to bind with higher affinity (−1,146 and −877 kcal/mol, respectively) (FIGS. 11 and 12A-C).

Figure 13:
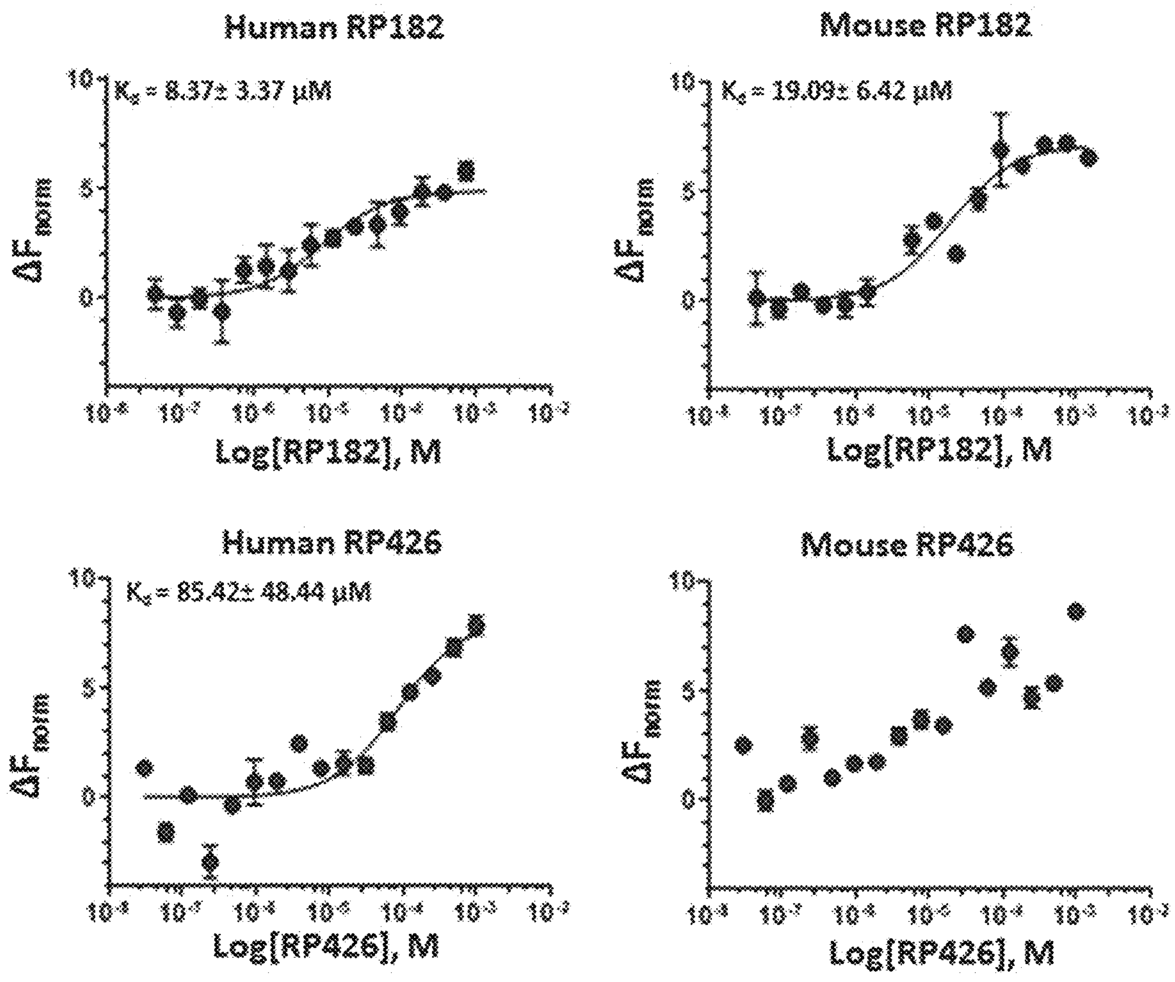
FIG. 13 shows Microscale Thermophoresis (MST) shifts of human (left) and murine (right) MRC1/CD206 at increasing concentrations of RP-182. KD model response curves are fit to the MST data of three independent experiments; control peptide RP-426 shown on bottom. Error bars represent standard deviations of the means.

Next, using microscale thermophoresis (MST), binding of RP-182 to human CD206 was measured and determined a KD of ~8 μM. The binding affinity of RP-426 to CD206 was about ten times lower (KD=85 μM) (FIG. 13). A KD of ~19 μM was measured for binding of RP-182 to murine CD206. Binding of RP-182, but not control peptide RP-426, to endogenous CD206 in human and murine macrophages was confirmed on bone marrow derived macrophages polarized into the M2 phenotype expressing CD206 by cellular thermal shift assay (CETSA) (FIGS. 14A-D). CETSA assesses target engagement of ligands via thermostability shifting of target protein(s) in a cell-based context. Human and murine M2-polarized macrophages incubated with RP-182, but not with RP-426, showed changed thermostability (>4 degrees) of CD206 compared to vehicle control, indicating interaction of RP-182 and the CD206 receptor in the natural environment (FIGS. 14A-D).

Figure 15A:
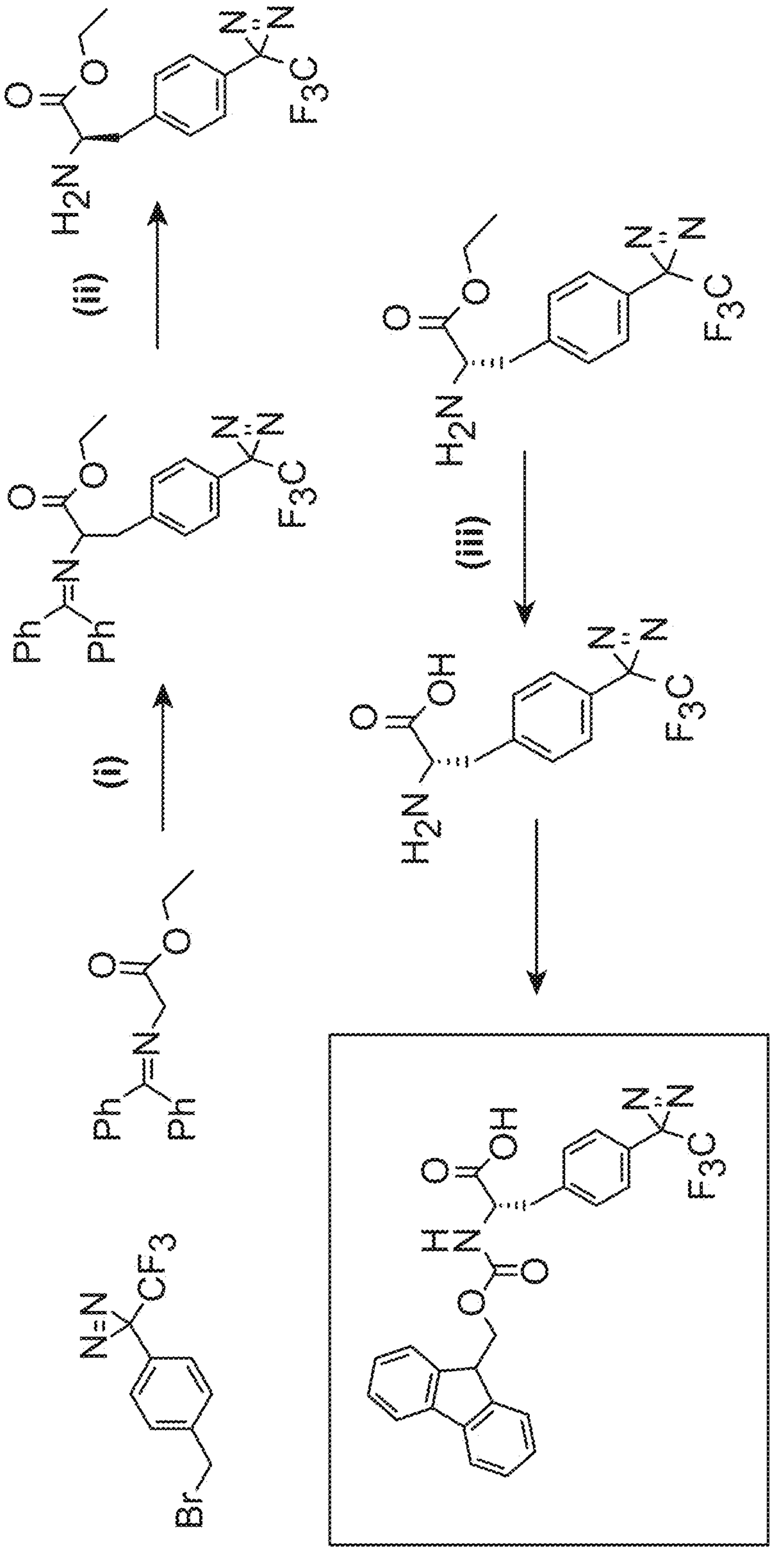
FIG. 15A shows abbreviated synthesis scheme of RP-182 analogues with diazirine-containing phenylalanine and biotin. Synthesis of diazirinyl D-phenylalanine derivative and Fmoc-diazirine-containing phenylalanine (enantiomers were resolved using a chiral column (Chiralpac IB 4.6×250 mm, 100% EOH; 1 ml/min)). Fmoc solid-phase peptide synthesis, and coupling with biotinylated linkers.
Figure 15A:
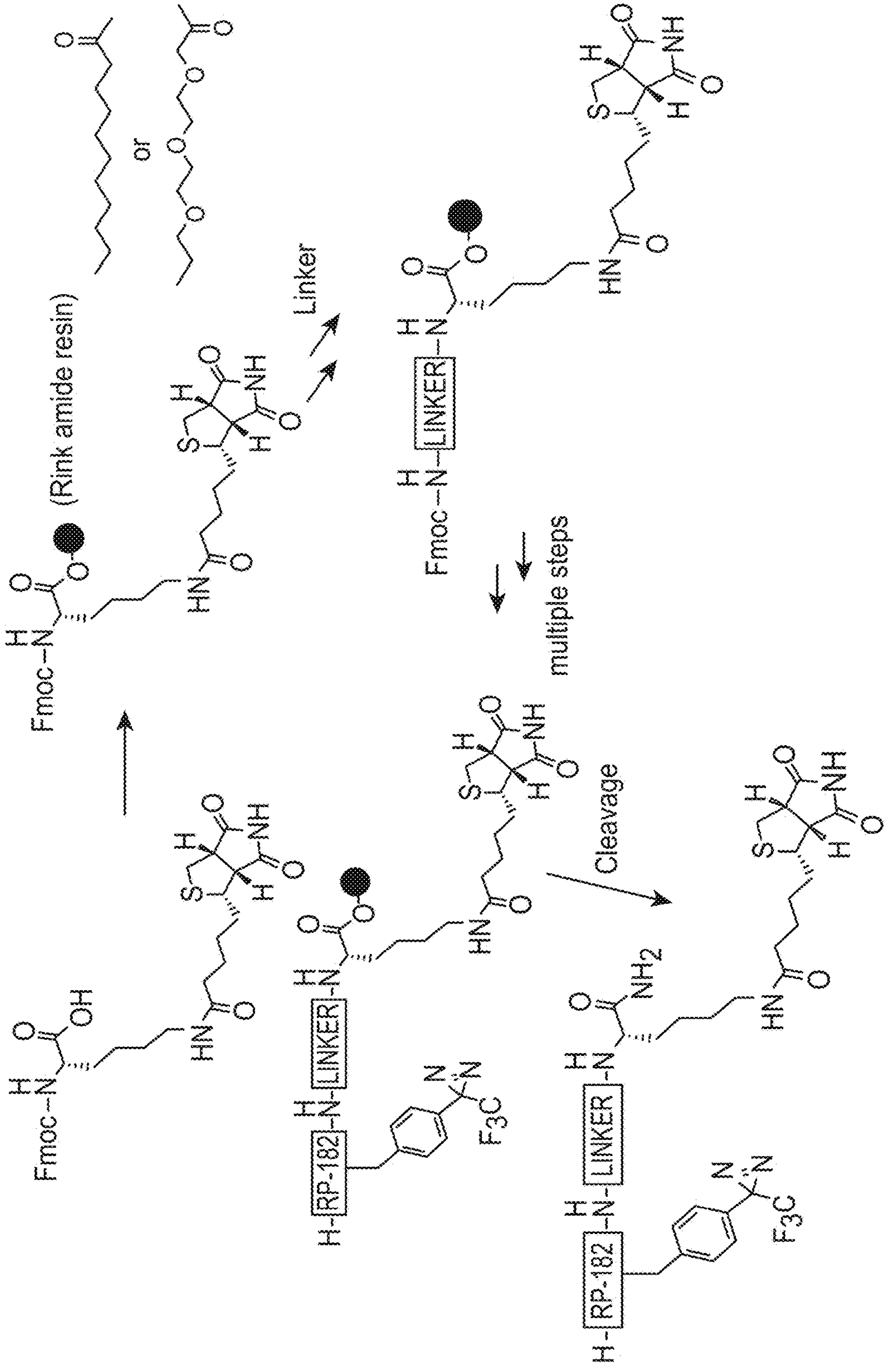
Figure 15B:
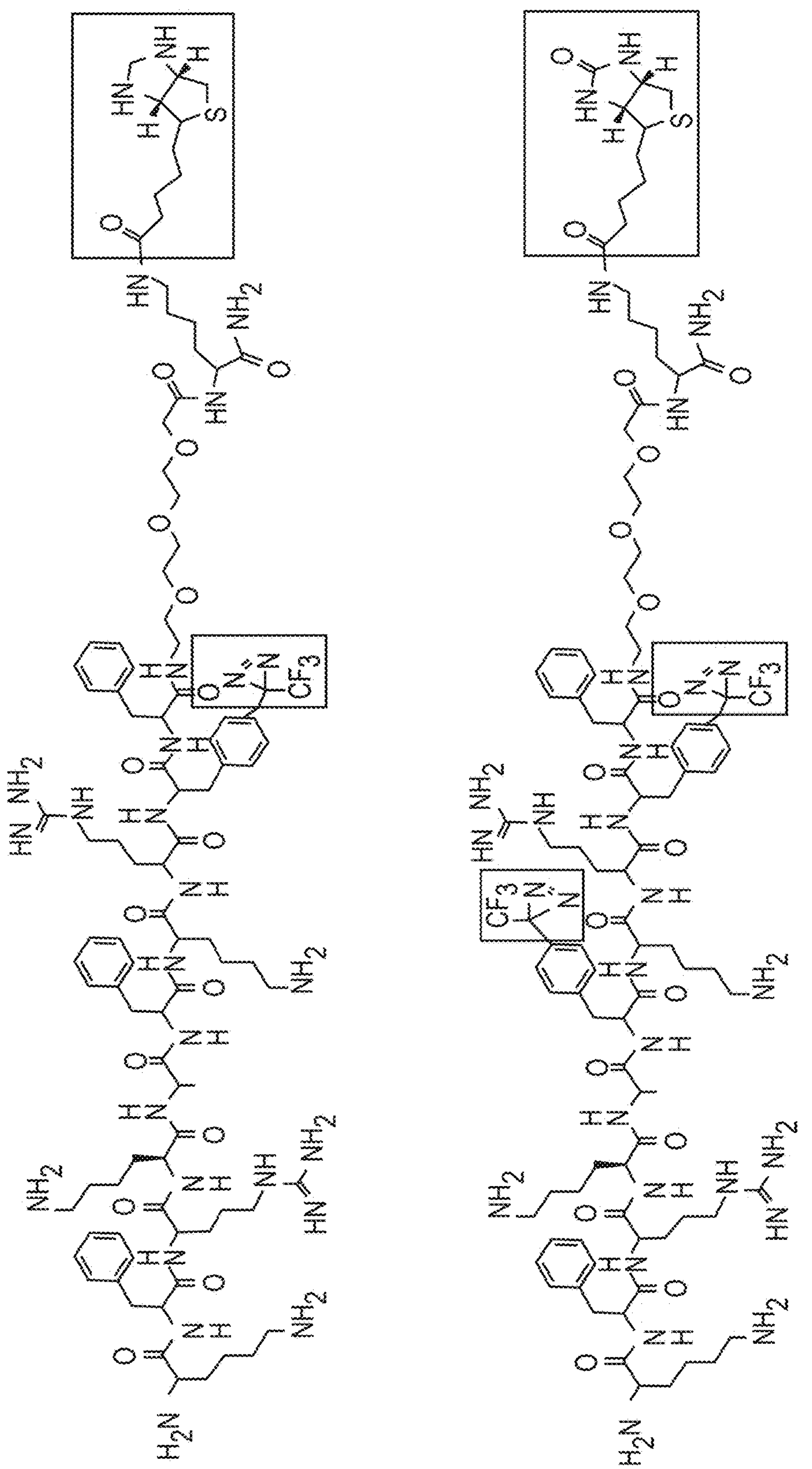
FIG. 15B shows derivatives of RP-182 harboring diazirine group and biotin via PEG (NCGC-00510433 and -35) or hydrocarbon (NCGC-00510432 and -34) linkers were tested for in vitro binding to recombinant MRC1/CD206 via microscale thermophoresis (MST) assay. Measured KD constants shown on the right. NCGC-00510434 was used for all further pulldown experiments.
Figure 16:
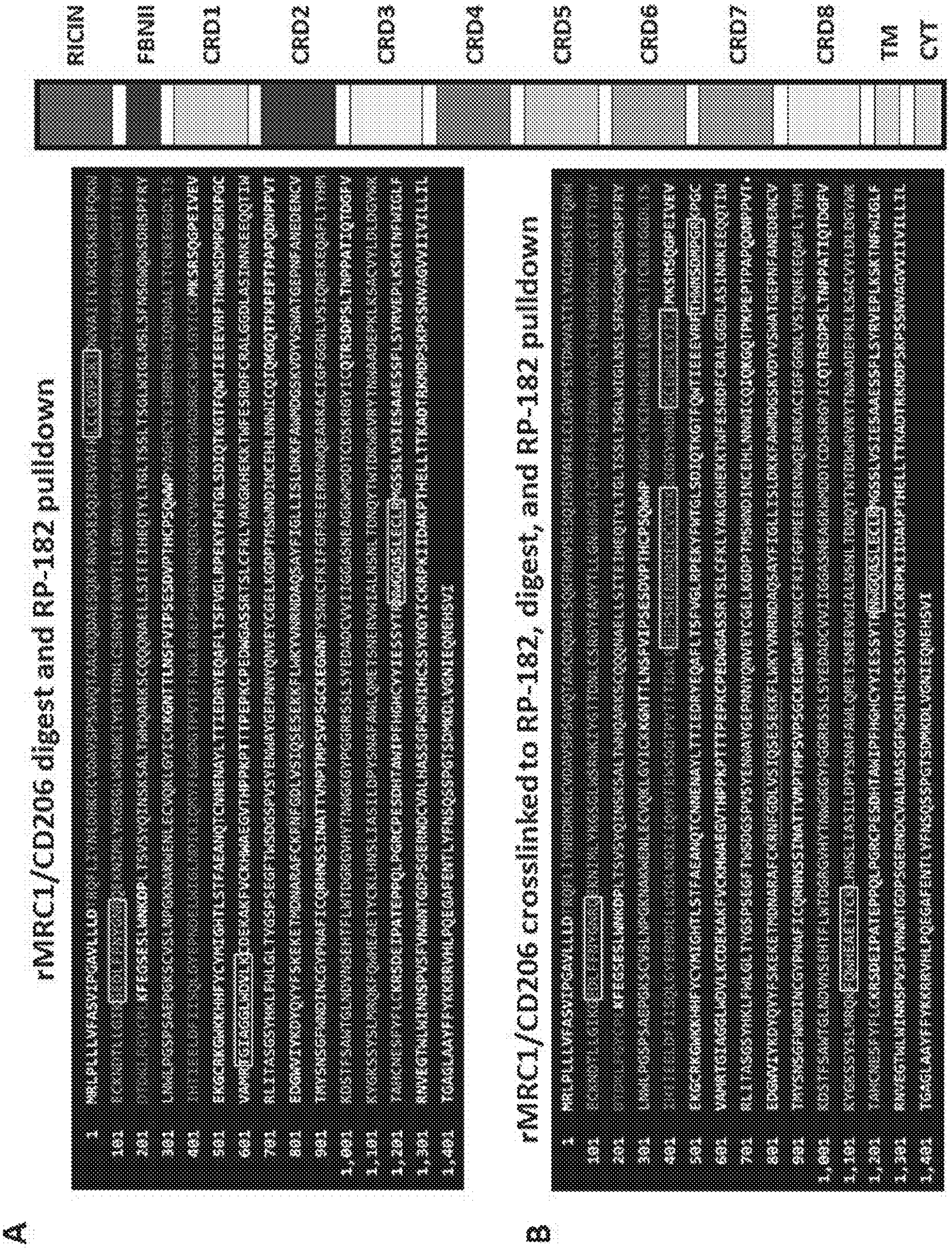
FIG. 16 shows Mapping of binding region of RP-182 to MRC1/CD206 via crosslinking followed by pulldown and proteomic analysis identifies fragment NFGDLVSIQSESEKK within the carbohydrate recognition domain 5 (CRD5; CTLD5) as the binding region of RP-182 to CD206. A. Peptide fragments (highlighted in rectangles) from full length rMRC1/CD206 pulled down with biotinylated diazirine RP-182 analogue NCGC-00510434 after trypsin digestion. B. Peptide fragments of MRC1/CD206 identified after crosslink to the RP-182 analogue, digestion, and pulldown as measured by decreased MRC1/CD206 fragments in the supernatant by mass spectrometry. Carbohydrate recognition domain 5 (CRD5; CTLD5) fragment NFGDLVSIQSESEKK (highlighted in red) was identified by both approaches. C. MS/MS spectrum of MRC1/CD206 CRD5 peptide NFGDLVSIQSESEKK precipitated by biotin-coupled RP-182. Panel A. LC/MS/MS chromatography showing the retention of CRD5 peptide, Panel B, MS1 full scan showing the peptide's triply charged ion m/z=560.9519 (monoisotopic), panel C, MS2 fragment scan showing the spectrum of monoisotopic m/z: 560.95319 Da (+0.34 mmu/+0.61 ppm). RT: 27.01 min. Spectrum was obtained by nano-HPLC-MS/MS analysis.

To further map the binding region of RP-182, mass spectrum studies were performed of recombinant CD206 cross-linked to RP-182 derivative NCGC-00510434. NCGC-00510434, which displays similar KD binding to recombinant CD206 as wild type RP-182, contained a diazirine-substituted phenylalanine and a C-terminally attached biotin (FIGS. 15A-B). Fragment analysis of trypsin-digested CD206 pulled-down with NCGC-00510434 identified CRD5 sequence NFGDLVSIQSESEKK, which aligned with peptide analysis of CD206 covalently crosslinked to NCGC-00510434, followed by digestion, pulldown and sequencing of peptide fragments, as well as the CRD5 motif previously predicted by in silico studies using the CD206 SAXS structure to be the binding region of RP-182 (FIG. 16).

In summary. RP-182 is a synthetic HDP derived from a conserved homology sequence found across a diverse range of peptide and protein regulators involved in innate immune processes. It selectively induces a conformational switch from the open to the closed state in the mannose receptor MRC1/CD206 which is different from the conformational change of CRD3 associated with lower pH or the binding of collagen to the fibronectin II domain.

Example 2: Effect of RP-182 on Cell Function

It was found that RP-182 induces a program of phagocytosis, autophagy, and apoptosis in human and murine M2 macrophages.

Figure 17:
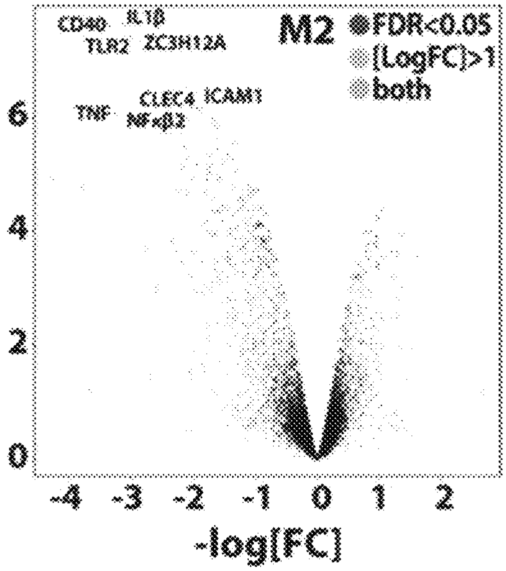
FIG. 17 shows a volcano plot of RNASeq analysis of vehicle- vs RP-182-treated M2 macrophages.
Figure 18:
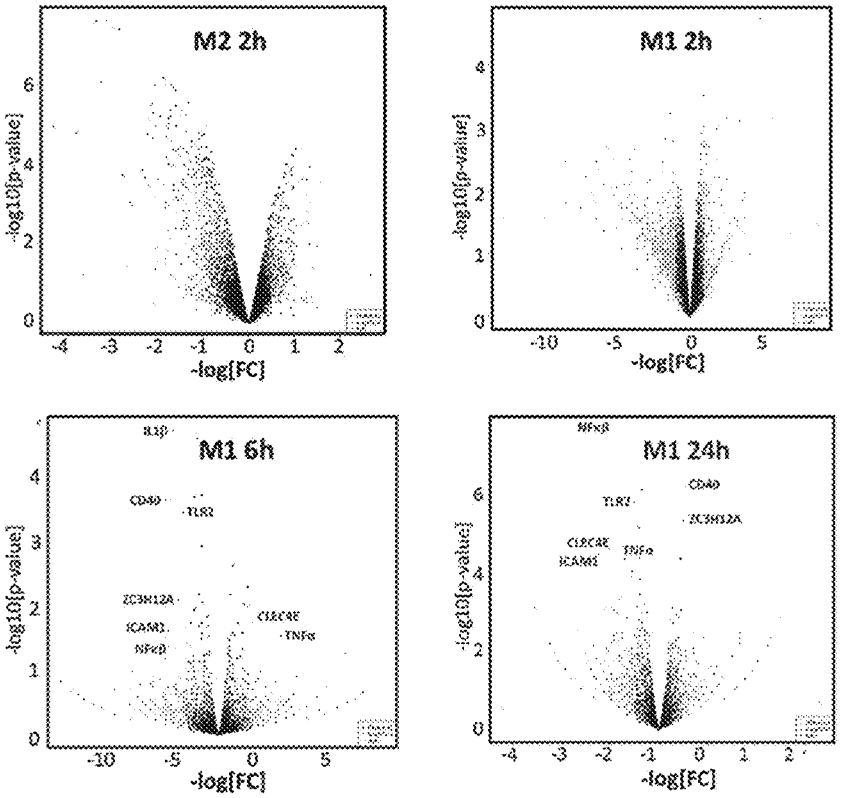
FIG. 18 shows Gene expression changes induced by RP-182 in M1- and M2-polarized BMDMs. Volcano plots of RNASeq analysis of vehicle- vs RP-182-treated M1 and M2 macrophages, treatment times indicated on top. Differentially expressed genes identified by EdgeR analysis with false discovery rate (FDR) $q<0.05$, $-1<\text{Log }2[FC]>1$ are shown (FC, fold change). Summary of identified DEGs shown on right.
Figure 19:
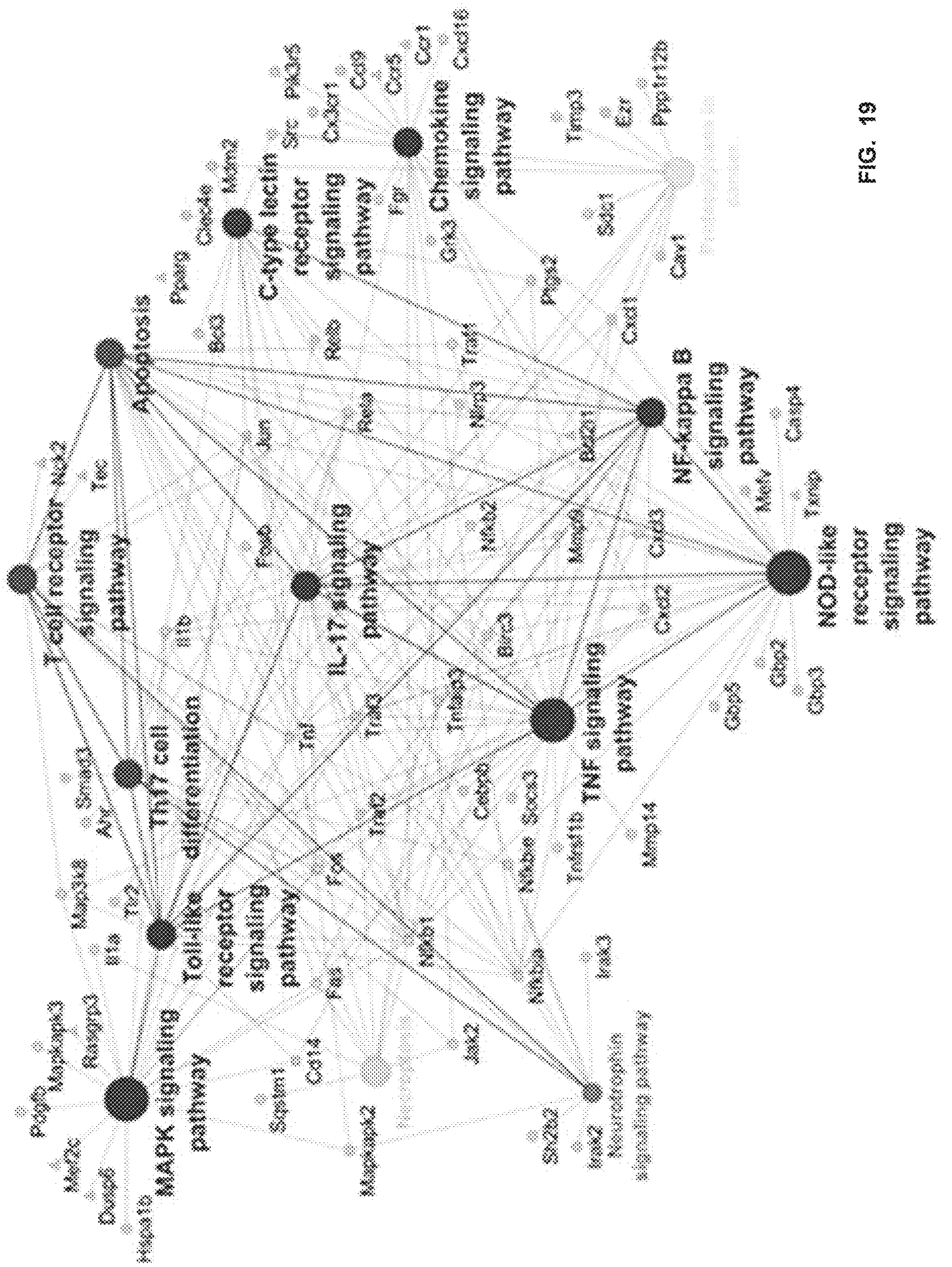
FIG. 19 shows Cytoscape® Functional GO Enrichment and Network Analyses of DEGs of vehicle vs RP-182-treated M2 BMDMs.

To investigate the impact of RP-182 binding and the induced conformational change of CD206 on cell function, first the effects of RP-182 were examined by global RNASeq analysis. Volcano blot analysis of gene expression changes between vehicle- and RP-182-treated M2 BMDMs showed differentially expressed genes (DEGs) skewed towards upregulation. Seven among the eight top DEGs were cytokines or regulators of the classical pro-inflammatory M1 phenotype showing ≥10- to 100-fold increased expression levels after 2 hours treatment (FIG. 17). Transcriptomic changes following RP-182 treatment in myeloid progenitors of murine bone marrow-derived macrophages (BMDM) polarized into M1 and M2 phenotypes occurred selectively in M2-polarized macrophages with no genes differentially expressed in M1 macrophages after 2 hours, six DEGs after 6 hours, and 8 after 24 hours of treatment with RP-182 (FIG. 18). Cytoscape® Functional GO Enrichment and Network Analyses identified pathways of inflammation and macrophage activation upregulated in RP-182-treated M2 BMDMs including C-type lectin receptor, NF-kB, TNF, or Toll-like receptor (TLR) signaling (FIG. 19).

Figure 20:
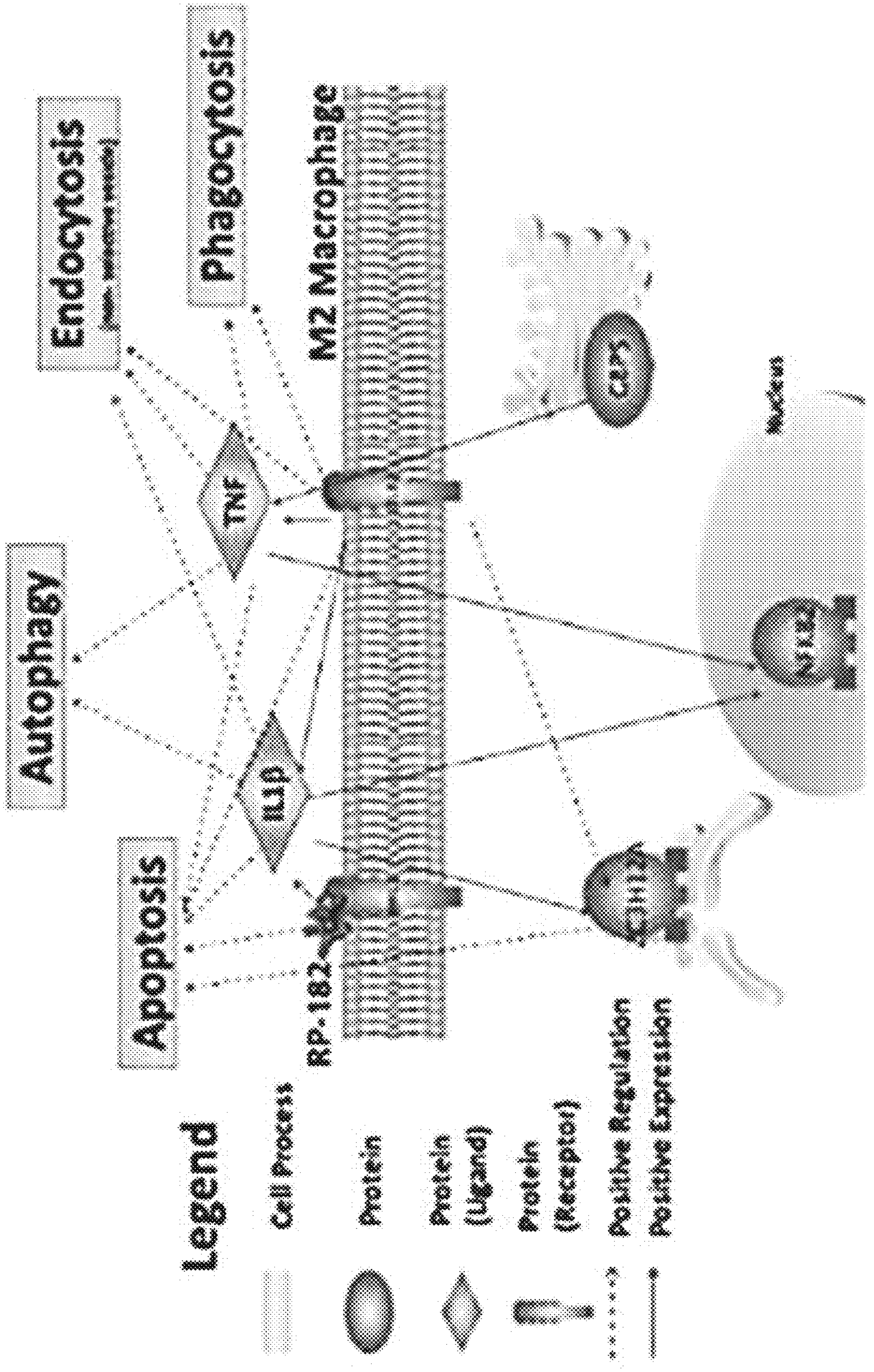
FIG. 20 shows Pathway Studio® graph of GO Cell Processes of most common genes across enriched gene sets in RP-182-treated M2 BMDMs.
Figure 21A:
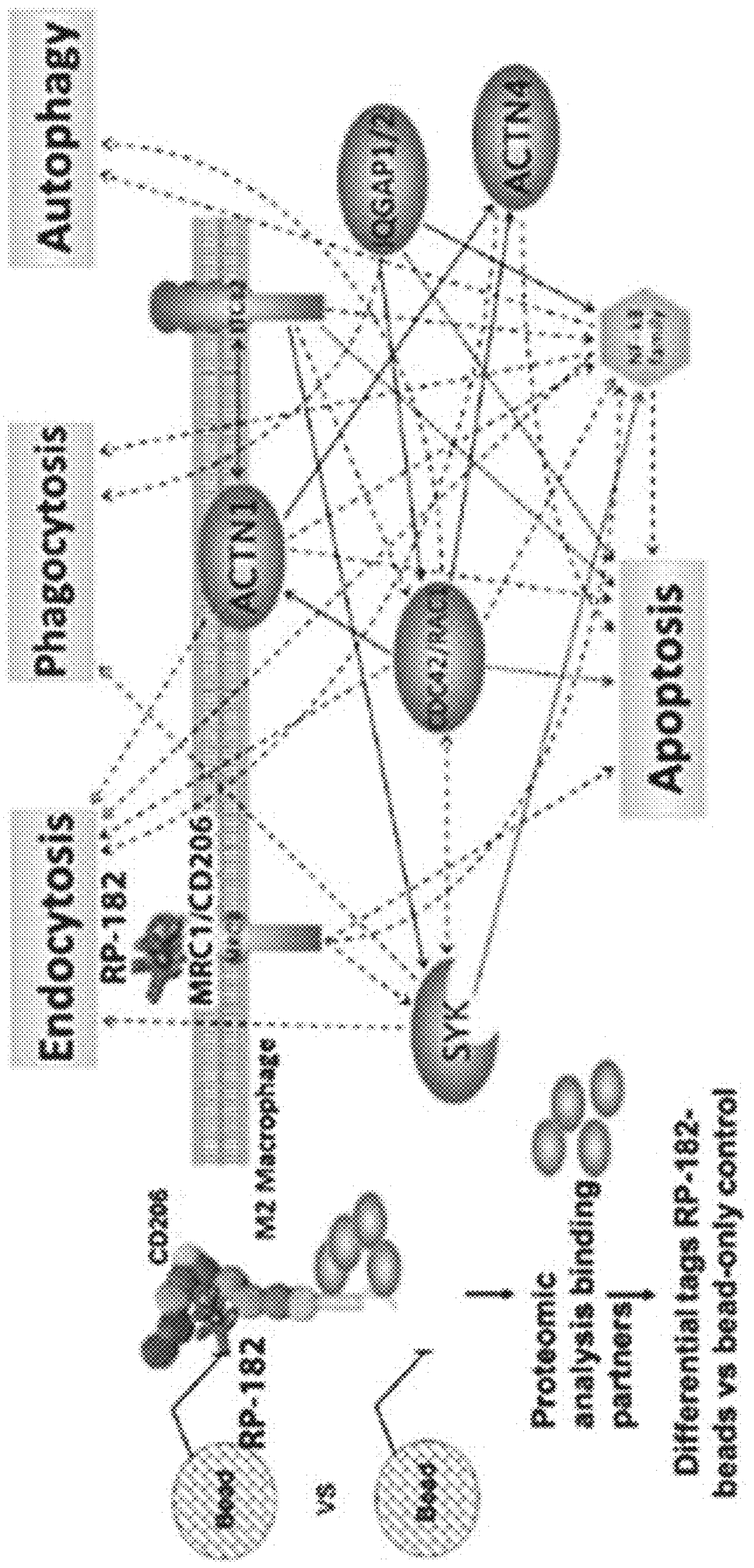
FIG. 21A shows protein network and related cellular processes of CD206 interactome induced by RP-182 in M2 macrophages
Figure 21C:
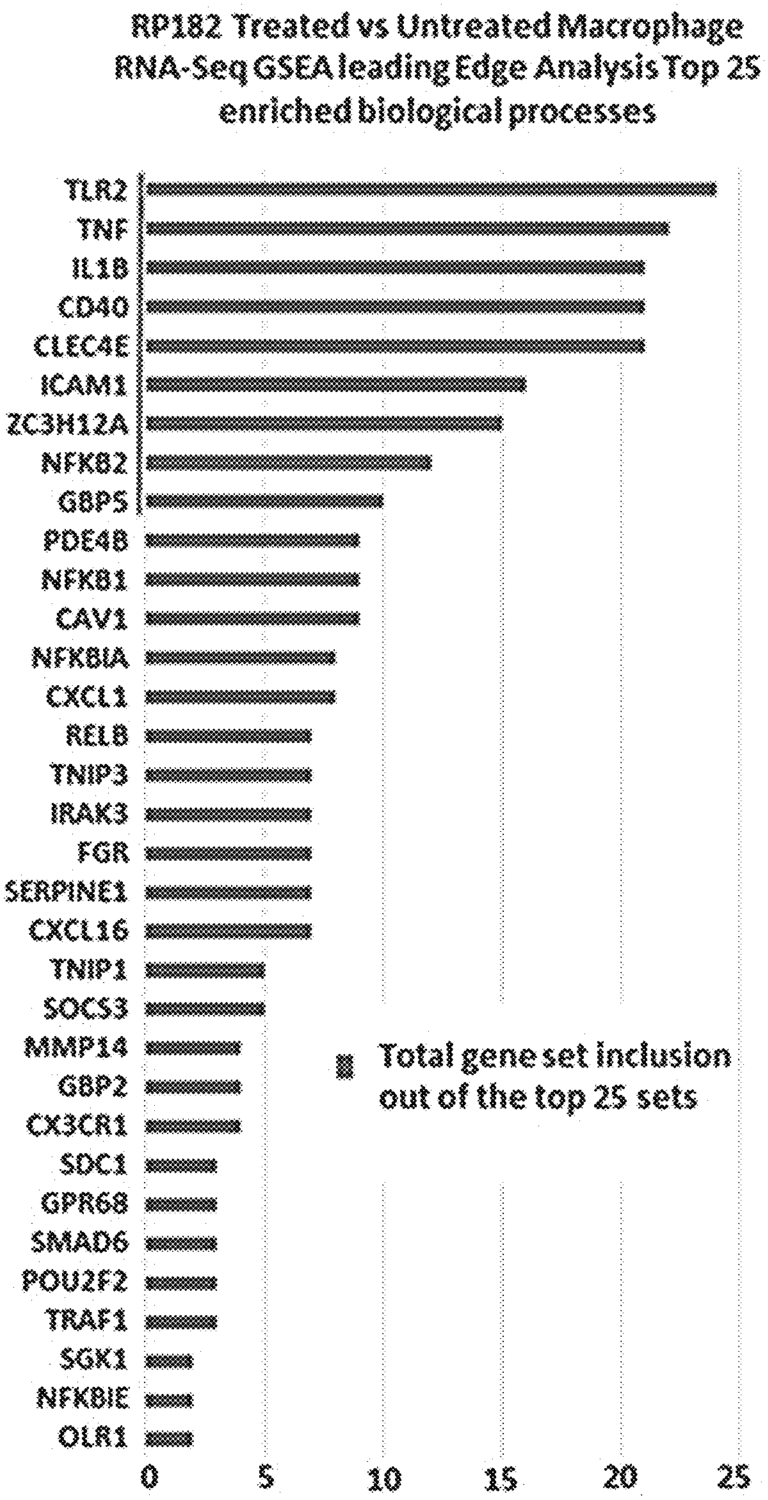
FIG. 21C shows RP182 treated vs. untreated macrophage RNA-Seq
Figure 21E:
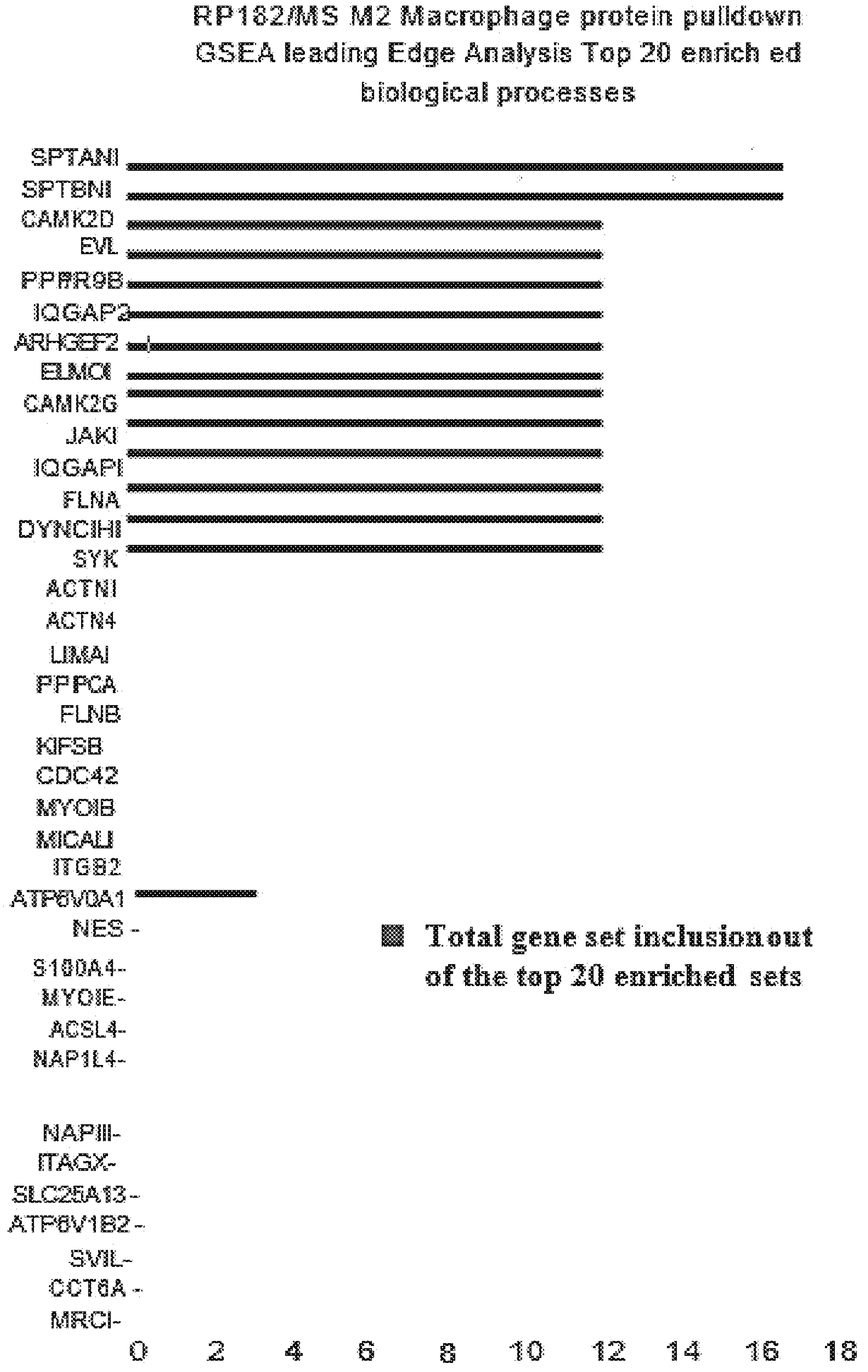
FIG. 21E shows RP182/MS M2 macrophage protein pulldown

The most commonly represented genes identified by Leading Edge Analysis after Gene Set Enrichment Analysis (GSEA) were imputed into Pathway Studio® which identified processes of endocytosis, phagocytosis, autophagy, and apoptosis as top biological pathways affected by RP-182 in M2 macrophages (FIG. 20). Proteomic analysis of binding partners in CD206 complexes pulled down after 10 minutes of treatment with RP-182 compared to bead-only control showed enrichment of proteins involved in similar cell processes (FIG. 21A, FIG. 4, and FIGS. 21B-E).

Figure 22:
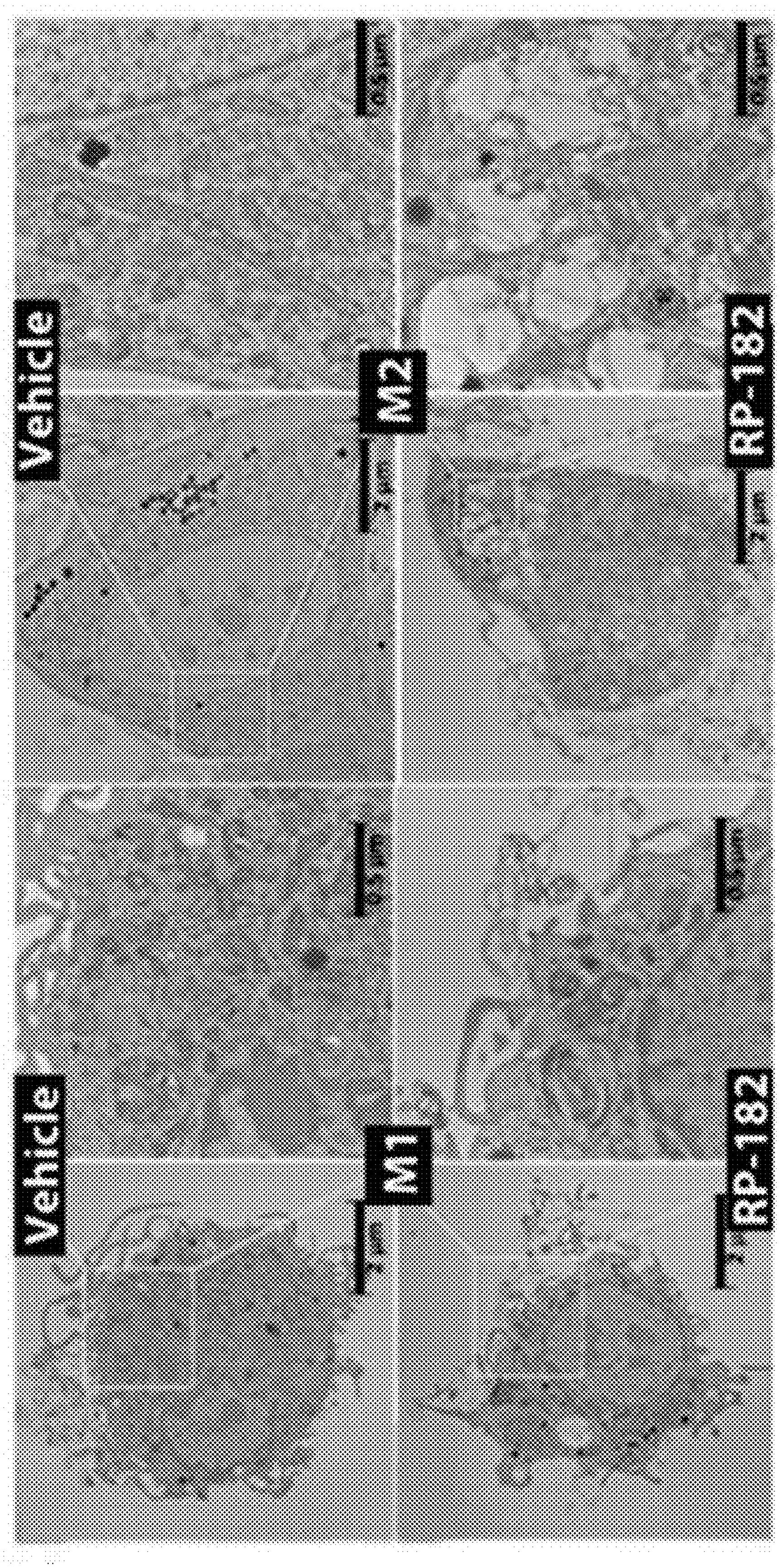
FIG. 22 shows electron microscopy images (at 1,000×; zoom 2.400×) of M1- and M2-polarized BMDMs.
Figure 23:
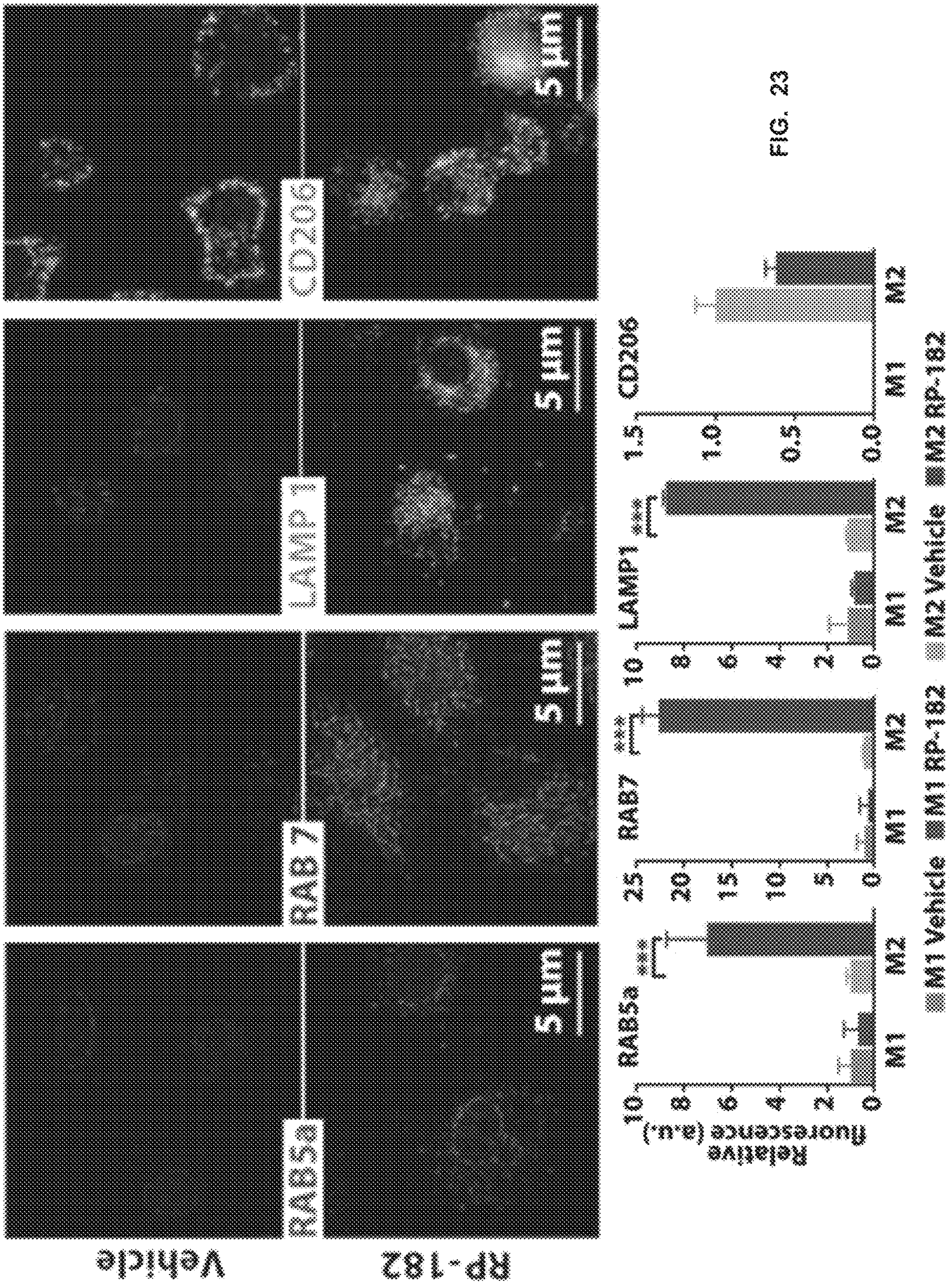
FIG. 23 shows immunofluorescence images of BMDMs polarized into M2 stained with anti-Rab5. Rab7. LAMP-1, and CD206 antibodies, nuclei with DAPI. Quantification of induced fluorescence on bottom. For all figures, data shown are representative of three independent experiments and normalized to corresponding vehicle treatment unless indicated otherwise.
Figure 24:
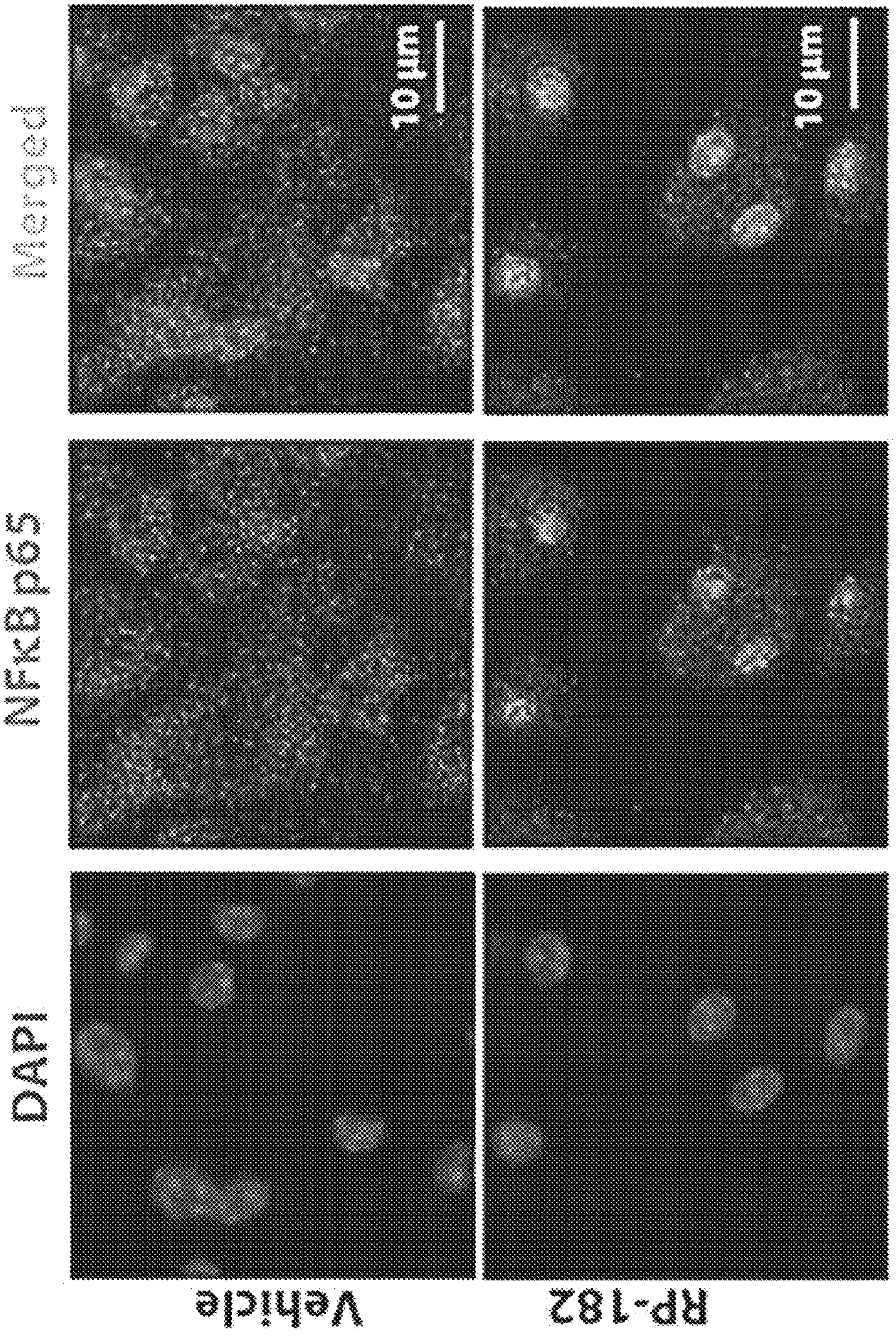
FIG. 24 shows that RP-182 activates phagocytosis and phagolysosome formation in M2- but not M1-polarized human macrophages derived from peripheral blood mononuclear cells (PBMC)s of healthy volunteers. Immunofluorescence of human macrophages derived from CD14-positive PBMCs of healthy donors and polarized into M1 and M2 populations stained with anti-Rab5, Rab7, LAMP-1, and CD206 antibodies. Representative images at 40×. Quantification of RP-182-induced Rab5, Rab7, LAMP-1, and CD206 expression levels in M1 (blue bars) and M2 (red bars) BMDMs is shown on the left. Fluorescence (bright objects) was normalized to the number of nuclei (DAPI), and vehicle-treated signal was set to 1. At least 100 cells in ≥5 independent fields were measured. Macrophages were treated with 20 μM RP-182 for 2 hours.
Figure 25A:
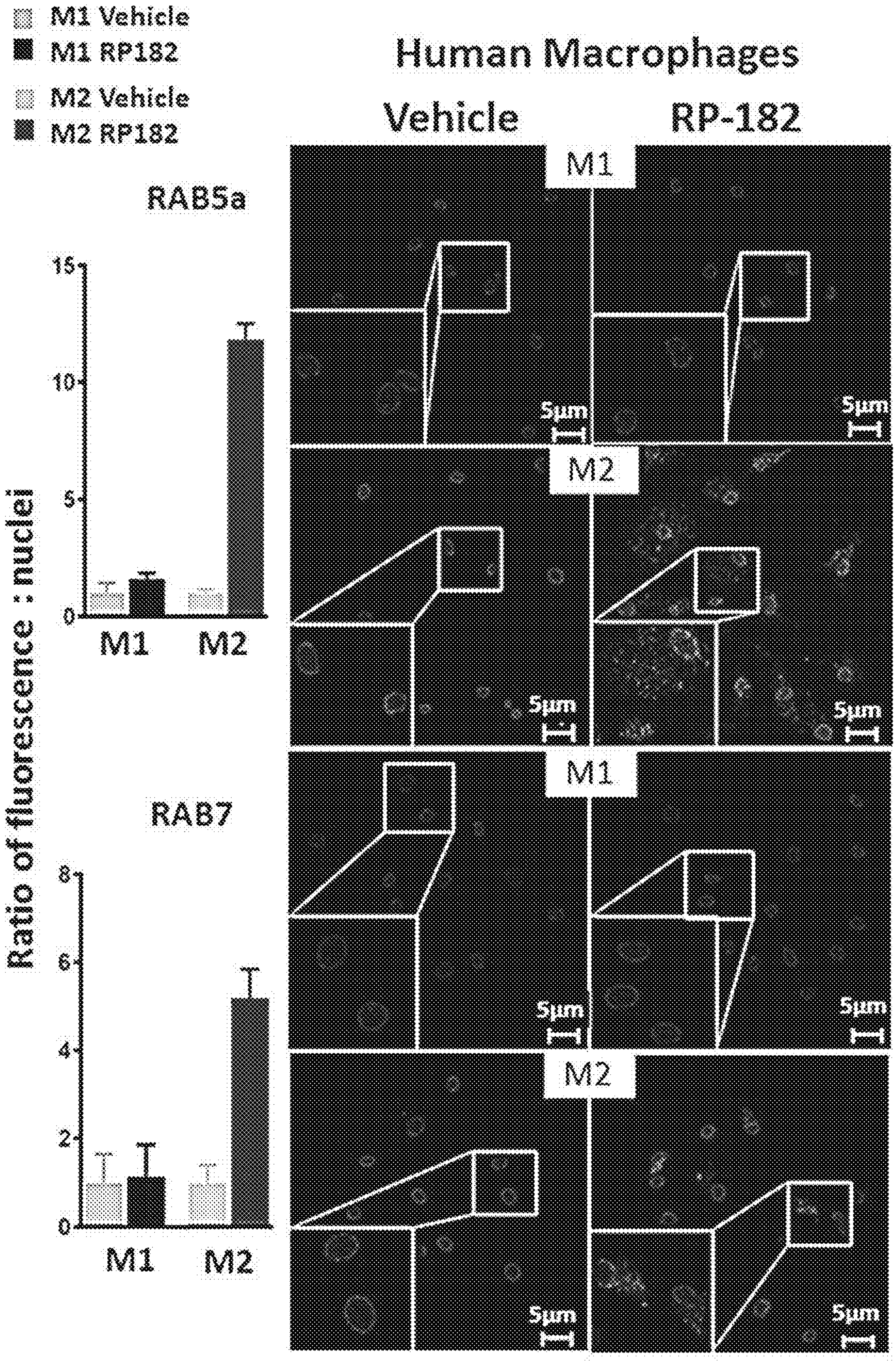
FIG. 25A shows that RAB5a and RAB7 RP-182 activates phagocytosis and phagolysosome formation in M2- but not M1-polarized human macrophages derived from peripheral blood mononuclear cells (PBMC)s of healthy volunteers. Immunofluorescence of human macrophages derived from CD14-positive PBMCs of healthy donors and polarized into M1 and M2 populations stained with anti-Rab5, Rab7, LAMP-1, and CD206 antibodies. Representative images at 40×. Quantification of RP-182-induced Rab5, Rab7, LAMP-1, and CD206 expression levels in M1 (blue bars) and M2 (red bars) BMDMs is shown on the left. Fluorescence (bright objects) was normalized to the number of nuclei (DAPI), and vehicle-treated signal was set to 1. At least 100 cells in 25 independent fields were measured. Macrophages were treated with 20 μM RP-182 for 2 hours.
Figure 25B:
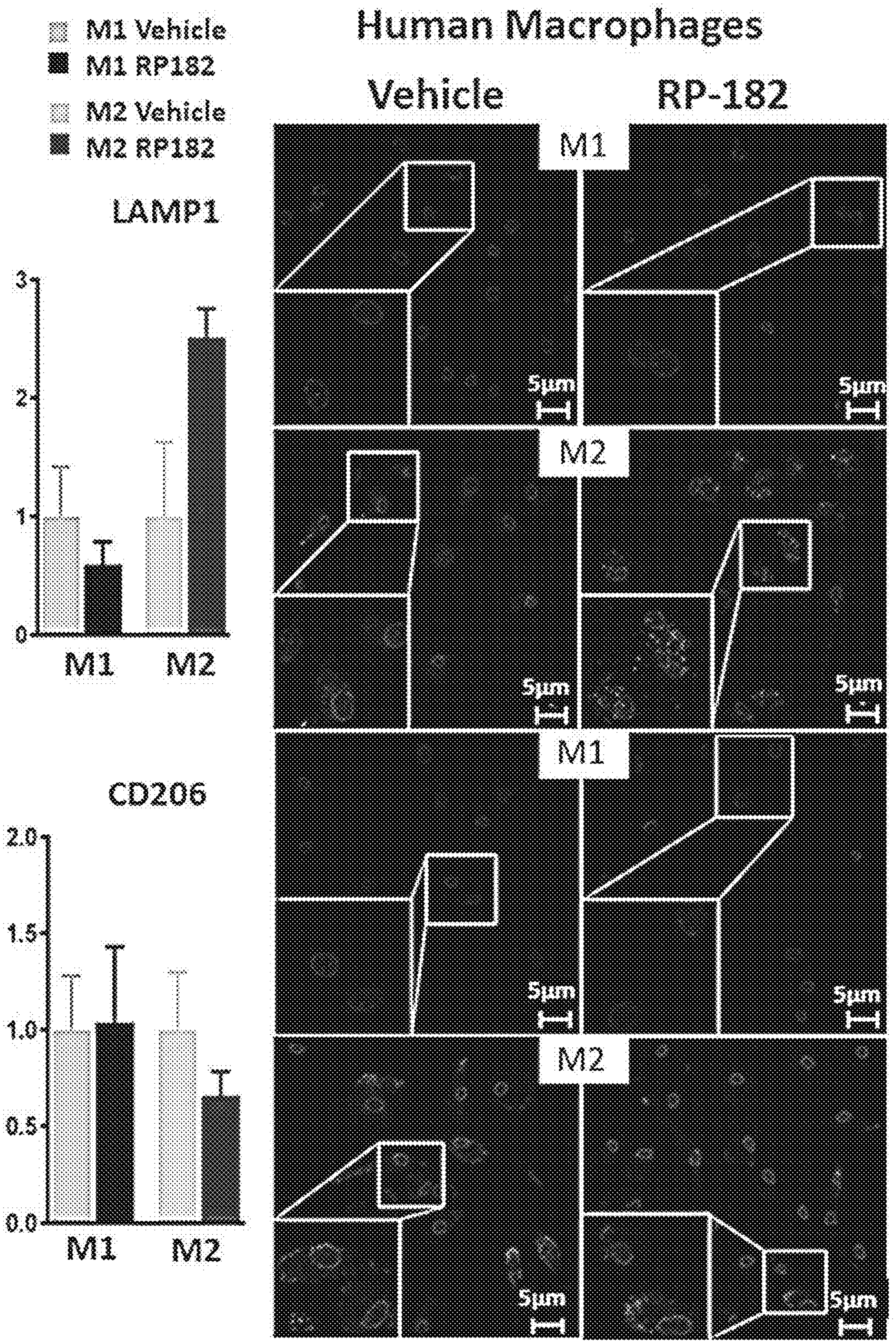
FIG. 25B shows that MAP1 and CD206 RP-182 activates phagocytosis and phagolysosome formation in M2- but not M1-polarized human macrophages derived from peripheral blood mononuclear cells (PBMC)s of healthy volunteers. Immunofluorescence of human macrophages derived from CD14-positive PBMCs of healthy donors and polarized into M1 and M2 populations stained with anti-Rab5. Rab7. LAMP-1, and CD206 antibodies. Representative images at 40×. Quantification of RP-182-induced Rab5. Rab7. LAMP-1, and CD206 expression levels in M1 (blue bars) and M2 (red bars) BMDMs is shown on the left. Fluorescence (bright objects) was normalized to the number of nuclei (DAPI), and vehicle-treated signal was set to 1. At least 100 cells in ≥5 independent fields were measured. Macrophages were treated with 20 μM RP-182 for 2 hours.
Figure 26:
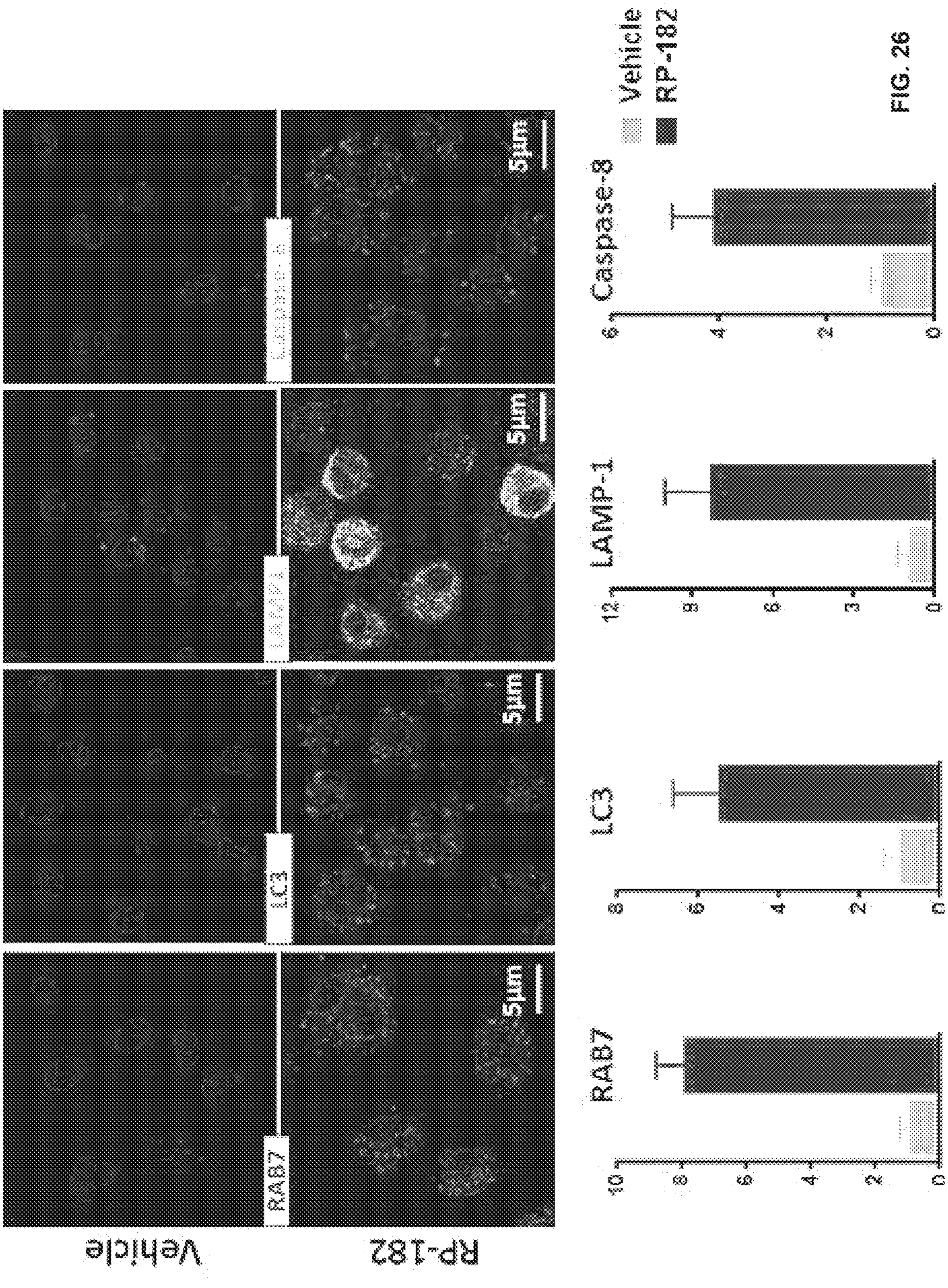
FIG. 26 shows RP-182 activates phagocytosis, autophagy, and apoptosis in BMDMs co-cultured with conditioned media from PANC1 cells. Representative images at 40× on top. Quantification of RP-182-induced Rab7, LC-3, LAMP-L. and cleaved caspase 8 expression levels (red bars) cells is shown on bottom. Fluorescence (bright objects) was normalized to the number of nuclei (DAPI), and vehicle-treated signal was set to 1. At least 100 cells in 25 independent fields were measured. Macrophages were treated with 20 μM RP-182 for 2 hours.
Figure 27A:
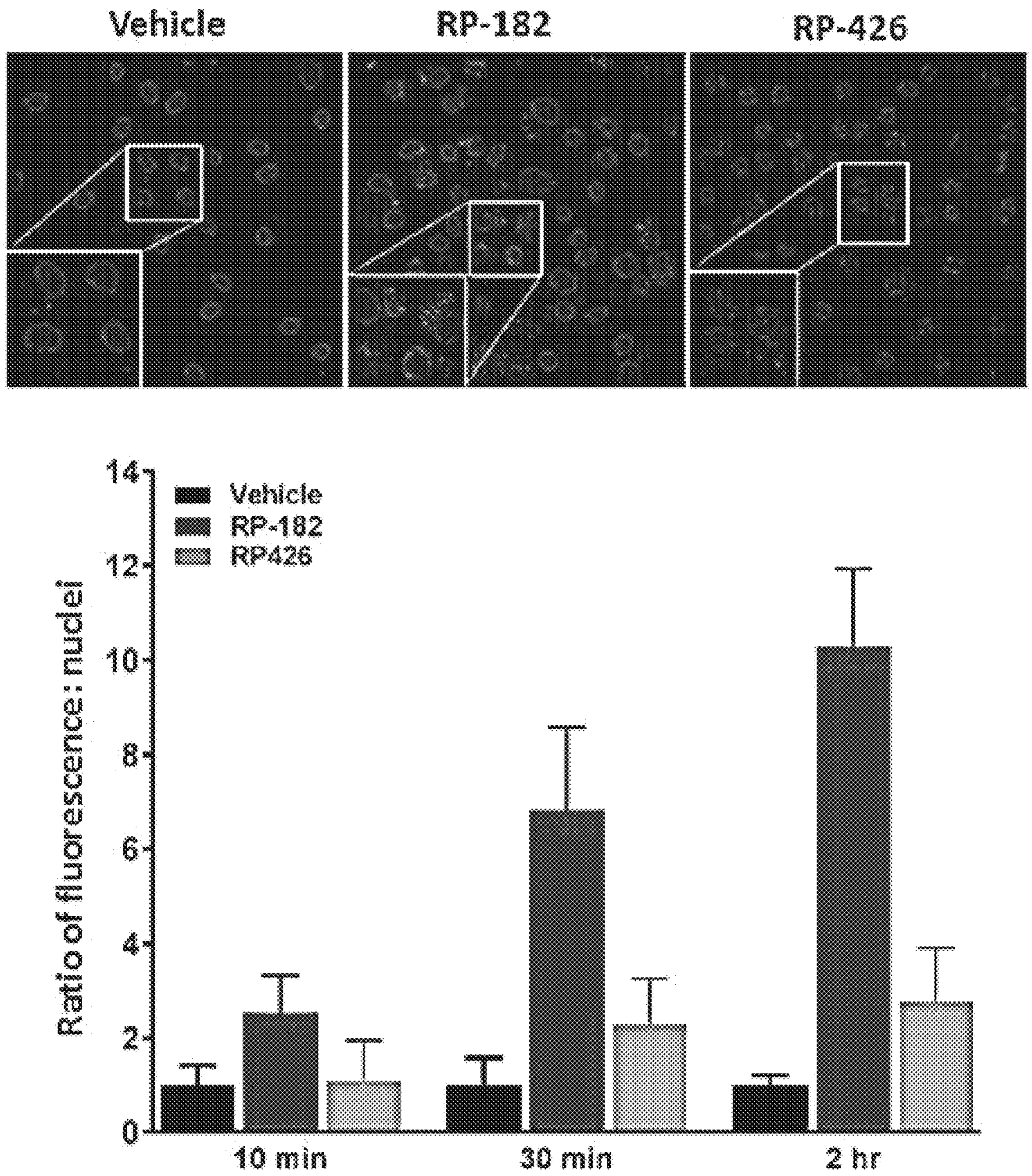
FIG. 27A shows RP-182 but not control peptide RP-426 induces phagocytosis in M2-polarized BMDMs. A. Rab7 levels by immunocytochemistry in M2-polarized macrophages treated with vehicle, 20 μM of RP-182 or RP-426. Fluorescence (bright objects) was normalized to number of nuclei (DAPI), and vehicle-treated was set at 1. At least 100 cells in 25 independent fields were measured.
Figure 27B:
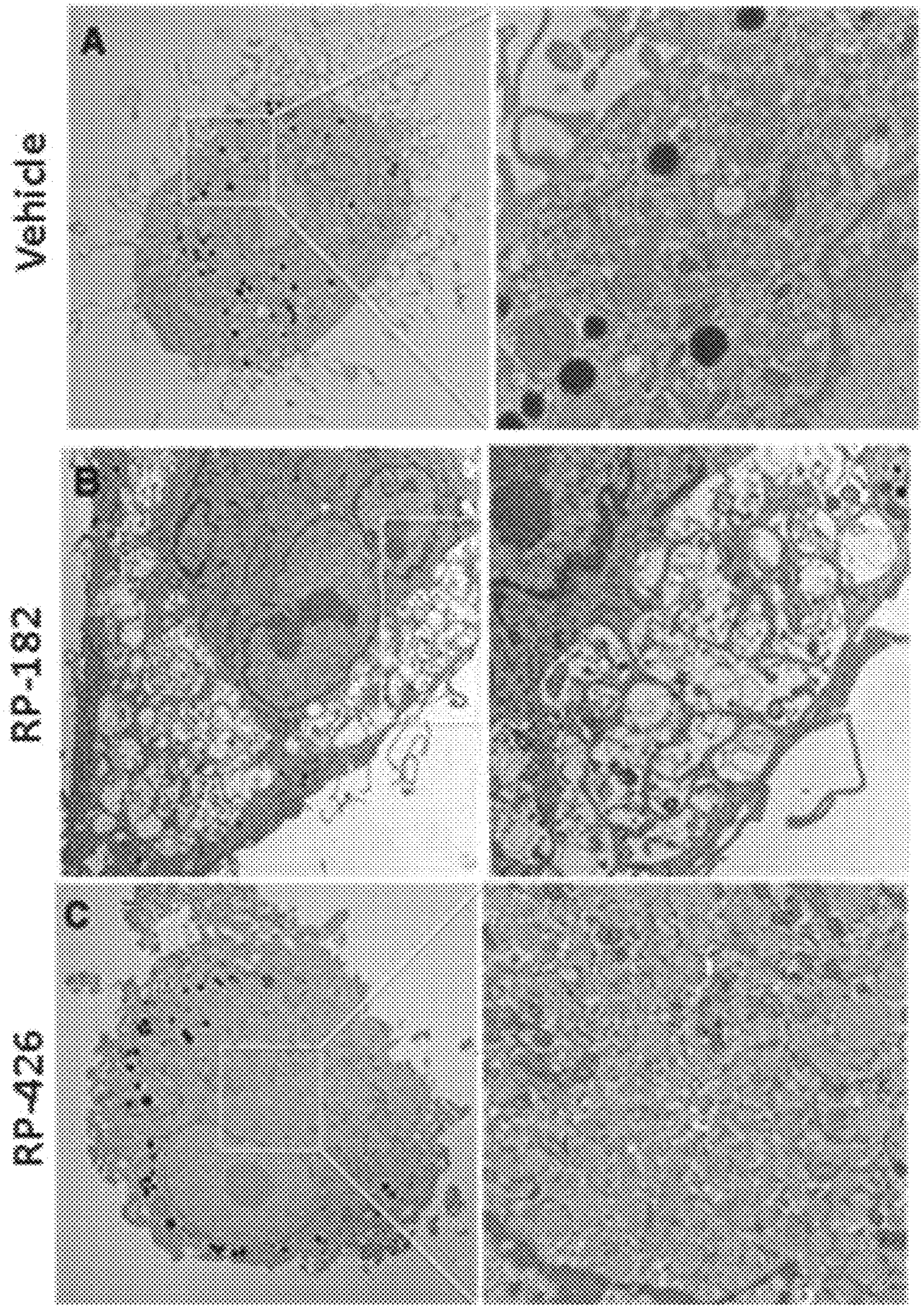
FIG. 27B shows induction of phagosomes in RP-182-treated but not RP-426-treated M2 macrophages. Electron microscopy images (representative image at 1,000× magnification shown on left; zoom 2,400× on right), shows phagosome with internal membrane structures.
Figure 28:
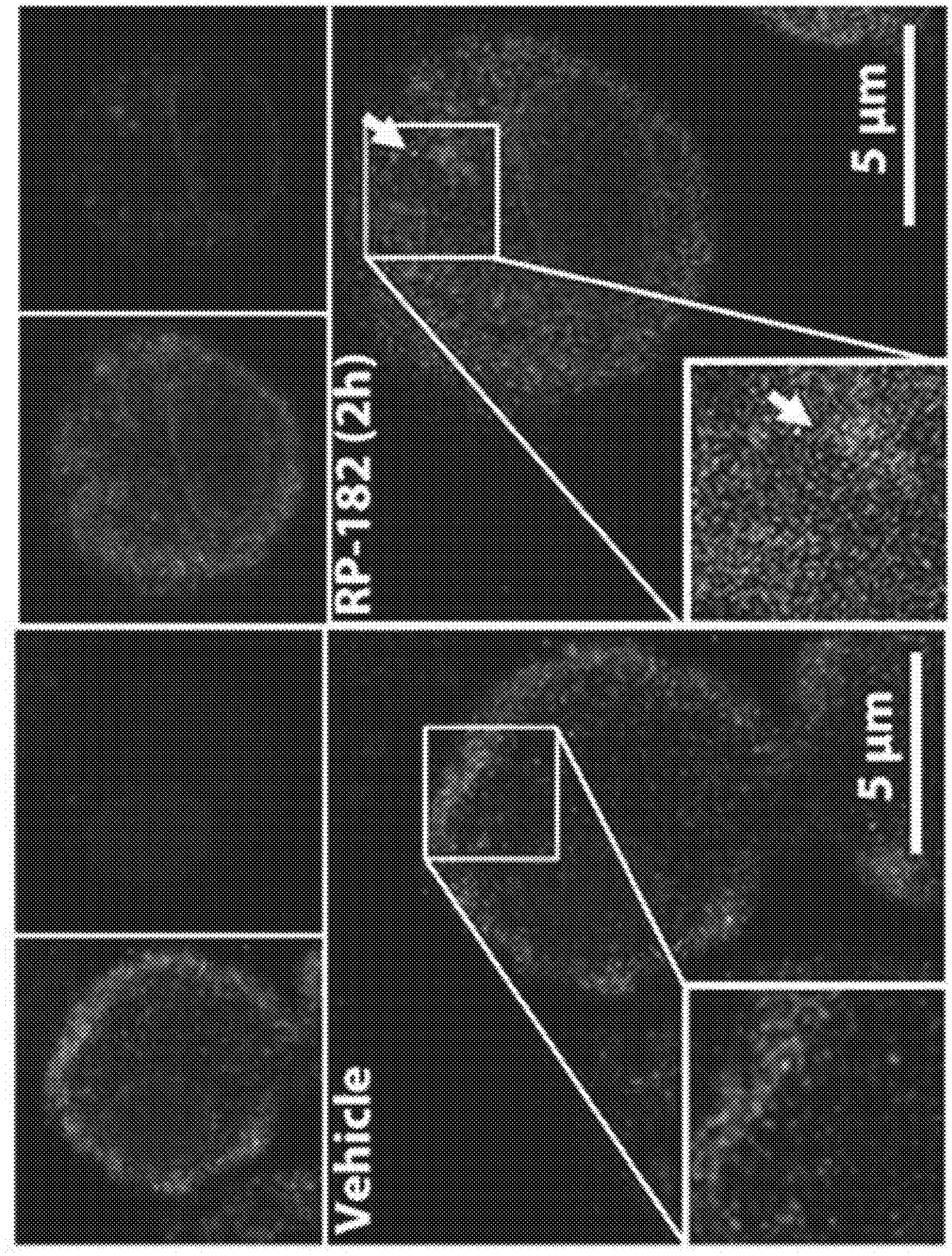
FIG. 28 shows immunofluorescence images of M2 BMDMs stained with anti-NF-kB/p65.
Figure 29:
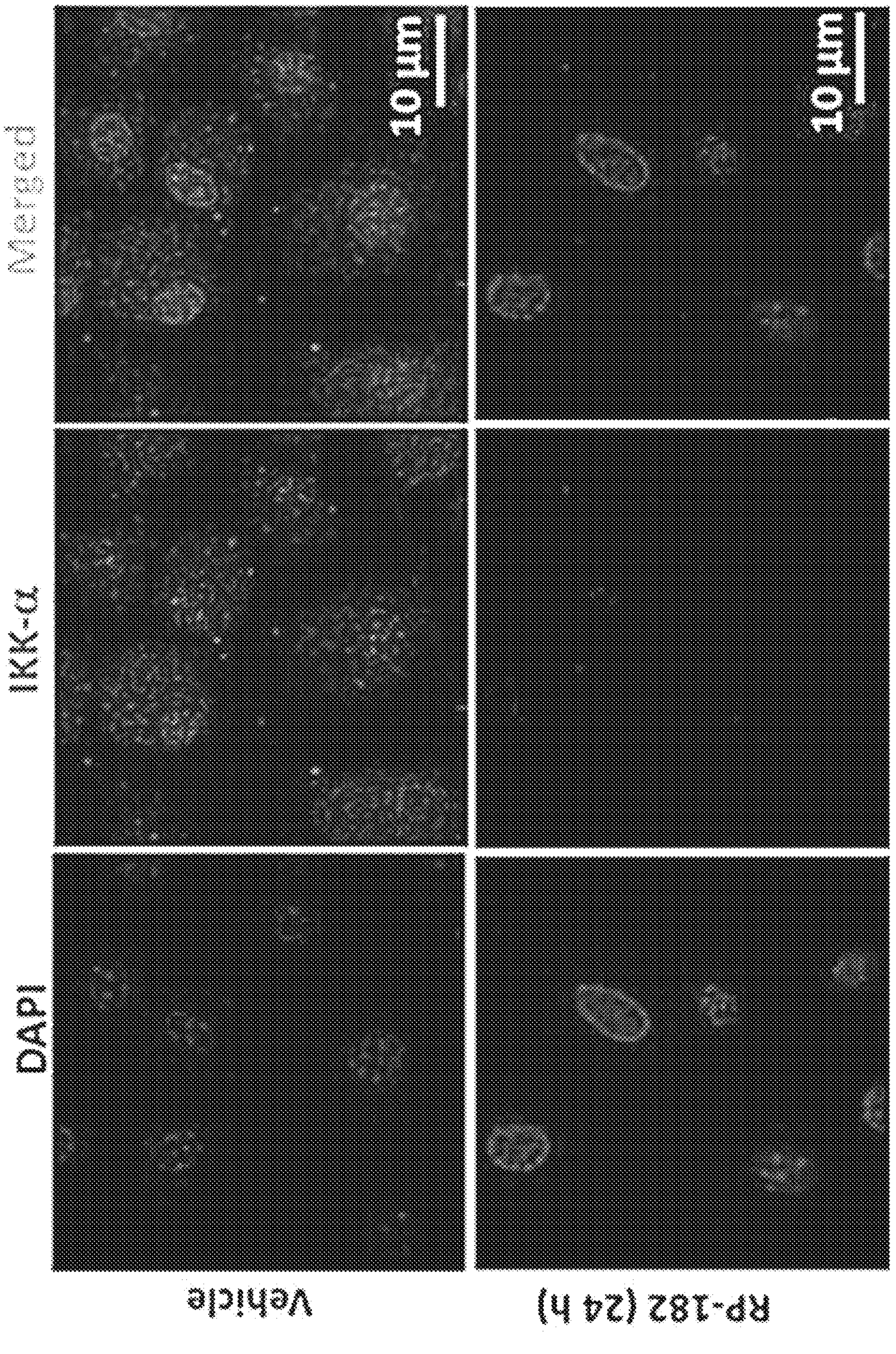
FIG. 29 shows that RP-182 reduces cytoplasmic expression of the negative regulator of macrophage activation and inflammation IKKα subunit of the IkappaB kinase (IKK) complex and activates autophagy and caspase 8 in M2-polarized BMDMs. A. Immunofluorescent staining of IKKα in M2 BMDMs after 2 hours treatment with vehicle and RP-182.

To confirm results of above analyses, BMDMs were evaluated and polarized into M1 and M2 by electron microscopy. RP-182 induced phagosomes in M2- but not M1-polarized BMDMs (FIG. 22). M2-selective induction of phagocytosis was confirmed by upregulation of the early and late endosomal markers Rab5a and Rab7, and the lysosomal-associated membrane protein 1 (LAMP-1) (FIG. 23). Upon treatment with RP-182, CD206 was increasingly detected in the cytoplasm and induced Rab7-positive phagosomes co-stained with CD206, findings in line with the known internalization of the mannose receptor (FIG. 24). Selective induction of phagosomes in the M2 phenotype upon treatment with RP-182 was equally observed in M2-polarized CD14+ peripheral monocytes isolated from healthy volunteers (FIG. 25A-B) and in BMDMs polarized into an 'in vitro TAM-like' phenotype after co-culture with conditioned media from cancer cells (FIG. 26). Control peptide RP-426 did not induce phagocytosis (FIG. 27A-B). RP-182 activated NF-kB signaling (FIG. 28 and FIG. 29).

Figure 30:
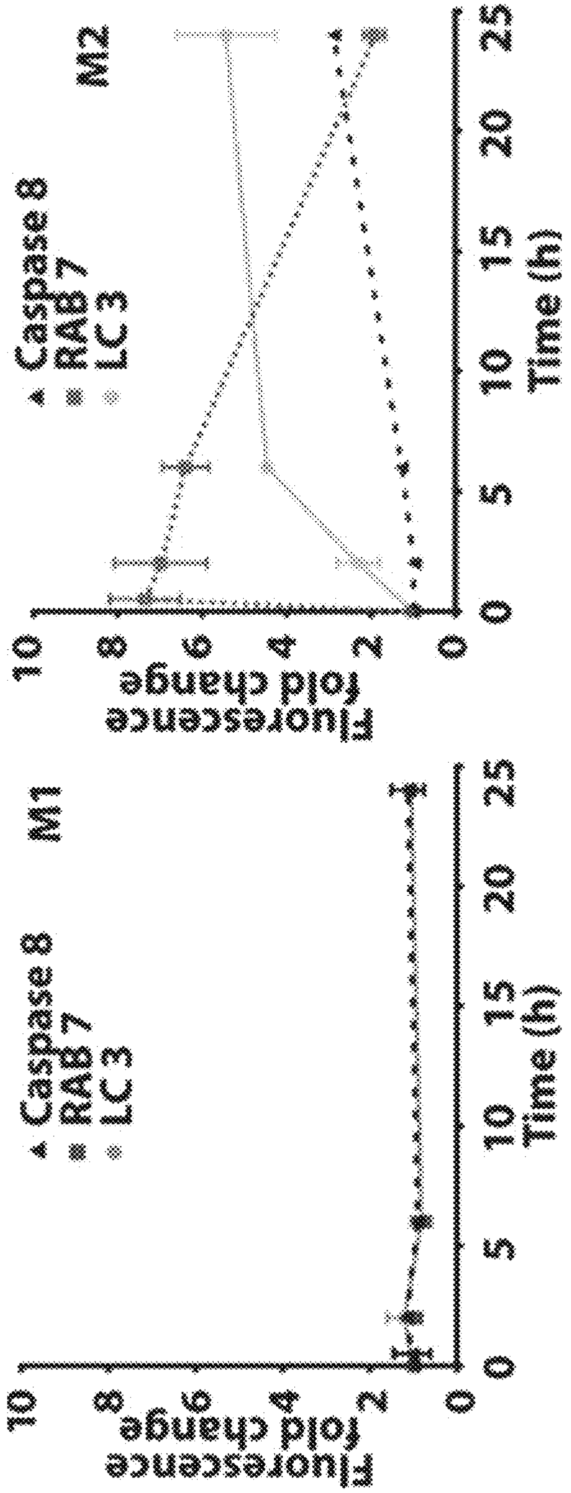
FIG. 30 shows quantification of activation of phagocytosis, autophagy, and apoptosis in M1 and M2 macrophages over time.
Figure 31:
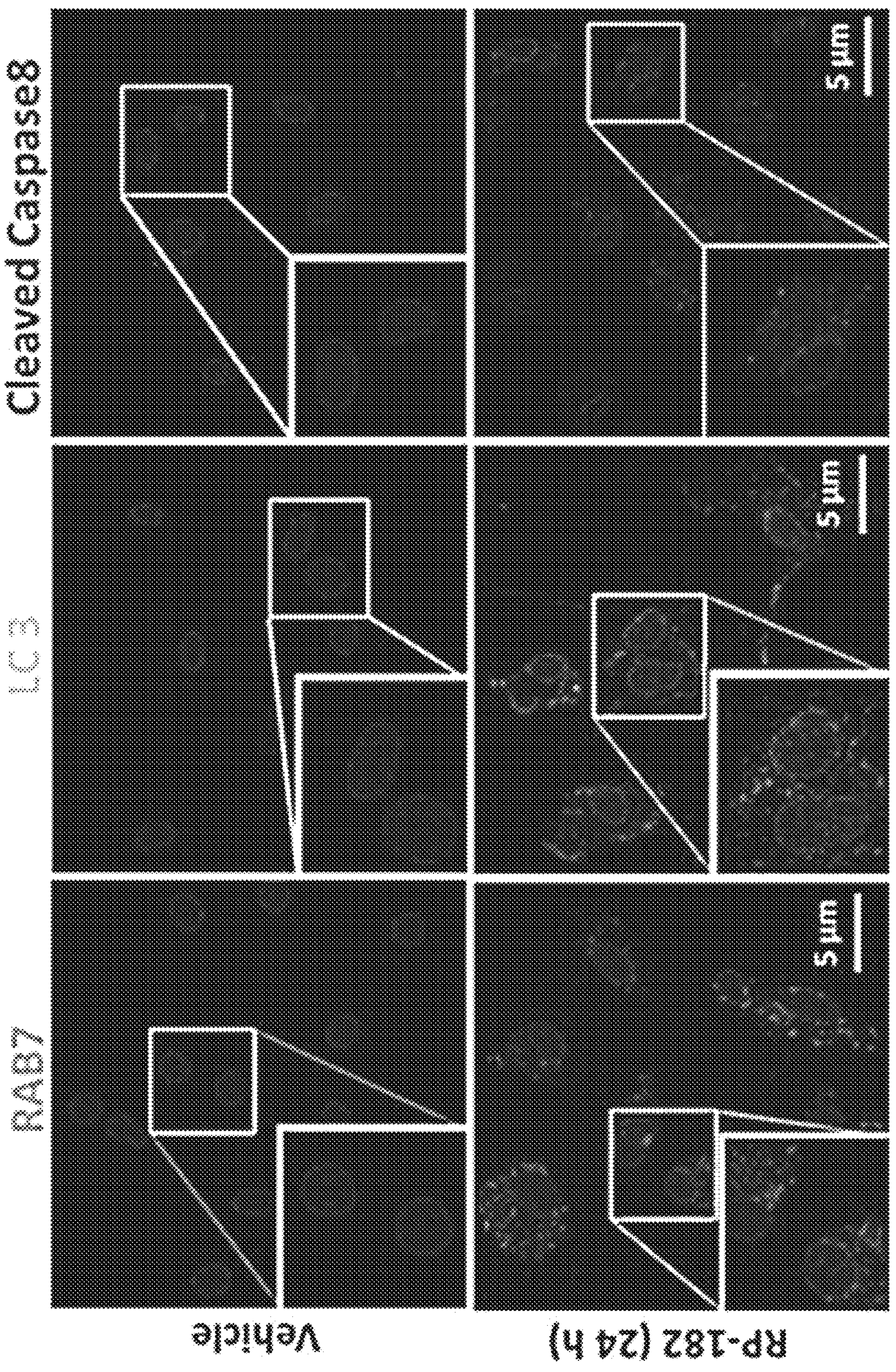
FIG. 31 shows activation of autophagy and apoptosis in M2 macrophages by RP-182 measured by immunofluorescent staining of LC3 and cleaved caspase 8. Representative immunofluorescent images of vehicle- and RP-182-treated M2 macrophages at 24 hours.
Figure 32:
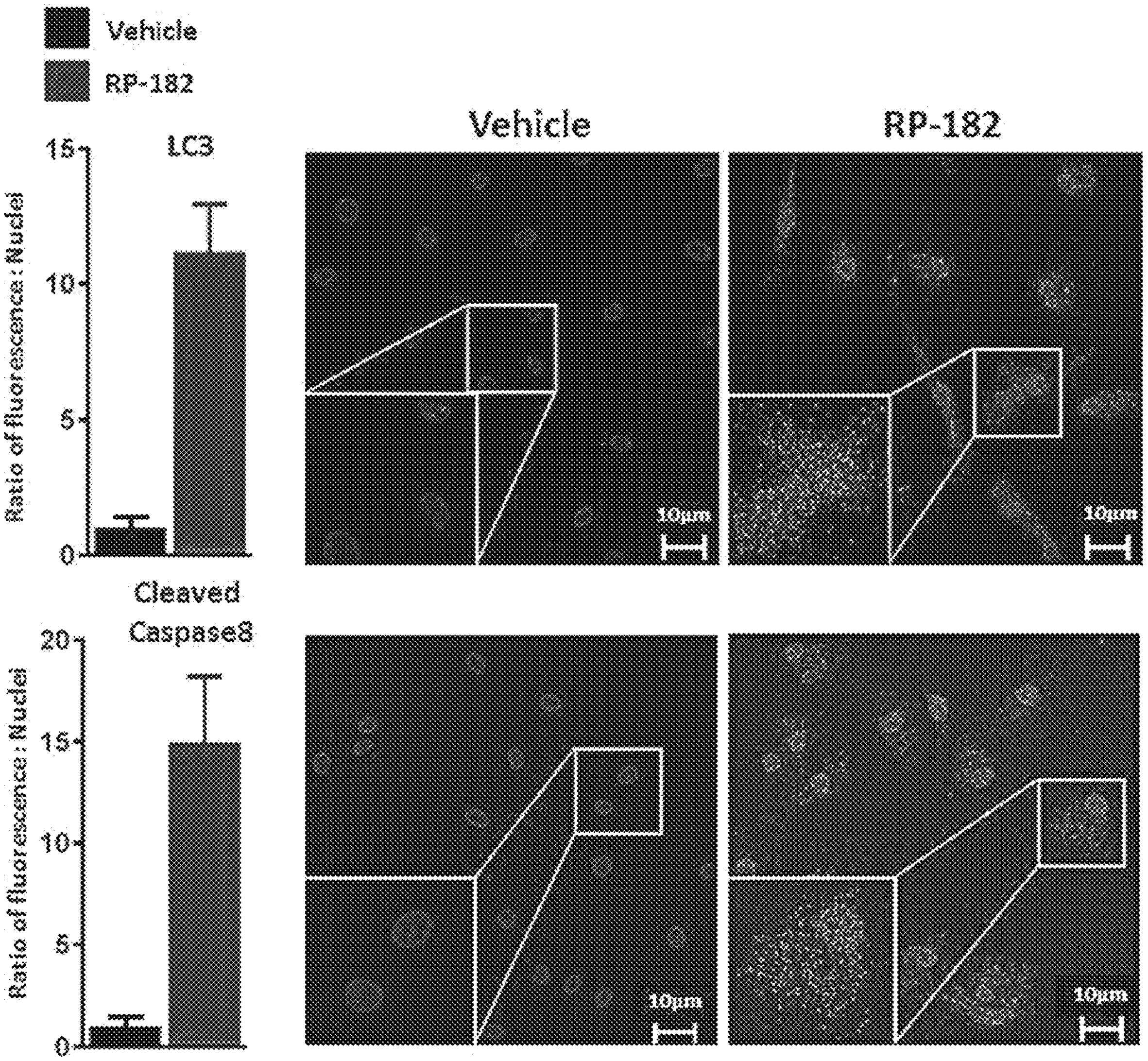
FIG. 32 shows RP-182 activates autophagy and apoptosis in human M2 macrophages. LC3 and cleaved caspase 8 levels were measured by immunocytochemistry staining of human M2 macrophages after 24 hours treatment with RP-182. Measured fluorescence (bright objects) was normalized to number of nuclei (DAPI), and fold change relative to vehicle control was plotted. Error bars are standard deviations of n≥2 independent experiments, ≥50 cells in 5 independent fields were measured.
Figure 33:
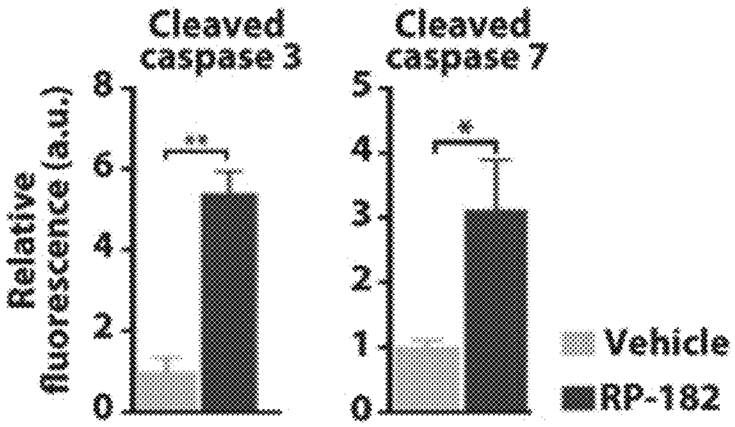
FIG. 33 shows quantification of cleaved caspase 3 and 7 levels after 24 hours treatment.
Figure 34:
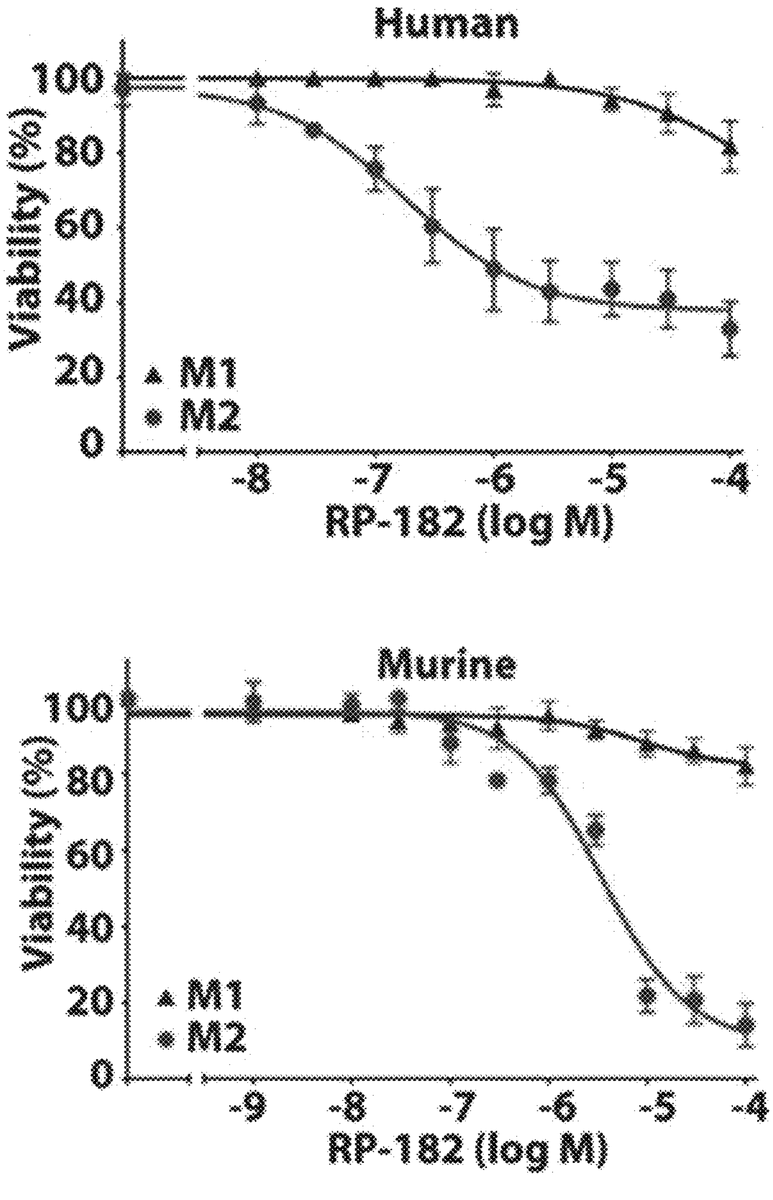
FIG. 34 shows cell viability of human and murine M1 (blue curves) and M2 (red curves) macrophages after 48 hours treatment with RP-182 relative to vehicle treatment.
Figure 35:
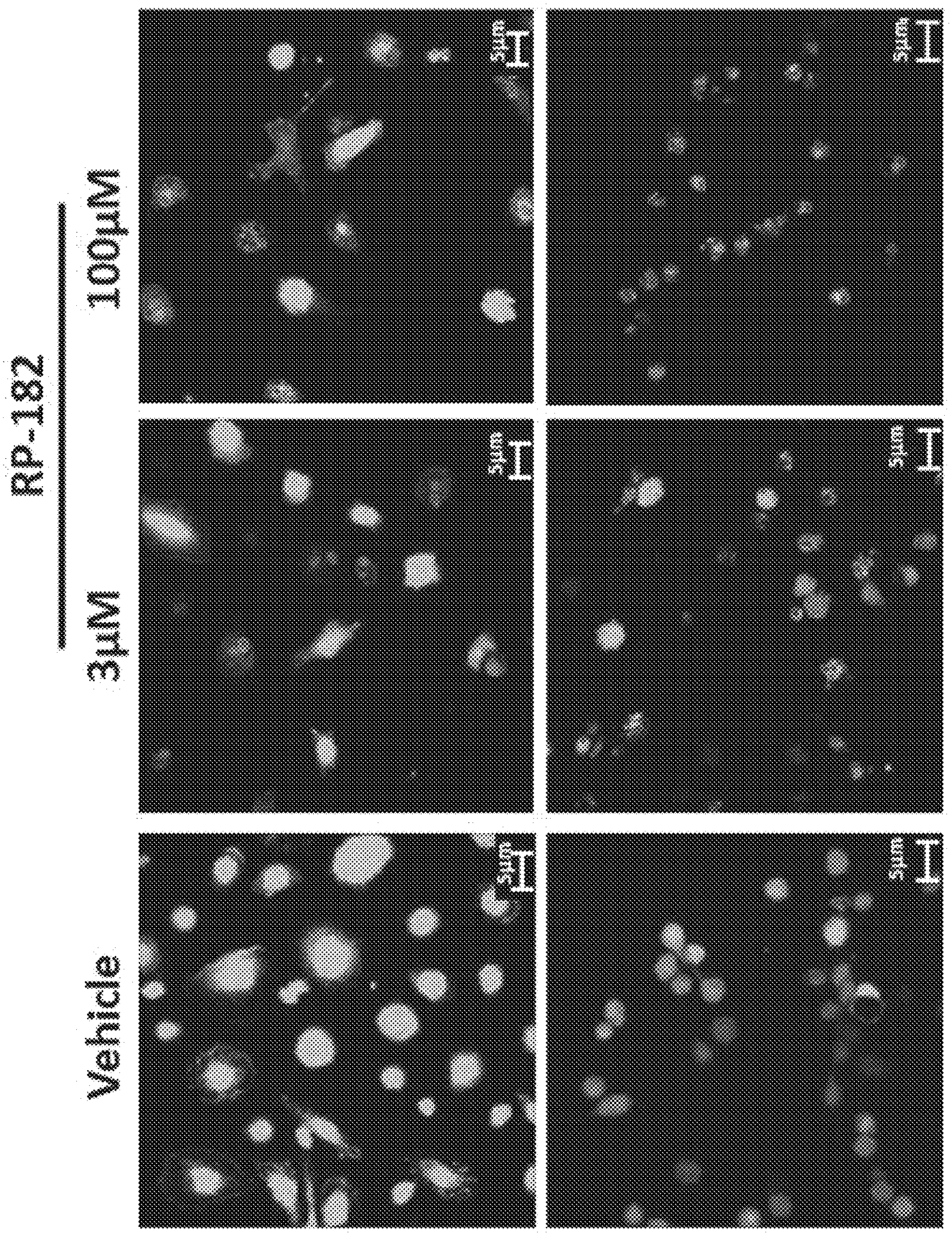
FIG. 35 shows RP-182 but not RP-426 induces cell death in M2-polarized macrophages. A. Representative images of M2 BMDMs treated with vehicle or RP-182 and stained after 48 hours using dual calcein AM (green)-ethidium homodimer (red). Viability for dose response curves shown in FIG. 2K was calculated as ratio of live cells (positive calcein AM and negative red staining) and dead cells (absent green, positive red staining).
Figure 36:
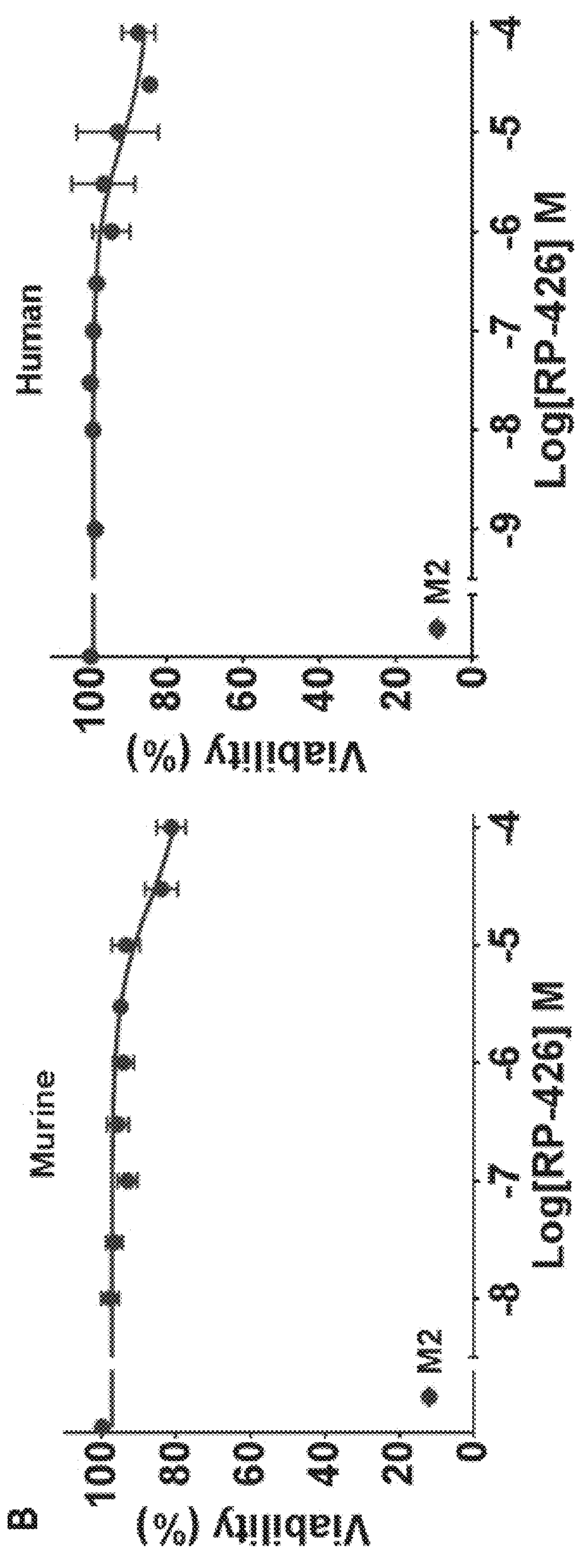
FIG. 36 shows dose-response curves of control peptide RP-426 in human (left) and murine (right) M2-polarized macrophages. Ratios of viable cells were normalized to vehicle-treated control, error bars represent standard deviations of two independent experiments in triplicates.
Figure 37:
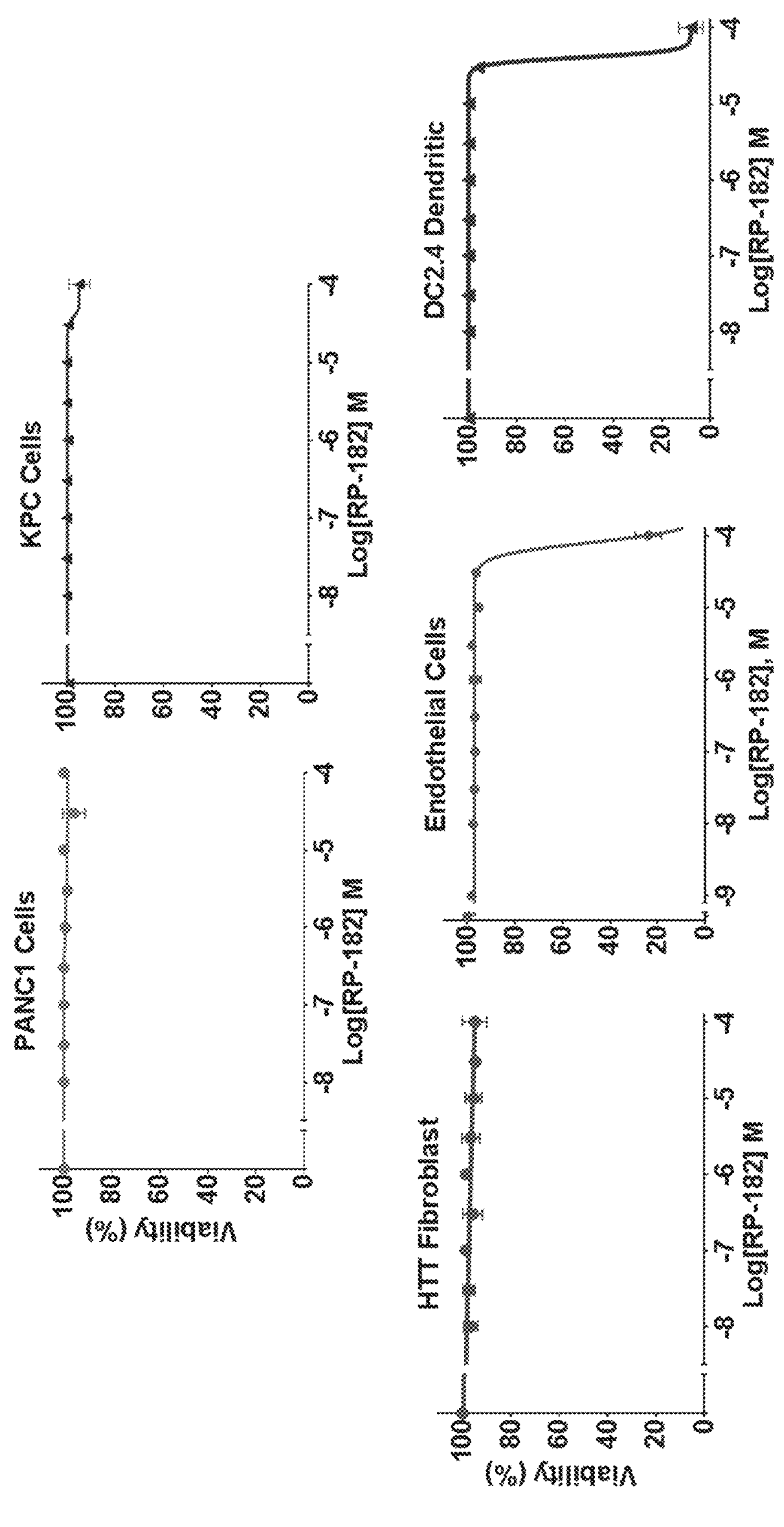
FIG. 37 shows RP-182 does not inhibit cell growth of pluripotent progenitor cells, cancer cells, fibroblasts, or endothelial or dendritic cells. Dose-response curves of RP-182 in human pancreas cancer cells PANC1, murine KPC, human fibroblasts, endothelial, and DC2.4 dendritic cells. Cells were stained after 48 hours using dual calcein AM (green)-ethidium homodimer (red) and experiments were conducted in parallel with RP-182 testing in M2 BMDMs as positive control. Representative curves of N=2 independent experiments conducted are shown.

Next, treatment time was extended to 24 hours and measured induction of autophagy and apoptosis across several timepoints. RP-182 sequentially induced phagocytosis, autophagy, and apoptosis in M2 macrophages with no effect on M1 cells (FIG. 30 and FIGS. 31 and 32). RP-182 also induced cleaved caspase 3 and 7, known downstream substrates of activated caspase 8 (FIG. 33). Upon 48 hours exposure to increasing concentrations of RP-182 using a double staining cell viability assay, RP-182 led to a reduction in M2- but not M1-polarized macrophages with calculated potency (IC50) for human M2 and murine M2 of 1.1 and 3.4 μM, respectively (FIG. 34 and FIG. 35). Control peptide RP-426 did not show any activity (FIG. 36), and RP-182 did not affect growth of mesenchymal stem cells, murine and human cancer cells, fibroblasts, or endothelial and D2.4 dendritic cells (FIG. 37).

Example 3: Effect Of RP-182 on M2 Macrophages

It was found that RP-182 reprograms M2 macrophages towards a M1-like phenotype. The observation that viable cell fractions after 48 hours of treatment with RP-182 at highest concentrations were greater than the initial fraction of CD206 negative cells (31% viable cells after max response vs 6.8% CD206-negative cells in human M2 macrophages; 17.2% viable cells vs 12.7% CD206-negative cells in M2 BMDMs) led us to examine a possible second mechanism of action of RP-182. It was speculated that M2 macrophages reprogrammed by RP-182 towards a M1-like phenotype may lose CD206 expression and might not be subject to the cell killing function of RP-182.

Figure 38:
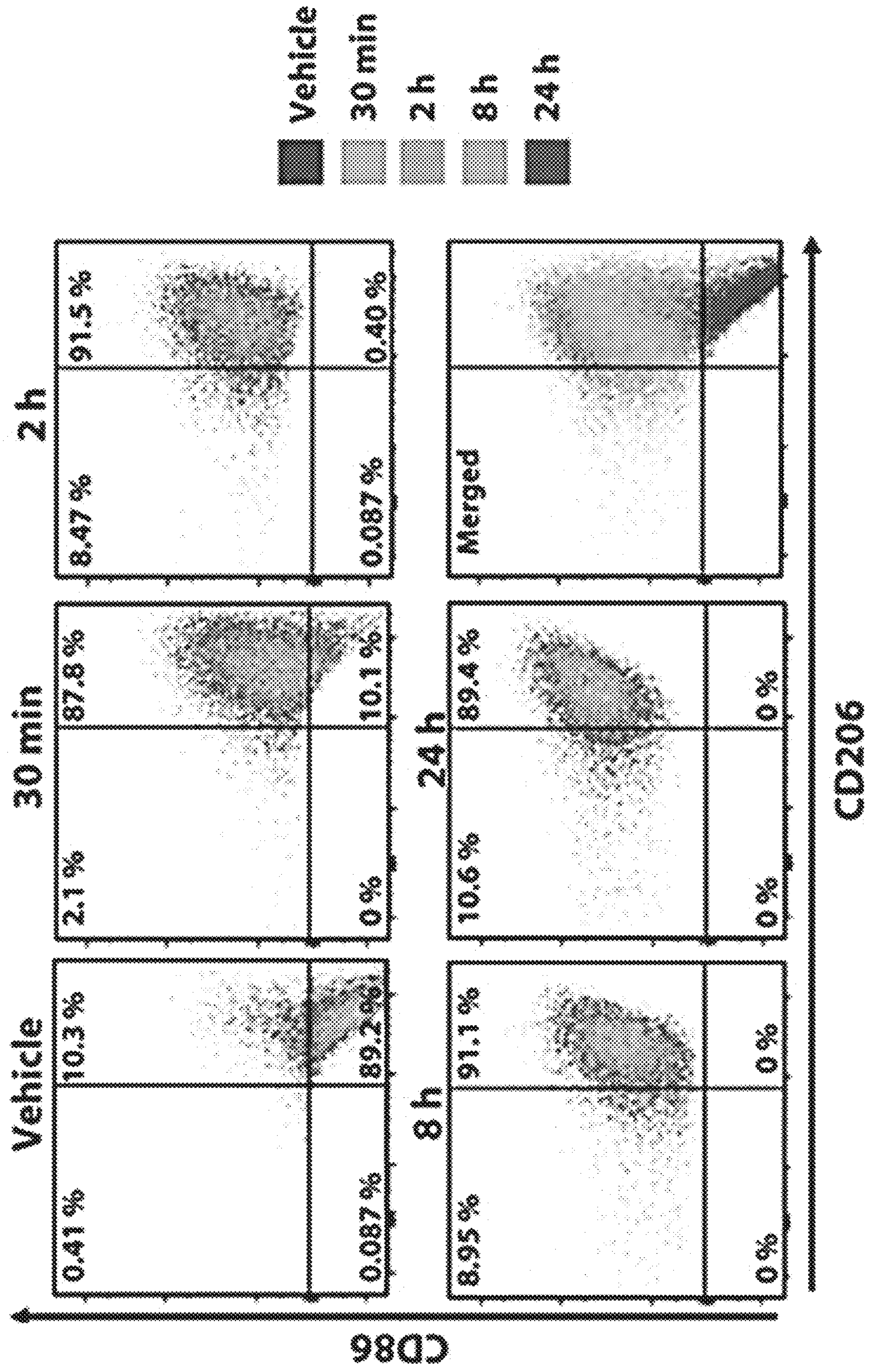
FIG. 38 shows flow cytometry plots of CD86 and CD206-positive CD11B+F4/80+Gr-1-macrophage fractions of M2 BMDMs after treatment with vehicle or RP-182 at indicated timepoints.
Figure 39A:
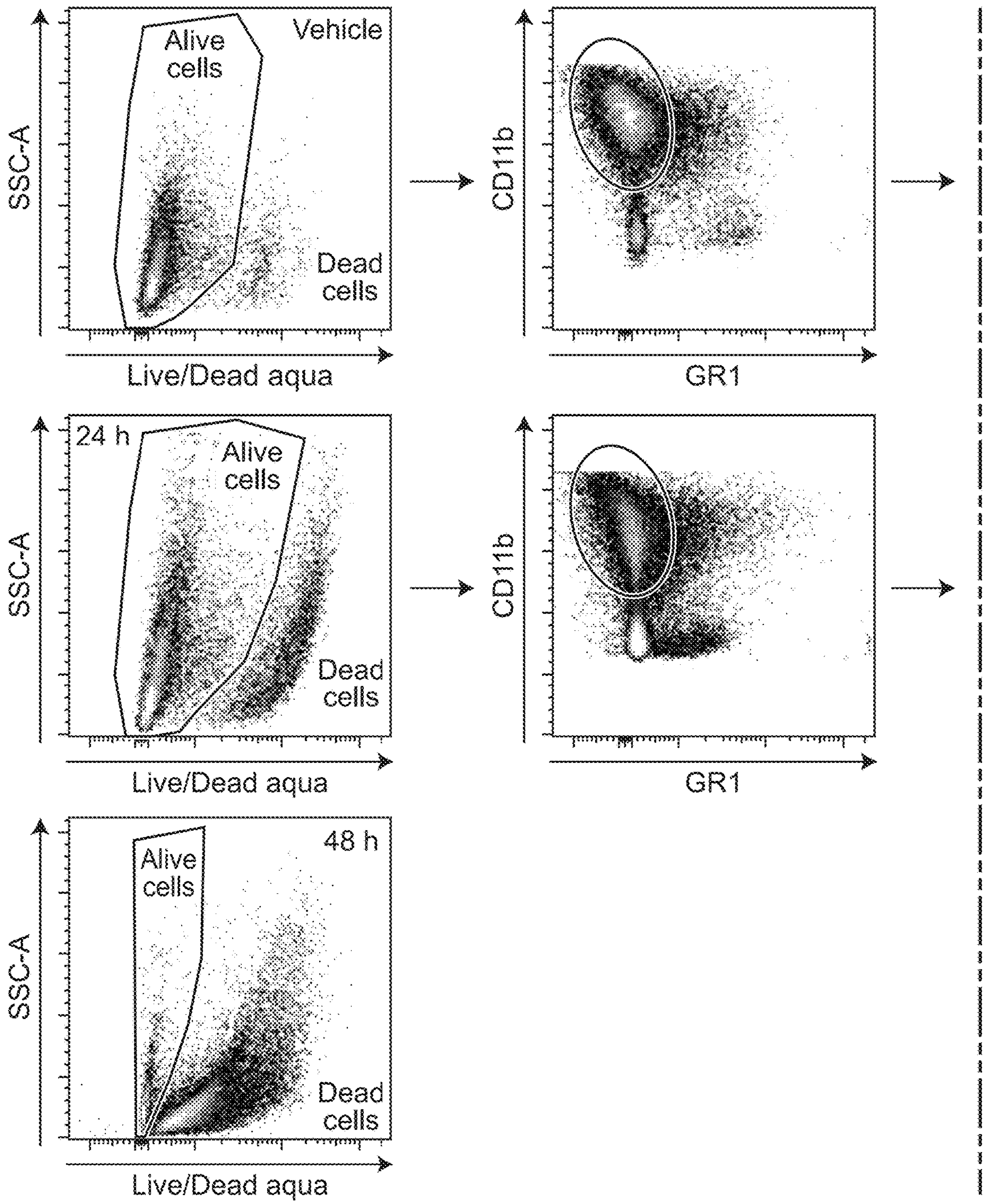
FIG. 39A shows gating strategy for the determination of CD86+ and CD206-positive CD11b+F4/80+Gr-1− macrophage fractions. A. Representative flow cytometry plots depicting gating strategy for determination of CD86 and CD206-positive macrophages after treatment with vehicle. RP-182 for 24 (middle) and 48 hours (bottom). Alive cells circled in black
Figure 39A:
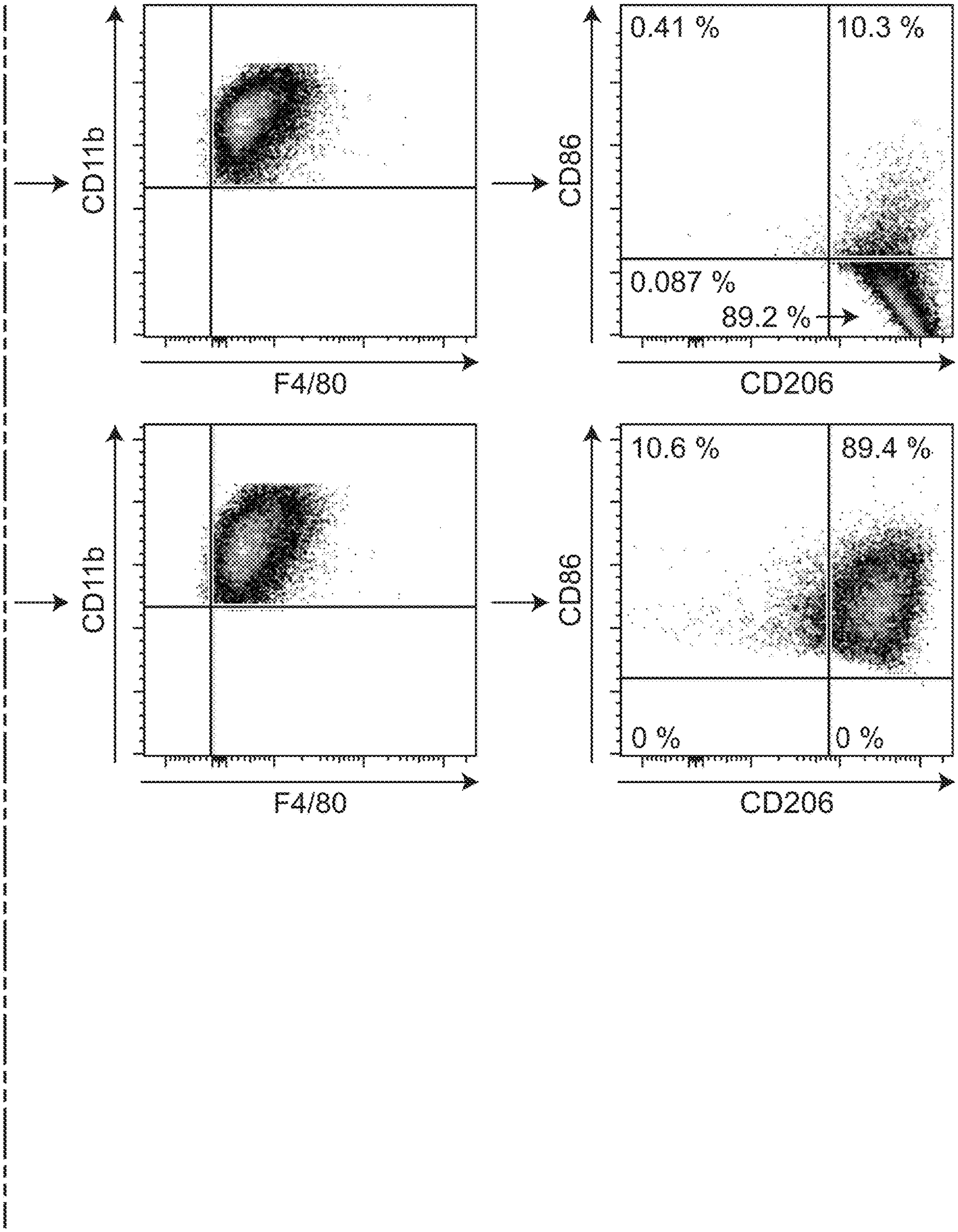
Figure 39B:
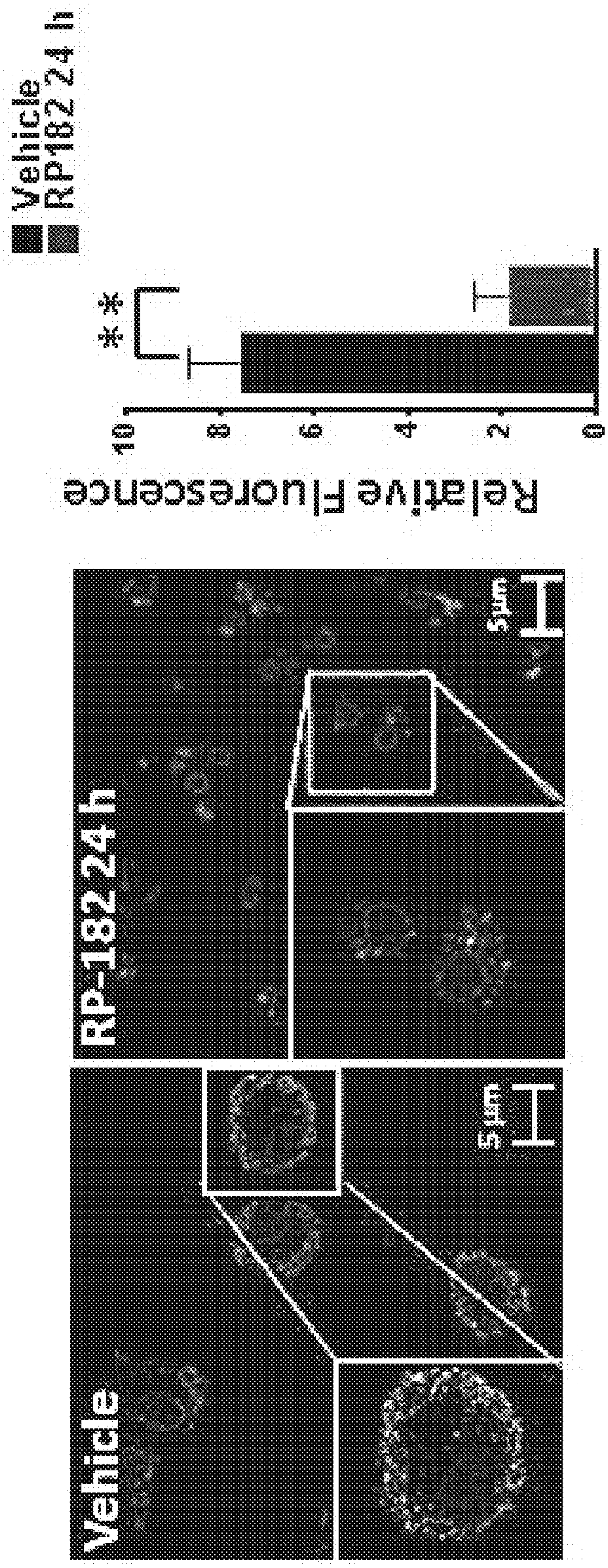
FIG. 39B shows representative immunocytometry images of M2 BMDMs stained with CD206 (left) and quantification (right) of total anti-CD206 immunofluorescence signal intensity in M2 BMDMs after 24 hours treatment with RP-182 or vehicle.
Figure 40A:
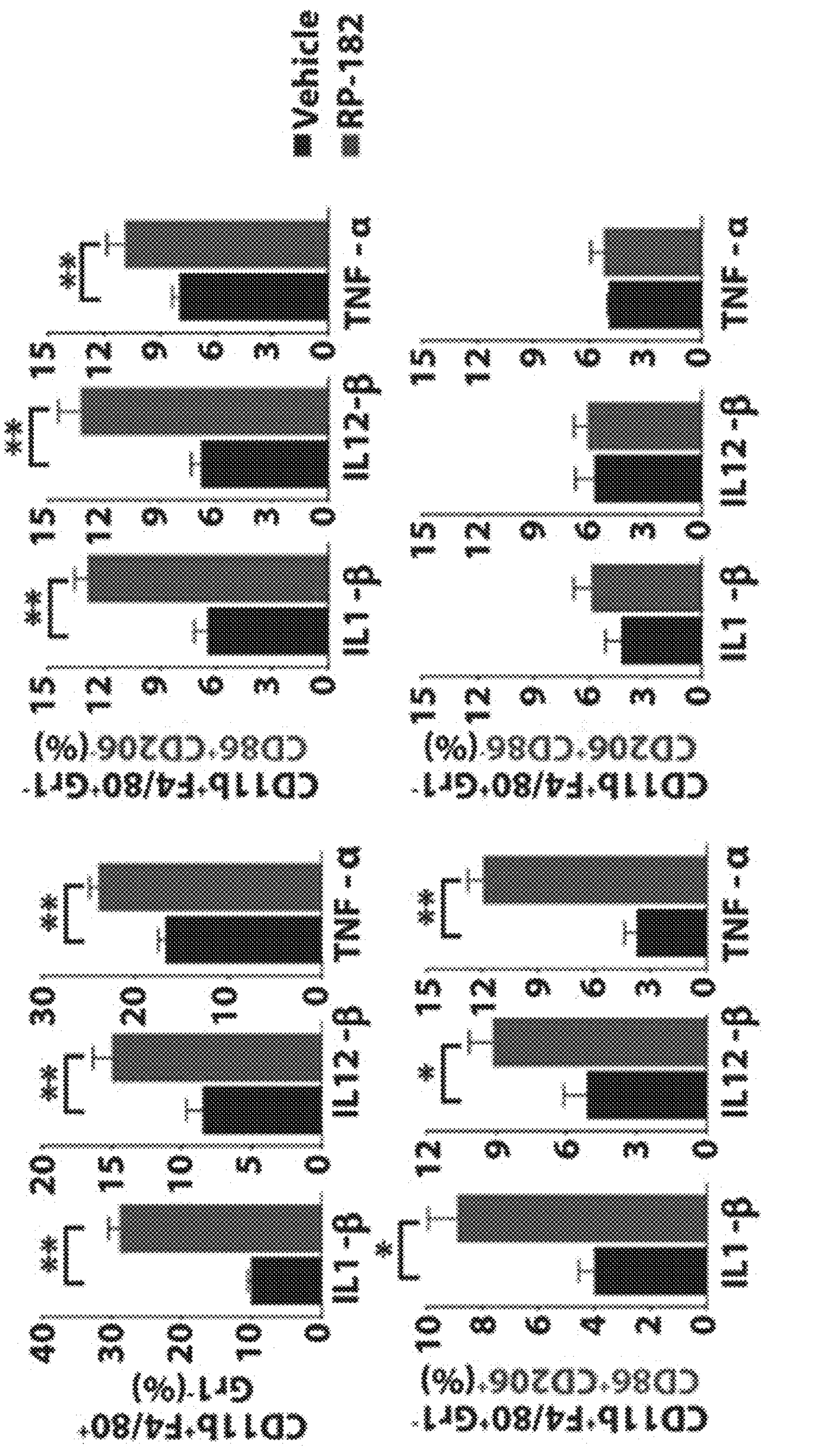
FIG. 40A shows quantification of fractions of IL-10, IL-12p40, and TNF-α positive CD11b+F4/80+Gr-1− cells, and of CD86+CD206−, CD86+CD206+ double positive, and CD86-CD206+ subpopulations of M2 BMDMs by flow cytometry.
Figure 40B:
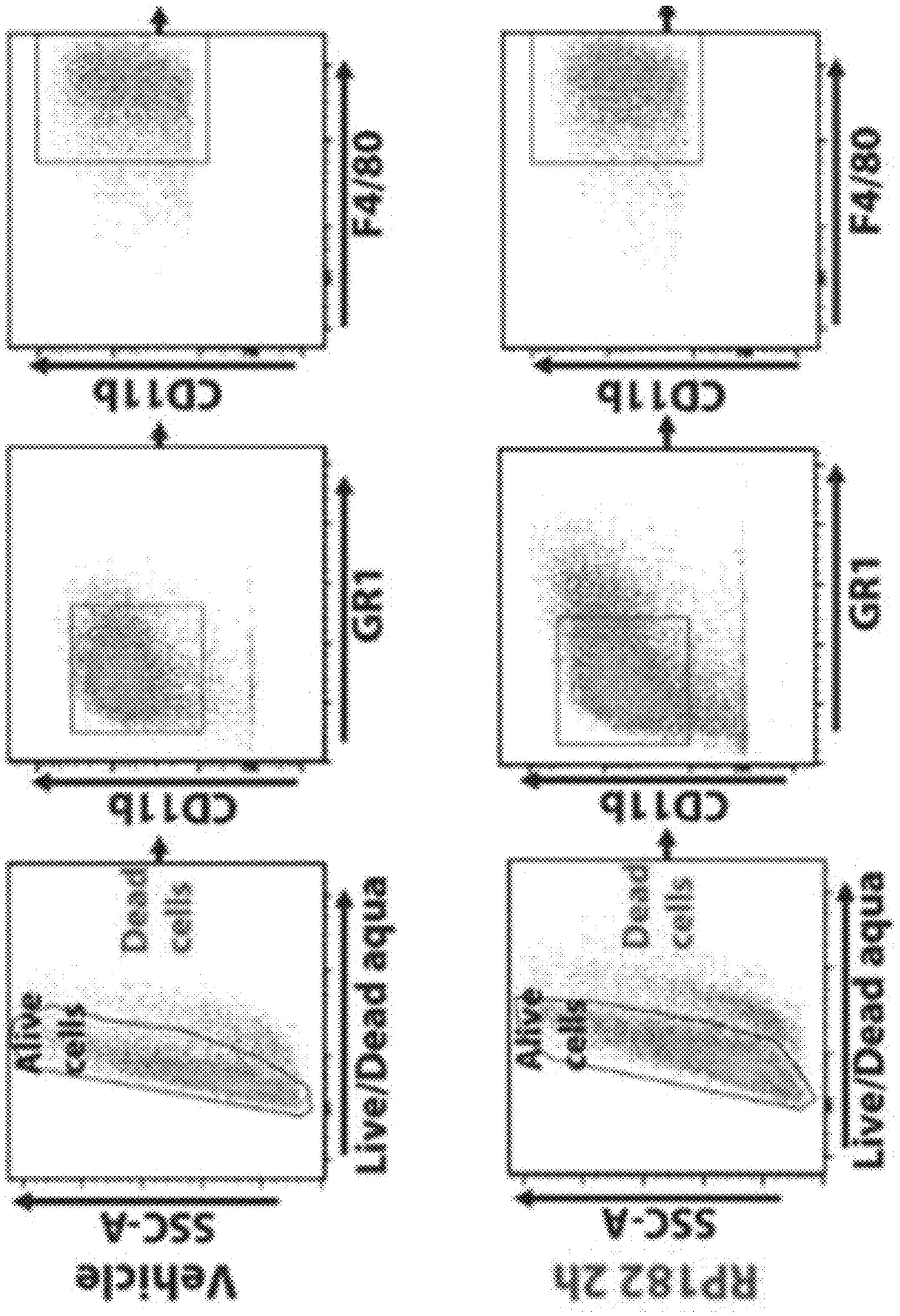
FIG. 40B shows flow cytometry plots fractions of IL-10, IL-12p40, and TNF-α positive CD11b+F4/80+Gr-1− cells, and of CD86+CD206−, CD86+CD206+ double positive, and CD86-CD206+ subpopulations of M2 BMDMs.
Figure 40C:
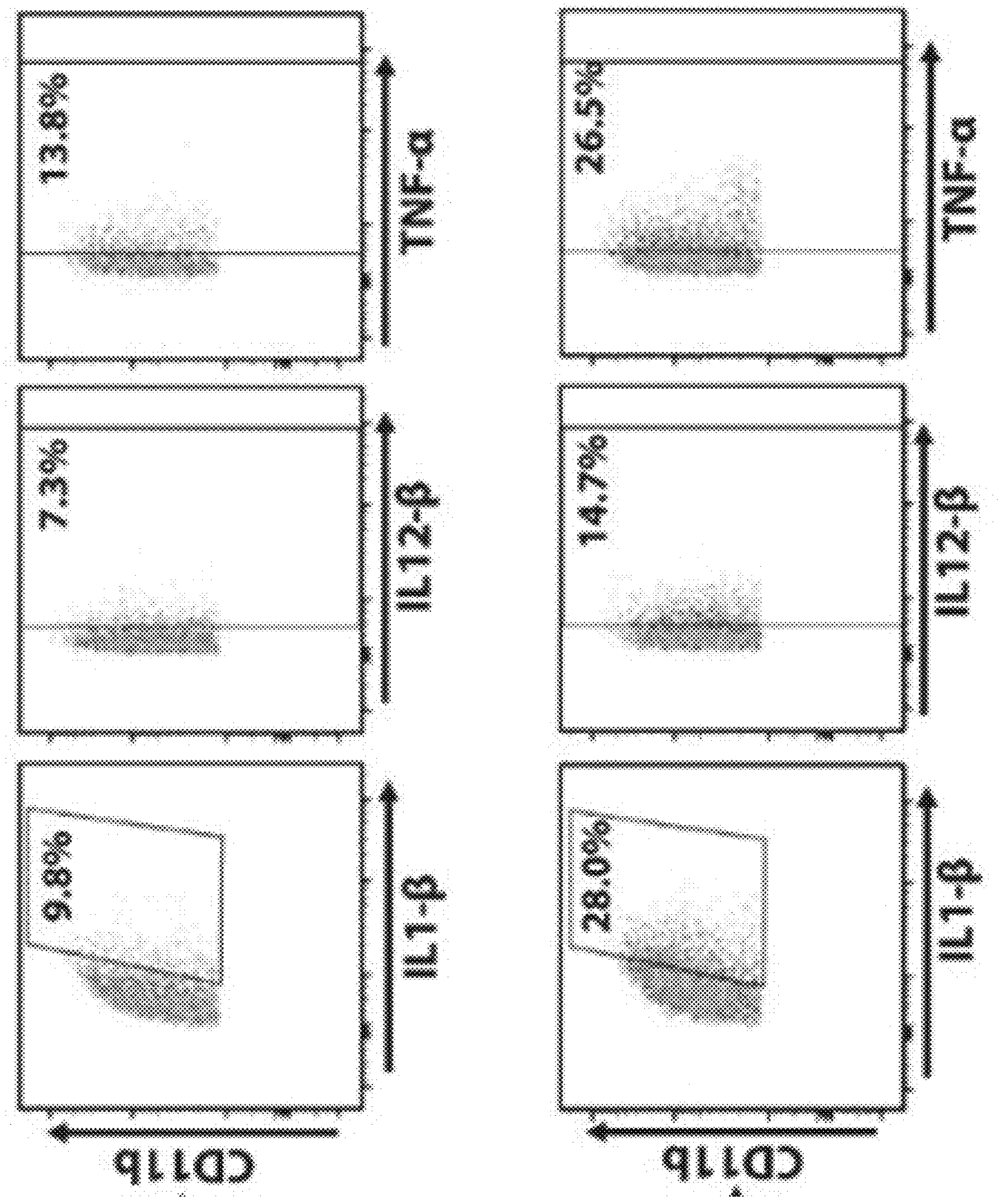
FIG. 40C shows flow cytometry plots fractions of IL-10, IL-12p40, and TNF-α.

Flow cytometry experiments of CD11b+F4/80+Gr-1− macrophages gated on alive cells using the M1 marker CD86 and M2 marker CD206 showed rapid induction of CD86 expression with an increase in the CD86+CD206+ double-positive macrophages fraction (87.8% vs 10.3% in vehicle-treated control) within 30 min upon treatment with RP-182 (FIG. 38 and FIGS. 39A-B). Expression of CD86 was followed by loss of CD206 expression resulting in a CD86+ M1-like fraction not expressing the M2 marker CD206 of 10.6% after 24 hours of treatment (FIG. 38). Increased CD86 expression in M2 BMDMs treated with RP-182 was accompanied by upregulation of M1 cytokines and markers, including IL-1β, IL-12, TNFα, and inducible nitric oxide synthase (iNOS) expressed by M1 macrophages (FIG. 40A-C).

Figure 41:
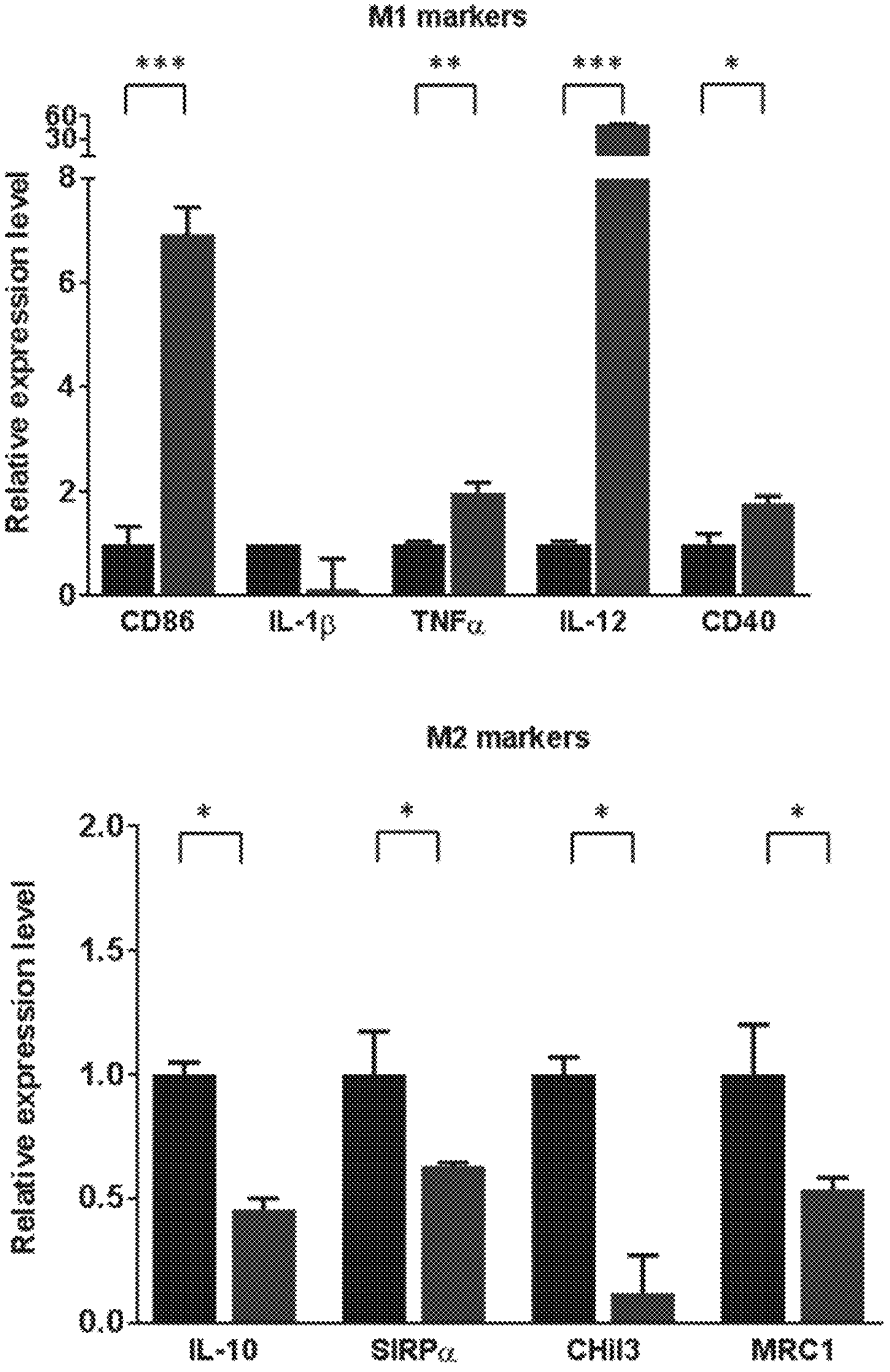
FIG. 41 shows M1 and M2 gene expression profile in CD11 b+F4/80+Gr-1-CD206+M2 BMDMs isolated by fluorescence activated cell sorting (FACS) after 2 hours treatment with vehicle (black bars) and RP-182 (red bars). Relative transcript levels by qRT-PCR after normalization to internal housekeeping genes, vehicle-treated signal was set to 1. N≥3 per group, in triplicates, error bars indicate SEM.
Figure 42:
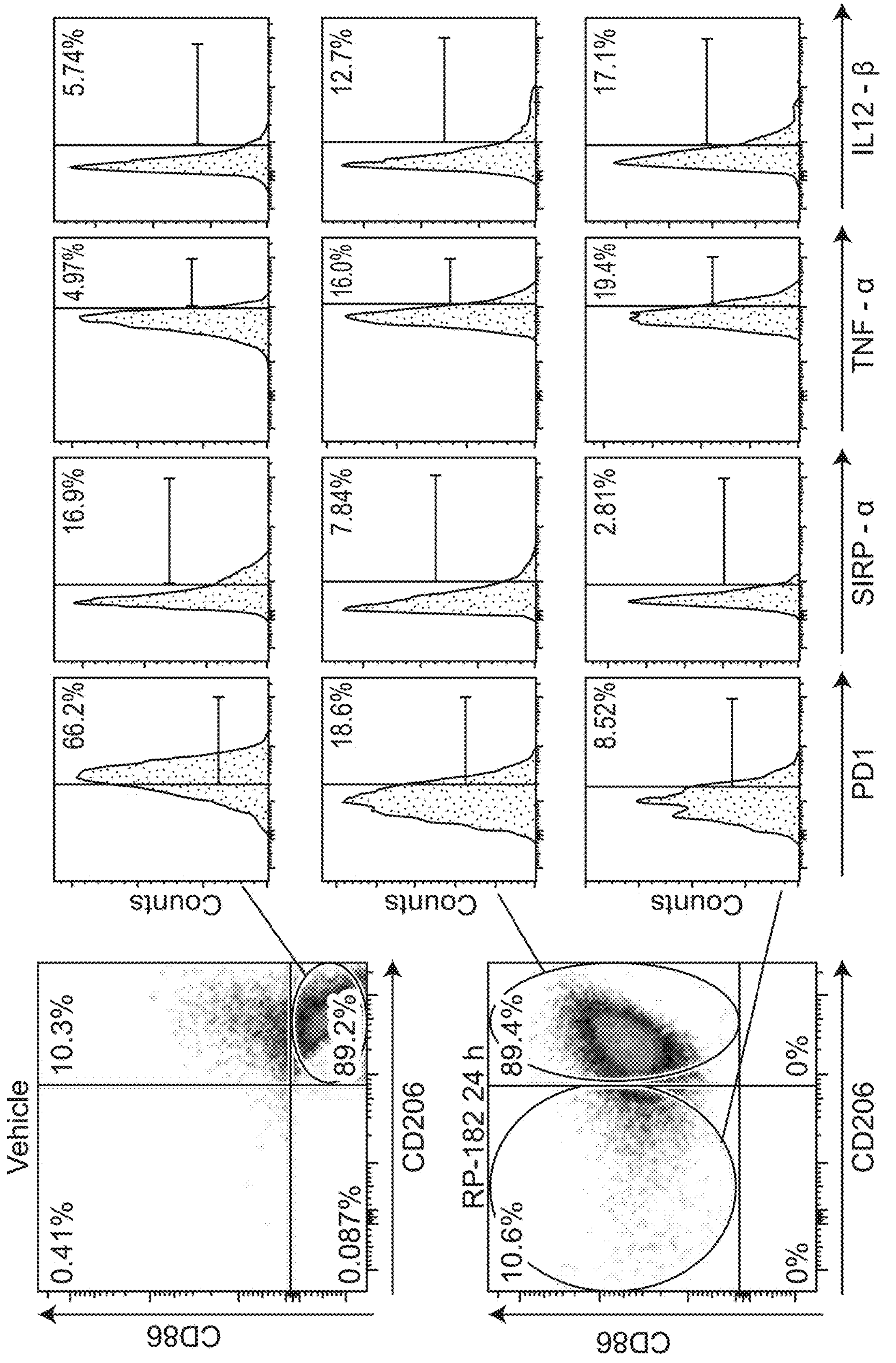
FIG. 42 shows immune checkpoint and M1 cytokine positive macrophage populations in vehicle-treated CD86−CD206+ M2 BMDMs, and RP-182-treated CD86+CD206− and CD86+CD206+ subpopulations. Univariate histograms with percentage positive cell fractions, quantifications of N=3 independent experiments are shown.
Figure 42:
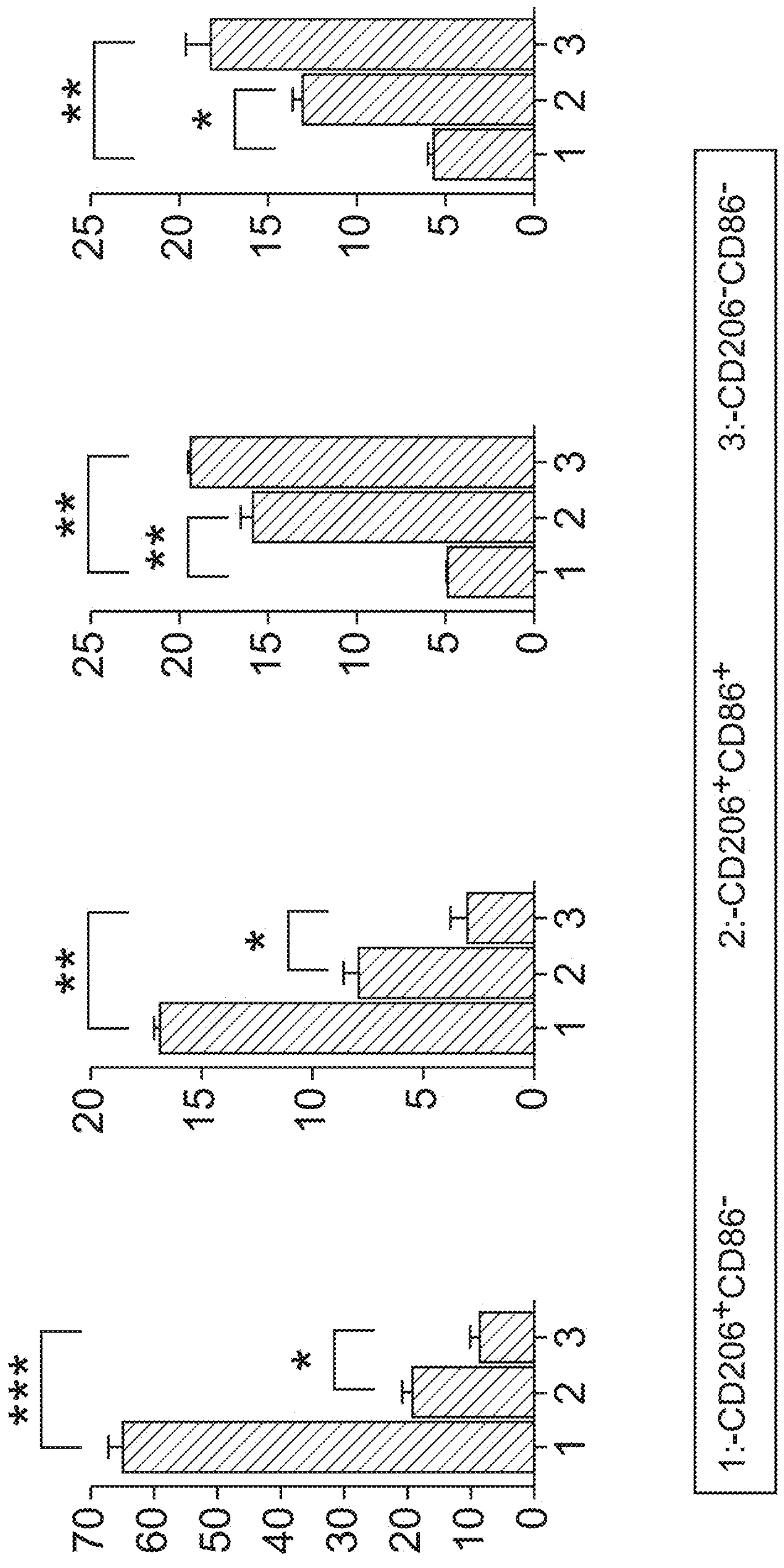
Figure 43:
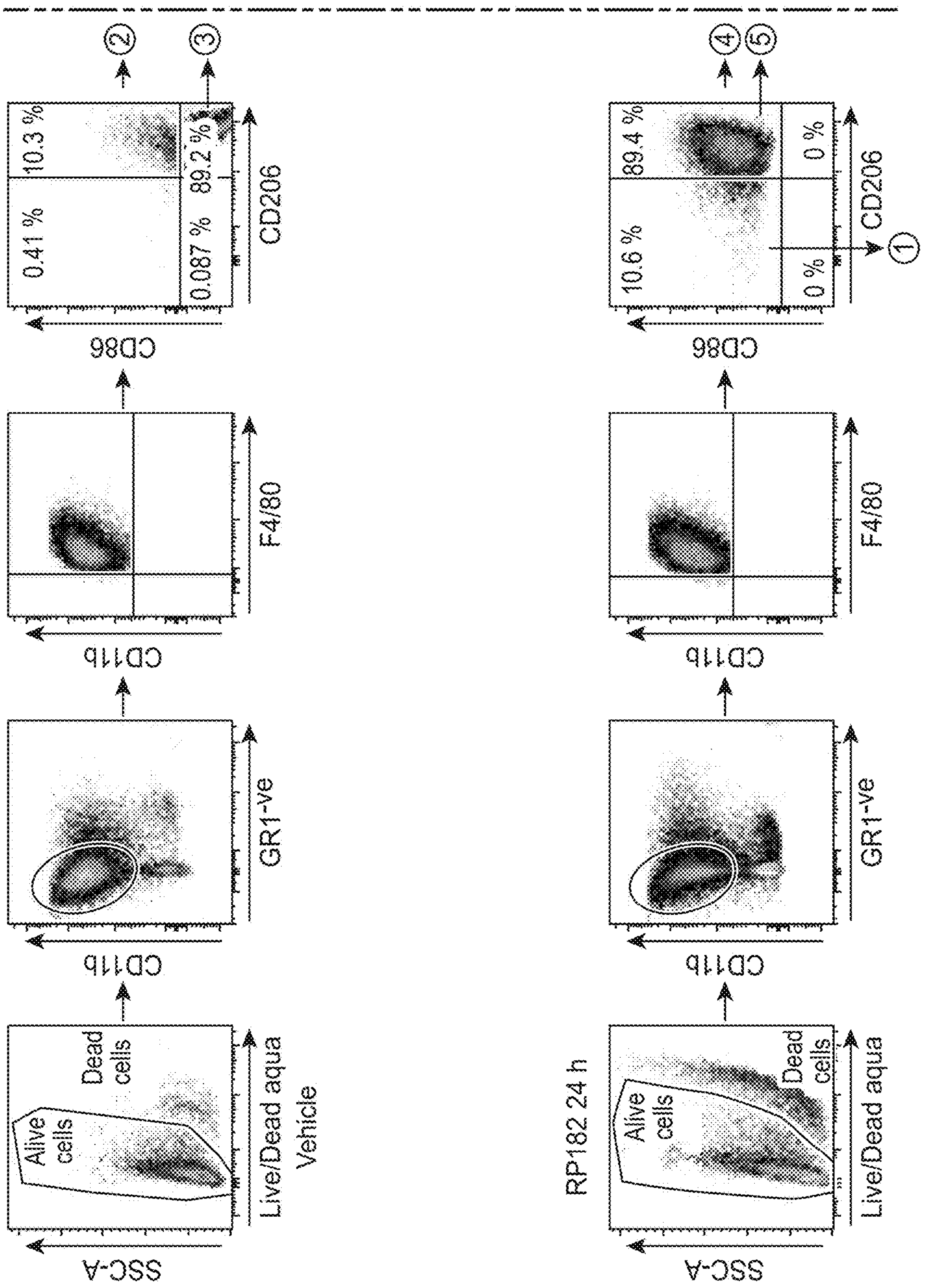
FIG. 43 shows representative flow cytometry plots of employed gating strategy including univariate histograms (with percentage of positive cell fractions) for determination of SIRPα checkpoint-positive as well as TNFα-positive macrophage cell fractions in vehicle-treated CD86-CD206+ (top row) and RP-182-treated (bottom) CD86+CD206+ (double positive) and CD86+CD206− positive M2 BMDMs. Quantification of N=3 independent experiments done in triplicates shown on bottom. 1: CD86−CD206+ fraction treated with vehicle; 2: CD86+CD206+ double positive fraction treated with RP-182; 3: CD86+CD206− positive cell fraction treated with RP-182.
Figure 43:
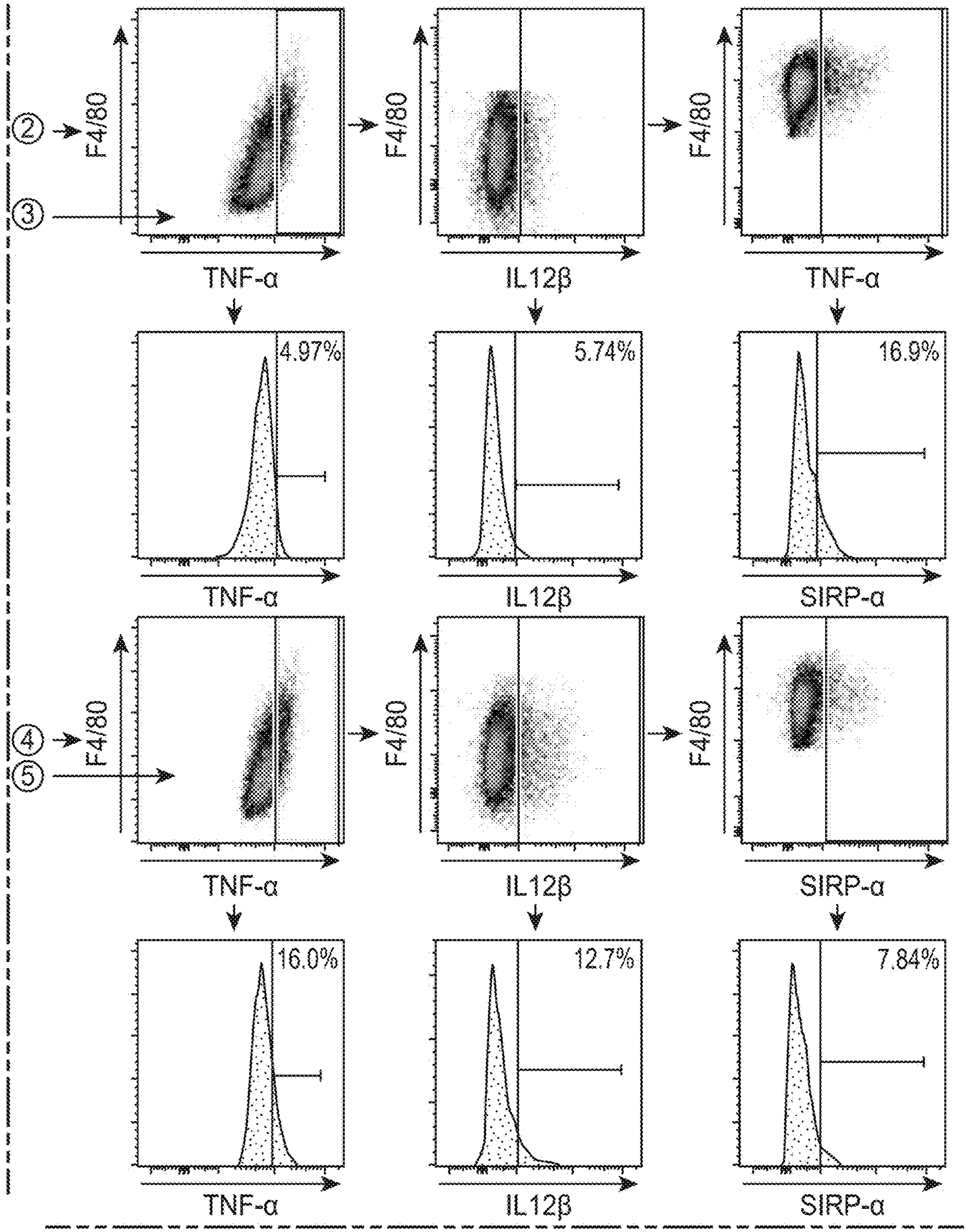
Figure 43:
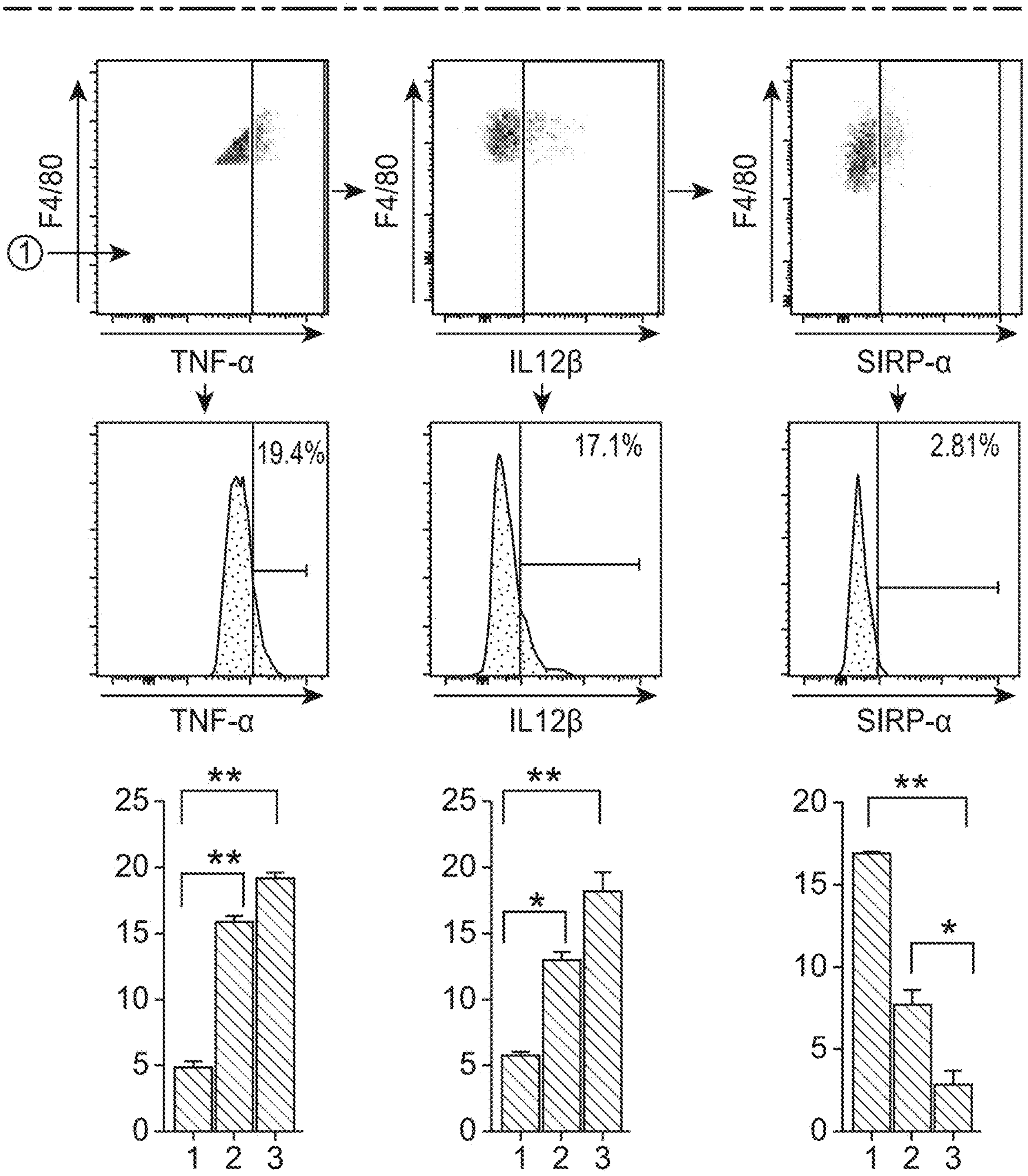

Induction of M1 and loss of M2 markers was also observed in M2 BMDMs treated with RP-182 isolated by fluorescence-activated cell sorting (FACS) (FIG. 41). The increase in M1 cytokine expression was selective for CD86+ macrophages and not observed on CD206+CD86− cells (FIG. 40A-C). The induced M1-like CD86+CD206− and double positive CD206+CD86+ macrophage cell populations showed decreased number of cells staining positive for the PD-1 (8.52% and 18.6% vs 66.2%) and inhibitory regulatory membrane glycoprotein signal regulatory protein α (SIRPα) (2.81% and 7.84% vs 16.9%) immune checkpoints compared to vehicle-treated CD86-CD206+M2 cells (FIG. 42 and FIG. 43). The phenotypic switch induced by RP-182 towards M1 was accompanied by elevated M1 function as the fraction of macrophages involved in bacterial phagocytosis, a function more commonly associated with the M1 phenotype, increased from 20.4 to 81.3 percent after treatment with RP-Macrophage fractions staining positive for the M1 cytokines TNFα and IL-12 were increased (19.4% and 16.0% vs 4.97%, and 17.1% and 12.7% vs 5.74%, respectively) compared to vehicle control.

Figure 44:
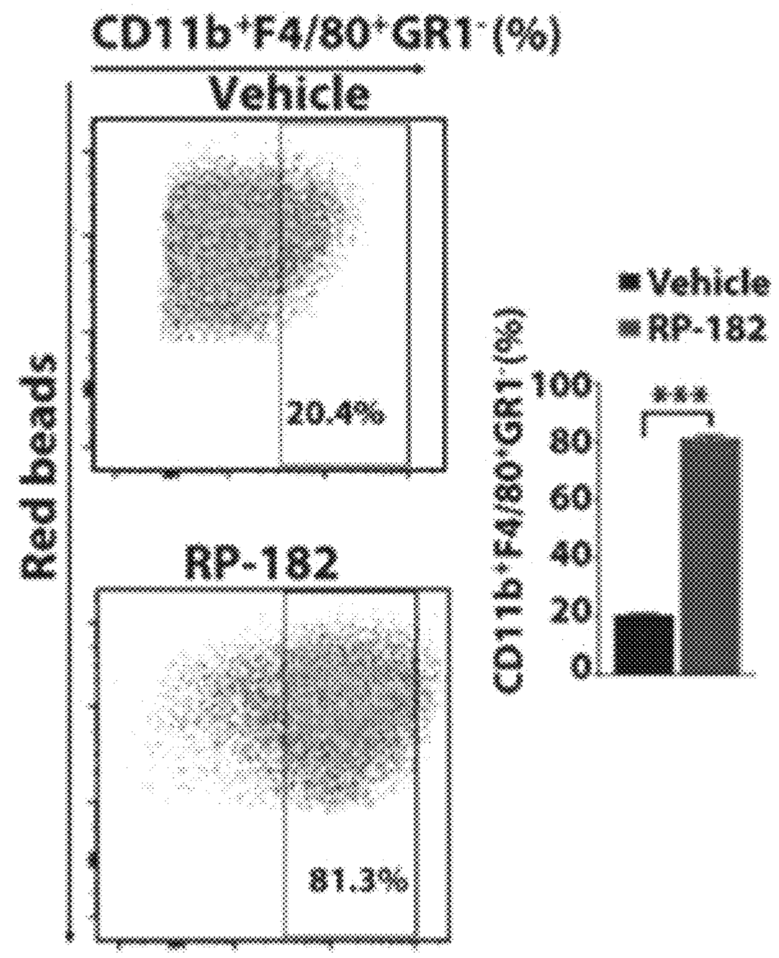
FIG. 44 shows flow cytometry analysis and quantification of CD11b+F4/80+Gr-1− cell fractions with phagocytosed *E. coli*-covered latex beads, quantification of N=3 independent experiments.
Figure 45:
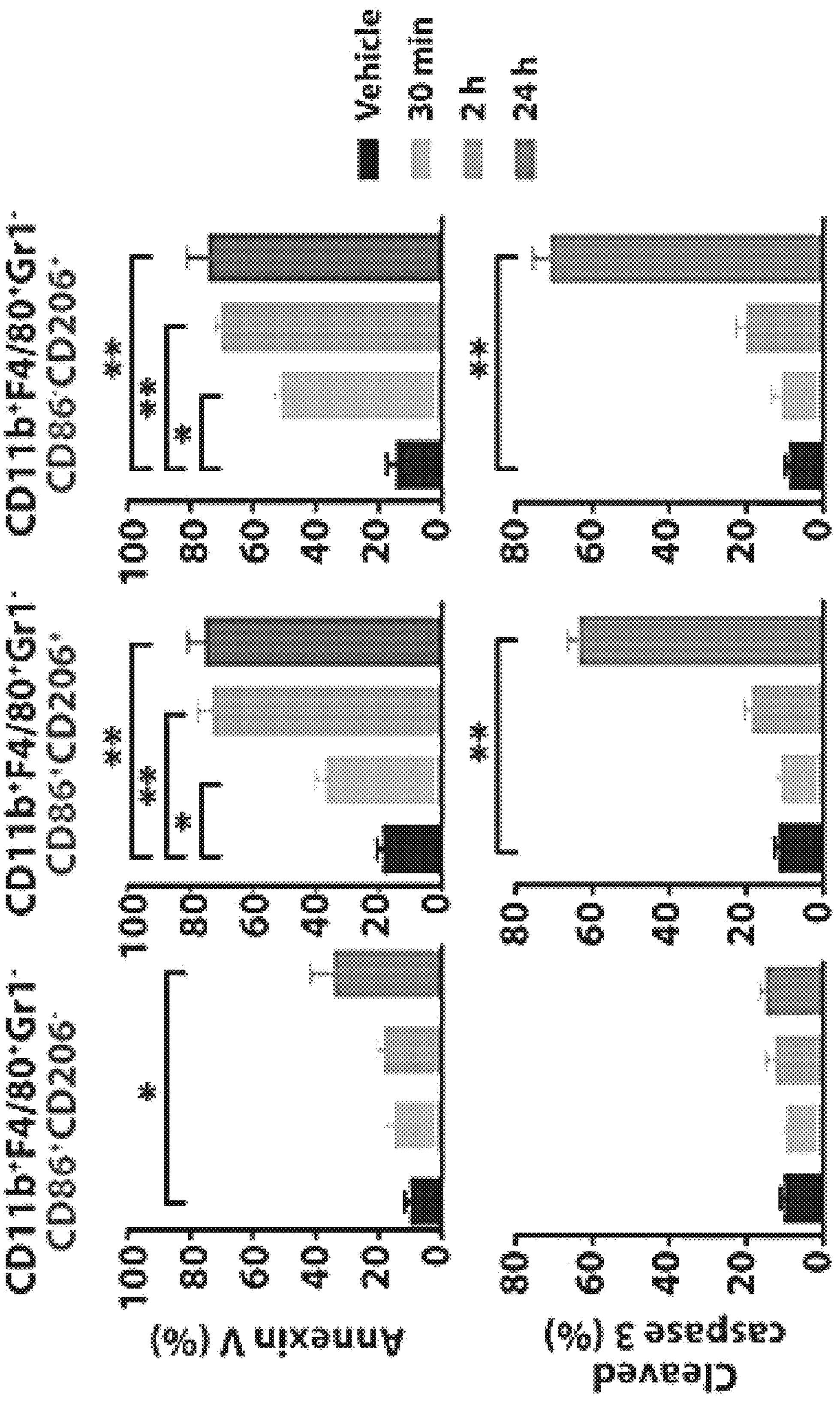
FIG. 45 shows quantification of annexin V-positive (top) and cleaved caspase 3-positive cell fractions (bottom) of CD86+CD206−. CD206+CD86+, and CD86−CD206+ M2 BMDMs treated with RP-182 at indicated time points.
Figure 46:
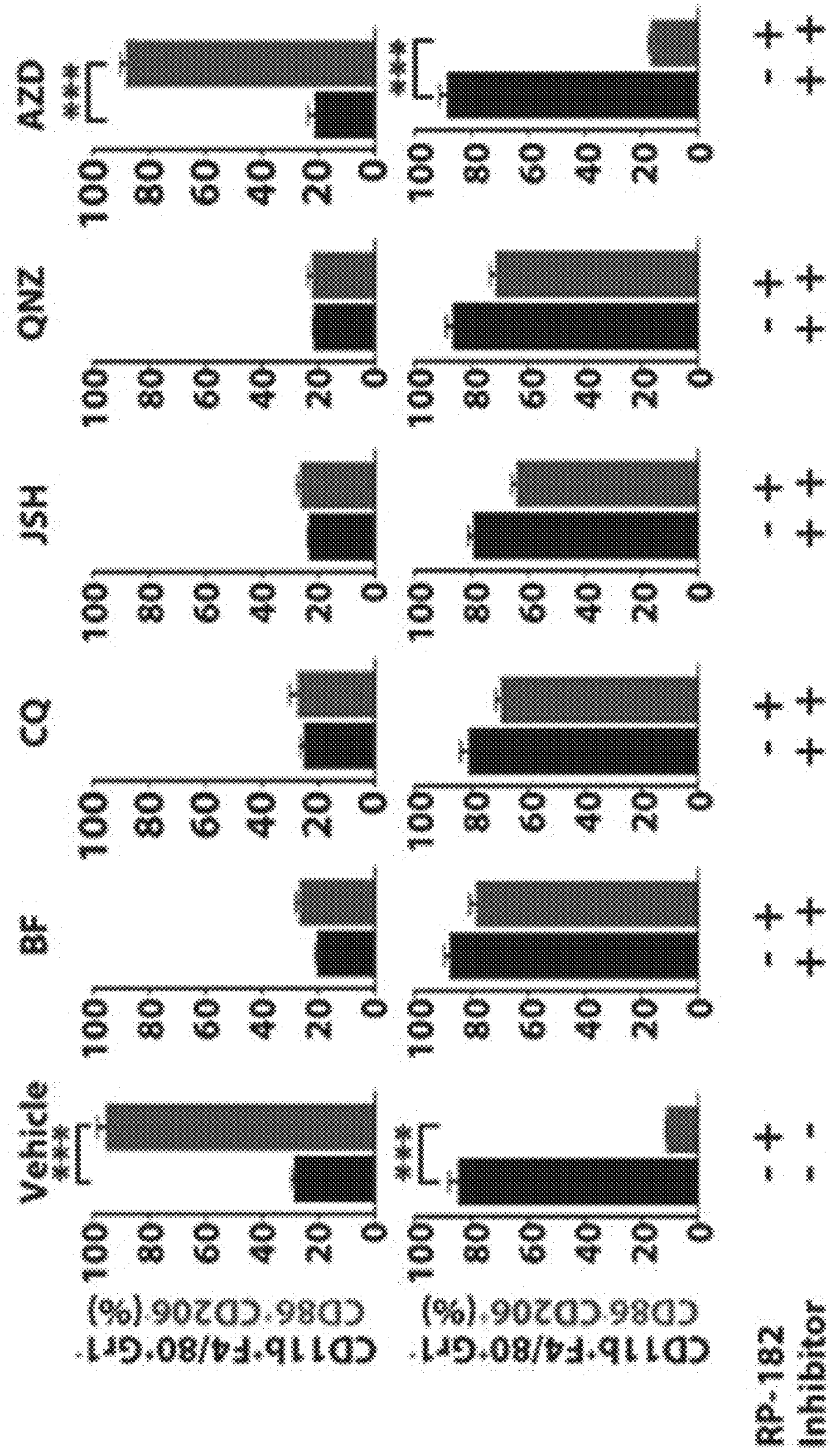
FIG. 46 shows quantification of vehicle- and RP-182-treated CD86+ (top) and CD206+ (bottom) CD11b+F4/80+Gr-1− BMDM-M2 cells co-incubated with NF-kB inhibitors JSH-23 and QNZ (EVP4593) and autophagy inhibitors bafilomycin (BF) and chloroquine (CQ). MEK inhibitor AZD6244 (selumetinib; AZD) shown as negative control).

The phenotypic switch induced by RP-182 towards M1 was accompanied by increased bacterial phagocytosis, a function more commonly associated with the M1 phenotype (FIG. 44). Of note, the rate of apoptosis in the reprogrammed M1-like CD86+CD206− cell macrophages after treatment with RP-182 was significantly lower than in the CD206+CD86− positive and CD206+CD86+ double-positive cells possibly indicating that (1) CD206 negative cells escape the direct cell killing of RP-182 and (2) RP-182 reprograms M2 macrophages towards a M1-like phenotype (FIG. 45). Both, pharmacological blockade of RP-182-induced NF-kB signaling and autophagy, previously shown to be induced by RP-182, suppressed reprogramming effect of RP-182 towards the M1 phenotype (FIG. 46).

Figure 47:
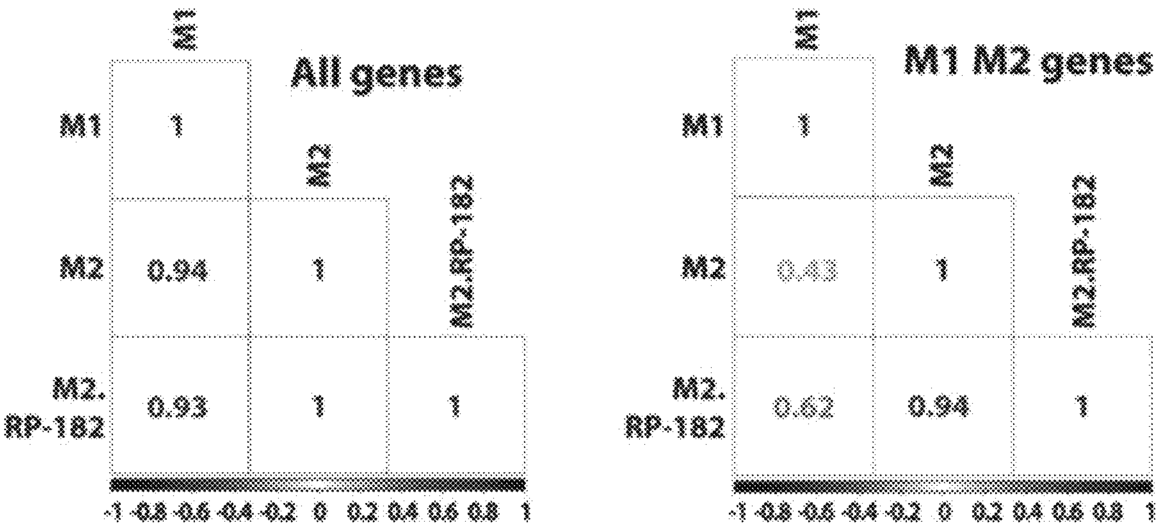
FIG. 47 shows Pearson's correlation analysis of gene expression matrices between samples using global RNASeq data (left) and M1 M2 marker set derived from BMDMs (right). Values ranges from 0 to 1, a high value between samples indicates high degree of correlation between two sample sets.

To examine whether gene expression changes induced by RP-182 support reprogramming of M2 BMDMs towards a M1-like phenotype, gene expression matrices were analyzed from RNASeq data. Pearson's correlation analysis of gene expression matrices derived from global RNASeq data of RNA isolated from M1, M2, and M2 BMDMs treated with RP-182 showed a high degree of similarity between the three datasets. Using a M1 M2 marker set previously described for characterization of macrophage phenotypes in BMDMs, M2 macrophages displayed greater similarity after RP-182 treatment to untreated M1 than to untreated M2 cells (FIG. 47). In summary, in addition to induction of phagocytosis, autophagy, and apoptosis in M2 macrophages, the synthetic HDP RP-182 induces a shift towards a M1-like phenotype.

Example 4: Mechanism of Action of RP-182

The mechanism of action of RP-182 was investigated, showing that the action is dependent on CD206 and initiates Rac1/Cdc42 activation and IQGAP1 recruitment.

Figure 48A:
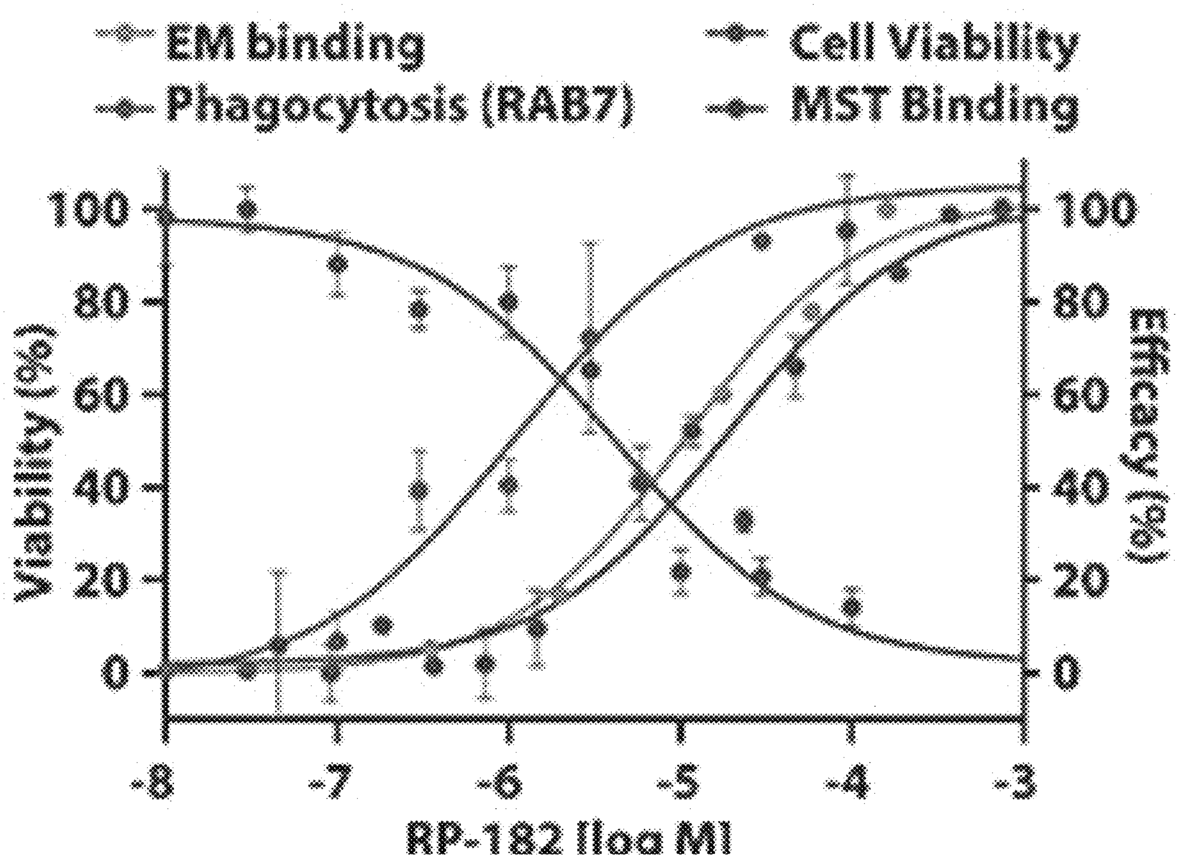
FIG. 48A shows biological activity of RP-182 is CD206-dependent and initiates activation of Rac1/CDC42 signaling. A. RP-182 dose-response curves of binding to recombinant CD206 (MST assay; red curve), induction of the closed conformation of CD206 (electron microscopy; green curve), induction of phagocytosis (anti-Rab7; purple), and M2 cell viability (blue) in M2 BMDMs.
Figure 48B:
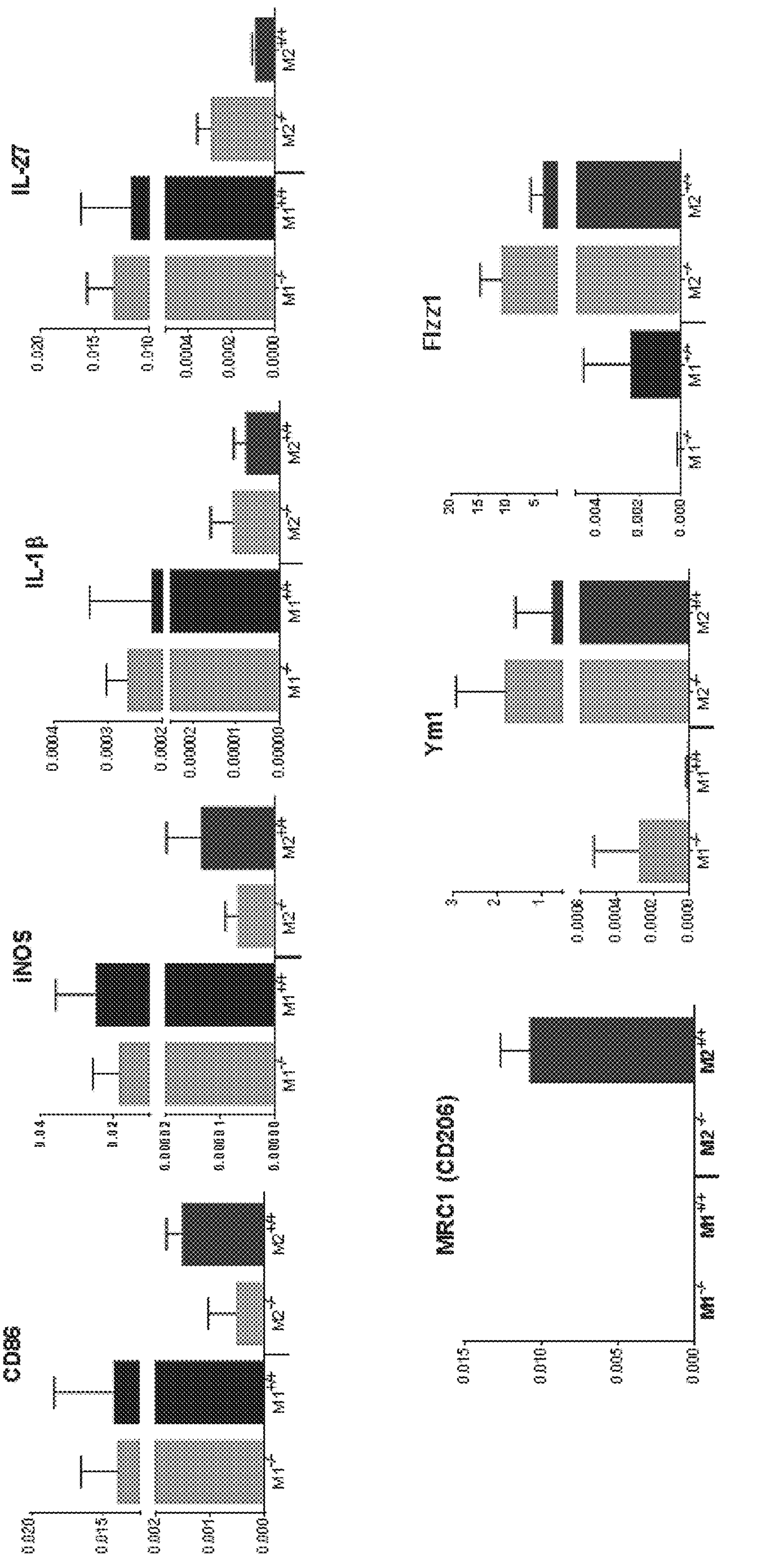
FIG. 48B shows M1 and M2 gene expression profiles of BMDMs isolated from B6.129P2-Mrc1tm1Mnz/J (CD206−/−) and wild type C57BL/6 mice (CD206+/+) after polarization into M1 and M2. Similar M1 and M2 gene expression profiles of BMDMs isolated CD206−/− and wild type C57BL/6 mice (CD206+/+) after polarization into M1 and M2. Relative gene expression levels measured by qRT-PCR of M1 markers CD86, iNOS. IL-1β, and IL-27 and M2 markers CD206, Fizz1, and YM1 in M1 (blue color) and M2 populations (red color) of CD206−/− and CD206+/+ BMDMs. For quantification of the relative expression levels see materials and methods. Mean±SEM of n≥3 per group is shown.
Figure 49:
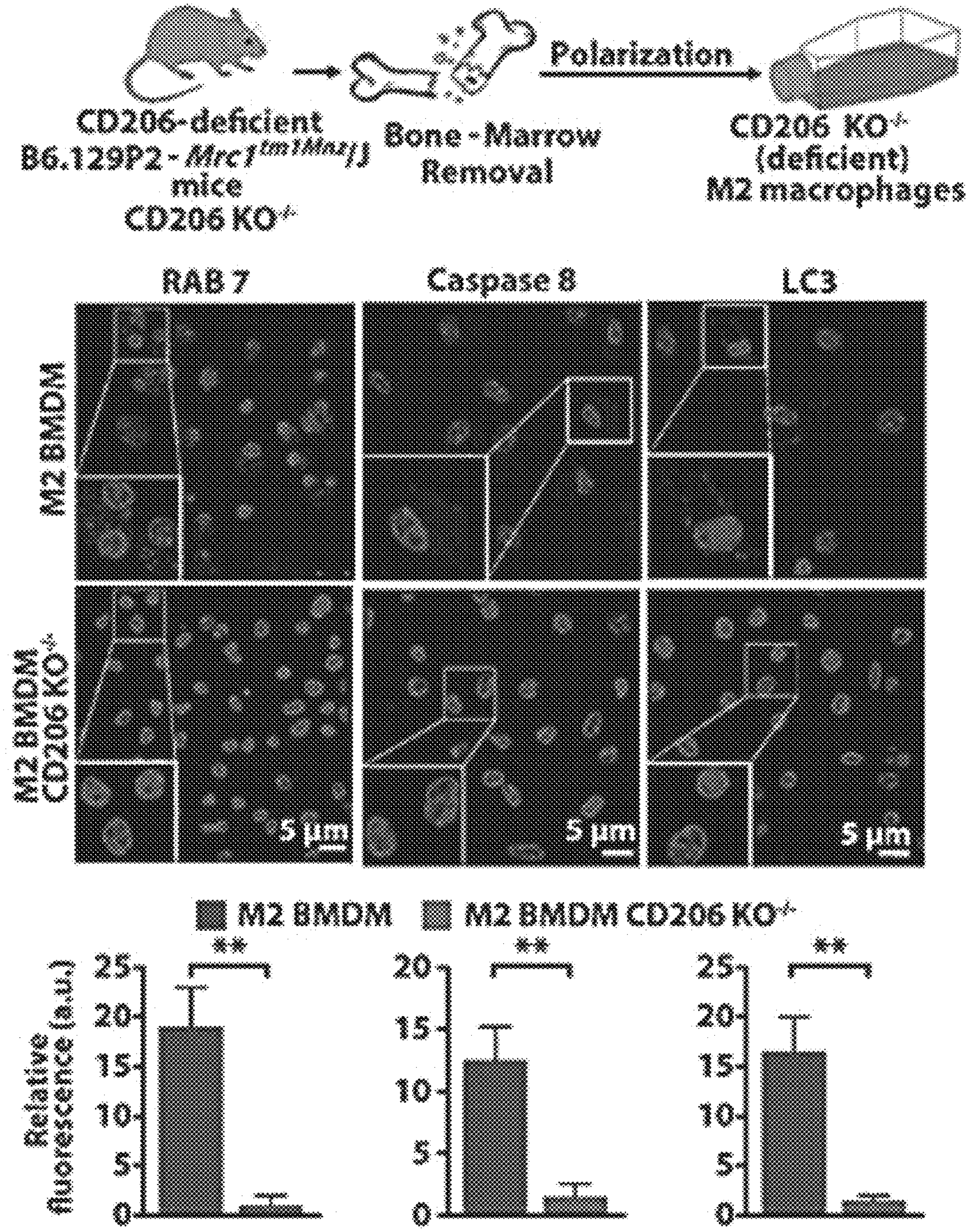
FIG. 49 shows immunofluorescence images of BMDMs derived from wild type and CD206−/− mice polarized into M2 stained with anti-Rab7. LC3, and cleaved caspase 8, quantification of three independent experiments on bottom.

When overlaying pharmacodynamic readouts of RP-182 treatment, the close EC50 and IC50 activities of RP-182 suggest a shared mechanism of action mediated by a common CD20 target (FIG. 48A). To show that the M2-selective action of RP-182 is indeed MRC1/CD206- dependent. BMDMs were isolated from B6.129P2-Mrc1tm1Mnz/J mice, which are deficient of CD206 (24). It was first confirmed that with the exception of CD206, there was upon polarization into M1 and M2 populations no difference in the expression profile of M1 and M2 markers between CD206 wt and CD206−/− BMDMs (FIG. 48B). In contrast to M2-polarized macrophages from wild type mice, M2-polarized macrophages isolated from B6.129P2-Mrc1tm1Mnz/J mice failed to show induction of phagocytosis, autophagy, or apoptosis (FIG. 49), did not respond to RP-182 (FIG. 50), and showed no induction of M1 cytokines upon treatment with RP-182 (FIG. 50).

Figure 50:
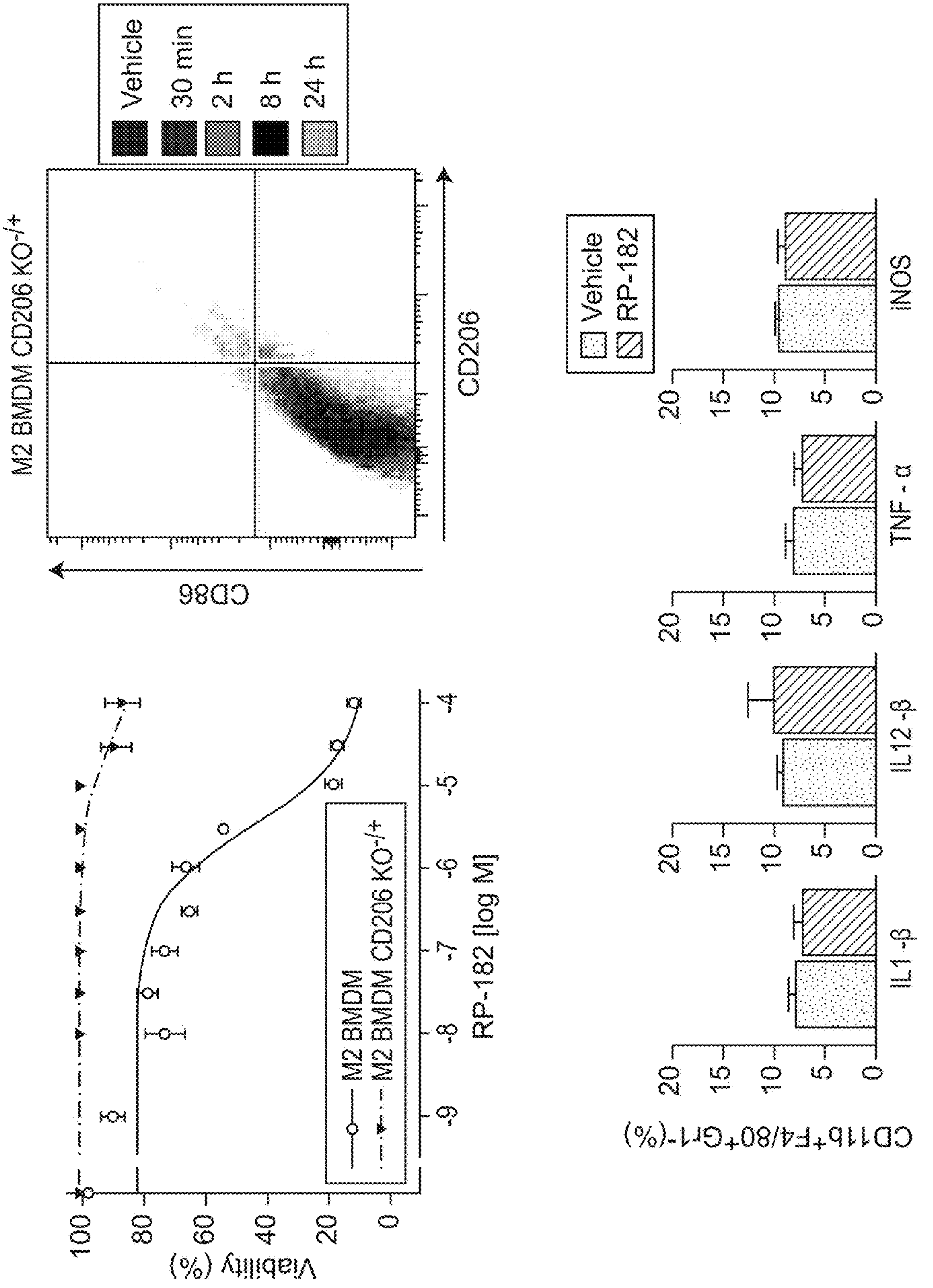
FIG. 50 shows cell viability of M2 BMDMs derived from $CD206^{wt}$ (red curve) and $CD206^{-/-}$ (brown curve) mice. D. Flow cytometry plots of CD86+ and CD206+ fractions (top) and quantification of M1 marker-positive cells in CD11 b+F4/80+Gr− 1− M2-BMDMs isolated from $CD206^{-/-}$ mice. Mean % positive cells of N=3 independent experiments in triplicates are shown.
Figure 52A:
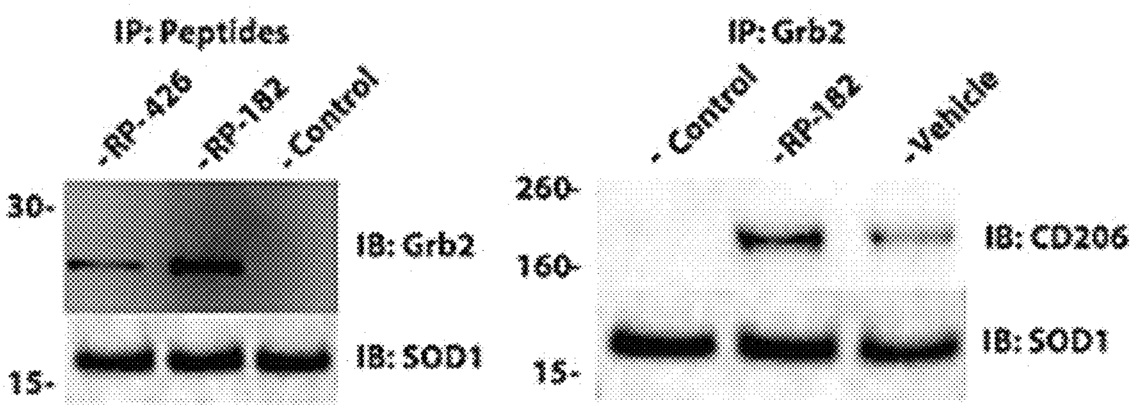
FIG. 52A shows immunoblot of lysates immunoprecipitated with biotinylated peptides (left) or with anti-GRB2 antibody (right). Proteins visualized using anti-GRB2 and anti-CD206 antibodies. Preloading control superoxide dismutase 1 (SOD1) shown on bottom
Figure 52B:
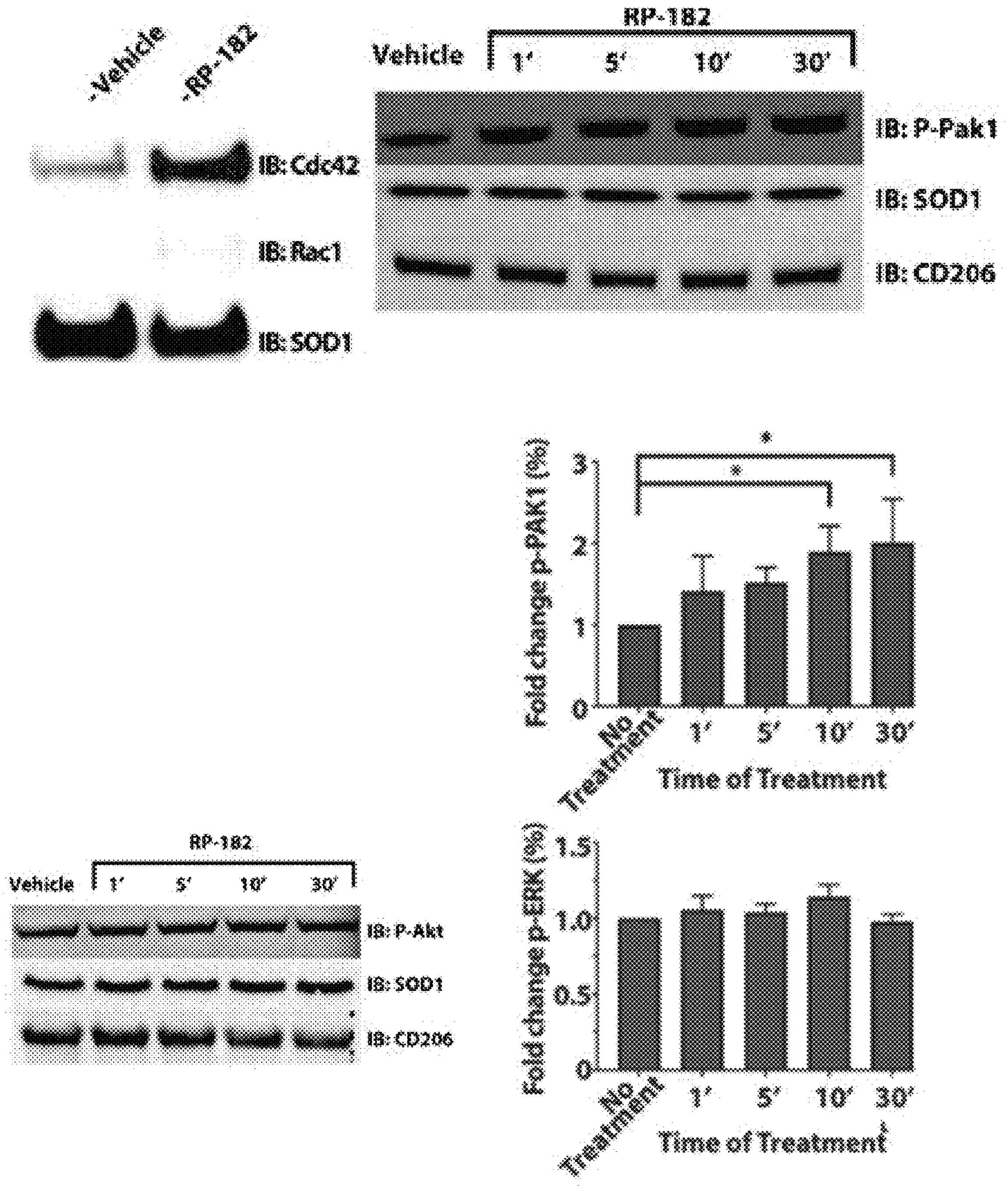
FIG. 52B shows immunoblot analysis of lysates from M2 BMDMs immunoprecipitated for active GTP-bound form of Rac1/CDC42 and visualized with anti-CDC42 or anti-Rac1 antibodies (left). Immunoblots of M2 lysates with anti-phospho-Pak1 and anti-phospho-AKT on the right. Quantification of band intensities summarizes N=3 independent experiments.
Figure 53:
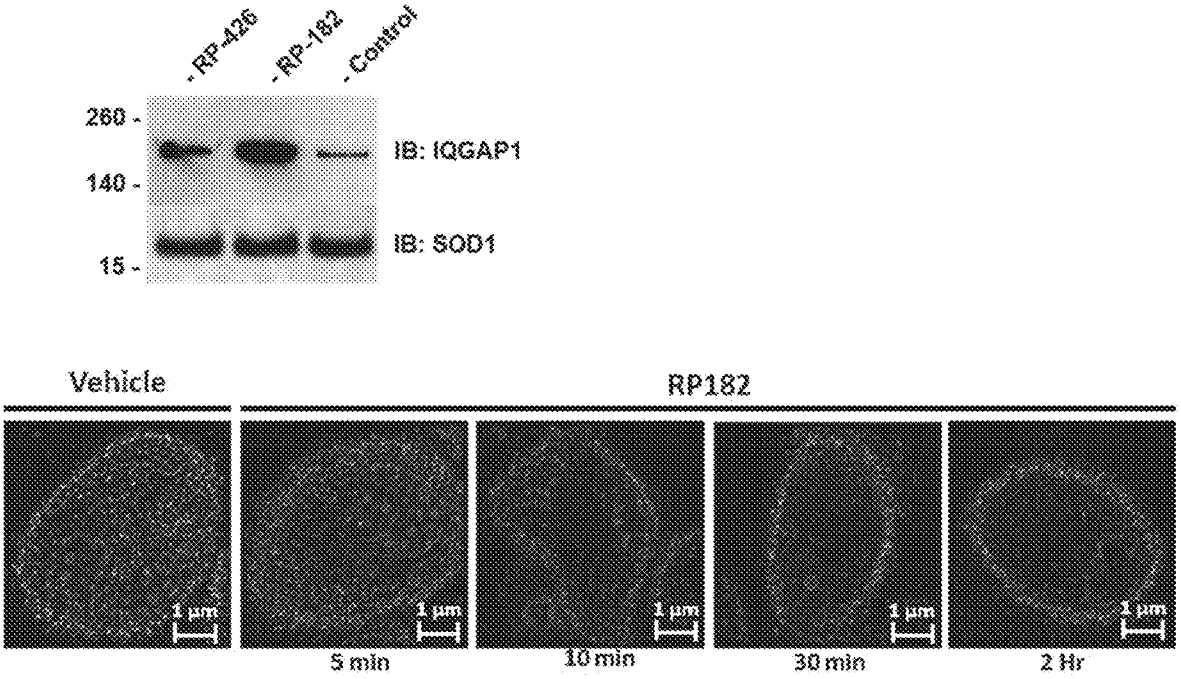
FIG. 53 shows RP-182 induces binding of IQGAP1 to CD206 and recruitment of IQGAP1 to the cell membrane of M2-polarized macrophages. A. Lysates from M2 BMDMs treated with biotinylated RP-182, biotinylated control peptide RP-426, or vehicle control for 10 minutes were precipitated with streptavidin magnetic beads, and proteins visualized with anti-IQGAP1 antibody. Preloading control superoxide dismutase 1 (SOD1) levels shown on bottom. B. Membrane recruitment of IQGAP1 by RP-182. Immunofluorescence staining of M2 BMDMs for IQGAP1, timepoints after administration of RP-182 indicated on bottom.
Figure 54A:
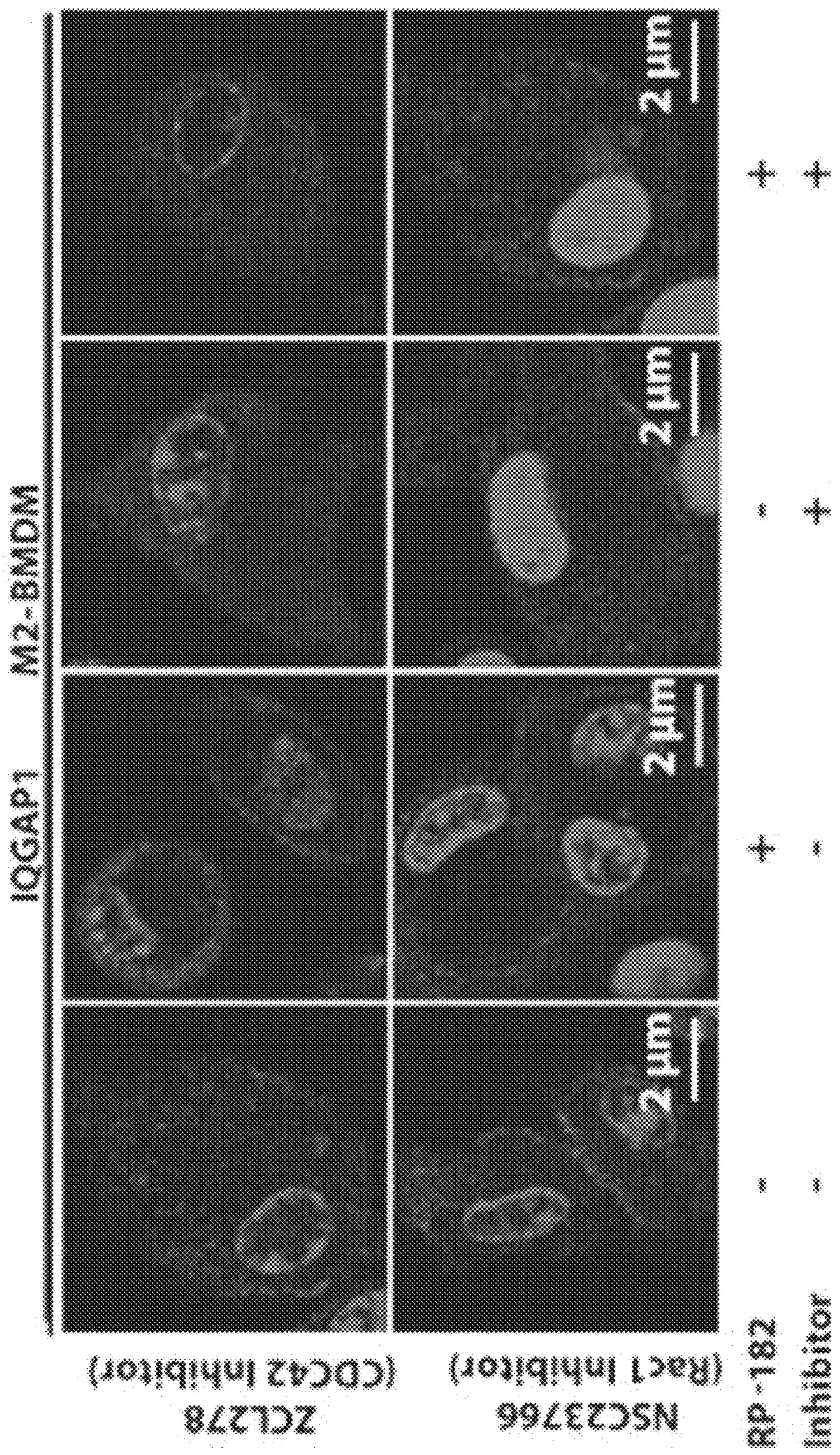
FIG. 54A shows immunofluorescence images after anti-IQGAP1 staining of M2 BMDMs treated with RP-182 and pre-incubated with indicated inhibitors.
Figure 54B:
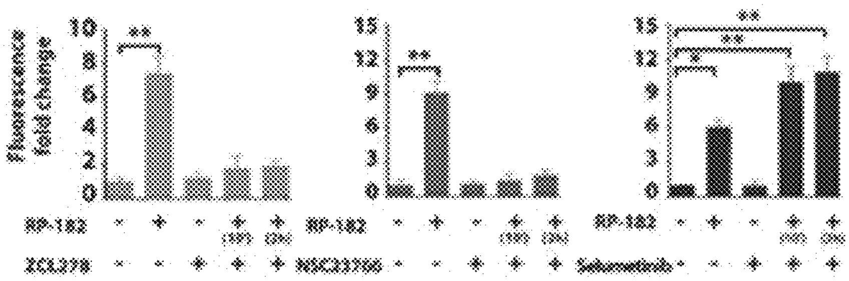
FIG. 54B shows quantification of Rab7 immunofluorescence levels of M2 BMDMs treated with RP-182 and preincubated with ZCL278 (left). NSC23766 (middle), and negative control selumetinib (right). Data shown are representative of two independent experiments and normalized to corresponding vehicle treatment unless indicated otherwise.
Figure 55A:
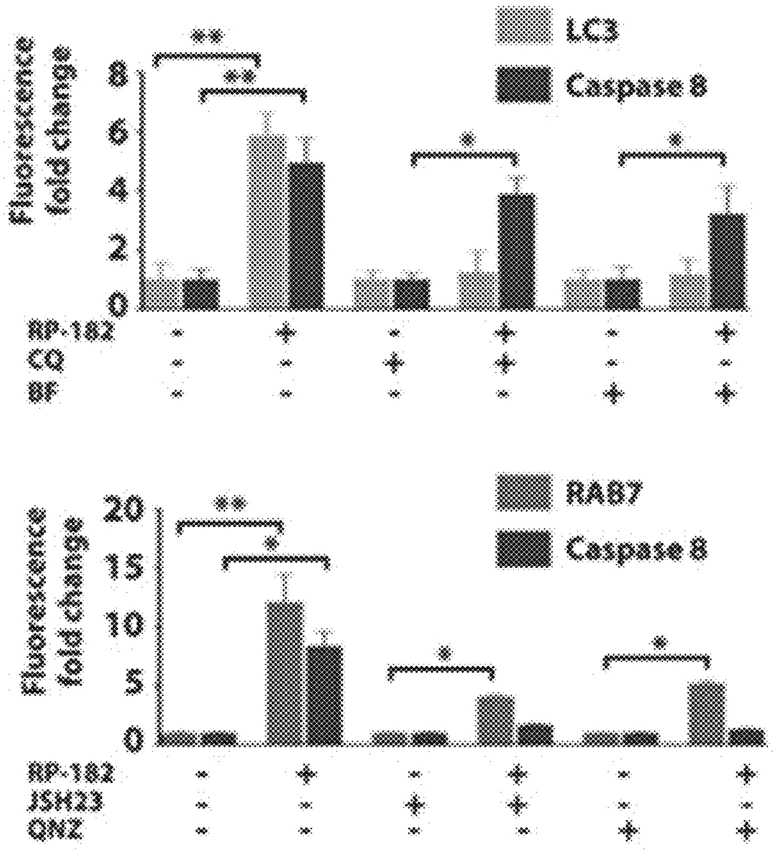
FIG. 55A shows LC3 and cleaved caspase 8 expression in M2 macrophages pre-incubated with chloroquine (CQ) and bafilomycin (BF). N=2, in triplicates.
Figure 55B:
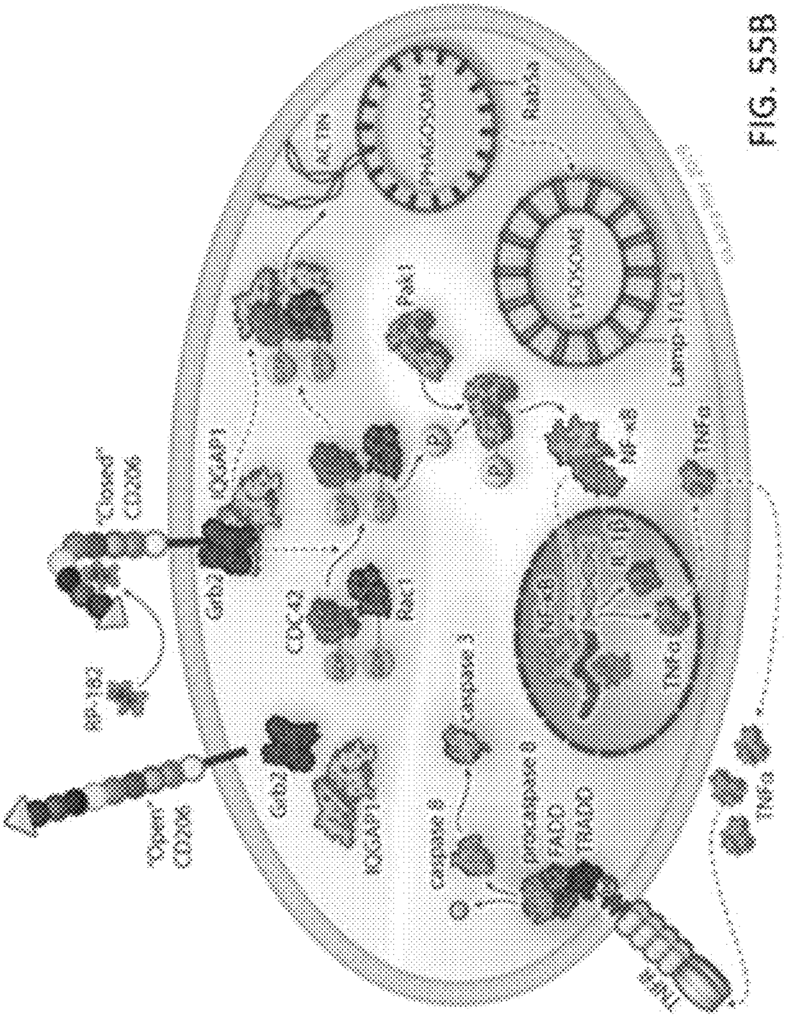
FIG. 55B shows quantification of phagocytosis (Rab7) and cleaved caspase 8 levels in M2 BMDMs in presence of NF-kB inhibitors JSH23 and QNZ. N=2, in triplicates. K. Schematic diagram of RP-182 functions in M2 macrophages.
Figure 56:
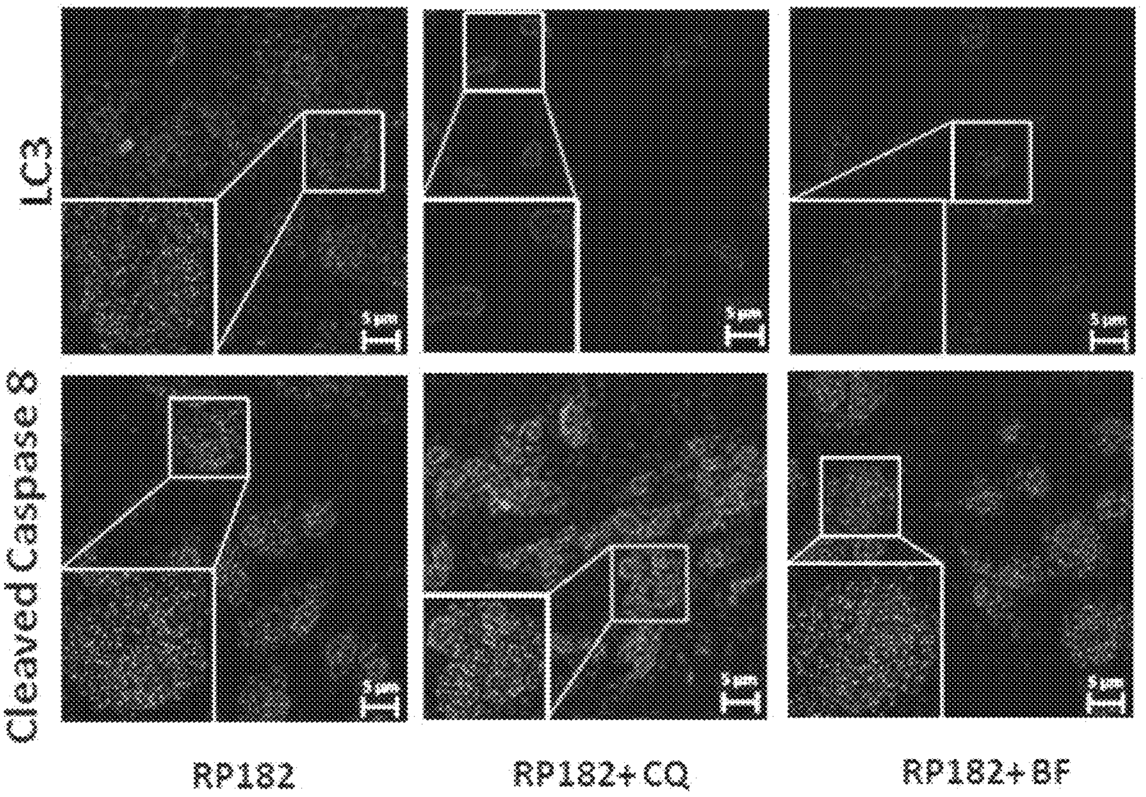
FIG. 56 shows induction of cleaved caspase 8 expression in M2 macrophages treated with RP-182 is not dependent on induction of autophagy. Representative images of LC3 and cleaved caspase 8 immunofluorescence levels in M2 BMDMs treated for 2 hours with 20 μM RP-182 and pre-incubated with autophagy inhibitors chloroquine (CQ) and bafilomycin (BF).
Figure 57:
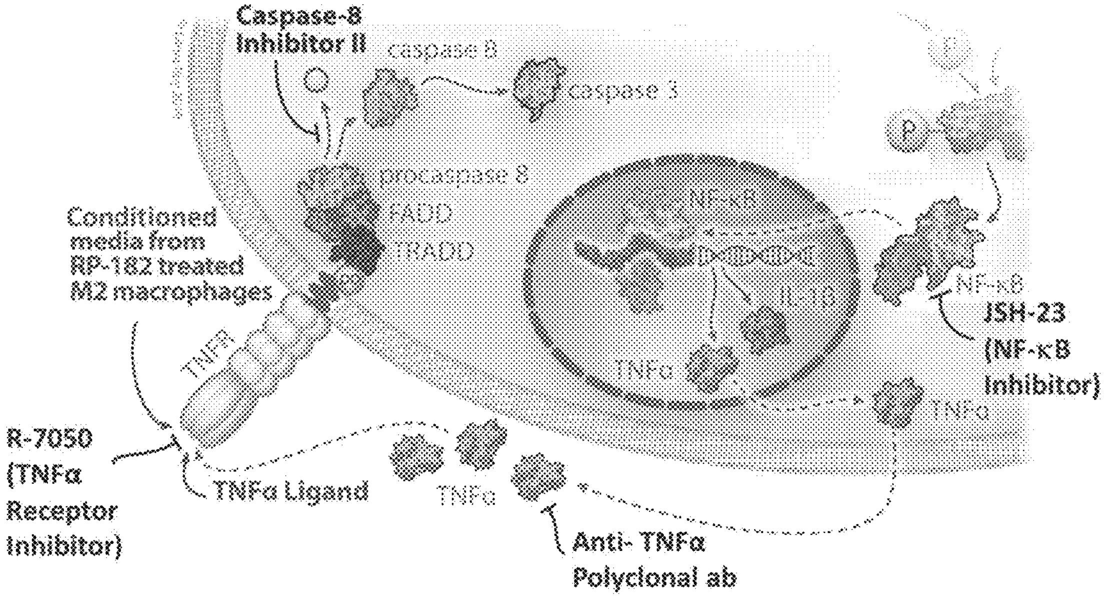
FIG. 57 shows blockade of RP-182-induced TNF signaling abrogates autocrine activation of apoptosis in M2-polarized macrophages. A. Cartoon depicting employed interference with RP-182-induced TNF signaling.

To better understand the downstream MRC1/CD206 signaling mechanism induced by RP-182, the proteomic analysis of MRC1/CD206 complexes was revisited from M2-polarized BMDMs treated with vehicle or biotinylated RP-182 (FIG. 50; FIG. 51). Previous studies identified growth factor receptor-bound protein 2 (GRB2) as an intracellular signaling adaptor molecule of mannose CD206 receptor activation of the CD206 receptor by mycobacteria induces phagocytosis via GRB2 recruitment as well as activation of the Rac1/CDC42/Pak1 signaling cascade, regulators which were GRB2 was highly enriched in the CD206 pulldown from RP-182-treated BMDMs. Co-immunoprecipitation and immunoblotting studies in M2 macrophages showed that binding of RP-182 to CD206 recruits GRB2 and activates Rac1/CDC42/Pak1 signaling (FIGS. 52A-B). As control we tested the phospho-AKT levels in RP-182 treated M2 macrophages and no activation of this pathway was identified. IQ motif containing GTPase activating proteins 1 and 2 (IQGAP1 and 2), which were 9- and 76-fold enriched in CD206 complexes pulled down from RP-182-treated cells compared to control, have previously been shown to be effectors of small GTPases Rac1/CDC42 in cytoskeletal dynamics stabilizing the GTP-bound, active state of Rac1/CDC42 and to be involved in endocytosis/phagocytosis. In M2 BMDMs, RP-182 increased the binding of IQGAP1 to the CD206 complex and induced membranous recruitment within 10 minutes (FIG. 53). Blockade of Rac1/CDC42 signaling abrogated RP-182-induced IQGAP1 membrane translocation and induction of phagocytosis (FIGS. 54A-B). Treatment with autophagy inhibitors prevented induction of RP-182-induced LC3 expression, but did not affect caspase 8 induction, suggesting that caspase 8 activation, which did not occur in the presence of NF-kB inhibitors, is not part of an autophagolysosomal cascade but driven by NF-kB activation mediated by Rac1/CDC42-Pak1 signaling activation (FIGS. 55A-B and FIG. 56). Indeed, induction of apoptosis was mediated by RP-182-induced autocrine TNFα signaling triggered by NF-kB activation. Blockade of TNFα signaling abrogated induction of caspase 8 and 3 activation, while conditioned media from RP-182-treated M2 BMDMs activated apoptosis which was not observed in the presence of anti-TNFα antibodies (FIG. 57).

These data suggest that RP-182 binding to CD206 recruits GRB2 and the Rac1/CDC42 effector IQGAP1 and activates Rac1/CDC42/Pak1 signaling promoting phagocytosis and autophagy and co-stimulates NF-kB signaling which is associated with induction of apoptosis via autocrine TNFα signaling (FIGS. 55A-B).

Example 5: Association of CD206 Expression Status with Intratumoral Immunity

The association of CD206 expression status with intratumoral immunity was assessed, and it was found that CD206$^{high}$ expression status is associated with decreased intratumoral immunity in human and murine pancreatic cancers.

Figure 58:
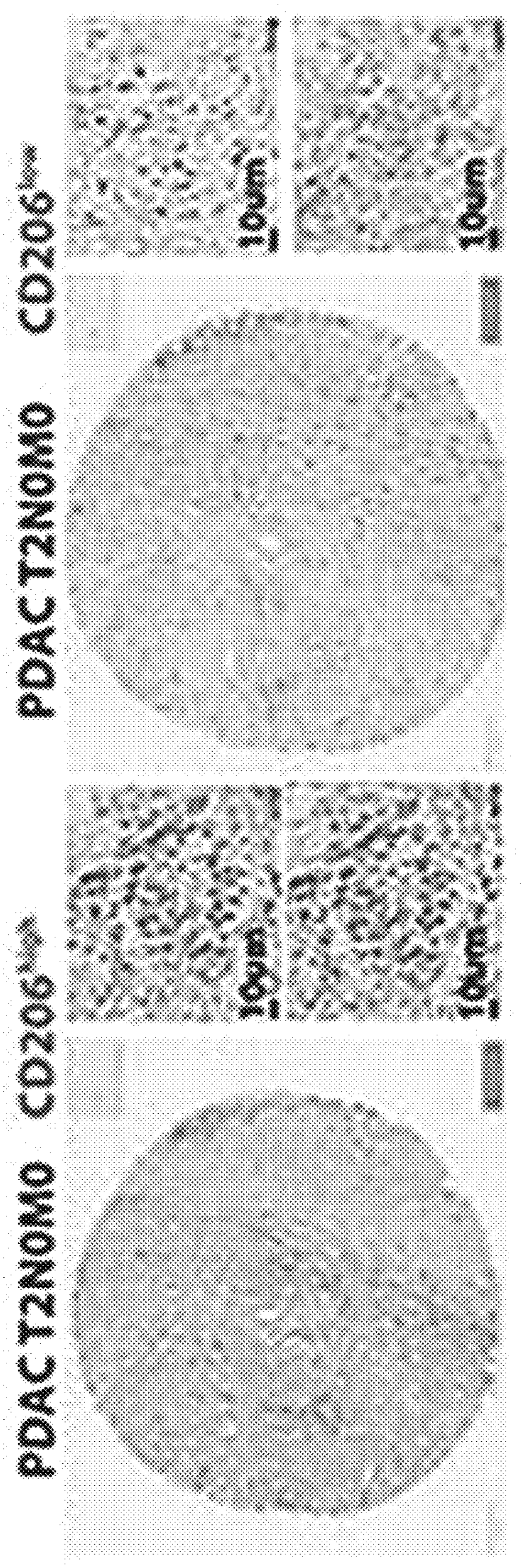
FIG. 58 shows immunohistochemical staining of CD206 in $CD206^{high}$ and $CD206^{low}$ PDAC (at 10×, inlets at 40× at right).
Figure 59:
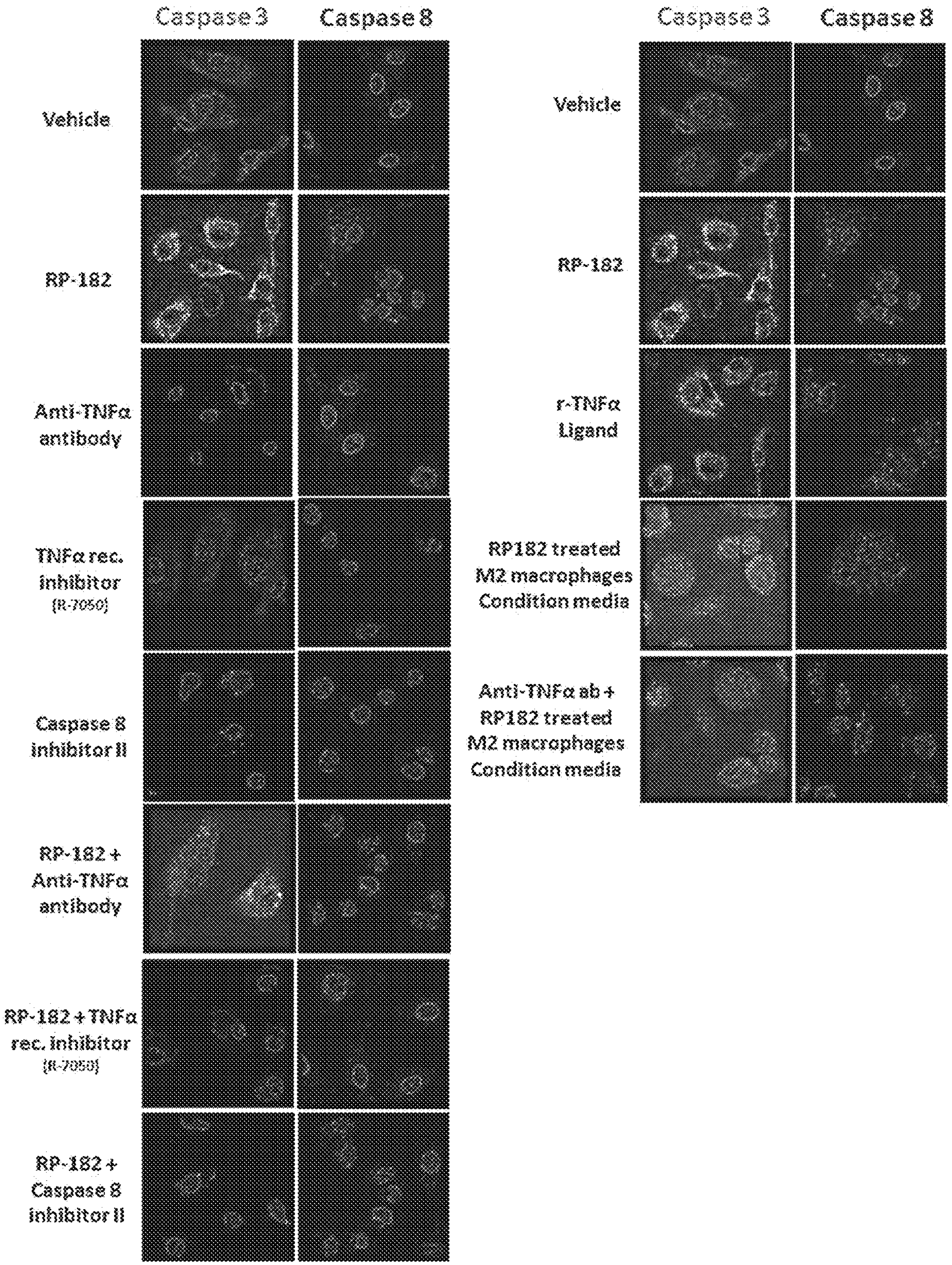
FIG. 59 shows immunofluorescence images of M2 BMDMs stained with anti-cleaved caspase 3 and anti-cleaved caspase 8 antibodies. Lack of caspase 8 and lack of, or reduced (with anti-TNFα antibody), caspase 3 activation upon addition of neutralizing anti-TNFα antibodies, small molecule-mediated blockade of the TNF receptor (TNFR1), or for caspase 3 activation blockade of caspase 8 to M2 BMDMs treated with RP-182 (panel on left). Controls with anti-TNFα antibody. TNFR1 inhibitor R-7050, and caspase 8 inhibitor alone are shown on top. Cleaved caspase 8 and 3 staining of M2 BMDMs upon addition of conditioned media (panel on right). The addition of conditioned media from M2 BMDMs treated with RP-182 or recombinant TNFα to M2 BMDMs strongly activated caspase 8 and 3, an effect which was reduced through the addition of neutralizing TNFα to the conditioned media (bottom). TNFα, recombinant TNFα ligand; α-TNF, anti-TNFα antibody; CM, conditioned media; TNFR1i, TNF receptor inhibitor R-7050.
Figure 60:
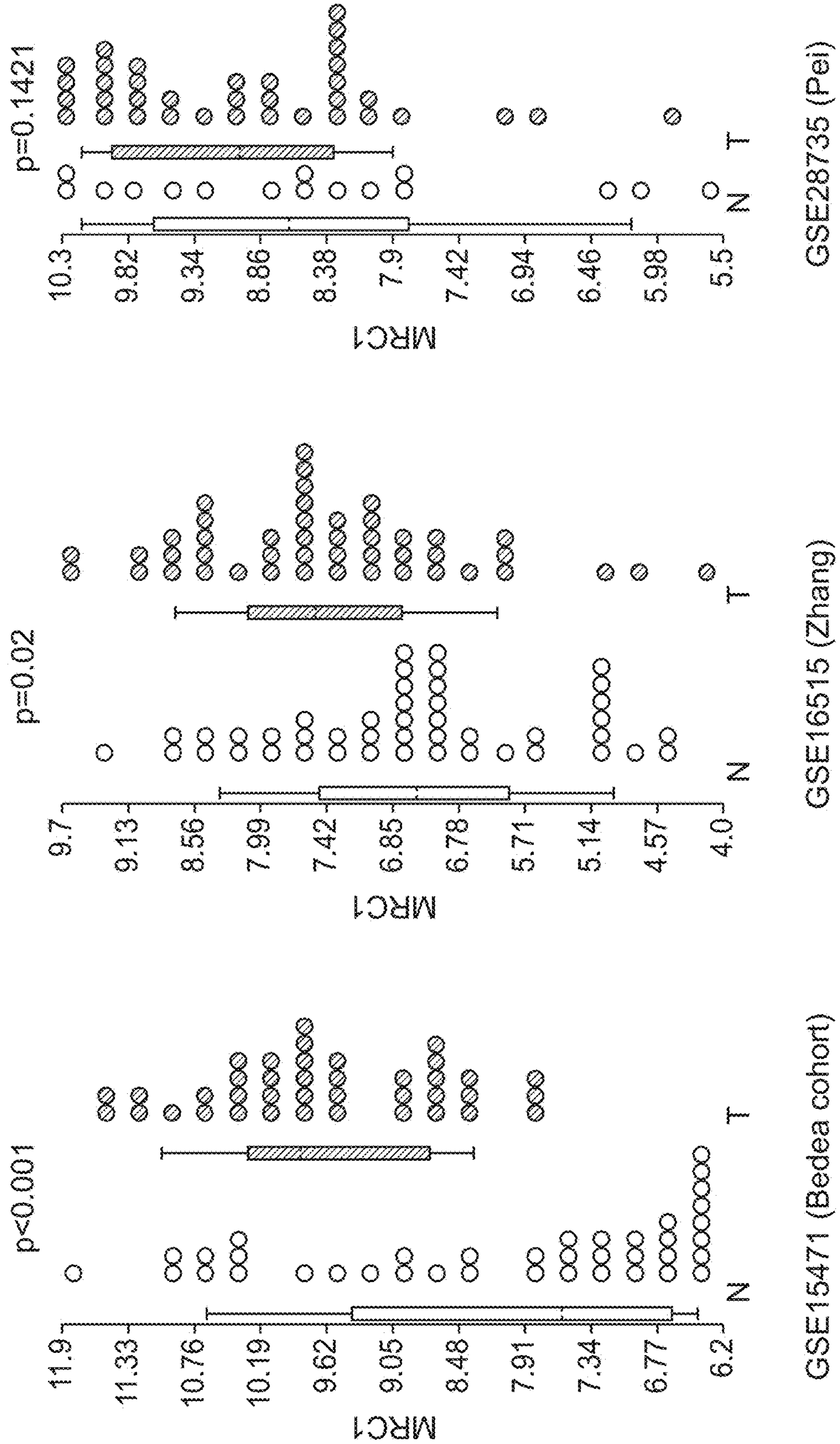
FIG. 60 shows CD206 expression in human pancreas cancer. A. CD206 is overexpressed in two out of three clinical pancreas cancer sample sets compared to matched uninvolved normal glandular tissue. MRC1/CD206 gene expression levels from gene sets GSE15471. GSE16515, and GSE28735. B. Tissue microarray (TMA) of 80 cases of adenocarcinoma of the pancreas, representative images at ×10 magnification of original cores shown on top, waterfall plot indicates percent CD206 positive cells of total cells ranked from highest (left) to lowest (right) for each case. Bottom shows representative images at ×40 magnification of CD206high (left) and CD206low (right) cases.

CD206 expression status as a surrogate for M2 macrophage population varied considerably across clinical pancreas cancer resection specimens (FIG. 58 and FIG. 59). CD206 was found to be overexpressed in two of three available independent gene expression sets of clinical pancreatic cancer specimens compared to matched uninvolved normal pancreas with gene set GSE28735 showing a trend towards higher CD206 expression in the tumors (gene sets GSE15471, GSE16515, and GSE28735; FIG. 60).

Figure 61:
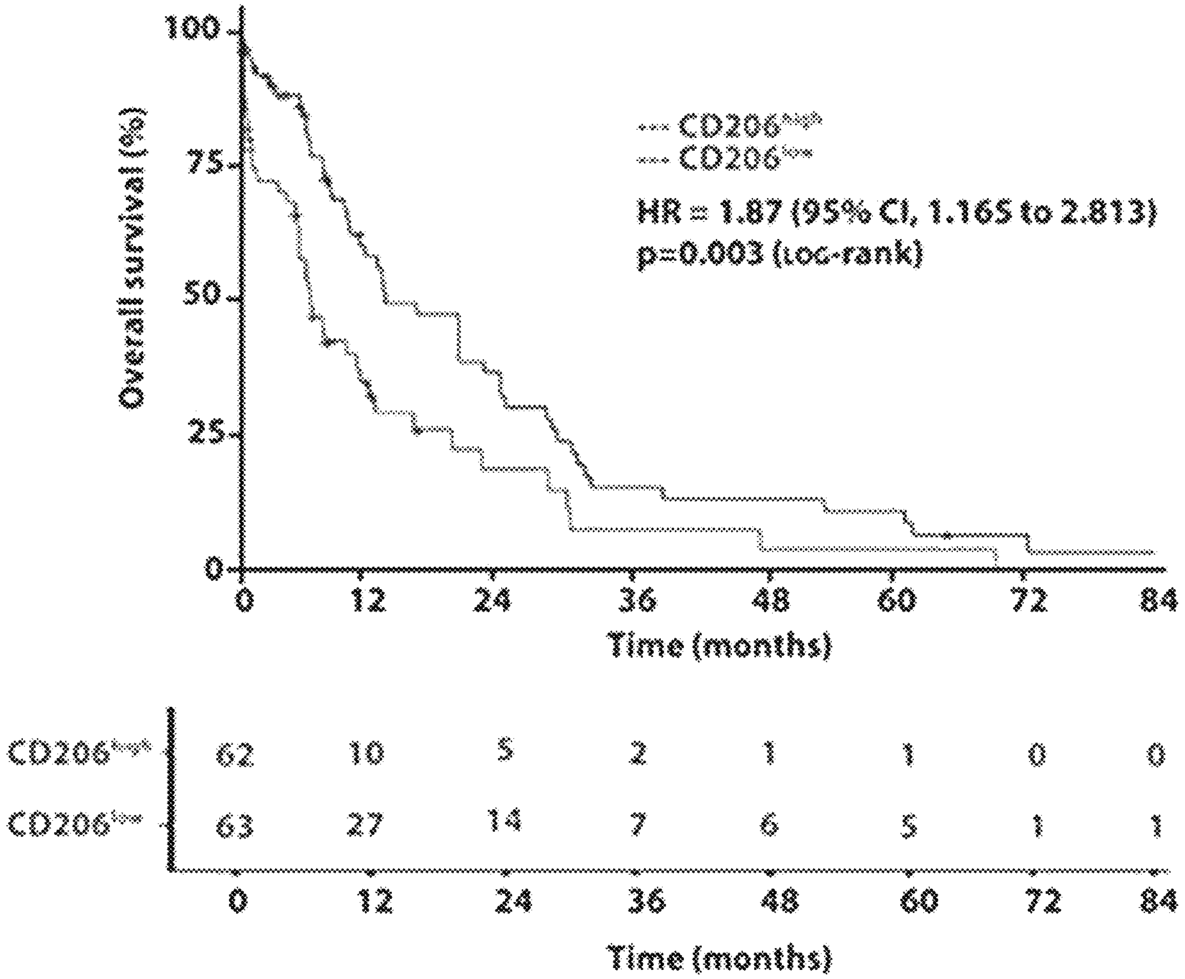
FIG. 61 shows Kaplan-Meier plots of overall survival of 125 patients afflicted with PDAC stratified by CD206 expression. Log-rank test, 2-tailed.
Figure 62:
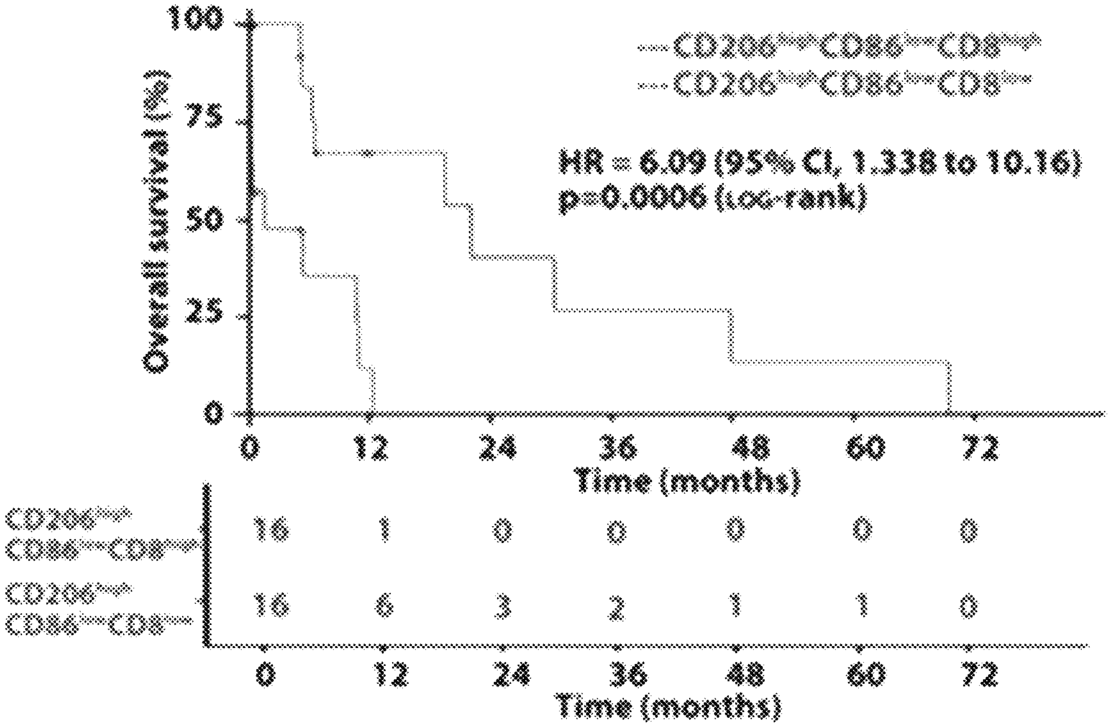
FIG. 62 shows Kaplan-Meier analysis of patients with CD206high TAMs stratified by CD8high vs CD8low.

Overall survival (OS) of patients with pancreatic cancers was more unfavorable in the CD206high clinical cases (HR 1.87, 95% confidence interval (CI) 1.165 to 2.813; log-rank test; p=0.003) (FIG. 61). Infiltrating CD8+ T cells measured by CD8 transcript levels separated outcome of clinical cases with high M2-like populations further (HR 6.09, 95% CI, 1.338 to 10.16; log-rank test; p=0.0006) (FIG. 62).

Figure 63A:
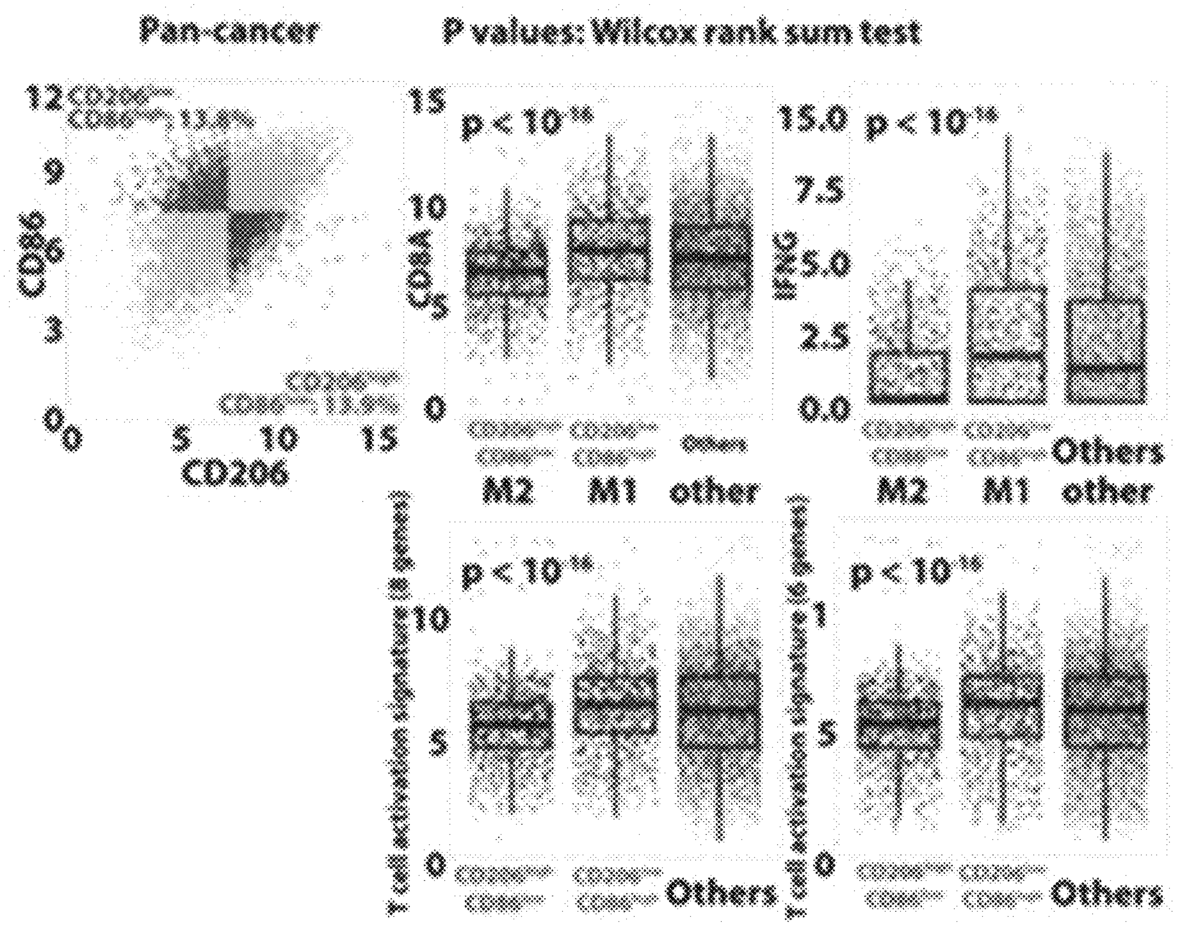
FIG. 63A shows correlation of CD8A. INFG expression, 8 and 6 gene CD8 T cell activation signatures (bottom) and M2 marker expression levels in clinical specimens from TCGA cancer dataset. Samples across all cancers were divided into CD206high and CD86low using median of all specimens.
Figure 63B:
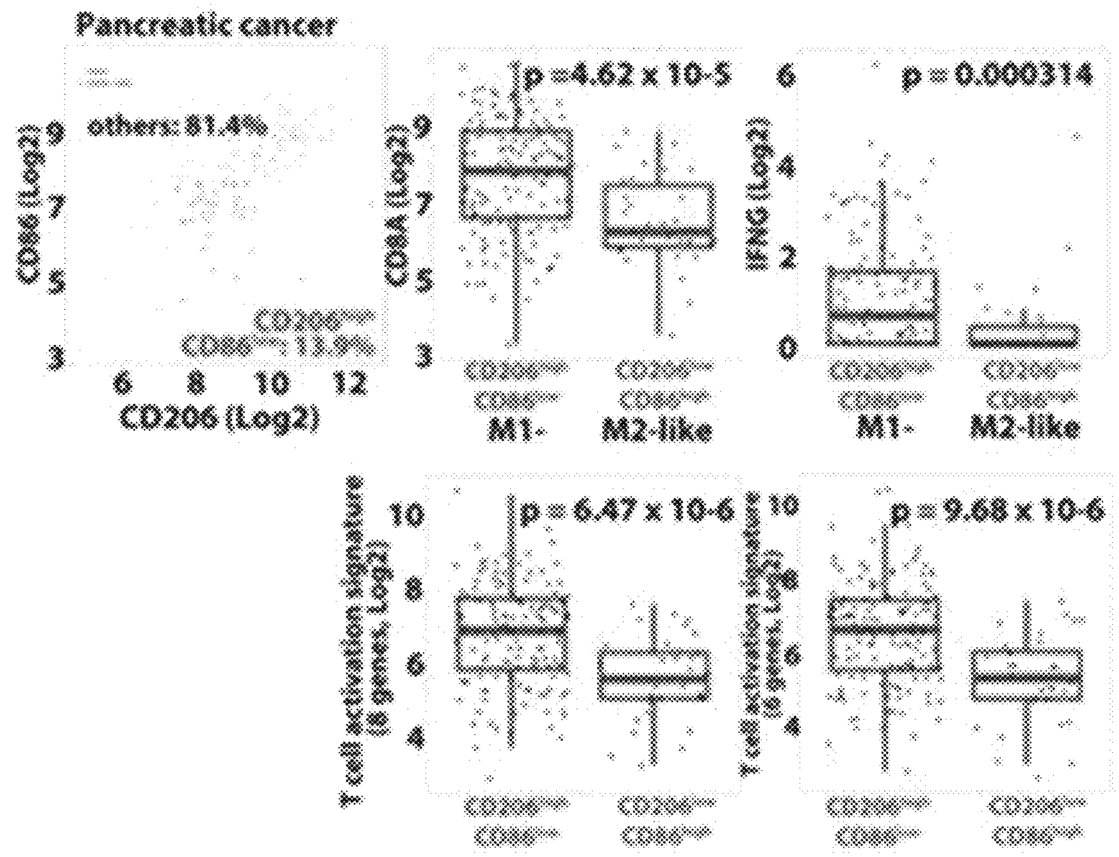
FIG. 63B shows correlation of CD8A, INFG expression, 8 and 6 gene CD8 T cell activation signatures (bottom) and M2 marker expression levels in clinical specimens from TCGA cancer dataset. Samples across all cancers were divided into CD206high and CD86low using median of all specimens. Correlation of macrophage subtypes and CD8+ T cell function in pancreas cancer TCGA dataset.

To examine whether the adverse disease outcome in CD206high cases is supported by immune subpopulation correlations in human pancreatic cancers, or across solid organ cancers, correlations of intratumoral macrophage subsets and surrogates of intratumoral CD8+ T cell function were investigated in TCGA pan-cancer and pancreatic adenocarcinoma data sets. After selecting tumors with M2-high fractions and low abundance of M1-like macrophages, there was a negative correlation with CD8 transcripts as well as measures of CD8+ T cell function including low expression of two previously described T cell activation response signatures (FIGS. 63A-B). To study the association of CD206 and clinical outcome further, we generated murine pancreatic cancers in CD206-deficient B6.129P2-Mrc1tm1Mnz/J mice.

Figure 64:
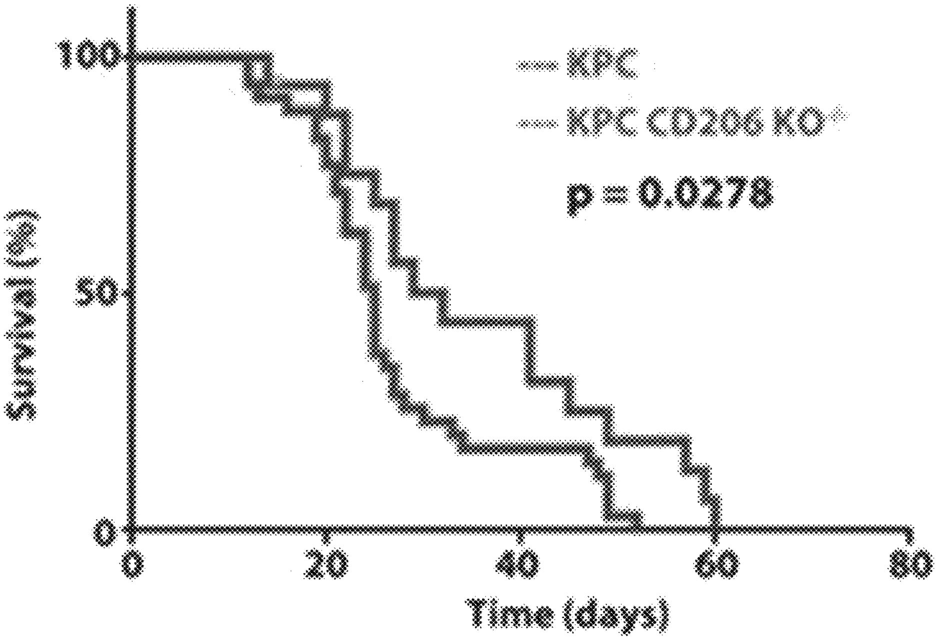
FIG. 64 shows Kaplan-Meier analysis of KPC tumors allografted in CD206−/− B6.129P2-Mrc1tm1Mnz/J mice (red curve) and in C57B/L wild type mice (black curve). Log-rank, 2-tailed.
Figure 65:
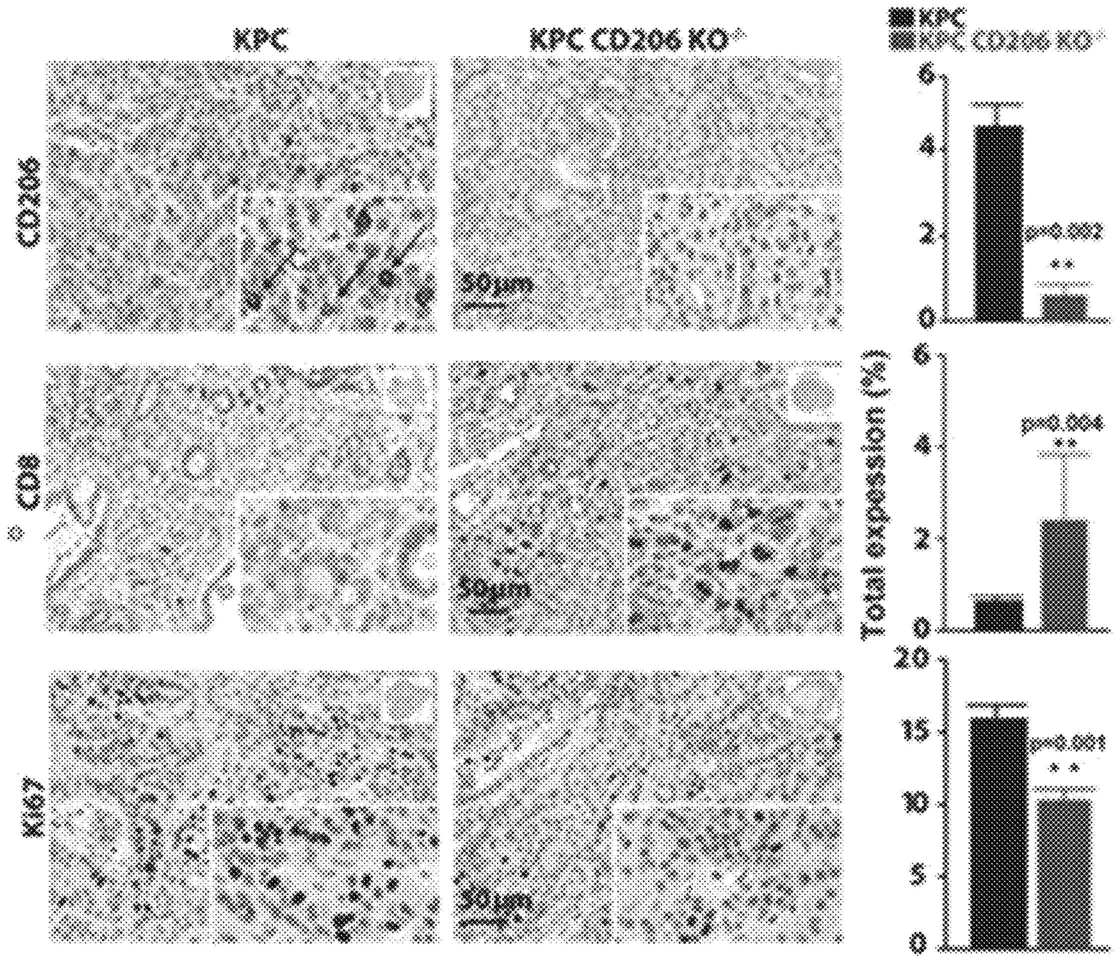
FIG. 65 shows immunohistochemical staining of KPC wild type (KPC) and KPC tumors generated in CD206−/− B6.129P2-Mrc1tm1Mnz/J mice (KPC CD206 KO−/−), quantification on right (N≥4 per group).
Figure 66:
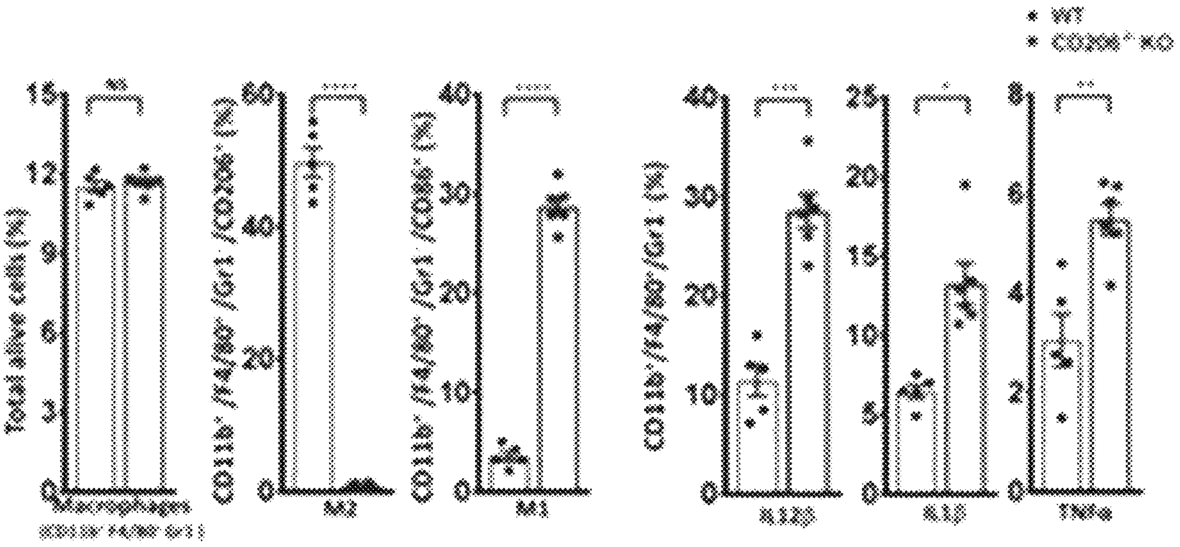
FIG. 66 shows quantification of flow cytometry of TAM subpopulations in KPC tumors grown in C57B/L6 wild type and CD206−/− mice (N≥5 per group).

There was a discernable difference in survival of KPC CD206−/− vs CD206 wild type allografts with CD206-deficient tumors showing prolonged overall survival (median OS of KPC CD206−/− vs CD206 wild type, 32 vs 25 days; p=0.0278; FIG. 64). KPC tumors in CD206−/− mice showed absent CD206 expression and, in line with the negative correlation of CD206high and CD8 T cell function in the human cancer specimens, significantly increased intratumoral CD8+ T cell numbers compared to KPC tumors generated in CD206-proficient C57B1/L6 wild type mice (FIG. 65). In summary, CD206-positive M2-like TAMs are negatively correlated with intratumoral T cell function. Pancreatic cancers allografted into CD206-deficient B6.129P2-Mrc1tm1Mnz/J mice have attenuated cancer progression compared to tumors generated in CD206-wildtype mice and share immunogenic traits including increased intratumoral CD8+ T cells observed in human CD206low tumors. KPC tumors in CD206−/− mice attracted an equal number of TAMs compared to KPC tumors grown in wild type mice, of note there was a significant shift towards a M1-like phenotype in the TAM population of CD206−/− mice (FIG. 66).

Example 6: Effect of RP-182 on Tumors and Tumor Microenvironments

Figure 67A:
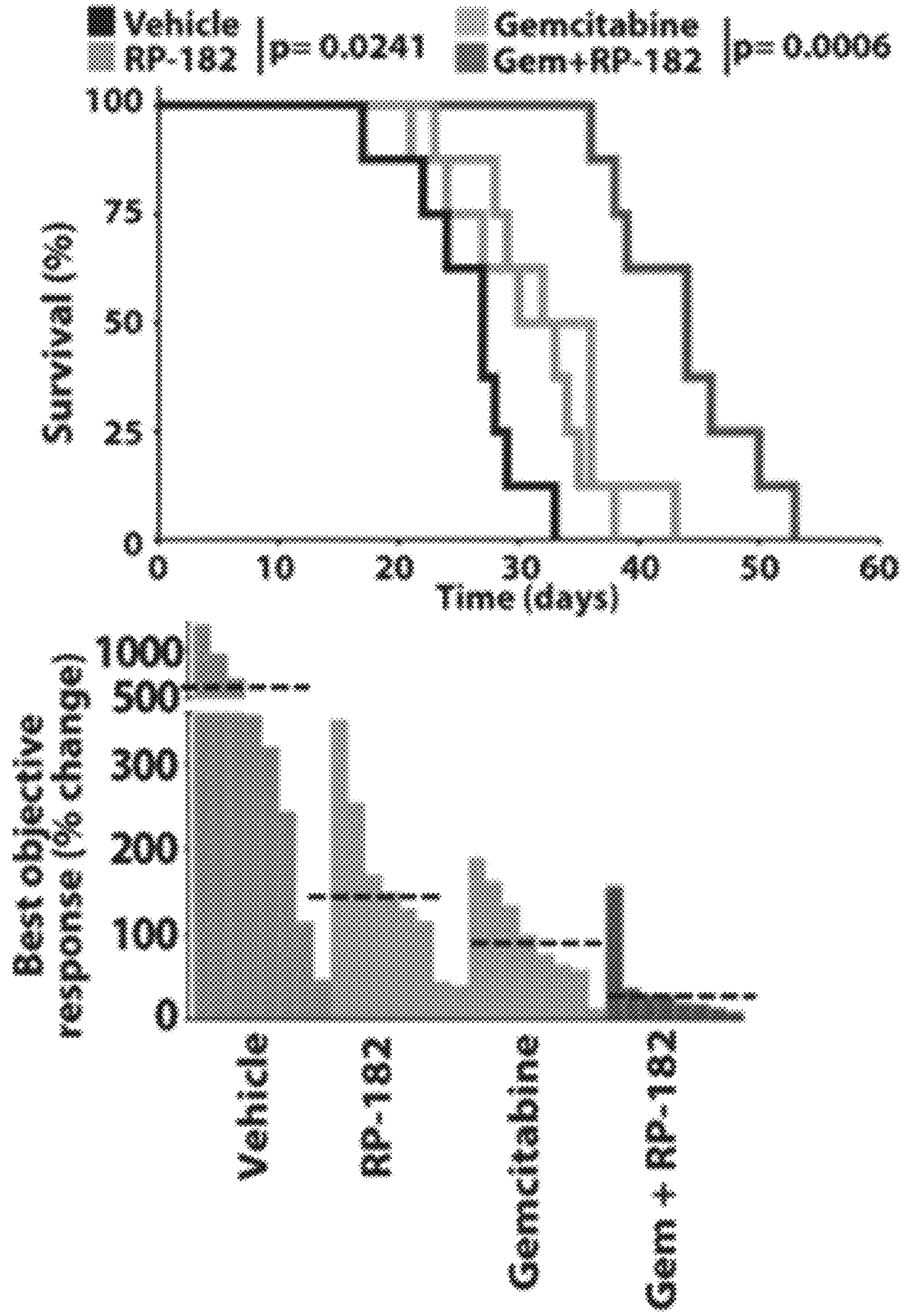
FIG. 67A shows Kaplan Meier analysis of KP16 mice. Log-rank test, 2-tailed. B. Waterfall plot of best objective response.
Figure 68:
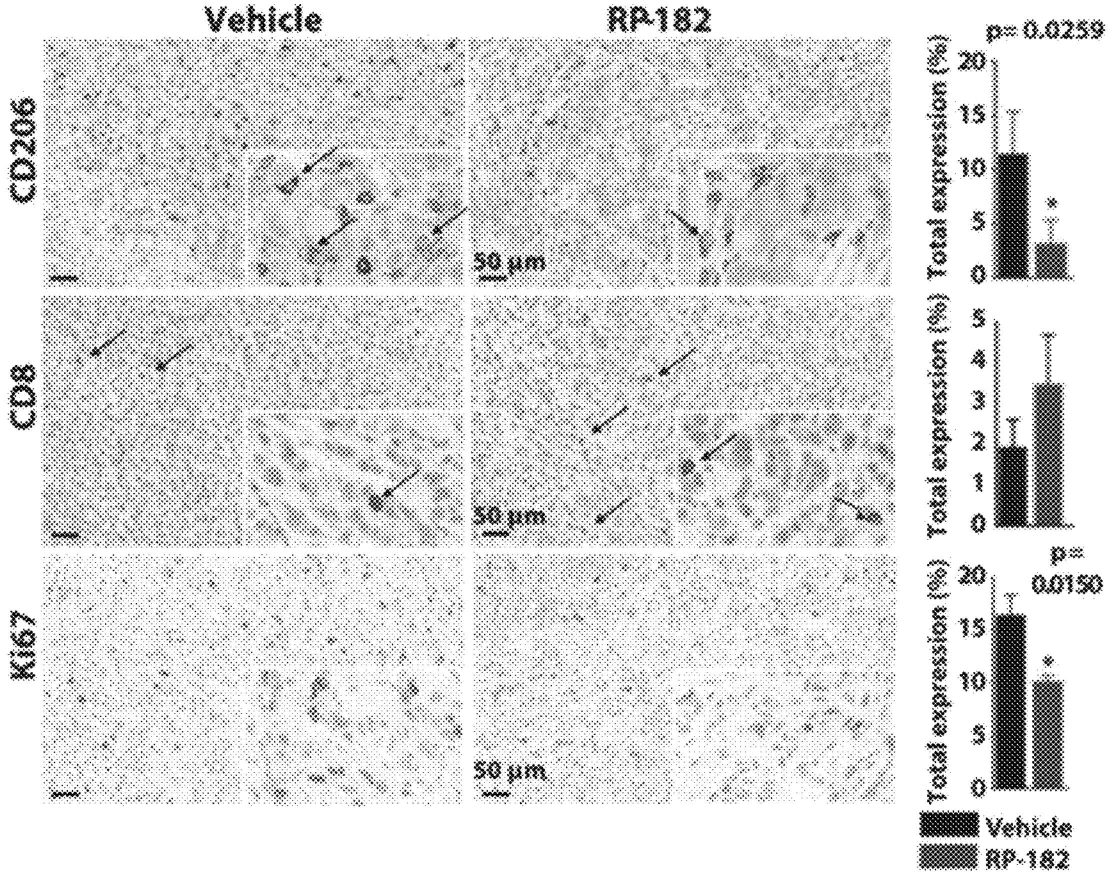
FIG. 68 shows images of immunohistochemical stains of tumors from KP16 mice treated with vehicle or RP-182, quantification depict mean percent positive cells by computer-based tissue analysis of N=4/group. Arrows indicate membranous staining of CD206-positive cells or CD8+ T cells.
Figure 69:
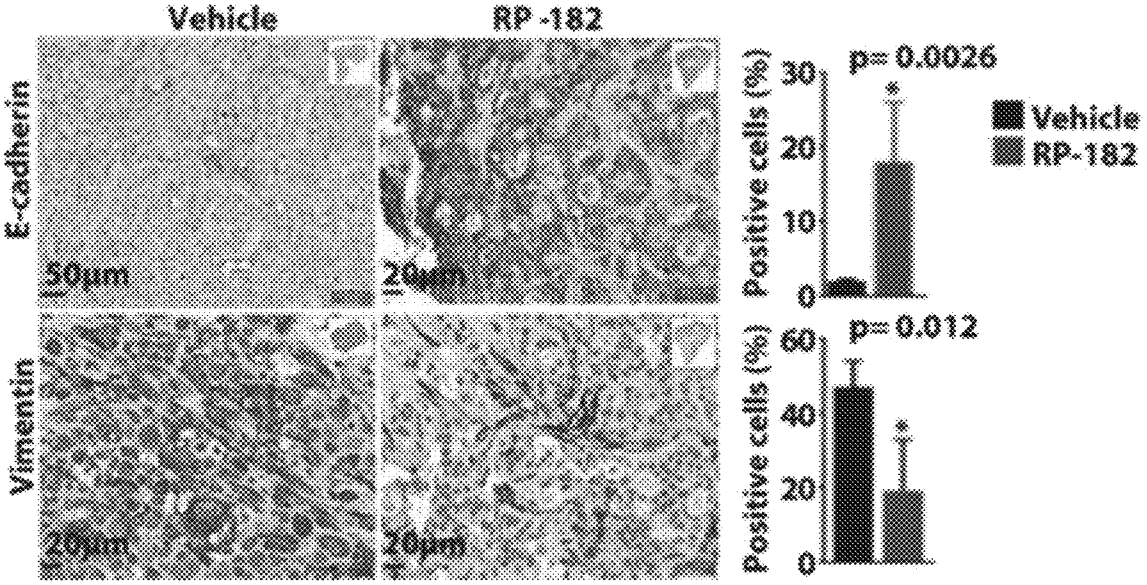
FIG. 69 shows immunohistochemical staining of E-cadherin and vimentin, quantification of N≥4 per group on right.

The effect of RP-182 on tumors was studied, and it was found that RP-182 mediates anti-tumor activity and reprograms the tumor microenvironment. RP-182 was tested in the autochthonous genetically engineered Ras-driven KP16 and KPC models of pancreas cancer. Kaplan-Meier analysis and tumor growth measurements showed extension of survival and anti-tumor activity of RP-182 monotherapy yielding similar gains in survival and tumor suppression as gemcitabine (median overall survival (OS) of 20.5 vs 32 days in vehicle vs RP-182-treated KPC animals; p=0.0125, and 27 vs 31.5 days in KP16 animals; p=0.0241) (FIGS. 67A-B). Animals treated with the combination of RP-182 and gemcitabine were afforded in both models the greatest extension of survival with outcome in the combination cohort improved compared to single-agent treatment (34 vs 44 days in gemcitabine vs combination group in KP16 mice; p=0.0006 and 24.5 vs 42.6 days in KPC; p=0.0002, respectively) (FIG. 67A-B). Tumor tissues harvested at study endpoint showed reduced stromal CD206-positive macrophages and decreased nuclear Ki67 expression (FIG. 68). RP-182 induced E-cadherin expression and reduced expression of the epithelial-to-mesenchymal transition (EMT) marker vimentin (FIG. 69).

Figure 70:
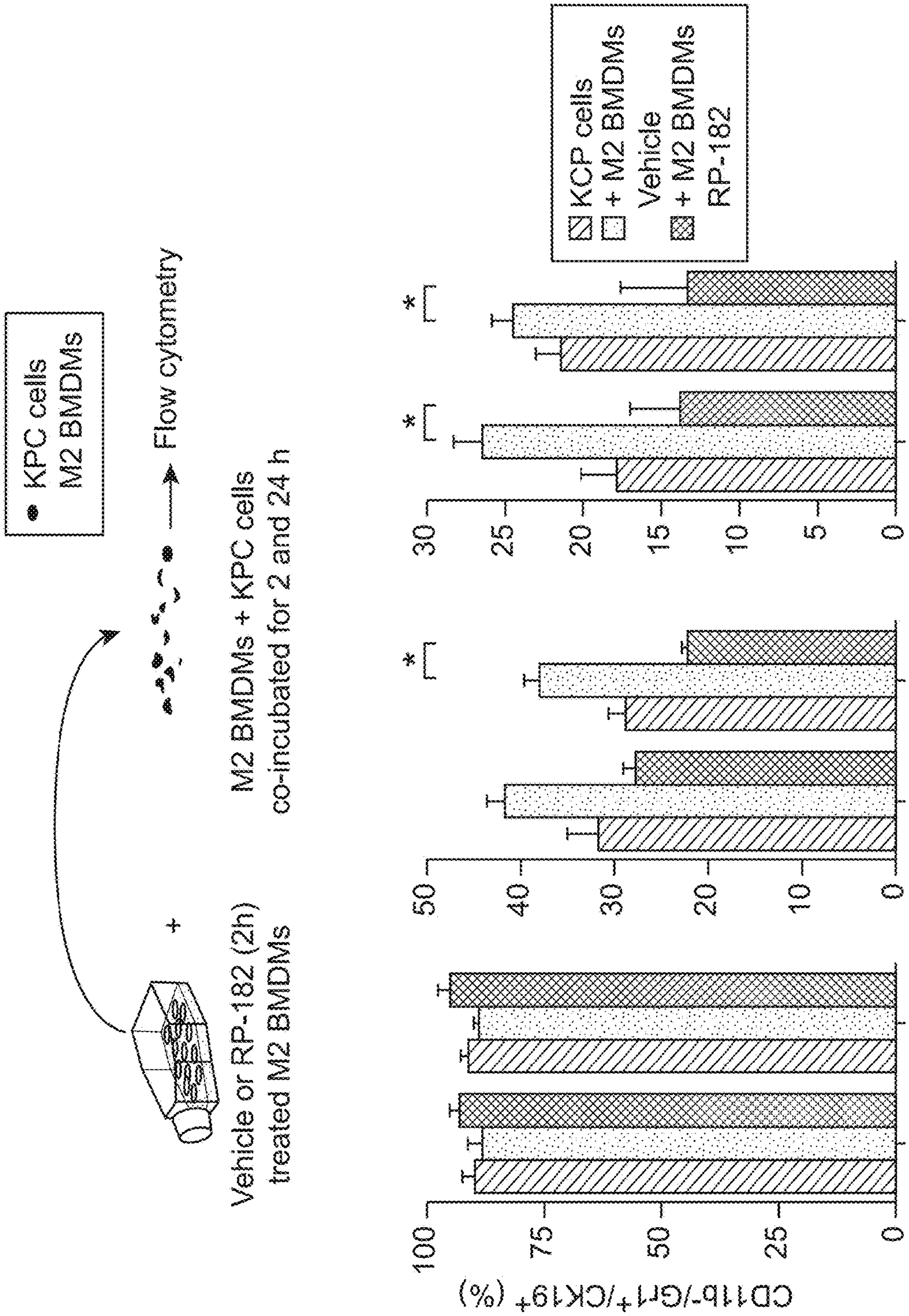
FIG. 70 shows treatment with RP-182 reduces induction of expression of EMT markers vimentin and SNAIL in KPC cancer cells upon co-culture of M2-polarized macrophages. Flow cytometry analysis of Ecadherin, vimentin, and SNAIL2-positive cancer cell fractions after co-culture with no cells (blue bars). M2 BMDMs treated with vehicle (black), and M2 BMDMs pre-treated with 20 μM RP-182 for 2 hours. Percent positive cells were gated on live CD11b-CK19-9+ cells; results from two independent experiments conducted in triplicates are shown.
Figure 71:
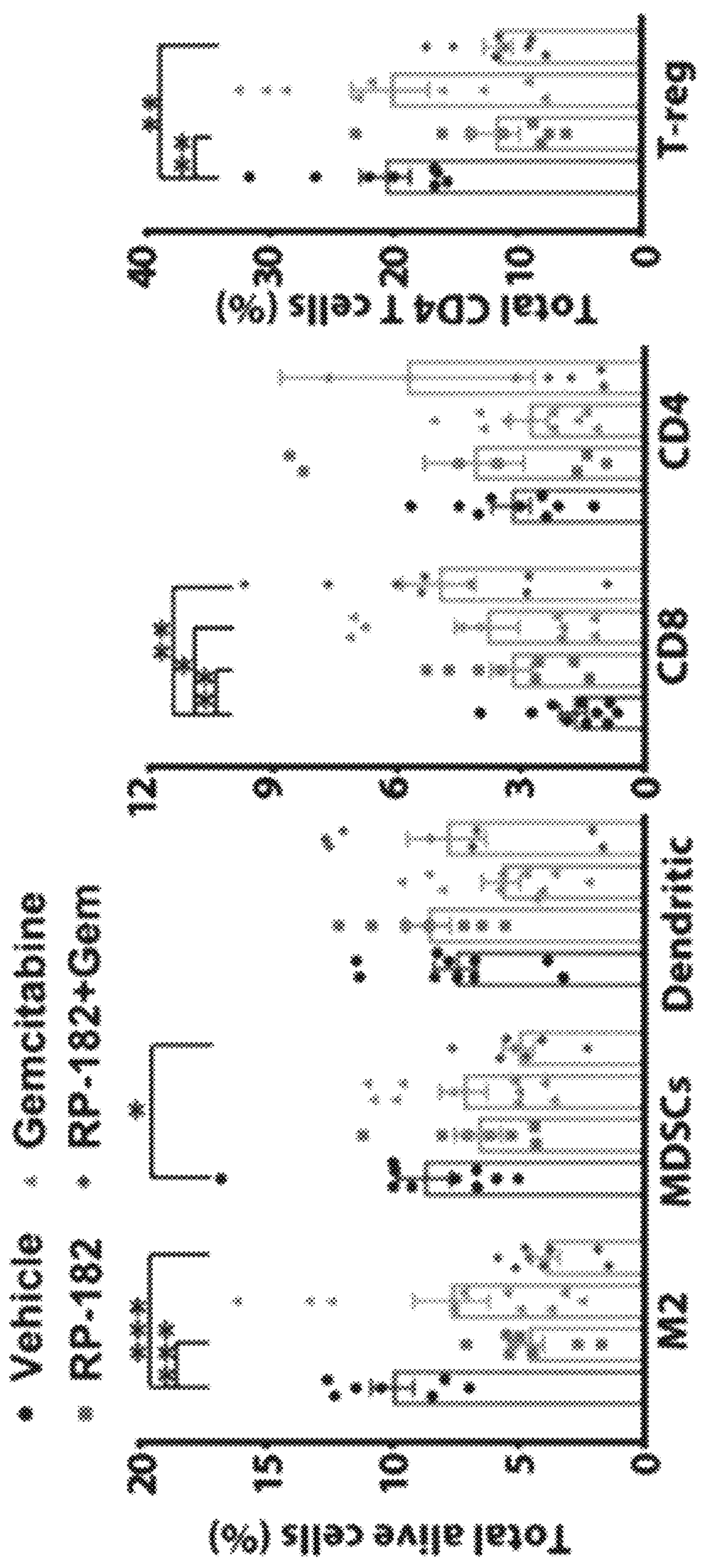
FIG. 71 shows percentage of CD206-positive M2 macrophage. MDSCs, dendritic, CD8-and CD4-positive cell fractions of total cells in KP16 tumors treated for 7 days. Fraction of FoxP3− positive Tregs of CD4+ T cells shown on the right. Representative flow cytometry plots shown on bottom.
Figure 72:
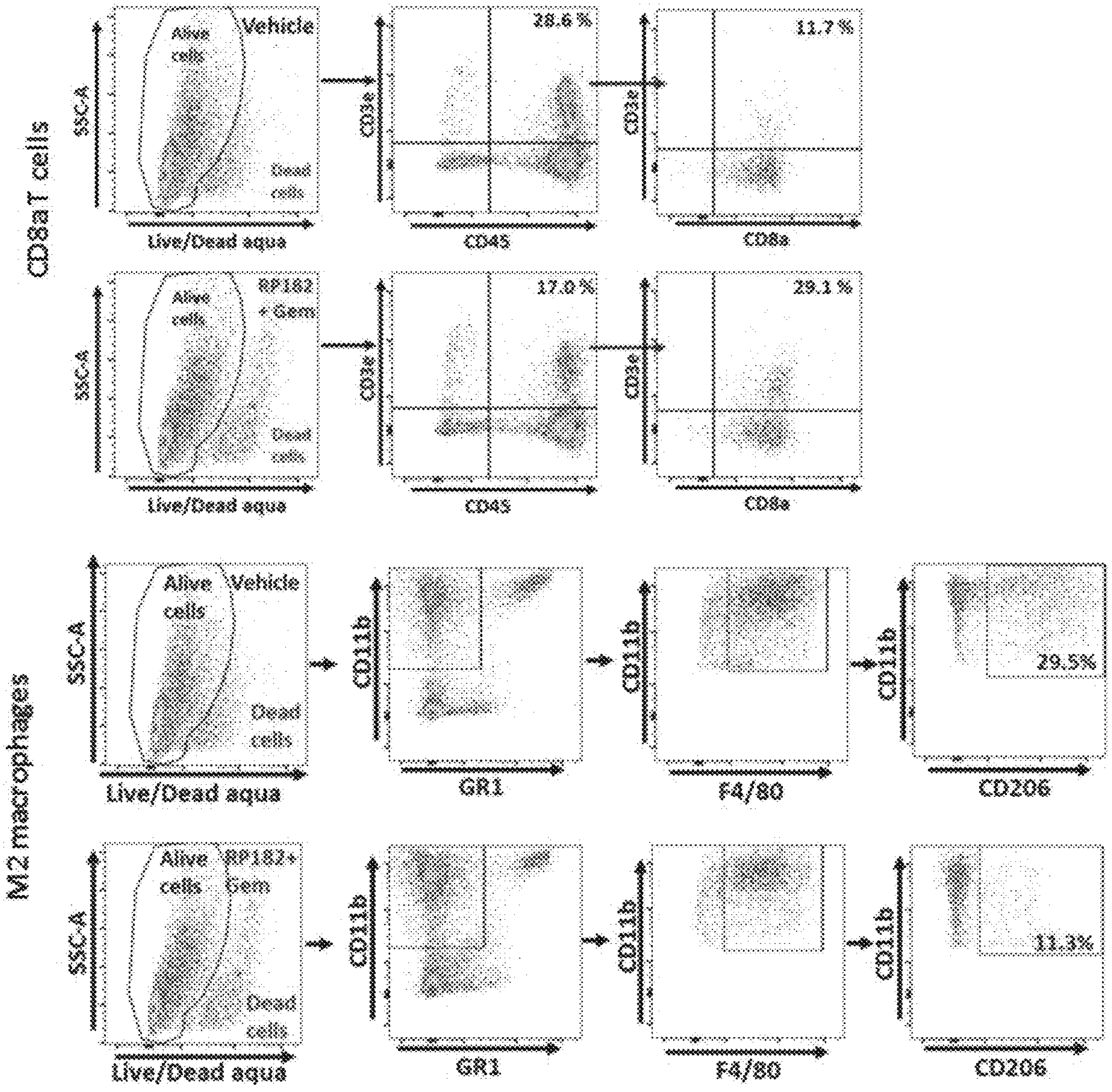
FIG. 72 shows gating strategy for the identification of tumor infiltrating CD8+ T cell (top) and CD206high M2-like TAM fraction in pancreatic tumor digests. Representative flow cytometry plots depicting gating strategy for determination of tumor infiltrating CD8a T cells and CD206-positive TAMs from KP16 animals after treatment with vehicle and RP-182 for 1 week. For final percentages shown in FIG. 6G percentages were normalized to total live cells.
Figure 73:
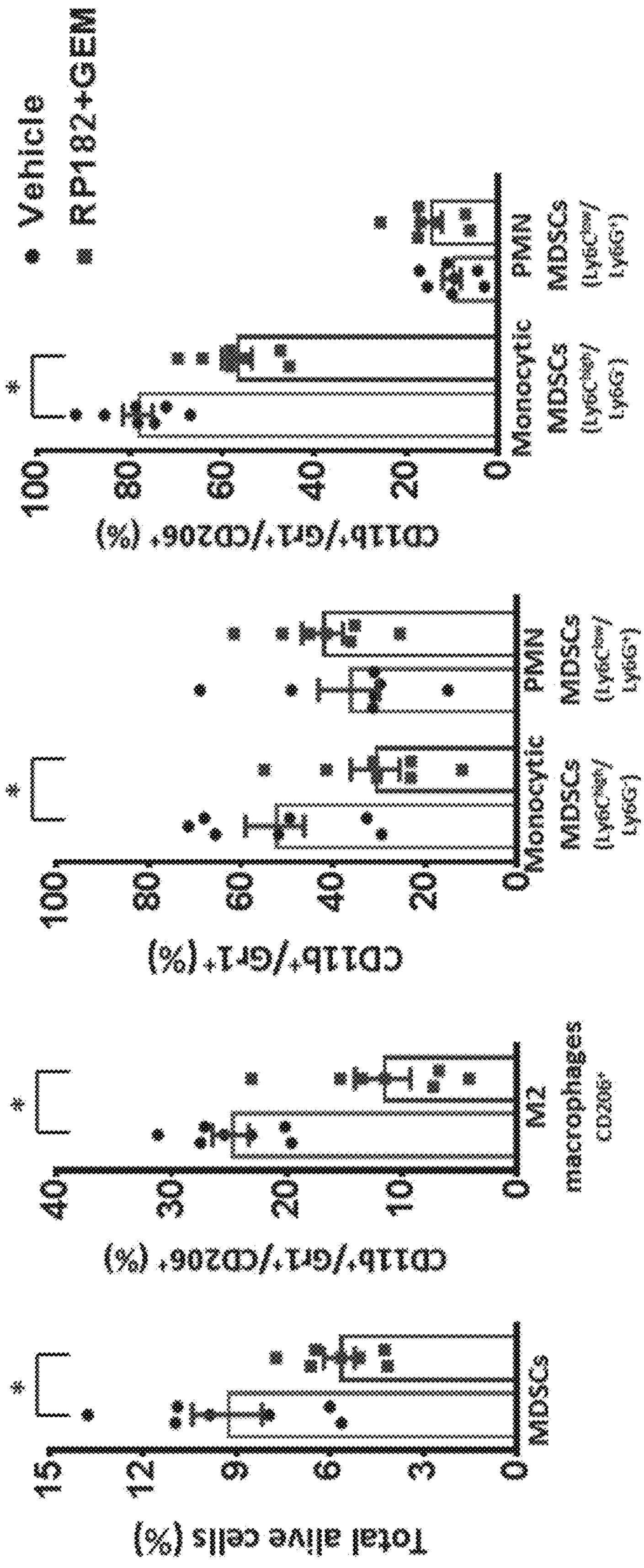
FIG. 73 shows RP-182 in combination with gemcitabine reduces CD206high monocytic MDSCs in authochtonous KPC tumors. Quantification of MDSC cell fractions by flow cytometry of tumor digests of KPC mice treated with vehicle and RP-182 in combination with gemcitabine for 7 days. % cells for each examined individual tumor are shown. Monocytic MDSCs, M-MDSC determined by CD11b+Gr-1+ Ly6ChighLy6G− cells; polymorphonuclear (PMN) MDSCs determined by CD11b+Gr-1+Ly6ClowLy6G+ cells.

In vitro, the expression of the EMT markers vimentin and SNAIL in murine pancreatic cancer cells induced upon co-culture with M2 BMDMs was reduced when macrophages were pretreated with RP-182 compared to vehicle control (FIG. 70). Flow cytometry studies of tumor digests from KP16 mice treated for 7 days with RP-182 alone, and RP-182 in combination with gemcitabine confirmed reduced M2-like TAM fractions in RP-182 and RP-182 in combination with gemcitabine-treated mice (10.3% vs 4.61%, p=0.001 and 10.3 vs 3.91%, p=0.0003 respectively) (FIG. 71). RP-182 also decreased immune suppressive CD4 positive T regulatory (Tregs), and in combination with gemcitabine myeloid-derived suppressor cells (MDSCs) (8.75 vs 4.99%, p=0.015). Either alone or in combination with gemcitabine. RP_182 increased intratumoral CD8+ T cells (1.74 vs 3.40%, p=0.032 and 1.74 vs 4.99%, p=0.020, respectively) (FIG. 71 and FIG. 72). The reduction in the MDSC population occurred nearly exclusively in the CD206high monocytic MDSC subset whereas CD206low polymorphonuclear MDSCs did not show any change (FIG. 73).

Figure 74:
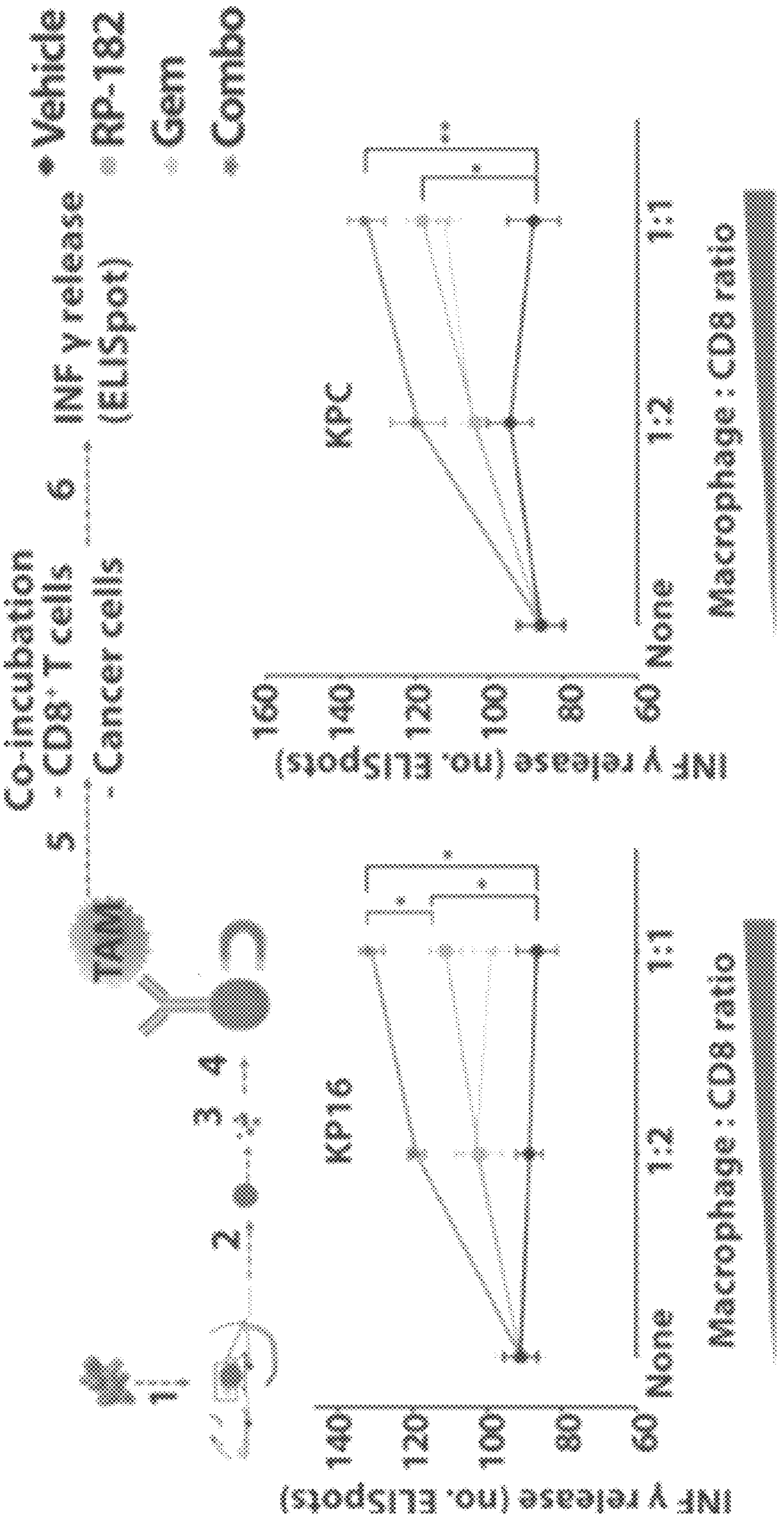
FIG. 74 shows INFγ-positive T cells after addition of TAMs isolated from KP16 and KPC tumors added to co-cultured cancer and splenic CD8+ T cells from tumor bearing mice.
Figure 75:
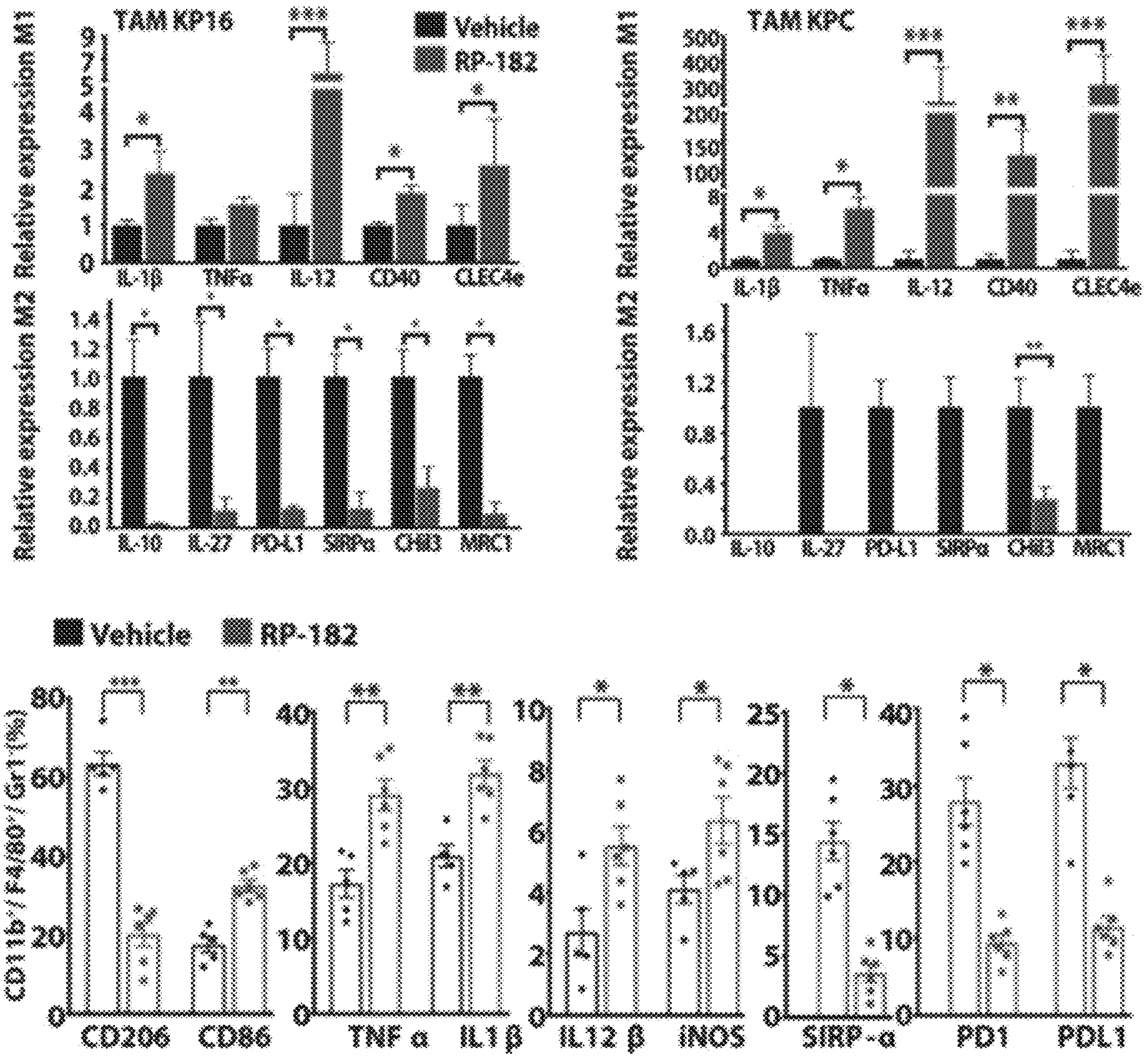
FIG. 75 shows quantification of qRT-PCR analysis of M1 and M2 gene expression levels of TAMs isolated from KPC and KP16 tumors (N≥3 per group, in triplicate). Quantification of percentage of CD206- and CD86-positive macrophages of CD11 b+F4/80+/Gr-1− TAMs, analysis of cell fractions of TAMs expressing M1 cytokines and immune checkpoints shown on the right.
Figure 76:
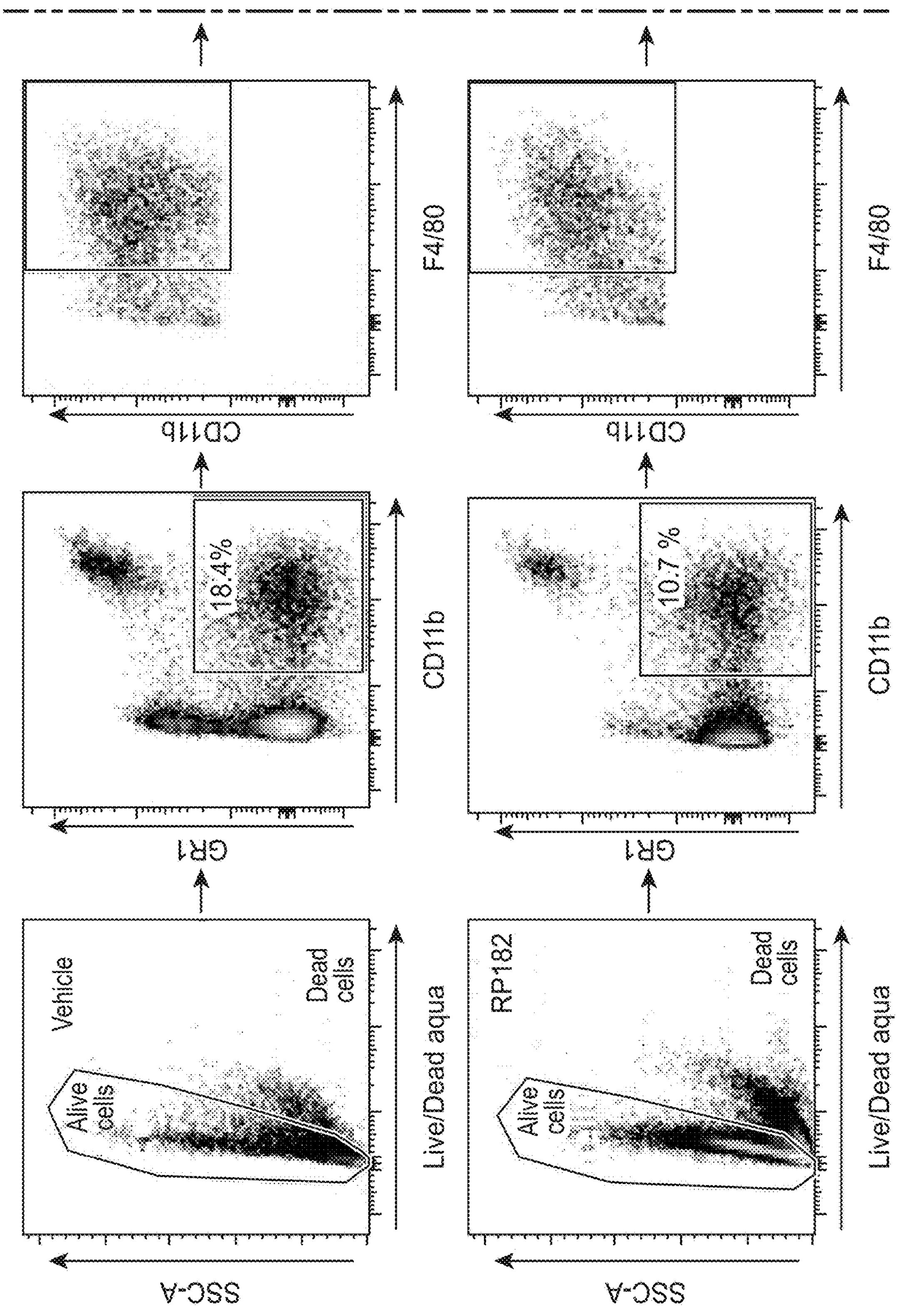
FIG. 76 shows RP-182-induced M1-like CD86+ TAM populations in KPC mice have increased M1 cytokine and decreased PD-1 and SIRPα-positive cell fractions. Flow cytometry analysis of KPC treated with vehicle (top) and RP-182 (bottom) for 7 days, percent positive cells for PD-1, SIRPα, and TNFα of CD11b+F4/80+Gr-1− TAMs are shown (N≥5 per group).
Figure 76:
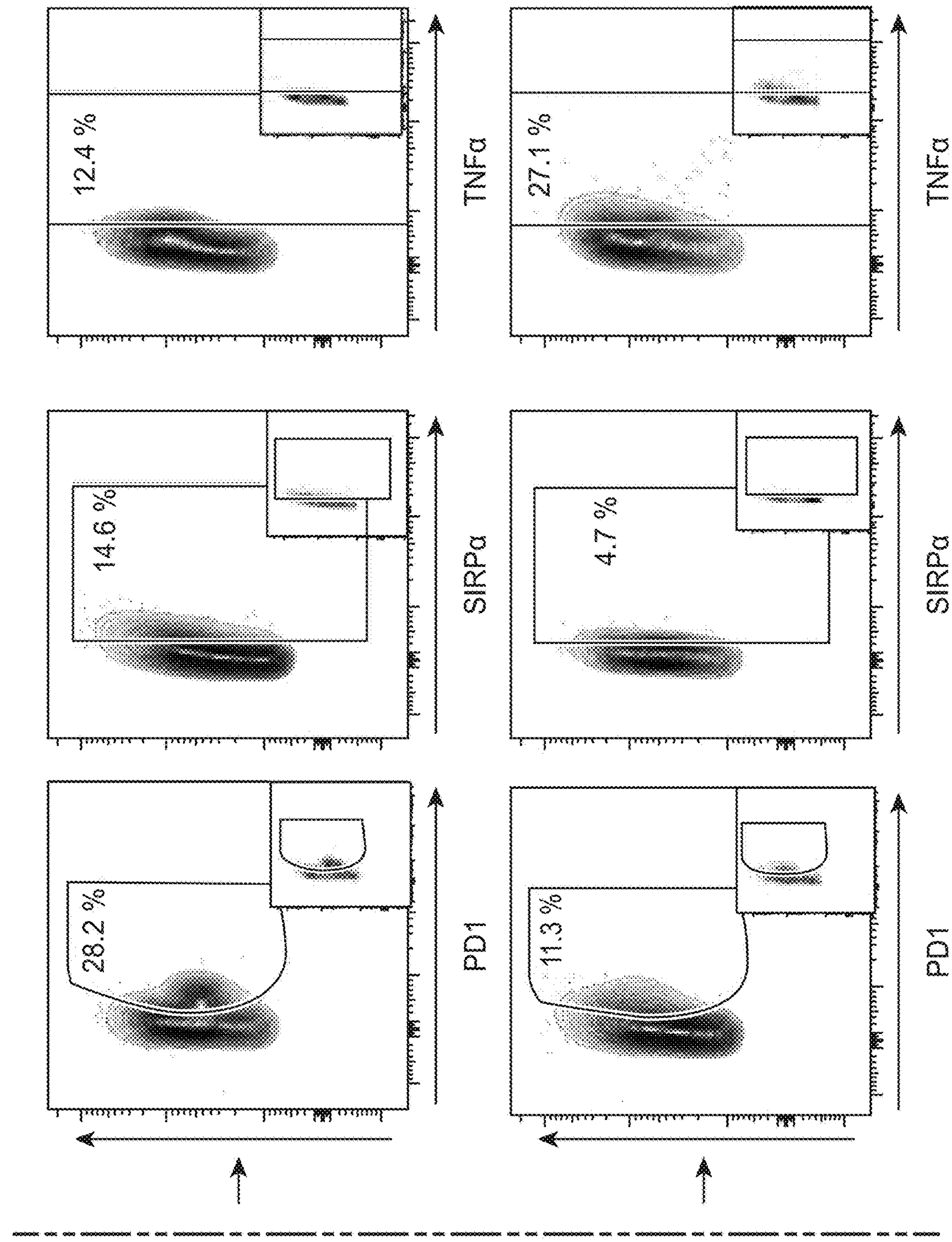
Figure 77:
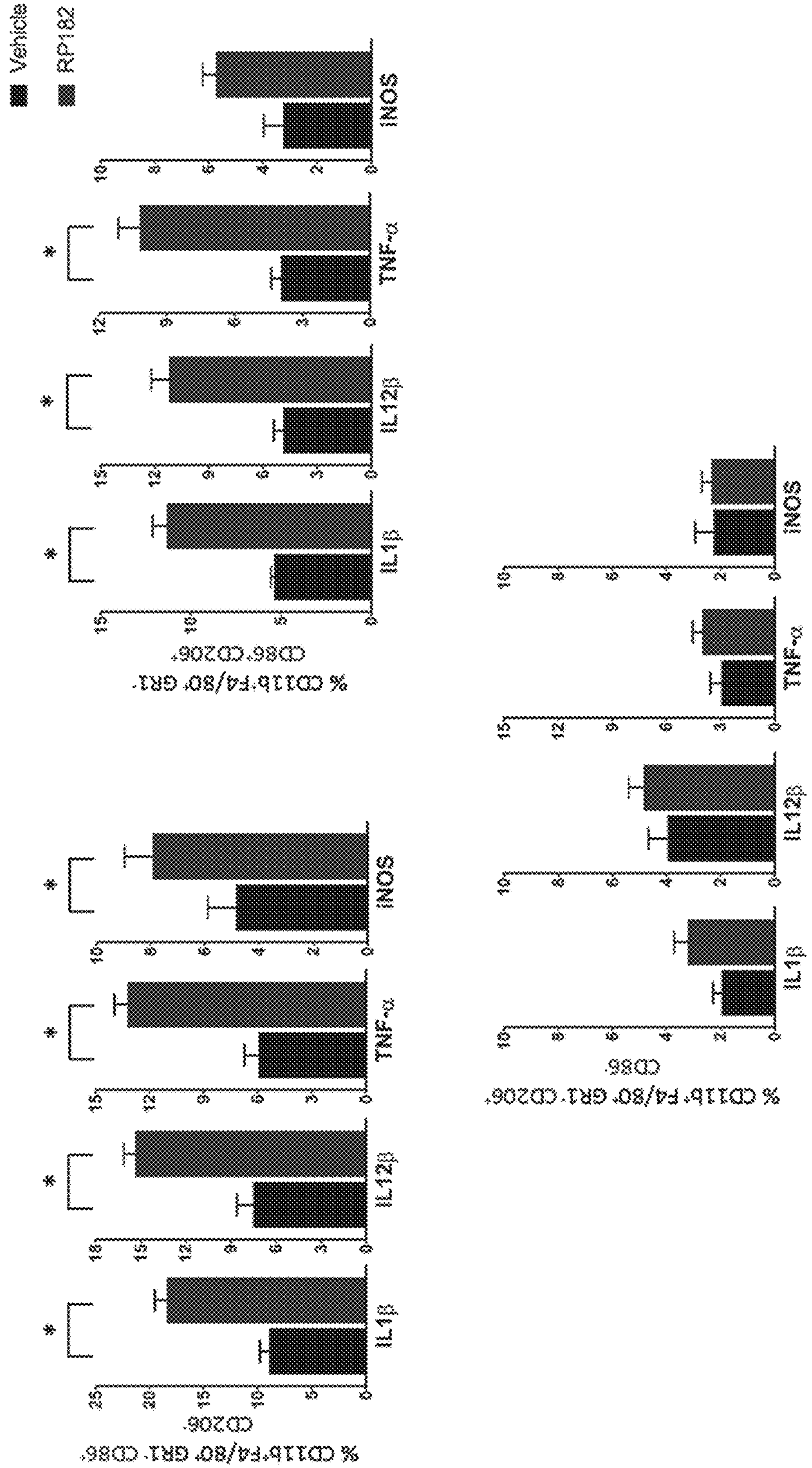
FIG. 77 shows RP-182-induced M1-like CD86+ TAM populations in KPC mice have increased M1 cytokine positive cell fractions. Increased cell fractions staining positive for M1 cytokines IL-1β, IL-12. TNFα and M1 marker iNOS in RP-182-induced double positive CD86+CD206+ and CD86+CD206− TAMs but not in the CD86-CD206+ TAM population. Flow cytometry analysis of KPC treated with vehicle and RP-182 for 7 days, percent positive cell fractions of CD86+CD206−, CD86+CD206+, and CD86−CD206+ macrophage populations are shown (N≥5 per group).

Next, equal numbers of TAMs were isolated from treated murine KPC and KP16 pancreatic tumors and evaluated their impact on T cell function. Whereas TAMs isolated from vehicle-treated animals did not induce increments of interferon gamma (INFγ) release, TAMs isolated from animals treated with RP-182, or RP-182 in combination with gemcitabine, showed activating T cell function (FIG. 74), suggesting a switch of the TAM population towards an anti-tumor, pro-inflammatory M1-like phenotype. Indeed, gene expression analysis of TAMs isolated from tumors of RP-182-treated animals and flow cytometry analysis of the TAM population confirmed a switch from decreased M2- to an increased M1-fraction in RP-182-administered animals (FIG. 75 and FIG. 76). Increased fractions of macrophages staining positive for the M1 cytokines IL-1β, IL-1β, TNFα and M1 marker iNOS were observed in RP-182-induced double positive CD86+CD206+ and the CD86+CD206− M1-like cells but not in the CD86-CD206+M2-like TAMs (FIG. 77), findings in line with the reprogramming effect of RP-182 observed on M2 BMDMs in vitro.

Figure 78:
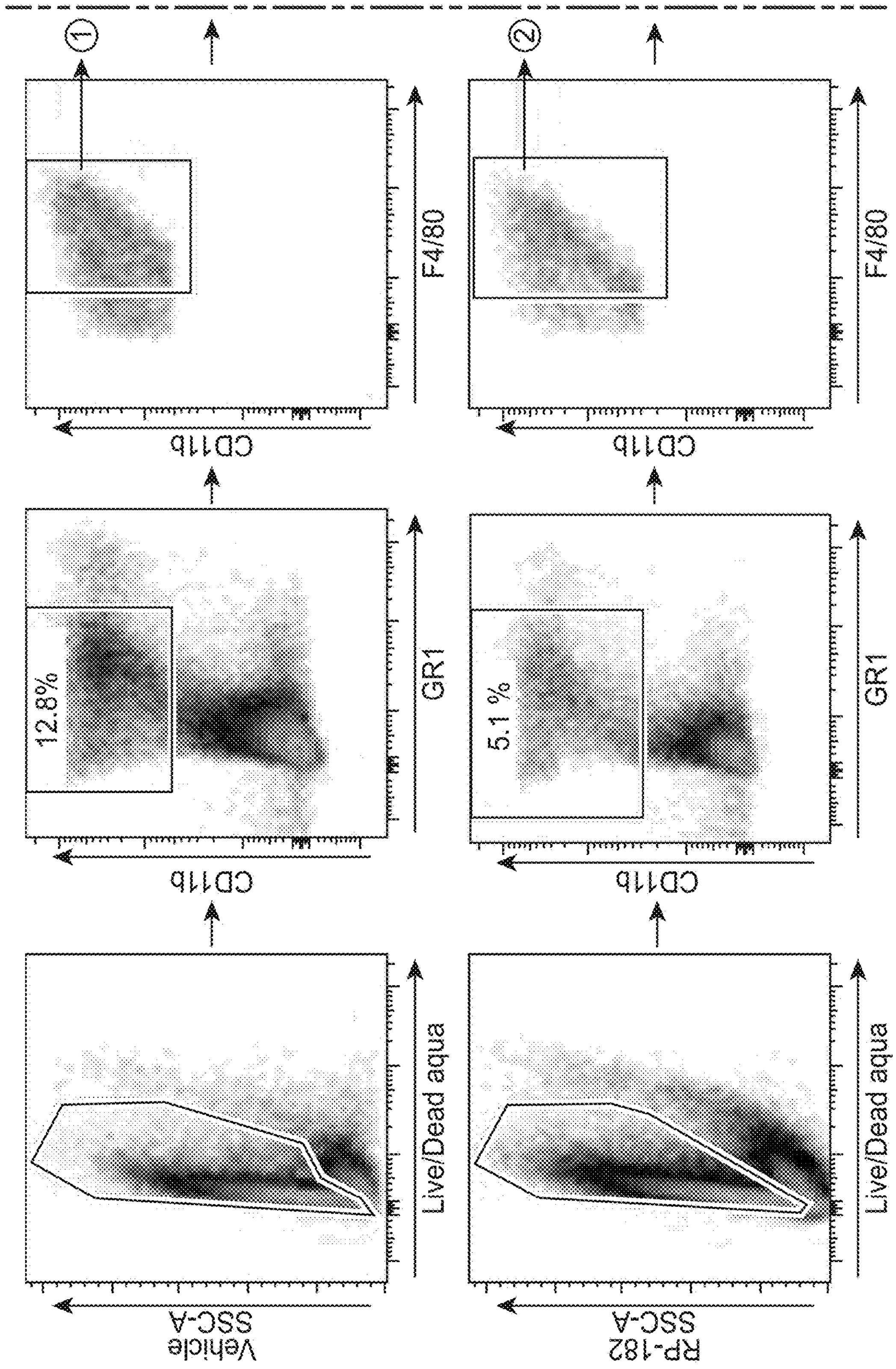
FIG. 78 shows flow cytometry plots including employed gating strategy to determine cleaved caspase 3, Rab7, and LAMP1-positive CD11b+F4/80+Gr-1− TAM fractions in KPC tumors of vehicle and RP-182-treated mice. Quantification of % positive TAM fractions in N≥7 mice per group shown on bottom.
Figure 78:
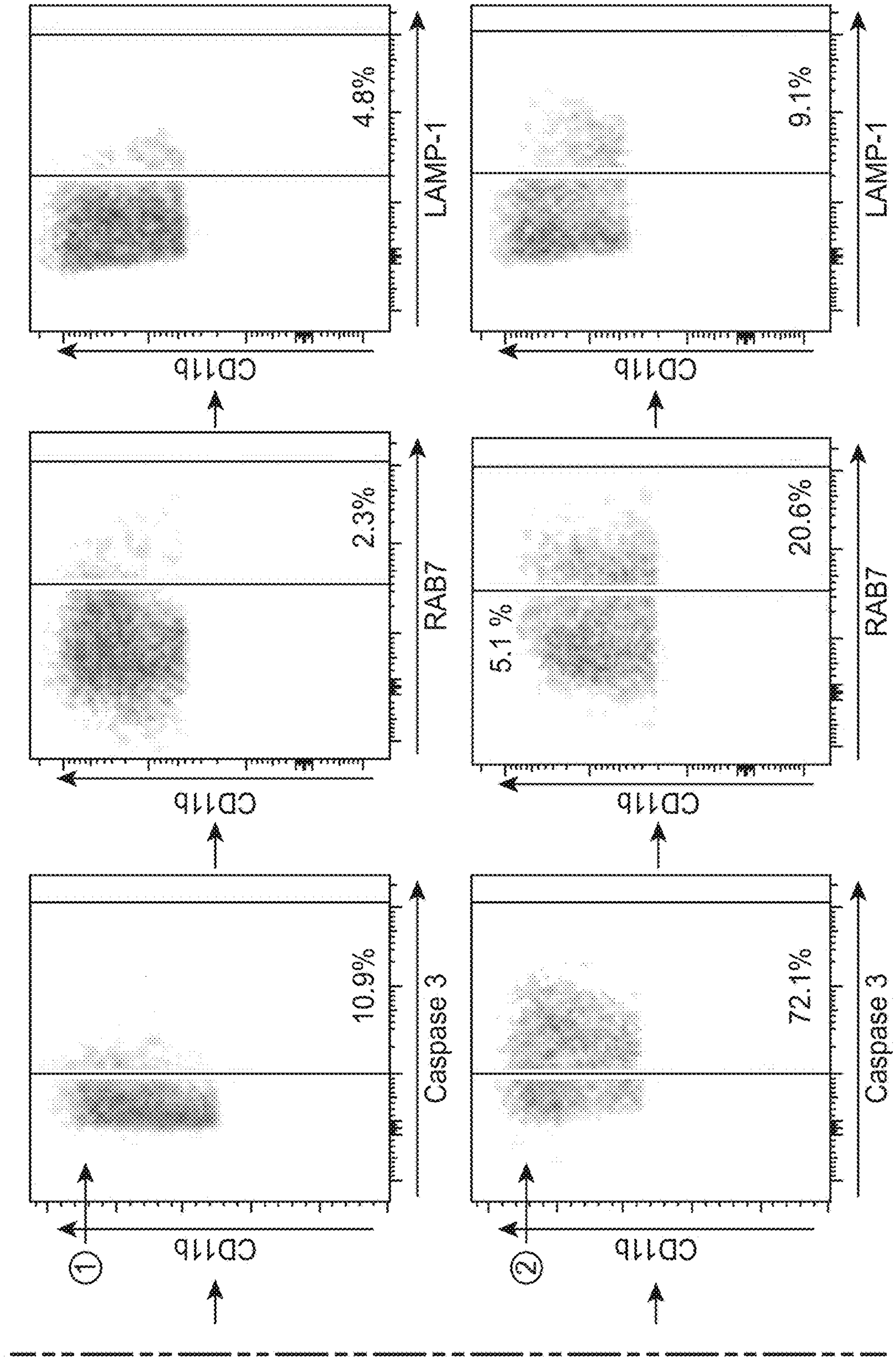
Figure 78:
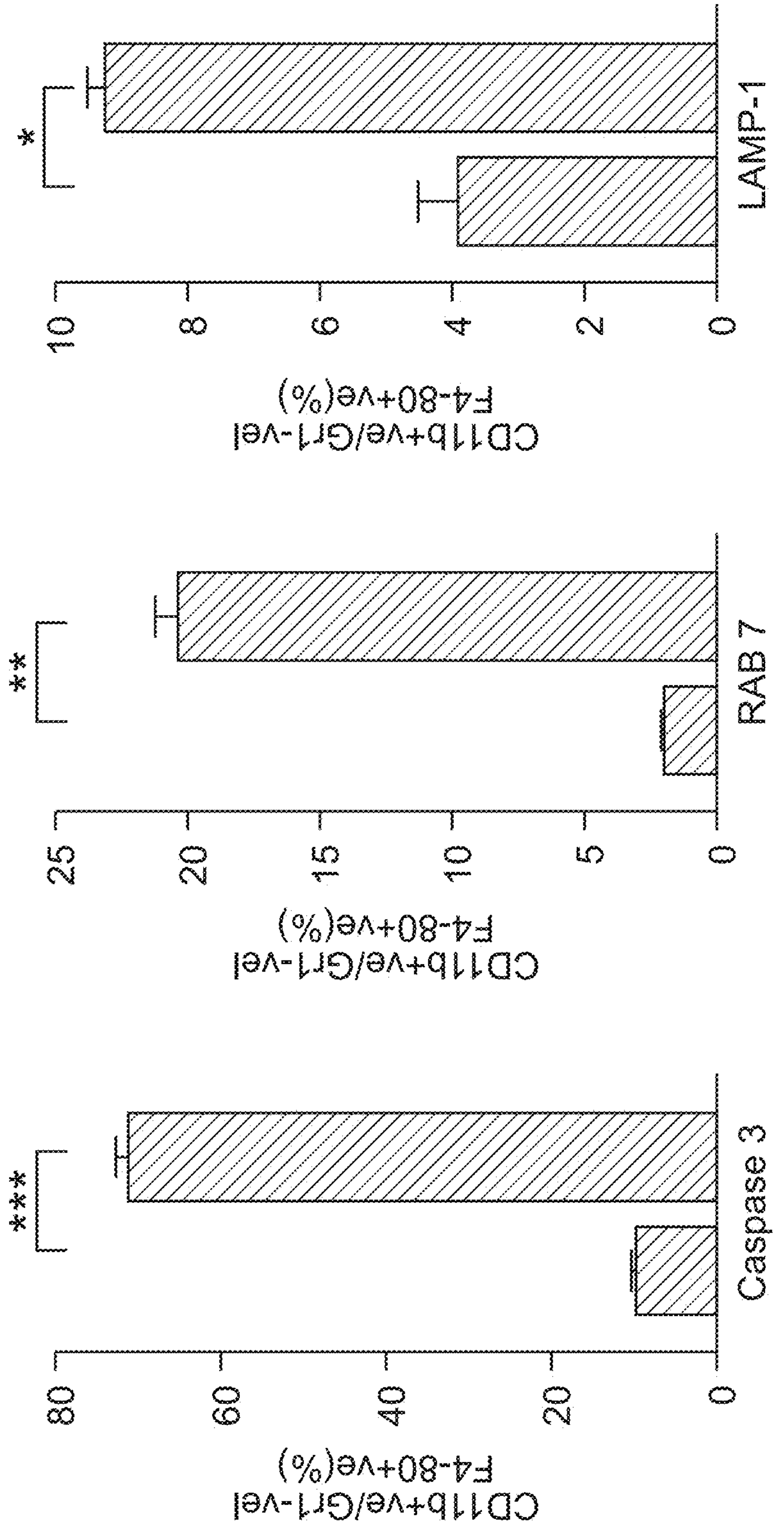
Figure 79:
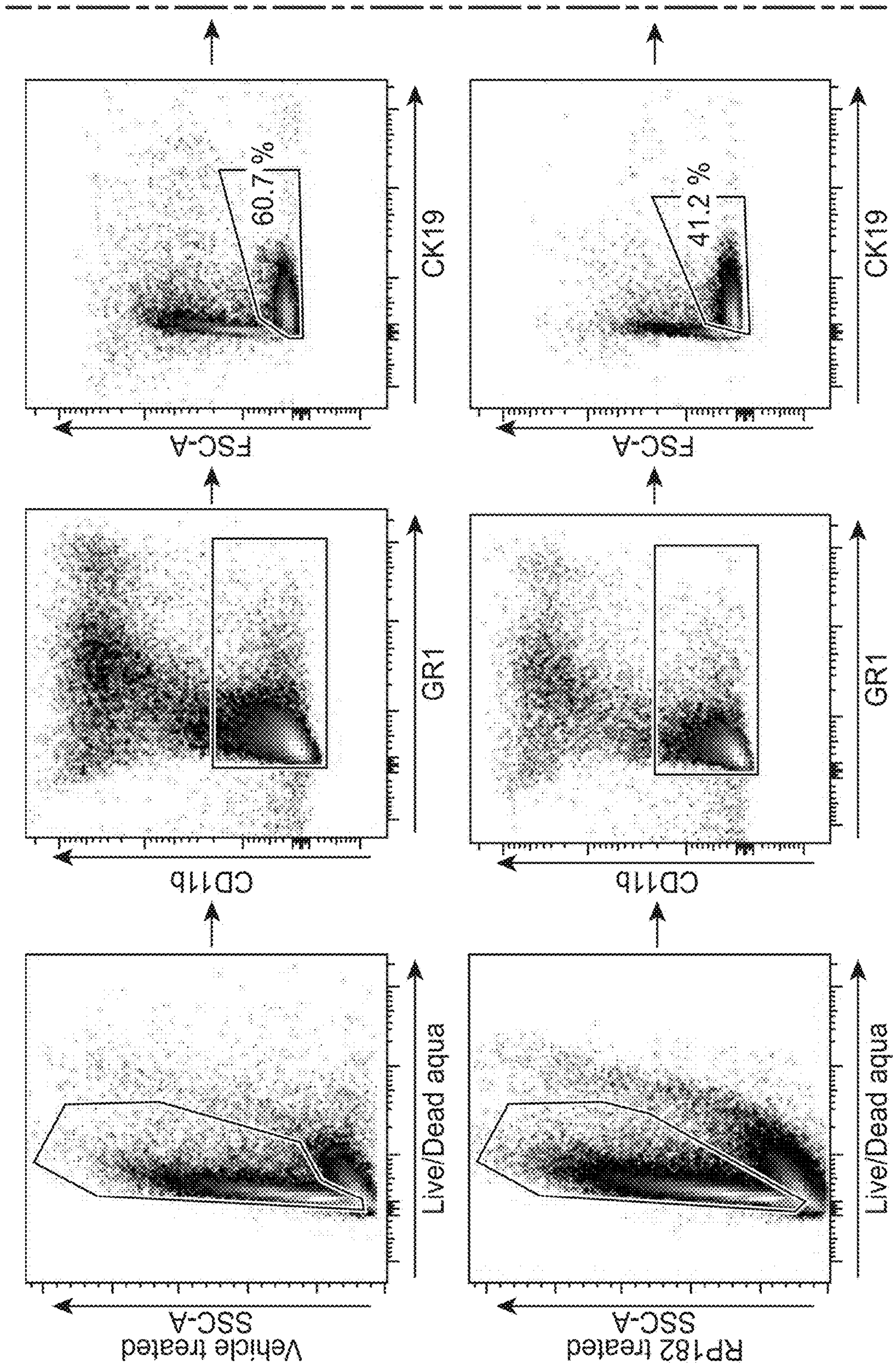
FIG. 79 shows analysis of apoptosis, phagocytosis, and phagolysosome formation by flow cytometry in CD11b-CK19+ cancer cells of tumor digests of KPC mice treated for 7 days with vehicle (top) and RP-182 (bottom). Flow cytometry plots including employed gating strategy for the determination of cleaved caspase 3, Rab7, and LAMP1-positive CD11b-CK19+ cell fractions of vehicle-treated and RP-182-treated mice. Quantification shown on bottom, bar graph indicates mean of percent fraction of N≥7 animals per group.
Figure 79:
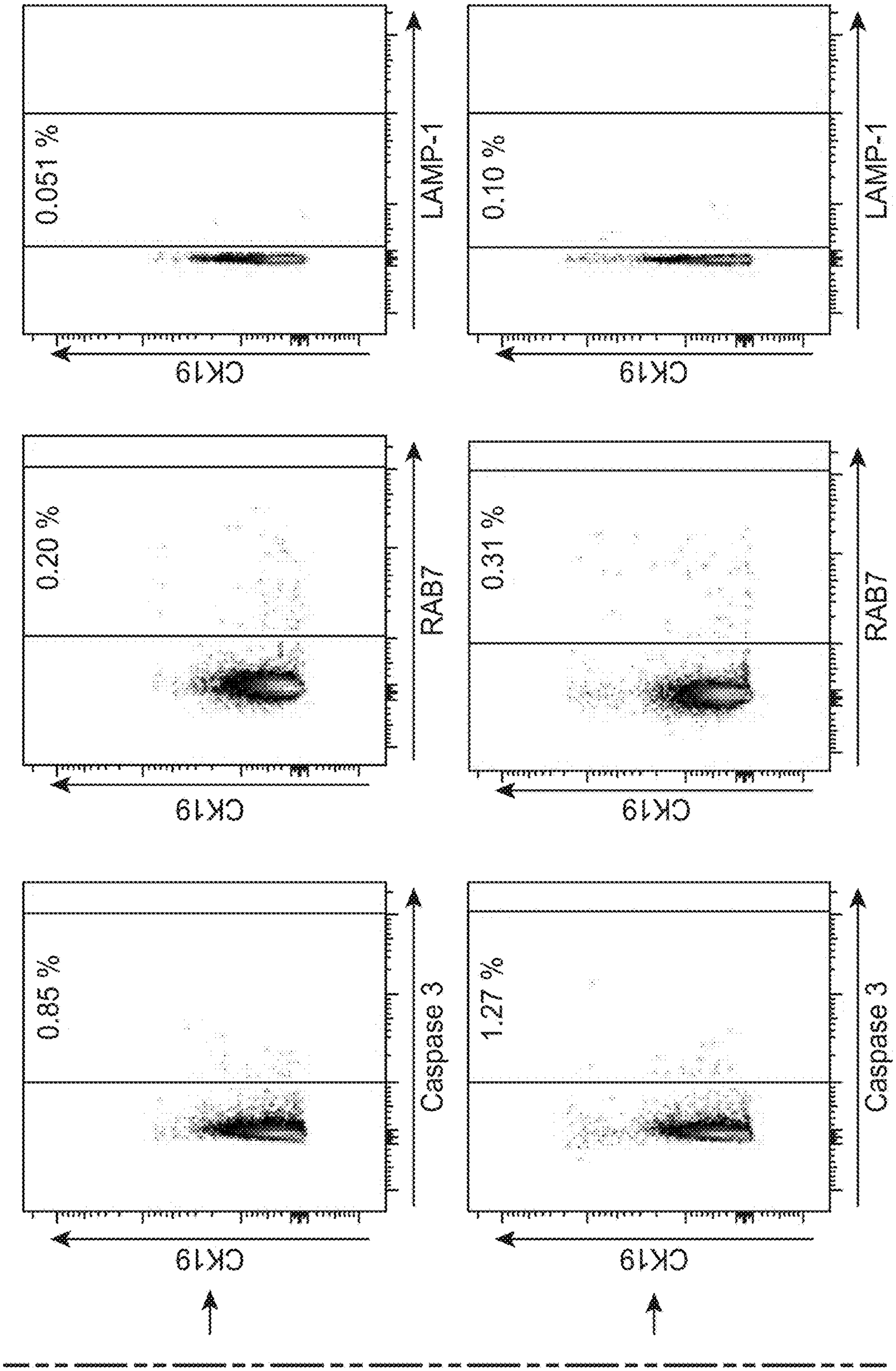
Figure 79:
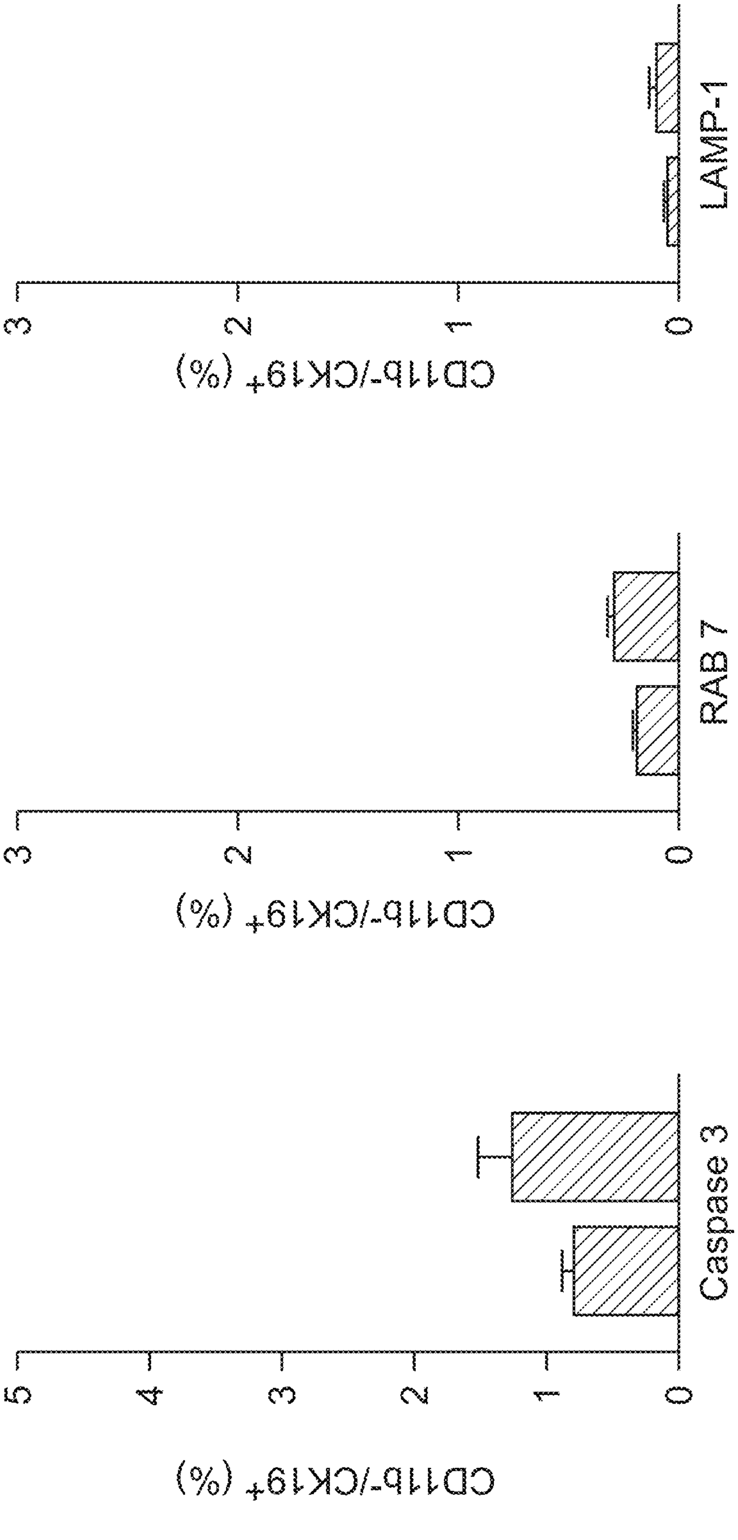
Figure 80:
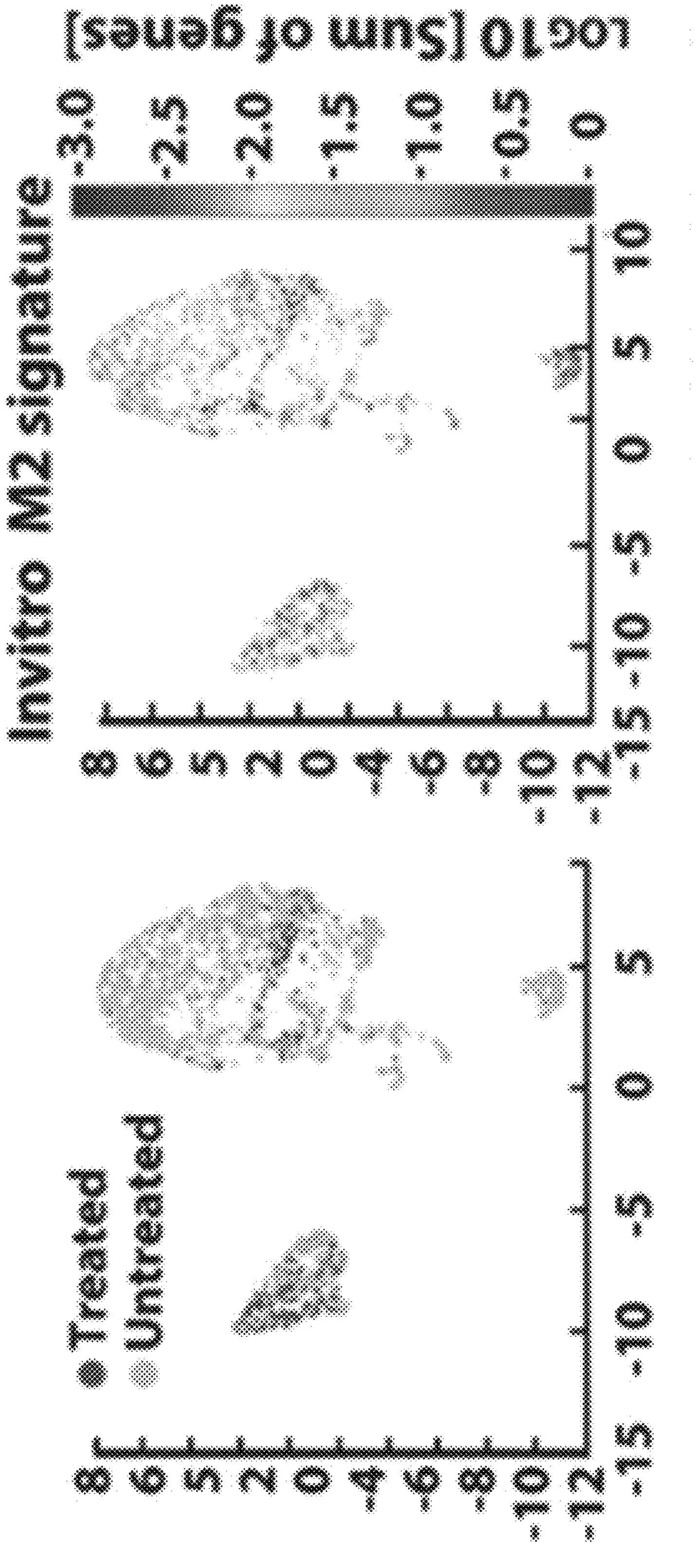
FIG. 80 shows T-distributed Stochastic Neighbor Embedding (t-SNE) plots after tumor single cell sequencing of CD11b+ and filtering out KRT19+, CD11c+, Ly6G+ cells (N=4/group) of vehicle- (light blue) vs RP-182-treated (dark blue) tumors, color bar indicates log 10[molecules/cell]. Increased expression levels of RP-182-induced DEGs identified in M2 BMDMs in vitro ('in vitro gene M2 signature') project onto CD11b+ KRT19-CD11c-Ly6G− cluster from RP-182-treated tumors (right), color bar indicates log 10[sum of in vitro gene expression changes].
Figure 81:
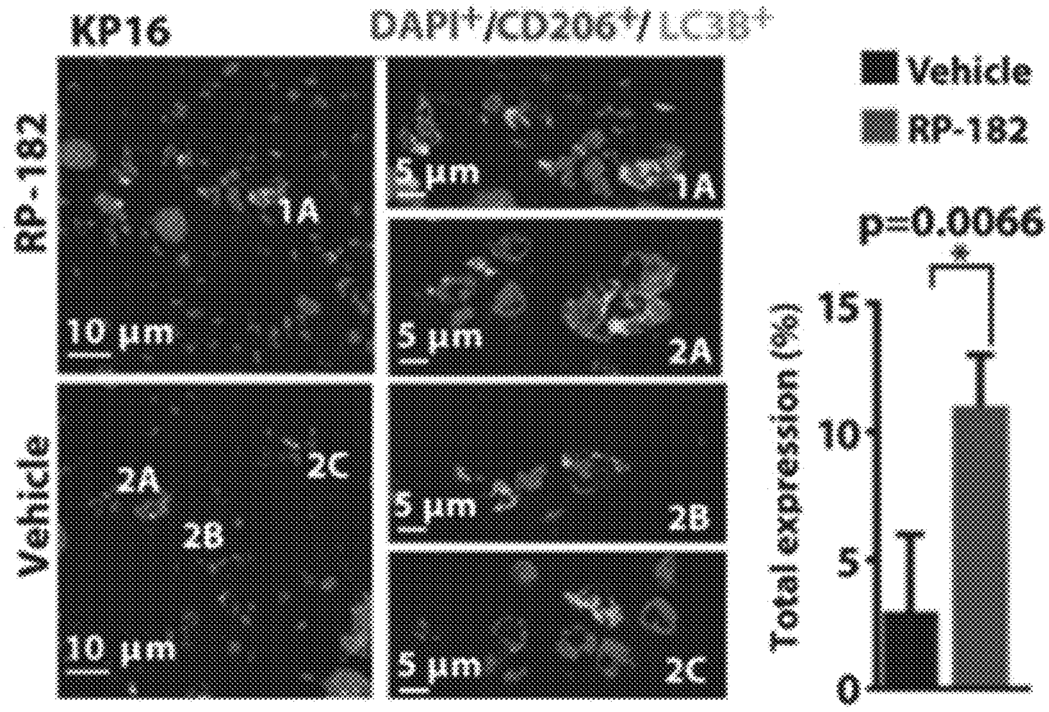
FIG. 81 shows images of immunofluorescence of KP16 tumors treated with RP-182 (top) and vehicle (bottom) co-stained with anti-CD206 (red) and anti-LC3 (green), computer-based quantification of co-staining cells (of total cells, N=4/group).
Figure 82:
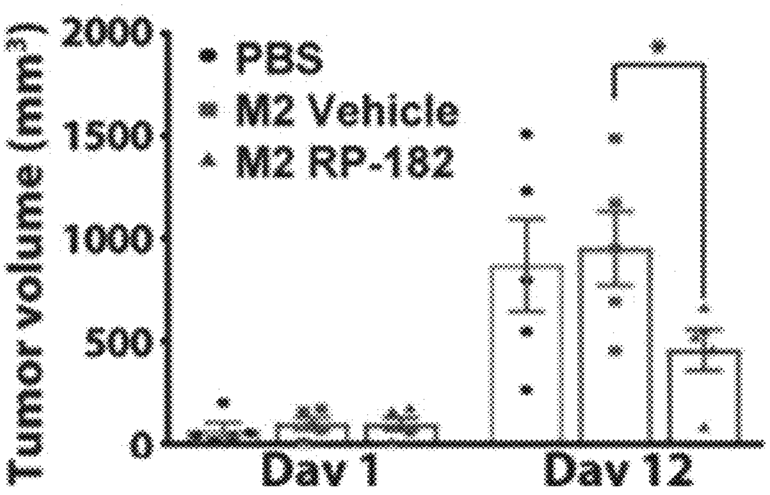
FIG. 82 shows tumor growth after intratumoral cell transfer of M2 BMDMs into KPC allografts (N=5).

In line with RP-182's mechanism of action in vitro, cleaved caspase 3. Rab7, and LAMP-1 positive TAM fractions were significantly higher in RP-182 vs vehicle-treated tumors (10.9 vs 72.1%, 2.7 vs 19.8%, and 3.9 vs 9.2%, respectively) (FIG. 78). Induction of apoptosis and phagocytosis was selective for CD11 b+F4/80+Gr-1− macrophages as CD11b-CK19-9+ cancer cells showed only minimal or no changes (FIG. 79). Furthermore, when applying the previously differentially expressed gene (DEG) set obtained from RP-182-treated vs untreated M2 BMDMs onto whole transcriptome analysis of single cells from KPC tumor digests, there was a significant enrichment of genes altered by RP-182 in vitro in the TAM cell cluster formed by the treated cohort (FIG. 80). Dual staining of RP-182-treated tumors with the markers LC3 and CD206 showed that RP-182 induced autophagosome formation in CD206-positive TAMs phenocopying the induced LC3 expression in human and murine M2-like macrophages in vitro (FIG. 81). RP-182-induced changes in M2 macrophages were associated with a tumor growth restricting impact upon intratumoral in vivo transfer of M2 BMDMs pretreated with RP-182 (FIG. 82).

Figure 83:
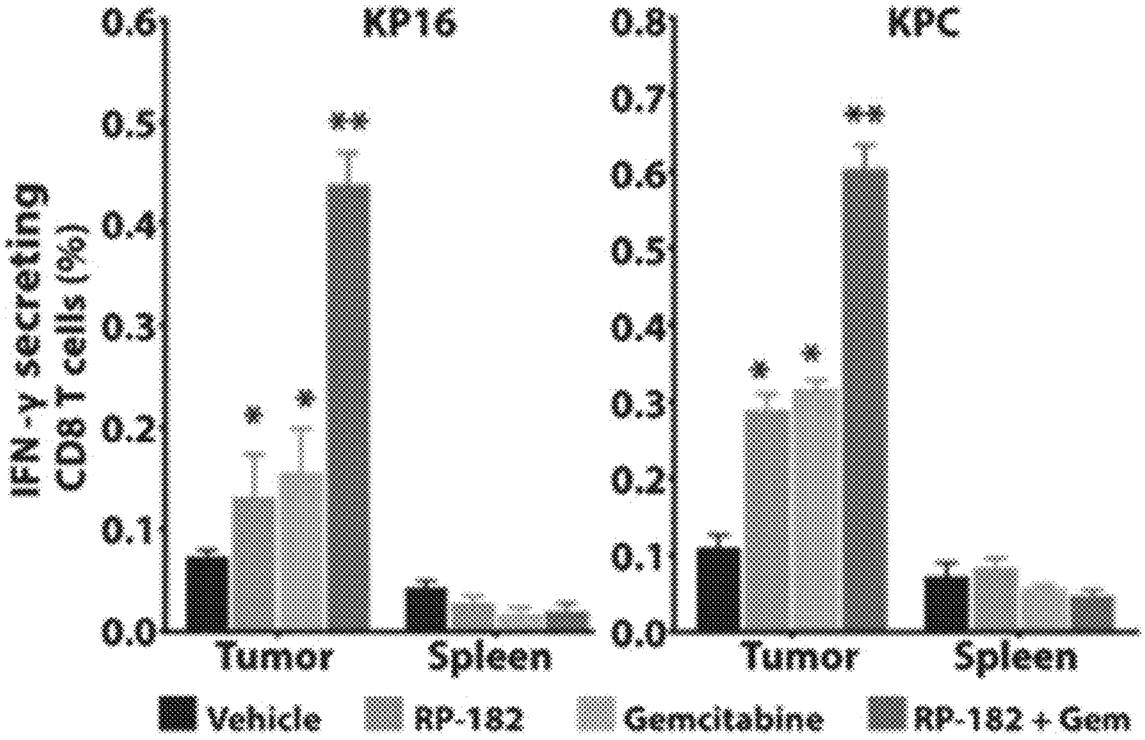
FIG. 83 shows quantification of EliSpots (INFγ-secreting CD8+ T cells of added total CD8+ T cells) after co-culture of KP16 (left) and KPC cancer cells (right) and CD8+ T cells isolated from tumors and spleens.

Example 7: RP-182 Cooperation with Immune Checkpoint Inhibition and Effect on Antitumor Immunogenicity and Disease Outcomes The effects of RP-182 on intratumoral T cell function were examined by measuring antigen recognition and T cell activation via interferon gamma (INFγ) release upon co-culture with KPC and KP16 cancer cells (EliSpot assay). Intratumoral T cells from animals treated with RP-182, and RP-182 in combination with gemcitabine, showed significantly stronger activation upon co-culture with cancer cells compared to T cells isolated from animals treated with vehicle control suggesting improved tumor antigen recognition following RP-182 treatment (FIG. 83). Improved T cell function was selective for T cells isolated from tumors and not observed in T cells isolated from spleens.

Figure 84:
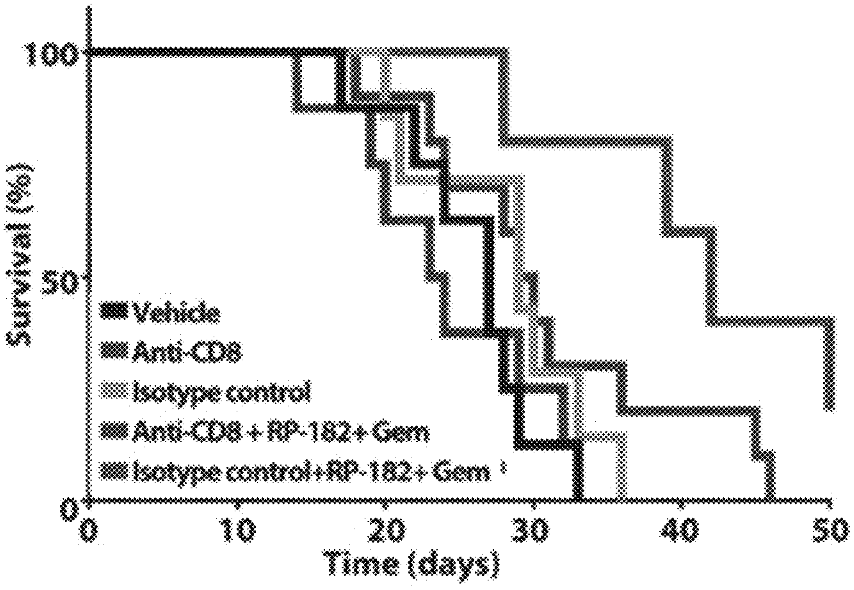
FIG. 84 shows Kaplan-Meier analysis of KP16 mice treated with anti-CD8 neutralizing antibody, anti-IgG2 isotype control, and indicated combinations.
Figure 85:
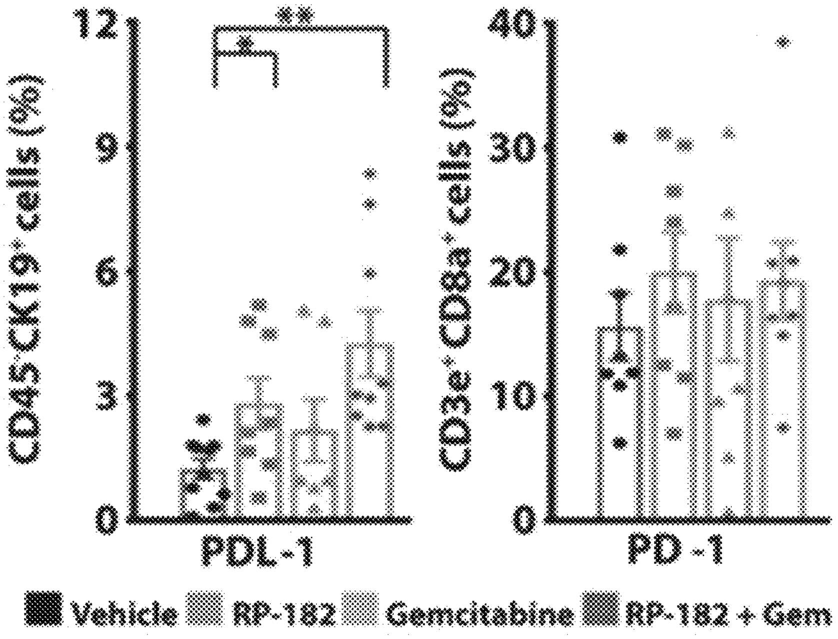
FIG. 85 shows quantification of flow cytometry analysis of CD45-CK19+ cancer cells expressing PD-L1 (left) and PD-1 expression on CD45+CD3e+CD8+ T cells (right) in KP16 tumors.
Figure 86:
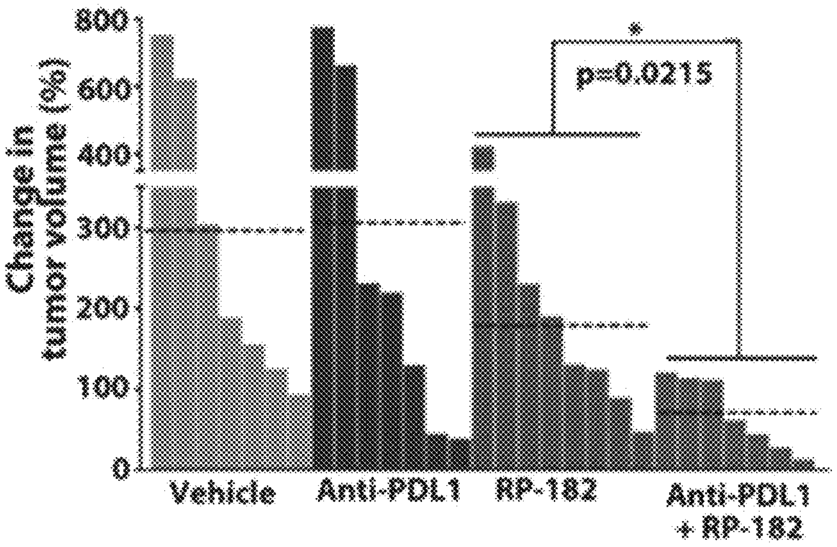
FIG. 86 shows best objective response (BOR) of KP16 tumors treated with vehicle (grey bars), anti-PD-L1 injections (purple). RP-182 (red), and anti-PD-L1 in combination with RP-182. N≥7 animals/group.

To link the above increased tumor cell recognition to the observed anti-tumor activity in vivo, the efficacy studies were repeated with RP-182 and gemcitabine treatment in mice depleted of CD8+ T cells. Mice void of CD8+ T cells and treated with RP-182 and gemcitabine displayed a reduction in extension of survival when compared to mice treated with isotype control, indicating the involvement of CD8+ T cells in RP-182's mechanism of action (FIG. 84). Murine pancreatic cancers showed increased PD-L1 expression on CK19-positive cancer cells upon treatment with RP-182 (FIG. 85). To test whether these elevated levels of checkpoint expression can be exploited for combination therapies, and whether anti-TAM therapy via RP-182 might cooperate with PD-L1 immune checkpoint inhibition in pancreas cancer not known to respond to single agent anti-PD-1/PD-L1 therapy. RP-182 was combined with anti-PD-L1 treatment. Anti-tumor activity of the combination was enhanced compared to single agent therapy (p=0.0215) (FIG. 86).

Figure 87:
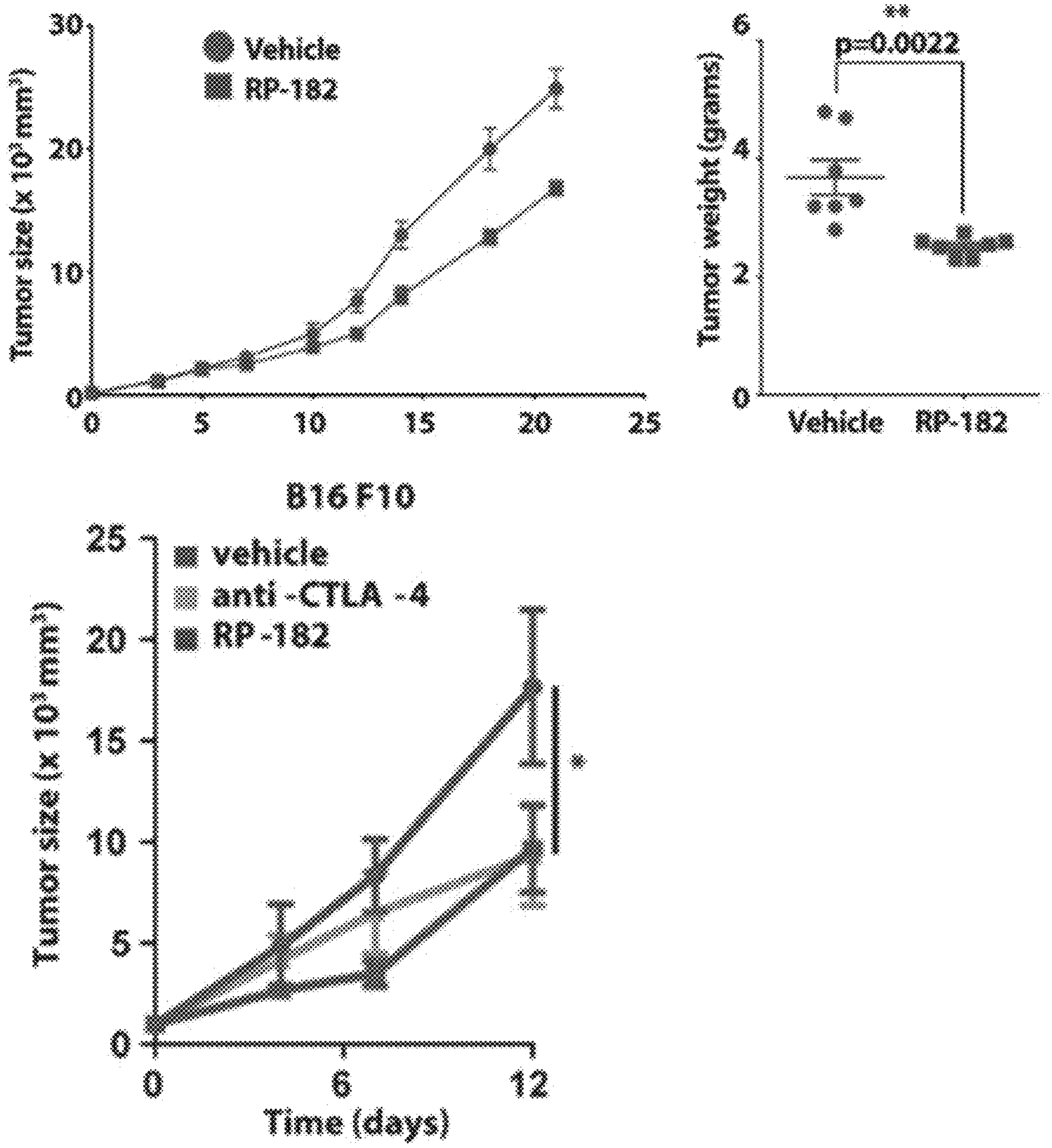
FIG. 87 shows tumor growth of CT-26 allografts, tumor weights at study endpoint shown on right. Tumor growth of murine B16 melanoma tumors.

Next, it was examined whether the above anti-tumor activity extends onto additional cancer models including patient-derived xenotransplantation models. RP-182 reduced growth of CT-26 colon tumors and murine B16 melanomas, where it showed equal efficacy as standard anti-CTLA4 checkpoint therapy (FIG. 87). Using previously genotyped human pancreatic cancer tissues from NCI's Patient-Derived Models Repository (PDMR; https://pdmr-.cancer.gov/), patient-derived xenotransplants (PDX) with CD206high and CD206low expression levels were generated and treated with vehicle, control peptide RP-426, or RP-182. While RP-182 reduced tumor growth in the CD206high PDX models compared to vehicle and RP-426 control, there was no effect in the CD206low models.

Figure 88A:
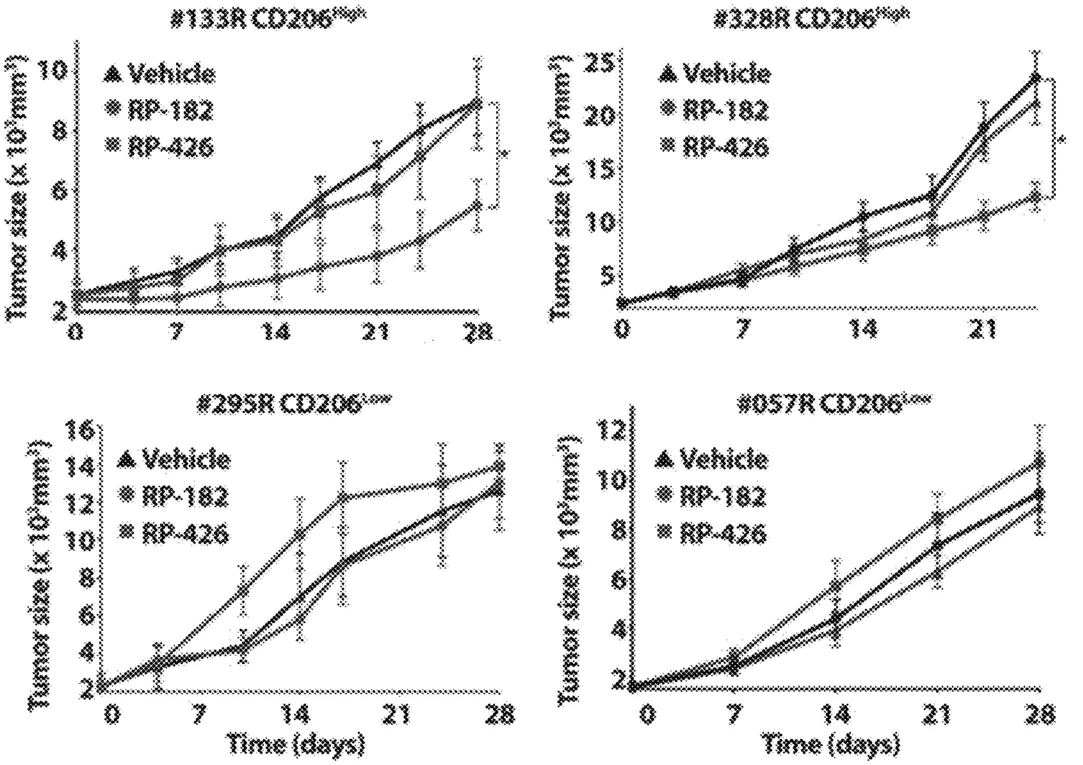
FIG. 88A shows pancreas cancer patient-derived xenotransplantation models with CD206high (#133R, #328R) and CD206low (#295R, #057R) expression levels treated with RP-182, RP-426, and vehicle-control. N≥7/group. H. RP-182 administration rescues mice with chemically induced pulmonary fibrosis. Quantification of total body weights and Kaplan-Meier survival analysis is shown. N=6/group, error bars indicate standard deviations.
Figure 88B:
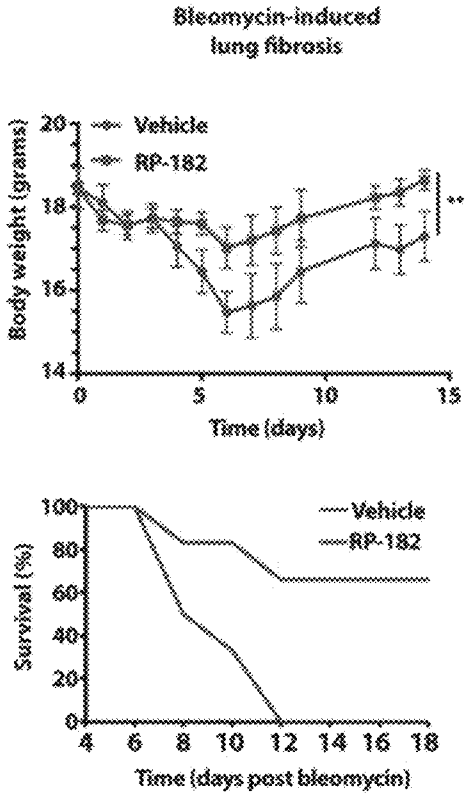
FIG. 88B shows pulmonary inflammatory infiltrates after bleomycin installation. Images of H&E stains, quantification of measured weights of excised lungs on right. N=4/group.
Figure 88C:
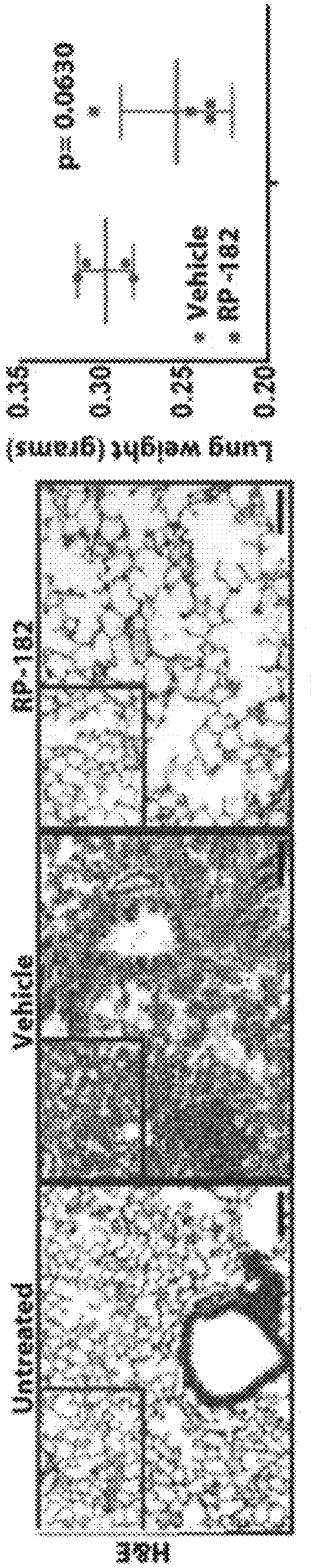
FIG. 88C shows images of Masson's trichrome staining, quantification of surface area (in μm2) of 100 mm2 examined lung surface on right.
Figure 89:
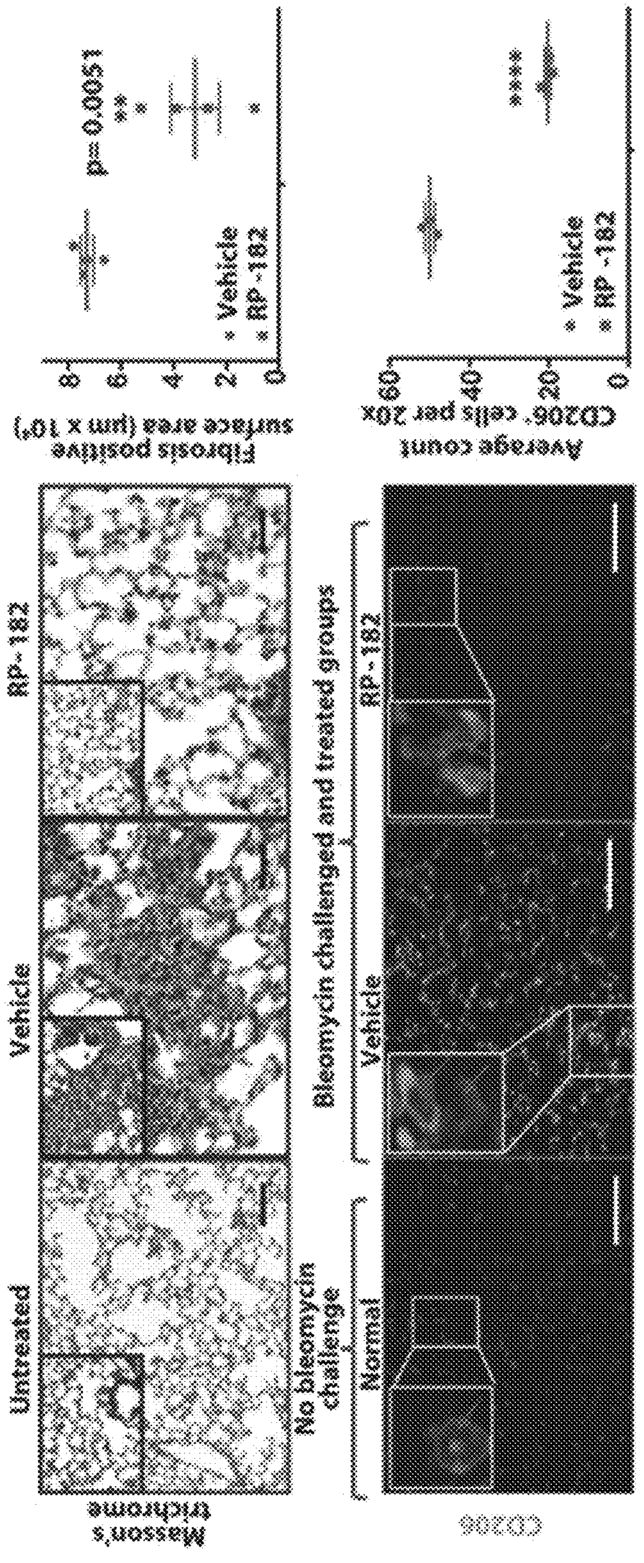
FIG. 89 shows reduction of CD206-positive alveolar cell infiltrate in RP-182-treated mice. Immunofluorescence lung field images of non-instilled and bleomycin-instilled mice treated with vehicle or RP-182 stained with DAPI and anti-CD206 (green). Quantification of number of CD206-positive cells shown on right, N=4/group.

Considering that CD206-positive, alternatively activated macrophages are involved in other disease processes, RP-182 was tested in a bleomycin lung fibrosis model next. Treatment with RP-182 resulted in increased animal weight and improved overall survival and diminished pulmonary fibrosis (FIGS. 88A-C). Correlative lung tissue studies showed reduction of M2-like macrophages measured by expression levels of CD206 (FIG. 89). These findings suggest that RP-182 modulates macrophage activity across several murine and human cancer models and possibly includes non-cancerous disease models driven by CD206-positive macrophages overall suggesting a wide applicability. CD206 expression status may aid future selection of tumors most likely to respond.

Example 8: Effect of RP-182 on Cancer Cell Phagocytosis by M1-Like Macrophages

Figure 90:
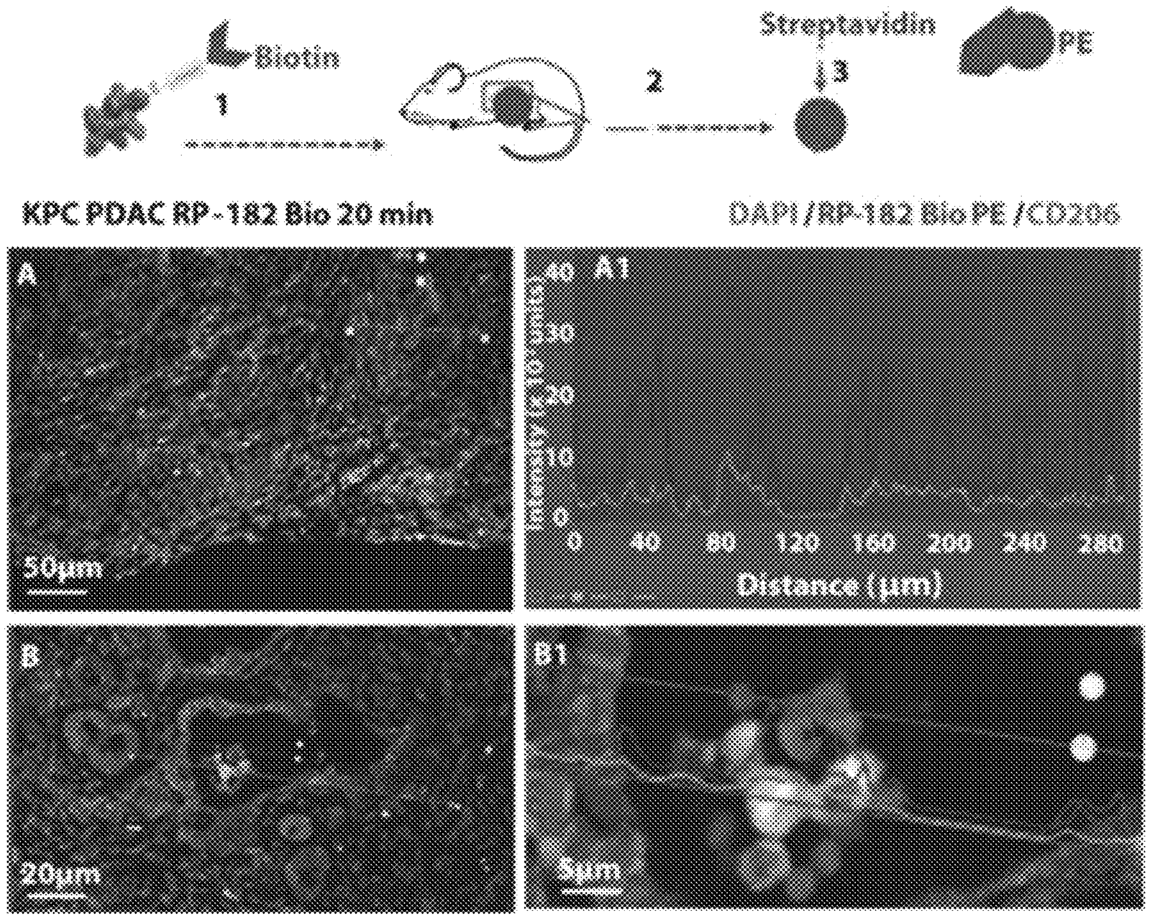
FIG. 90 shows immunofluorescence images of KPC tumors treated with biotinylated RP-182 and co-stained with anti-CD206 (green), streptavidin (red), and DAPI (blue). Laser intensity profiles (A1) of linear scanning of random tissue section measuring intensity (fluorescence intensity, y-axis) across distance (in pin; x-axis). Co-localization of CD206 expressing cells (green) and bio-RP-182 (red channel) (B1) generating yellow/purple emission.
Figure 91:
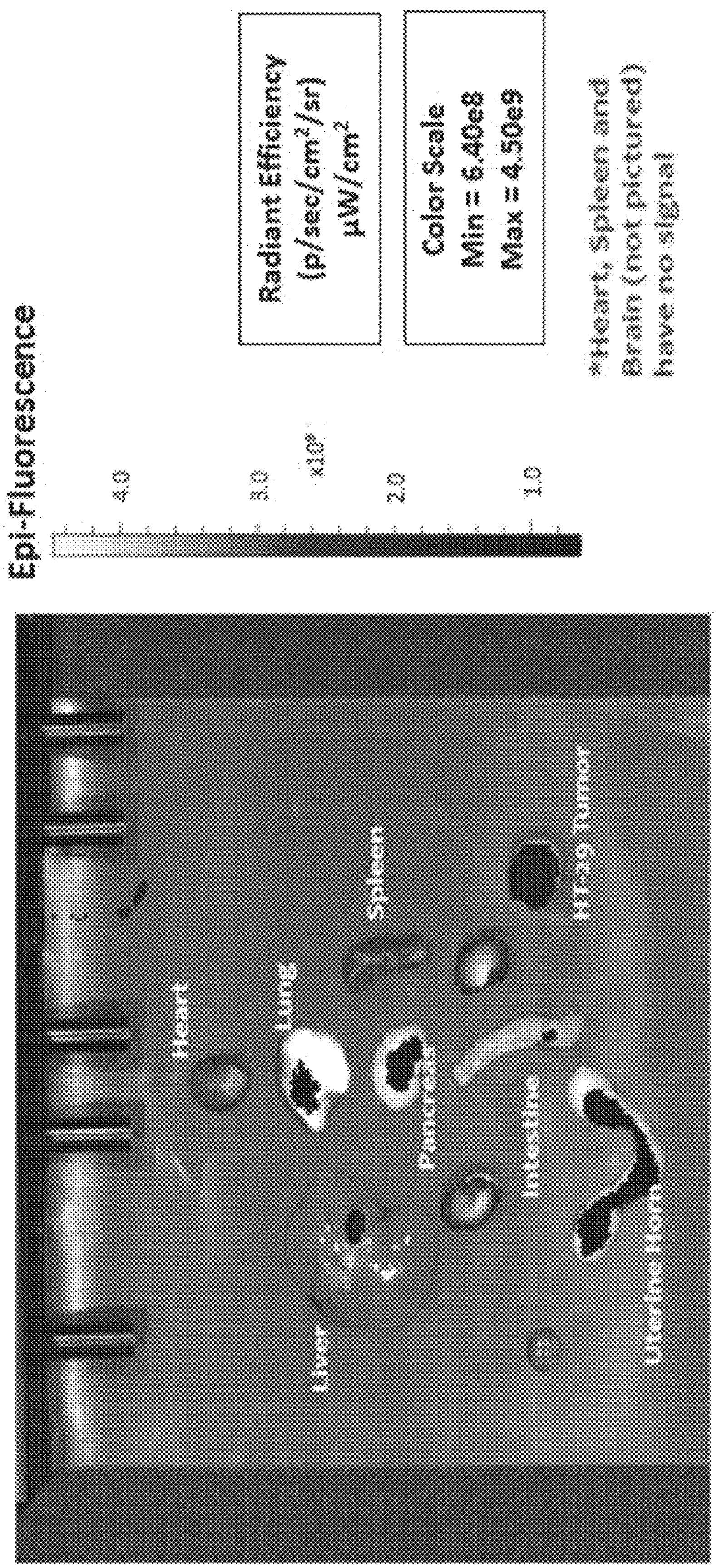
FIG. 91 shows tissue distribution of RP-182 after imaging of indicated organs including subcutaneous grown CT-26 tumor in BALB/c mice that were excised at 10 min after administration of Alexa-488 labelled peptide RP-182 at 20 mg/kg via intraperitoneal injection. Fluorescence in manually set regions of interest was quantified by Living Image, color scale of intensity of emitted photons shown on right.

To confirm that RP-182 is able to efficiently engage CD206 positive target cells in pancreatic tumors after systemic administration, KPC mice were dosed with 20 mg/kg of RP-182 carrying a biotin. Tumors were harvested, embedded, and co-stained with anti-CD206 antibody probes and AlexaFluor-streptavidin to detect intratumoral RP-182 (NCGC-00510434; FIG. 15B). Multicolor confocal microscopy measuring staining intensities across linear sectional distances (in pm) showed remarkable co-localization of RP-182 with CD206-positive cells in the microenvironment of pancreatic KPC tumors suggesting RP-182 is binding its target (FIG. 90). Photon xenogene quantification of AlexaFluor480-RP-182 in organs showed significant enrichment in tumor and kidney compared to other organs (FIG. 91). Fourteen-day toxicity studies of continuous dosing of up to 30 mg/kg daily dosing of RP-182 did not show hematological changes in total blood of dosed animals or any change in total body or selective organ weights.

Figure 92:
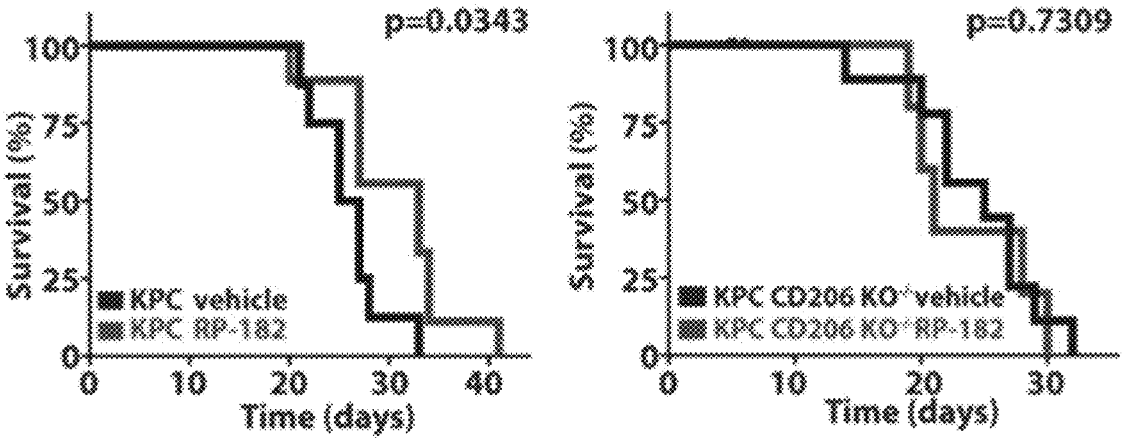
FIG. 92 shows Kaplan-Meier analysis of KPC wild type (left) and KPC CD206 KO−/− allografts (right) treated with vehicle (black curve) or RP-182 (red). Phase-contrast images of M2 BMDMs incubated with carboxyfluorescein succinimidyl ester (CFSE)-labelled cancer cells (green). Inlet (at 100×) shows representative macrophage with engulfed green-labelled cancer cell and induced cytoplasmatic vacuoles and vesicles
Figure 93:
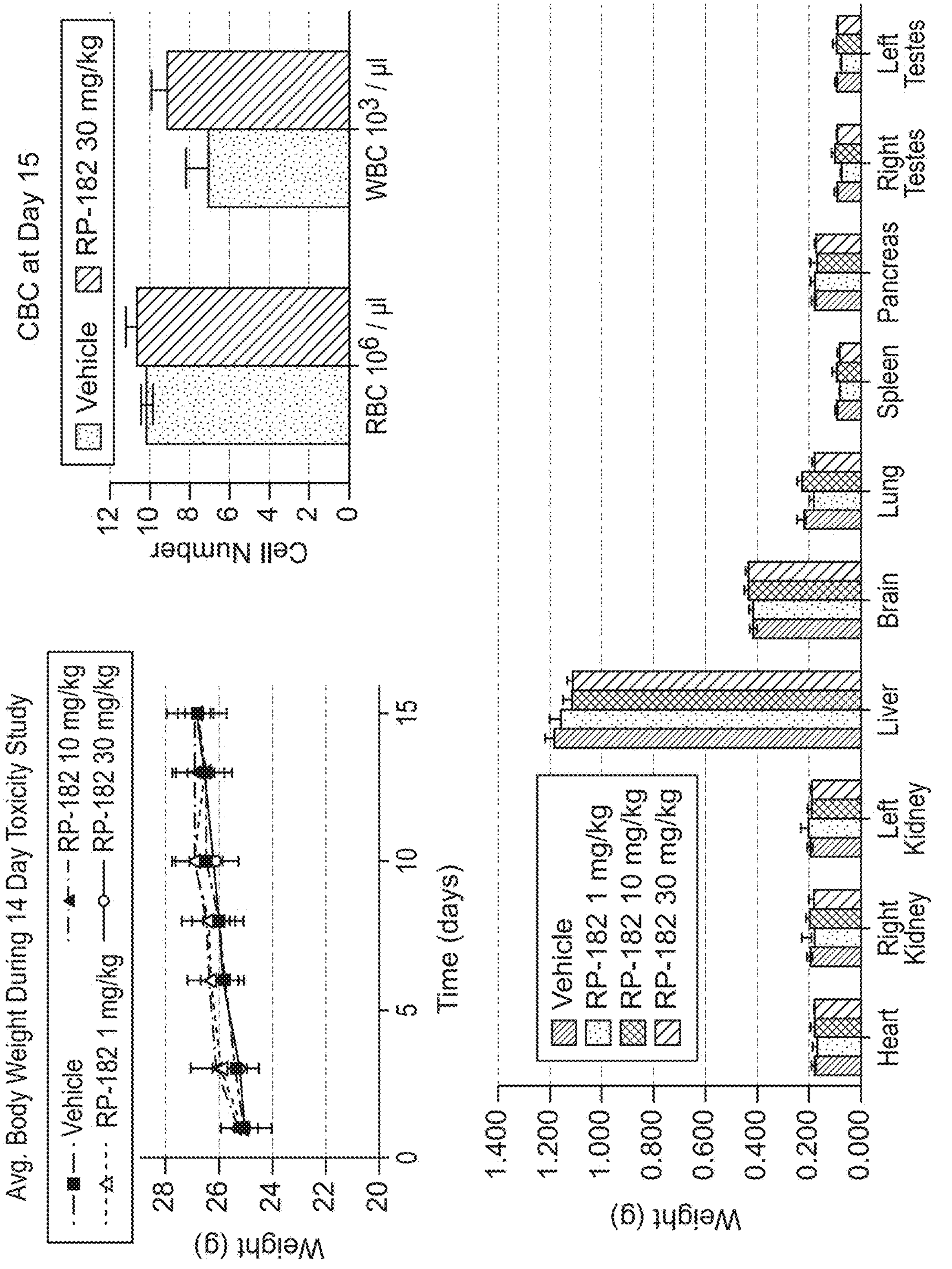
FIG. 93 shows toxicity measures after daily 14-day administration of increasing concentrations of RP-182. Body weights after 14-day daily administration of RP-182 (left) and red and white blood cell counts (RBC, WBC) of vehicle and RP-182-treated mice at 30 mg/kg (right). C. Individual organ weights (in grams) of mice treated for 14 days with indicated daily doses of RP-182, n≥7/group.

In line with its selectivity for its target CD206 and CD206 expressing M2 macrophages, treatment with RP-182 mediated a survival gain C57BL/6 wild type mice allografted with KPC tumors but not in CD206-deficient B6.129P2-Mrc1tm1Mnz/J mice with KPC tumors lacking the target receptor of RP-182 (FIG. 92). The smaller impact of RP-182 on overall survival compared to autochthonous KPC tumors shown in FIG. 67B might be due to differences between spontaneous KPC tumors and KPC tumors generated from allografted cells. RP-182 did not produce discernible hematological changes in total blood of dosed animals or any change in total body or selective organ weights upon preliminary toxicity testing (FIG. 93).

Figure 94A:
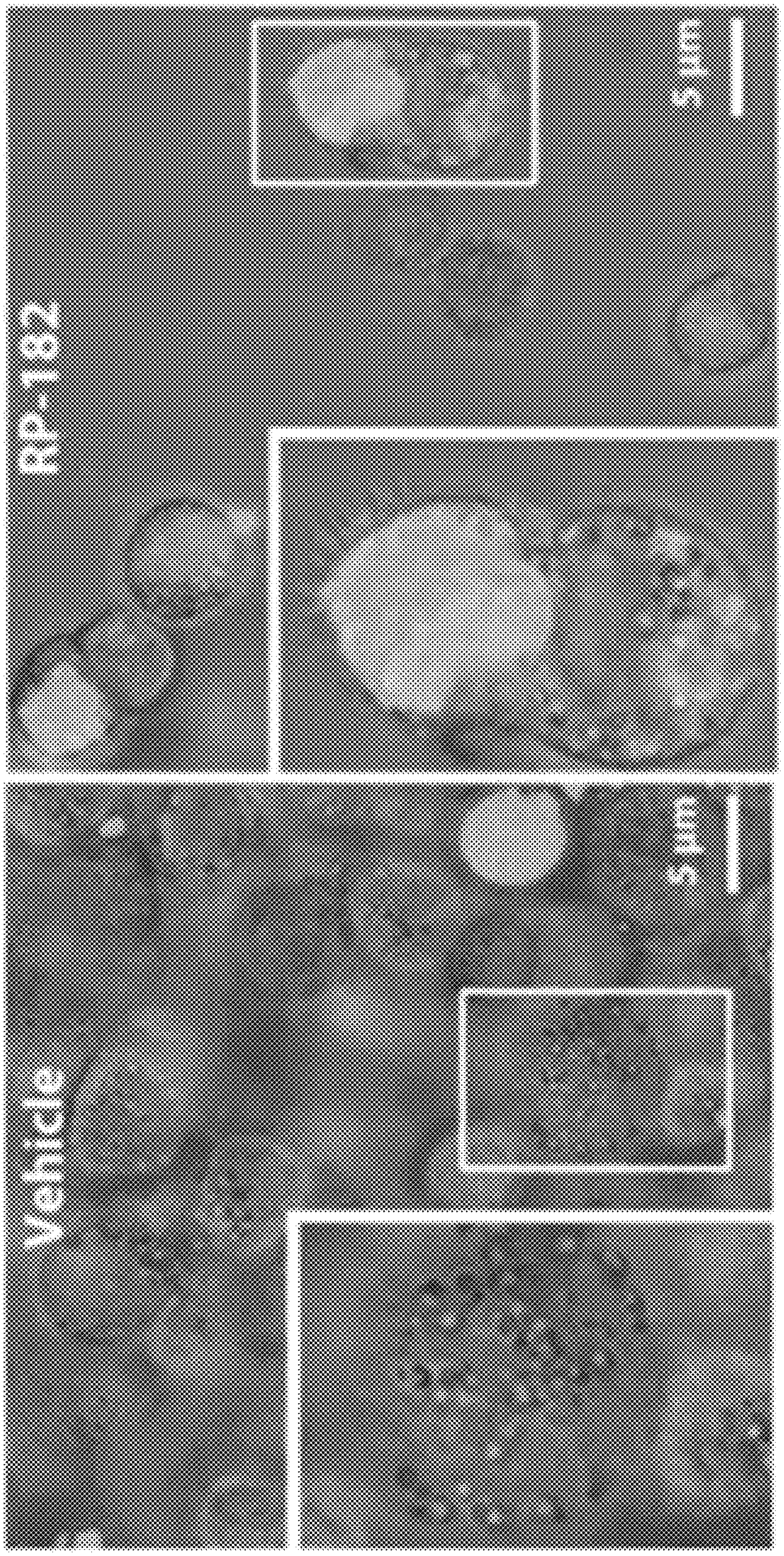
FIG. 94A shows Phase-contrast images of M2 BMDMs incubated with carboxyfluorescein succinimidyl ester (CFSE)-labelled cancer cells (green). Inlet (at 100×) shows representative macrophage with engulfed green-labelled cancer cell and induced cytoplasmatic vacuoles and vesicles.
Figure 94B:
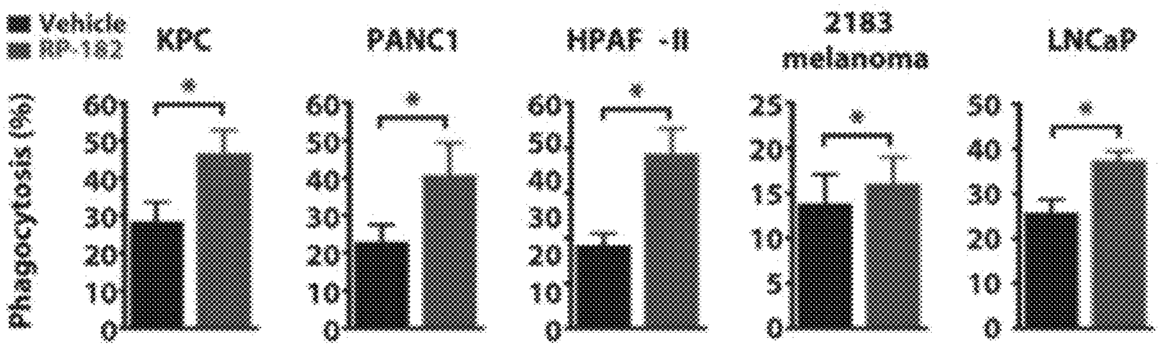
FIG. 94B shows Quantification of number of CFSE-positive macrophages of total number of M2 BMDMs (%, phagocytic index).
Figure 95:
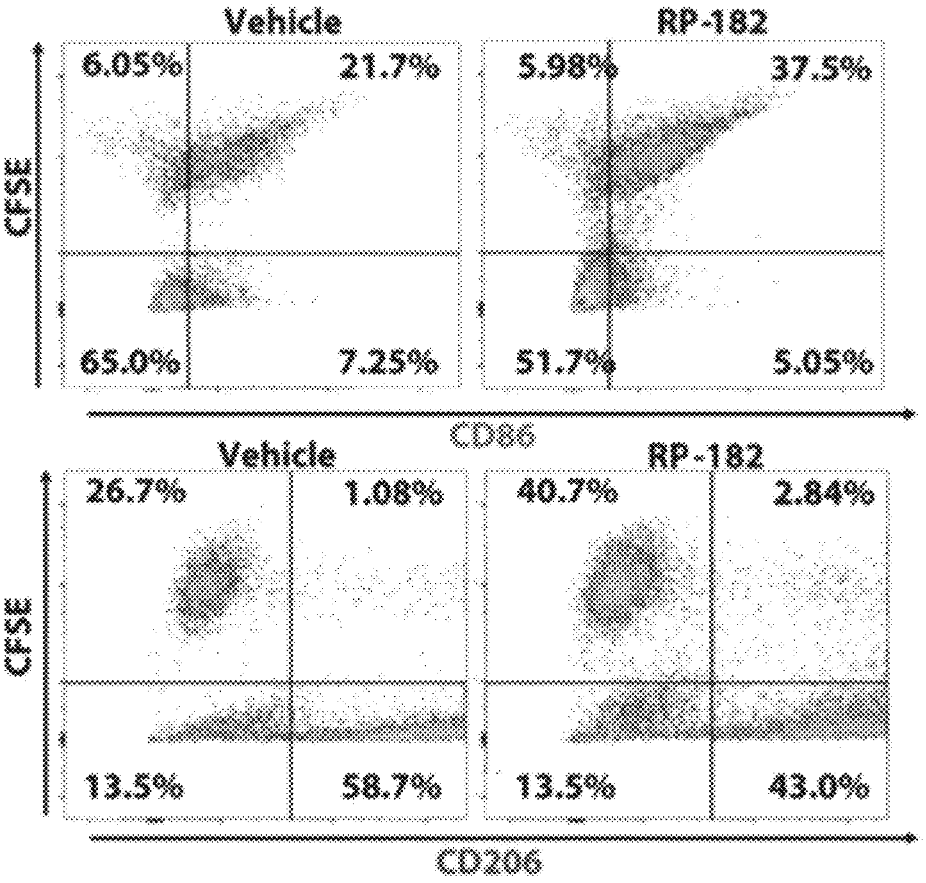
FIG. 95 shows Flow cytometry plots of CFSE-positive CD11 b+F4/80+Gr-1-CD86+ (top) and CD206+ BMDMs after addition of CFSE-labelled KPC cancer cells and treatment with vehicle or RP-182.

The loss of the SIRPα receptor involved in the 'do-not-eat me' signaling of innate immune cells on macrophages isolated from murine pancreatic tumors treated with RP-182 (FIG. 75) prompted us to explore whether T cell-independent innate mechanisms of RP-182 such as cancer cell phagocytosis might contribute to the anti-tumor activity of RP-182. Thus, phagocytosis was measured of several different human and murine cancer cell lines labelled with the green fluorescent dye carboxyfluorescein succinimidyl ester (CFSE) in M2 BMDMs treated with RP-182 next RP-182 increased cancer cells phagocytosis (measured by engulfed CSFE-positive cells; phagocytic index after 2 hours treatment with RP-182) of several murine and human cancer cell lines by 28.2 to 46.6% (FIGS. 94A-B). Cancer cell phagocytosis was exclusively observed at baseline in the CD86-positive M1 population, and increased after exposure to RP-182 (FIG. 95). While the increase in cancer cell phagocytosis by M1 macrophages is similar to the fraction of reprogrammed CD86 positive M1 cells, it cannot be ruled out that the reduction of suppressive M2 cues releasing inhibition of M1 function is, in part, responsible for the observed increased cancer cell phagocytosis effect of RP-182.

Figure 96:
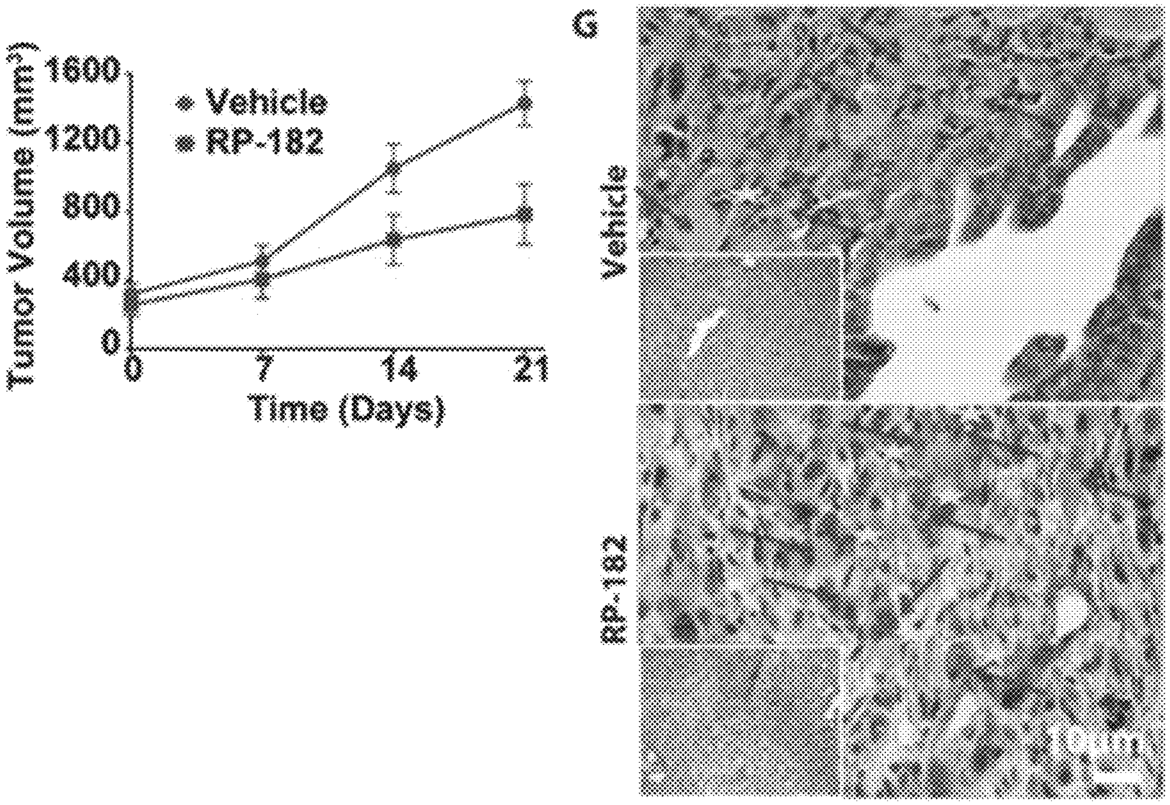
FIG. 96 shows tumor growth of KPC xenografts (N≥7/group).
Figure 97:
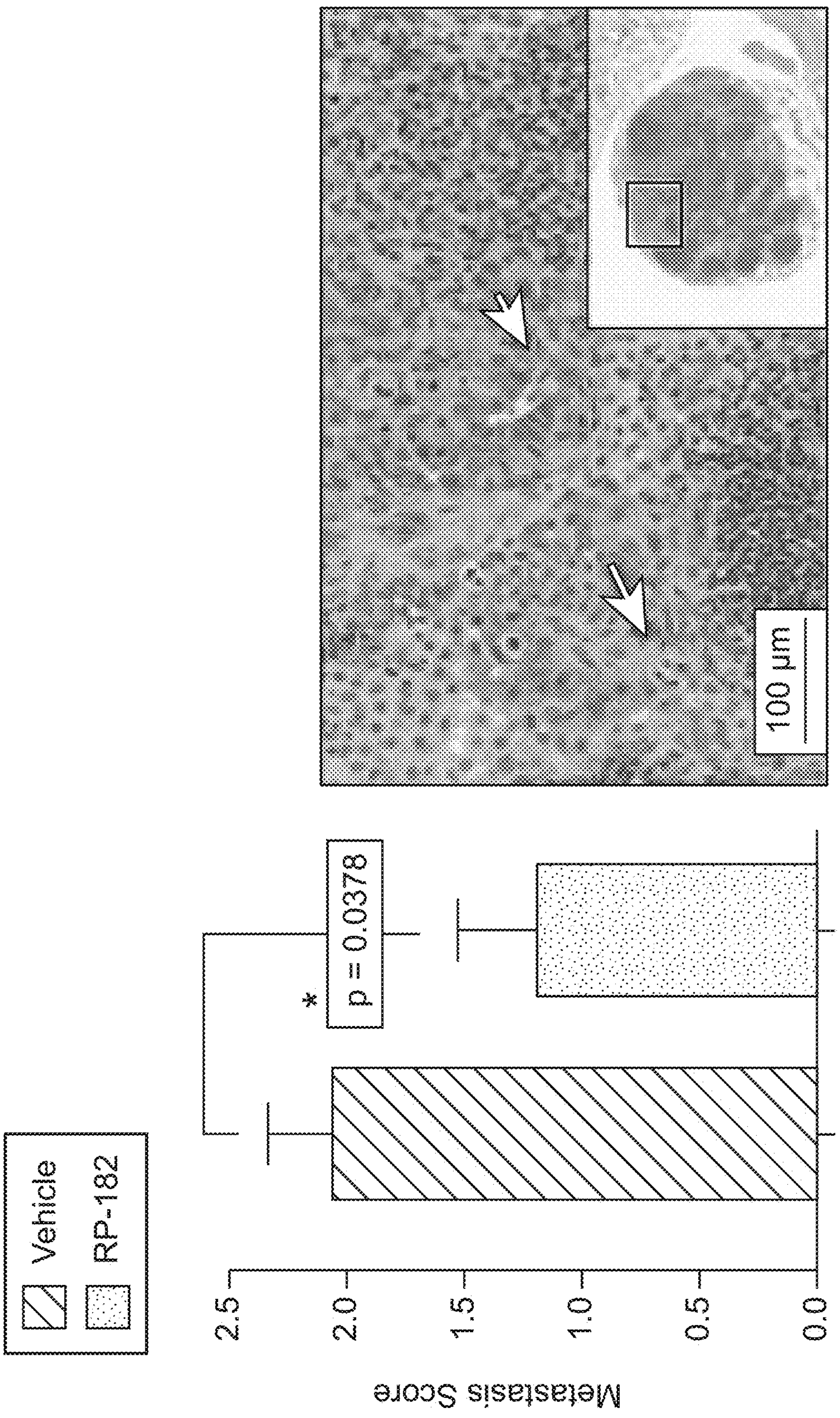
FIG. 97 shows RP-182 restricts tumor growth of MDA-MB231 breast cancer and C4-2 prostate cancer xenografts grown in T cell deficient nu/J mice. A. MDA-MB231 tumors (N≥7/group) grown in nu/J mice treated with vehicle (red), RP-182 (purple), gemcitabine (green), and the combination (brown) shown on left, impact of RP-182 treatment onto lymph node metastasis in MDA-MB231 mice after 42 days of treatment shown right. Analysis shows fraction of lymph nodes involved by cancer per examined total number of lymph nodes in draining basin. Representative H&E staining of metastatic cancer in involved lymph node shown on right, green arrows highlight cancer cells with abnormal mitotic figures. B. Tumor growth of C4-2 prostate cancer xenografts grown in T cell deficient nu/J mice.
Figure 98:
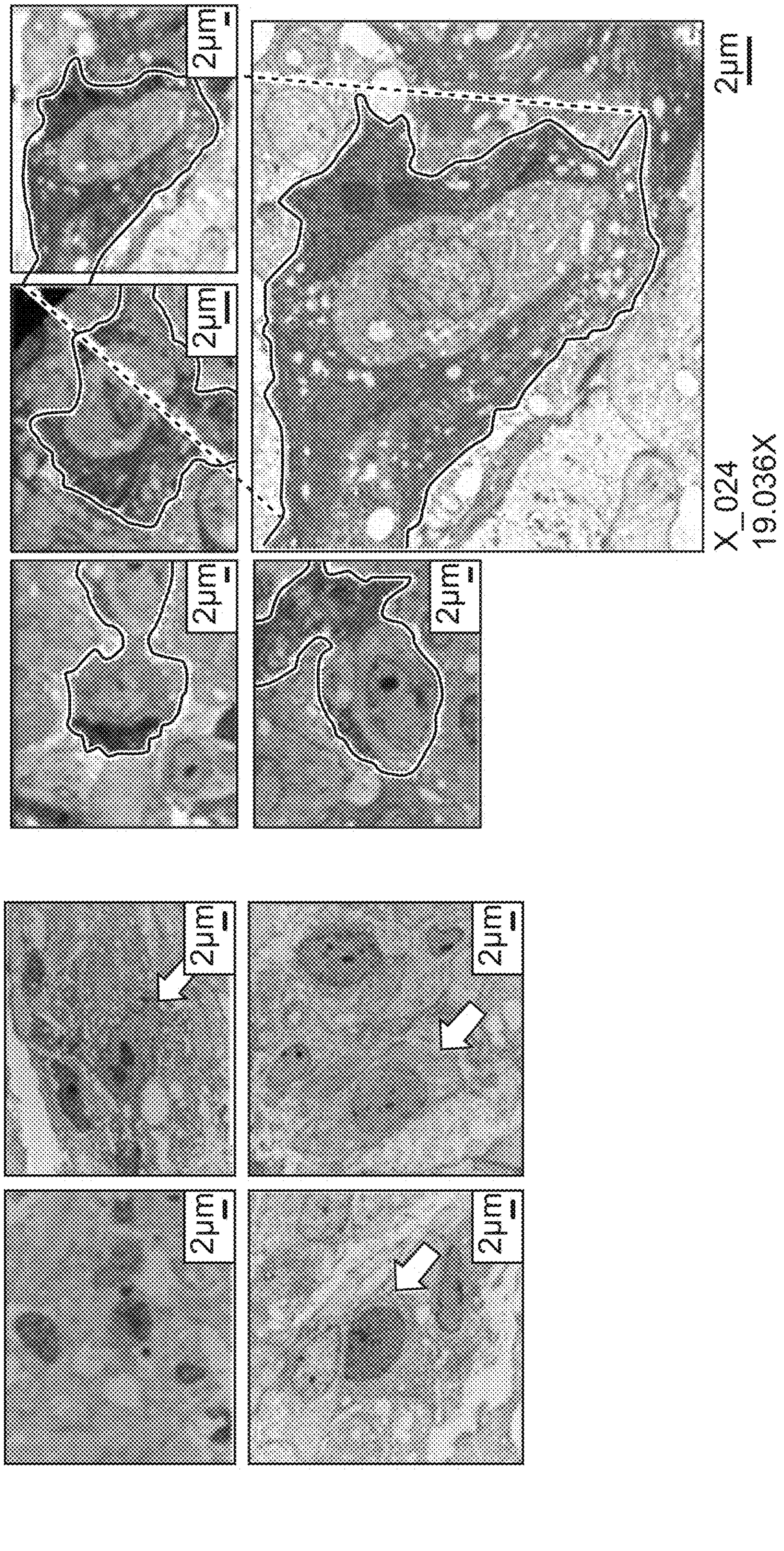
FIG. 98 shows transmission electron microscopy of KP16 tumors treated with vehicle and RP-182. TAMs with intracellular vesicles indicated by arrow, clasping of cancer cell and partial or complete cancer cell phagocytosis events highlighted in red.

To show that the induced cancer cell phagocytosis as an innate mechanism of action of RP-182 is involved in RP-182's anti-tumor activity, KPC, MDA-MB231 breast and C4-2 prostate tumors were established in homozygous nu/J mice which are deficient of mature T lymphocytes and unable to mount cell-mediated anti-tumor immune responses but retain B cell, natural killer (NK), and myeloid cell function. RP-182 monotherapy reduced tumor growth across these tumor models, and improved anti-tumor activity of the standard gemcitabine model and reduced metastatic dissemination in the MDA-MB231 model (FIG. 96: FIG. 97). H&E review of RP-182-treated tumors revealed features of macrophage activation and cancer cell phagocytosis. Upon treatment with RP-182 TAMs lost their ballooned, eosinophilic cytoplasm displaying increased hematoxylin uptake with numerous intracellular inclusions of nuclear material or cellular debris. Tissue sections interrogated by electron microscopy showed multiple complete inclusions of cancer cells in TAMs, partial phagocytosis of cancer cells, or clasping of activated macrophages onto cancer cells compared to vehicle-treated tumors (FIG. 98).

Thus, RP-182 enhances via CD206 adaptive and innate immune cell functions in tumors to-date not known to be responsive to immune checkpoint blockade.

Discussion

Tumor-associated macrophages, which successfully recognize and infiltrate affected tissues, are positioned to be able to initiate a profound, anti-tumor immune response. Unfortunately, many tumors are able to alter the behavior of these cells and coax them into supporting vascularization, tumor growth, invasion, and metastasis.

RP-182 was selectively killing these problematic macrophages, initiating an apoptotic process that then depletes them at tumor sites. Evaluation of RP-182's biological actions within M2-macrophages and other immune cells showed that this peptide also alters the function of these macrophages shifting them from an immune-suppressive state into a pro-inflammatory, phagocytosing phenotype able to mediate immune anti-tumor activity. The activation of phagocytosis, autophagy, and NF-kB signaling within RP-182-responding macrophages rapidly leads to upregulation of M1 markers followed by downregulation of M2 markers. These phenotypic changes are accompanied by improved phagocytic function, and notably by a reduction of their overall immunosuppressive character. Both, the reprogramming towards a M1 phenotype of cells which lose MRC1/CD206 expression and escape apoptosis together with the induction of cell death in MRC1/CD206-carrying macrophages upon longer exposure with RP-182 robustly shifts the TAM population toward a M1 phenotype which restores immune surveillance in the tumor microenvironment. The mannose receptor MRC1/CD206 is expressed on the cell surface and intimately connected to its main functions of phagocytosis of pathogenic micro-organisms through recognition of their surface, mannose-containing glycoproteins (MGPs) as well as its scavenger function, in particular collagen, at sites of tissue injury.

RP-182 activates via the mannose receptor MRC1/CD206 phagocytosis and autophagy in M2-like macrophages, which reverts these cells into an anti-tumor M1-like phenotype with elevated M1 cytokine production and the ability to phagocytose cancer cells. In addition, RP-182 induces via an autocrine positive feedforward loop involving TNFα signaling induction of apoptosis via cleaved caspase 8 promoting the depletion of this population and further shifting the balance towards the pro-inflammatory, anti-tumor M1 phenotype. RP-182 was tested in a lung fibrosis model characterized by the extravasation of CD206-positive alveolar macrophages. The observed decreased deposition of collagen and reduced fibrosis associated with the therapeutic merit of RP-182 in this inflammatory model appears consistent with the known anti-fibrotic activity of activated M2 macrophages.

Kinetically, induction of phagocytosis and autophagy by RP-182 in CD206-positive M2-like macrophages was followed by induction of apoptosis, reduction of M2-like macrophages in the TAM population, and increased CD8 cytotoxic T cell infiltration and function. The altered TAM phenotype was also associated with a less-EMT-like cancer phenotype in RP-182-treated tumors. Of note, the increased M1 population transformed from M2-like cells improved innate anti-tumor immunity via increased cancer cell phagocytosis both in vitro and in vivo. Results from the studies in human CD206high vs CD206low PDX models and in CD206−/− knockout allografts suggest that CD206 levels might be used as a future biomarker for this approach.

In summary, the results presented herein show that biophysical similarities beyond primary amino acid sequence alignments can detect previously unknown homologies between HDPs and regulators of the innate immune system and that these motifs can be used to design effective therapeutics. RP-182 is a 10mer synthetic HDP derived from screening for biophysical homologies across HDPs and mediators involving innate immune processes. A conformational switch of the mannose receptor MRC1/CD206 by RP-182 reprograms M2-like TAM in the tumor stroma and improves intratumoral innate and adaptive anti-tumor immunity and tumor control.

Materials and Methods

Peptides, Cell Lines, and Chemical Sources

Peptides were synthesized by Poly Peptide Laboratories, San Diego, CA. Peptides included RP-182, KFRKAFKRFF; RP-832C, RWKFGGFKWR; RP-185, FFKKFFKKFK; AVP, EKLSAFRNFF; LL37F1, FFRKSKEKIG; and RP-426 KARKAAKRAF. PANC-1 (CRL-1469), HPAF-II (CRL-1997), and LNCaP cells (CRL-1740) were purchased from the American Type Culture Collection (ATCC, Manassas, VA), primary murine KP16 and KPC pancreas cancer cell lines were derived from fresh tumor tissue and the primary patient-derived low-passage melanoma line 2183 was provided. In accordance with AACR practices, cells were authenticated by SNP genotyping using Illumina MiSeq sequencing and confirmed to be mycoplasma-free. Mesenchymal Stem Cells, human fibroblasts, and endothelial cells were purchased from Cellular Dynamics International Inc., and DC2.4 mouse dendritic cells were purchased from Millipore Sigma. The cells were maintained according to instructions from supplier or in RPMI 1640 medium with 10% (v/v) FBS and incubated at 37° C. in a 5.0% CO2 atmosphere. Small molecule inhibitors were purchased from Selleckchem Inc. (Houston, TX) and included nuclear factor 'kappa-light-chain-enhancer' of activated B-cells (NF-kB) inhibitors JSH-23 (Cat #S7351), QNZ (EVP4593) (Cat #S4902), mitogen-activated protein kinase (MAPK) inhibitor selumetinib (AZD6244) (Cat #S1008), Ras-related C3 botulinum toxin substrate 1 (Rac1) GTPase inhibitor NSC 23766 (Cat #S8031), and cell division control protein 42 homolog (CDC42) inhibitor ZCL278 (Cat #S7293).

Synthesis of Peptide Analogs

The diazirine containing biotinylated RP-182 analog (NCGC-00510434) and biotinylated RP-426 were synthesized and purified to >95% purity commercially by RS Synthesis LLC (Louisville, KY). The Fmoc-diazirine-containing phenylalanine analog was prepared as shown in FIGS. 15A-B. Separation of the enantiomers was resolved on a chiral column (Chiralpac IB 4.6×250 mm, 100% EOH; 1 ml/min). The biotin was introduced on the side chain of a lysine residue that was coupled to either polyethylene glycol (PEG) or hydrocarbon polyether linkers (see FIGS. 15A-B).

Recombinant Human and Mouse MRC1/CD206

Recombinant human CD206 was purchased from R&D Systems(Cat #2534-MR/CF). Recombinant mouse CD206 was produced by Protein Expression Laboratory (FNLCR, Frederick. MD). Briefly, mouse CD206 (NM_008625.2) cDNA fragment encoding 23-1387 sequence was optimized for human codon usage and generated in pDEST vector with N-terminal honeybee melittin signal peptide and C-terminal 6×His tag. Protein was transiently expressed in Expi293E cells and purified from the supernatant, collected 72 h post transfection, using nickel affinity chromatography. CD206 was eluted in 20 mM HEPES, pH 7.2, 300 mM NaCl, 250 mM imidazole and dialyzed into PBS, pH 7.4. For electron microscopy experiments, the mouse CD206 was further purified by size exclusion chromatography and eluted in PBS, pH 7.4.

Biophysical Homology Screening

To screen for phylogenetically conserved homologies beyond primary amino acid structures the design heuristic Molly font was used (FIG. 1). Chemical properties of amino acids captured by Molly font include amino acid volume encoded by circle size (measured in cubic Angstroms (radius of gyration) in H2O) and the hydrophobicity/hydrophilicity of amino acids converted to a color scale. The most hydrophobic amino acids are depicted in the most intense cyan color, while those that are less hydrophobic are proportionally less concentrated cyan (FIG. 1). Amino acids that are most hydrophilic possess the deepest magenta color and a graduated scale of less intense magenta color is used for amino acids of lower hydrophilic character. Implicit in this scheme is that, within a particular cue, i.e., among hydrophobic or hydrophilic amino acids of very similar properties, exchanges would be more likely to occur (generating the variability one observes in proteins of similar function from evolutionarily distant organisms) subject to the specific structural constraints imposed on each particular protein for it to retain its functionality. Representative glyphs included as mnemonic symbols characterize additional chemical properties of amino acids, including charge of amino acids ("+" or a "−" sign) incorporated within their glyph, and dissociation constant of their ionizable protons encoded by the thickness of the glyph. Numerical values are the energies in kcal/mol required to move the amino acid side chain from the interior of lipid bilayer to the outside aqueous environment (32).

In Silico Docking

Protein-protein interactions of α-helices derived from identified biophysical homology sequences with putative target receptors were evaluated by in silico docking utilizing ClusPro® server (Boston University, MA), which performs direct docking in three computational steps: (1) rigid body docking by sampling billions of conformations, (2) root-mean-square deviation (RMSD) based clustering of the 1,000 lowest energy structures generated to find the largest clusters, that will represent the most likely models of the complex, and (3) refinement of selected structures using energy minimization. Docking with each energy parameter set results in ten models defined by centers of highly populated clusters of the lowest energy docked structures. Consideration of the centers of the largest clusters of these low energy structures, rather than simply low energy structures, is unique to ClusPro® and implicitly accounts for some of the entropic effects aligning cluster populations to cluster probabilities under natural assumptions. Structures were compared by ranking plotted binding coefficients that combines cluster probabilities with binding energies.

MRC1/CD206 Modeling

The protein sequence (1,456 aa) for human MRC1/CD206 was obtained from UniProt (UniProt ID P22897-1 NCBI ID: NP_002429.1) and includes two N-terminus domains (Ricin-B-type Lectin and a Fibronectin type-II) followed by eight C-type lectin domains (numbered 1 to 8), a transmembrane domain (TM), and a cytoplasmic domain. The Iterative Threading and ASSEmbly Refinement software, I-TASSER (https://zhanglab.ccmb.med.umich.edu/I-TASSER/), was used to generate 3D models of CD206. I-TASSER utilizes a hierarchical approach that identifies 3D templates from the RCSB-PDB (http://www.rcsb.org) using a multiple threading approach. Full-length models will eventually be constructed by iterative template fragment assembly simulations.

To assist modeling, we extracted from UniProt (www.uniprot.org) the cysteine residue positions that participate in the disulfide bonds and supplied this list as distance restraints during I-TASSER modeling. The top threading RCSB-PDB template IDs identified by I-TASSER were 5ao5, 3jav, 5ao6 and 4igl. The normalized B-factor values for the models fluctuated around zero, indicating acceptable local accuracy of the model(s). Model confidence was measured by C-score, and the C-score for models ranged between −5 and 2, where higher values indicates higher confidence. The top 4 models had the following C-scores, −0.35, −1.93, −2.89 and −2.97. The top 4 models were analyzed and based on the comparison of Small Angle X-ray Scattering model (SAXS) and the I-TASSER predicted secondary structure confidence and C-scores, the top-ranked I-TASSER model was identified as a possible structural fold for CD206.

Small-Angle X-Ray Scattering (SAXS) Data Collection and Analysis

SAXS data was collected at the 121D-B beamline of the Advanced Photon Source (APS), Argonne National Laboratory, Lemont, IL. Photon energy was 13.3-KeV and sample-to-detector distance was 2 m to achieve a q range of $0.005<q<0.90$ Å-1, where $q=(4\pi/\lambda)\sin\theta$, and $2\theta$ is the scattering angle. Concentration series measurements for CD206 in buffer containing 50 mM Hepes, 100 mM NaCl, 1 mM DTT were carried out to extrapolate the data to infinite dilution for removing the scattering contribution due to interparticle interactions (concentration effect). Thirty 2D-image frames were recorded for sample solution and their matching buffer using a flow cell, with the exposure time of 0.75-1 sec to minimize radiation damage and to yield optimal signal-to-noise ratio. The 2D images were reduced to 1D scattering profiles and averaged using the Matlab software package at the beamlines.

The buffer background subtraction and intensity extrapolation to infinite dilution were carried out using MatLab script developed by 12-ID-B beamline. The radius of gyration (Rg) was generated from Guinier plot in the range of $qRg<1.3$. For comparison, Rg was also calculated in real and reciprocal spaces using program GNOM (https://www.embl-hamburg.de/biosaxs/manuals/gnom.htm). The pair—distance distribution function P(r) and maximum dimension (Dmax) were also calculated using GNOM. The molecular weights were estimated using two methods based on Porod volume, Vporod, and correlation volume, Vc. Based on the silico models of CD206 monomer derived from iTASSER, the fit of dimer of CD206 to SAXS experimental data were calculated using the program CORAL.

Electron Microscopy

Purified recombinant mouse CD206 full length protein as well as the complexes with the peptides RP-182, RP-185, RP-832C, AVP1, LL37F1 and RP-426 were analyzed by negative stain electron microscopy. A 3 μL aliquot containing ~0.01 mg/mL of the sample was applied for 20 seconds onto a carbon-coated 200 Cu mesh grid that had been glow discharged at 30 mA for 30 sec, then negatively stained with 0.7% (w/v) uranyl formate for 40 sec. Data for the CD206 unbound and the complexes with RP-182, RP-426 and RP-832C were collected using a FEI T20 electron microscope operating at 200 kV, with an electron dose of ~40 e-/Å2 and a magnification of 100.000× that resulted in a pixel size of 2.19 Å at the specimen plane. Images were acquired with an Eagle 2k×2k CCD camera (http://FEI.com) using a nominal defocus of 1500 nm and the SerialEM software (54). Data for the complexes with RP-185, AVP1 and LL37F1 were collected using a FEI Talos electron microscope operating at 200 KV, with an electron dose of ~40 e-/Å2 and a magnification of 73,000× that resulted in a pixel size of 1.98 Å at the specimen plane. Images were acquired with a Ceta 4k×4k CCD camera (http://FEI.com) using a nominal defocus of 1200 nm and the EPU software. For electron microscopy data processing, particles were selected from the micrographs, extracted, and a reference-free 2D class averages were obtained using RELION 2.1.0.

Microscale thermophoresis and cellular thermal shift assays.

The binding of RP-182 and RP426 peptides to purified recombinant MRC1/CD206 was evaluated by microscale thermophoresis (MST) using a label-free approach. Specifically, two-fold serial dilutions of the peptides were prepared in PBS and incubated with the same volume of 250 nM recombinant human and mouse CD206 in PBS. After a 5 min incubation at room temperature (RT), measurements were carried out in standard capillaries using a Monolith NT. Labelfree instrument (Nanotemper Technologies) with 40% LED excitation power, 40% IR-laser power, and laser on and off times of 30 s and 5 s, respectively. KD values were calculated by fitting the T-Jump signal of the thermograph using MOAffinity analysis software (Nanotemper Technologies).

The target engagement of the peptides in macrophages was assessed using the cellular thermal shift assay (CETSA) following the Jafari et al. protocol with minor modifications. Briefly, a suspension of M2-polarized macrophages was prepared using Cell dissociation buffer (Gibco BRL) for 5 minutes at RT followed by one wash step in DMEM (Gibco, Cat. #11965118). Aliquots of 6×105 cells were incubated with 100 μM RP-182, 100 μM RP-426, or the equivalent volume of PBS, for 45 min at 37° C. After treatment, cells were collected by centrifugation for 5 min at 300× g and re-suspended in 600 μL DMEM. Fifty μL aliquots of the cell suspension were heated for 3 min in a temperature range of 37 to 64° C. with 3° C. steps, cooled at RT for 3 min, and lysed in 10 μL DMEM containing NP-40 (1%(v/v) final concentration) and Halt protease inhibitor cocktail (ThermoFisher, Cat. #78430) supported by three freeze-thaw cycles. Samples were centrifuged at 20,000×g for 20 min at 4° C., and the supernatant was subsequently analyzed by western blot using 12-230 kDa Peggy Sue separation module (ProteinSimple, Cat #, SM-S001) and Peggy Sue instrument (Protein Simple) with following settings: electrophoresis 250 volts for 45 min; blocking, 23 min; primary antibody, 30 min; secondary antibody, 30 min. Quantitative analysis of CD206 level was performed using anti-CD206 antibody at 1:70 concentration multiplexed with anti-SOD1 antibody at 1:300 dilution, as internal control for normalization, and Compass software (ProteinSimple, San Jose, CA).

MRC1/CD206 Fragment Analysis by LC-MS/MS

To identify the binding domain of MRC1/CD206 to RP-182, we utilized two different approaches. First, 5 μg of trypsin (Thermo Scientific. Cat #90057) digested fragments of recombinant human CD206 was incubated with biotinylated RP-182 (NCGC-00510434) immobilized to magnetic beads (Thermo Scientific, Cat #65001) or bead alone for 4 h at RT. Samples on the beads were eluted after washing the beads three times in PBS containing 0.05% Tween-20 PBS-T), desalted using C18-ziptip (Millipore, ZTC18S960), and analyzed by LC-MS/MS. Second, RP-182 analog with diazirine and biotin (NCGC-00510434) was cross-linked by photo-labeling to full length recombinant CD206 and then digested with trypsin. In detail, 50 μg MRC1/CD206 protein was incubated with 100 μM NCGC-00510434 or PBS, incubated 5 min at RT, photo-labeled for 30 min on ice and digested with trypsin. Samples were incubated with streptavidin magnetic beads for 4 h at RT. Beads were collected and washed three times with PBS-T. Samples on the beads were processed as described above and analyzed by LC-MS/MS.

The LC-MS/MS analysis of samples were carried out using a Thermo Scientific Q-Exactive hybrid Quadrupole-Orbitrap Mass Spectrometer and a Thermo Dionex UltiMate 3000 RSLCnano System. Peptide mixture from each sample was loaded onto a peptide trap cartridge, eluted onto a reversed-phase PicoFrit column (New Objective, Woburn, MA) using a linear gradient of acetonitrile (3-36%) in 0.1%(v/v) formic acid, ionized and sprayed into the mass spectrometer, using a Nanospray Flex Ion Source ES071 (Thermo Scientific) under the following settings: spray voltage 1.8 kV, capillary temperature 250° C. For peptide identification and protein assembly, data were analyzed using the Thermo Proteome Discoverer 1.4.1 platform (Thermo Scientific, Bremen, Germany). Database search against CD206 sequence was performed based on the SEQUEST algorithms through the Proteome Discoverer 1.4.1 platform. Carbamidomethylation of cysteines was set as a fixed modification, and Oxidation and Deamidation Q/N-deamidated (+0.98402 Da) were set as dynamic modifications. The minimum peptide length was specified to be five amino acids with maximum false peptide discovery rate of 0.01. The precursor and fragment mass tolerance was set to 15 ppm and 0.05 Da, respectively.

Proteomic Analysis of CD206 Complex by LC-MS/MS

To identify proteins involved in downstream signaling induced by RP-182 via CD206, 5×106 M2 cells per treatment were re-suspended into 3 mL RPMI media and incubated with 100 μM biotinylated RP-182 or PBS for 30 min at 37° C. Cells were pelleted and lysed with 500 μL Pierce IP Lysis buffer (Thermo Scientific, Cat #87787) with protease and phosphatase inhibitors (Thermo Scientific, Cat #78440) for 15 min at 4° C., then cleared by centrifugation at 15,000×g for 15 minutes at 4° C. Supernatants were transferred to new tubes and incubated with 20 μL streptavidin magnetic beads (Thermo Scientific, Cat #65001) for 30 minutes at 4° C. Beads were collected and washed four times with PBS-T. Samples on the beads were separated by SDS-PAGE, reduced with DTT, alkylated with iodoacetamide and digested with MS grade trypsin. Digested peptide mixture were concentrated and desalted using C18 Zip-Tip, reconstituted in 20 μL of 0.1% formic acid and analyzed by LC-MS/MS as described above.

Raw data files were screened against a mouse protein sequence database using the Proteome Discoverer 1.4 software (Thermo Scientific, San Jose. CA) based on the SEQUEST algorithm. Carbamidomethylation (+57.021 Da) of cysteines was a fixed modification, and Oxidation/+15.995 Da (M). Deamidated/+0.984 Da (N, Q), Methyl/+14.016 Da (K. R), Acetyl/+42.011 Da (K), Phospho/+79.966 Da (S, T. Y), Dimethyl/+28.031 Da (K, R) were set as dynamic modifications. The minimum peptide length was specified to be five amino acids. The precursor mass tolerance was set to 15 ppm, whereas fragment mass tolerance was set to 0.05 Da. The maximum false peptide discovery rate was specified as FDR<0.01.

Murine and Human Macrophages

Figure 14A:
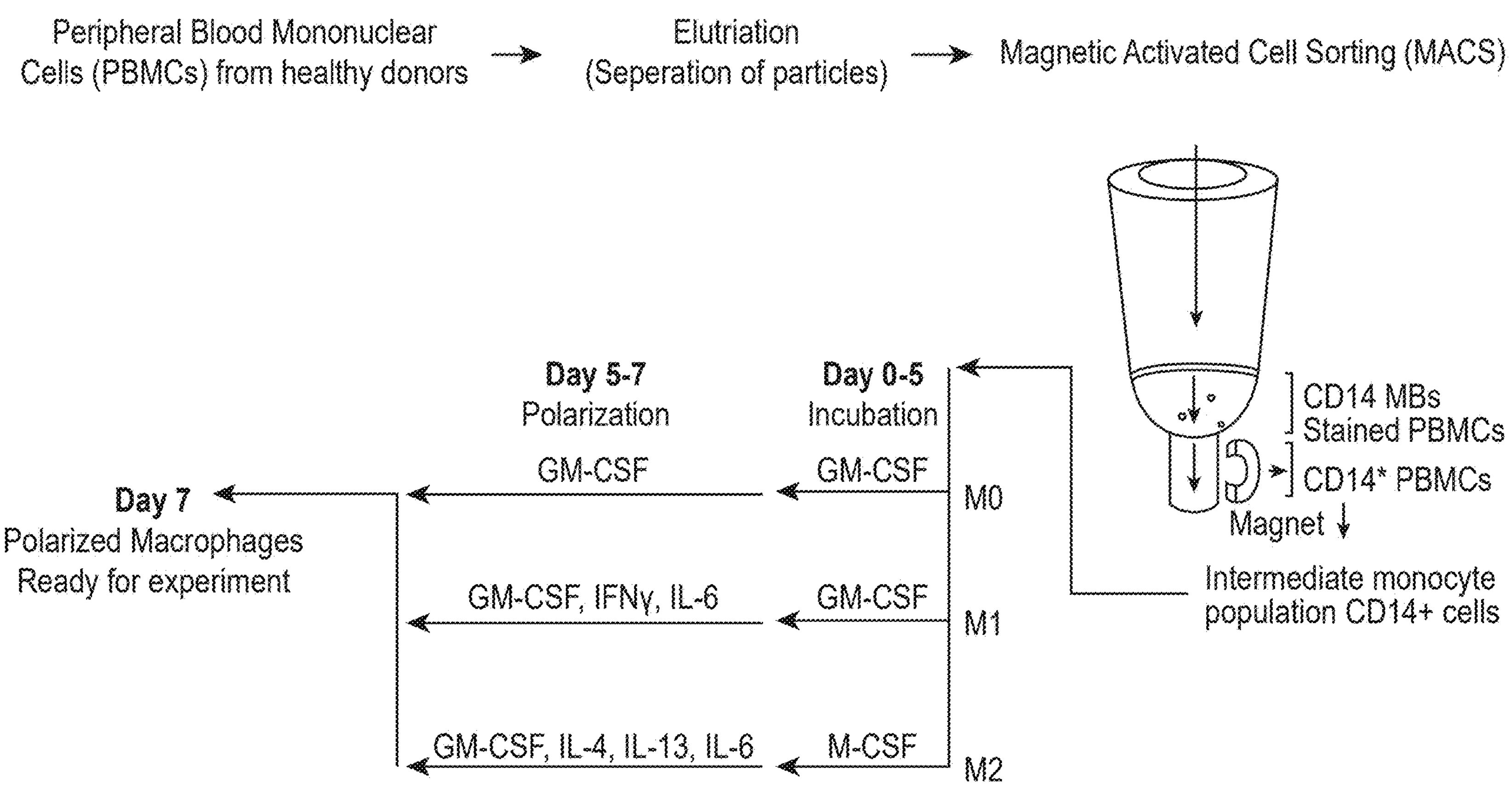
FIG. 14A shows the human peripheral blood monocyte-derived macrophage polarization protocol.
Figure 14A:
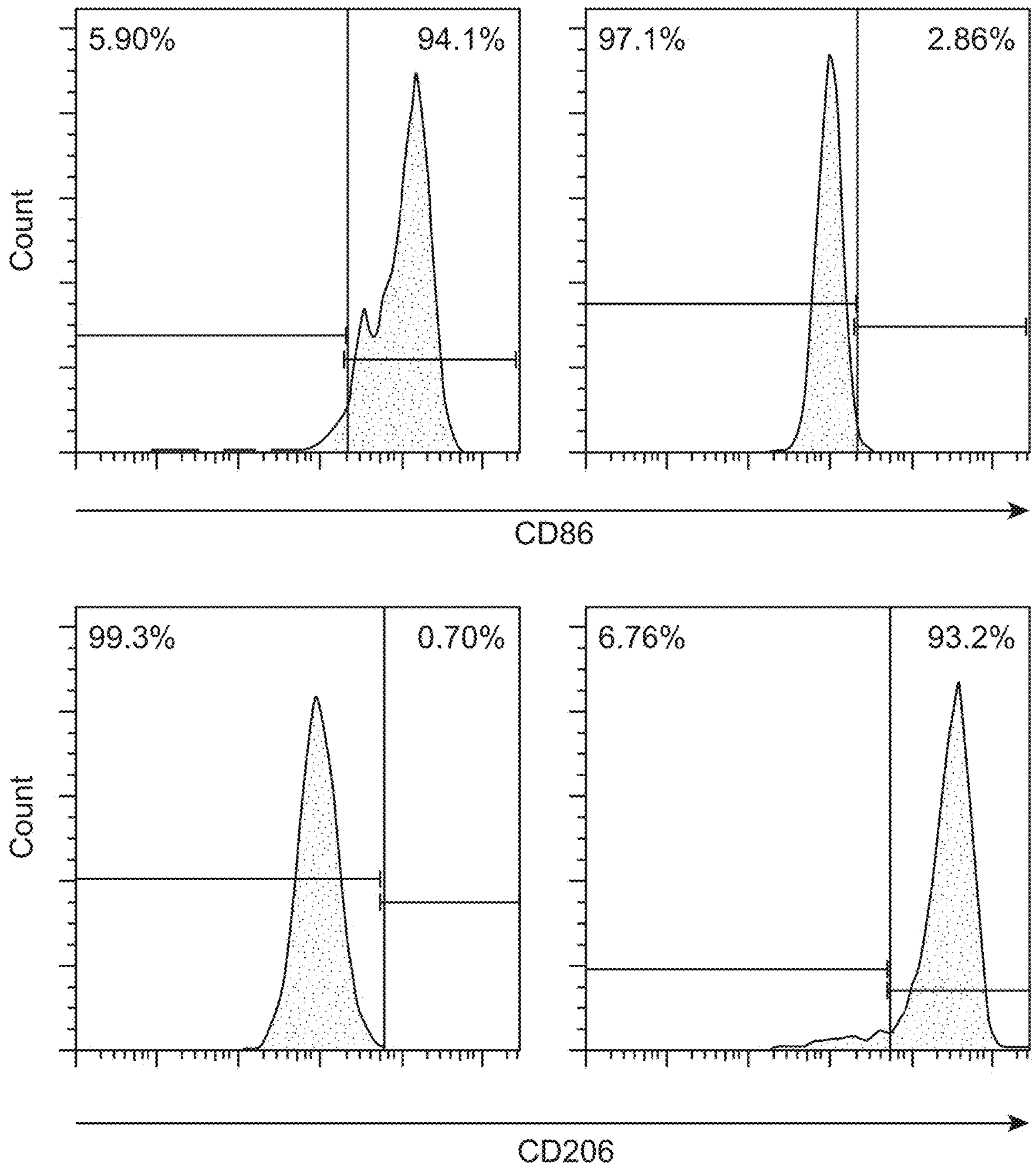
Figure 14B:
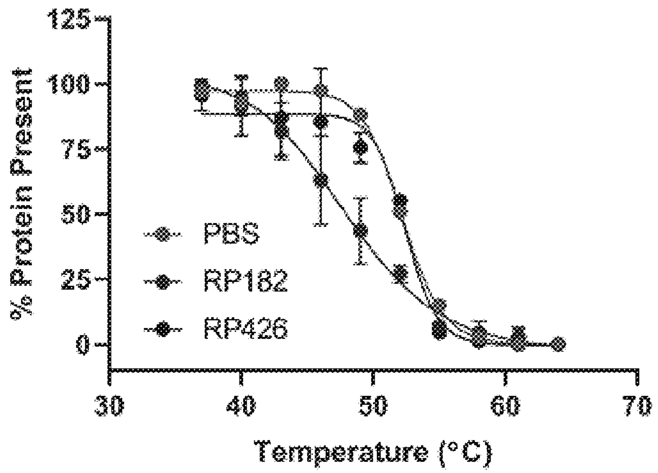
FIG. 14B shows the cellular Thermal Shift Assay (CETSA) of human macrophages.
Figure 14C:
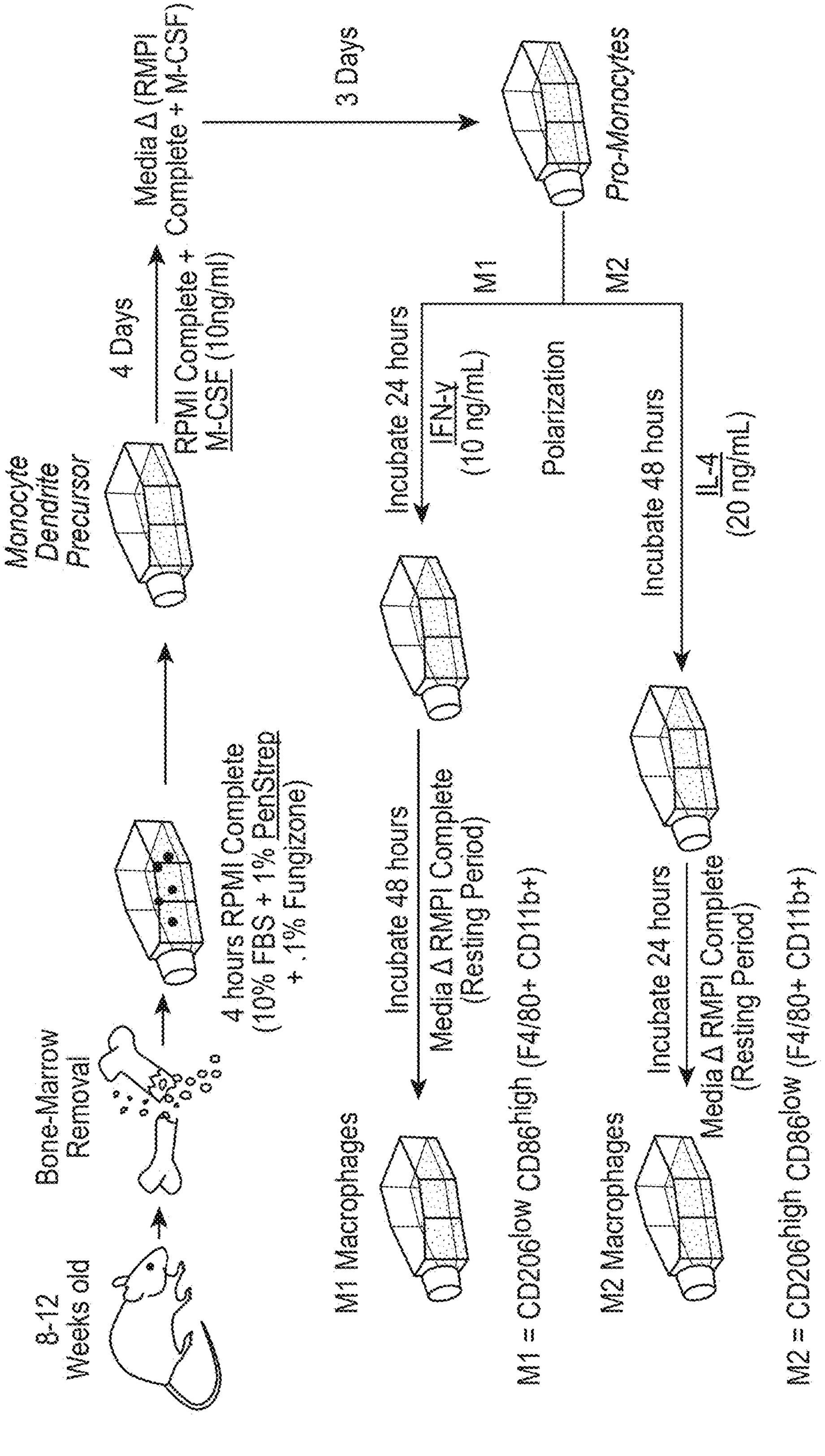
FIG. 14C shows the murine bone marrow-derived macrophage (BMDM) polarization protocol.
Figure 14C:
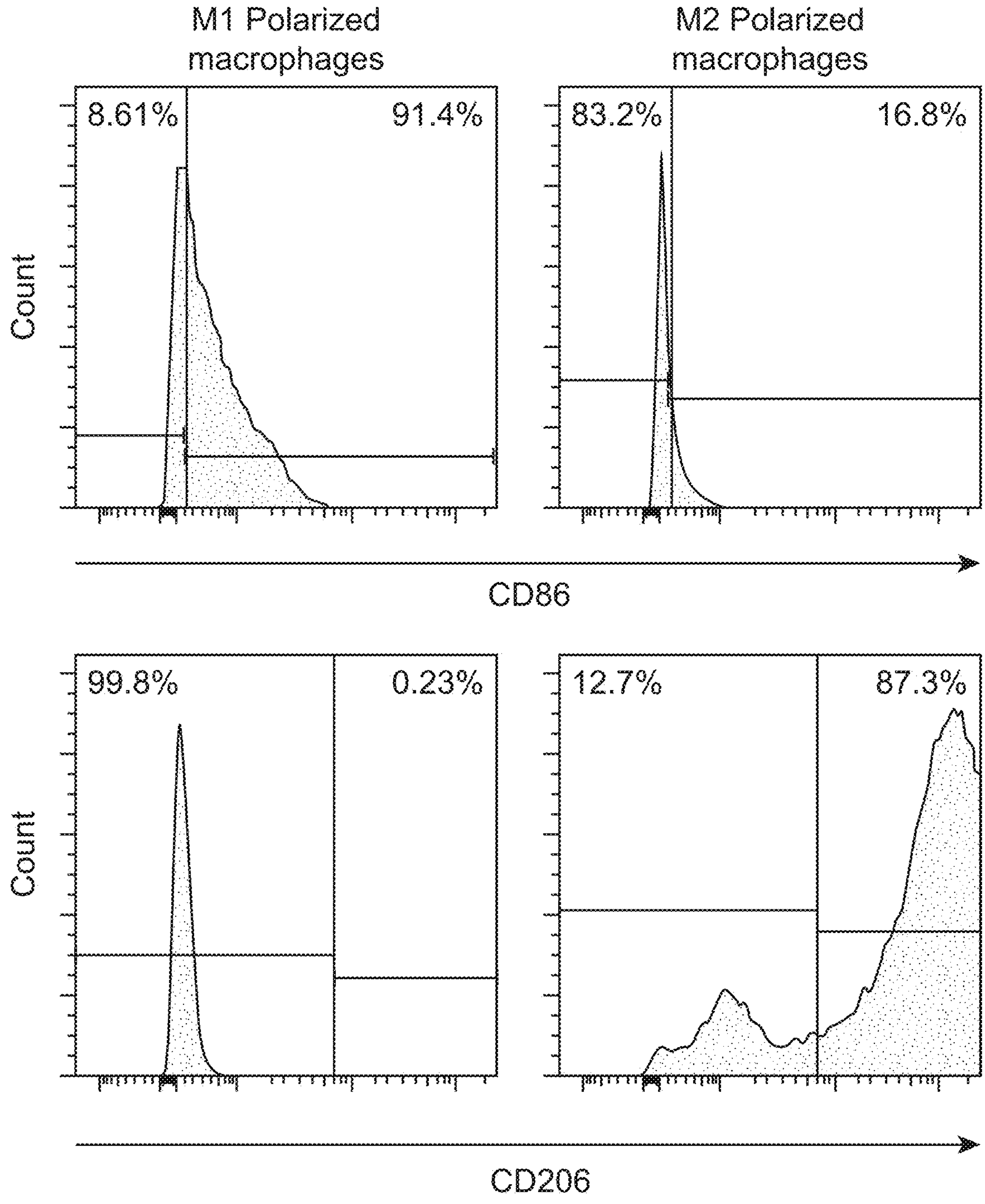
Figure 14D:
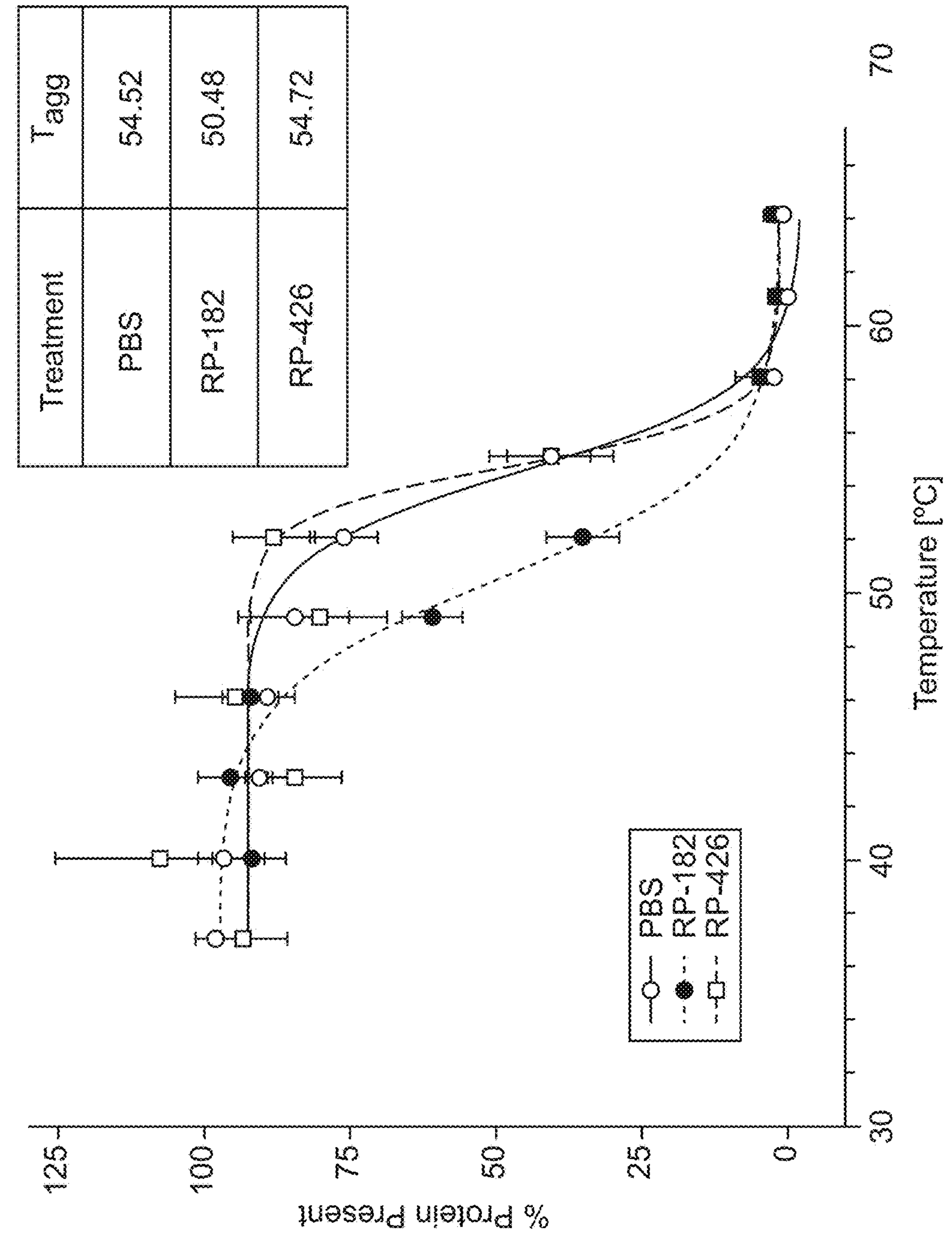
FIG. 14D shows Cellular Thermal Shift Assay (CETSA) of murine macrophages.
Figure 14D:
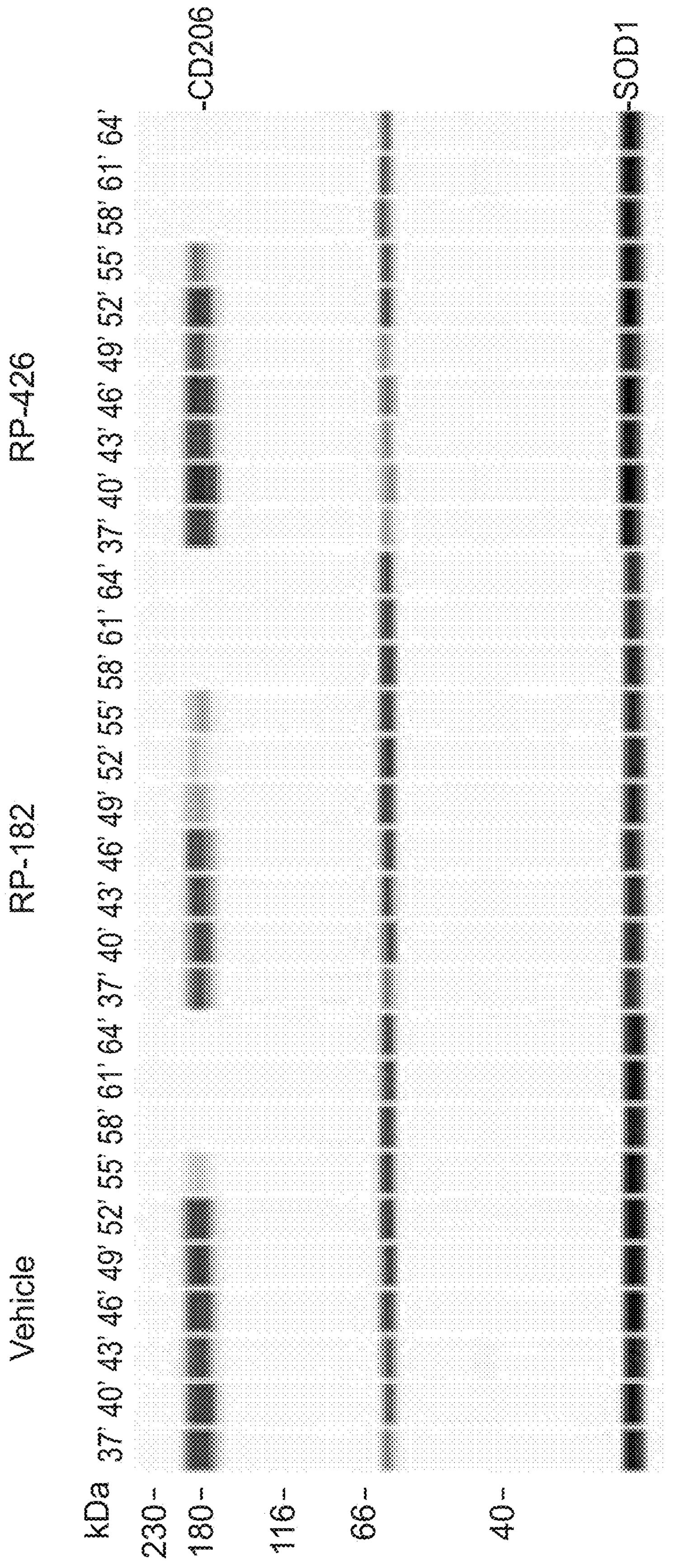

Murine monocyte precursor cells were obtained by flushing out the bone marrow from the femur bones of 6-8 week old healthy C57B/L mice. Experiments were conducted according to protocols and policies approved by the Institutional Animal Care and Use Committee (ACUC) of the National Institutes of Health (ACUC protocol SB-210-3) and NIHs policy on humane care and use of laboratory animals (https://olaw.nih.gov/home.htm). After 1 week of incubation at 37° C. with 5% CO2, bone marrow progenitors were polarized into M1 and M2 macrophages with the use of respective cytokines as shown in FIG. 14A. Human macrophages were obtained from peripheral blood mononuclear cells (PBMCs) acquired from de-identified healthy human donors from the NIH, Department of Transfusion Medicine (DTM) (under Institutional Review Board (IRB)-approved NIH protocol 99-C-0168) using Classical Monocyte Isolation Kit, human (Cat #130-117-337 MACS Miltenyi Biotec, San Diego, CA) and were depleted of CD14 positive cells and polarized into M1 and M2 macrophages with the use of cytokines, as described in FIG. 21B-E (57). Recombinant mouse M-CSF (Cat #PMC2044) and IFN-γ Recombinant Human Protein (Cat #PHC4033) was purchased from ThermoFisher Scientific, recombinant mouse INFγ (Cat #485-M1-100), mouse IL-4 (Cat #404-ML-050), Recombinant Human IL-4 Protein (Cat #204-IL-050), Recombinant Human IL-13 Protein (Cat #213-ILB-025), and Recombinant Human IL-6 Protein (Cat #206-IL-050) from R&D Systems (Minneapolis, MN.). Human Granulocyte Macrophage Colony Stimulating Factor (hGM-CSF) (Cat #8922SC), human Macrophage Colony Stimulating Factor (hM-CSF) (Cat #8929SC) purchased from Cell Signaling and Lipopolysaccharides from *Escherichia coli* 0111:B4 (Cat #L3012-5MG) was purchased from Sigma Aldrich.

RNA Sequencing (RNASeq) Experiments and Data Analysis

Total RNA was harvested from M1- and M2-polarized macrophages treated for 2 h with 20 μM RP-182 or vehicle and subject to global RNASeq analysis on the Illumina NextSeq500 sequencer. Reads were trimmed to remove adapter sequences as well as reads less than 25 base pairs (bp) using the Trimmomatic ver 0.32 tool. Trimmed reads were mapped to mouse genome mm10 using STAR aligner. Transcriptome bam along with genome bam was created to use for RSEM quantification (accurate transcript quantification from RNASeq data with or without a reference genome).

EdgeR (Empirical Analysis of Digital Gene Expression Data; v3.30.09) analysis was conducted in R which is based on a negative binomial model and count data. In the edgeR analysis, low count transcripts were excluded manually and only genes with at least 1 count per million were used for further analysis. A normalization factor was calculated using the trimmed mean of M values (TMM) method, and the dispersion parameter for each gene was estimated as the Cox-Reid common dispersion method. The GLM (Generalized Linear M) likelihood ratio test is based on fitting negative binomial GLMs with Cox-Reid dispersion estimates in order to take known sources of variation into account. Significant DEGs were detected with a cut-off value of false discovery rate (FDR)<0.05 and log 2 fold change>1.

Functional GO Enrichment and Network Analyses: Differentially expressed genomic features (p<0.05; q≤0.05) in M2 macrophages after RP-182 treatment were imported into Cytoscape (v. 3.7.1) to assess functional gene ontology enrichment and visualize GO term interaction network. After import, setsApp (v. 2.2.0) plug-in was used to separate features by up- or down-regulation. Once separated, functional analysis and network construction were completed using the ClueGO plug-in (v. 2.5.4). A two-sided (enrichment/depletion) hypergeometric test with Bonferroni step down was used to determine KEGG pathways (v. 27.02.2019) enrichment. Analysis thresholds included: enrichment significance of p<0.05, a minimum of 5% gene inclusion and a kappa score threshold of ≥0.4. ClueGO uses kappa scores to determine likelihood of GO term interactions and groupings.

For Pathway Studio® analysis, differentially expressed gene sets of RP-182– vs vehicle-treated M2 BMDMs were calculated. DESeq2 Analysis (version 1.22.2; in R) yielded 1,224 differentially expressed genes (DEGs) at p<0.05 and 382 DEGS at FDR adjusted q≤0.05 and were used for Gene Ontology analysis at Mouse Genome Informatics (http://www.informatics.jax.org/). Gene set enrichment analysis of top 25

DEGs generated p-values for enrichment and enrichment score which were both incorporated into ranking metric. Leading Edge Analysis was used to identify most common genes across enriched gene sets that remained consistent despite ranking metric change which were imputed into Pathway Studio® finder (https://www.pathwaystudio.com/).

Single-Cell RNA-Sequencing

Normal pancreas and pancreatic tumors from treated and untreated KPC mice were harvested, and single cell suspensions were prepared using mouse tumor dissociation kit (#130-096-730, MACS Miltenyi Biotec, San Diego, CA) and a Gentle Macs Agitator (Miltenyi Biotec, San Diego, CA) as per company protocol. 9,000-12.000 cells were used to generate single-cell barcoded cDNA libraries using the 10× Genomics Chromium Controller. Single Cell 5' Library and Gel Bead Kit (10× Genomics, Cat #1000006) was used to generate gene expression libraries. Manufacturer's instructions were followed for generating the libraries, which were then sequenced on multiple runs of Illumina NextSeq500 with V2 chemistry. Sequencing runs for the gene expression libraries were setup as 26 cycles+8 cycles+57 cycles non-symmetric runs.

Single Cell Transcriptome

For single cell gene expression libraries, de-multiplexing, alignment to the mm10 transcriptome, gene-barcode matrices generation were using the 10× Genomics Cellranger toolkit (v2.2.0) for each data set. Library batches were normalized using the CellRanger Aggregate function to aggregate all treated and untreated tumor samples datasets together, and the resulting gene-barcode matrices were fed into Seurat(v2.3.4). Each sample in the sample set was preprocessed in Seurat (v2.3.4) by removing genes that were detected in fewer than 3 cells and removing cells that had fewer than 100 genes detected. The samples were then further processed by using the global-scaling normalization method LogNormalize, that normalizes the gene expression measurements for each cell by the total expression, multiplies this number by a scale factor (10,000 by default), and log-transforms the result. The number of principal components to use for analysis was estimated on each sample set by using the calcPCA function in URD while setting the mp.factor parameter to 2. The total number of significant principal components identified by this algorithm was taken as the estimated number of principal components to use in Seurat. Dimensionality reduction was carried out in Seurat via principal component analysis followed by clustering t-SNE visualization using the top significant components. Major clusters were denoted by differentially expressed canonical marker genes, and these were subjected to additional rounds of cluster refinement. For the CD11b+ and Krt19, CD11c, and Ly6G negative cells, the marker gene ITGAM was used to identify CD11b+ cells, the cells co-expressing the Krt19 gene (cytokeratin-19), ITGAX (CD11c), and LY6G were removed. The filtered gene-barcode matrix for CD11b+ and Krt19, ITGAX, and LY6G negative cells were used for cluster refinement and analysis. Differential expression analysis was performed using EdgeR program. Differentially expressed genes from RP-182 treated M2 BMDMs (adjusted p-values<0.05) were ranked and a fold-change cut-off (−1<Log(FC)>1) was applied. All genes above the fold-change p-value threshold reported by EdgeR were submitted to GSEA program, compared to their counterparts from the bulk RNASeq dataset, and marker genes discriminating a specific subpopulations were identified using the FindMarkers function. The top markers ranked by Bonferroni adjusted p-values are displayed on a log (10) fold-change color scale, normalized across all cells.

Co-Immunoprecipitation Experiments

M2 macrophages were re-suspended in RPMI media and treated with 100 μM peptide or PBS for 10 min at 37° C. Cells were pelleted and lysed with 500 μL Pierce IP Lysis buffer (Thermo Scientific, Cat #87787) containing protease and phosphatase inhibitors (Thermo Scientific, Cat #78440). To pull-down CD206 associated proteins via biotinylated RP-182 or RP-426, 50 μL of streptavidin beads (Thermo Scientific, Cat #65001) were added to cleared cell lysates and incubated for 30 min with gentle mixing at RT. Supernatants from the beads were collected after washing the beads four times with PBS containing 0.05% Tween-20, incubating in PBS with 0.1% SDS and boiling for 5 min at 95° C. To validate GRB2 interacting proteins, 25 μg anti-GRB2 antibody was immobilized onto agarose resin using the Pierce Classic IP Kit (Thermo Scientific, Cat #26146) and co-immunoprecipitation was performed following the manufacturer's protocol. Specifically, lysates were incubated with the immobilized antibody overnight at 4° C. with gentle rotation. The columns were washed three times with PBS containing 0.25% Triton X100, and eluted using supplied elution buffer (Thermo Scientific, Cat #21027). Samples were visualized by western blotting using indicated antibodies. Activated forms of the RhoGTPases Rac1 and CDC42 (GTP-Rac1 and GTP-CDC42) were measured with the RhoA/Rac1/Cdc42 combo activation assay kit following the manufacturer's instruction (Abeam, Cambridge, MA).

Immunofluorescence Assays

Immunocytochemistry analysis was carried out using Zeiss LSM 880 confocal microscope. 50,000 myeloid progenitors were seeded onto 8-well chamber slides, polarized into M1 and M2 macrophages. Cells were treated with 20 μM RP-182 for 2 h at 37° C. followed by fixation with 4% paraformaldehyde for 15 min, permeabilization with 0.3% Triton for 5 min, and blocking with 3% BSA in PBS for 1 h. After blocking, cells were incubated with respective primary antibody (Tables 6A-D) for 1 h at RT. Staining with secondary antibodies was carried out for 1 h at RT, followed by washing and addition of DAPI with mounting media (H-1200 Vectashield, Burlingame. CA). Images were taken at 63× magnification, and three separate images for each treatment group containing about 200 cells were analyzed using ImagePro software (Media Cybernetics, Rockville, MD). The number of automatically counted bright objects (fluorescence of secondary antibodies for specific proteins) was normalized to the number of DAPI stained nuclei. For relative comparison, the fluorescence ratio for vehicle treated cells was set to 1.

Cell Viability Assay

Dose-response curves in terms of cell viability were determined using the Live/Dead Viability Cytotoxicity Kit (#L3224, ThermoFisher Scientific. Grand Island, NY). Macrophages were seeded onto glass bottom 96 well plates and polarized into M1 and M2. Cells were treated with different concentrations of RP-182 and control peptide RP-426 ranging from 0.01 μM to 100 μM for 48 hours. After drug treatment, 100 μL mixture of 2 μM calcein-AM and 4 μM ethidium homodimer was added and incubated for 1 h. The images were taken in a similar fashion explained in the immunofluorescence assay. 200 cells were counted manually from 3 different random regions across the three technical replicates and percentage of alive cells was calculated using GraphPad Prism version 7.0.

Animal Models

Colonies of transgenic mice were established at the National Cancer Institute (NCI) in Bethesda, MD, and all animal experiments were conducted according to protocols and policies approved by the Institutional Animal Care and Use Committees (ACUC) of the National Institutes of Health. All animal studies were conducted under ACUC-approved protocols SB-210 and SB-211. Mice with individual genes for Pdx-1-cre, LSL-KrasG12D/+, Trp53R172H/+, and Ink4a(p16)/Arf(p19) flox/flox were obtained from NCI's Mouse Repository. Frederick National Laboratory of Cancer Research. https://frederick.cancer-.gov/science/technology/mouserepositoiy) and crossed to create animals with the triple genotype of Pdx-1-cre; LSL-KrasG12D/+; Ink4a(p16)/Arf(p19)flox/flox (KP16) or Pdx-1-cre; LSL-Kras GI2D/+; LSL– Trp53R172H/+ (KPC) (49, 60). B6.129P2-Mrc1tm1Mnz/J mice were obtained from The Jackson Laboratory (JAX stock #007620) (61). Genotypes were verified using PCR methods performed by Transnetyx, Inc. (Cordova, TN).

Human pancreatic cancer tissues for xenotransplantation were obtained from the NCI Patient-Derived Models Repository (PDMR; https://pdmr.cancer.govf) initiative and subcutaneously implanted into NOD-scid IL2Rgammanull (NSG) immuno-deficient mice (F0 generation). After tumors reached 2 cm, tumors were explanted, cut into equal pieces, and re-generated in another generation (F1 generation). Treatment experiments were carried out in F2 mice.

Syngeneic murine models of cancer included the murine CT-26 colon cancer and B16 melanoma models. Approximately 1×106 CT-26 cells/100 μL media were implanted subcutaneously into 6 to 8-week old BALB/c mice. When tumors reach ~50 mm3 volume, mice were started on treatment as outlined below. Tumor volume (mm3) was calculated as (L×W2)/2, with L=length (mm) and W=width (mm) during two-dimensional caliper measurements and total body weights were recorded twice per week. Two hours after the last injections, mice were sacrificed, tumors excised, weighed, and fixed in formalin. Similarly, 0.5×106 murine B16 melanoma cells were subcutaneously injected into the flank of BALB/c animals and treatment was started upon tumors reaching ~50-100 mm3 volume. 0.5×106 human breast MDA-MB23, prostate C4-2, or KPC cells were subcutaneously injected into the flank of homozygous female athymic (nu/J) nude mice. KPC tumors were treated for 3 weeks after tumors reached 250 mm3, C4-2 tumors were treated for 4 weeks and MDA-MB231 tumors for 6 weeks after tumors had reached 100 mm3 volume, at which point the draining lymph node basin was removed for H&E staining determination of locoregional metastatic index (number lymph nodes involved by cancer per total number of excised and examined lymph nodes in draining basin).

Animal Imaging

Mice with the KP16 and KPC genotypes were imaged with ultrasound weekly, starting at six weeks of life. Ultrasound imaging was performed using a 40 mHz transducer and a Vevo700 ultrasound machine (Visualsonics. Toronto, Canada). Mice were anesthetized with Isoflurane (Baxter. Deerfield. IL), shaved, and injected intraperitoneally with 1.5 ml of normal saline (eBioscience. San Jose, CA). B-mode images were recorded to obtain tumor measurements.

Treatment Protocols

KP16 and KPC mice were treated for 7 days prior to harvest of tumors used in flow cytometry, pull down of immune cells, or immune assays, or until a predefined study endpoint. All animal treatments started after ultrasound confirmed a pancreatic tumor measuring≥4-5 mm and randomization of individual animals to treatment groups. Animal survival was measured from the first day of treatment until death. Animals in control and treatment cohorts were allowed to progress under continuous treatment administration until they reached study end-point (determined as 20% weight loss, recognizable signs of morbidity, general lack of reflexes, abnormal posture, loss of ability to ambulate, labored respiration, inability to drink or feed) where, in order to avoid animal suffering, animals were euthanized in accordance with ACUC animal care guidelines. For experiments in KP16 and KPC mice, normal saline as vehicle, 20 mg/kg RP-182 (PolyPeptide Group, San Diego, CA), 50 mg/kg Gemcitabine (Fresenius Kabi, Lake Zurich, IL), or RP-182 in combination with gemcitabine was injected intraperitoneally (IP) with final volume of 200 μL was administered. RP-182 was injected every other day and gemcitabine was injected 2 times a week. Anti-PD-L1 (Biolegend, Cat. #124329) was administered three times weekly at 150 μg per mouse via intraperitoneal injection. Mice were treated IP with 100 μg anti-CTLA-4 antibody (Bioxcell; 9D9) twice a week. For CD8 depletion, two doses of 100 μg anti-mCD8 (Bioxcell, Cat. #BE0061) per mouse on day 1 and 5 were administered. Rat isotype control IgG1 (Bioxell, Cat. #BE0090) was given at equivalent doses at the same schedule. Mice with CT-26, MDA-MB231, C4-2, and B16 tumors received 10 mg/kg RP-182 via IP injection daily for tumor growth studies, gemcitabine dosing was unchanged, the docetaxol dose delivered to the C4-2 model was docetaxel dosed 2.5 mg/kg daily for 7 days and then discontinued. For intratumoral injections, 50,000 BMDMs pretreated for 2 hours with vehicle or 20 μM RP-182 were injected on days 2,5,7, and 9 into KPC tumors≥500 mm3 grown in C57B/L wild type mice. Prior to injection, M2 BMDMs grown and polarized on T75 flasks were washed ×2, lifted and counted, and resuspended in HBSS for injection volume of <50 μL.

Bleomycin Lung Fibrosis Model

To facilitate intratracheal bleomycin installation, animals were anesthetized for a short period of time. A single dose of 0.5 mg/kg (1-4 U/mg) bleomycin in sterile isotonic saline (total volume 50 μL) was intratracheally administered via a 22 gauge plastic cannula to a total of n=12 BALB/c mice, and the same volume of sterile saline was administered to control group of mice (N=6 mice). Mice instilled with bleomycin were randomized on day 1 to receive 20 mg/kg RP via daily IP injection or vehicle control. Mice underwent daily weight measures, and animal survival was measured from the first day of treatment until death. Animals were allowed in control and RP-182-treatment cohorts to progress under continuous treatment conditions until they reached study end-point (determined as 20% weight loss, recognizable signs of morbidity, general lack of reflexes, abnormal posture, loss of ability to ambulate, labored respiration, inability to drink or feed, determined as moribund with poor survival as per study veterinarian) where, in order to avoid animal suffering, animals were euthanized in accordance with ACUC animal care guidelines. Only 'warm' necropsy specimens (lungs) were used for tissue analysis. Lungs were weighed prior to fixation in formalin and embedding in paraffin, and stained with H&E, Masson's trichrome, and anti-CD206. ImageJ was used to quantify the level of fibrosis between the vehicle and RP-182-treated group.

Flow Cytometry Analysis

Multicolor flow cytometry analysis was performed after 7 days of treatment with RP-182, gemcitabine, the combination, or vehicle. After animal euthanasia, pancreatic tumors were harvested, washed with PBS, and minced with a scalpel. Tumors were digested using mouse tumor dissociation kit (#130-096-730, MACS Miltenyi Biotec, San Diego, CA) and a Gentle Macs Agitator (Miltenyi Biotec, San Diego. CA) as per company protocol. Tumor lysates were passed through a 70 μm filter, washed in PBS, and stained for flow cytometry analysis. BMDMs subject to flow cytometry were treated with RP-182 and control peptides for 2 or 24 hours at 37° C. prior to staining. Cells were stained with the Live/Dead Fixable Blue Dead Cell Stain Kit (ThermoFisher Scientific), and antibodies coupled to flourophores as listed in Tables 6A-D (antibodies for flow cytometry). Stained cells were washed with FACS buffer prior to sample acquisition by the BD LSRFortessa SORP I flow cytometer (BD Bioscience). Flow cytometry data was analyzed using FlowJo software (TreeStar, Ashland, OR).

Histology

Harvested tumors were prepared for histological analysis using standard protocols and 4% paraformaldehyde. In addition to H&E staining, tumors were interrogated by immunocytochemistry and immunohistochemistry using antibodies listed in Tables 6A-D (antibodies for tissue staining). A commercially available pancreatic carcinoma tissue microarray (TMA) with 80 single cores per case (70 from adenocarcinoma pancreas, 10 normal pancreas) was purchased from US Biomax, Inc., Derwood, MD (Cat. No. PA801) for anti-CD206 staining. Brightfield images (immunostaining) were acquired using an Aperio ScanScope XT (Aperio, Vista. CA, USA) for whole slide scanning at 40× magnification and analyzed using ImageScope Analysis. Quantitative analysis was performed using the Aperio membrane algorithm. For immunofluorescence analysis, slides were de-paraffinized as follows: 5 min Xylene immersion twice, 5 min 100% ethanol twice, 5 min 95% ethanol, 5 min 80% ethanol. 5 min 70% ethanol, 5 min rehydration in water. Following antigen retrieval after 60 min incubation at 60° C., slides were blocked with $H_2O_2$ peroxidase, washed twice in PBS Blocking solution with FBS or NGS for 30 min, and incubated with the primary antibodies overnight at 4° C.

Alexa 488 anti-mouse or Alexa 594 anti-rabbit secondary antibodies were incubated for 30 min at 27° C. Following DAPI counterstaining for 1 min, slides were then cover slipped with glycerol mounting media. Images were collected and analyzed using Zeiss AxioScan imaging.

TCGA Gene Expression Data Analysis

Genomic data from TCGA project are available from the National Cancer Institute's Genomic Data Commons (https://gdc.cancer.gov/). Gene-level gene expression data from RNA-seq experiments of all tumors (N=9,452) and adenocarcinoma of the pancreas (N=125) were included in analyses and correlated with individual gene expression levels and immune signature scores as previously shown (62, 63).

Isolation of Tumor-Associated Macrophages and Bone Marrow Derived Macrophages (BMDM) and qRT-PCR TAM's were isolated from tumor digests derived from KP16 and KPC tumors using the EasySep™ Mouse PE positive selection kit (Cat. #18554, StemCell), EasySep™ Mouse custom enrichment kit (Cat. #19709. StemCell) and CD11b (clone M1/70, BD Biosciences), Gr1 (clone RB6-8C5, Biolegend) antibodies. Following tumor harvest and digestion, Gr-1 positive cells were first removed prior to isolation of CD1 1b− positive macrophages via magnetic cell isolation. Total RNA from TAM isolates and bone-marrow derived macrophage (BMDM) was extracted using RNeasy Mini Kit (Ref: #74104, Qiagen). Bone marrow derived macrophages were sorted for CD11 b+GR 1-F4/80+ CD206+ population using fluorescence activated cell sorting (FACS) FACS sorter and lysates from the same cells used for RT-PCR. Superscript III First-Strand (Ref: #18080-051, Invitrogen) synthesis system for RT-PCR was used to generate cDNA. Following first strand cDNA synthesis, individual primer master mix (IL1b-Mm00434228_m1, TNFα-Mm00443258_m1, IL12-Mm01288989_m1, CD40-Mm00441891_m1, CLEC4e-Mm01183703_m1, CD86-Mm00444540, IL10-Mm01288386_m1, IL27-Mm00461162, PDL1-Mm00452054_m1, SIRPα-Mm00455928, Chil3-Mm00657889_m1, MRC1-Mm01339362_m1, actb-Mm02619580_g1; gapdh-Mm99999915_g1; TaqMan Assays. ThermoFisher Scientific) was added and qRT-PCR reactions were carried out and read in a BioRad CFX96 cycler. Target gene expression was calculated using 'relative gene expression=2-(ΔCt)', where ΔCt is the cycle number of target genes (Cttarget) normalized to a reference/housekeeping gene (Ctreference). Individual qRT-PCR reactions were run in triplicate, and graphs were generated by GraphPad Prism.

ELISpot Assays

T-cell reactivity to cancer cells was assessed in 20-hour co-culture assays in flat-bottom 96-well PVDF-membrane microtiter plates (Cat. #MAIPSWU10, EMD Millipore). CD8a+ T cells were isolated with the EasySep™ Mouse CD8a Positive Selection Kit II (Cat. #18953. StemCell) from single-cell suspensions of whole digested tumors or spleens. 1×105 KP16 cancer cells were co-cultured with 4×104 isolated CD8a+ T cells, positive controls included CD8a+ T cells with PMA/ionomycin, while negative controls contained CD8a+ T cells only. Visualization of immobilized cytokine as 'ImmunoSpots' was carried out according to the manufacturer's instructions (Cat. #3321-2A, Mabtech), ELISpots were read and quantified in an ImmunoSpot S6 universal analyzer (C.T.L.). 4×104 CD8+ T cells after pulldown were added to 1×105 KP16 cancer cells and Elispots were then analyzed. In the triple co-culture experiment, 4×104 TAMs, isolated from tumor and spleen from tumor-bearing animals via CD11b pulldown following negative selection for Gr-1, were added to 1×105 KP16 cancer cells and 4×104 CD8+ T cells isolated from spleen of tumor-bearing mice. T-cell reactivity to cancer cells was assessed after 20-hour co-culture as above.

Phagocytosis Assay

The ability of BMDM's and TAM's to phagocytose cancer cells was analyzed by confocal microscopy and flow cytometry. Cancer cell lines including KPC, PANC1, HPAF-II (pancreatic cancer), the primary melanoma tissue culture line 2183, and LNCaP (prostate cancer) were labelled with CFSE (5-(and -6)-carboxyfluorescein diacetate, succinimidyl ester) dye (#C1157, ThermoFisher Scientific, Grand Island. NY) for 1 hour at 37° C. and 5% CO2 according to manufacturer's instruction. CFSE labeled cancer cells were added onto RP-182 or vehicle (2 hours) pretreated BMDMs and incubated for 6 hours prior to twice washing to remove excess cancer cells. Images were taken using Zeiss LSM 880 confocal microscope at 63× using green and phase contrast channels. For flow cytometry, CFSE-labelled cancer cells were incubated with RP-182 and vehicle-pretreated macrophages (2 hours) cultured on T75 flasks for 4 hours. Excess CFSE-labelled cells were washed, macrophages were harvested from T75 flasks and analyzed on BD LSRFortessa SORP I flow cytometer (BD Bioscience). For the phagocytosis functional assay involving beads, the pHrodo™ Red *E. coli* BioParticles™ Phagocytosis Kit was used (#A10025, ThermoFisher Scientific, Grand Island, NY). Macrophage polarization, treatments, and analysis for flow and immunofluorescence assays were done in similar fashion explained in the previous experiment.

Statistical Analysis

Data was statistically analyzed using SPSS software version 16 (IBM, Armonk, NY). Tumor volumes were compared between all four groups using best objective response (BOR), best response recorded from the start of the study treatment compared to any of the follow-up measurements, or absolute measurements (in mm3). Continuous data, including tumor volumes, gene expression levels, or immune cell population percentages, was compared using student's t-test in GraphPad Prism. The log-rank test was used to compare Kaplan-Meier curves. Error bars indicate standard error of the means (SEM) unless otherwise indicated. Calculated p values were given by number and asterisk(s) with * indicating $p<0.05$, $p<0.01$, and *$p<0.001$.

Notwithstanding the appended claims, the disclosure is also defined by the following clauses:

1. A method of modulating macrophage activity, the method comprising:
   contacting a macrophage with a CD206-binding agent to modulate activity of the macrophage.
2. The method of clause 1, wherein the CD206-binding agent binds to a site selected from fibronectin II domain of CD206, C-type lectin carbohydrate recognition domain 3 (CRD3) of CD206, C-type lectin carbohydrate recognition domain 4 (CRD4) of CD206 and C-type lectin carbohydrate recognition domain 5 (CRD5) of CD206.
3. The method of clause 1, wherein the CD206-binding agent binds to CD206 with a binding energy of at least −650 kcal/mol.
4. The method of clause 1, wherein the macrophage activity that is modulated is macrophage polarization.
5. The method of clause 1, wherein viability of the macrophage is reduced.

6. The method of clause 1, wherein the macrophage is a M2 macrophage or a tumor associated macrophage (TAM).
7. The method of clause 1, wherein the CD206-binding agent inhibits macrophage activity.
8. The method of clause 1, wherein the CD206-binding agent induces apoptosis of the macrophage.
9. The method of clause 1, wherein the CD206-binding agent stimulates phagocytosis.
10. The method according to any one of clauses 1-9, wherein the macrophage is in vitro.
11. The method according to any one of clauses 1-9, wherein the macrophage is in vivo.
12. The method of any one of clauses 1-11, wherein the CD206-binding agent is an immunomodulatory peptide.
13. The method of clause 12, wherein the immunomodulatory peptide is of 5 to 18 amino acid residues in length, the peptide comprising: a striapathic region of alternating hydrophilic and hydrophobic modules that adopts an amphipathic conformation under physiological conditions.
14. The method of clause 13, wherein the striapathic region comprises:
    3 or more hydrophobic modules; and
    2 or more hydrophilic modules each comprising at least one cationic residue;
    wherein the immunomodulatory peptide specifically binds CD206.
15. The method of any one of clauses 12-14, wherein the immunomodulatory peptide comprises a sequence defined by one of the formulae:

$$[J_{1a}J_{1b}]\text{-}[X_{1a}X_{1b}]\text{-}[J_{2a}J_{2b}]\text{-}[X_{2a}X_{2b}]\text{-}[J_{3a}]\text{-}[X_{3a}];\text{ and}$$

$$[X_{3a}]\text{-}[J_{3a}]\text{-}[X_{2b}X_{2a}]\text{-}[J_{2b}J_{2a}]\text{-}[X_{1b}X_{1a}]\text{-}[J_{1b}J_{1a}];$$

wherein:
    $J_{1a}$, $J_{1b}$, $J_{2a}$, $J_{2b}$ and $J_{3a}$ are each independently selected from phenylalanine, tryptophan, alanine, valine, and glycine; and
    $X_{1a}$, $X_{1b}$, $X_{2a}$, $X_{2b}$ and $X_{3a}$ are each independently selected from lysine, arginine, histidine, aspartic acid, glutamic acid, asparagine and glutamine.
16. The method of clause 15, wherein:
$J_{1a}$, $J_{1b}$, $J_{2a}$, $J_{2b}$ and $J_{3a}$ are each phenylalanine; and
$X_{1a}$, $X_{1b}$, $X_{2a}$, $X_{2b}$ and $X_{3a}$, are each independently selected from lysine and arginine.
17. The method of any one of clauses 12-16, wherein the immunomodulatory peptide comprises
    a) a sequence selected from:
        KFRKAFKRFF (RP182);
        FFRKFAKRFK (RP183);
        FFKKFFKKFK (RP185);
        FFKKFFKKFK (RP186); and
        FFKKFFKKFK (RP233); or
    b) a sequence having one or two amino acid substitutions relative to the sequence defined in a).
18. The method of clause 17, wherein the immunomodulatory peptide comprises the amino acid sequence KFRKAFKRFF (RP182)
19. The method of clause 17, wherein the immunomodulatory peptide comprises the amino acid sequence FFRKFAKRFK (RP183).
20. The method of clause 17, wherein the immunomodulatory peptide comprises the amino acid sequence FFKKFFKKFK (RP185).
21. The method of any one of clauses 12-16, wherein the immunomodulatory peptide comprises:
    a) a peptide sequence selected from:
        RWKFGGFKWR (RP832C);
        FKWRGGRWKF (RP837C);
        FWKRGGRKWF (RP837A);
        FWKRFV (RP837N);
        FVRKWR (RP837C1);
        FAOOFAOOFO (RP850):
        FWKRFVRKWR (RP837);
        FWKKFVKKWK (RP841);
        WWHHWWHHWH (RP847);
        WWRHWWHRWR (RP848);
        WWKHWWHKWK (RP849);
        GDRGIKGHRGF (RP842);
        LYKKIIKKLL (RP846);
        FYPDFFKKFF (RP844);
        FFRKSKEKIG (RP853);
        FFRHFATHLD (RP845); and
        EKLSAFRNFF (RP843); or
    b) a sequence having one or two amino acid substitutions relative to the sequence defined in a).
22. The method of clause 21, wherein the one or two amino acid substitutions defined in b) consist of a highly conservative substitution of a cationic amino acid of the sequence.
23. The method of clause 21, comprising the peptide sequence selected from: RWKFGGFKWR (RP832C), FKWRGGRWKF (RP837C) and FWKRGGRKWF (RP837A).
24. The method of clause 21, comprising the peptide sequence selected from FWKRFV (RP837N) and FVRKWR (RP837C1).
25. The method of clause 21, comprising a peptide sequence selected from FAOOFAOOFO (RP850), FWKRFVRKWR (RP837) and FWKKFVKKWK (RP841).
26. The method of clause 21, comprising a peptide sequence selected from WWHHWWHHWH, WWRHWWHRWR and WWKHWWHKWK (RP847-849).
27. The method of clause 21, comprising the peptide sequence GDRGIKGHRGF (RP842).
28. The method of clause 21, comprising the peptide sequence LYKKIIKKLL (RP846).
29. The method of clause 21, comprising the peptide sequence FYPDFFKKFF (RP844).
30. The method of clause 21, comprising the peptide sequence FFRKSKEKIG (RP853).
31. The method of clause 21, comprising the peptide sequence FFRHFATHLD (RP845).
32. The method of clause 21, comprising the peptide sequence EKLSAFRNFF (RP843).
33. A method of inhibiting growth of a CD206-expressing cell, the method comprising contacting a target CD206-expressing cell with a CD206-binding agent to inhibit growth of the cell.
34. The method of clause 33, wherein the target CD206-expressing cell is a cancer cell.
35. The method of clause 34, wherein the cancer cell is a pancreatic cancer cell, a prostate cancer cell, a colon cancer cell, a skin cancer cell or breast cancer cell.
36. The method of any one of clauses 33-35, wherein the contacting the target CD206-expressing cell comprises administering to a subject in need thereof a therapeutically effective amount of the CD206-binding agent to treat the subject for cancer.

37. The method of clause 36, wherein the cancer is a solid tumor cancer.
38. The method of clause 37, wherein the cancer is a cholangiocarcinoma, pancreatic, prostate, colon, breast, bladder or skin.
39. The method of any one of clauses 36-38, wherein the CD206-binding agent is an immunomodulatory peptide.
40. The method of clause 39, wherein the immunomodulatory peptide is of 5 to 18 amino acid residues in length, the peptide comprising: a striapathic region of alternating hydrophilic and hydrophobic modules that adopts an amphipathic conformation under physiological conditions.
41. The method of clause 40, wherein the striapathic region comprises:
 3 or more hydrophobic modules; and
 2 or more hydrophilic modules each comprising at least one cationic residue;
 wherein the immunomodulatory peptide specifically binds CD206.
42. The method of any one of clauses 39-41, wherein the immunomodulatory peptide comprises a sequence defined by one of the formulae:

$[J_{1a}J_{1b}]$-$[X_{1a}X_{1b}]$-$[J_{2a}J_{2b}]$-$[X_{2a}X_{2b}]$-$[J_{3a}]$-$[X_{3a}]$; and $[X_{3a}]$-$[J_{3a}]$-$[X_{2b}X_{2a}]$-$[J_{2b}J_{2a}]$-$[X_{1b}X_{1a}]$-$[J_{1b}J_{1a}]$;

wherein:
 $J_{1a}$, $J_{1b}$, $J_{2a}$, $J_{2b}$ and $J_{3a}$ are each independently selected from phenylalanine, tryptophan, alanine, valine, and glycine; and
 $X_{1a}$, $X_{1b}$, $X_{2a}$, $X_{2b}$ and $X_{3a}$ are each independently selected from lysine, arginine, histidine, aspartic acid, glutamic acid, asparagine and glutamine.
43. The method of clause 42, wherein:
$J_{1a}$, $J_{1b}$, $J_{2a}$, $J_{2b}$ and $J_{3a}$ are each phenylalanine; and
$X_{1a}$, $X_{1b}$, $X_{2a}$, $X_{2b}$ and $X_{3a}$ are each independently selected from lysine and arginine.
44. The method of any one of clauses 39-43, wherein the immunomodulatory peptide comprises
 a) a sequence selected from:
  KFRKAFKRFF (RP182);
  FFRKFAKRFK (RP183);
  FFKKFFKKFK (RP185);
  FFKKFFKKFK (RP186); and
  FFKKFFKKFK (RP233); or
 b) a sequence having one or two amino acid substitutions relative to the sequence defined in a).
45. The method of clause 44, wherein the immunomodulatory peptide comprises the amino acid sequence KFRKAFKRFF (RP182)
46. The method of clause 44, wherein the immunomodulatory peptide comprises the amino acid sequence FFRKFAKRFK (RP183).
47. The method of clause 44, wherein the immunomodulatory peptide comprises the amino acid sequence FFKKFFKKFK (RP185).
48. The method of any one of clauses 39-43, wherein the immunomodulatory peptide comprises:
 a) a peptide sequence selected from:
  RWKFGGFKWR (RP832C);
  FKWRGGRWKF (RP837C);
  FWKRGGRKWF (RP837A);
  FWKRFV (RP837N);
  FVRKWR (RP837C1);
  FAOOFAOOFO (RP850);
  FWKRFVRKWR (RP837);
  FWKKFVKKWK (RP841);
  WWHHWWHHWH (RP847);
  WWRHWWHRWR (RP848);
  WWKHWWHKWK (RP849);
  GDRGIKGHRGF (RP842);
  LYKKIIKKLL (RP846);
  FYPDFFKKFF (RP844);
  FFRKSKEKIG (RP853);
  FFRHFATHLD (RP845); and
  EKLSAFRNFF (RP843); or
 b) a sequence having one or two amino acid substitutions relative to the sequence defined in a).
49. The method of clause 48, wherein the one or two amino acid substitutions defined in b) consist of a highly conservative substitution of a cationic amino acid of the sequence.
50. The method of clause 48, comprising the peptide sequence selected from: RWKFGGFKWR (RP832C), FKWRGGRWKF (RP837C) and FWKRGGRKWF (RP837A).
51. The method of clause 48, comprising the peptide sequence selected from FWKRF-V (RP837N) and FVRKWR (RP837C1).
52. The method of clause 48, comprising a peptide sequence selected from FAOOFAOOFO (RP850), FWKRFVRKWR (RP837) and FWKKFVKKWK (RP841).
53. The method of clause 48, comprising a peptide sequence selected from WWHHWWHHWH, WWRHWWHRWR and WWKHWWHKWK (RP847-849).
54. The method of clause 48, comprising the peptide sequence GDRGIKGHRGF (RP842).
55. The method of clause 48, comprising the peptide sequence LYKKIIKKLL (RP846).
56. The method of clause 48, comprising the peptide sequence FYPDFFKKFF (RP844).
57. The method of clause 48, comprising the peptide sequence FFRKSKEKIG (RP853).
58. The method of clause 48, comprising the peptide sequence FFRHFATHLD (RP845).
59. The method of clause 48, comprising the peptide sequence EKLSAFRNFF (RP843).
60. A method of treating a subject for a condition associated with chronic inflammation, the method comprising:
 administering a therapeutically effective amount of a CD206-binding agent to a subject to treat the subject for the condition associated with chronic inflammation.
61. The method of clause 60, wherein the condition associated with chronic inflammation is selected from scleroderma or multiple sclerosis, irritable bowel disease, ulcerative colitis, colitis, Crohn's disease, idiopathic pulmonary fibrosis, asthma, keratitis, arthritis, osteoarthritis, rheumatoid arthritis, auto-immune diseases, a feline or human immunodeficiency virus (FIV or HIV) infection, cancer, age-related inflammation and/or stem cell dysfunction, graft-versus-host disease (GVHD), keloids, obesity, diabetes, diabetic wounds, other chronic wounds, atherosclerosis, Parkinson's disease, Alzheimer's disease, macular degeneration, gout, gastric ulcers, gastritis, mucositis, toxoplasmosis, and chronic viral or microbial infections.

62. The method of any one of clauses 60-61, wherein the CD206-binding agent is administered in conjunction with another drug known to be effective in treating the condition.
63. The method of clause 62, wherein the condition is cancer.
64. The method of clause 63, wherein the cancer is pancreatic, prostate, colon, breast or skin.
65. The method of clause 64, further comprising administering an effective amount of a chemotherapeutic agent, antibody agent or cell therapy to the subject.
66. The method of clause 65, wherein the chemotherapeutic agent, antibody agent or cell therapy is selected from steroids, anthracyclines, thyroid hormone replacement drugs, thymidylate-targeted drugs, antibodies, checkpoint inhibitor drugs. Chimeric Antigen Receptor/T cell therapies, and other cell therapies.
67. The method of clause 60, wherein the condition associated with chronic inflammation is a fibrosis or scleroderma.
68. The method of any one of clauses 60-67, wherein the CD206-binding agent is an immunomodulatory peptide.
69. The method of clause 68, wherein the immunomodulatory peptide is of 5 to 18 amino acid residues in length, the peptide comprising: a striapathic region of alternating hydrophilic and hydrophobic modules that adopts an amphipathic conformation under physiological conditions.
70. The method of clause 69, wherein the striapathic region comprises:
    3 or more hydrophobic modules; and
    2 or more hydrophilic modules each comprising at least one cationic residue;
    wherein the immunomodulatory peptide specifically binds CD206.
71. The method of any one of clauses 68-70, wherein the immunomodulatory peptide comprises a sequence defined by one of the formulae:

$$[J_{1a}J_{1b}]\text{-}[X_{1a}X_{1b}]\text{-}[J_{2a}J_{2b}]\text{-}[X_{2a}X_{2b}]\text{-}[J_{3a}]\text{-}[X_{3a}];\text{ and}$$

$$[X_{3a}]\text{-}[J_{3a}]\text{-}[X_{2b}X_{2a}]\text{-}[J_{2b}J_{2a}]\text{-}[X_{1b}X_{1a}]\text{-}[J_{1b}J_{1a}];$$

wherein:
    $J_{1a}$, $J_{1b}$, $J_{2a}$, $J_{2b}$ and $J_{3a}$ are each independently selected from phenylalanine, tryptophan, alanine, valine, and glycine; and
    $X_{1a}$, $X_{1b}$, $X_{2a}$, $X_{2b}$ and $X_{3a}$ are each independently selected from lysine, arginine, histidine, aspartic acid, glutamic acid, asparagine and glutamine.
72. The method of clause 71, wherein:
$J_{1a}$, $J_{1b}$, $J_{2a}$, $J_{2b}$ and $J_{3a}$ are each phenylalanine; and
$X_{1a}$, $X_{1b}$, $X_{2a}$, $X_{2b}$ and $X_{3a}$ are each independently selected from lysine and arginine.
73. The method of any one of clauses 68-72, wherein the immunomodulatory peptide comprises
    a) a sequence selected from:
        KFRKAFKRFF (RP182);
        FFRKFAKRFK (RP183);
        FFKKFFKKFK (RP185);
        FFKKFFKKFK (RP186); and
        FFKKFFKKFK (RP233); or
    b) a sequence having one or two amino acid substitutions relative to the sequence defined in a).
74. The method of clause 73, wherein the immunomodulatory peptide comprises the amino acid sequence KFRKAFKRFF (RP182)
75. The method of clause 73, wherein the immunomodulatory peptide comprises the amino acid sequence FFRKFAKRFK (RP183).
76. The method of clause 73, wherein the immunomodulatory peptide comprises the amino acid sequence FFKKFFKKFK (RP185).
77. The method of any one of clauses 68-72, wherein the immunomodulatory peptide comprises:
    a) a peptide sequence selected from:
        RWKFGGFKWR (RP832C);
        FKWRGGRWKF (RP837C);
        FWKRGGRKWF (RP837A);
        FWKRFV (RP837N);
        FVRKWR (RP837C);
        FAOOFAOOFO (RP850);
        FWKRFVRKWR (RP837);
        FWKKFVKKWK (RP841);
        WWHHWWHHWH (RP847);
        WWRHWWHRWR (RP848);
        WWKHWWHKWK (RP849);
        GDRGIKGHRGF (RP842);
        LYKKIIKKLL (RP846);
        FYPDFFKKFF (RP844);
        FFRKSKEKIG (RP853);
        FFRHFATHLD (RP845); and
        EKLSAFRNFF (RP843); or
    b) a sequence having one or two amino acid substitutions relative to the sequence defined in a).
78. The method of clause 77, wherein the one or two amino acid substitutions defined in b) consist of a highly conservative substitution of a cationic amino acid of the sequence.
79. The method of clause 77, comprising the peptide sequence selected from: RWKFGGFKWR (RP832C), FKWRGGRWKF (RP837C) and FWKRGGRKWF (RP837A).
80. The method of clause 77, comprising the peptide sequence selected from FWKRFV (RP837N) and FVRKWR (RP837C1).
81. The method of clause 77, comprising a peptide sequence selected from FAOOFAOOFO (RP850). FWKRFVRKWR (RP837) and FWKKFVKKWK (RP841).
82. The method of clause 77, comprising a peptide sequence selected from WWHHWWHHWH. WWRHWWHRWR and WWKHWWHKWK (RP847-849).
83. The method of clause 77, comprising the peptide sequence GDRGIKGHRGF (RP842).
84. The method of clause 77, comprising the peptide sequence LYKKIIKKLL (RP846).
85. The method of clause 77, comprising the peptide sequence FYPDFFKKFF (RP844).
86. The method of clause 77, comprising the peptide sequence FFRKSKEKIG (RP853).
87. The method of clause 77, comprising the peptide sequence FFRHFATHLD (RP845).
88. The method of clause 77, comprising the peptide sequence EKLSAFRNFF (RP843).
89. A method of converting a phenotype of a macrophage from an M2 phenotype to an M1 phenotype, the method comprising contacting a macrophage having an M2 phenotype with a CD206-binding agent in a manner sufficient to convert the phenotype of the macrophage to an M1 phenotype.
90. The method of clause 89, wherein contacting the CD206-binding agent induces a conformational change in a CD206 receptor of the macrophage sufficient to convert the phenotype of the macrophage to an M1 phenotype.

91. The method of clause 89-90, wherein converting the phenotype of the macrophage comprises inducing expression of CD86 by the macrophage.

92. The method of any one of clauses 89-91, wherein converting the phenotype of the macrophage comprises reducing expression of CD206 or CD163 by the macrophage.

93. The method of any one of clauses 89-92, wherein converting the phenotype of the macrophage comprises converting the macrophage to a phenotype that exhibits upregulation of M1 cytokines and markers.

94. The method of clause 93, wherein M1 cytokine and marker is selected from the group consisting of IL-1β, IL-12. TNFα and nitric oxide synthetase.

95. The method of any one of clauses 89-94, wherein converting the phenotype of the macrophage comprises converting the macrophage to a phenotype that exhibits decreased expression of signal regulatory protein α (SIRPα)

96. The method of any one of clauses 89-95, wherein the CD206-binding agent binds to a site selected from fibronectin II domain of CD206, C-type lectin carbohydrate recognition domain 3 (CRD3) of CD206, C-type lectin carbohydrate recognition domain 4 (CRD4) of CD206 and C-type lectin carbohydrate recognition domain 5 (CRD5) of CD206.

97. The method according to any one of clauses 89-96, wherein the macrophage is contacted with the CD206-binding agent in vivo.

98. The method according to any one of clauses 89-97, wherein the macrophage is contacted with the CD206-binding agent in vitro.

99. The method of any one of clauses 89-98, wherein the CD206-binding agent is an immunomodulatory peptide.

100. The method of clause 99, wherein the immunomodulatory peptide is of 5 to 18 amino acid residues in length, the peptide comprising: a striapathic region of alternating hydrophilic and hydrophobic modules that adopts an amphipathic conformation under physiological conditions.

101. The method of clause 100, wherein the striapathic region comprises:

3 or more hydrophobic modules; and 2 or more hydrophilic modules each comprising at least one cationic residue;

wherein the immunomodulatory peptide specifically binds CD206.

102. The method of any one of clauses 99-101, wherein the immunomodulatory peptide comprises a sequence defined by one of the formulae:

$$[J_{1a}J_{1b}]\text{-}[X_{1a}X_{1b}]\text{-}[J_{2a}J_{2b}]\text{-}[X_{2a}X_{2b}]\text{-}[J_{3a}]\text{-}[X_{3a}];\text{ and}$$

$$[X_{3a}]\text{-}[J_{3a}]\text{-}[X_{2b}X_{2a}]\text{-}[J_{2b}J_{2a}]\text{-}[X_{1b}X_{1a}]\text{-}[J_{1b}J_{1a}];$$

wherein:

$J_{1a}$, $J_{1b}$, $J_{2a}$, $J_{2b}$ and $J_{3a}$ are each independently selected from phenylalanine, tryptophan, alanine, valine, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine.

103. The method of clause 102, wherein:

$J_{1a}$, $J_{1b}$, $J_{2a}$, $J_{2b}$ and $J_{3a}$ are each phenylalanine; and $X_{1a}$, $X_{1b}$, $X_{2a}$, $X_{2b}$ and $X_{3a}$ are each independently selected from lysine and arginine.

104. The method of any one of clauses 99-103, wherein the immunomodulatory peptide comprises a) a sequence selected from:
KFRKAFKRFF (RP182);
FFRKFAKRFK (RP183);
FFKKFFKKFK (RP185);
FFKKFFKKFK (RP186); and
FFKKFFKKFK (RP233); or b) a sequence having one or two amino acid substitutions relative to the sequence defined in a).

105. The method of clause 104, wherein the immunomodulatory peptide comprises the amino acid sequence KFRKAFKRFF (RP182)

106. The method of clause 104, wherein the immunomodulatory peptide comprises the amino acid sequence FFRKFAKRFK (RP183).

107. The method of clause 104, wherein the immunomodulatory peptide comprises the amino acid sequence FFKKFFKKFK (RP185).

108. The method of any one of clauses 99-103, wherein the immunomodulatory peptide comprises:

a) a peptide sequence selected from:
RWKFGGFKWR (RP832C);
FKWRGGRWKF (RP837C);
FWKRGGRKWF (RP837A);
FWKRFV (RP837N);
FVRKWR (RP837C1);
FAOOFAOOFO (RP850);
FWKRFVRKWR (RP837);
FWKKFVKKWK (RP841):
WWHHWWHHWH (RP847);
WWRHWWHRWR (RP848);
WWKHWWHKWK (RP849);
GDRGIKGHRGF (RP842);
LYKKIIKKLL (RP846);
FYPDFFKKFF (RP844);
FFRKSKEKIG (RP853);
FFRHFATHLD (RP845); and
EKLSAFRNFF (RP843); or b) a sequence having one or two amino acid substitutions relative to the sequence defined in a).

109. The method of clause 108, wherein the one or two amino acid substitutions defined in b) consist of a highly conservative substitution of a cationic amino acid of the sequence.

110. The method of clause 108, comprising the peptide sequence selected from: RWKFGGFKWR (RP832C), FKWRGGRWKF (RP837C) and FWKRGGRKWF (RP837A).

111. The method of clause 108, comprising the peptide sequence selected from FWKRFV (RP837N) and FVRKWR (RP837C1).

112. The method of clause 108, comprising a peptide sequence selected from FAOOFAOOFO (RP850), FWKRFVRKWR (RP837) and FWKKFVKKWK (RP841).

113. The method of clause 108, comprising a peptide sequence selected from WWHHWWHHWH, WWRHWWHRWR and WWKHWWHKWK (RP847-849).

114. The method of clause 108, comprising the peptide sequence GDRGIKGHRGF (RP842).

115. The method of clause 108, comprising the peptide sequence LYKKIIKKLL (RP846).

116. The method of clause 108, comprising the peptide sequence FYPDFFKKFF (RP844).

117. The method of clause 108, comprising the peptide sequence FFRKSKEKIG (RP853).

118. The method of clause 108, comprising the peptide sequence FFRHFATHLD (RP845).

119. The method of clause 108, comprising the peptide sequence EKLSAFRNFF (RP843).

120. A method of treating a subject for a neoplastic condition, the method comprising administering to a therapeutically effective amount of a CD206-binding agent to a subject diagnosed as having a neoplastic condition to treat the neoplastic condition in the subject.

121. The method of clause 120, wherein the neoplastic condition is a solid-tumor cancer.

122. The method of any one of clauses 120-121, wherein the neoplastic condition is a cancer selected from the group consisting of pancreatic cancer, prostate cancer, colon cancer, breast cancer and skin cancer.

123. The method of any one of clauses 120-122, further comprising administering an effective amount of a chemotherapeutic agent, antibody agent or cell therapy to the subject.

124. The method of clause 123, wherein the chemotherapeutic agent, antibody agent or cell therapy is selected from steroids, anthracyclines, thyroid hormone replacement drugs, thymidylate-targeted drugs, antibodies, checkpoint inhibitor drugs, Chimeric Antigen Receptor/T cell therapies, and other cell therapies.

125. The method of clause 124, wherein the chemotherapeutic agent is a non-pepitidic compound that reduces proliferation of cancer cells.

126. The method of any one of clauses 124-125, wherein the chemotherapeutic agent is a compound selected from the group consisting of alkylating agents, metal complexes, nitrosoureas, antimetabolites, antitumor antibiotics, plant (vinca) alkaloids, hormone modulators, steroid hormones.

127. The method of clause 126, wherein the antibody agent is a chemotherapeutic antibody agent.

128. The method of clause 127, wherein the antibody agent is an antibody raised against a tumor-associated antigen selected from the group consisting of CD20. CD30, CD33, CD52, EpCAM, CEA, gpA33, Mucins, TAG-72, CAIX, PSMA, Folate-binding protein. Gangliosides (e.g., GD2, GD3, GM2, etc.), Le y, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP and Tenascin.

129. The method of 124, wherein the immune checkpoint inhibitor is an inhibitory compound that targets one or more of PD1, PD-L1, CTLA4, TIM3, LAG3, VISTA, BTLA, TIGIT, LAIR1, CD160, 2B4 and TGFRβ.

130. The method of any one of clauses 120-129, wherein the CD206-binding agent is an immunomodulatory peptide.

131. The method of clause 130, wherein the immunomodulatory peptide is of 5 to 18 amino acid residues in length, the peptide comprising: a striapathic region of alternating hydrophilic and hydrophobic modules that adopts an amphipathic conformation under physiological conditions.

132. The method of clause 131, wherein the striapathic region comprises:
   3 or more hydrophobic modules; and
   2 or more hydrophilic modules each comprising at least one cationic residue;
   wherein the immunomodulatory peptide specifically binds CD206.

133. The method of any one of clauses 130-132, wherein the immunomodulatory peptide comprises a sequence defined by one of the formulae:

$$[J_{1a}J_{1b}]-[X_{1a}X_{1b}]-[J_{2a}J_{2b}]-[X_{2a}X_{2b}]-[J_{3a}]-[X_{3a}];\text{ and}$$

$$[X_{3a}]-[J_{3a}]-[X_{2b}X_{2a}]-[J_{2b}J_{2a}]-[X_{1b}X_{1a}]-[J_{1b}J_{1a}];$$

wherein:
   $J_{1a}$, $J_{1b}$, $J_{2a}$, $J_{2b}$ and $J_{3a}$ are each independently selected from phenylalanine, tryptophan, alanine, valine, and glycine; and
   $X_{1a}$, $X_{1b}$, $X_{2a}$, $X_{2b}$ and $X_{3a}$ are each independently selected from lysine, arginine, histidine, aspartic acid, glutamic acid, asparagine and glutamine.

134. The method of clause 133, wherein:
   $J_{1a}$, $J_{1b}$, $J_{2a}$, $J_{2b}$ and $J_{3a}$ are each phenylalanine; and
   $X_{1a}$, $X_{1b}$, $X_{2a}$, $X_{2b}$ and $X_{3a}$ are each independently selected from lysine and arginine.

135. The method of any one of clauses 130-134, wherein the immunomodulatory peptide comprises
   a) a sequence selected from:
      KFRKAFKRFF (RP182);
      FFRKFAKRFK (RP183);
      FFKKFFKKFK (RP185);
      FFKKFFKKFK (RP186); and
      FFKKFFKKFK (RP233); or
   b) a sequence having one or two amino acid substitutions relative to the sequence defined in a).

136. The method of clause 135, wherein the immunomodulatory peptide comprises the amino acid sequence KFRKAFKRFF (RP182)

137. The method of clause 135, wherein the immunomodulatory peptide comprises the amino acid sequence FFRKFAKRFK (RP183).

138. The method of clause 135, wherein the immunomodulatory peptide comprises the amino acid sequence FFKKFFKKFK (RP185).

139. The method of any one of clauses 130-134, wherein the immunomodulatory peptide comprises:
   a) a peptide sequence selected from:
      RWKFGGFKWR (RP832C);
      FKWRGGRWKF (RP837C);
      FWKRGGRKWF (RP837A);
      FWKRFV (RP837N);
      FVRKWR (RP837C);
      FAOOFAOOFO (RP850);
      FWKRFVRKWR (RP837);
      FWKKFVKKWK (RP841);
      WWHHWWHHWH (RP847);
      WWRHWWHRWR (RP848);
      WWKHWWHKWK (RP849);
      GDRGIKGHRGF (RP842);
      LYKKIIKKLL (RP846);
      FYPDFFKKFF (RP844);
      FFRKSKEKIG (RP853);
      FFRHFATHLD (RP845); and
      EKLSAFRNFF (RP843); or
   b) a sequence having one or two amino acid substitutions relative to the sequence defined in a).

140. The method of clause 139, wherein the one or two amino acid substitutions defined in b) consist of a highly conservative substitution of a cationic amino acid of the sequence.

141. The method of clause 139, comprising the peptide sequence selected from: RWKFGGFKWR (RP832C), FKWRGGRWKF (RP837C) and FWKRGGRKWF (RP837A).

142. The method of clause 139, comprising the peptide sequence selected from FWKRFV (RP837N) and FVRKWR (RP837C1).

143. The method of clause 139, comprising a peptide sequence selected from FAOOFAOOFO (RP850), FWKRFVRKWR (RP837) and FWKKFVKKWK (RP841).

144. The method of clause 139, comprising a peptide sequence selected from WWHHWWHHWH, WWRHWWHRWR and WWKHWWHKWK (RP847-849).

145. The method of clause 139, comprising the peptide sequence GDRGIKGHRGF (RP842).

146. The method of clause 139, comprising the peptide sequence LYKKIIKKLL (RP846).

147. The method of clause 139, comprising the peptide sequence FYPDFFKKFF (RP844).

148. The method of clause 139, comprising the peptide sequence FFRKSKEKIG (RP853).

149. The method of clause 139, comprising the peptide sequence FFRHFATHLD (RP845).

150. The method of clause 139, comprising the peptide sequence EKLSAFRNFF (RP843).

151. A method of combination therapy, the method comprising administering to a subject in need thereof:
   a CD206-binding agent; and
   one or more of a chemotherapeutic agent, antibody agent, an immune checkpoint inhibitor drug or cell therapy.

152. The method of clause 151, wherein the chemotherapeutic agent is a non-pepitidic compound that reduces proliferation of cancer cells.

153. The method of clause 151, wherein the chemotherapeutic agent is a compound selected from the group consisting of alkylating agents, metal complexes, nitrosoureas, antimetabolites, antitumor antibiotics, plant (vinca) alkaloids, hormone modulators, steroid hormones.

154. The method of clause 151, wherein the antibody agent is a chemotherapeutic antibody agent.

155. The method of clause 154, wherein the antibody agent is an antibody raised against a tumor-associated antigen selected from the group consisting of CD20. CD30, CD33, CD52, EpCAM. CEA, gpA33, Mucins, TAG-72, CAIX, PSMA, Folate-binding protein, Gangliosides (e.g., GD2, GD3, GM2, etc.). Le y, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP and Tenascin.

156. The method of clause 151, wherein the immune checkpoint inhibitor is an inhibitory compound that targets one or more of PD1, PD-L1, CTLA4. TIM3, LAG3, VISTA, BTLA, TIGIT. LAIR1, CD160, 2B4 and TGFRβ.

157. The method of any one of clauses 151-156, wherein the CD206-binding agent is an immunomodulatory peptide.

158. The method of clause 157, wherein the immunomodulatory peptide is of 5 to 18 amino acid residues in length, the peptide comprising: a striapathic region of alternating hydrophilic and hydrophobic modules that adopts an amphipathic conformation under physiological conditions.

159. The method of clause 158, wherein the striapathic region comprises:
   3 or more hydrophobic modules; and
   2 or more hydrophilic modules each comprising at least one cationic residue;
   wherein the immunomodulatory peptide specifically binds CD206.

160. The method of any one of clauses 157-159, wherein the immunomodulatory peptide comprises a sequence defined by one of the formulae:

$$[J_{1a}J_{1b}]\text{-}[X_{1a}X_{1b}]\text{-}[J_{2a}J_{2b}]\text{-}[X_{2a}X_{2b}]\text{-}[J_{3a}]\text{-}[X_{3a}];\text{ and}$$

$$[X_{3a}]\text{-}[J_{3a}]\text{-}[X_{2b}X_{2a}]\text{-}[J_{2b}J_{2a}]\text{-}[X_{1b}X_{1a}]\text{-}[J_{1b}J_{1a}];$$

wherein:
   $J_{1a}$, $J_{1b}$, $J_{2a}$, $J_{2b}$ and $J_{3a}$ are each independently selected from phenylalanine, tryptophan, alanine, valine, and glycine; and
   $X_{1a}$, $X_{1b}$, $X_{2a}$. $X_{2b}$ and $X_{3a}$ are each independently selected from lysine, arginine, histidine, aspartic acid, glutamic acid, asparagine and glutamine.

161. The method of clause 160, wherein:
   $J_{1a}$, $J_{1b}$, $J_{2a}$, $J_{2b}$ and $J_{3a}$ are each phenylalanine; and
   $X_{1a}$, $X_{1b}$, $X_{2a}$, $X_{2b}$ and $X_{3a}$ are each independently selected from lysine and arginine.

162. The method of any one of clauses 157-161, wherein the immunomodulatory peptide comprises
   a) a sequence selected from:
      KFRKAFKRFF (RP182);
      FFRKFAKRFK (RP183);
      FFKKFFKKFK (RP185);
      FFKKFFKKFK (RP186); and
      FFKKFFKKFK (RP233); or
   b) a sequence having one or two amino acid substitutions relative to the sequence defined in a).

163. The method of clause 162, wherein the immunomodulatory peptide comprises the amino acid sequence KFRKAFKRFF (RP182)

164. The method of clause 162, wherein the immunomodulatory peptide comprises the amino acid sequence FFRKFAKRFK (RP183).

165. The method of clause 162, wherein the immunomodulatory peptide comprises the amino acid sequence FFKKFFKKFK (RP185).

166. The method of any one of clauses 157-161, wherein the immunomodulatory peptide comprises:
   a) a peptide sequence selected from:
      RWKFGGFKWR (RP832C);
      FKWRGGRWKF (RP837C);
      FWKRGGRKWF (RP837A);
      FWKRFV (RP837N);
      FVRKWR (RP837C1);
      FAOOFAOOFO (RP850);
      FWKRFVRKWR (RP837);
      FWKKFVKKWK (RP841);
      WWHHWWHHWH (RP847);
      WWRHWWHRWR (RP848);
      WWKHWWHKWK (RP849);
      GDRGIKGHRGF (RP842);
      LYKKIIKKLL (RP846);
      FYPDFFKKFF (RP844);
      FFRKSKEKIG (RP853);
      FFRHFATHLD (RP845); and
      EKLSAFRNFF (RP843); or
   b) a sequence having one or two amino acid substitutions relative to the sequence defined in a).

167. The method of clause 166, wherein the one or two amino acid substitutions defined in b) consist of a highly conservative substitution of a cationic amino acid of the sequence.

168. The method of clause 166, comprising the peptide sequence selected from: RWKFGGFKWR (RP832C), FKWRGGRWKF (RP837C) and FWKRGGRKWF (RP837A).

169. The method of clause 166, comprising the peptide sequence selected from FWKRFV (RP837N) and FVRKWR (RP837C1).

170. The method of clause 166, comprising a peptide sequence selected from FAOOFAOOFO (RP850), FWKRFVRKWR (RP837) and FWKKFVKKWK (RP841).

171. The method of clause 166, comprising a peptide sequence selected from WWHHWWHHWH, WWRHWWHRWR and WWKHWWHKWK (RP847-849).

172. The method of clause 166, comprising the peptide sequence GDRGIKGHRGF (RP842) or LYKKIIKKLL (RP846).

173. The method of clause 166, comprising the peptide sequence FYPDFFKKFF (RP844).

174. The method of clause 166, comprising the peptide sequence FFRKSKEKIG (RP853).

175. The method of clause 166, comprising the peptide sequence FFRHFATHLD (RP845).

176. The method of clause 166, comprising the peptide sequence EKLSAFRNFF (RP843).

177. An active agent that binds to an activity modulating domain of CD206.

178. The active agent according to clause 177, wherein the active agent binds to an activity modulating domain of CD206 selected from fibronectin 11 domain of CD206, C-type lectin carbohydrate recognition domain 3 (CRD3) of CD206. C-type lectin carbohydrate recognition domain 4 (CRD4) of CD206 and C-type lectin carbohydrate recognition domain 5 (CRD5) of CD206.

179. The active agent of clause 178, wherein the active agent binds to CRD5 domain of CD206.

180. The active agent of clause 178, wherein the active agent binds to fibronectin II domain of CD206.

181. The active agent of clause 178, wherein the active agent binds to CRD3 domain of CD206.

182. The active agent of any one of clauses 177 to 181, wherein the active agent is an immunomodulatory peptide.

183. The active agent of clause 182, wherein the immunomodulatory peptide is of 5 to 18 amino acid residues in length, the peptide comprising: a striapathic region of alternating hydrophilic and hydrophobic modules that adopts an amphipathic conformation under physiological conditions.

184. The active agent of clause 183, wherein the striapathic region comprises:

3 or more hydrophobic modules; and 2 or more hydrophilic modules each comprising at least one cationic residue;

wherein the immunomodulatory peptide binds to the activity modulating domain of CD206.

185. The active agent of any one of clauses 182-184, wherein the immunomodulatory peptide comprises a sequence defined by one of the formulae:

$[J_{1a}J_{1b}]$-$[X_{1a}X_{1b}]$-$[J_{2a}J_{2b}]$-$[X_{2a}X_{2b}]$-$[J_{3a}]$-$[X_{3a}]$; and $[X_{3a}]$-$[J_{3a}]$-$[X_{2b}X_{2a}]$-$[J_{2b}J_{2a}]$-$[X_{1b}X_{1a}][J_{1b}J_{1a}]$;

wherein:

$J_{1a}$, $J_{1b}$, $J_{2a}$, $J_{2b}$ and $J_{3a}$ are each independently selected from phenylalanine, tryptophan, alanine, valine, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine.

186. The active agent of clause 182 or 183, wherein the immunomodulatory peptide comprises a sequence defined by one of the formulae:

$[X_{1a}]$-$[J_{2a}]$-$[X_{2a}]$-$[J_{2a}]$-$[X_{3a}]$-$[J_{3a}]$ $[J_{3a}]$-$[X_{3a}]$-$[J_{2a}]$-$[X_{2a}]$-$[J_{1a}]$-$[X_{1a}]$ $[J_{1a}J_{1b}]$-$[X_{1a}X_{1b}]$-$[J_{2a}J_{2b}]$;

$[J_{1a}J_{1b}]$-$[X_{1a}X_{1b}]$-$[J_{2a}]$-$[X_{2a}]$;

$[X_{3a}]$-$[J_{3a}]$-$[X_{2b}X_{2a}]$-$[J_{2b}J_{2a}]$;

$[J_{1a}J_{1b}]$-$[X_{1a}]$-$[J_{2a}J_{2b}]$-$[X_{2a}]$; and $[X_{1a}]$-$[J_{1a}J_{1b}]$-$[X_{2a}]$-$[J_{2a}J_{2b}]$;

wherein:

$J_{1a}$, $J_{1b}$, $J_{2a}$, $J_{2b}$ and $J_{3a}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine.

187. The active agent of clause 185 or 186, wherein:

$J_{1a}$, $J_{1b}$, $J_{2a}$, $J_{2b}$ and $J_{3a}$ are each phenylalanine; and $X_{1a}$, $X_{1b}$, $X_{2a}$, $X_{2b}$ and $X_{3a}$ are each independently selected from lysine and arginine.

188. The active agent of clause 185, wherein the immunomodulatory peptide comprises a) a sequence selected from:

KFRKAFKRFF (RP182);

FFRKFAKRFK (RP183);

FFKKFFKKFK (RP185);

FFKKFFKKFK (RP186); and

FFKKFFKKFK (RP233); or b) a sequence having one or two amino acid substitutions relative to the sequence defined in a).

189. The active agent of clause 188, wherein the immunomodulatory peptide comprises the amino acid sequence KFRKAFKRFF (RP182)

190. The active agent of clause 188, wherein the immunomodulatory peptide comprises the amino acid sequence FFRKFAKRFK (RP183).

191. The active agent of clause 189, wherein the immunomodulatory peptide comprises the amino acid sequence FFKKFFKKFK (RP185).

192. The active agent of clause 183, wherein the immunomodulatory peptide comprises:

a) a peptide sequence selected from:

RWKFGGFKWR (RP832C);

FKWRGGRWKF (RP837C);

FWKRGGRKWF (RP837A);

FWKRFV (RP837N);

FVRKWR (RP837C1);

FAOOFAOOFO (RP850);

FWKRFVRKWR (RP837);

FWKKFVKKWK (RP841);
WWHHWWHHWH (RP847);
WWRHWWHRWR (RP848);
WWKHWWHKWK (RP849);
GDRGIKGHRGF (RP842);
LYKKIIKKLL (RP846):
FYPDFFKKFF (RP844);
FFRKSKEKIG (RP853);
FFRHFATHLD (RP845); and
EKLSAFRNFF (RP843); or b) a sequence having one or two amino acid substitutions relative to the sequence defined in a).

193. The active agent of clause 192, wherein the one or two amino acid substitutions defined in b) consist of a highly conservative substitution of a cationic amino acid of the sequence.

194. The active agent of clause 192, comprising the peptide sequence selected from: RWKFGGFKWR (RP832C), FKWRGGRWKF (RP837C) and FWKRGGRKWF (RP837A).

195. The active agent of clause 192, comprising the peptide sequence selected from FWKRFV (RP837N) and FVRKWR (RP837C1).

196. The active agent of clause 192, comprising a peptide sequence selected from FAOOFAOOFO (RP850), FWKRFVRKWR (RP837) and FWKKFVKKWK (RP841).

197. The active agent of clause 192, comprising a peptide sequence selected from WWHHWWHHWH, WWRHWWHRWR and WWKHWWHKWK (RP847-849).

198. The active agent of clause 183, comprising a peptide sequence selected from MVFRDVGNRN. LFWKRFVEFF, AIRRIPRRIR, LAERAFHRFF. DVRMRLRSEV. FFNRFANERH, GFRELFRQLD. SQLPAFKRFF. RRAELGFKWR, MFEREVKNAM, REVKNAMRRW, IENAAFKRFF. FYPDFFKKFF, and KKIRVRSLA 199. The active agent of clause 192, comprising the peptide sequence GDRGIKGHRGF (RP842).

200. The active agent of clause 192, comprising the peptide sequence LYKKIIKKLL (RP846).

201. The active agent of clause 192, comprising the peptide sequence FYPDFFKKFF (RP844).

202. The active agent of clause 192, comprising the peptide sequence FFRKSKEKIG (RP853).

203. The active agent of clause 192, comprising the peptide sequence FFRHFATHLD (RP845).

204. The active agent of clause 192, comprising the peptide sequence EKLSAFRNFF (RP843).

205. The active agent of clause 186, wherein the immunomodulatory peptide comprises:

a) a peptide sequence selected from:
AFKRFF (182-FN6);
FFKKFF (185-FN6);
FWKRFV (837-FN6);
WWVRRVV (WLUB-F1-N6);
IFKKIE (CEC-F1-N6)
FLRNLV (LL37F-3-N6);
FLHSAK (MAG-F1-N6);
FFHHIF (PISC-F-N6);
FFKKAA (PLEU-F-N6);
ALKKVF (PSEU-F-N6);
LYKKII (CXCL4-F-N6);
LFRRAF (IL24-FN6);
FLKRLL (IL7-FN6);
FFRRFA (ABCP-FN6);
FFRHFA (E1P-FN6);
AIRRIP (gP120-FN6);
AFHRFF (GP2B-FN6);
FFNRFA (MCPH-FN6);
AFKRFF (SPRA-FN6);
AFKRFF (TPRO-FN6);
IVRRAD (COL18-FN6);
FWRWFK (HX5/CPAP);
KFWRWF (HX6/YJPA):
WFRFWK (HX7/CLPB)
KWFRFW (HX8/ATG1);
AFHHFF (HEX16F/STPK);
FFRNFA (HEXF13/SIF1):
AFHRFF (HEX9F/THIF);
FFRQFA (HEXF1/ATPB);
AFNRFF (HEX2F/AATF);
WIQRMM (CXCL13-FN6);
WVQRVV (CXCL8-FN6);
AFRNFF (HEX3F/FBNA); and
TLRRFM (HEX18/HSHK); or b) a sequence having one or two amino acid substitutions relative to the sequence defined in a).

206. The active agent of clause 186, wherein the immunomodulatory peptide comprises:

a) a peptide sequence selected from:
DVRMRL (MCMV-FN6); and
RRAELG (TONB-FN6) or b) a sequence having one or two amino acid substitutions relative to the sequence defined in a).

207. The active agent of clause 182, wherein the immunomodulatory peptide comprises:

a) a peptide sequence selected from:
FWRWFA (HX1/MMPL);
AFWRWF (HX2/ABCT);
WFRFWA (HX3/GTRF);
AWFRFW (HX4/AXES);
VAVRIW (HX9/IDRF/AMIA);
FFRFFA (HEXF2/AMT1); and
AFFRFF (HEX13F/TGME); or b) a sequence having one or two amino acid substitutions relative to the sequence defined in a).

208. The active agent of clause 186, wherein the immunomodulatory peptide comprises:

a) a peptide sequence selected from:
FFKKFF; WWKKFF; FWKKWF; FFKKWW; WWKKWW; YYKKYY; IIKKYY; YIKKIY; YYKKII; IIKKII; MMKKMM; LLKKMM; MLKKLM; MMKKLL; LLKKLL; VVKKVV; AAKKVV; VAKKAV; VVKKAA; AAKKAA; GGKKGG; TTKKGG: GTKKTG; GGKKTT; TTKKTT; SSKKSS; CCKKSS; SCKKCS; SSKKCC; and CCKKCC; or b) a sequence having one or two amino acid substitutions relative to the sequence defined in a).

209. The active agent of clause 186, wherein the immunomodulatory peptide comprises:

a) a peptide sequence selected from:
FKFKFK; WKWKWK; YKYKYK; IKIKIK; MKMKMK; LKLKLK; VKVKVK; AKAKAK; GKGKGK; TKTKTK; SKSKSK; CKCKCK; KFKFKF; KWKWKW; KYKYKY; KIKIKI; KMKMKM; KLKLKL; KVKVKV; KAKAKA; KGKGKG; KTKTKT; KSKSKS; and KCKCKC; or b) a sequence having one or two amino acid substitutions relative to the sequence defined in a).

210. The active agent of clause 182, wherein the immunomodulatory peptide comprises a peptide from table 1.
211. The active agent of clause 210, wherein the immunomodulatory peptide comprises a peptide of table 1 truncated by 1 or 2 amino acids at the N-terminus.
212. The active agent of clause 210, wherein the immunomodulatory peptide comprises a peptide of table 1 truncated by 1 or 2 amino acids at the C-terminus.
213. The active agent of clause 182 or 183, wherein the immunomodulatory peptide comprises a sequence defined by one of the formulae:

$[J_{1a}]-[X_{2a}]-[J_{2a}]-[X_{3a}]-[J_{3a}]$ $[X_{1a}]-[J_{1a}]-[X_{2a}]-[J_{2a}]-[X_{3a}]$ $[X_{1a}]-[J_{1a}]-[X_{2a}]-[J_{2a}J_{2b}]$;

$[J_{1a}J_{1b}]-[X_{1a}]-[J_{2a}]-[X_{2a}]$;

$[X_{1a}]-[J_{1a}J_{1b}]-[X_{2a}]-[J_{2a}]$;

$[J_{1a}]-[X_{1a}]-[J_{2a}J_{2b}]-[X_{2a}]$; and $[J_{1a}J_{1b}]-[X_{2a}]-[J_{2a}J_{2b}]$;

wherein:
$J_{1a}$, $J_{1b}$, $J_{2a}$, $J_{2b}$ and $J_{3a}$ are each independently selected from phenylalanine, tryptophan, alanine, valine, leucine, isoleucine, methionine, tyrosine, threonine, serine, cysteine, proline, and glycine; and
$X_{1a}$, $X_{1b}$, $X_{2a}$, $X_{2b}$ and $X_{3a}$ are each independently selected from lysine, arginine, histidine, aspartic acid, glutamic acid, asparagine and glutamine.
214. The active agent of clause 213, wherein the immunomodulatory peptide comprises:
a) a peptide sequence selected from:
AFKRF; FFKKF; FWKRF; WVRRV; IFKKI; FLRNL; FLHSA; FFHHI; FFKKA; ALKKV; LYKKI; LFRRA; FLKRL; FFRRF; FFRHF; AIRRI; AFHRF; FFNRF; IVRRA; FWRWF; KFWRW; WFRFW; KWFRF; AFHHF; FFRNF; FFRQF; AFNRF; WIQRM; WVQRV; AFRNF; TLRRF; FKRFF; FKKFF; WKRFV; VRRVV; FKKIE; LRNLV; LHSAK; FHHIF; FKKAA; LKKVF; YKKII; FRRAF; LKRLL; FRRFA; FRHFA; IRRIP; FHRFF; FNRFA; VRRAD; WRWFK; FRFWK; FHHFF; FRNFA; FRQFA; FNRFF; IQRMM; VQRVV; FRNFF; LRRFM; DVRMR; VRMRL; RRAEL; RAELG; and RWKFG; or
b) a sequence having one or two amino acid substitutions relative to the sequence defined in a).
215. The active agent of clause 182, wherein the immunomodulatory peptide comprises:
a)
i) a peptide sequence selected from:
AFWRW; AWFRF; VAVRI; FFRFF; AFFRF; WRWFA; FRFWA; AVRIW; and FRFFA; or
ii) a sequence having one or two amino acid substitutions relative to the sequence defined in i); or
b)
i) a peptide sequence selected from:
FFKKF; WWKKF; FWKKW; FFKKW; WWKKW; YYKKY; IIKKY; YIKKI; YYKKI; IIKKI; MMKKM; LLKKM; MLKKL; MMKKL; LLKKL; VVKKV; AAKKV; VAKKA; VVKKA; AAKKA; GGKKG; TTKKG; GTKKT; GGKKT; TTKKT; SSKKS; CCKKS; SCKKC; SSKKC; and CCKKC; FKKFF; WKKFF; WKKWF; FKKWW; WKKWW; YKKYY; IKKYY; IKKIY; YKKII; IKKII; MKKMM; LKKMM; LKKLM; MKKLL; LKKLL; VKKVV; AKKVV; AKKAV; VKKAA; AKKAA; GKKGCG; TKKGCG; TKKTG; GKKTT; TKKTT; SKKSS; CKKSS; CKKCS; SKKCC; and CKKCC; or
ii) a sequence having one or two amino acid substitutions relative to the sequence defined in i).
216. The active agent of clause 213, wherein the immunomodulatory peptide comprises:
a) a peptide sequence selected from:
FKFKF; WKWKW; YKYKY; IKIKI; MKMKM; LKLKL; VKVKV; AKAKA; GKGKG; TKTKT; SKSKS; CKCKC; KFKFK; KWKWK; KYKYK; KIKIK; KMKMK; KLKLK; KVKVK; KAKAK; KGKGK; KTKTK; KSKSK; and KCKCK; or
b) a sequence having one or two amino acid substitutions relative to the sequence defined in a).
217. The active agent of clause 182 or 183, wherein the immunomodulatory peptide comprises a sequence defined by one of the formulae:

$[J_{1a}]-[X_{1a}]-[J_{2a}]-[X_{2a}]$ $[X_{1a}]-[J_{1a}]-[X_{2a}]-[J_{2a}]$ $[X_{1a}X_{2a}]-[J_{2a}J_{2b}]$; and $[J_{1a}J_{1b}]-[X_{1a}X_{2a}]$;

wherein:
$J_{1a}$, $J_{1b}$, $J_{2a}$, and $J_{2b}$, are each independently selected from phenylalanine, tryptophan, alanine, valine, leucine, isoleucine, methionine, tyrosine, threonine, serine, cysteine, proline, and glycine; and
$X_{1a}$, $X_{1b}$, $X_{2a}$, and $X_{2b}$ are each independently selected from lysine, arginine, histidine, aspartic acid, glutamic acid, asparagine and glutamine.
218. The active agent of clause 217, wherein the immunomodulatory peptide comprises:
a) a peptide sequence selected from:
AFKR; FFKK; FWKR; WVRR; IFKK; FLRN; FLHS; FFHH; ALKK; LYKK; LFRR; FLKR; FFRR; FFRH; AIRR; AFHR; FFNR; IVRR; FWRW; KFWR; WFRF; KWFR; AFHH; FFRN; FFRQ; AFNR; WIQR; WVQR: AFRN; TLRR: KRFF; KKFF: KRFV; RRVV; KKIE: RNLV; HSAK; HHIF; KKAA; KKVF; KKII; RRAF; KRLL; RRFA; RHFA; RRIP; HRFF; NRFA: RRAD; RWFK; RFWK; HHFF; RNFA; RQFA; NRFF; QRMM; QRVV; RNFF; RRFM; VRMR; RMRL; RAEL; AELG; and WKFG; or
b) a sequence having one or two amino acid substitutions relative to the sequence defined in a).
219. The active agent of clause 182, wherein the immunomodulatory peptide comprises:
a) a peptide sequence selected from:
FWRW; AFWR; WFRF; AWFR; VAVR; FFRF; AFFR; RWFA; WRWF; RFWA; FRFW; VRIW; RFFA; and FRFF; or
b) a sequence having one or two amino acid substitutions relative to the sequence defined in a).

220. The active agent of clause 217, wherein the immunomodulatory peptide comprises:
a) a peptide sequence selected from:
FFKK; WWKK; FWKK; YYKK; IIKK; YIKK; MMKK; LLKK; MLKK; VVKK; AAKK; VAKK; GGKK; TTKK; GTKK; SSKK; CCKK; SCKK; KKFF; KKWF; KKWW; KKYY; KKIY; KKII; KKMM; KKLM; KKLL; KKVV; KKAV; KKAA; KKGG; KKTG; KKTT; KKSS; KKCS; and KKCC; or
b) a sequence having one or two amino acid substitutions relative to the sequence defined in a).

221. The active agent of clause 217, wherein the immunomodulatory peptide comprises:
a) a peptide sequence selected from:
FKFK; WKWK; YKYK; IKIK; MKMK; LKLK; VKVK; AKAK; GKGK; TKTK; SKSK; CKCK; KFKF; KWKW; KYKY; KIKI; KMKM; KLKL; KVKV; KAKA; KGKG; KTKT; KSKS; and KCKC; or
b) a sequence having one or two amino acid substitutions relative to the sequence defined in a).

222. The active agent of any one of clauses 205 to 221, wherein the one or two amino acid substitutions defined in b) consist of a highly conservative substitution of a cationic amino acid of the sequence.

223. The active agent of any one of clauses 177 to 181, wherein the active agent is a small molecule active agent.

224. The active agent of clause 223, wherein the small molecule active agent is described by formula (I):

(I)

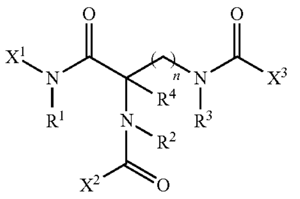

wherein:
$R^1$-$R^4$ are each independently selected from hydrogen, alkyl and substituted alkyl;
$X^1$ is selected from alkyl, substituted alkyl, aryl, substituted aryl, aralkyl, substituted aralkyl, heterocycle, substituted heterocycle, heteroaryl, substituted heteroaryl;
$X^2$ is selected from alkyl, substituted alkyl, aryl, substituted aryl, amino, substituted amino, heteroaryl, substituted heteroaryl, heterocycle, substituted heterocycle;
$X^3$ is selected from alkyl, substituted alkyl, aryl, substituted aryl, naphthyl, substituted naphthyl, heterocycle, substituted heterocycle, heteroaryl, substituted heteroaryl, aryl heterocycle, substituted aryl heterocycle; and
n is an integer from 1 to 10.
or a pharmaceutically acceptable salt or solvate thereof.

225. The active agent of clause 224, wherein the small molecule active agent is described by formula (Ia):

(Ia)

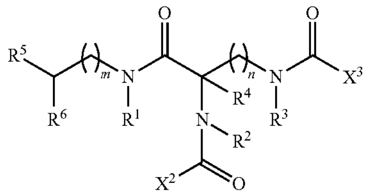

wherein:
$R^1$-$R^4$ are each independently selected from hydrogen, and alkyl;
$R^5$-$R^6$ are each independently selected from aryl and substituted aryl;
$X^2$ is selected from alkyl, and $NR^{2a}R^{2b}$ where R2a and R2b are independently selected from hydrogen, aryl, and substituted aryl;
$X^3$ is selected from aryl, substituted aryl, naphthyl, substituted naphthyl, carbazole, and substituted carbazole;
n is an integer from 1 to 6; and
m is an integer from 1 to 6.

226. The active agent of clause 225, wherein the small molecule active agent is a compound selected from the group consisting of:

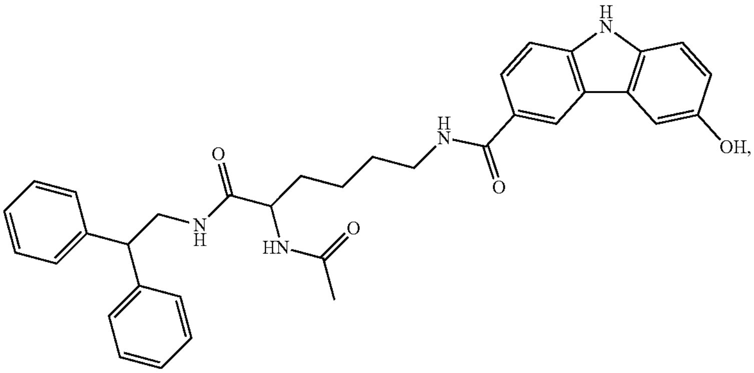
,

-continued
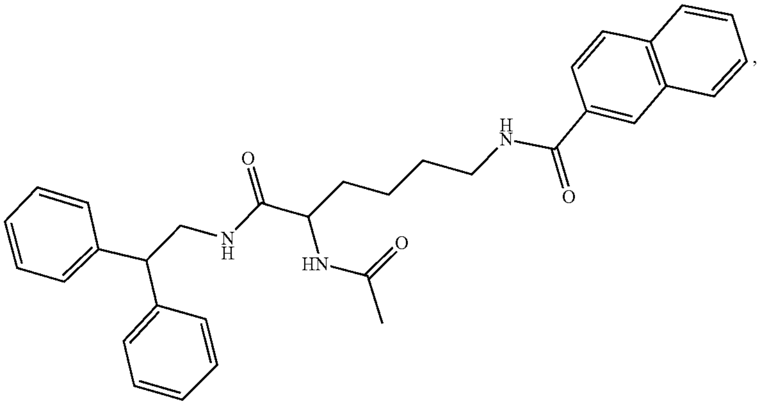
,
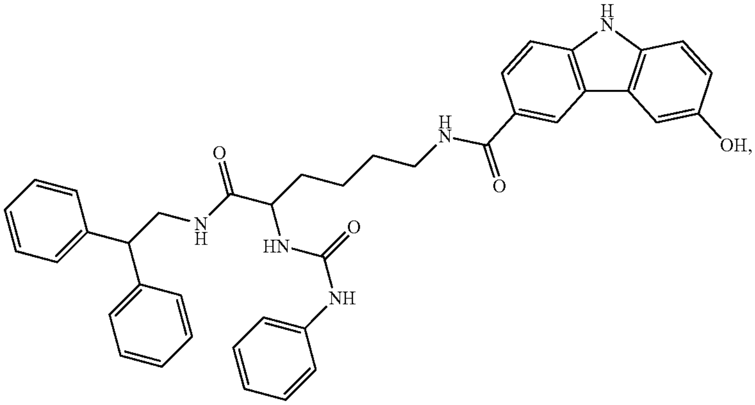
,
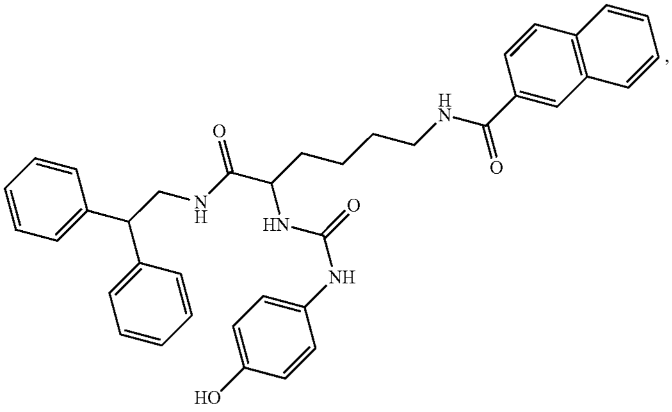
, and
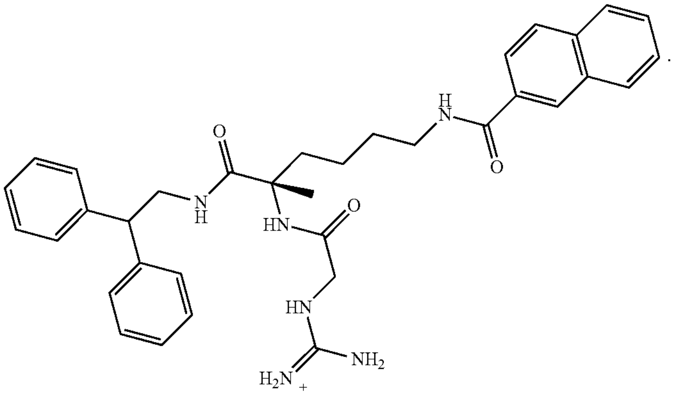
.

227. The active agent of clause 223, wherein the small molecule active agent is described by the formula (II):

(II)

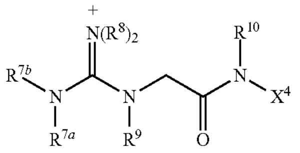

wherein:

$R^{7a}$, $R^{7b}$, $R^8$, $R^9$ and $R^{10}$ are each independently selected from hydrogen, alkyl and substituted alkyl; and $X^4$ is selected from alkyl, aryl, aralkyl, heterocycle, and heteroaryl, acyl, wherein $X^4$ is optionally further substituted with one or more groups selected from, alkyl, substituted alkyl, aryl, substituted aryl, amino, substituted amino, carboxamide, substituted carboxamide, heterocycle, substituted heterocycle, and a second compound of formula (II)

or a pharmaceutically acceptable salt or solvate thereof.

228. The active agent of clause 227, wherein the small molecule active agent is described by the formula (IIa):

(IIa)

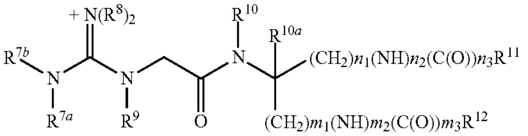

wherein:

$R^{7a}$, $R^{7b}$, $R^8$, $R^9$, $R^{10}$ and $R^{10a}$ are each independently selected from hydrogen, and alkyl;

$R^{11}$ and $R^{12}$ are each independently selected from aryl, substituted aryl, heteroaryl, substituted heteroaryl, naphthyl, substituted naphthyl, carbazole, and substituted carbazole:

$n_1$ and $m_1$ are each independently an integer from 1 to 10;

$n_2$ and $m_2$ are each independently 0 or 1; and $n_3$ and $m_3$ are each independently 0 or 1.

229. The active agent of clause 228, wherein the small molecule active agent is a compound selected from the group consisting of:

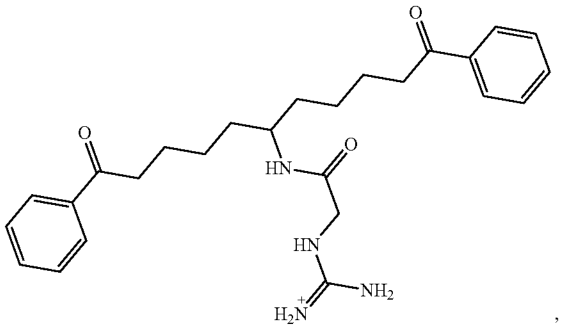

,

-continued

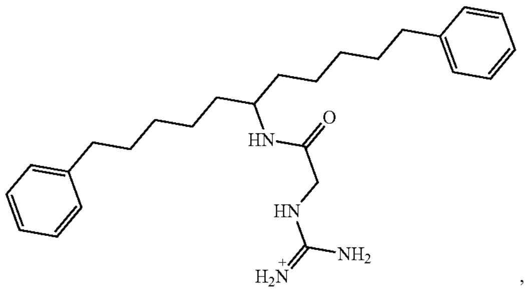

, and

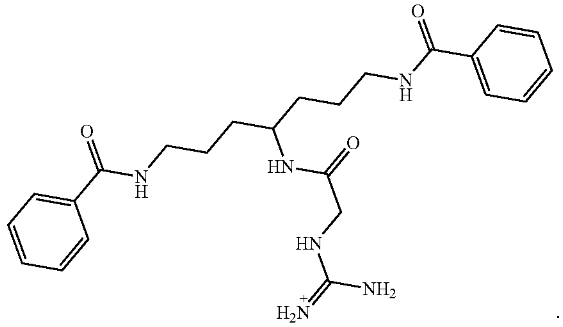

.

230. The active agent of clause 227, wherein the small molecule active agent is a compound selected from the group consisting of:

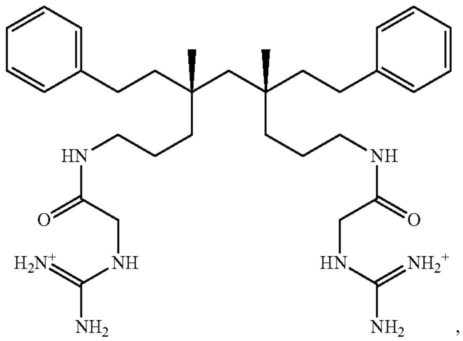

, and

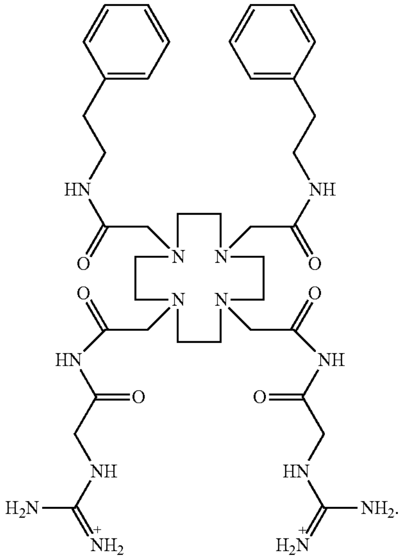

231. The active agent of clause 223, wherein the small molecule active agent is described by the formula (III):

(III)

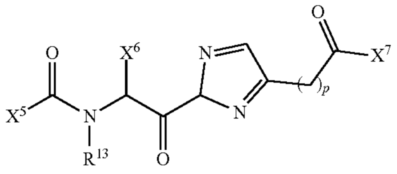

wherein:

$R^{13}$ is selected from hydrogen, alkyl and substituted alkyl; $X^5$ is selected from alkyl, substituted alkyl, aryl, substituted aryl, amino, substituted amino, heteroaryl, substituted heteroaryl, heterocycle, substituted heterocycle;

$X^6$ is selected from alkyl, substituted alkyl, aryl, substituted aryl, aralkyl, substituted aralkyl, heterocycle, substituted heterocycle, heteroaryl, substituted heteroaryl;

$X^7$ is selected from alkyl, substituted alkyl, aryl, substituted aryl, naphthyl, substituted naphthyl, heterocycle, substituted heterocycle, heteroaryl, substituted heteroaryl, aryl heterocycle, substituted aryl heterocycle; and p is an integer from 1 to 10, or a pharmaceutically acceptable salt or solvate thereof.

232. The active agent of clause 231, wherein the small molecule active agent is:

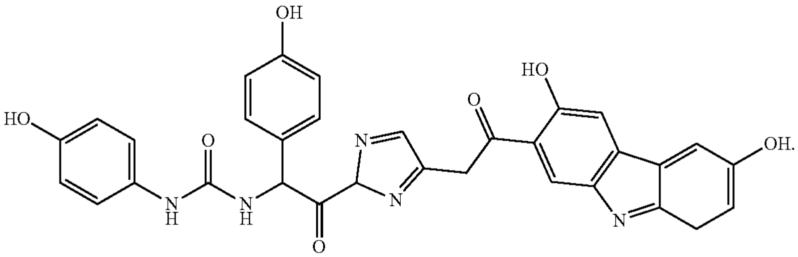 [SMILES: O=C(Nc1ccc(O)cc1)NC(C(=O)C1N=CC(CC(=O)c2cc3c(cc2O)C2=CC(O)=CCC2=N3)=N1)c1ccc(O)cc1]

233. The active agent of clause 177, wherein the active agent is a specific binding member.

234. The active agent of clause 233, wherein the specific binding member is an antibody, or a binding fragment thereof.

235. The active agent of clause 233 or 234, wherein the specific binding member targets a sequence of CD206 selected from the group consisting of NFGDLVSIQSESEKK, NDAQSAYFIGLLISL, SKEKETMDNARAF, and EDENCVTMYSNSGFWN.

236. The active agent of clause 235, wherein the specific binding member targets a NFGDLVSIQSESEKK sequence of CD206.

237. The active agent of clause 235, wherein the specific binding member targets a NDAQSAYFIGLLISL sequence of CD206.

238. The active agent of clause 235, wherein the specific binding member targets a SKEKETMDNARAF sequence of CD206.

239. The active agent of clause 235, wherein the specific binding member targets a EDENCVTMYSNSGFWN sequence of CD206.

240. A method comprising:

contacting a macrophage comprising CD206 with a compound, and determining if the compound binds to an activity modulating domain of CD206.

241. The method according to clause 240, further comprising determining the activity modulating domain of CD206 that binds the compound.

242. The method according clause 240 or 241, wherein the macrophage is a macrophage comprising one or more mutations in the activity modulating domains of CD206.

243. The method according to any one of clauses 240-242, wherein the activity modulating domain of CD206 is selected from the group consisting of fibronectin II domain of CD206, C-type lectin carbohydrate recognition domain 3 (CRD3) of CD206, C-type lectin carbohydrate recognition domain 4 (CRD4) of CD206 and C-type lectin carbohydrate recognition domain 5 (CRD5) of CD206.

244. The method of clause 243, wherein the activity modulating domain of CD206 is the CRD5 domain.

245. The method of clause 243, wherein the activity modulating domain of CD206 is the fibronectin II domain.

246. The method of clause 243, wherein the activity modulating domain of CD206 is the CRD3 domain.

247. The method of any one of clauses 243 to 246, wherein the compound is an immunomodulatory peptide.

248. The method of clause 247, wherein the immunomodulatory peptide is of 5 to 18 amino acid residues in length, the peptide comprising: a striapathic region of alternating hydrophilic and hydrophobic modules that adopts an amphipathic conformation under physiological conditions.

249. The method of clause 248, wherein the striapathic region comprises:

3 or more hydrophobic modules; and 2 or more hydrophilic modules each comprising at least one cationic residue;

wherein the immunomodulatory peptide hinds to the activity modulating domain of CD206.

250. The method of any one of clauses 247 to 249, wherein the immunomodulatory peptide comprises a sequence defined by one of the formulae:

$[Y_{1a}Y_{1b}]$-$[X_{1a}X_{1b}]$-$[Y_{2a}Y_{2b}]$-$[X_{2a}X_{2b}]$-$[Y_{3a}]$-$[X_{3a}]$;

and $[X_{3a}]$-$[Y_{3a}]$-$[X_{2b}X_{2a}]$-$[Y_{2b}Y_{2a}]$-$[X_{1b}X_{1a}]$-$[Y_{1b}Y_{1a}]$;

wherein:

$Y_{1a}$, $Y_{1b}$, $Y_{2a}$, $Y_{2b}$ and $Y_{3a}$ are each independently selected from phenylalanine, tryptophan, alanine, valine, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine.

251. The method of clause 247 or 248, wherein the immunomodulatory peptide comprises a sequence defined by one of the formulae:

$[X_{1a}]$-$[Y_{2a}]$-$[X_{2a}]$-$[Y_{2a}]$-$[X_{3a}]$-$[Y_{3a}]$ $[Y_{3a}]$-$[X_{3a}]$-$[Y_{2a}]$-$[X_{2a}]$-$[Y_{1a}]$-$[X_{1a}]$ $[Y_{1a}Y_{1b}]$-$[X_{1a}X_{1b}]$-$[Y_{2a}Y_{2b}]$;

$[Y_{1a}Y_{1b}]$-$[X_{1a}X_{1b}]$-$[Y_{2a}]$-$[X_{2a}]$;

$[X_{3a}]$-$[Y_{3a}]$-$[X_{2b}X_{2a}]$-$[Y_{2b}Y_{2a}]$;

$[Y_{1a}Y_{1b}]$-$[X_{1a}]$-$[Y_{2a}Y_{2b}]$-$[X_{2a}]$; and $[X_{1a}]$-$[Y_{1a}Y_{1b}]$-$[X_{2a}]$-$[Y_{2a}Y_{2b}]$;

wherein:

$Y_{1a}$, $Y_{1b}$, $Y_{2a}$, $Y_{2b}$ and $Y_{3a}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine.

252. The method of clause 250 or 251, wherein:

$Y_{1a}$, $Y_{1b}$, $Y_{2a}$, $Y_{2b}$ and $Y_{3a}$ are each phenylalanine; and $X_{1a}$, $X_{1b}$, $X_{2a}$, $X_{2b}$ and $X_{3a}$ are each independently selected from lysine and arginine.

253. The method of clause 250, wherein the immunomodulatory peptide comprises a) a sequence selected from:
KFRKAFKRFF (RP182);
FFRKFAKRFK (RP183);
FFKKFFKKFK (RP185);
FFKKFFKKFK (RP186); and
FFKKFFKKFK (RP233); or b) a sequence having one or two amino acid substitutions relative to the sequence defined in a).

254. The method of clause 253, wherein the immunomodulatory peptide comprises the amino acid sequence KFRKAFKRFF (RP182)

255. The method of clause 253, wherein the immunomodulatory peptide comprises the amino acid sequence FFRKFAKRFK (RP183).

256. The method of clause 253, wherein the immunomodulatory peptide comprises the amino acid sequence FFKKFFKKFK (RP185).

257. The method of clause 248, wherein the immunomodulatory peptide comprises:

a) a peptide sequence selected from:
RWKFGGFKWR (RP832C);
FKWRGGRWKF (RP837C);
FWKRGGRKWF (RP837A);
FWKRFV (RP837N);
FVRKWR (RP837C1);
FAOOFAOOFO (RP850);
FWKRFVRKWR (RP837);
FWKKFVKKWK (RP841);
WWHHWWHHWH (RP847);
WWRHWWHRWR (RP848);
WWKHWWHKWK (RP849);
GDRGIKGHRGF (RP842);
LYKKIIKKLL (RP846);
FYPDFFKKFF (RP844);
FFRKSKEKIG (RP853);
FFRHFATHLD (RP845); and
EKLSAFRNFF (RP843); or b) a sequence having one or two amino acid substitutions relative to the sequence defined in a).

258. The method of clause 257, wherein the one or two amino acid substitutions defined in b) consist of a highly conservative substitution of a cationic amino acid of the sequence.

259. The method of clause 257, comprising the peptide sequence selected from: RWKFGGFKWR (RP832C), FKWRGGRWKF (RP837C) and FWKRGGRKWF (RP837A).

260. The method of clause 257, comprising the peptide sequence selected from FWKRFV (RP837N) and FVRKWR (RP837C1).

261. The method of clause 257, comprising a peptide sequence selected from FAOOFAOOFO (RP850), FWKRFVRKWR (RP837) and FWKKFVKKWK (RP841).

262. The method of clause 257, comprising a peptide sequence selected from WWHHWWHHWH, WWRHWWHRWR and WWKHWWHKWK (RP847-849).

263. The method of clause 248, comprising a peptide sequence selected from MVFRDVGNRN, LFWKRFVEFF, AIRRIPRRIR, LAERAFHRFF, DVRMRLRSEV, FFNRFANERH, GFRELFRQLD, SQLPAFKRFF, RRAELGFKWR, MFEREVKNAM, REVKNAMRRW, IENAAFKRFF, FYPDFFKKFF, and KKIRVRSLA 264. The method of clause 257, comprising the peptide sequence GDRGIKGHRGF (RP842).

265. The method of clause 257, comprising the peptide sequence LYKKIIKKLL (RP846).

266. The method of clause 257, comprising the peptide sequence FYPDFFKKFF (RP844).

267. The method of clause 257, comprising the peptide sequence FFRKSKEKIG (RP853).

268. The method of clause 257, comprising the peptide sequence FFRHFATHLD (RP845).

269. The method of clause 257, comprising the peptide sequence EKLSAFRNFF (RP843).

270. The method of clause 251, wherein the immunomodulatory peptide comprises:

a) a peptide sequence selected from:
AFKRFF (182-FN6);
FFKKFF (185-FN6);
FWKRFV (837-FN6);
WVRRVV (WLUB-F1-N6);
IFKKIE (CEC-F1-N6)
FLRNLV (LL37F-3-N6);
FLHSAK (MAG-F1-N6);
FFHHIF (PISC-F-N6);
FFKKAA (PLEU-F-N6);
ALKKVF (PSEU-F-N6);
LYKKII (CXCL4-F-N6);
LFRRAF (IL24-FN6);
FLKRLL (IL7-FN6);
FFRRFA (ABCP-FN6);
FFRHFA (E1P-FN6);
AIRRIP (gP120-FN6);
AFHRFF (GP2B-FN6);
FFNRFA (MCPH-FN6);
AFKRFF (SPRA-FN6);
AFKRFF (TPRO-FN6);
IVRRAD (COL18-FN6);

FWRWFK (HX5/CPAP);
KFWRWF (HX6/YJPA);
WFRFWK (HX7/CLPB)
KWFRFW (HX8/ATG1);
AFHHFF (HEX16F/STPK);
FFRNFA (HEXF13/SIF1);
AFHRFF (HEX9F/THIF);
FFRQFA (HEXF1/ATPB);
AFNRFF (HEX2F/AATF);
WIQRMM (CXCL13-FN6);
WVQRVV (CXCL8-FN6);
AFRNFF (HEX3F/FBNA); and
TLRRFM (HEX18/HSHK); or b) a sequence having one or two amino acid substitutions relative to the sequence defined in a).

271. The method of clause 251, wherein the immunomodulatory peptide comprises:

a) a peptide sequence selected from:
DVRMRL (MCMV-FN6); and
RRAELG (TONB-FN6) or b) a sequence having one or two amino acid substitutions relative to the sequence defined in a).

272. The method of clause 247, wherein the immunomodulatory peptide comprises:

a) a peptide sequence selected from:
FWRWFA (HX1/MMPL);
AFWRWF (HX2/ABCT):
WFRFWA (HX3/GTRF);
AWFRFW (HX4/AXES);
VAVRIW (HX9/IDRF/AMIA);
FFRFFA (HEXF2/AMT1); and
AFFRFF (HEX13F/TGME); or b) a sequence having one or two amino acid substitutions relative to the sequence defined in a).

273. The method of clause 251, wherein the immunomodulatory peptide comprises:

a) a peptide sequence selected from:
FFKKFF; WWKKFF; FWKKWF; FFKKWW; WWKKWW; YYKKYY; IIKKYY; YIKKIY; YYKKII; IIKKII; MMKKMM; LLKKMM; MLKKLM; MMKKLL; LLKKLL; VVKKVV; AAKKVV: VAKKAV; VVKKAA; AAKKAA; GGKKGG; TTKKGG: GTKKTG; GGKKTT; TTKKTT; SSKKSS; CCKKSS; SCKKCS; SSKKCC; and CCKKCC; or b) a sequence having one or two amino acid substitutions relative to the sequence defined in a).

274. The method of clause 251, wherein the immunomodulatory peptide comprises:

a) a peptide sequence selected from:
FKFKFK; WKWKWK; YKYKYK; IKIKIK; MKMKMK; LKLKLK; VKVKVK; AKAKAK; GKGKGK; TKTKTK; SKSKSK; CKCKCK; KFKFKF; KWKWKW; KYKYKY; KIKIKI; KMKMKM; KLKLKL; KVKVKV; KAKAKA; KGKGKG; KTKTKT; KSKSKS; and KCKCKC; or b) a sequence having one or two amino acid substitutions relative to the sequence defined in a).

275. The method of clause 247, wherein the immunomodulatory peptide comprises a peptide from table 1.

276. The method of clause 275, wherein the immunomodulatory peptide comprises a peptide of table 1 truncated by 1 or 2 amino acids at the N-terminus.

277. The method of clause 275, wherein the immunomodulatory peptide comprises a peptide of table 1 truncated by 1 or 2 amino acids at the C-terminus.

278. The method of clause 247 or 248, wherein the immunomodulatory peptide comprises a sequence defined by one of the formulae:

$[J_{1a}]$-$[X_{2a}]$-$[J_{2a}]$-$[X_{3a}]$-$[J_{3a}]$ $[X_{1a}]$-$[J_{1a}]$-$[X_{2a}]$-$[J_{2a}]$-$[X_{3a}]$ $[X_{1a}]$-$[J_{1a}]$-$[X_{2a}]$-$[J_{2a}J_{2b}]$;

$[J_{1a}J_{1b}]$-$[X_{1a}]$-$[J_{2a}]$-$[X_{2a}]$;

$[X_{1a}]$-$[J_{1a}J_{1b}]$-$[X_{2a}]$-$[J_{2a}]$;

$[J_{1a}]$-$[X_{1a}]$-$[J_{2a}J_{2b}]$-$[X_{2a}]$; and $[J_{1a}J_{1b}]$-$[X_{2a}]$-$[J_{2a}J_{2b}]$;

wherein:

$J_{1a}$, $J_{1b}$, $J_{2a}$, $J_{2b}$ and $J_{3a}$ are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, $X_{2b}$ and $X_{3a}$ are each independently selected from lysine, arginine, histidine, aspartic acid, glutamic acid, asparagine and glutamine.

279. The method of clause 278, wherein the immunomodulatory peptide comprises:

a) a peptide sequence selected from:
AFKRF; FFKKF; FWKRF; WVRRV; IFKKI; FLRNL; FLHSA; FFHHI; FFKKA; ALKKV; LYKKI; LFRRA; FLKRL; FFRRF; FFRHF; AIRRI; AFHRF; FFNRF; IVRRA; FWRWF; KFWRW; WFRFW; KWFRF; AFHHF; FFRNF; FFRQF; AFNRF; WIQRM; WVQRV; AFRNF; TLRRF; FKRFF; FKKFF; WKRFV; VRRVV; FKKIE; LRNLV; LHSAK; FHHIF; FKKAA; LKKVF; YKKII; FRRAF; LKRLL; FRRFA; FRHFA; IRRIP; FHRFF; FNRFA; VRRAD; WRWFK; FRFWK; FHHFF; FRNFA; FRQFA; FNRFF; IQRMM; VQRVV; FRNFF; LRRFM; DVRMR; VRMRL; RRAEL; RAELG; and RWKFG; or b) a sequence having one or two amino acid substitutions relative to the sequence defined in a).

280. The method of clause 247, wherein the immunomodulatory peptide comprises:

a) a peptide sequence selected from:
AFWRW; AWFRF; VAVRI; FFRFF; AFFRF; WRWFA; FRFWA; AVRIW; and FRFFA; or b) a sequence having one or two amino acid substitutions relative to the sequence defined in a).

281. The method of clause 278, wherein the immunomodulatory peptide comprises:

a) a peptide sequence selected from:
FFKKF; WWKKF; FWKKW; FFKKW; WWKKW; YYKKY; IIKKY; YIKKI; YYKKI; IIKKI; MMKKM; LLKKM; MLKKL; MMKKL; LLKKL; VVKKV; AAKKV; VAKKA; VVKKA; AAKKA; GGKKG; TTKKG; GTKKT; GGKKT; TTKKT; SSKKS; CCKKS; SCKKC; SSKKC; and CCKKC; FKKFF; WKKFF; WKKWF; FKKWW; WKKWW; YKKYY; IKKYY; IKKIY; YKKII; IKKII; MKKMM; LKKMM; LKKLM; MKKLL; LKKLL; VKKVV; AKKVV; AKKAV; VKKAA; AKKAA; GKKGCG; TKKGCG; TKKTG; GKKTT; TKKTT; SKKSS; CKKSS; CKKCS; SKKCC; and CKKCC; or b) a sequence having one or two amino acid substitutions relative to the sequence defined in a).

282. The method of clause 278, wherein the immunomodulatory peptide comprises:

a) a peptide sequence selected from:
FKFKF; WKWKW; YKYKY; IKIKI; MKMKM; LKLKL; VKVKV; AKAKA; GKGKG; TKTKT; SKSKS; CKCKC; KFKFK; KWKWK; KYKYK; KIKIK; KMKMK; KLKLK; KVKVK; KAKAK; KGKGK; KTKTK; KSKSK; and KCKCK; or b) a sequence having one or two amino acid substitutions relative to the sequence defined in a).

283. The method of clause 247 or 248, wherein the immunomodulatory peptide comprises a sequence defined by one of the formulae:

$[J_{1a}]$-$[X_{1a}]$-$[J_{2a}]$-$[X_{2a}]$ $[X_{1a}]$-$[J_{1a}]$-$[X_{2a}]$-$[J_{2a}]$ $[X_{1a}X_{2a}]$-$[J_{2a}J_{2b}]$; and $[J_{1a}J_{1b}]$-$[X_{1a}X_{2a}]$;

wherein:

$J_{1a}$, $J_{1b}$, $J_{2a}$, and $J_{2b}$, are each independently selected from phenylalanine, tryptophan, alanine, valine, leucine, isoleucine, methionine, tyrosine, threonine, serine, cysteine, proline, and glycine; and $X_{1a}$, $X_{1b}$, $X_{2a}$, and $X_{2b}$ are each independently selected from lysine, arginine, histidine, aspartic acid, glutamic acid, asparagine and glutamine.

284. The method of clause 283, wherein the immunomodulatory peptide comprises:

a) a peptide sequence selected from:
AFKR; FFKK; FWKR; WVRR; IFKK; FLRN; FLHS; FFHH; ALKK; LYKK; LFRR; FLKR; FFRR; FFRH; AIRR; AFHR; FFNR; IVRR; FWRW; KFWR; WFRF; KWFR; AFHH; FFRN; FFRQ; AFNR; WIQR; WVQR: AFRN; TLRR: KRFF; KKFF: KRFV; RRVV; KKIE: RNLV; HSAK; HHIF; KKAA; KKVF; KKII; RRAF; KRLL; RRFA; RHFA; RRIP; HRFF; NRFA: RRAD; RWFK; RFWK; HHFF; RNFA; RQFA; NRFF; QRMM; QRVV; RNFF; RRFM; VRMR; RMRL; RAEL; AELG; and WKFG; or b) a sequence having one or two amino acid substitutions relative to the sequence defined in a).

285. The method of clause 247, wherein the immunomodulatory peptide comprises:

a) a peptide sequence selected from:
FWRW; AFWR; WFRF; AWFR; VAVR; FFRF; AFFR; RWFA; WRWF; RFWA; FRFW; VRIW; RFFA; and FRFF; or b) a sequence having one or two amino acid substitutions relative to the sequence defined in a).

286. The method of clause 283, wherein the immunomodulatory peptide comprises:

a) a peptide sequence selected from:
FFKK; WWKK; FWKK; YYKK; IIKK; YIKK; MMKK; LLKK; MLKK; VVKK; AAKK; VAKK; GGKK; TTKK; GTKK; SSKK; CCKK; SCKK; KKFF; KKWF; KKWW; KKYY; KKIY; KKII; KKMM; KKLM; KKLL; KKVV; KKAV; KKAA; KKGG; KKTG; KKTT; KKSS; KKCS; and KKCC; or b) a sequence having one or two amino acid substitutions relative to the sequence defined in a).

287. The method of clause 283, wherein the immunomodulatory peptide comprises:

a) a peptide sequence selected from:
FKFK; WKWK; YKYK; IKIK; MKMK; LKLK; VKVK; AKAK; GKGK; TKTK; SKSK; CKCK; KFKF; KWKW; KYKY; KIKI; KMKM; KLKL; KVKV; KAKA; KGKG; KTKT; KSKS; and KCKC; or b) a sequence having one or two amino acid substitutions relative to the sequence defined in a).

288. The method of any one of clauses 270 to 287, wherein the one or two amino acid substitutions defined in b) consist of a highly conservative substitution of a cationic amino acid of the sequence.

289. The method of any one of clauses 243 to 246, wherein the compound is a small molecule active agent.

290. The method of clause 289, wherein the small molecule active agent is described by formula (I):

(I)

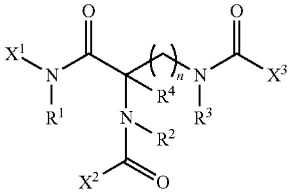

wherein:

$R^1$-$R^4$ are each independently selected from hydrogen, alkyl and substituted alkyl;

$X^1$ is selected from alkyl, substituted alkyl, aryl, substituted aryl, aralkyl, substituted aralkyl, heterocycle, substituted heterocycle, heteroaryl, substituted heteroaryl;

$X^2$ is selected from alkyl, substituted alkyl, aryl, substituted aryl, amino, substituted amino, heteroaryl, substituted heteroaryl, heterocycle, substituted heteroaryl;

$X^3$ is selected from alkyl, substituted alkyl, aryl, substituted aryl, naphthyl, substituted naphthyl, heterocycle, substituted heterocycle, heteroaryl, substituted heteroaryl, aryl heterocycle, substituted aryl heterocycle; and n is an integer from 1 to 10, or a pharmaceutically acceptable salt or solvate thereof.

291. The method of clause 290, wherein the small molecule active agent is described by formula (Ia):

(Ia)

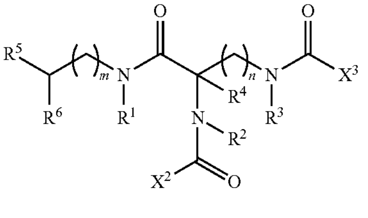

wherein:

$R^1$-$R^4$ are each independently selected from hydrogen, and alkyl;

$R^5$-$R^6$ are each independently selected from aryl and substituted aryl;

$X^2$ is selected from alkyl, and $NR^{2a}R^{2b}$, where R2a and R2b are independently selected from hydrogen, aryl, and substituted aryl;

$X^3$ is selected from aryl, substituted aryl, naphthyl, substituted naphthyl, carbazole, and substituted carbazole;

n is an integer from 1 to 6; and m is an integer from 1 to 6;

wherein in some instances the small molecule active agent is a compound selected from the group consisting of:

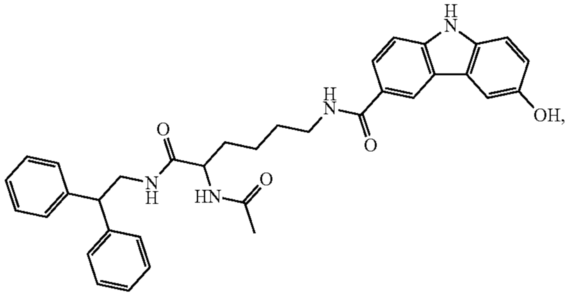

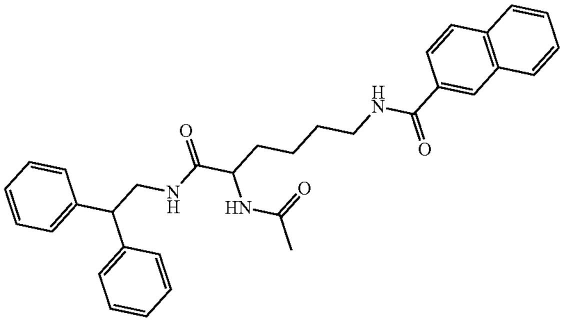

,

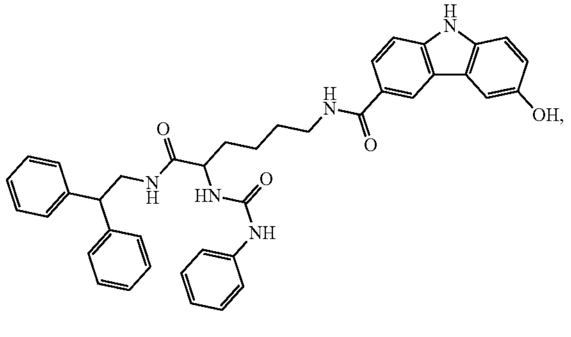

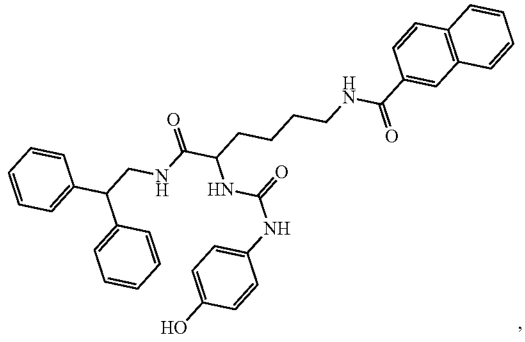

, and

-continued

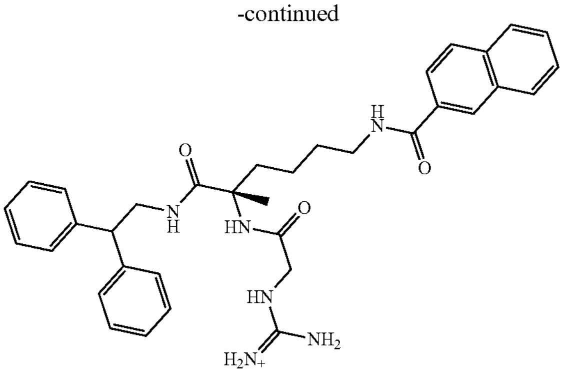

.

292. The method of clause 289, wherein the small molecule active agent is described by the formula (II):

(II)

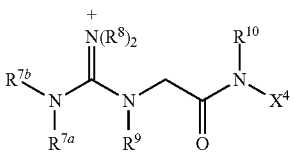

wherein:

$R^{7a}$, $R^{7b}$, $R^8$, $R^9$ and $R^{10}$ are each independently selected from hydrogen, alkyl and substituted alkyl; and $X^4$ is selected from alkyl, aryl, aralkyl, heterocycle, and heteroaryl, acyl, wherein $X^4$ is optionally further substituted with one or more groups selected from, alkyl, substituted alkyl, aryl, substituted aryl, amino, substituted amino, carboxamide, substituted carboxamide, heterocycle, substituted heterocycle, and a second compound of formula (II)

or a pharmaceutically acceptable salt or solvate thereof.

293. The method of clause 292, wherein the small molecule active agent is described by the formula (IIa):

(IIa)

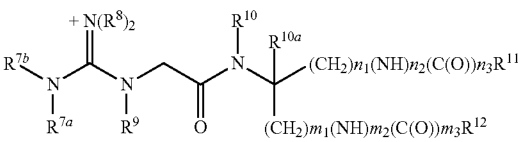

wherein:

$R^{7a}$, $R^{7b}$, $R^8$, $R^9$, $R^{10}$ and $R^{10a}$ are each independently selected from hydrogen, and alkyl;

$R^{11}$ and $R^{12}$ are each independently selected from aryl, substituted aryl, heteroaryl, substituted heteroaryl, naphthyl, substituted naphthyl, carbazole, and substituted carbazole;

n1 and m1 are each independently an integer from 1 to 10;

n2 and m2 are each independently 0 or 1; and n3 and m3 are each independently 0 or 1.

294. The method of clause 293, wherein the small molecule active agent is a compound selected from the group consisting of:

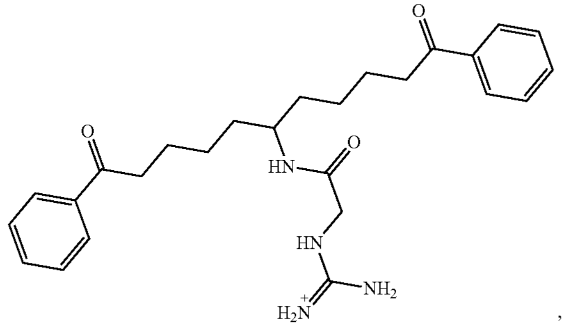

,

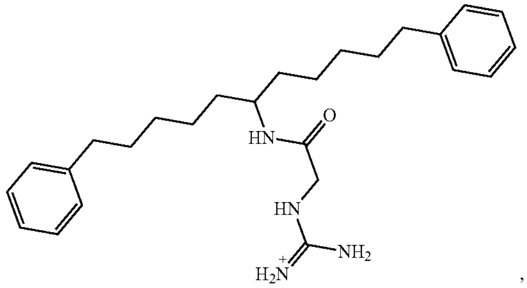

, and

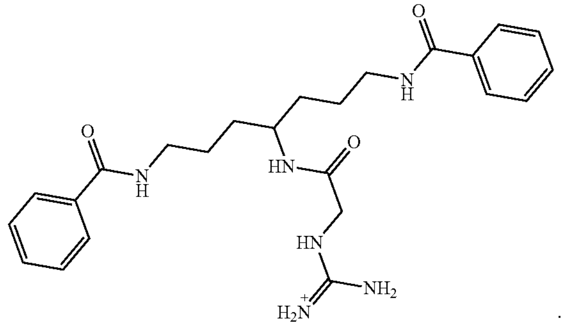

.

295. The method of clause 292, wherein the small molecule active agent is a compound selected from the group consisting of:

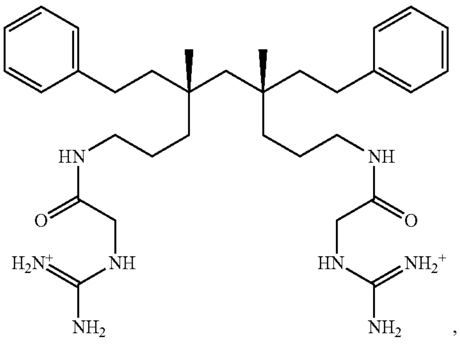

, and

-continued

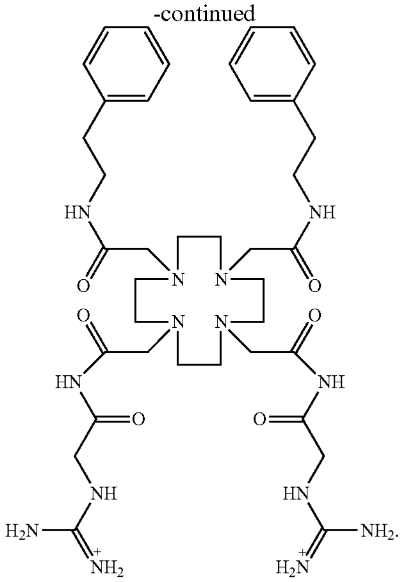

296. The method of clause 289, wherein the small molecule active agent is described by the formula (III):

(III)

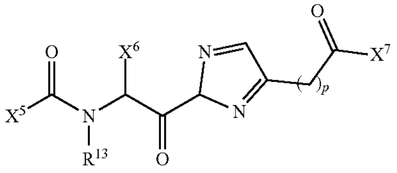

wherein:

$R^{13}$ is selected from hydrogen, alkyl and substituted alkyl;

$X^5$ is selected from alkyl, substituted alkyl, aryl, substituted aryl, amino, substituted amino, heteroaryl, substituted heteroaryl, heterocycle, substituted heteroaryl;

$X^6$ is selected from alkyl, substituted alkyl, aryl, substituted aryl, aralkyl, substituted aralkyl, heterocycle, substituted heterocycle, heteroaryl, substituted heteroaryl;

$X^7$ is selected from alkyl, substituted alkyl, aryl, substituted aryl, naphthyl, substituted naphthyl, heterocycle, substituted heterocycle, heteroaryl, substituted heteroaryl, aryl heterocycle, substituted aryl heterocycle; and p is an integer from 1 to 10, or a pharmaceutically acceptable salt or solvate thereof.

297. The method of clause 296, wherein the small molecule active agent is:

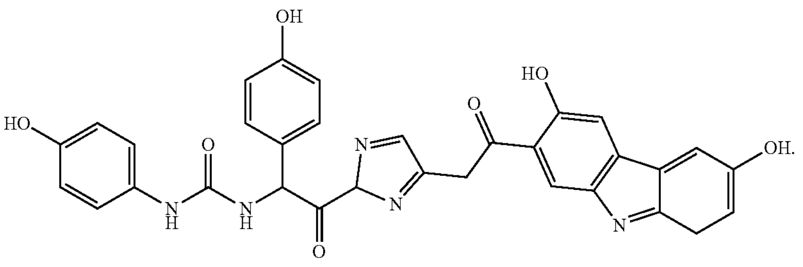 [SMILES: O=C(Nc1ccc(O)cc1)NC(C(=O)C1N=CC(CC(=O)c2cc3c(cc2O)C2=CC(O)=CCC2=N3)=N1)c1ccc(O)cc1]

298. The method of any one of clauses 243 to 246, wherein the compound is a specific binding member.
299. The method of any one of clauses 298, wherein the specific binding member is an antibody, or a binding fragment thereof.
300. The method of clause 298 or 299, wherein the specific binding member targets a sequence of CD206 selected from the group consisting of NFGDLVSIQSESEKK, NDAQSAYFIGLLISL, SKEKETMDNARAF, and EDENCVTMYSNSGFWN.
301. The method of clause 300, wherein the specific binding member targets a NFGDLVSIQSESEKK sequence of CD206.
302. The antibody of clause 300, wherein the specific binding member targets a NDAQSAYFIGLLISL sequence of CD206.
303. The antibody of clause 300, wherein the specific binding member targets a SKEKETMDNARAF sequence of CD206.
304. The antibody of clause 300, wherein the specific binding member targets a EDENCVTMYSNSGFWN sequence of CD206.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed:

1. A method of treating a subject for a condition, the method comprising:

administering a therapeutically effective amount of a CD206-binding agent that converts a macrophage M2 phenotype to M1 to a subject to treat the subject for the condition;

wherein:

the condition is a condition associated with chronic inflammation selected from the group consisting of scleroderma, Crohn's disease, fibrosis, idiopathic pulmonary fibrosis, asthma, arthritis, osteoarthritis, rheumatoid arthritis, breast cancer, colon cancer, pancreatic cancer, melanoma, prostate cancer, graft-versus-host disease (GVHD), diabetes, diabetic wounds, Alzheimer's disease, and macular degeneration, and the CD206-binding agent is described by formula (Ia):

(Ia)

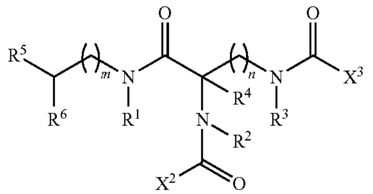

wherein:

$R^1$-$R^4$ are each independently selected from hydrogen, and alkyl;

$R^5$ and $R^6$ are each independently selected from optionally substituted aryl;

$X^2$ is selected from optionally substituted alkyl, optionally substituted heteroaryl, and $NR^{2a}R^{2b}$, where $R^{2a}$ and $R^{2b}$ are independently selected from hydrogen, and optionally substituted aryl;

$X^3$ is selected from optionally substituted aryl; and n is an integer from 1 to 6;

m is an integer of 3 or less, or a pharmaceutically acceptable salt or solvate thereof.

2. The method of claim 1, wherein the condition is pancreatic cancer or melanoma.

3. The method of claim 1, wherein the small molecule active agent is a compound selected from the group consisting of:

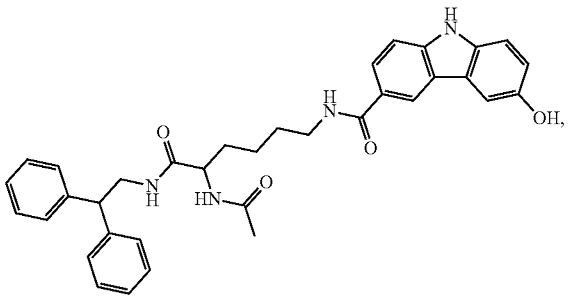

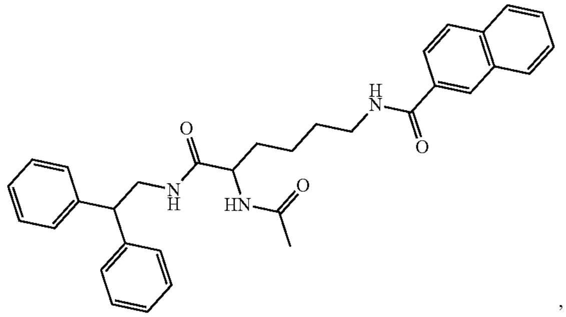

,

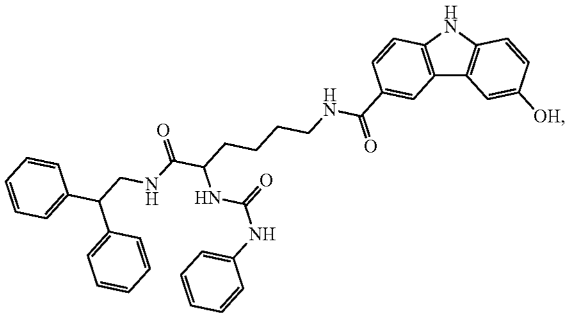

-continued

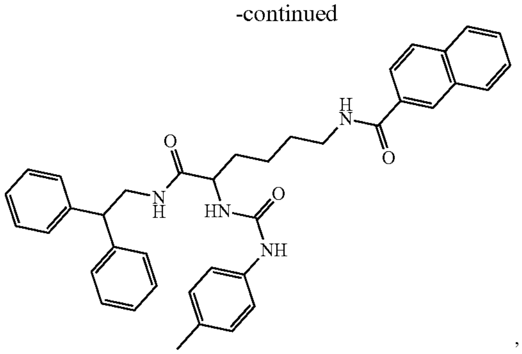

, and

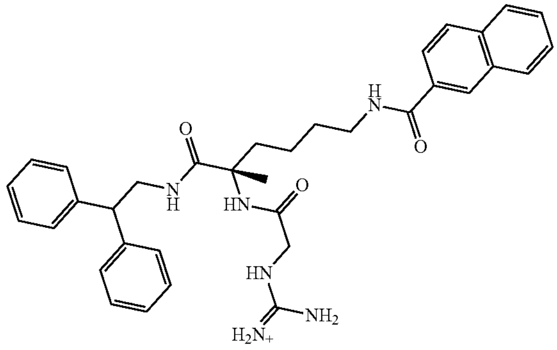

.

4. The method of claim 1, wherein $R^1$-$R^4$ are each hydrogen.

5. The method of claim 1, wherein $R^4$ is alkyl, and each of $R^1$-$R^3$ are hydrogen.

6. The method of claim 1, wherein $R^5$ and $R^6$ are each phenyl.

7. The method of claim 1, wherein $X^2$ is $C_1$-$C_6$ alkyl.

8. The method of claim 1, wherein $X^2$ is $C_1$-$C_6$ alkyl substituted with one or more groups selected from hydroxyl, amino, carboxamide, guanidine, acyl and halogen.

9. The method of claim 1, wherein $X^2$ is optionally substituted heteroaryl.

10. The method of claim 1, wherein $X^2$ is optionally substituted heteroaryl substituted with one or more groups selected from carbonyl and hydroxyl.

11. The method of claim 1, wherein $X^2$ is $NR^{2a}R^{2b}$, where $R^{2a}$ is an optionally substituted aryl group and $R^{2b}$ is H.

12. The method of claim 1, wherein $X^3$ is an optionally substituted carbazole.

13. The method of claim 1, wherein $X^3$ is an optionally substituted napthyl.

14. The method of claim 1, wherein m is 1 or 2.

* * * * *